United States Patent
Takeda et al.

(10) Patent No.: US 11,225,488 B2
(45) Date of Patent: Jan. 18, 2022

(54) ORGANIC COMPOUND, LIGHT-EMITTING ELEMENT, LIGHT-EMITTING DEVICE, ELECTRONIC DEVICE, DISPLAY DEVICE, AND LIGHTING DEVICE

(71) Applicant: Semiconductor Energy Laboratory Co., Ltd., Kanagawa-ken (JP)

(72) Inventors: Kyoko Takeda, Kanagawa (JP); Harue Osaka, Kanagawa (JP); Satoshi Seo, Kanagawa (JP); Tsunenori Suzuki, Kanagawa (JP); Naoaki Hashimoto, Kanagawa (JP); Yusuke Takita, Kanagawa (JP)

(73) Assignee: Semiconductor Energy Laboratory Co., Ltd.

( * ) Notice: Subject to any disclaimer, the term of this patent is extended or adjusted under 35 U.S.C. 154(b) by 621 days.

(21) Appl. No.: 16/090,477

(22) PCT Filed: Feb. 28, 2018

(86) PCT No.: PCT/IB2018/051255
§ 371 (c)(1),
(2) Date: Oct. 1, 2018

(87) PCT Pub. No.: WO2018/185571
PCT Pub. Date: Oct. 11, 2018

(65) Prior Publication Data
US 2021/0347782 A1    Nov. 11, 2021

(30) Foreign Application Priority Data

Apr. 7, 2017  (JP) .............................. JP2017-077076
Sep. 20, 2017  (JP) .............................. JP2017-179894
Dec. 1, 2017  (JP) .............................. JP2017-231424

(51) Int. Cl.
*C07D 495/04*    (2006.01)
*C07D 495/00*    (2006.01)
(Continued)

(52) U.S. Cl.
CPC ....... *C07D 491/048* (2013.01); *C07D 495/00* (2013.01); *H01L 51/0061* (2013.01);
(Continued)

(58) Field of Classification Search
None
See application file for complete search history.

(56) References Cited

U.S. PATENT DOCUMENTS 7,723,722 B2    5/2010  Kawakami et al.
8,134,147 B2    3/2012  Kawakami et al.
(Continued)

FOREIGN PATENT DOCUMENTS

CN    101659593 A    3/2010
CN    102924217 A    2/2013
(Continued)

OTHER PUBLICATIONS

SciFinder Search (Year: 2021).*
(Continued)

*Primary Examiner* — Vu A Nguyen
(74) *Attorney, Agent, or Firm* — Husch Blackwell LLP

(57) ABSTRACT

A novel organic compound is provided. Alternatively, an organic compound that exhibits light emission with favorable chromaticity is provided. Alternatively, an organic compound that exhibits blue light emission with favorable chromaticity is provided. Alternatively, an organic compound with favorable emission efficiency is provided. Alternatively, an organic compound having a high carrier-transport property is provided. Alternatively, an organic compound with favorable reliability is provided. An organic (Continued)

compound including at least one amino group in which any one of a substituted or unsubstituted dibenzofuranyl group, a substituted or unsubstituted dibenzothiophenyl group, and a substituted or unsubstituted carbazolyl group is bonded to any one of a substituted or unsubstituted naphthobisbenzofuran skeleton, a substituted or unsubstituted naphthobisbenzothiophene skeleton, and a substituted or unsubstituted naphthobenzofuranobenzothiophene skeleton is provided.

34 Claims, 125 Drawing Sheets

(51) Int. Cl.
  *H01L 51/00* (2006.01)
  *C07D 491/048* (2006.01)
(52) U.S. Cl.
  CPC ...... *H01L 51/0072* (2013.01); *H01L 51/0073* (2013.01); *H01L 51/0074* (2013.01)

(56) References Cited

U.S. PATENT DOCUMENTS

| | | | |
|---|---|---|---|
| 8,182,933 B2 | 5/2012 | Osaka et al. | |
| 8,278,655 B2 | 10/2012 | Kawakami et al. | |
| 8,530,672 B2 | 9/2013 | Kawakami et al. | |
| 8,673,459 B2 | 3/2014 | Seo et al. | |
| 8,816,098 B2 | 8/2014 | Kawakami et al. | |
| 8,940,416 B2 | 1/2015 | Osaka et al. | |
| 9,065,058 B2 | 6/2015 | Seo et al. | |
| 9,136,479 B2 | 9/2015 | Kawakami et al. | |
| 9,412,953 B2 | 8/2016 | Inoue et al. | |
| 9,447,111 B2 | 9/2016 | Kitamura et al. | |
| 9,496,503 B2 | 11/2016 | Takeda et al. | |
| 9,540,315 B2 | 1/2017 | Osaka et al. | |
| 9,586,972 B2 | 3/2017 | Kitamura et al. | |
| 9,634,263 B2 | 4/2017 | Ogita et al. | |
| 9,735,372 B2 | 8/2017 | Seo et al. | |
| 10,003,031 B2 | 6/2018 | Jang et al. | |
| 10,804,471 B2 | 10/2020 | Osaka et al. | |
| 10,833,282 B2 | 11/2020 | Seo et al. | |
| 2010/0032658 A1 | 2/2010 | Lee et al. | |
| 2011/0248246 A1 | 10/2011 | Ogita et al. | |
| 2014/0284578 A1 | 9/2014 | Takeda et al. | |
| 2015/0108440 A1 | 4/2015 | Jung et al. | |
| 2015/0166560 A1 | 6/2015 | Kitamura et al. | |
| 2015/0218184 A1 | 8/2015 | Kitamura et al. | |
| 2018/0201621 A1 | 7/2018 | Park et al. | |
| 2018/0282276 A1 | 10/2018 | Mun et al. | |
| 2019/0378992 A1* | 12/2019 | Skulason | C07C 211/61 |
| 2020/0181165 A1 | 6/2020 | Koo et al. | |
| 2021/0036226 A1 | 2/2021 | Osaka et al. | |

FOREIGN PATENT DOCUMENTS

| | | |
|---|---|---|
| CN | 111194320 A | 5/2020 |
| CN | 109928980 B | 3/2021 |
| EP | 1 972 619 A1 | 9/2008 |
| EP | 2145936 A | 1/2010 |
| JP | 2010-059147 A | 3/2010 |
| JP | 2013-232521 A | 11/2013 |
| JP | 2013-234151 A | 11/2013 |
| JP | 2014-045099 A | 3/2014 |
| JP | 2014-082247 A | 5/2014 |
| JP | 2014-237682 A | 12/2014 |
| JP | 2016-503761 | 2/2016 |
| KR | 2010-0007780 A | 1/2010 |
| KR | 2011-0022605 A | 3/2011 |
| KR | 2014-0023407 A | 2/2014 |
| KR | 2014-0023408 A | 2/2014 |
| KR | 2014-0024438 A | 2/2014 |
| KR | 2014-0024439 A | 2/2014 |
| KR | 2014-0024440 A | 2/2014 |
| KR | 2014-0071980 A | 6/2014 |
| KR | 2015-0046639 A | 4/2015 |
| KR | 2015-0048182 A | 5/2015 |
| KR | 2016-0115114 A | 10/2016 |
| KR | 2017-0022505 A | 3/2017 |
| TW | 201009046 | 3/2010 |
| TW | 201408670 | 3/2014 |
| TW | 201414717 | 4/2014 |
| WO | WO-2014/061464 | 4/2004 |
| WO | WO 2009/139358 A1 | 11/2009 |
| WO | WO 2012/033108 A1 | 3/2012 |
| WO | WO-2014/034393 | 3/2014 |
| WO | WO-2016/153198 | 9/2016 |
| WO | WO-2017/030307 | 2/2017 |
| WO | WO 2017/048025 A1 | 3/2017 |
| WO | WO 2018/097937 A1 | 5/2018 |

OTHER PUBLICATIONS

International Search Report re Application No. PCT/IB2018/051255, dated May 15, 2018.
Written Opinion re Application No. PCT/IB2018/051255, dated May 15, 2018.
Yamamoto, K. et al., "Synthesis and Properties of naphthobisbenzo[b]thiophenes: Structural Curvature of Higher Acene Frameworks for Solubility Enhancement and High-Order Orientation in Crystalline States," Tetrahedron Letters, Apr. 4, 2012, vol. 53, No. 14, pp. 1786-1789.
Indian Office Action (Application No. 201917041006) dated Apr. 12, 2021.
Chinese Office Action (Application No. 201880000701.1) dated Oct. 25, 2021.

* cited by examiner

[FIG. 1]
(A)
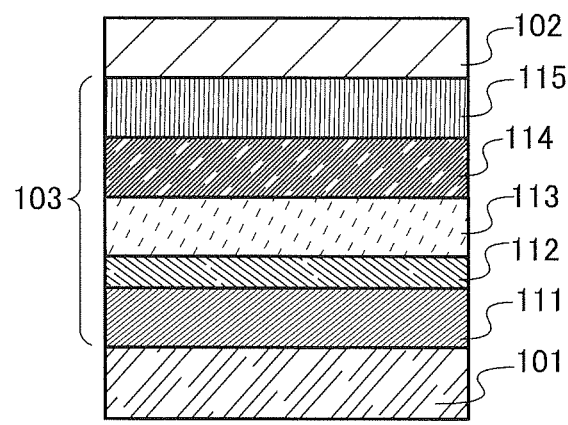
(B)
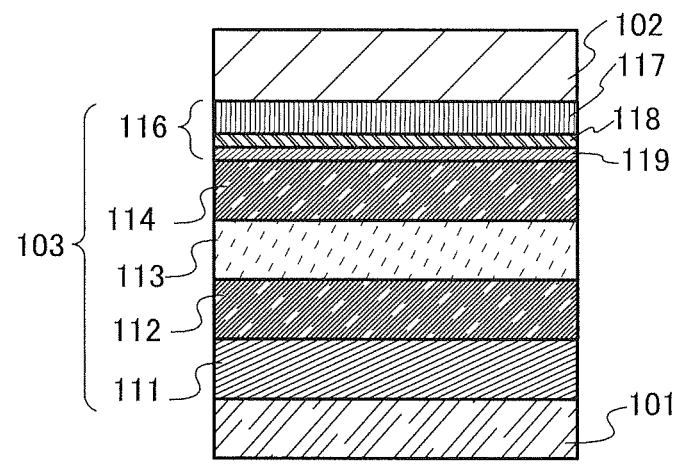
(C)
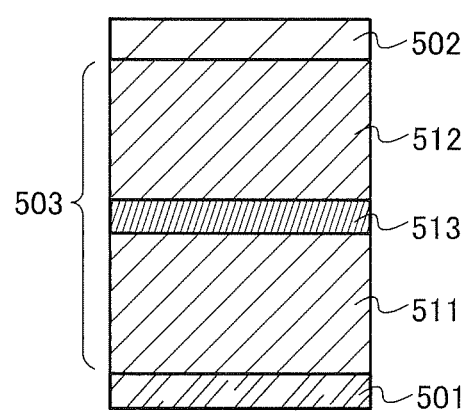

[FIG. 2]
(A)
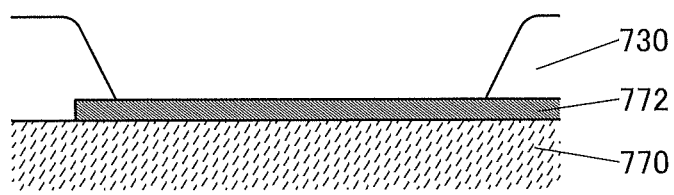
(B)
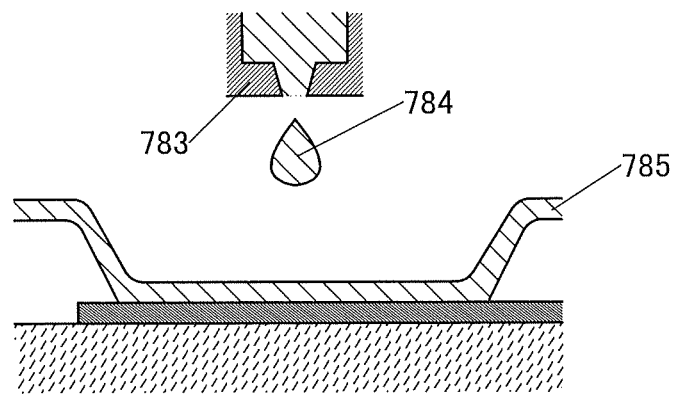
(C)
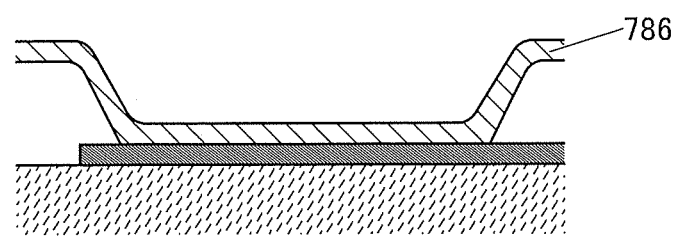
(D)
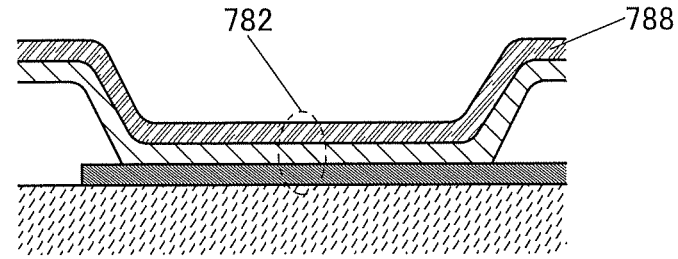

[FIG. 3]
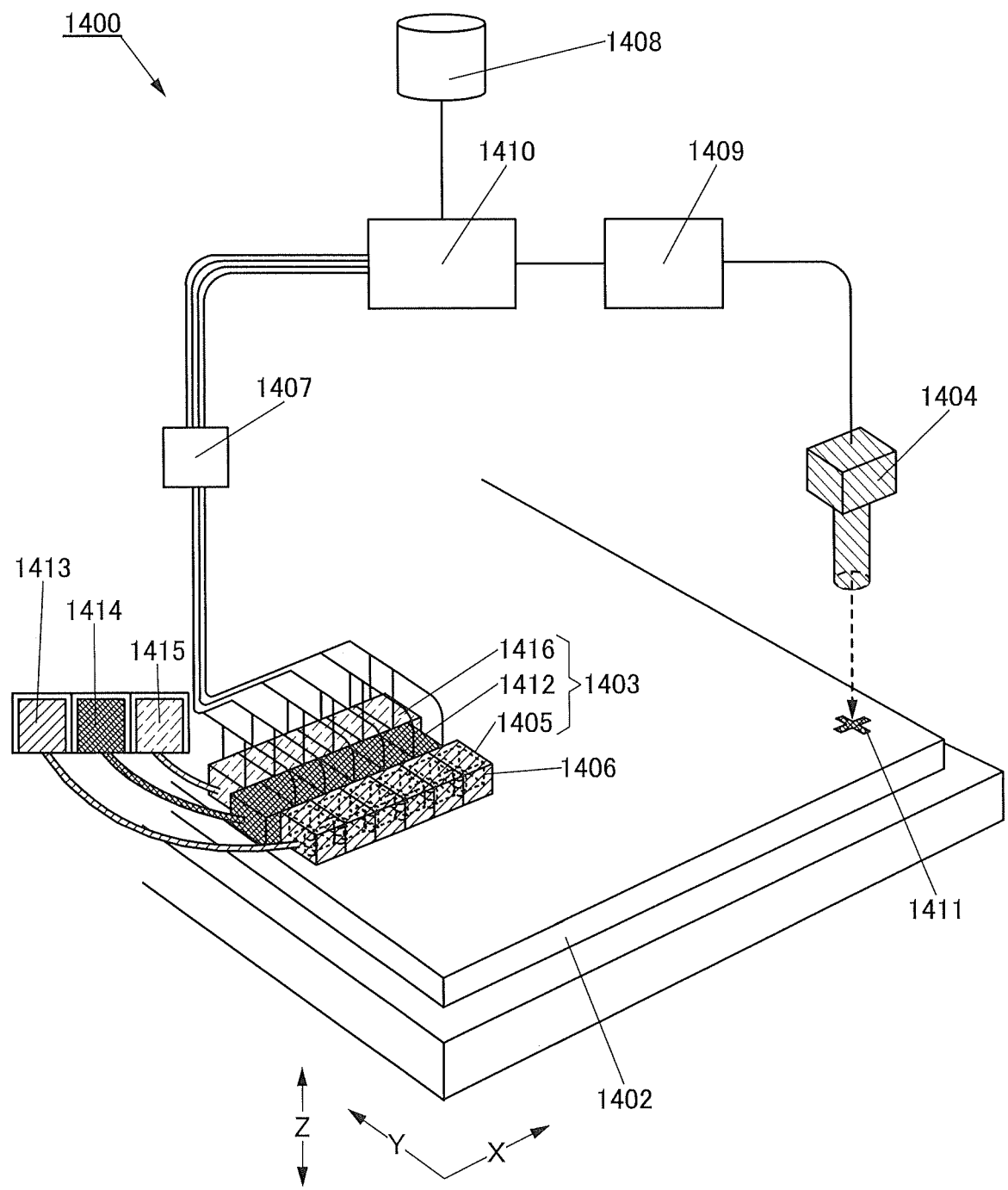

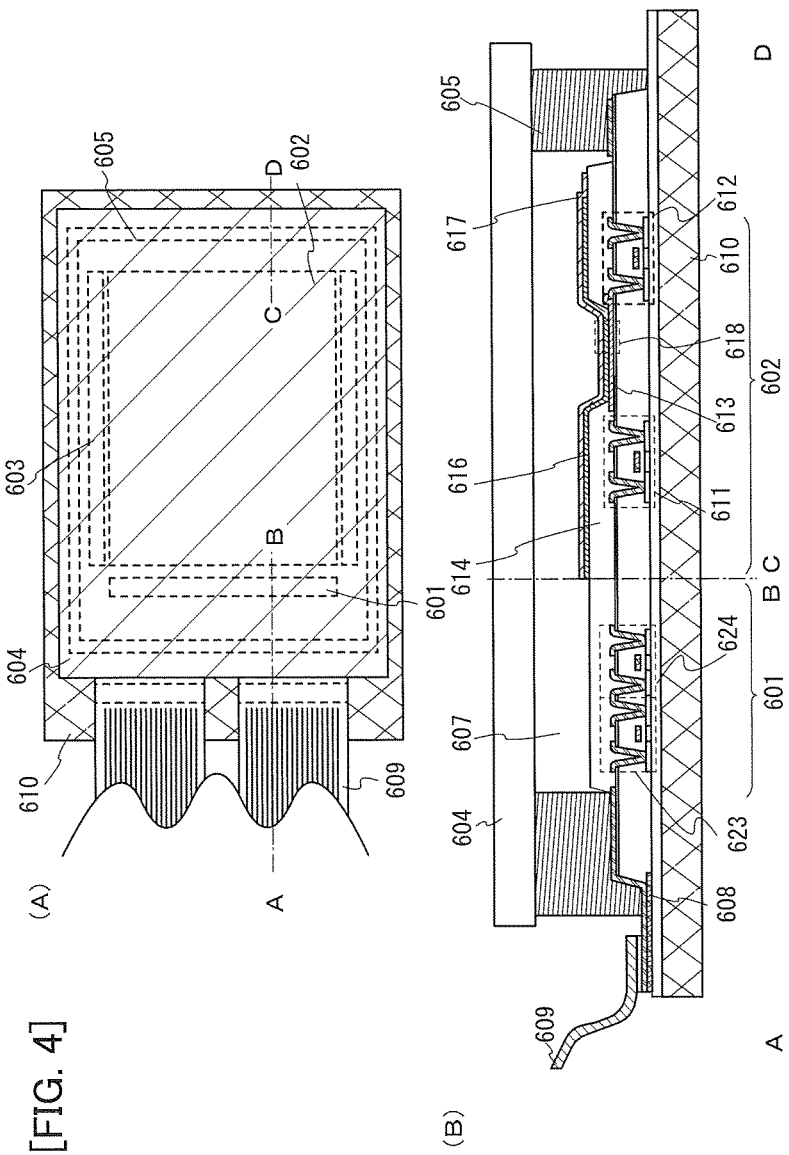
[FIG. 4]

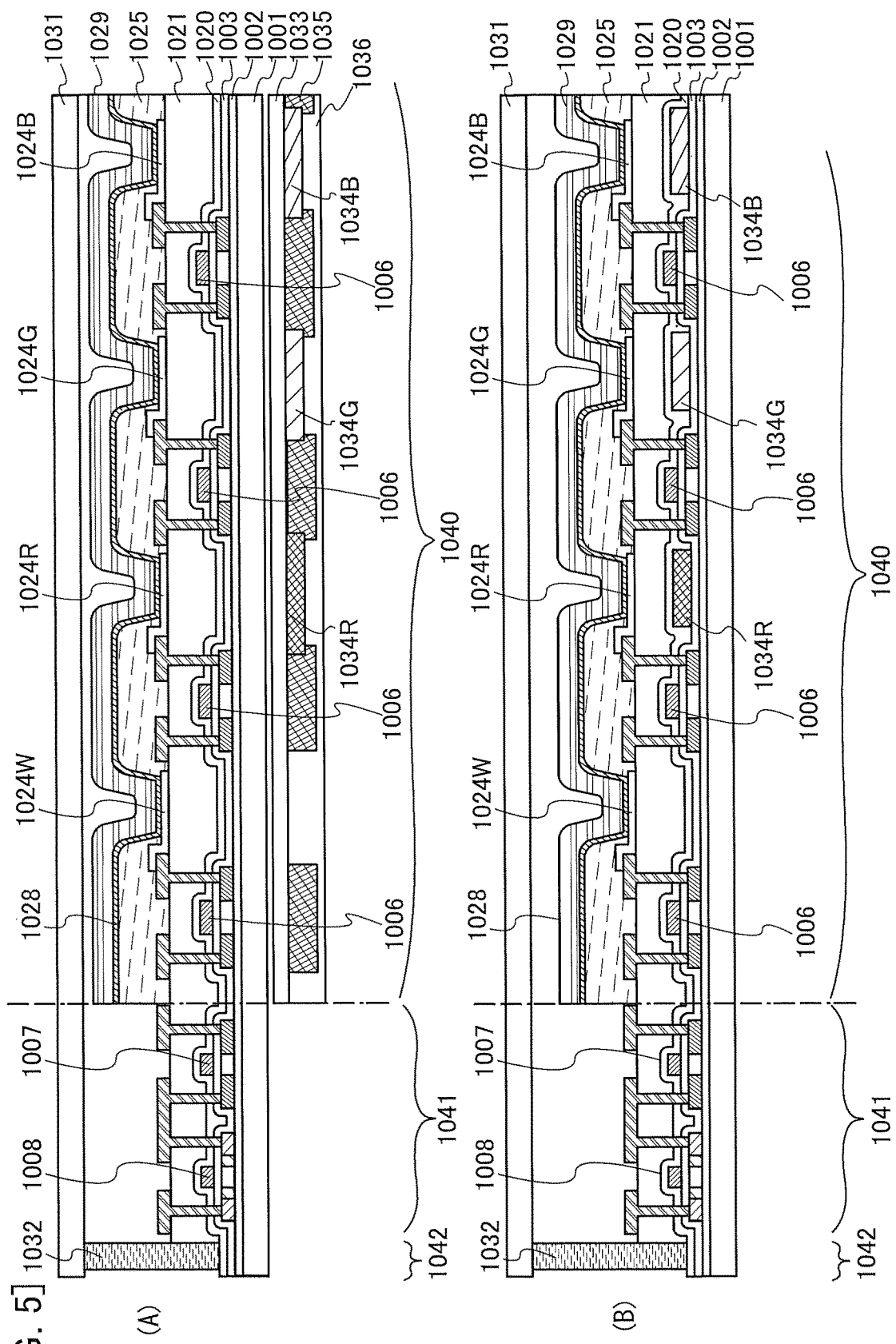

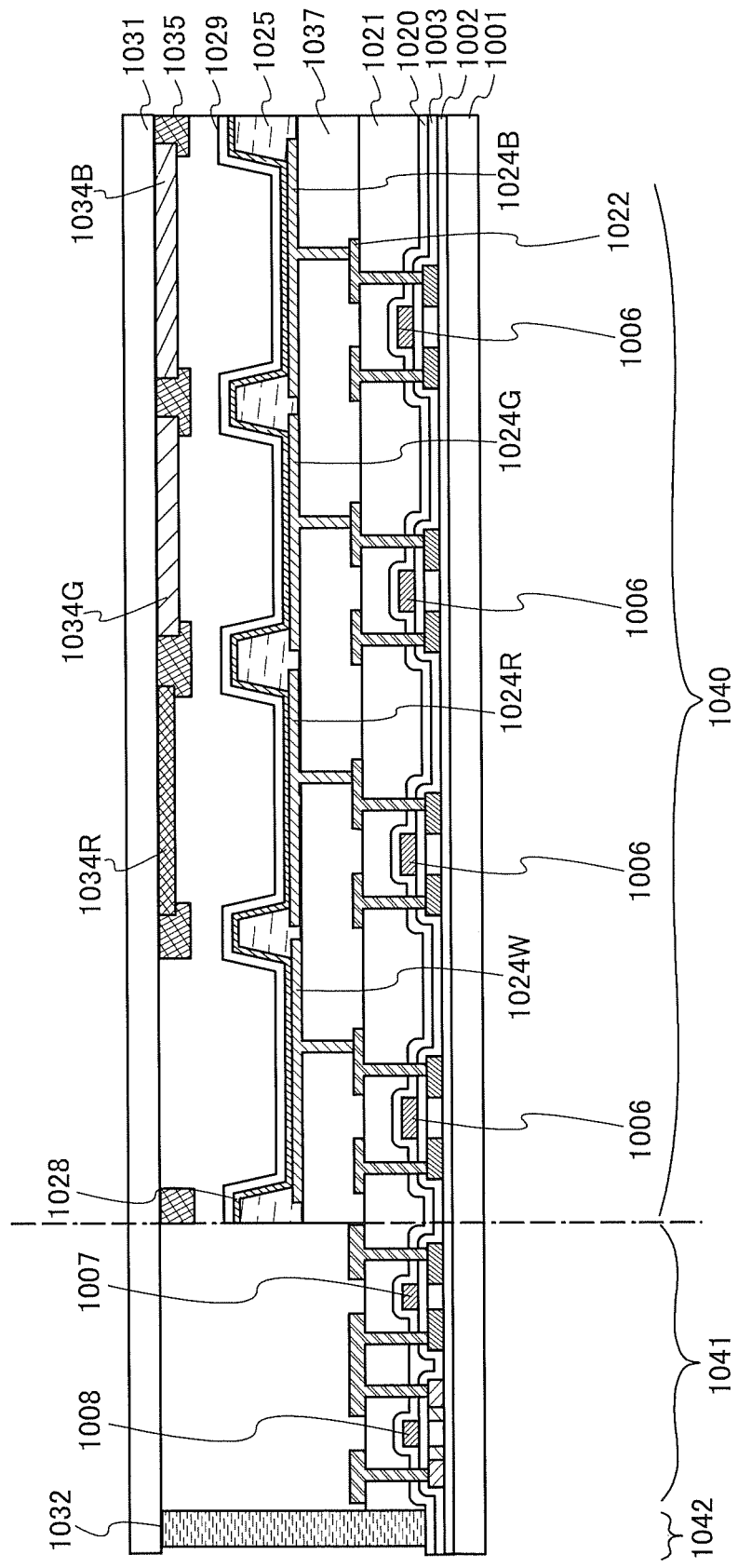
[FIG. 6]

[FIG. 7]
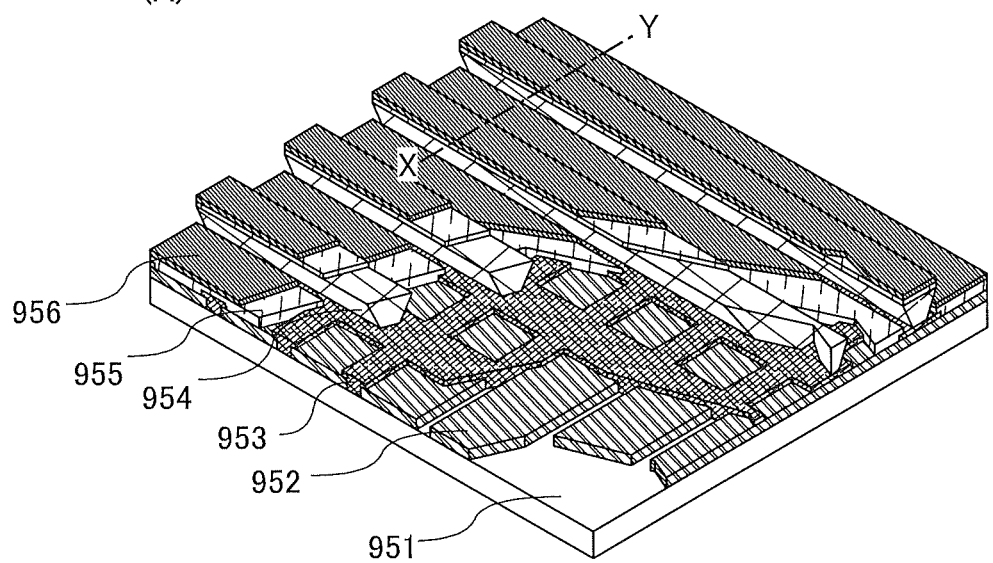
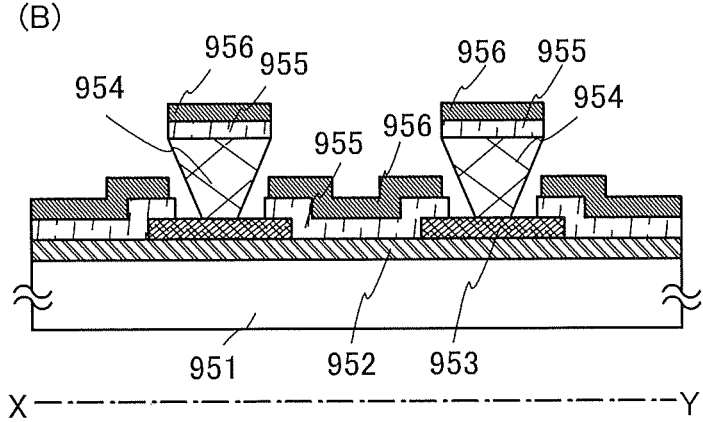

[FIG. 8]
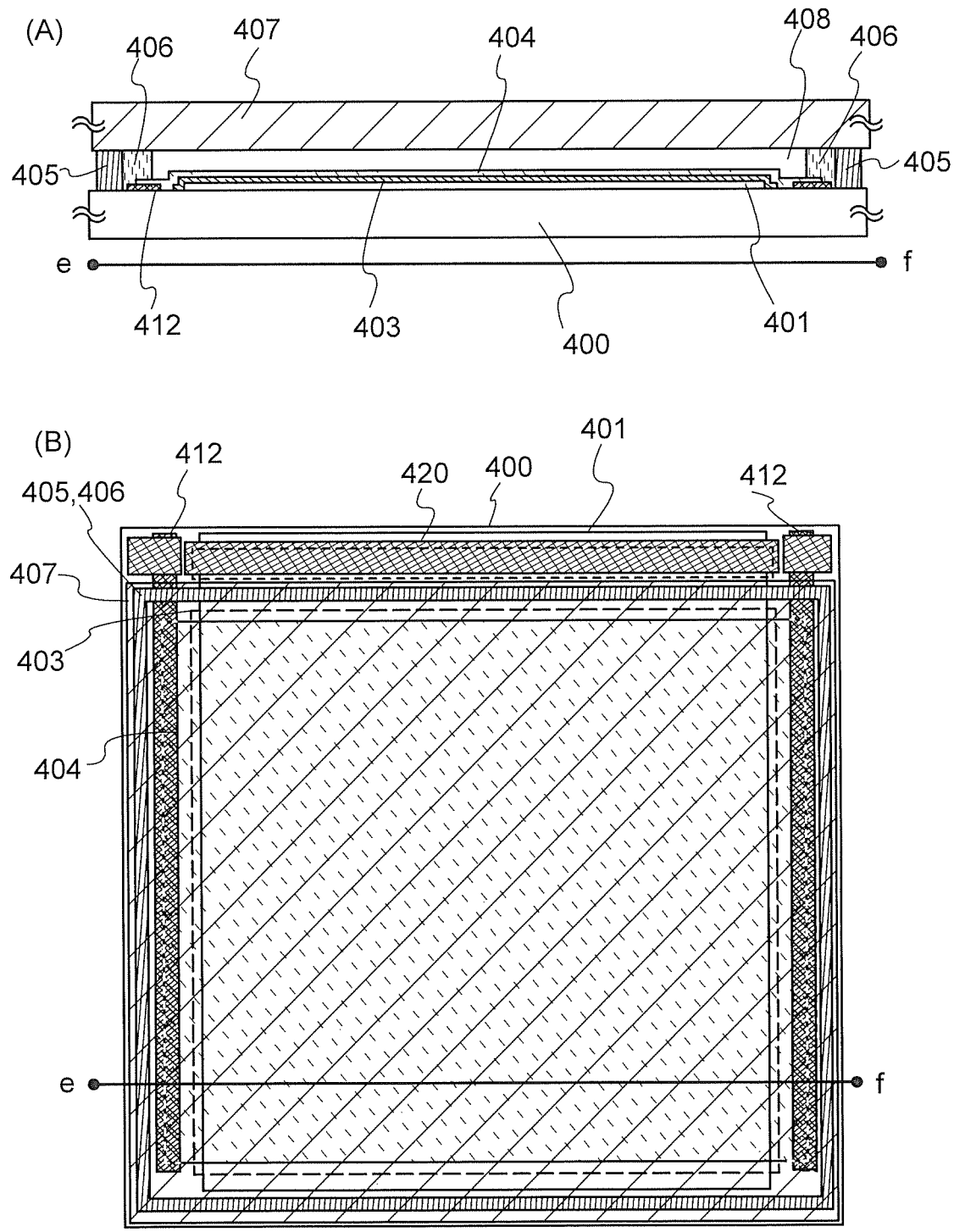

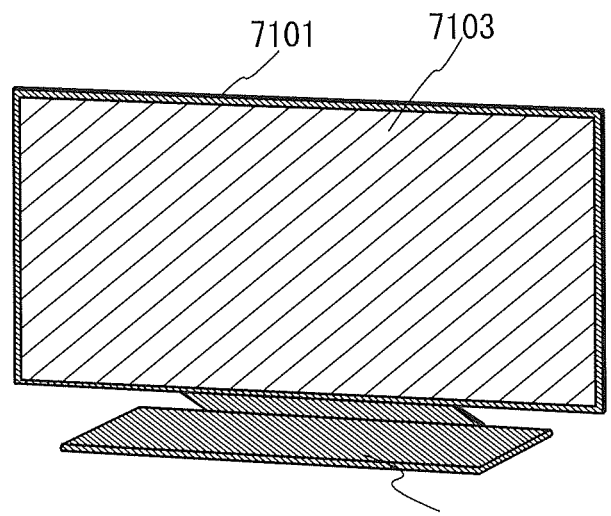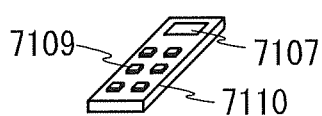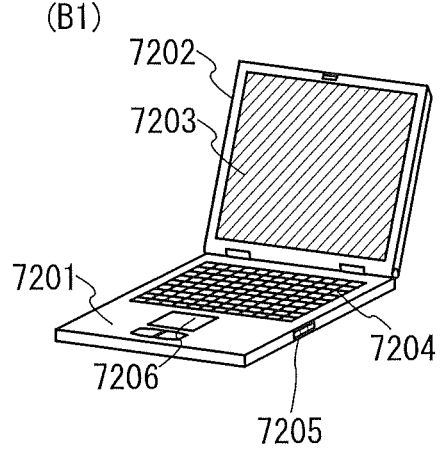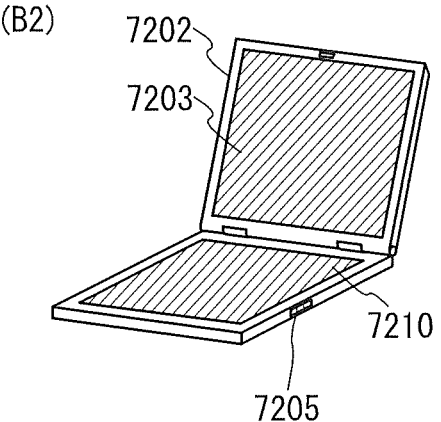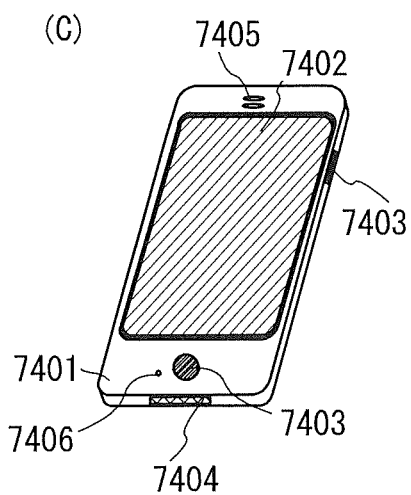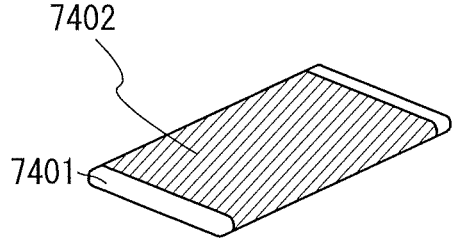

[FIG. 10]
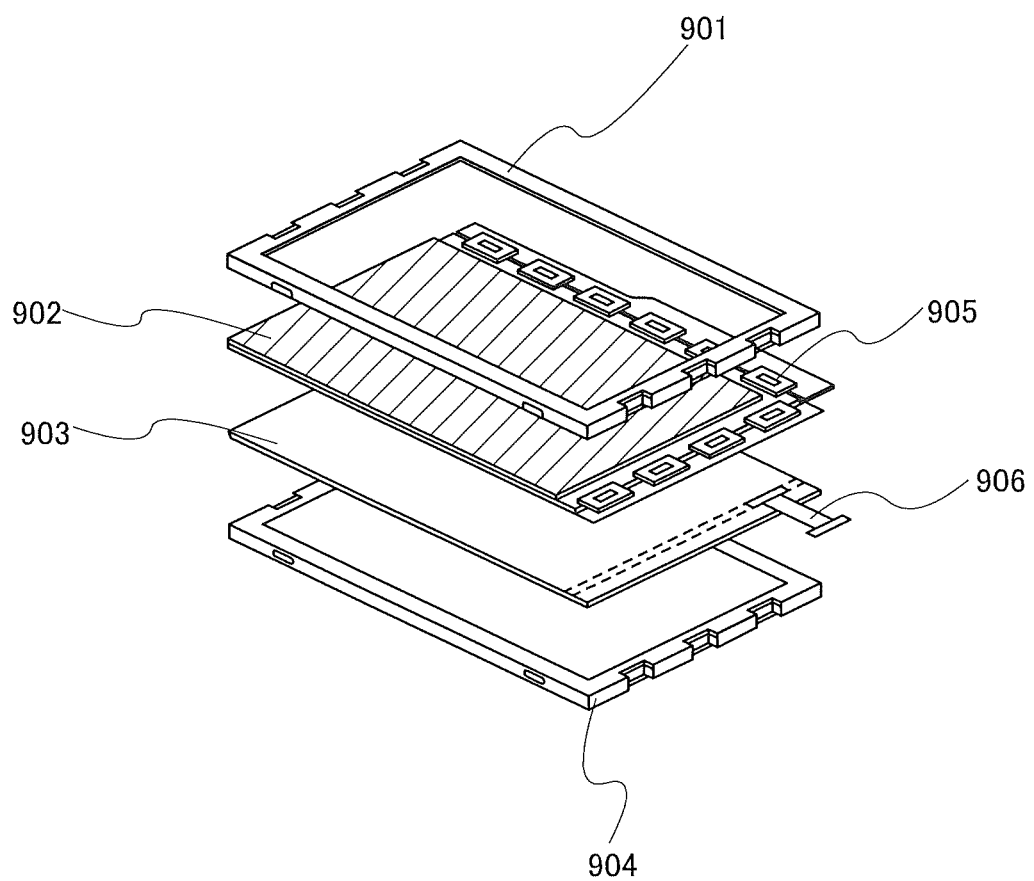

[FIG. 11]
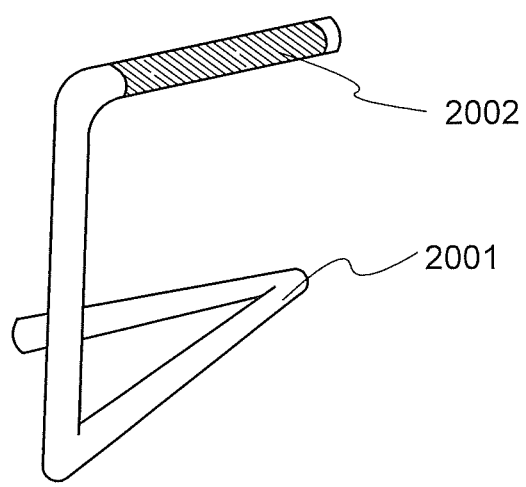

[FIG. 12]
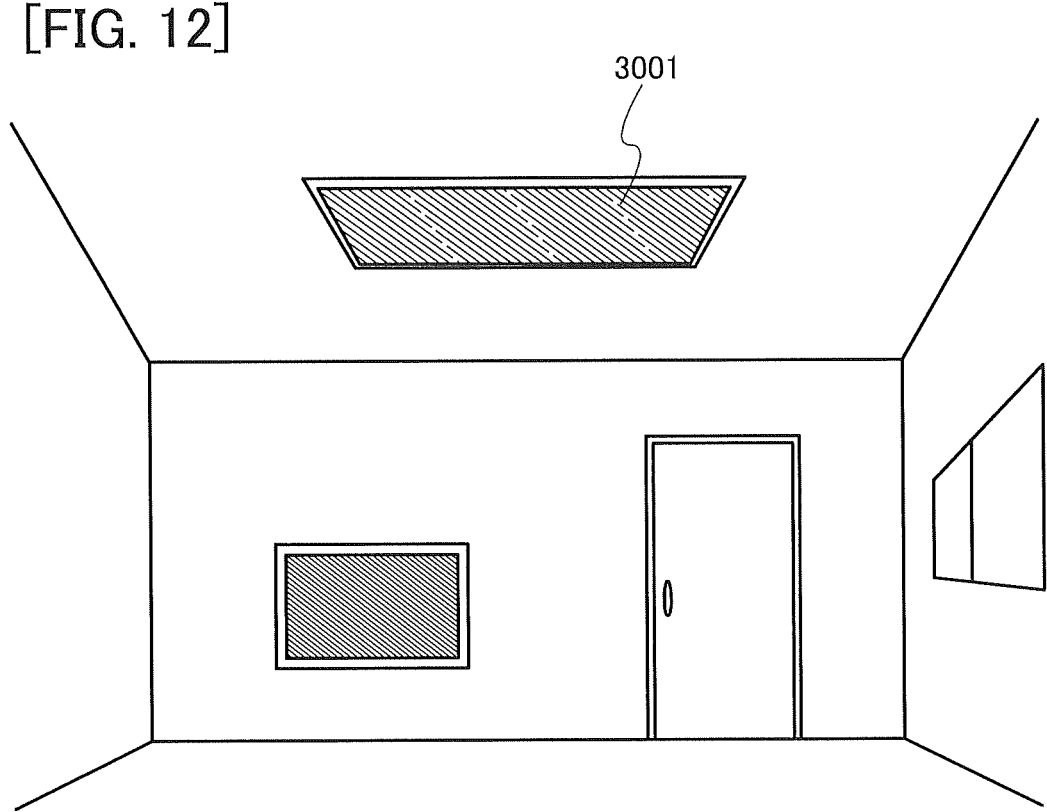

[FIG. 13]
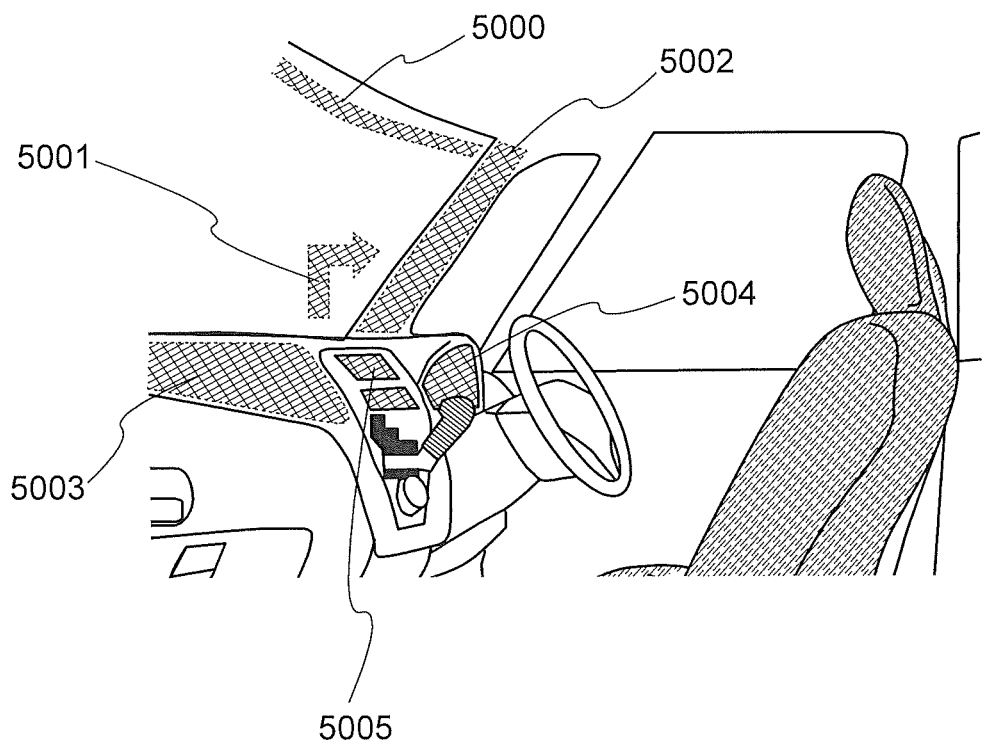

[FIG. 14]
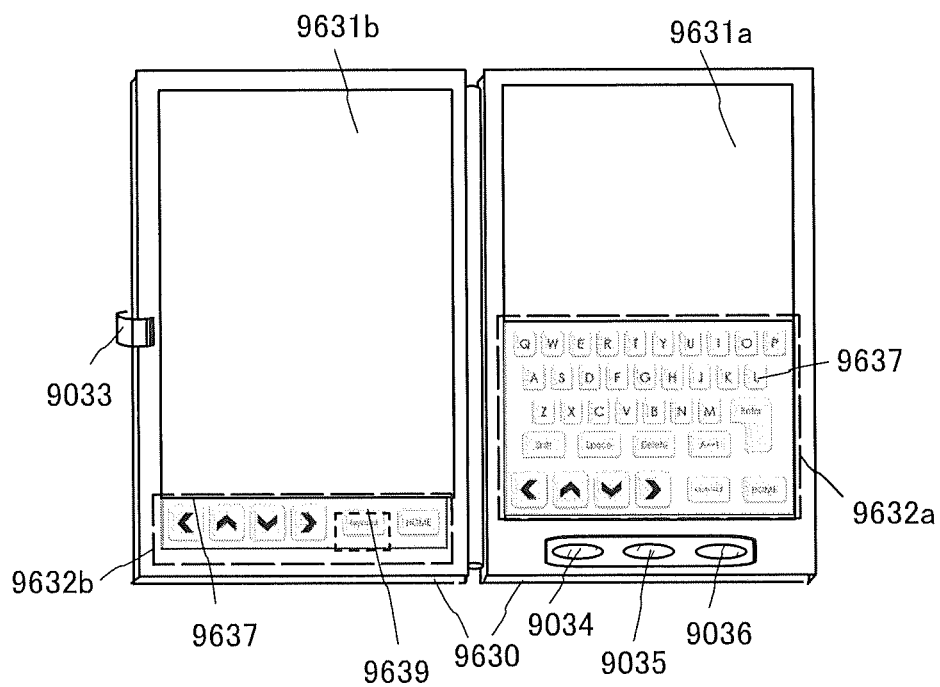
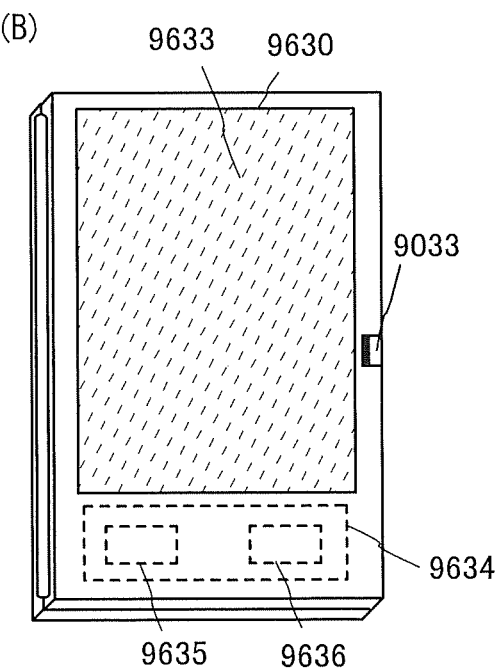
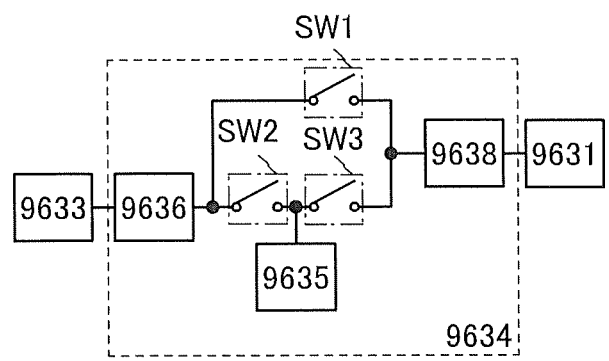

[FIG. 15]
(A)
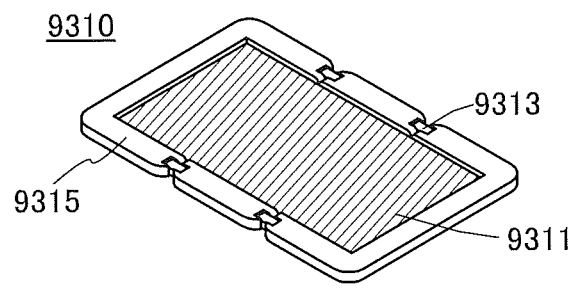
(B)
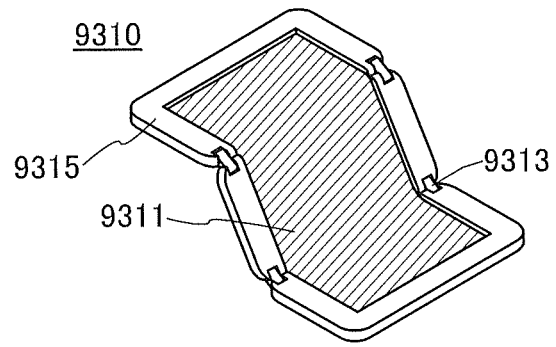
(C)
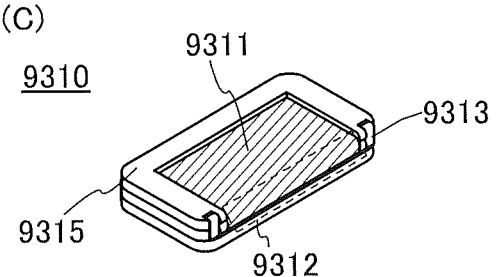

[FIG. 16]
(A)
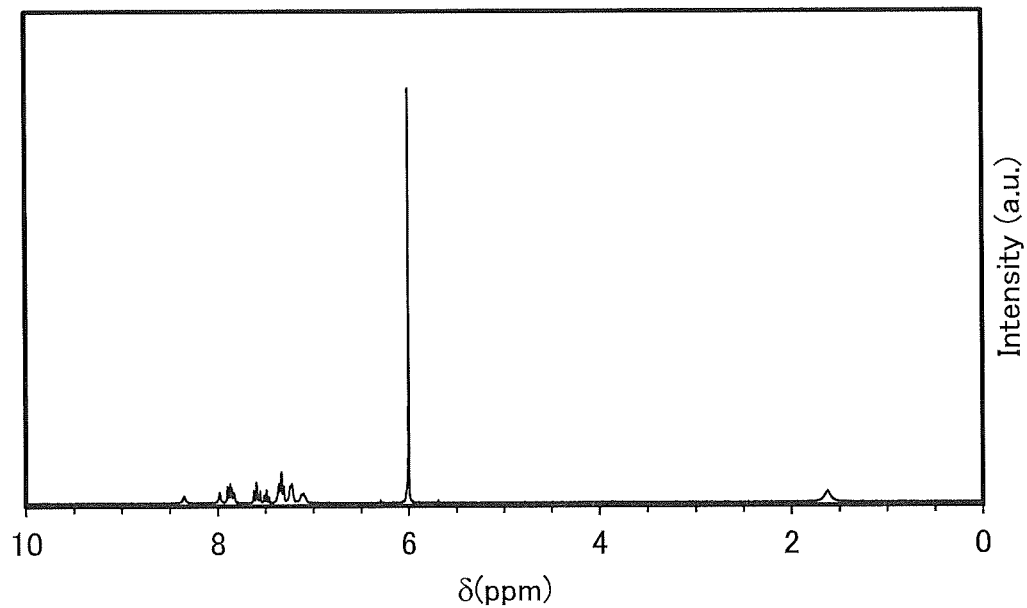
(B)
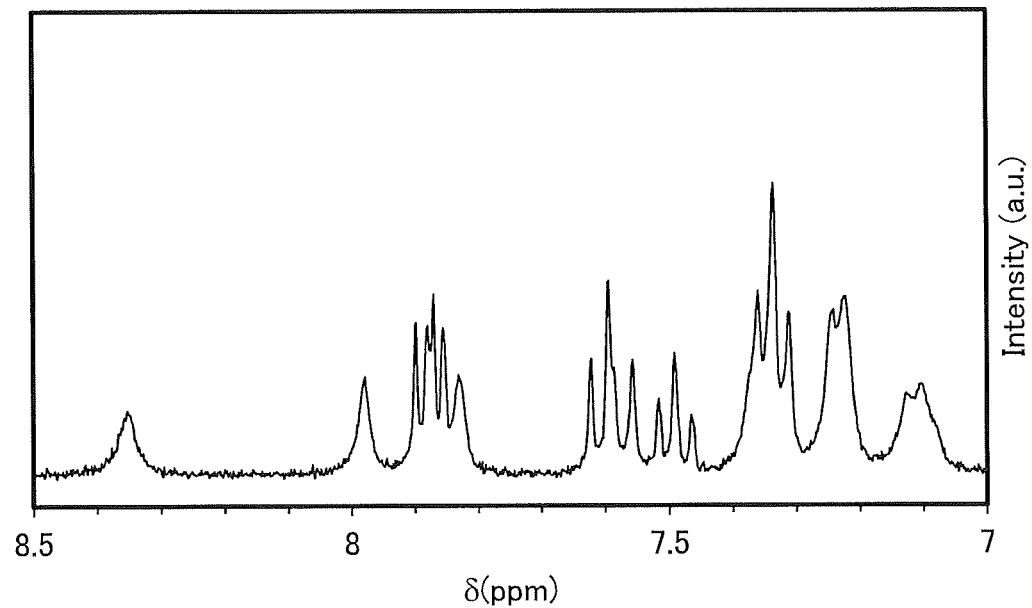

[FIG. 17]
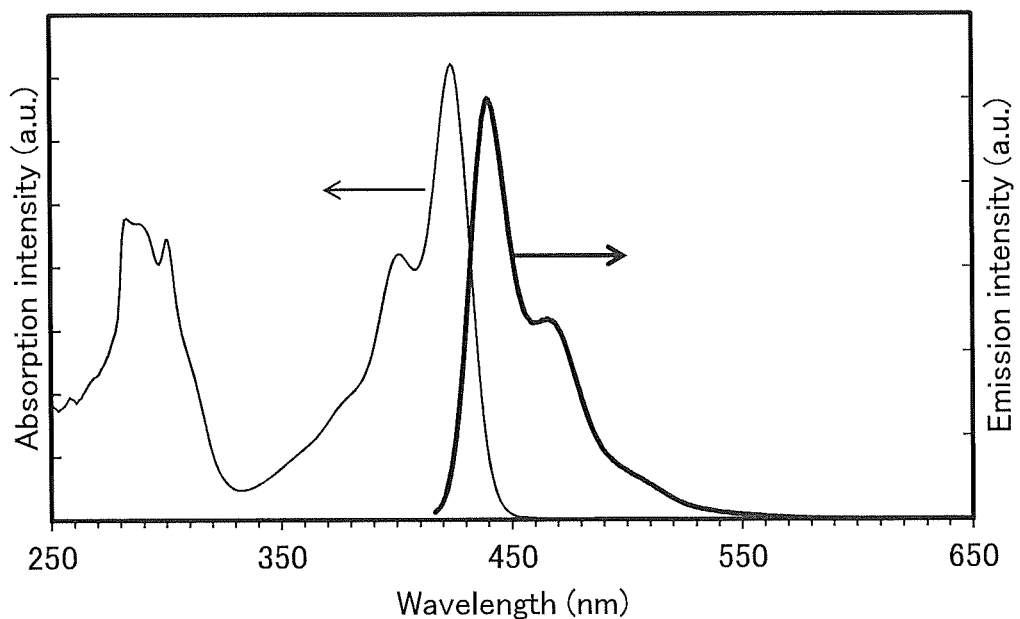
[FIG. 18]
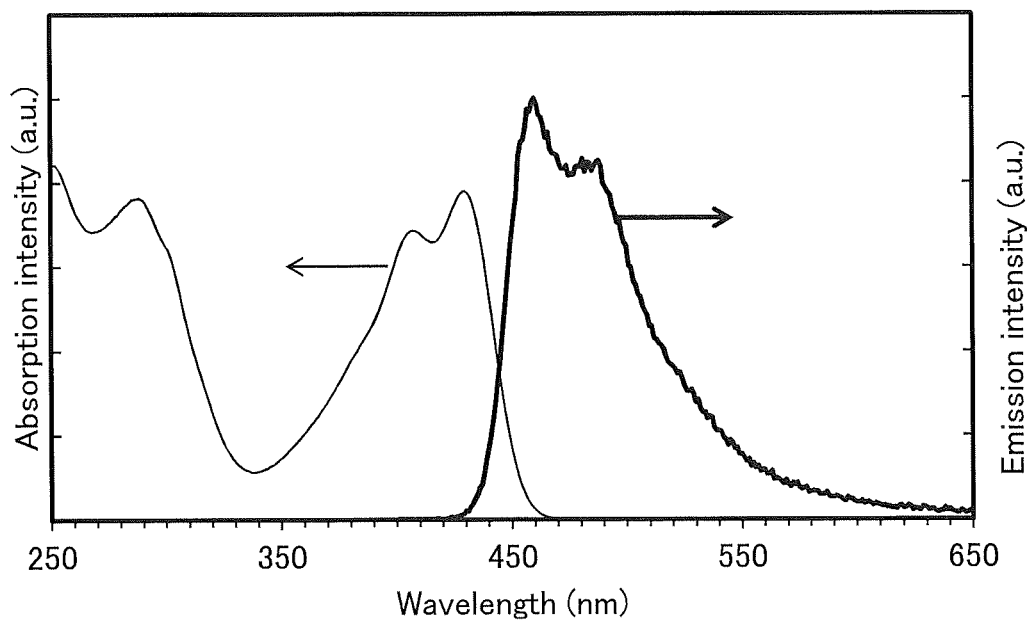

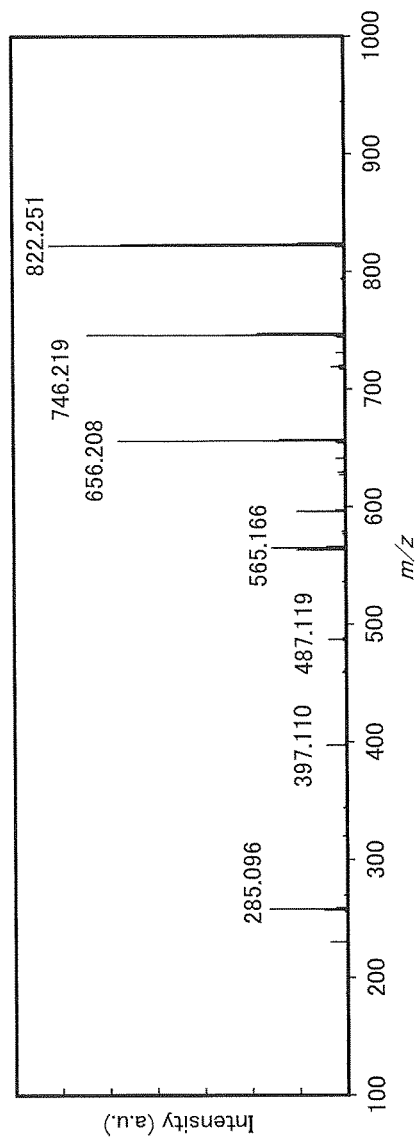
[FIG. 19]

[FIG. 20]
(A)
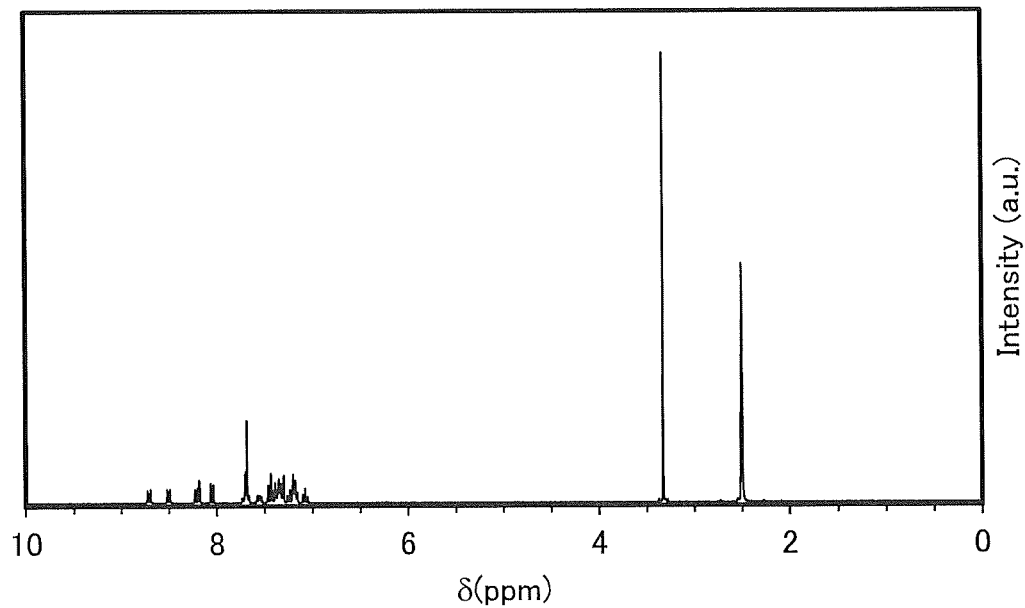
(B)
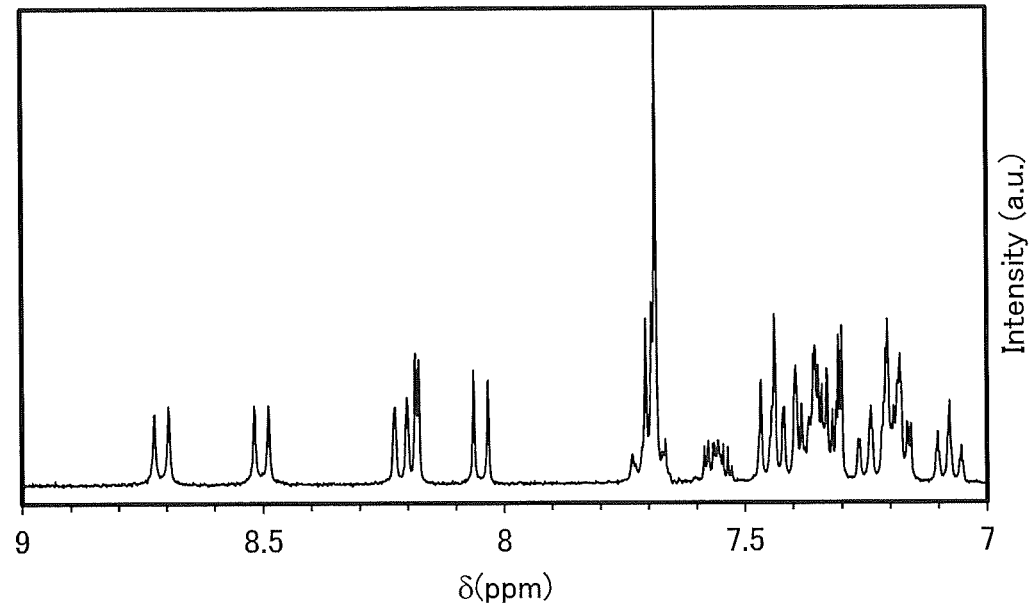

[FIG. 21]
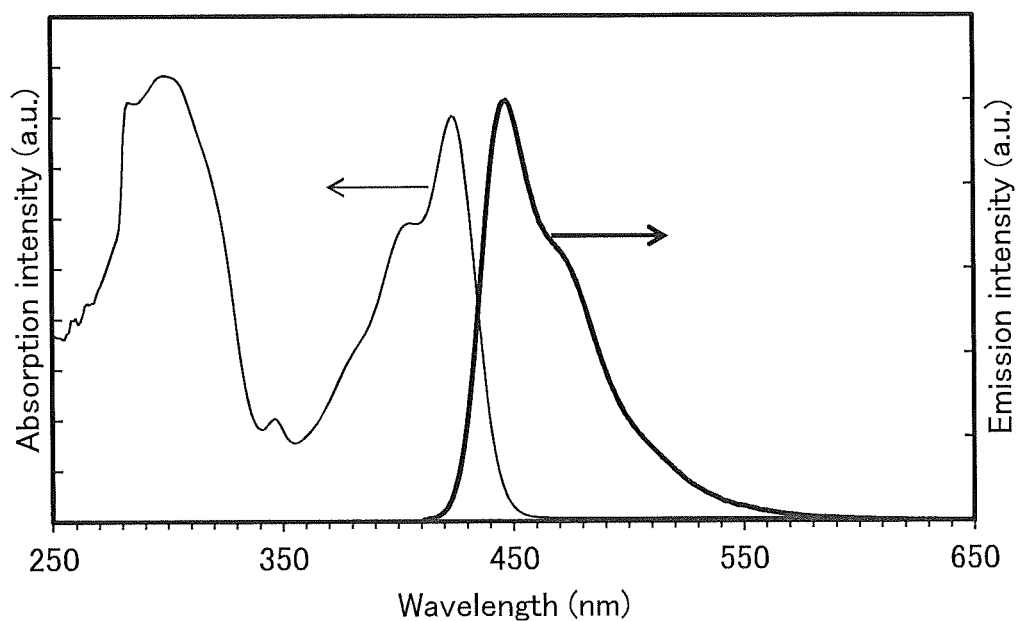
[FIG. 22]
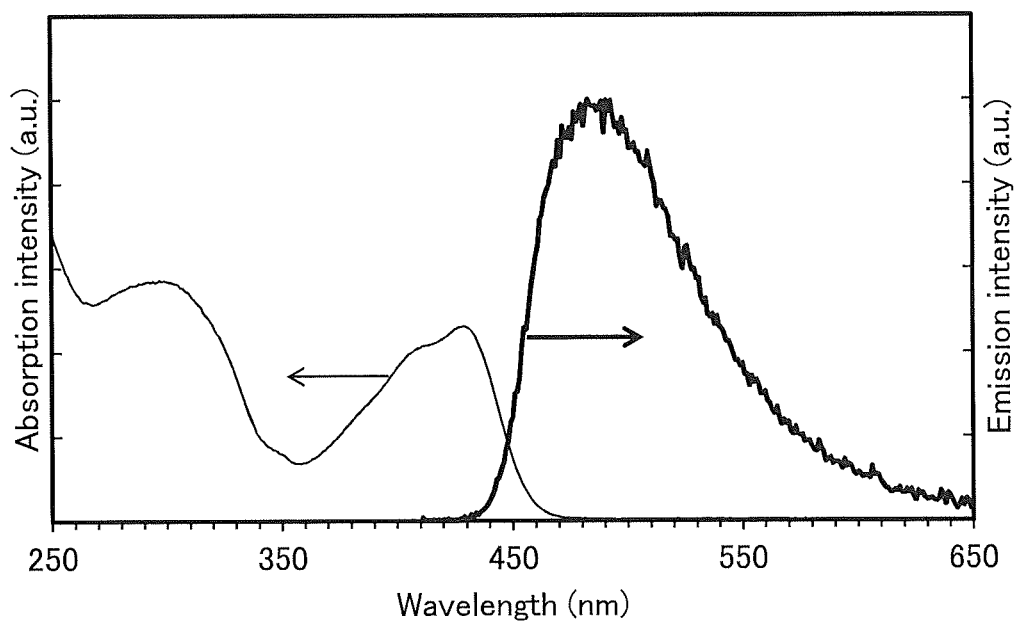

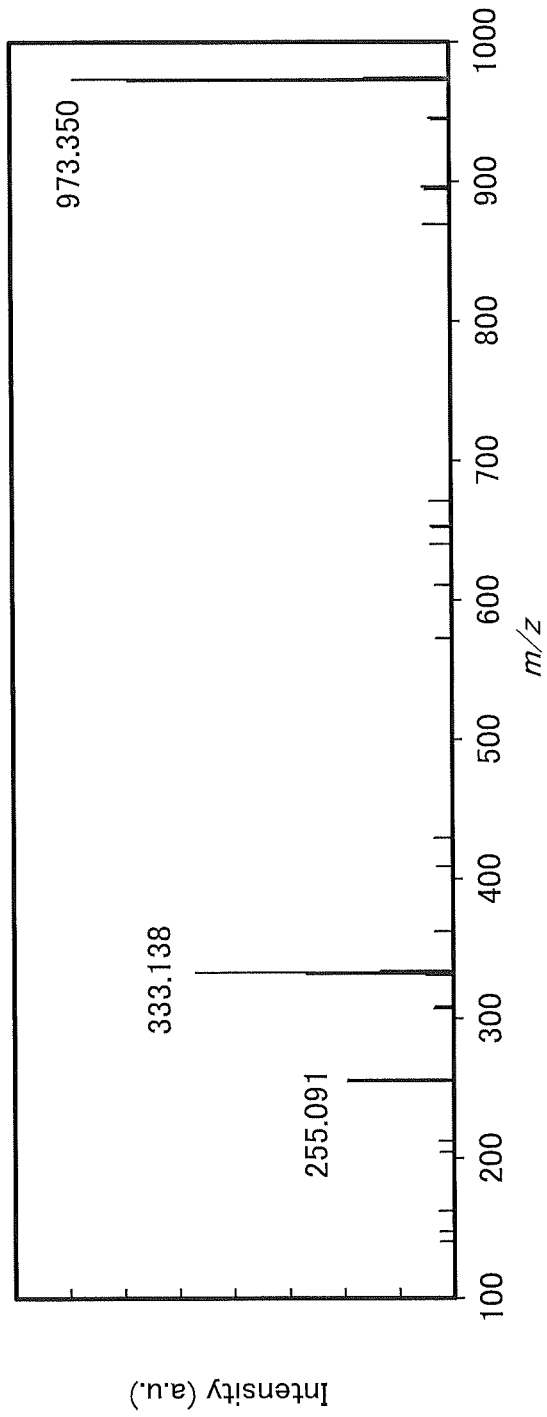
[FIG. 23]

[FIG. 24]
(A)
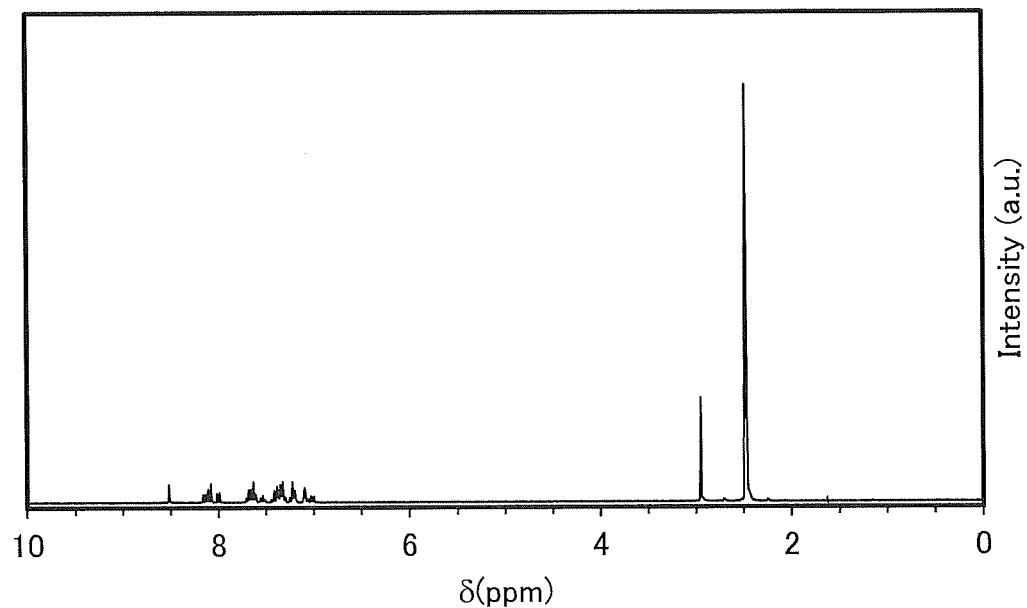
(B)
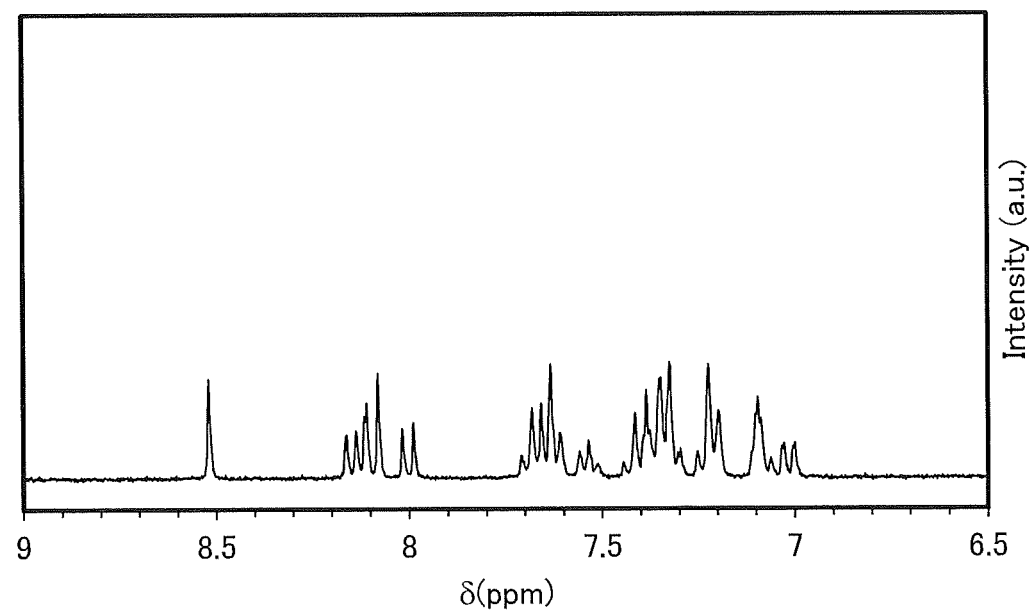

[FIG. 25]
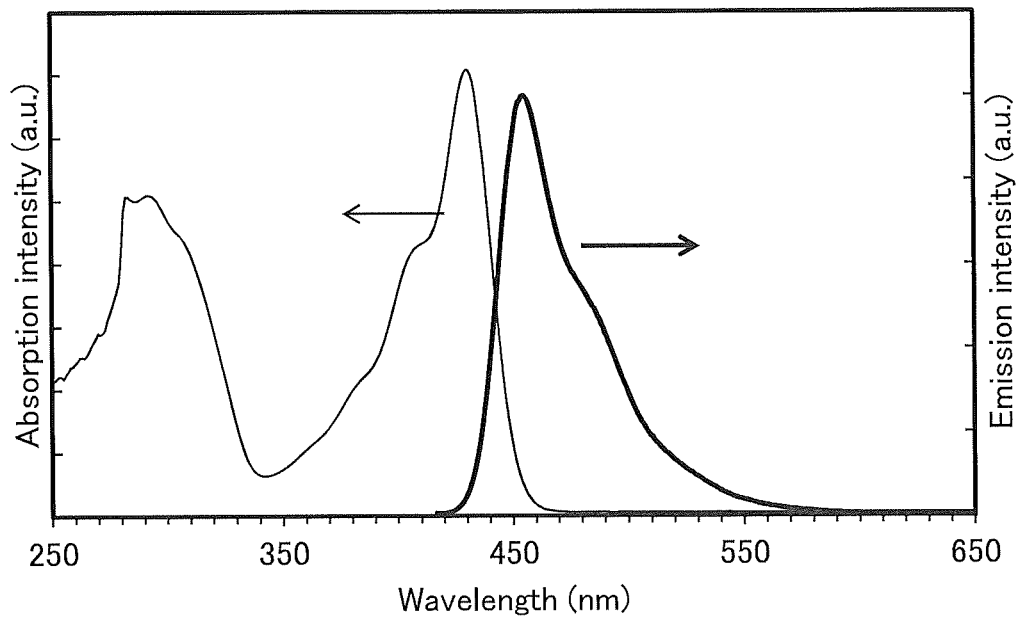
[FIG. 26]
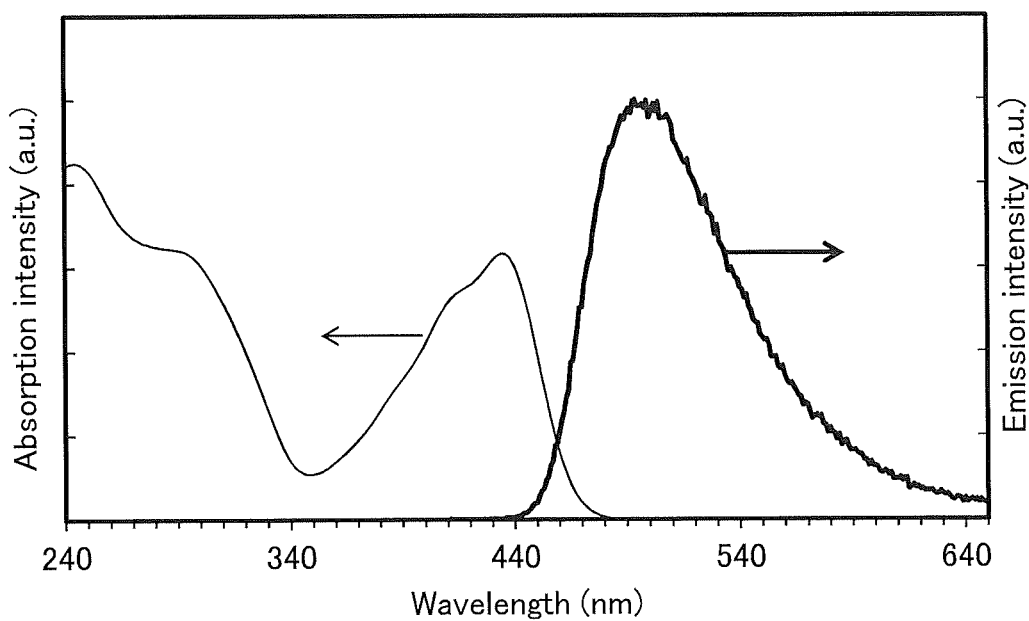

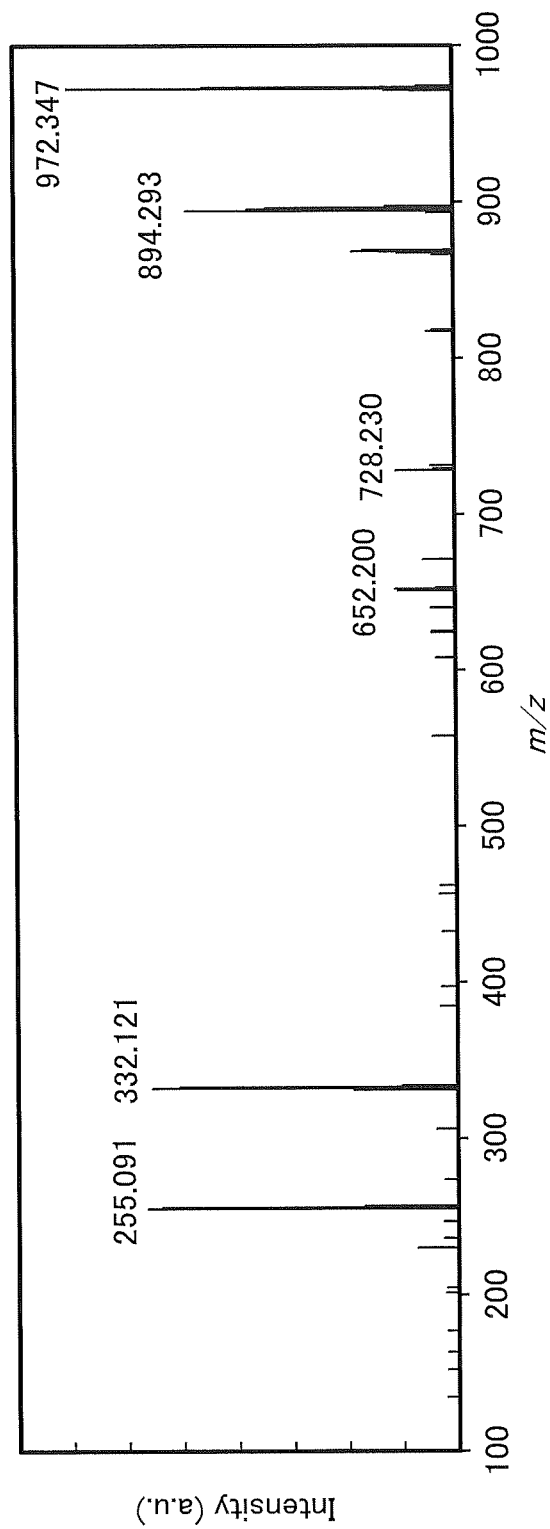
[FIG. 27]

[FIG. 28]
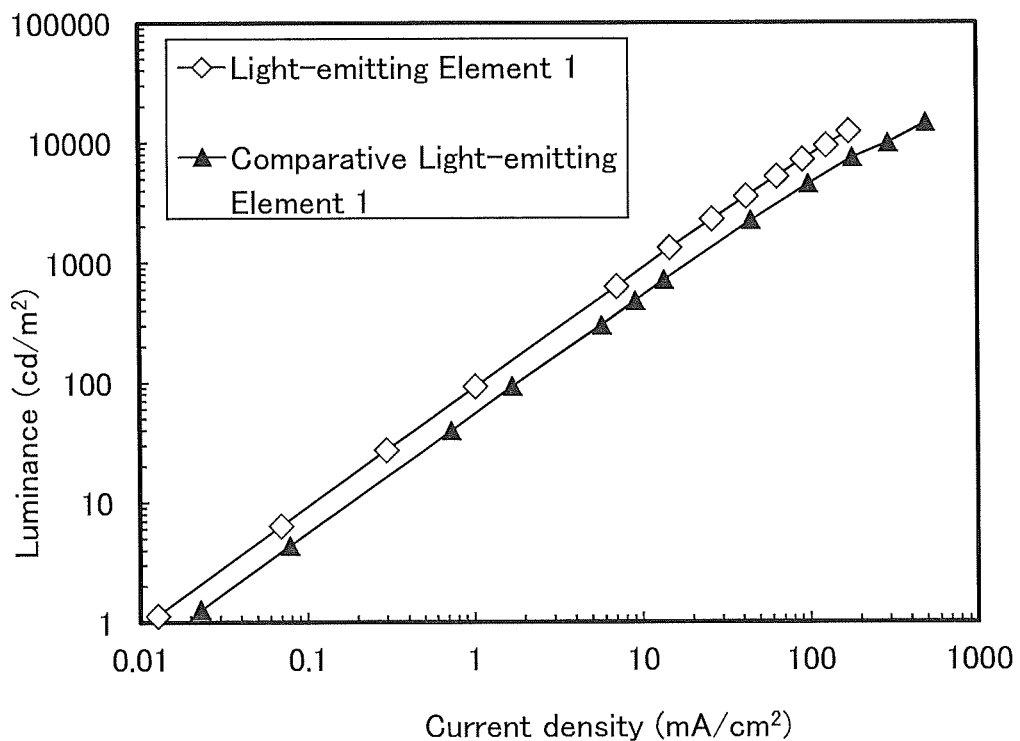
[FIG. 29]
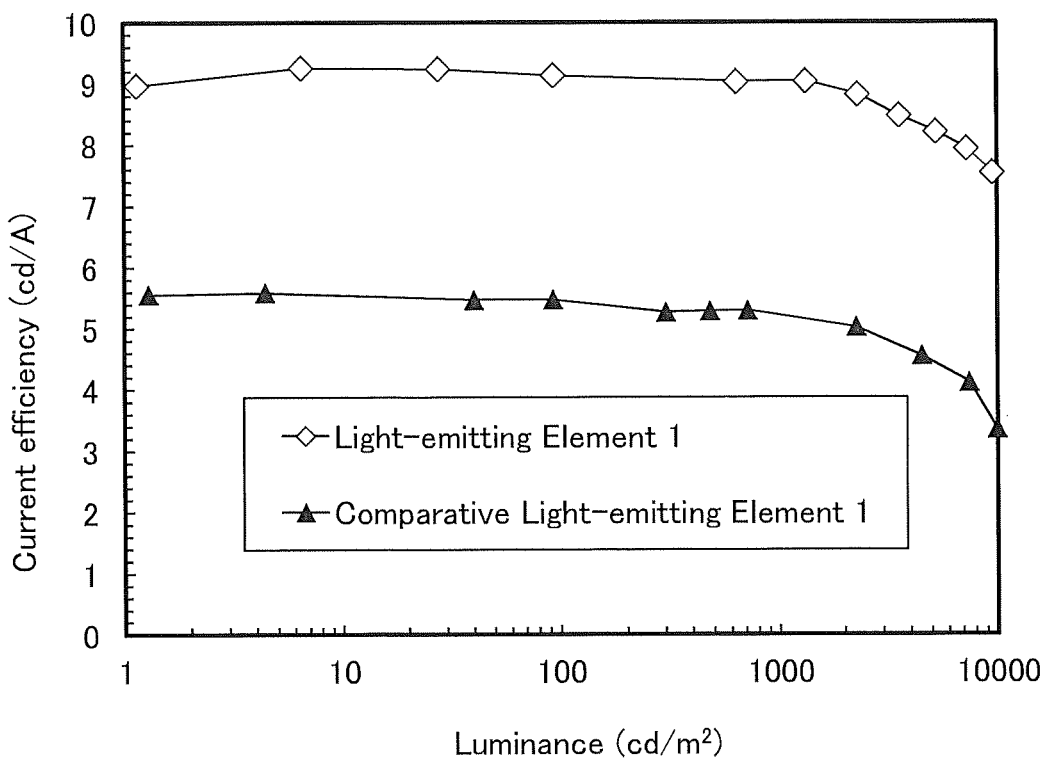

[FIG. 30]
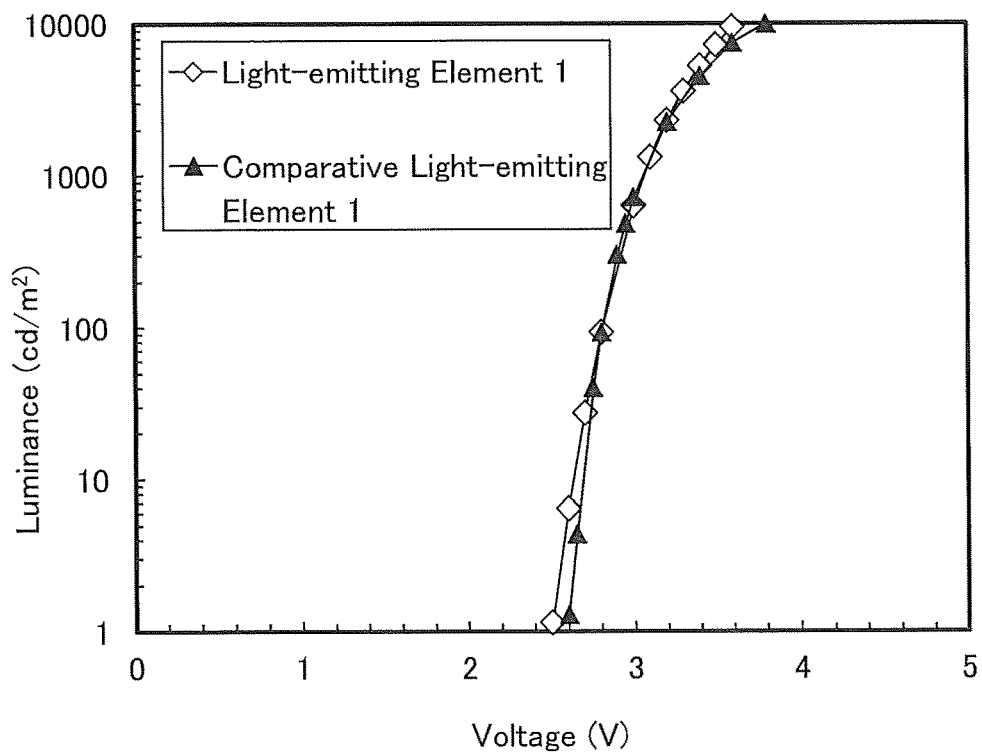
[FIG. 31]
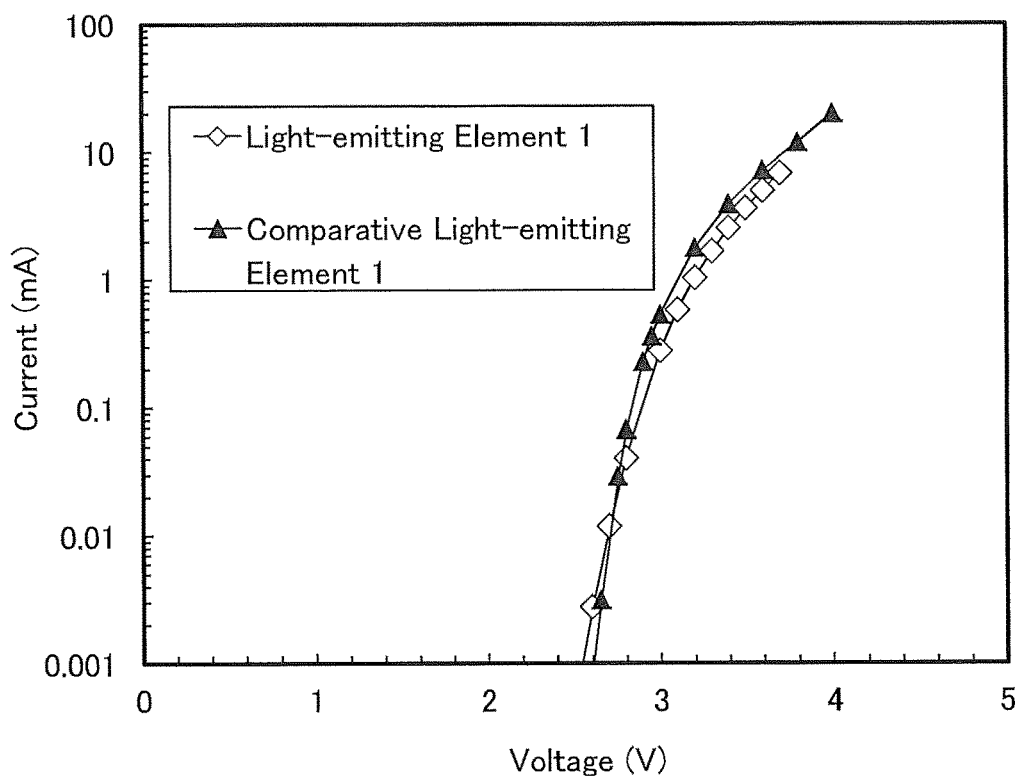

[FIG. 32]
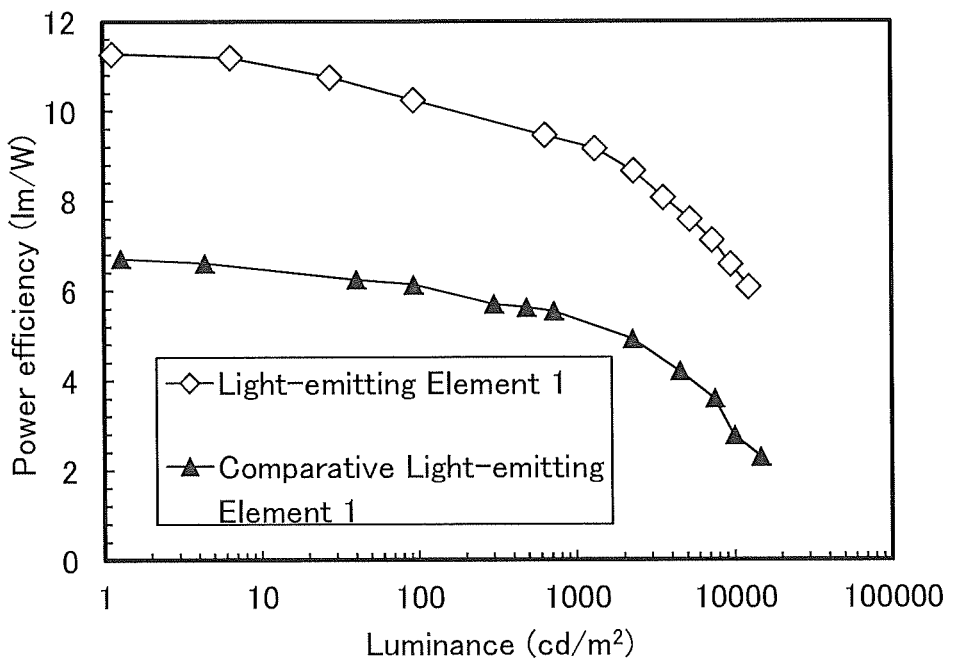
[FIG. 33]
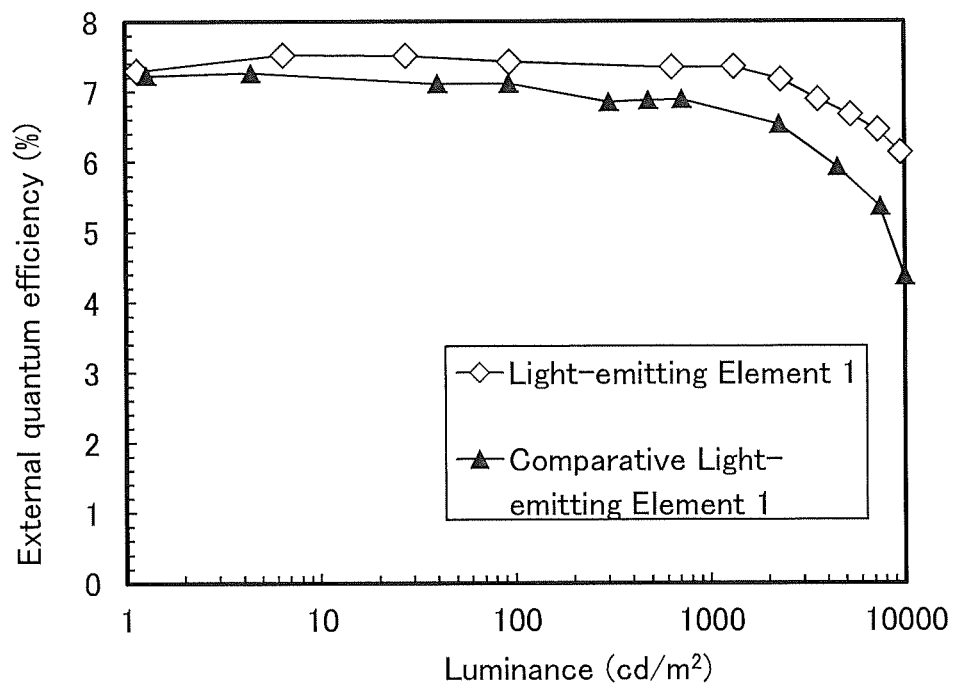

[FIG. 34]
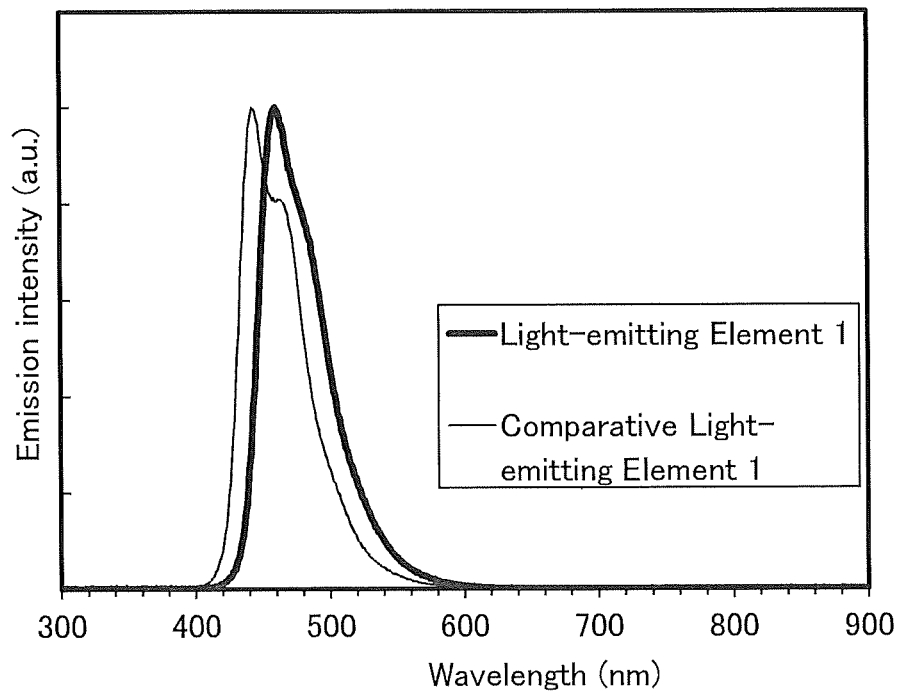
[FIG. 35]
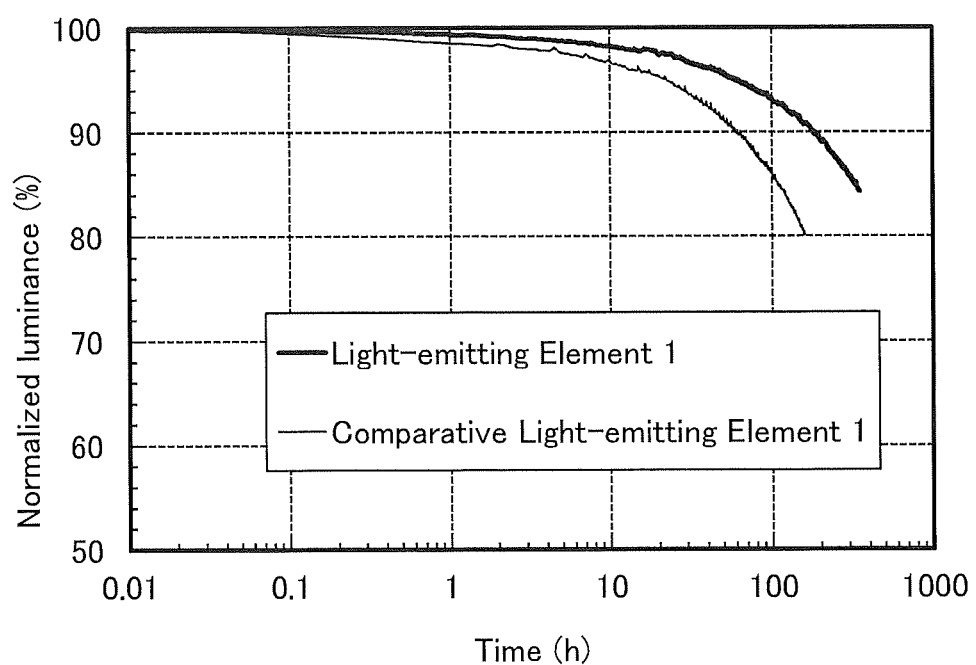

[FIG. 36]
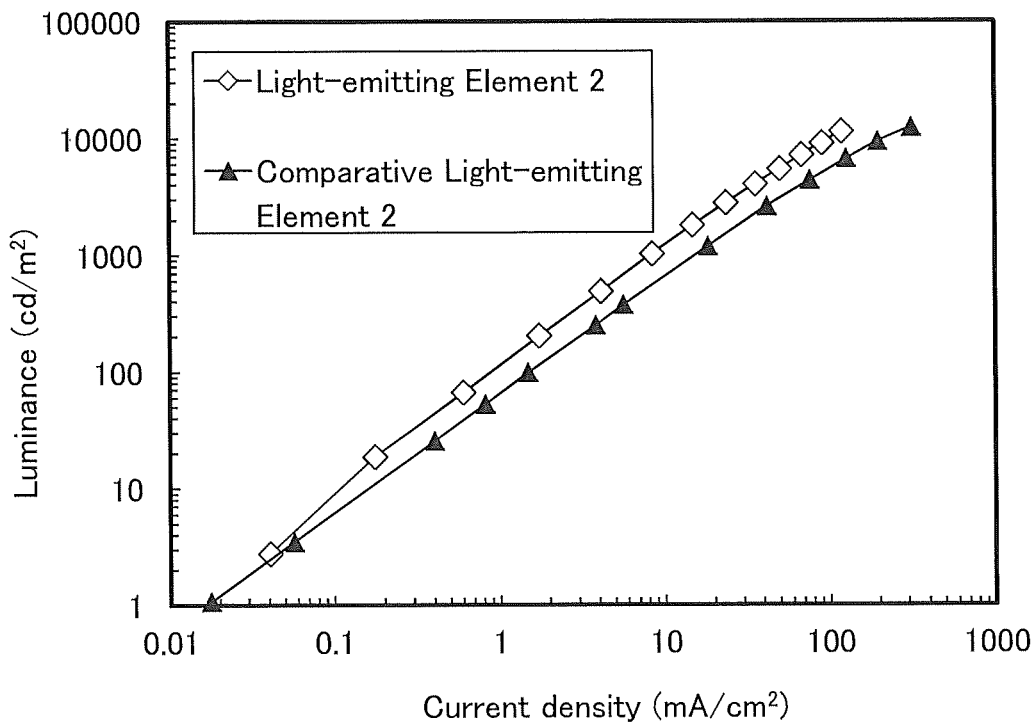
[FIG. 37]
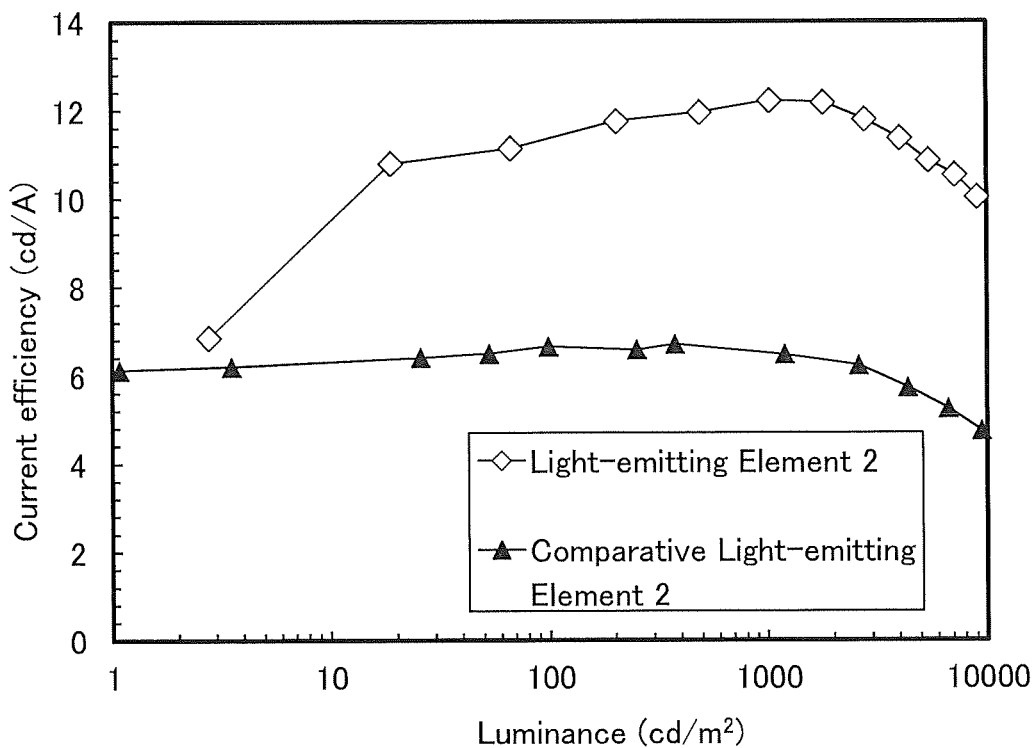

[FIG. 38]
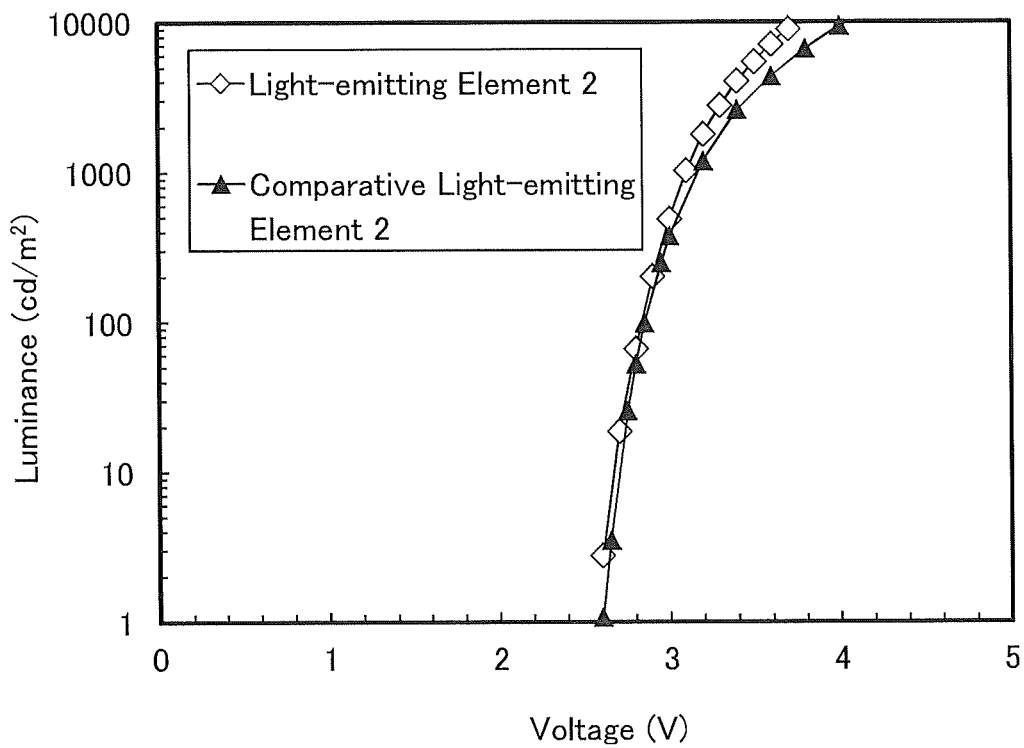
[FIG. 39]
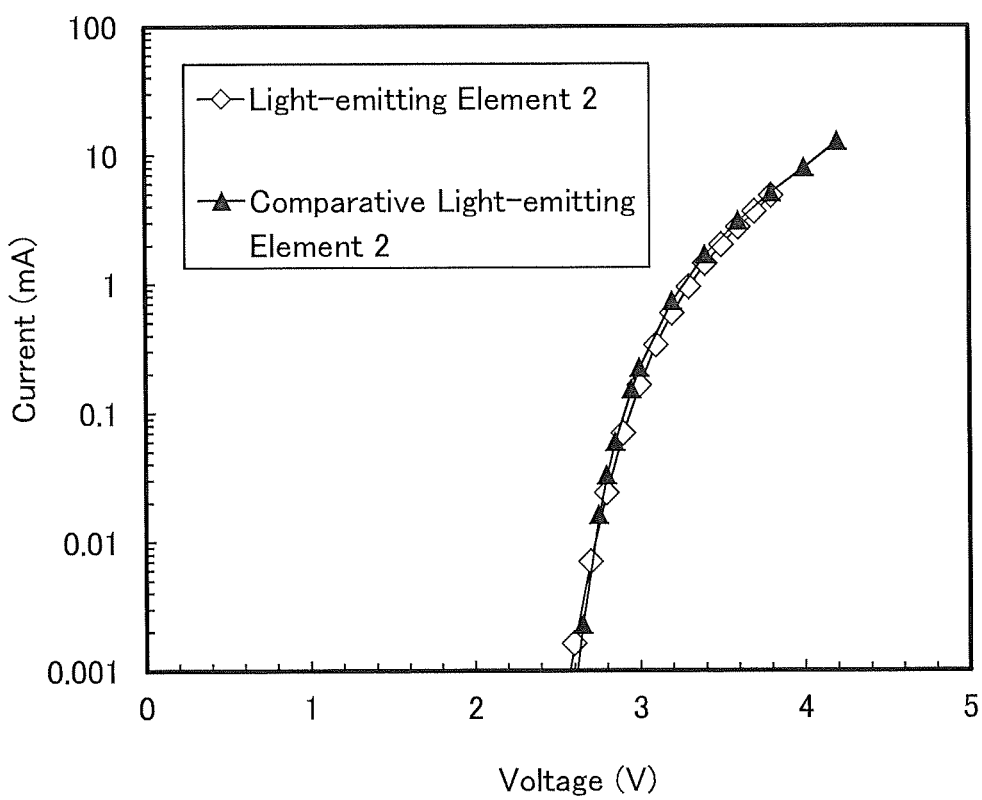

[FIG. 40]
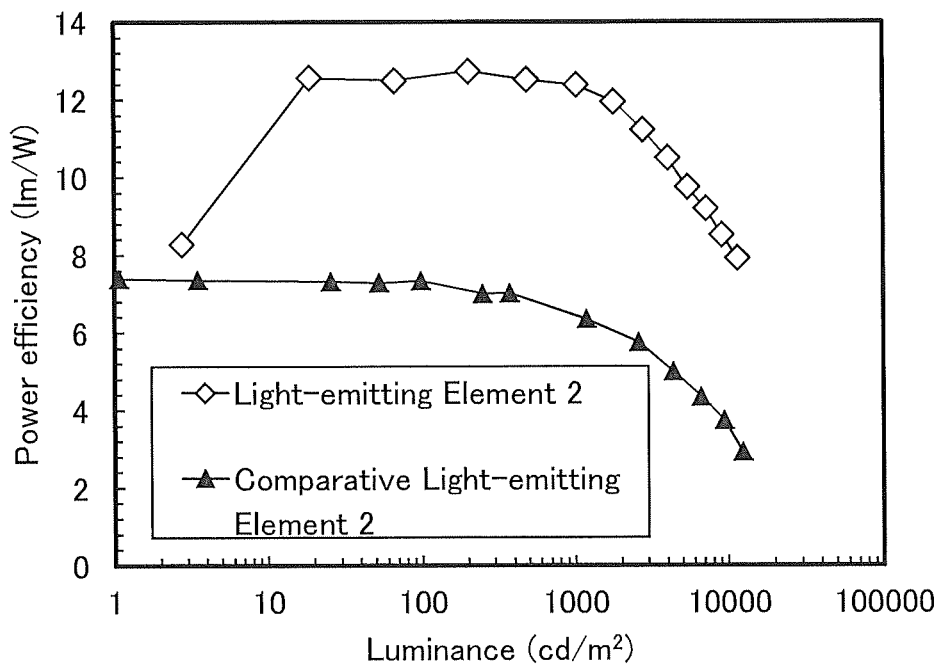
[FIG. 41]
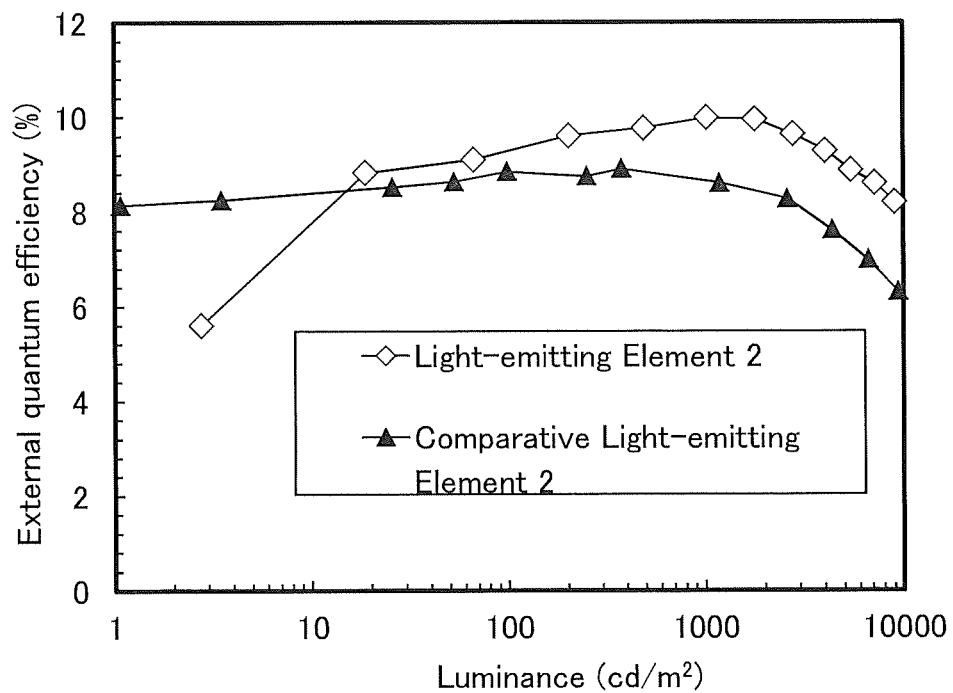

[FIG. 42]
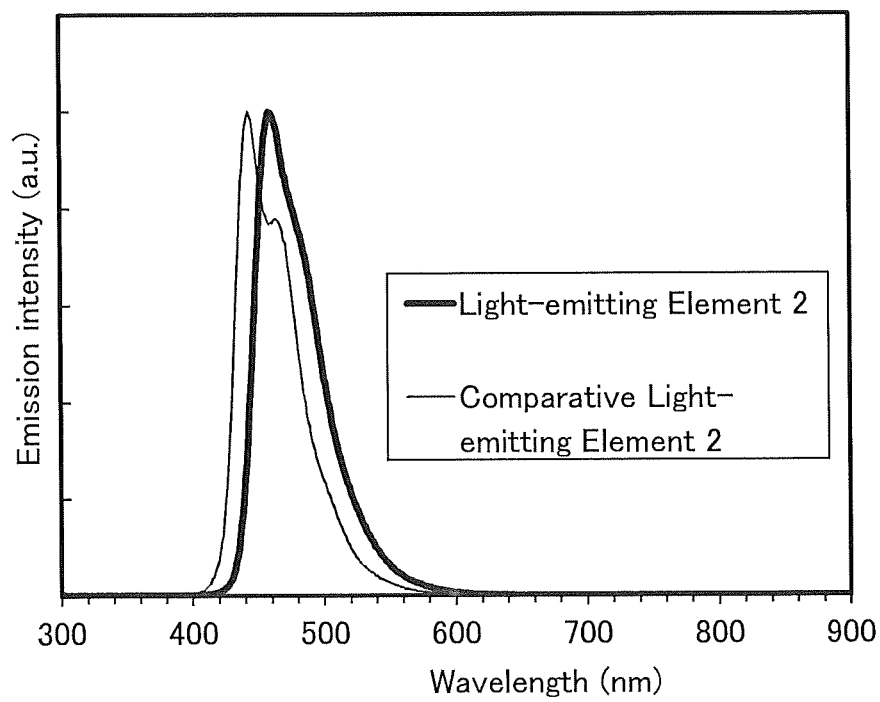
[FIG. 43]
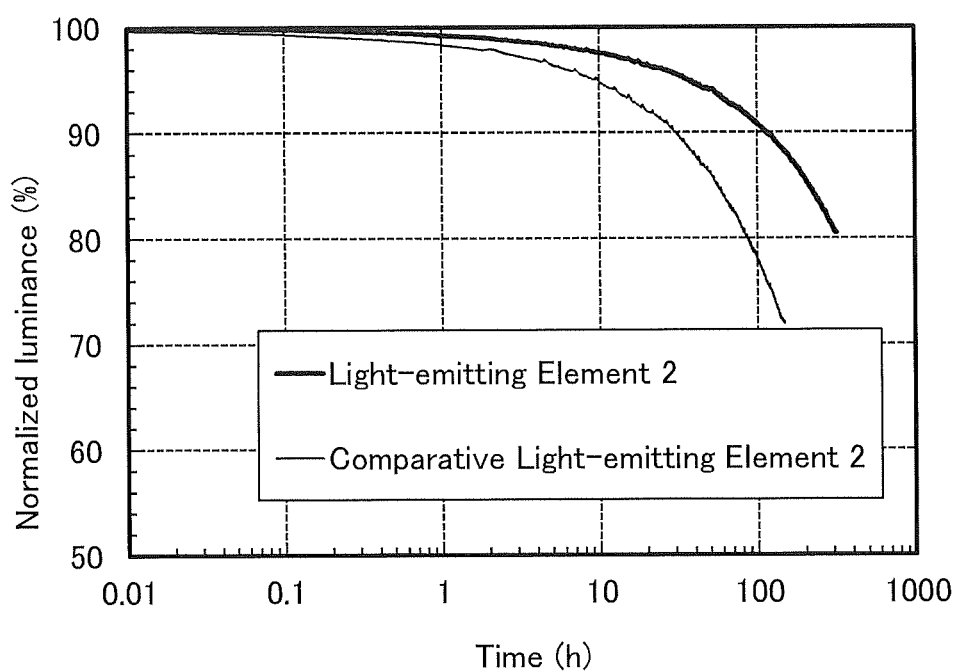

[FIG. 44]
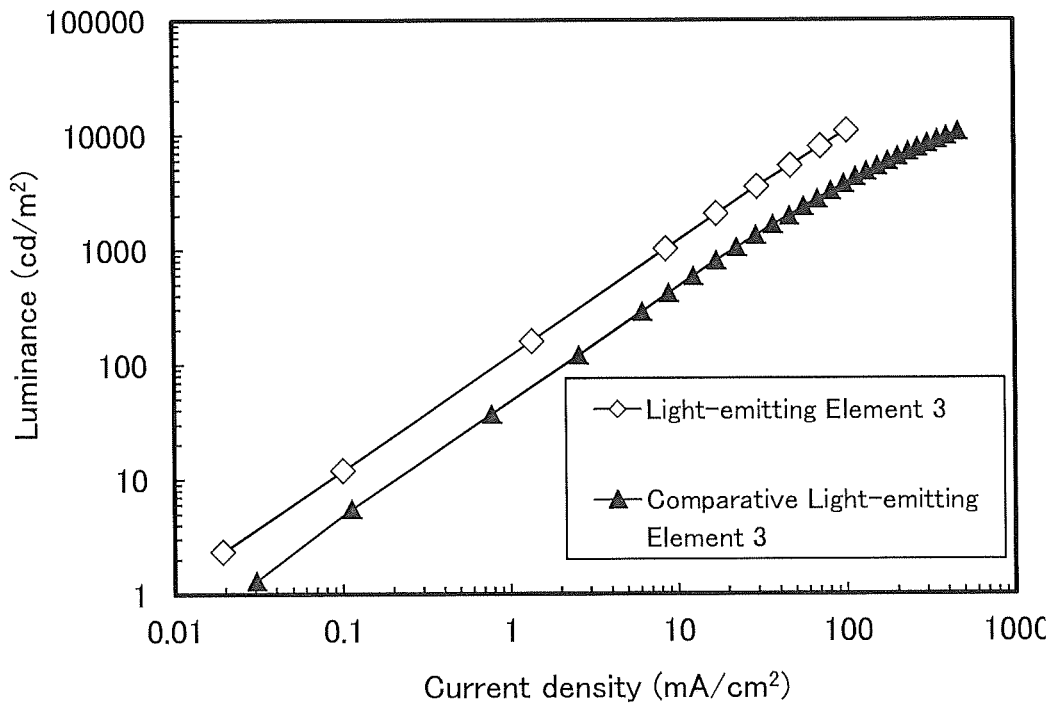
[FIG. 45]
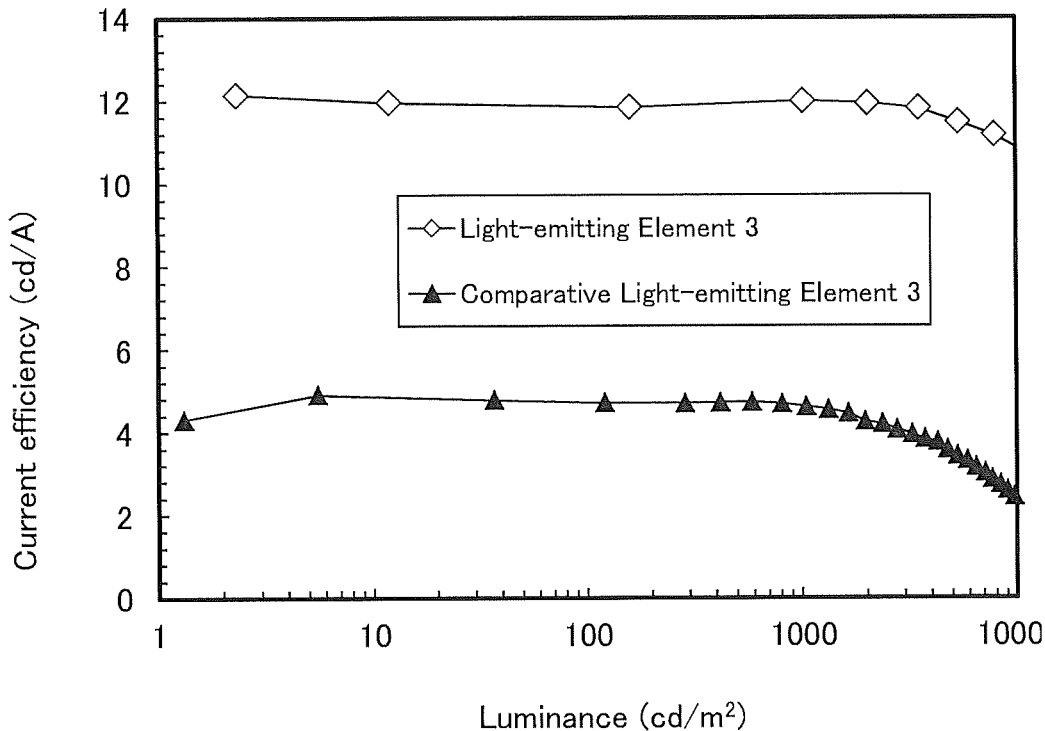

[FIG. 46]
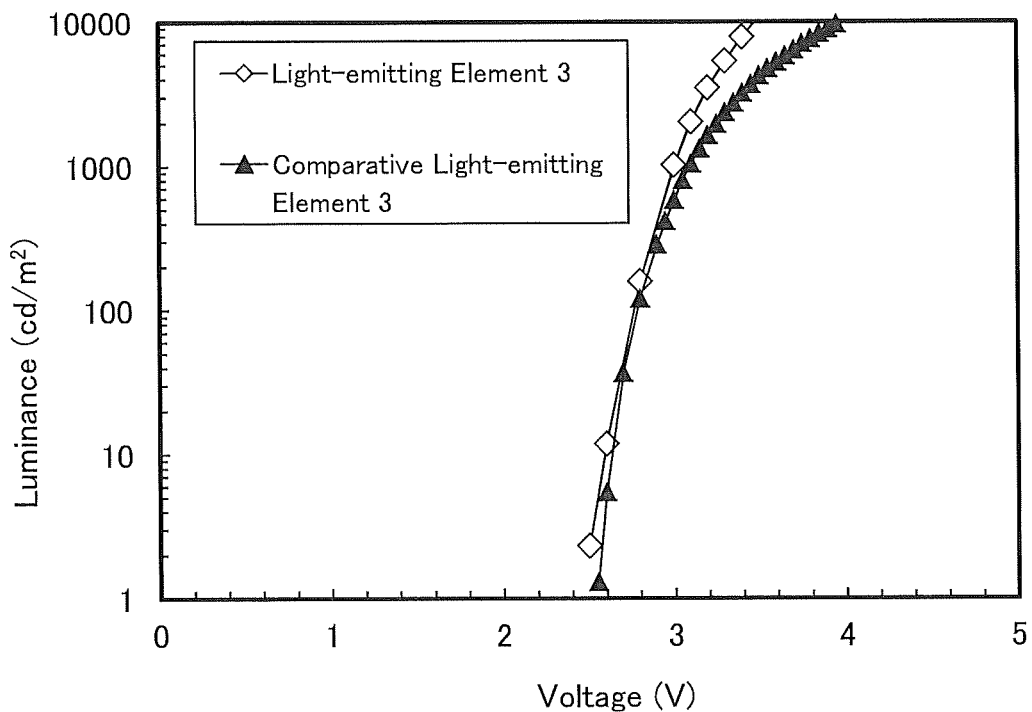
[FIG. 47]
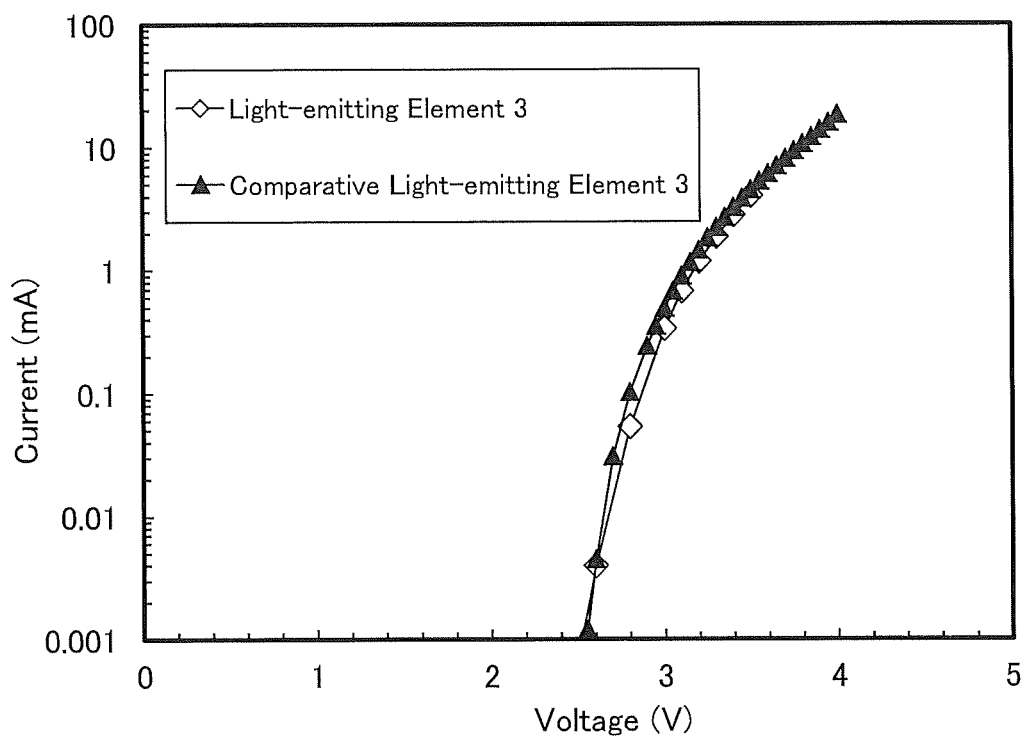

[FIG. 48]
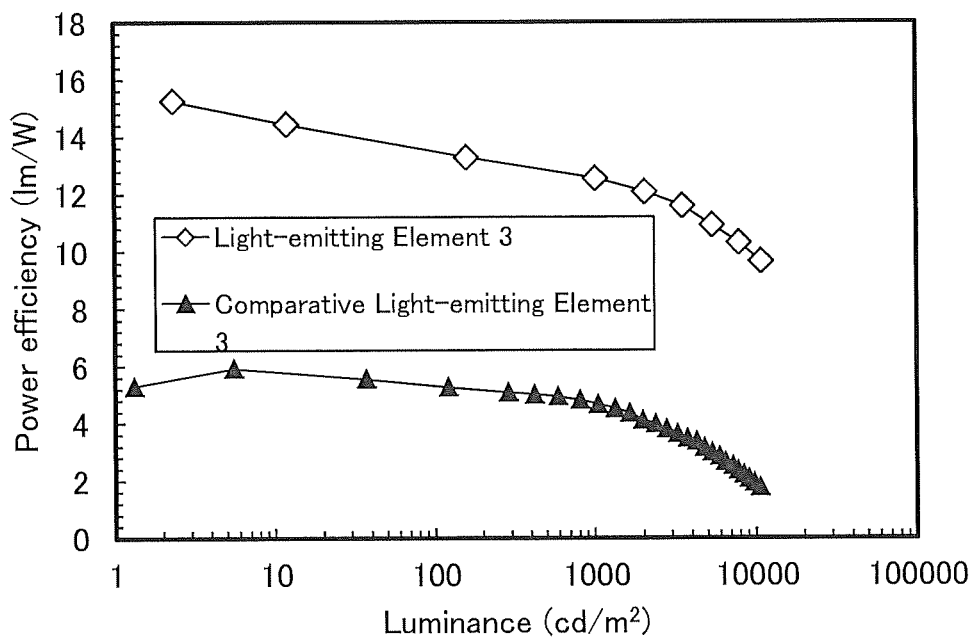
[FIG. 49]
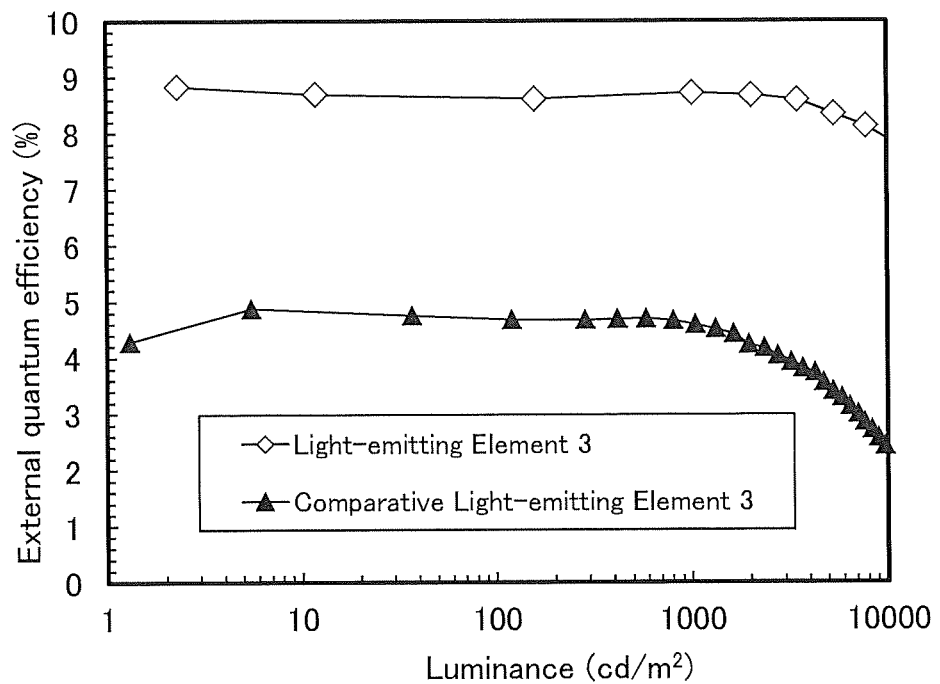

[FIG. 50]
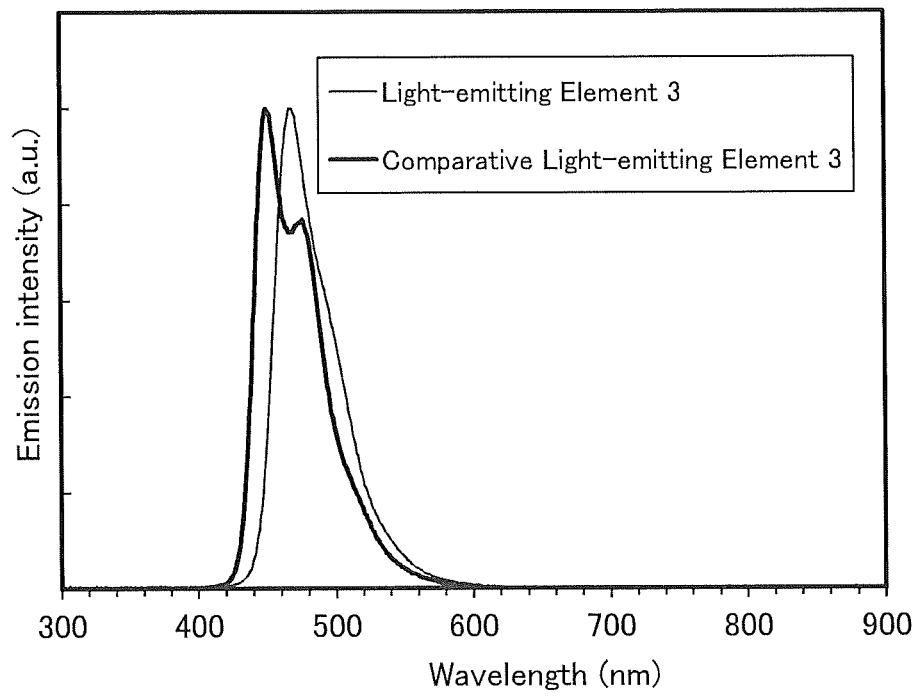
[FIG. 51]
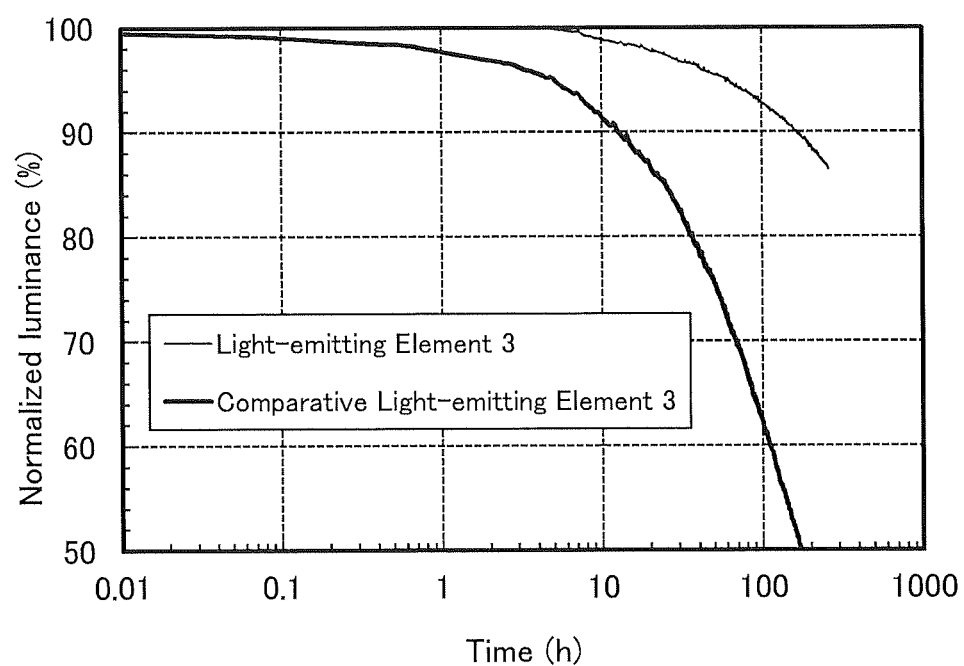

[FIG. 52]
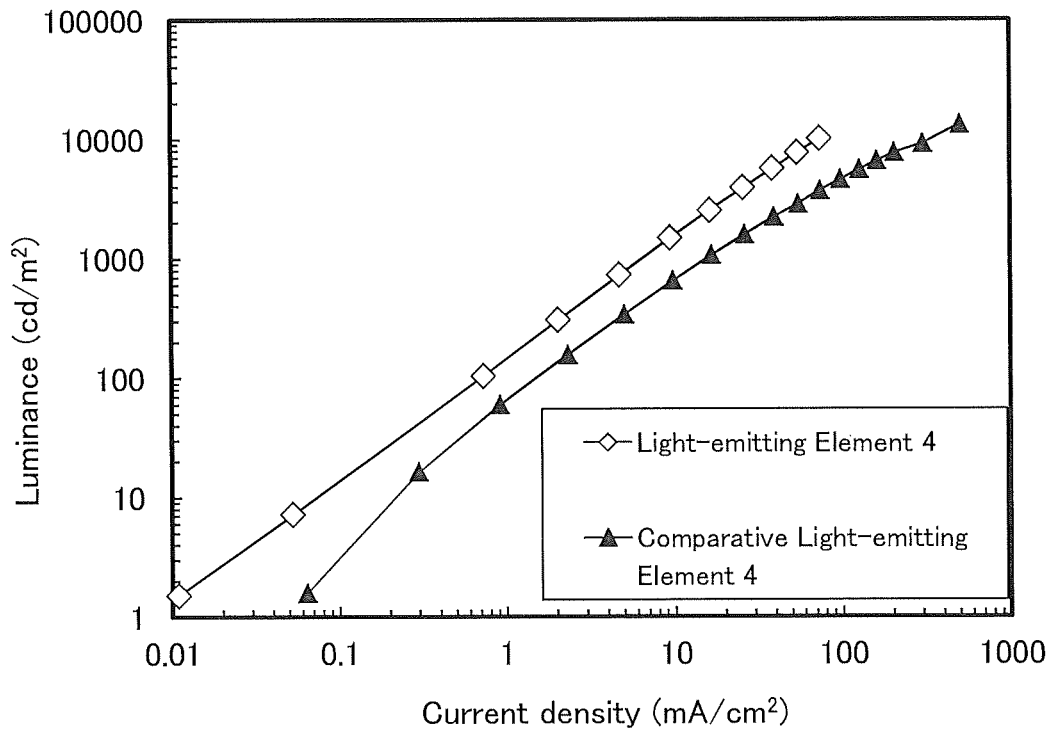
[FIG. 53]
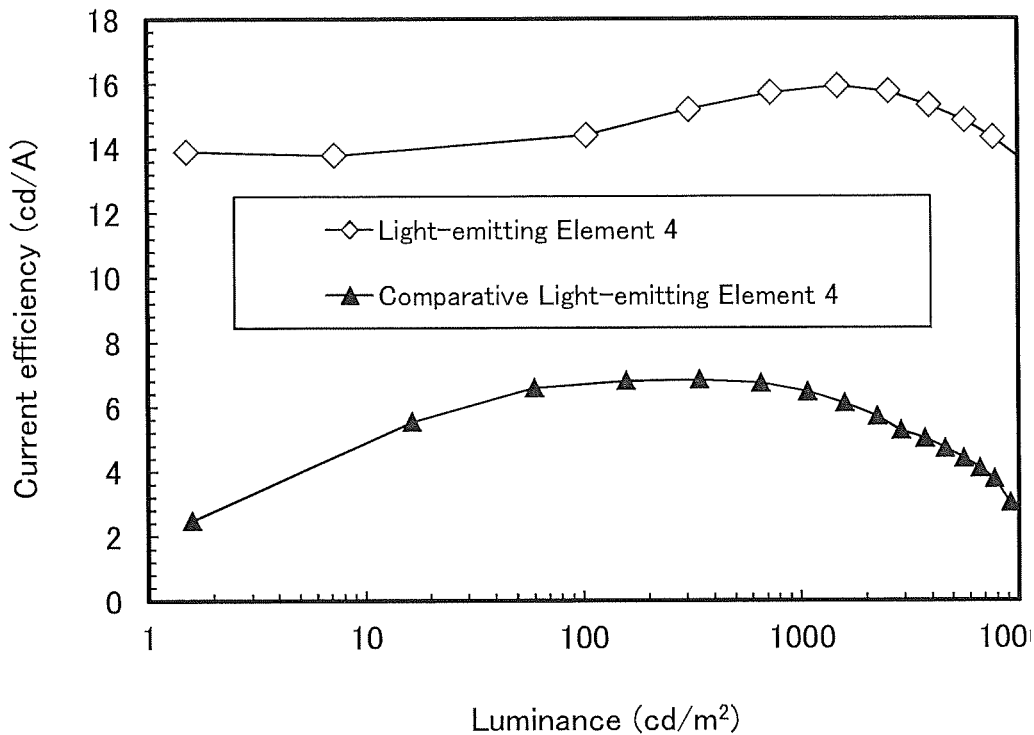

[FIG. 54]
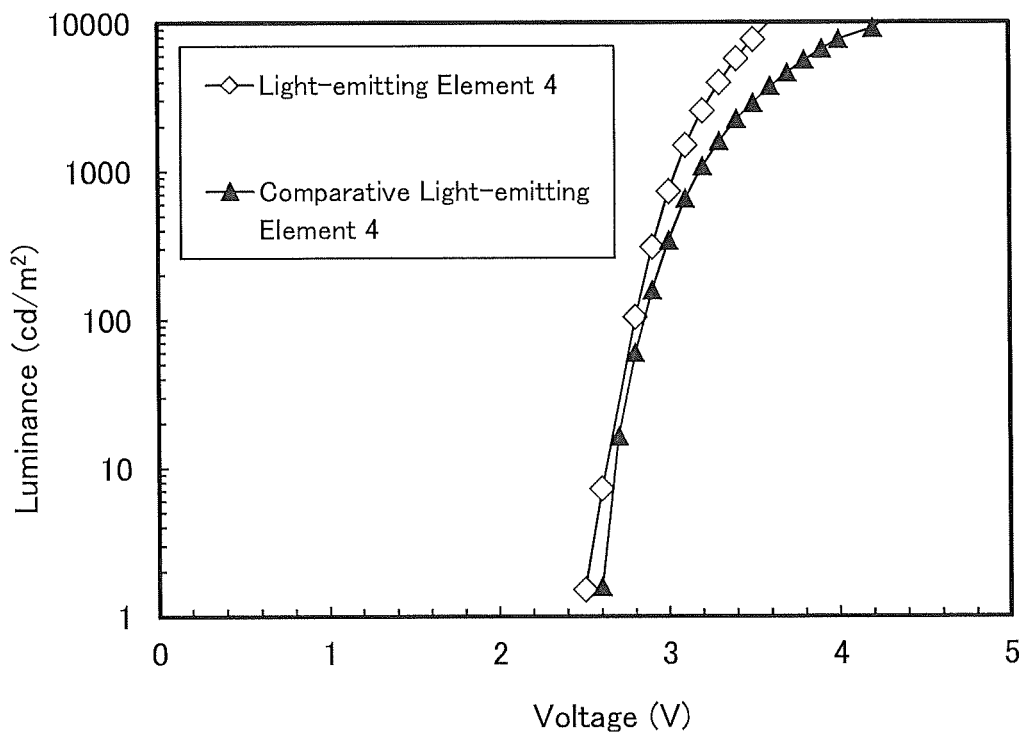
[FIG. 55]
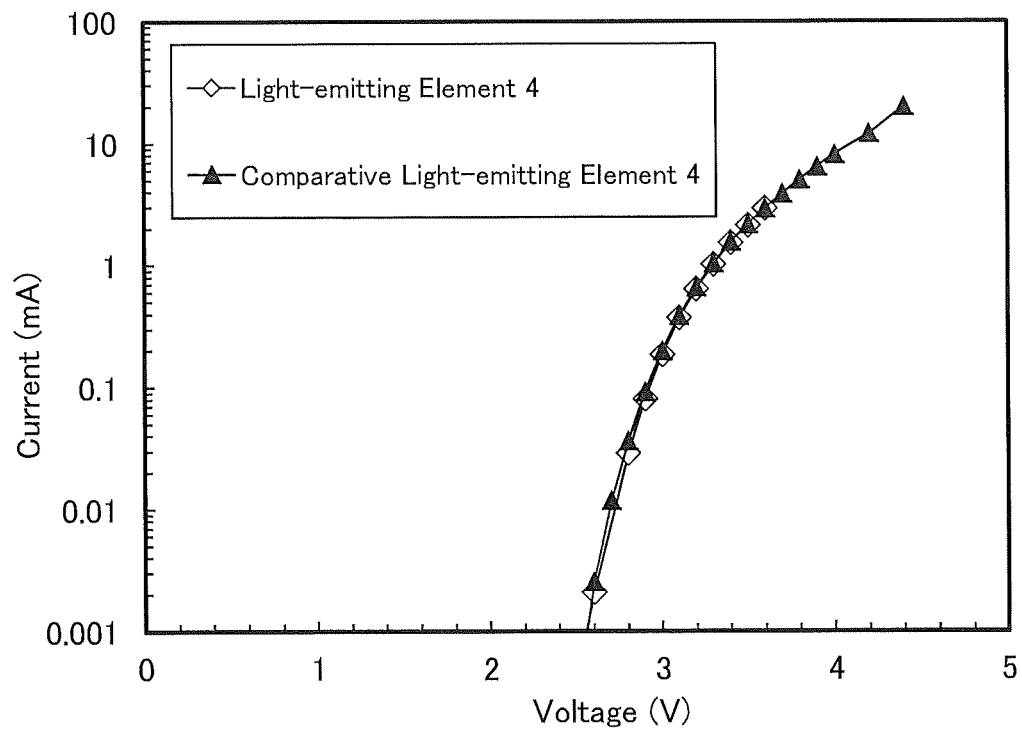

[FIG. 56]
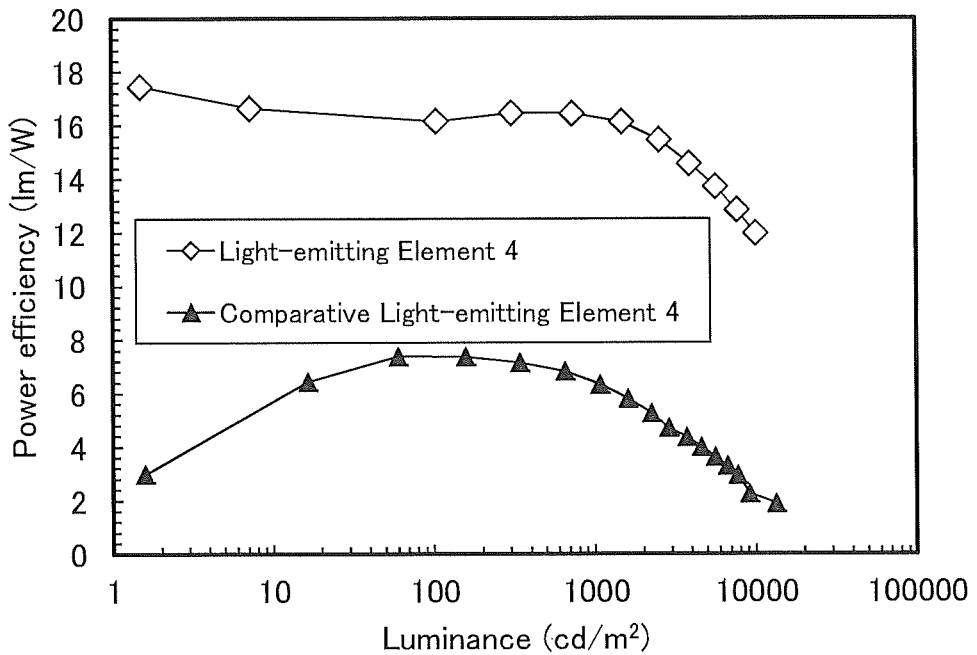
[FIG. 57]
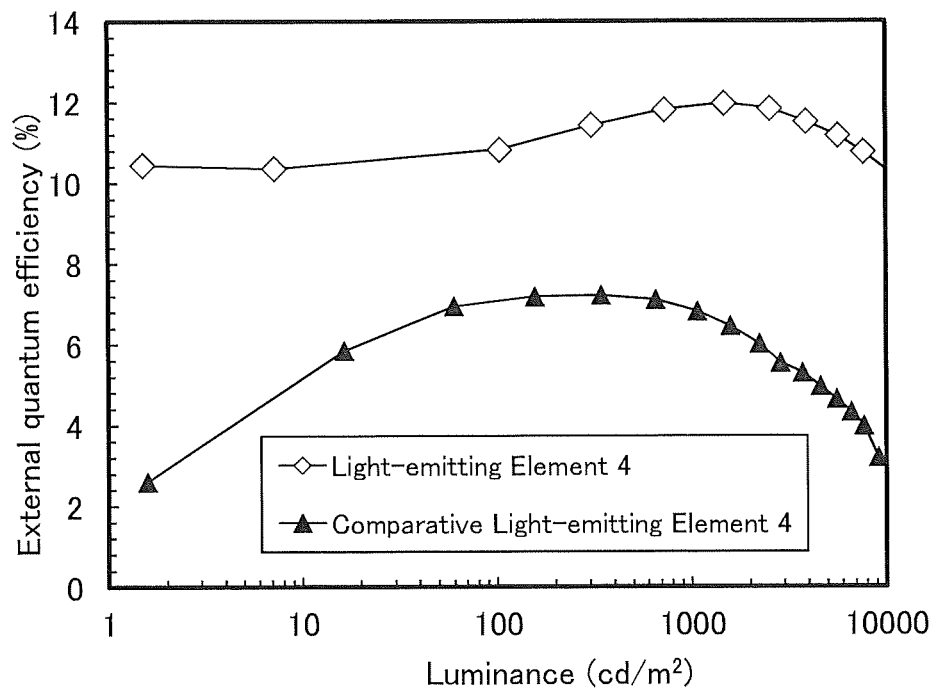

[FIG. 58]
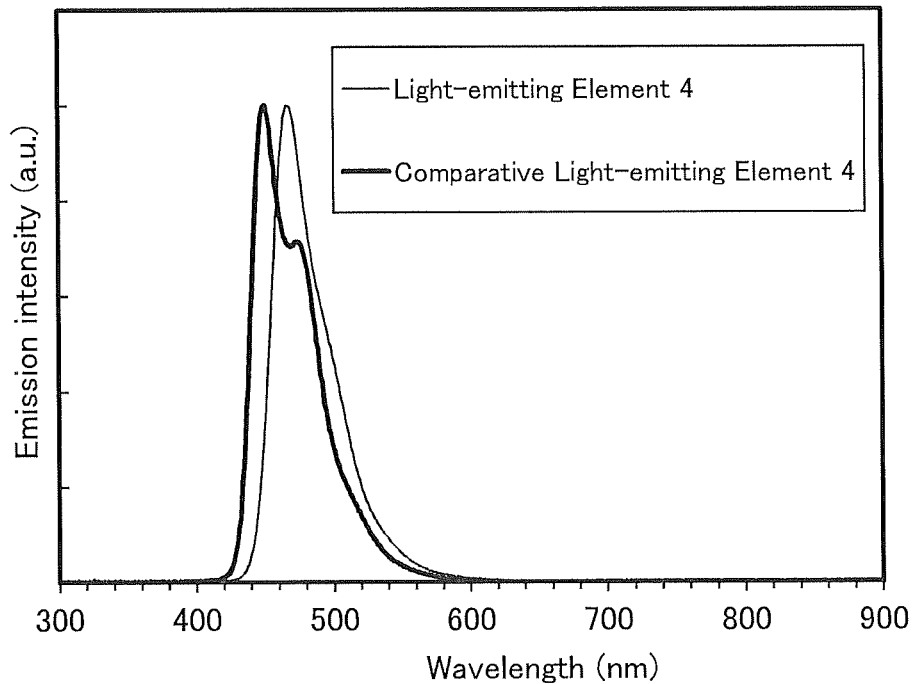
[FIG. 59]
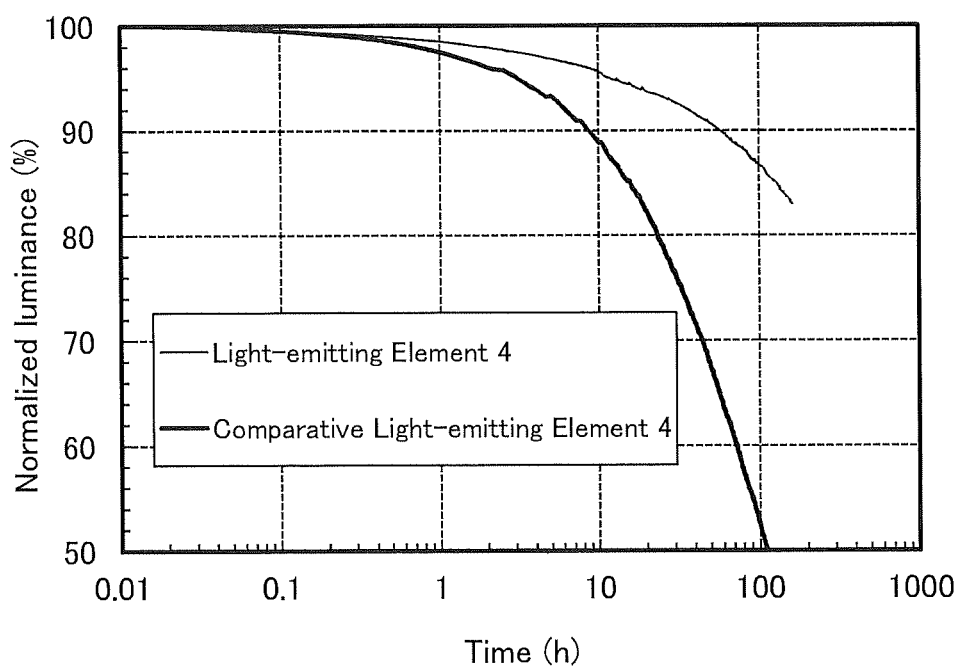

[FIG. 60]
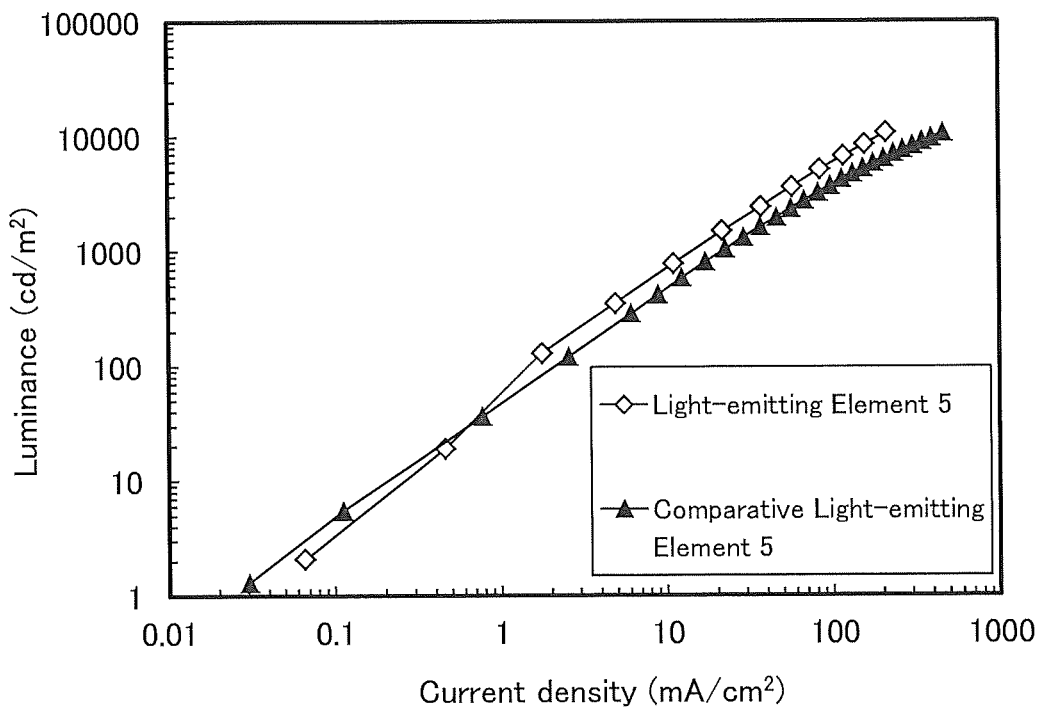
[FIG. 61]
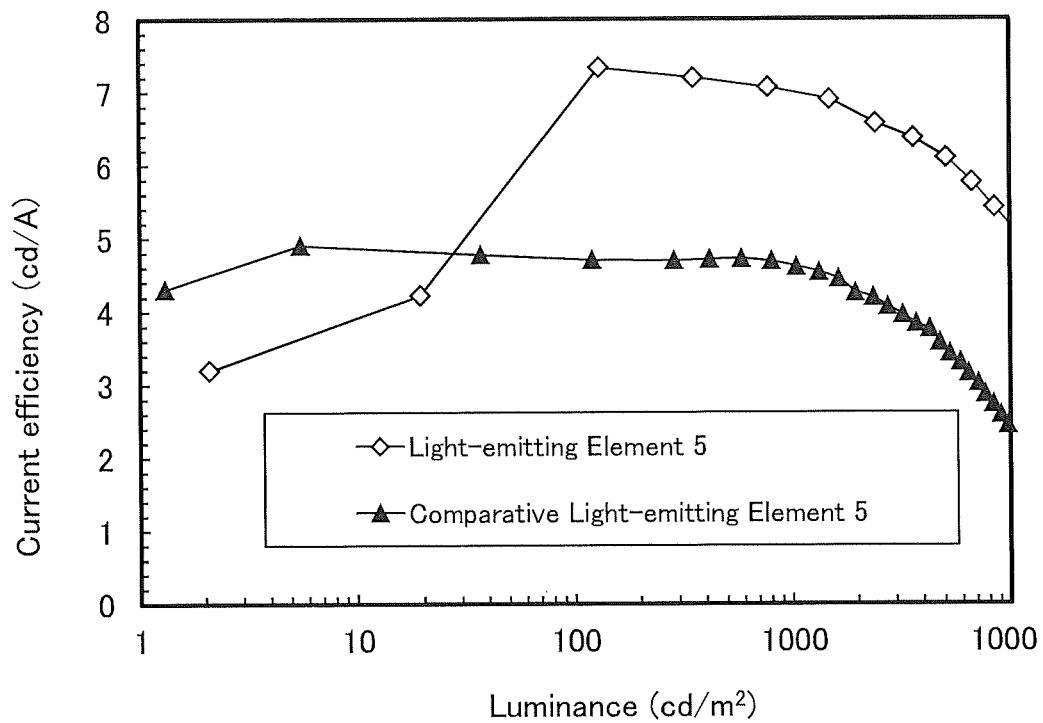

[FIG. 62]
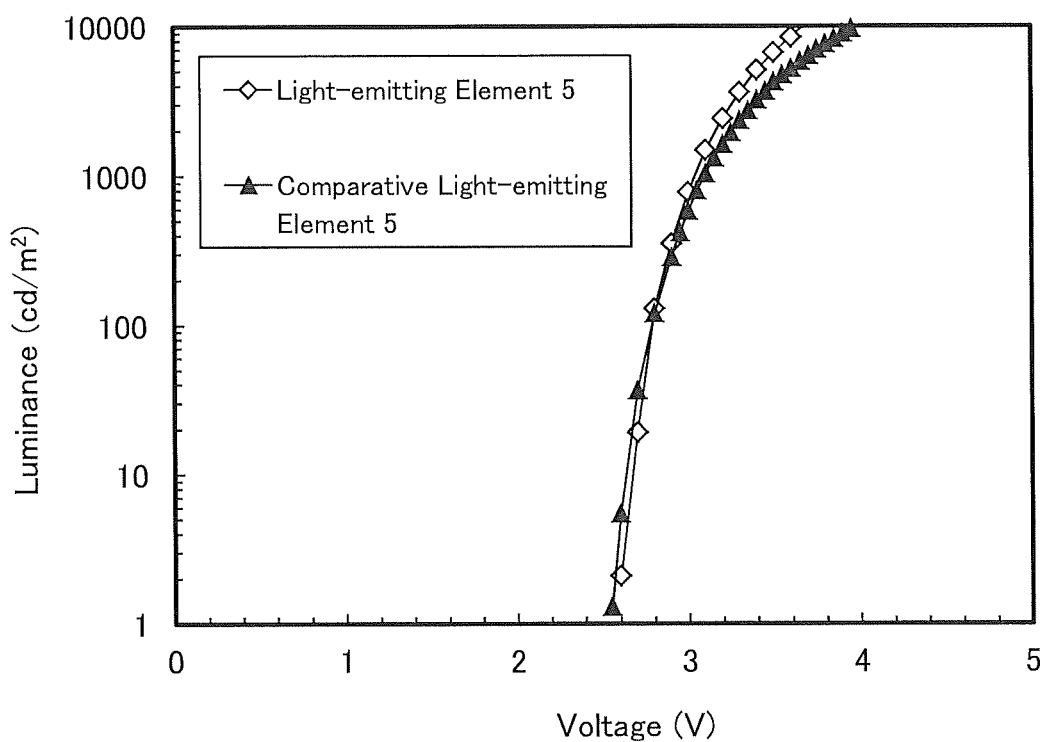
[FIG. 63]
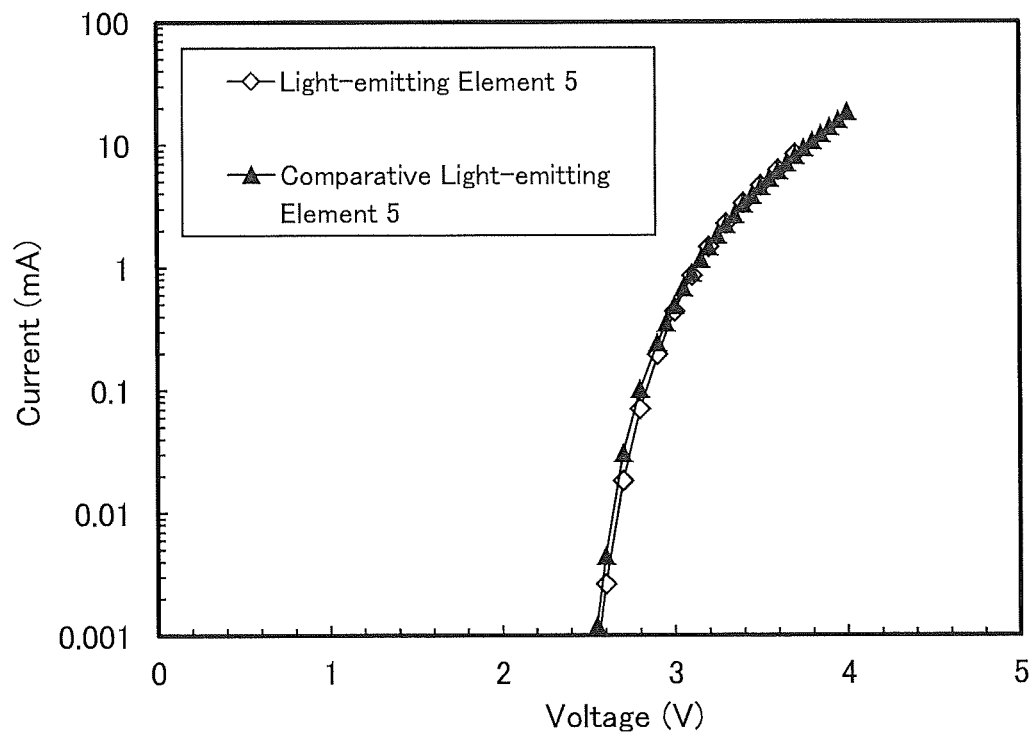

[FIG. 64]
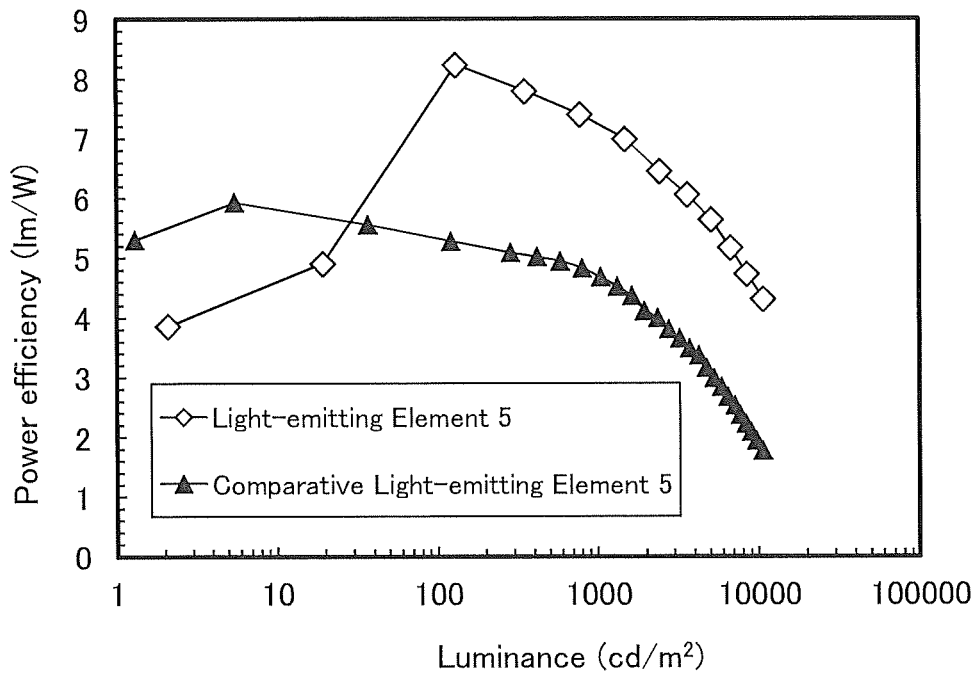
[FIG. 65]
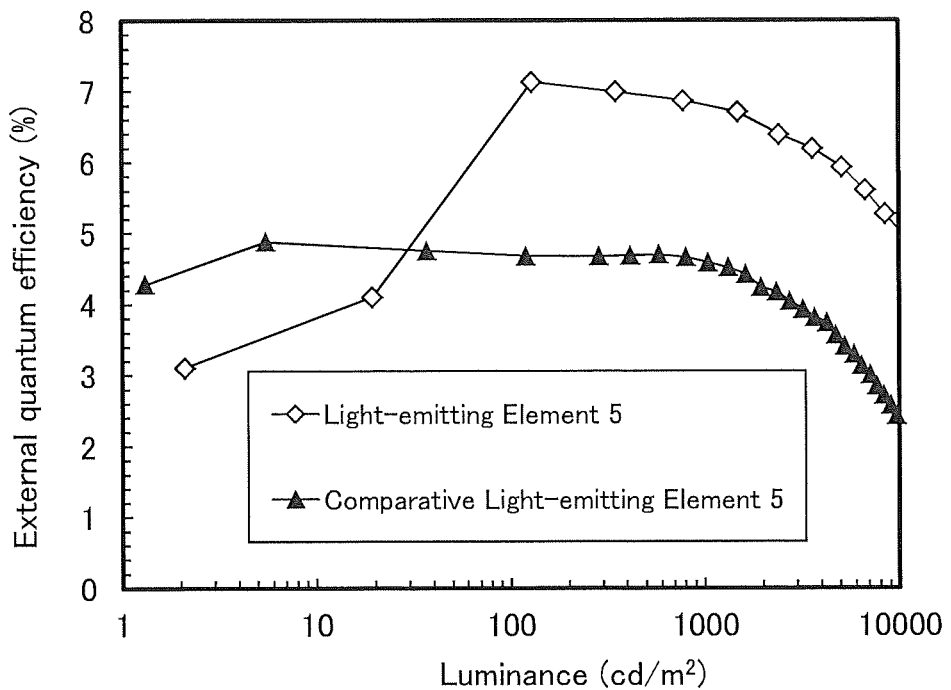

[FIG. 66]
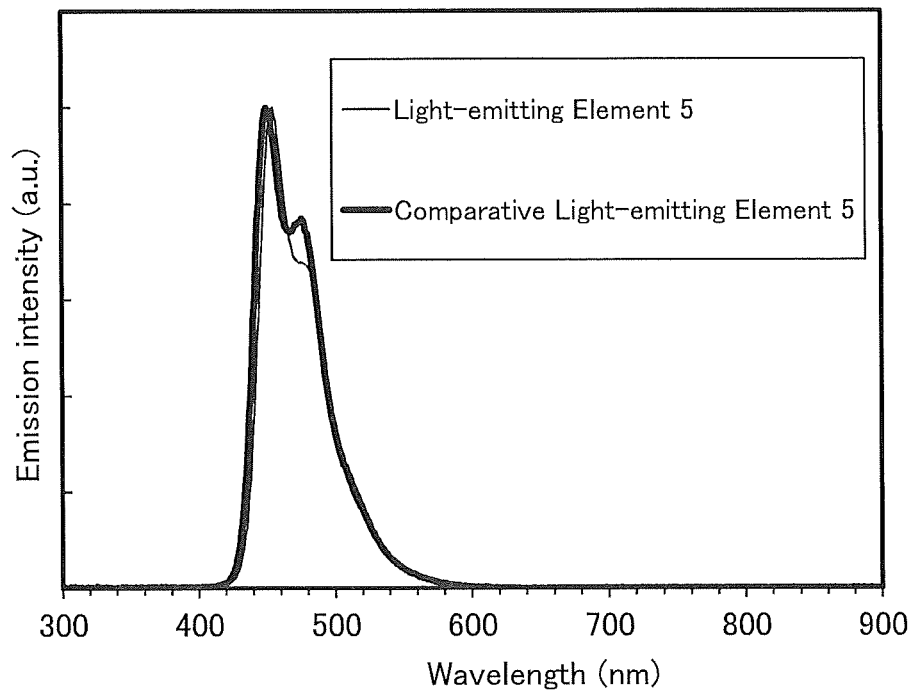
[FIG. 67]
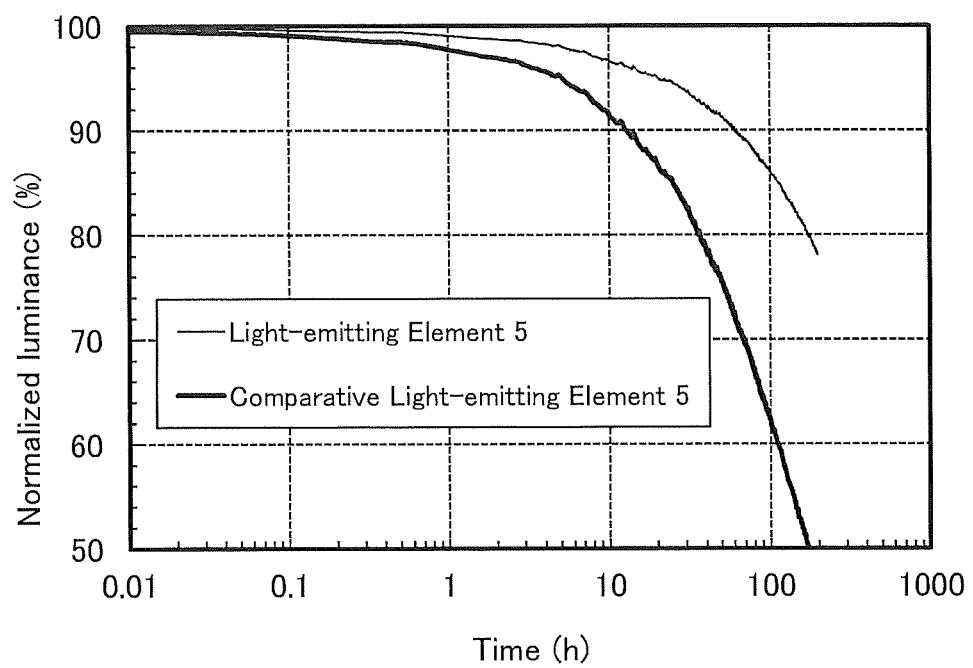

[FIG. 68]
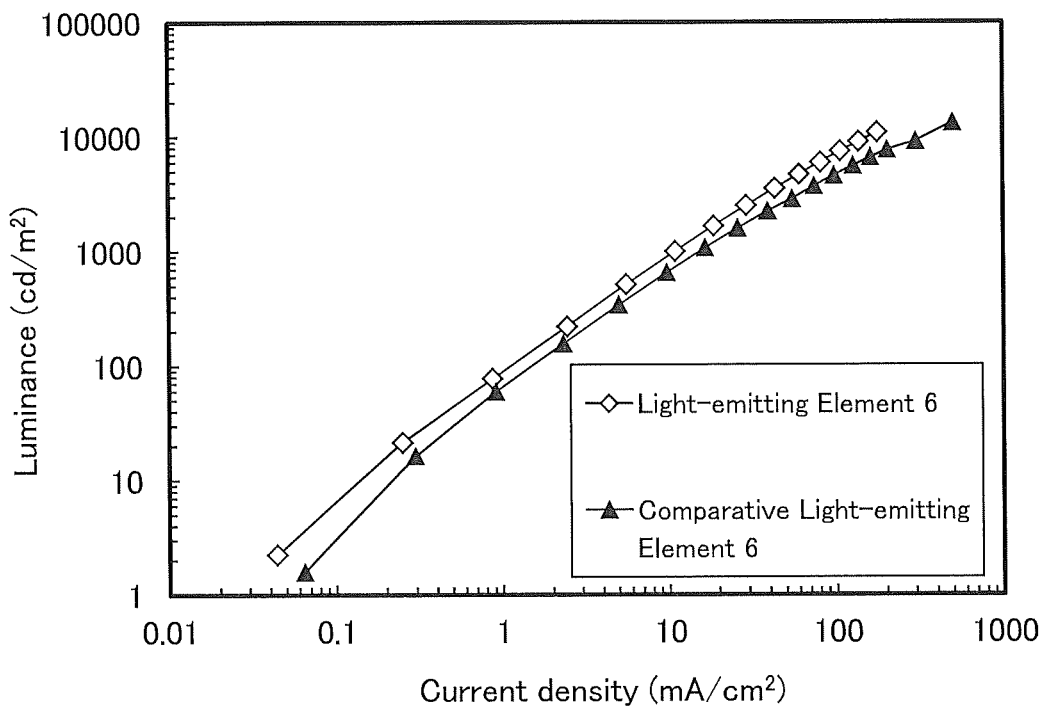
[FIG. 69]
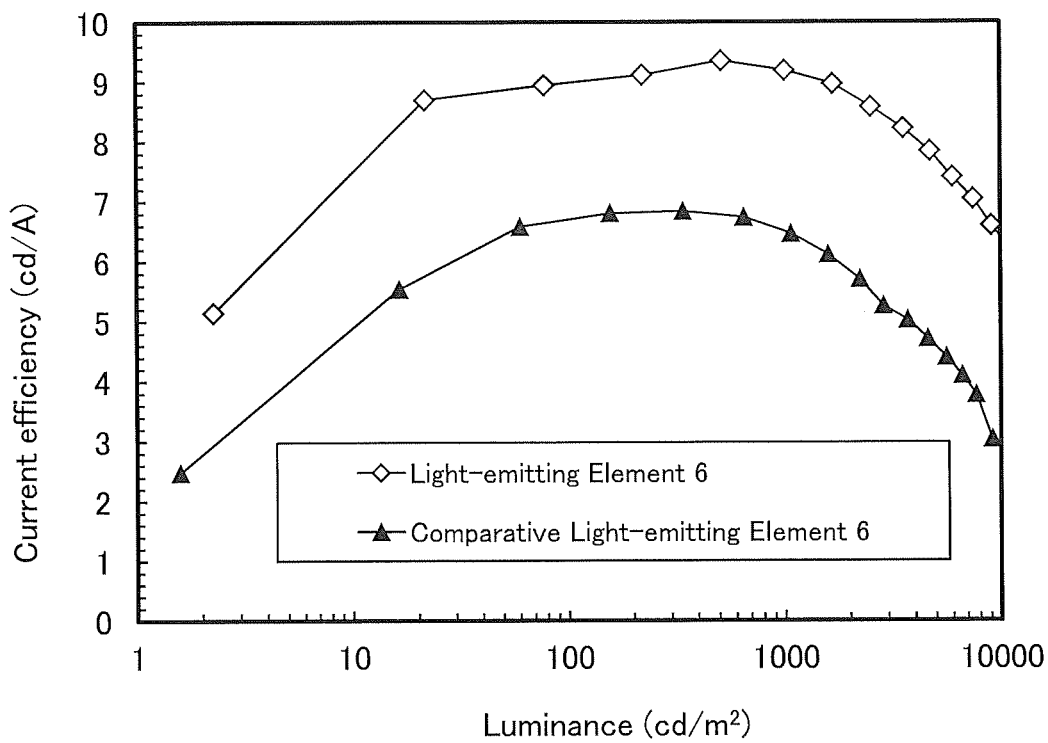

[FIG. 70]
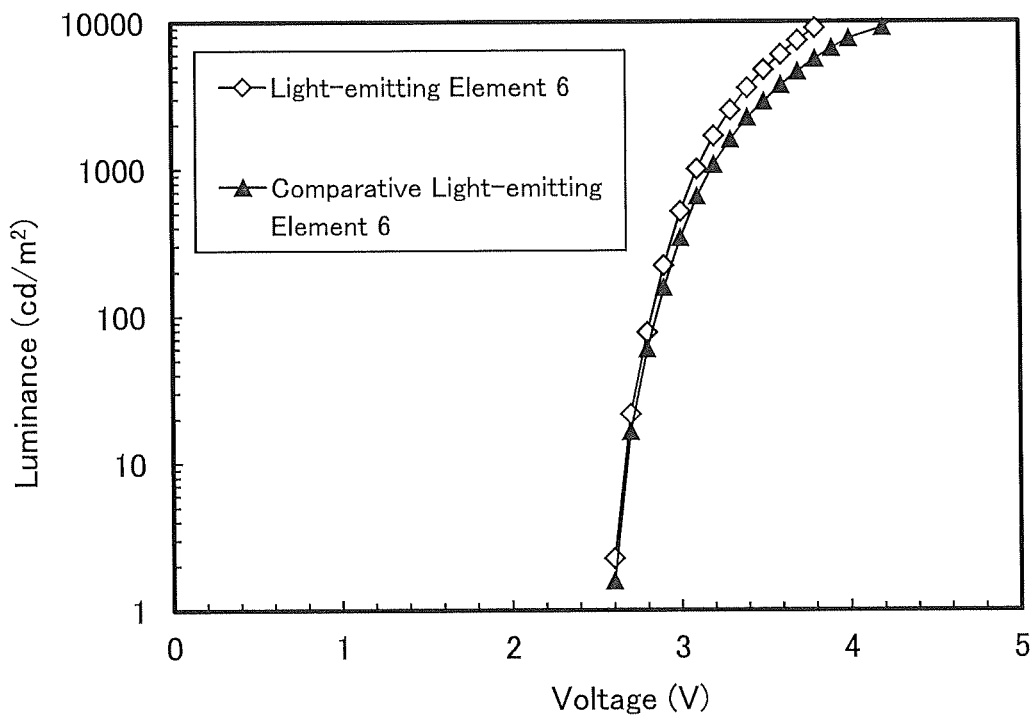
[FIG. 71]
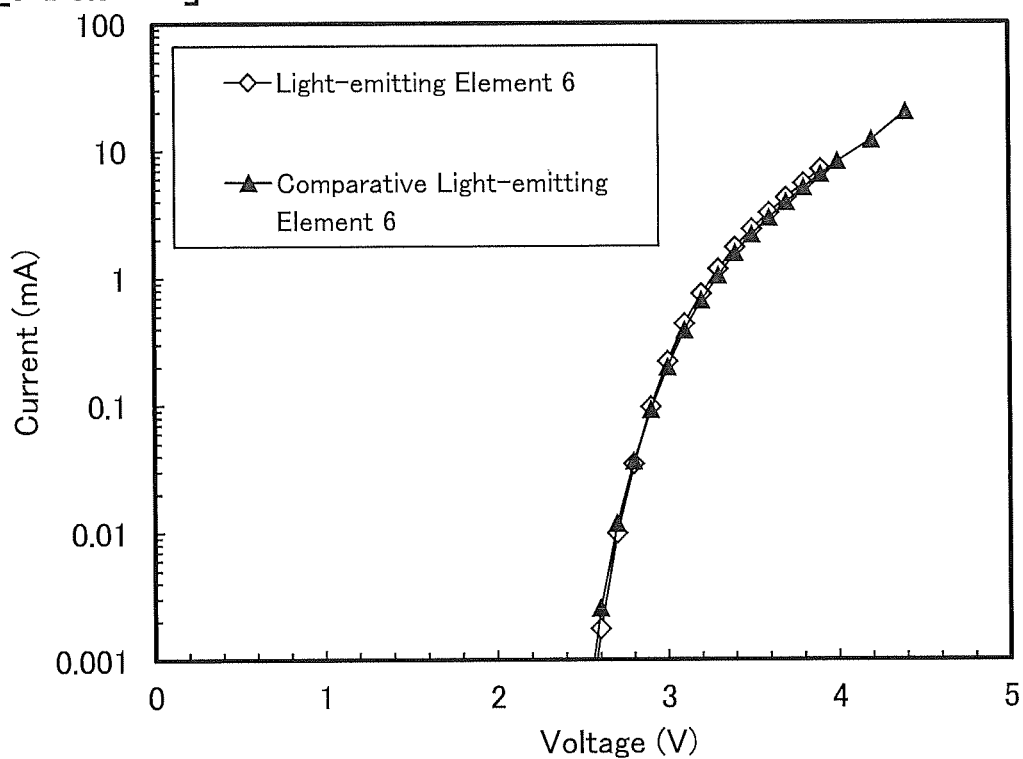

[FIG. 72]
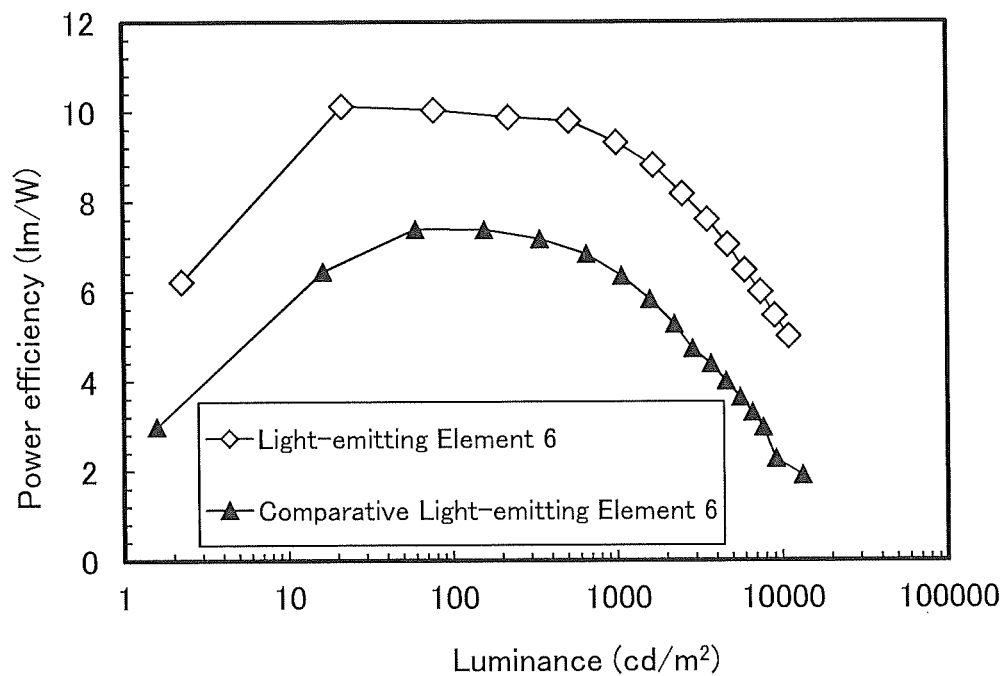
[FIG. 73]
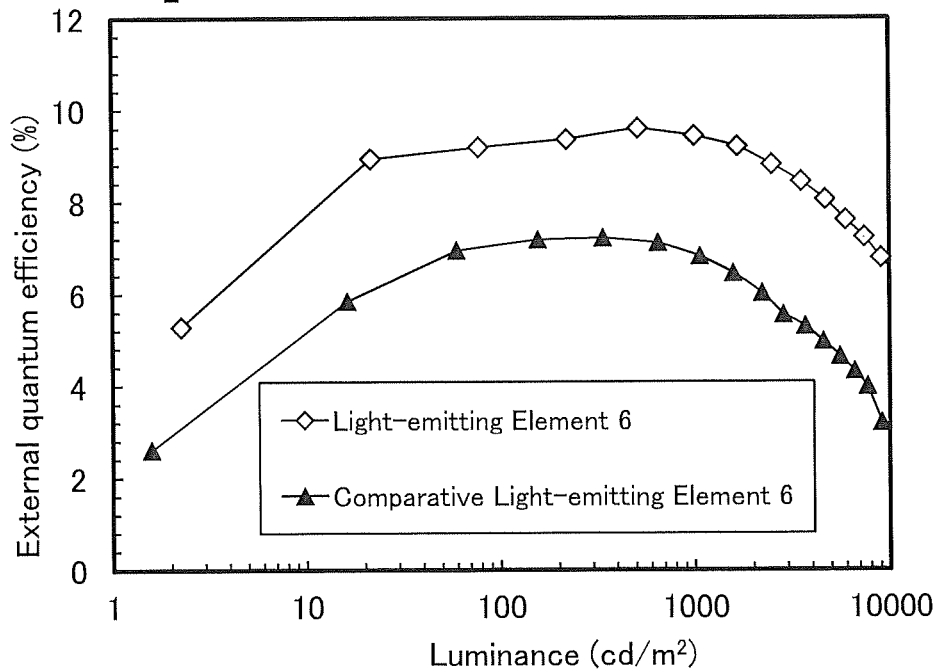

[FIG. 74]
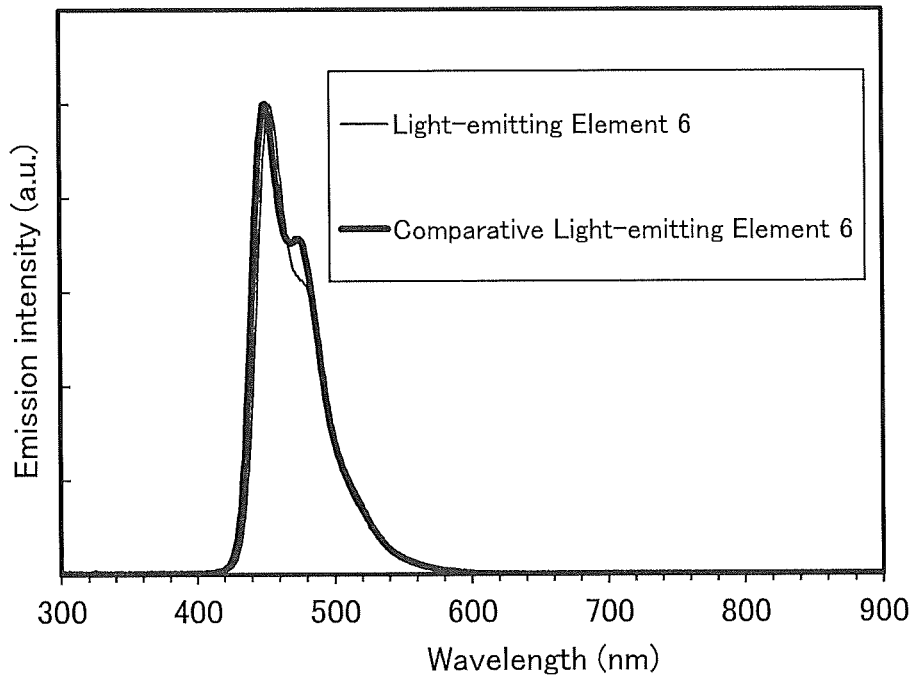
[FIG. 75]
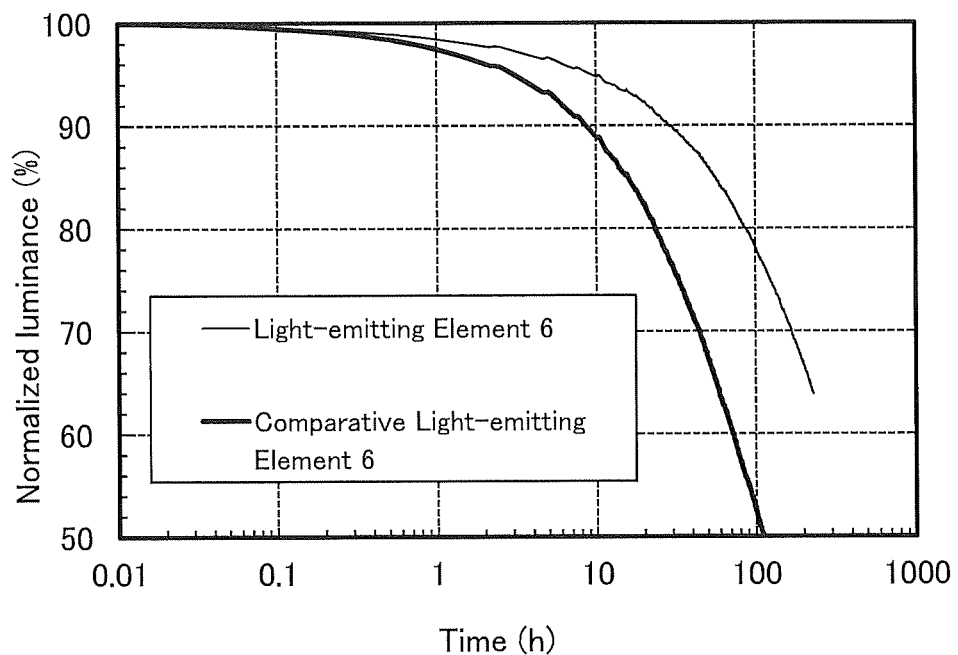

[FIG. 76]
(A)
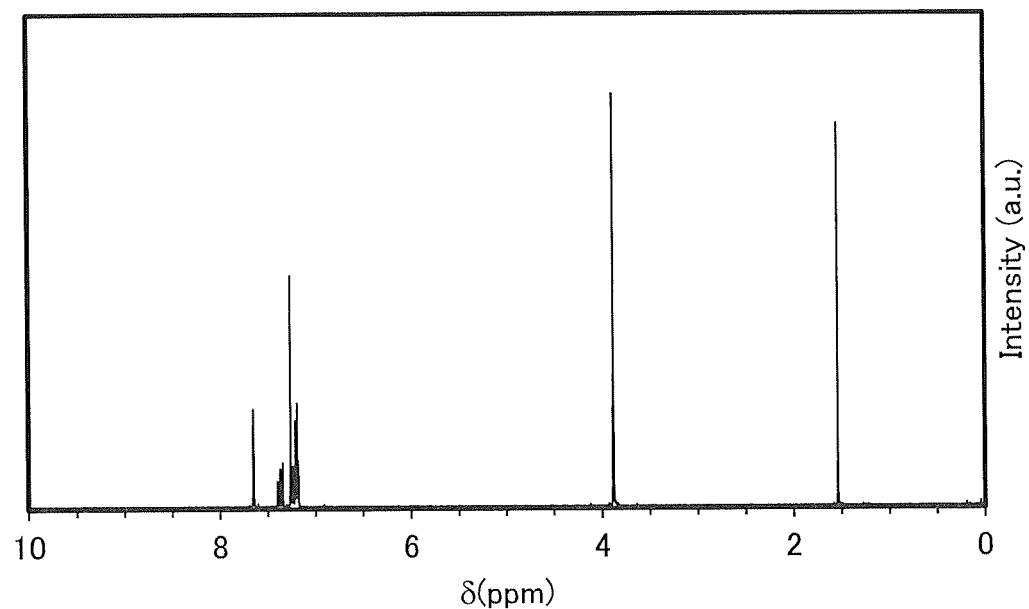
(B)
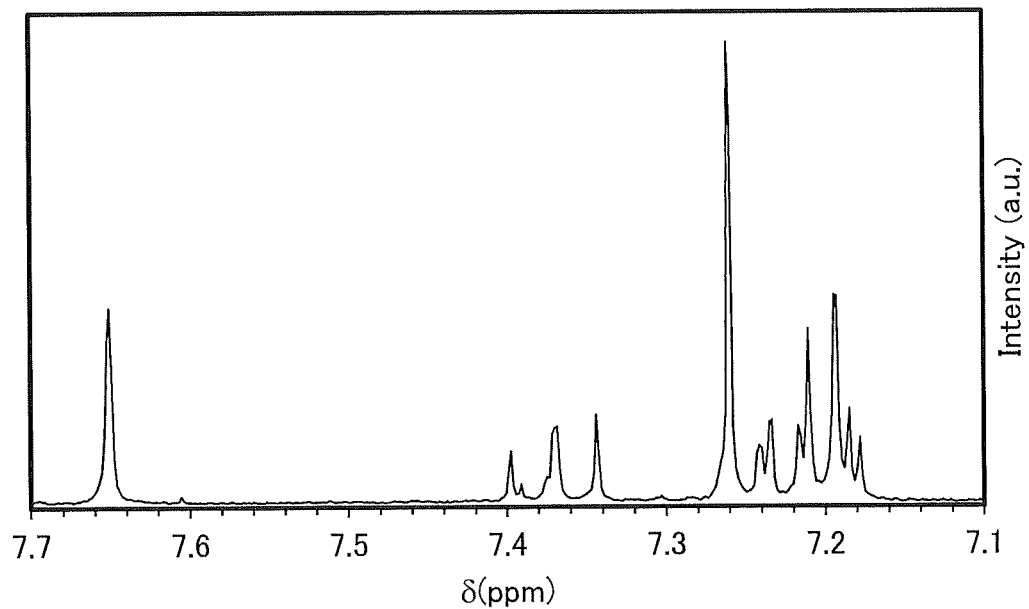

[FIG. 77]
(A)
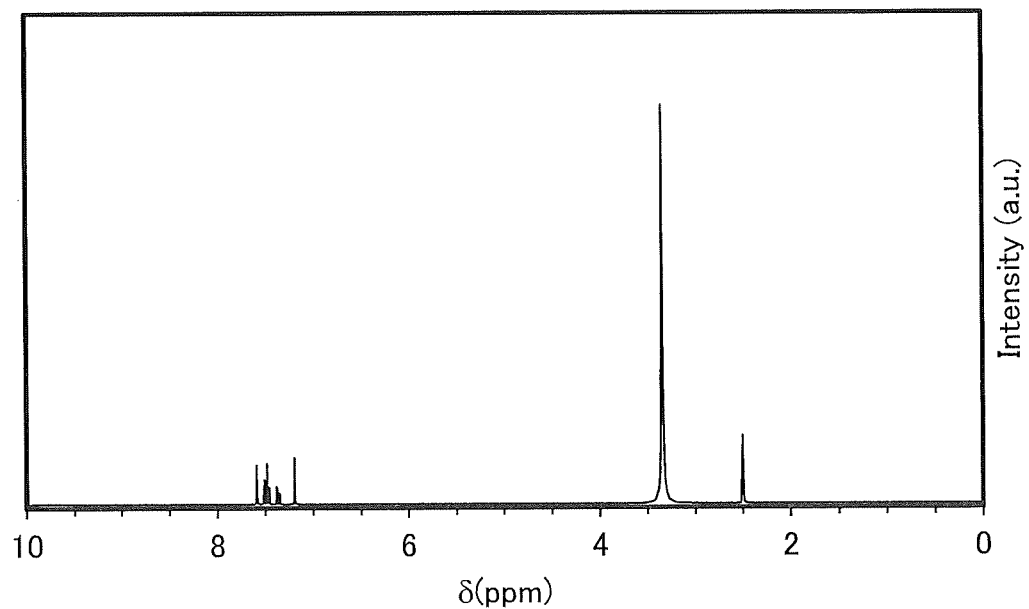
(B)
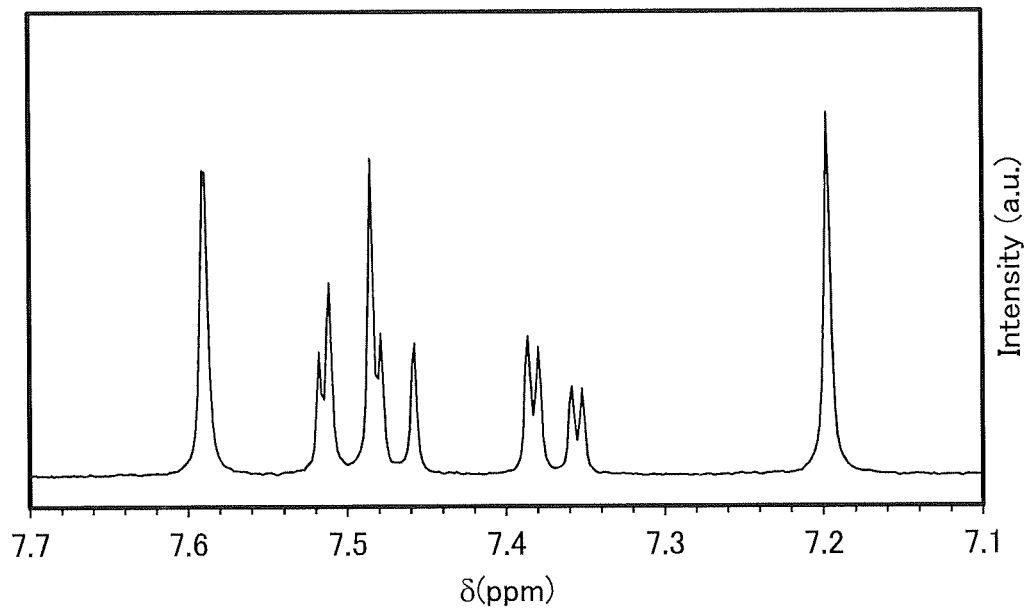

[FIG. 78]
(A)
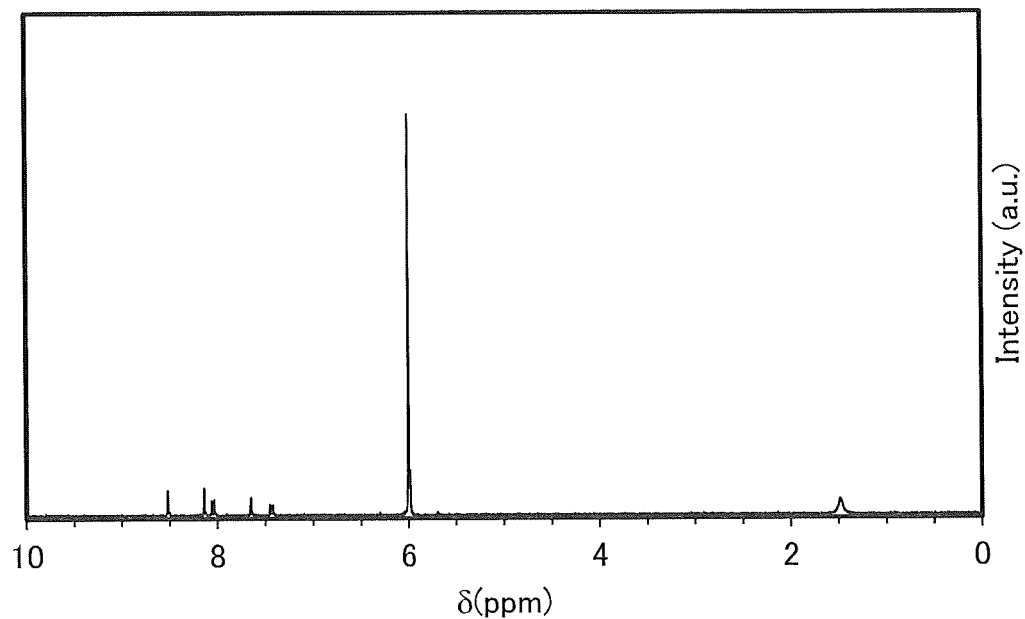
(B)
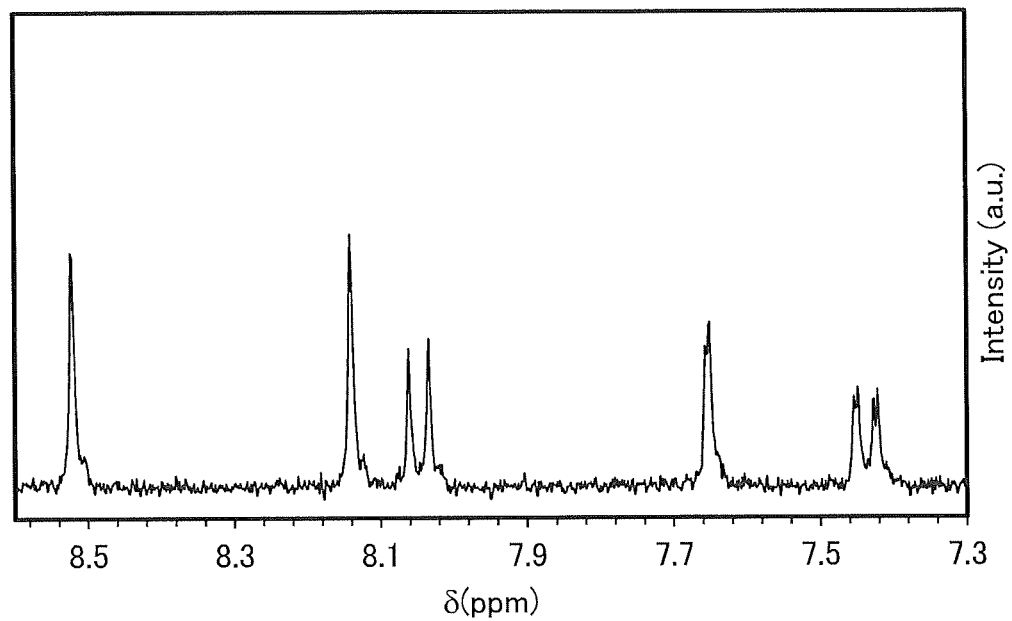

[FIG. 79]
(A)
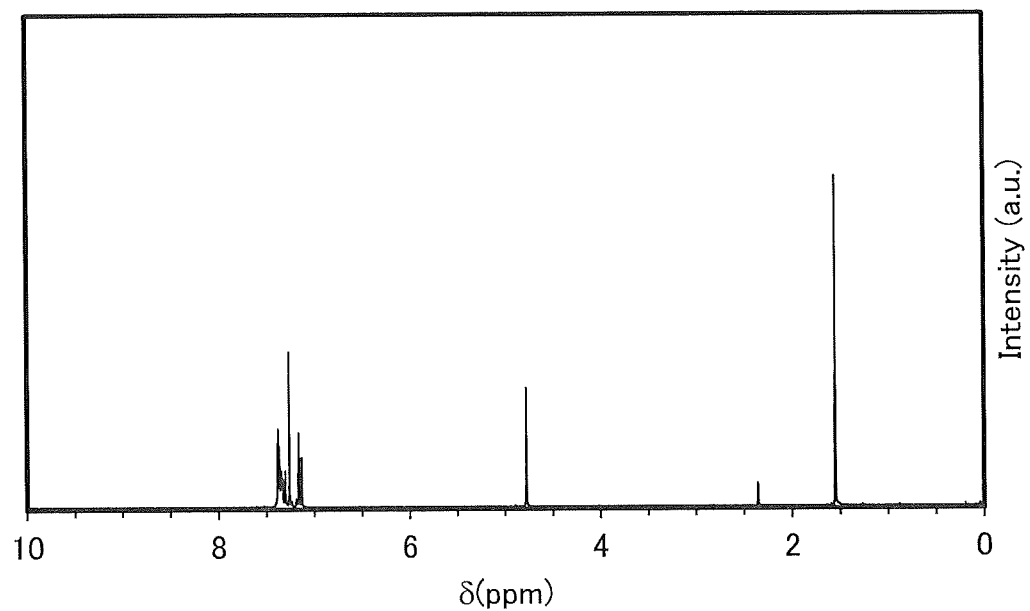
(B)
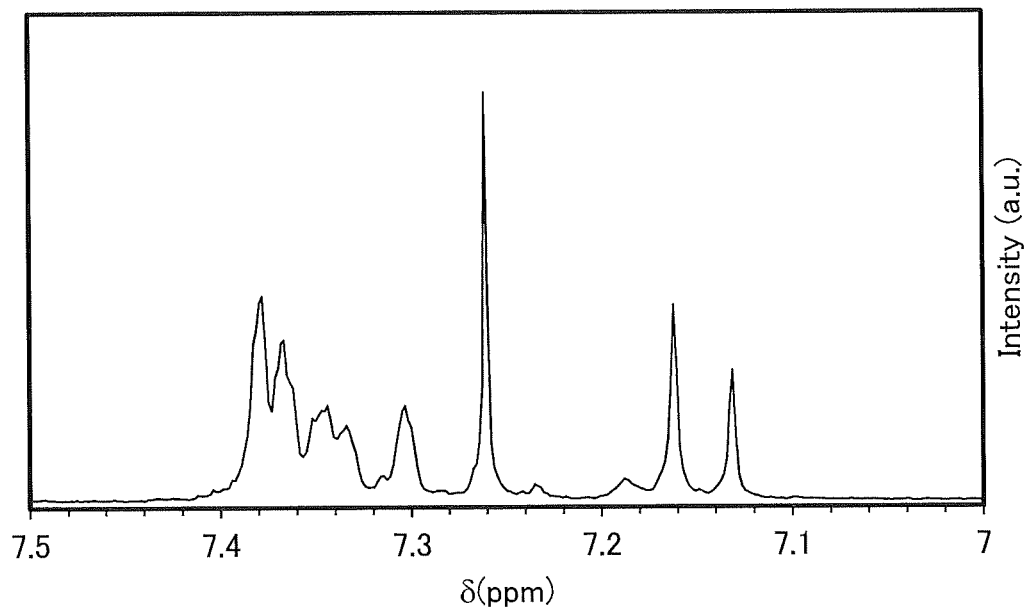

[FIG. 80]
(A)
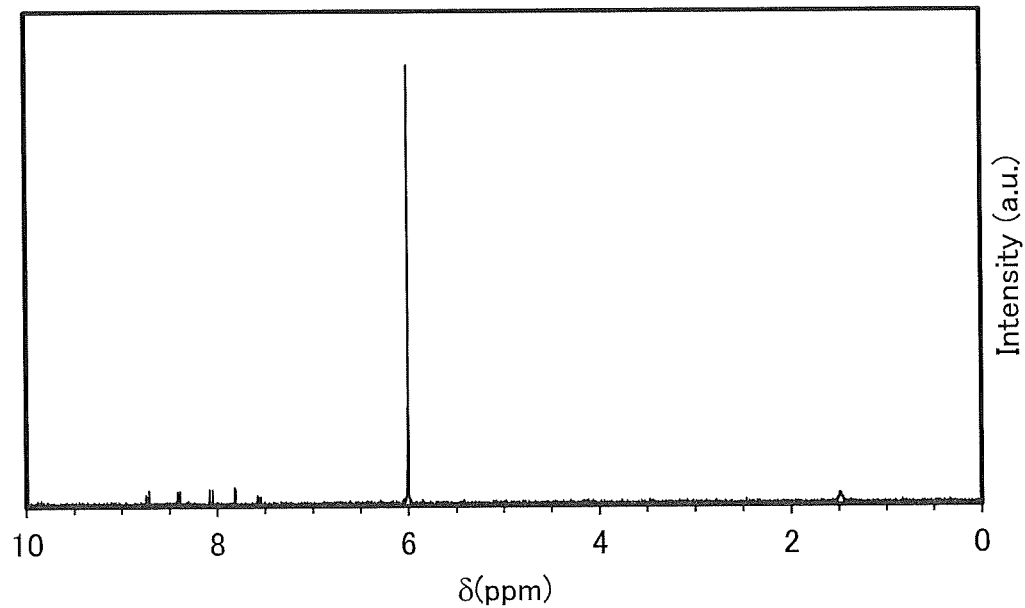
(B)
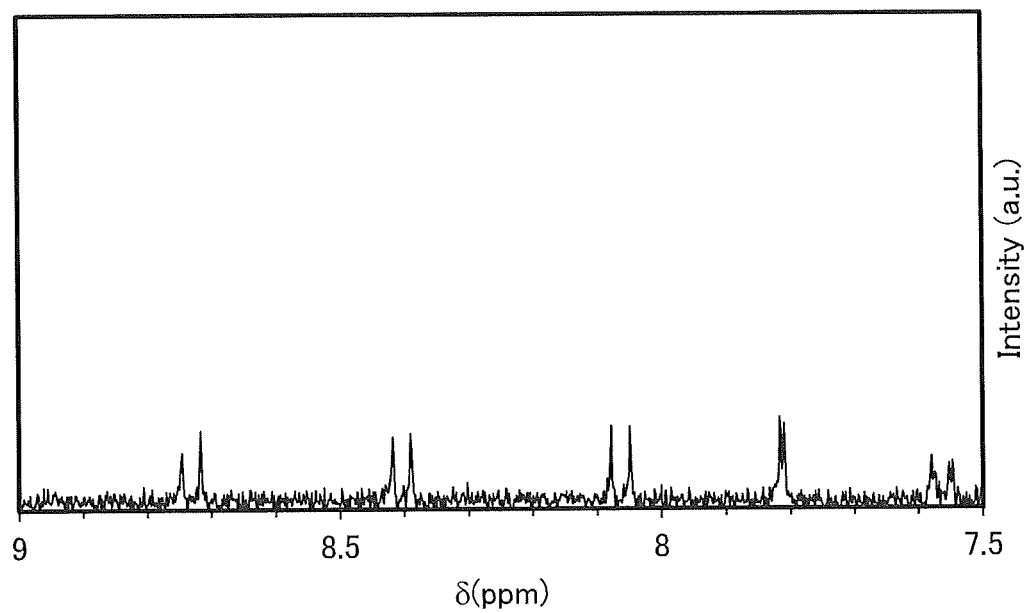

[FIG. 81]
(A)
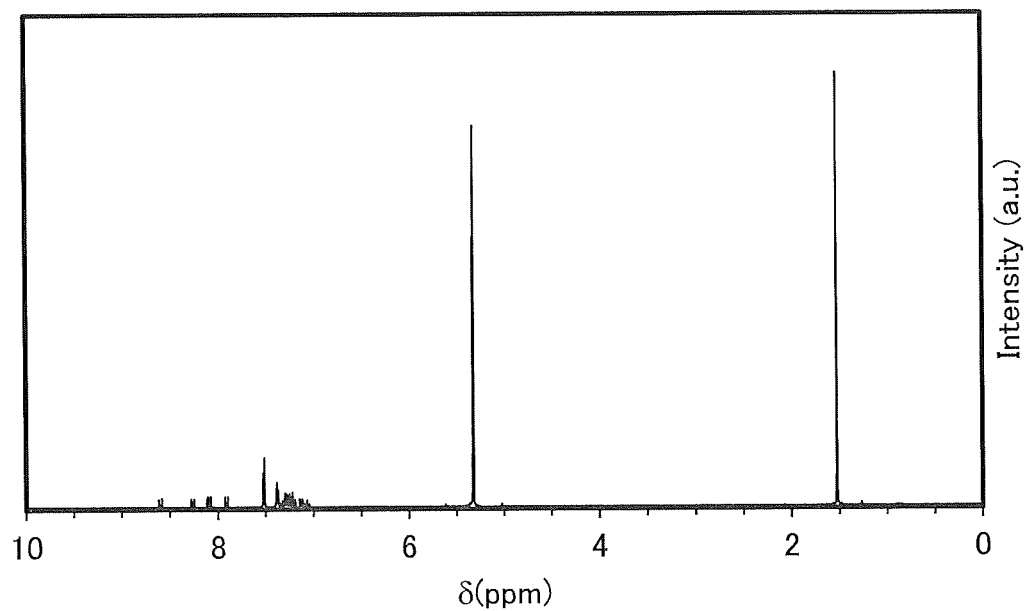
(B)
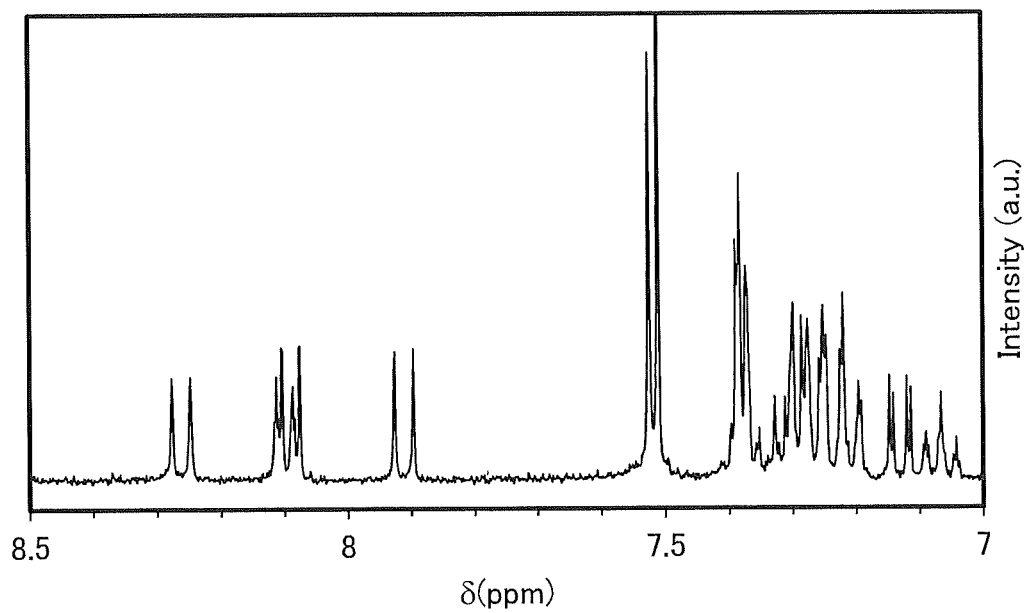

[FIG. 82]
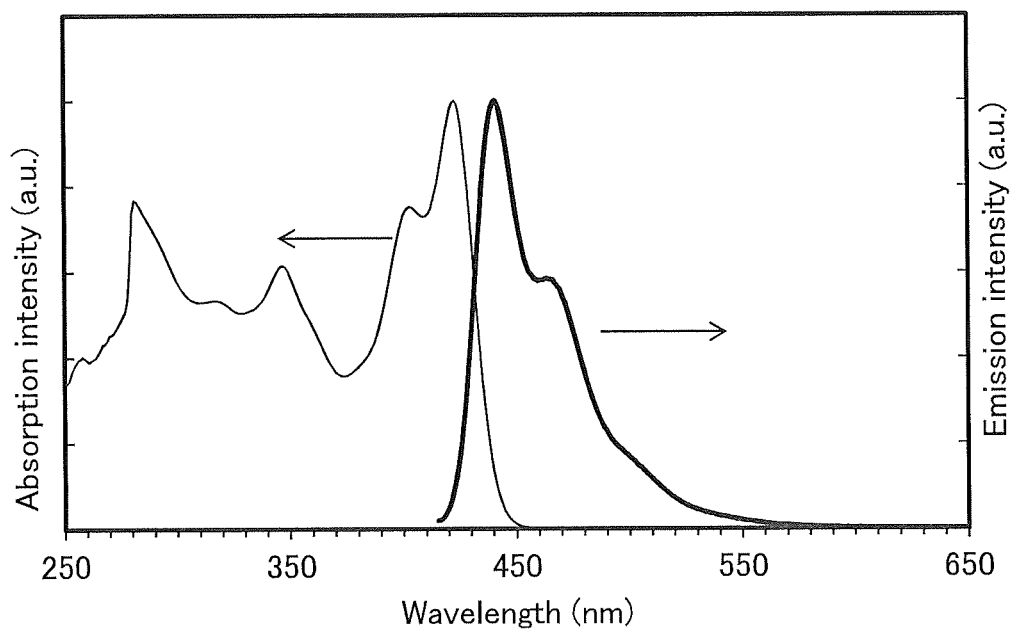

[FIG. 83]
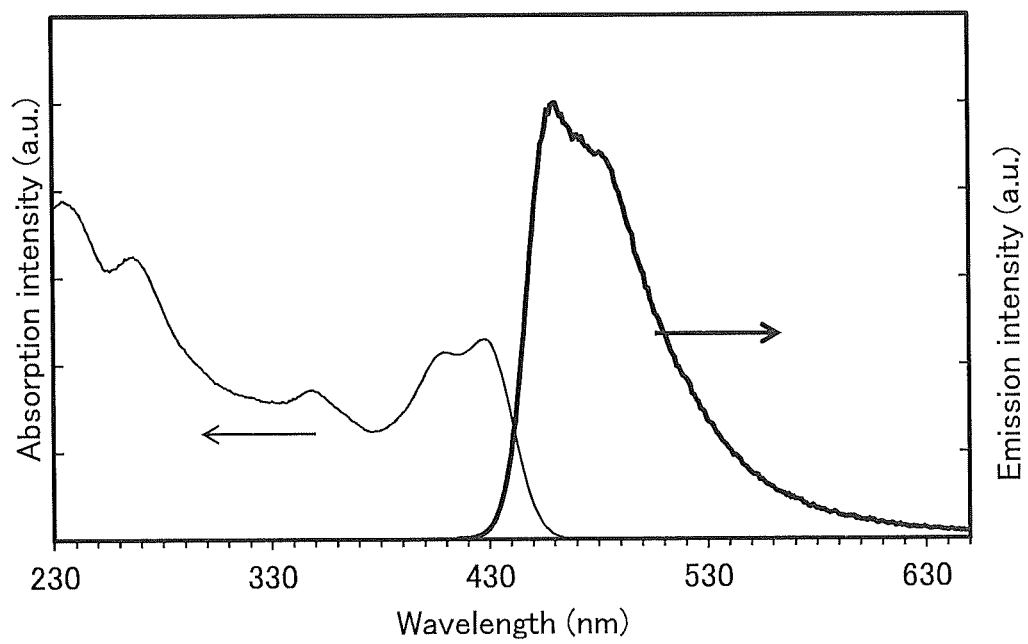

[FIG. 84]
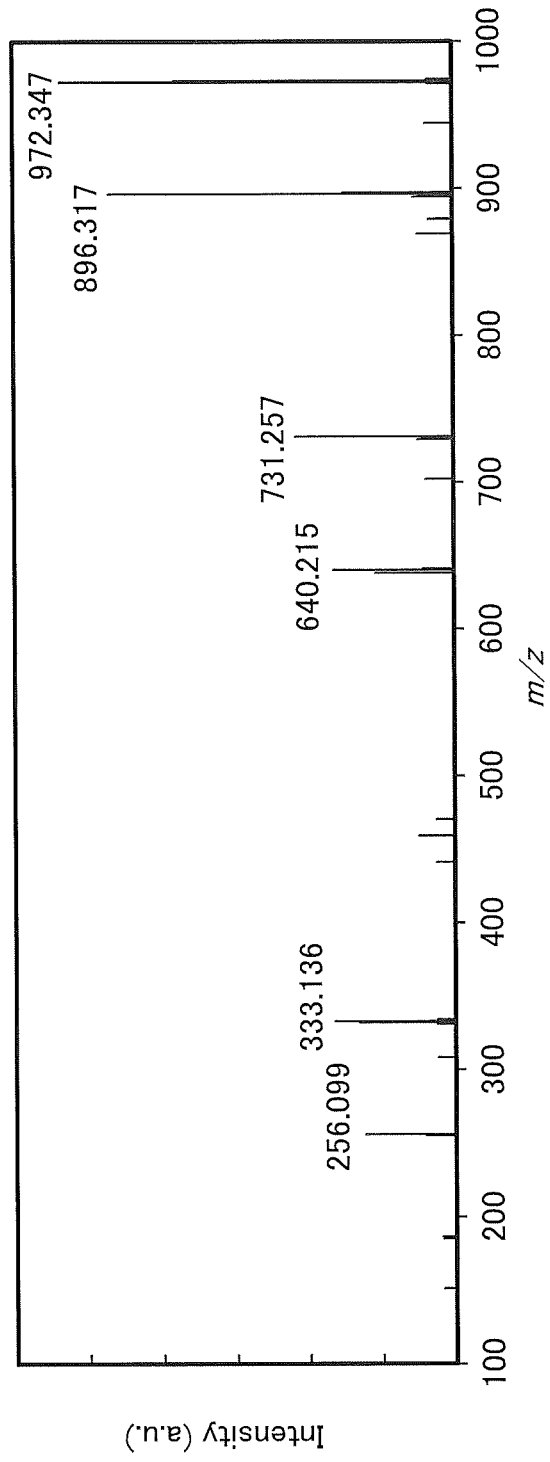

[FIG. 85]
(A)
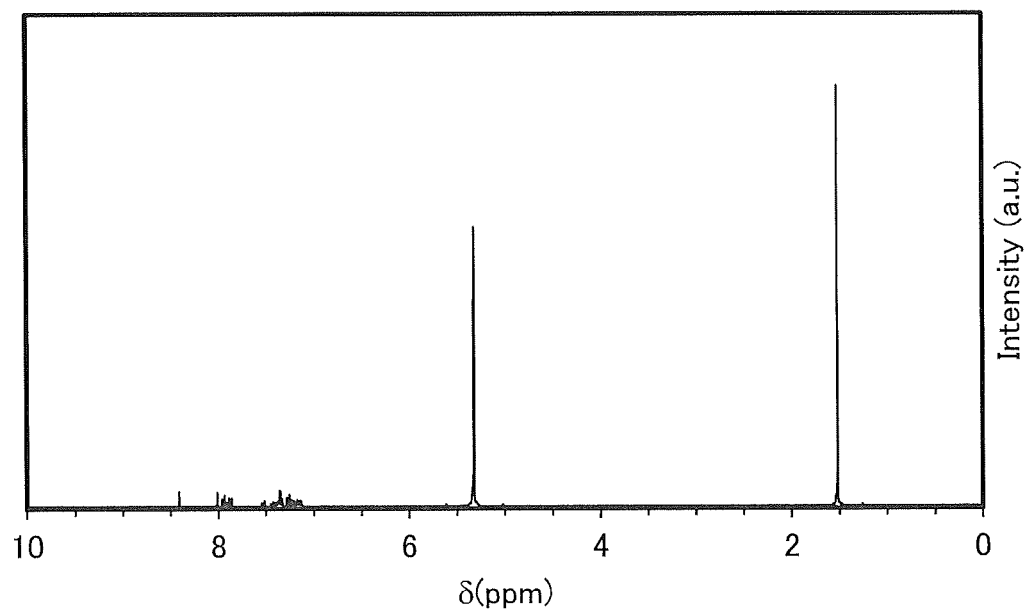
(B)
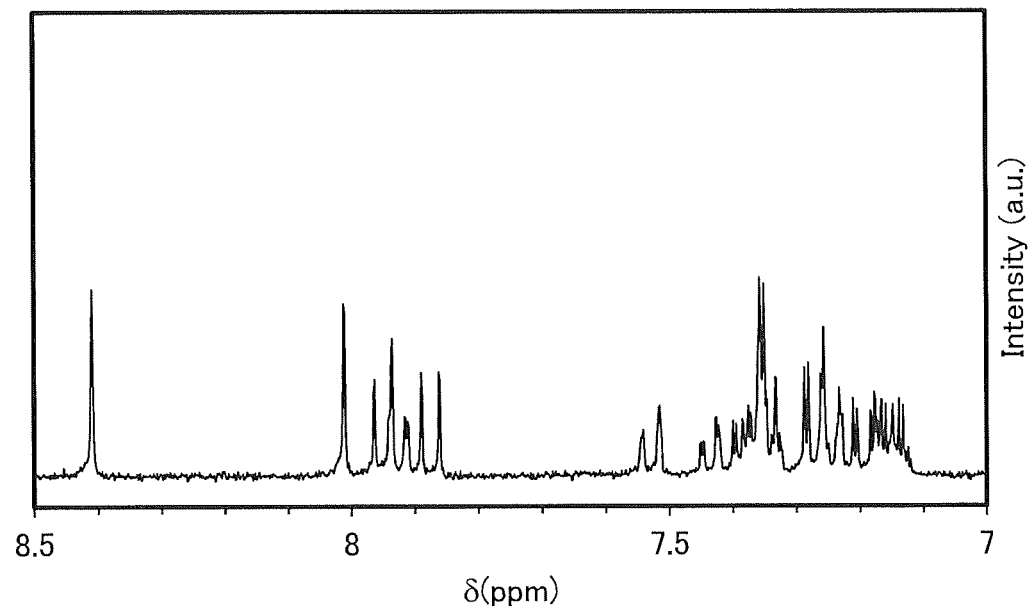

[FIG. 86]
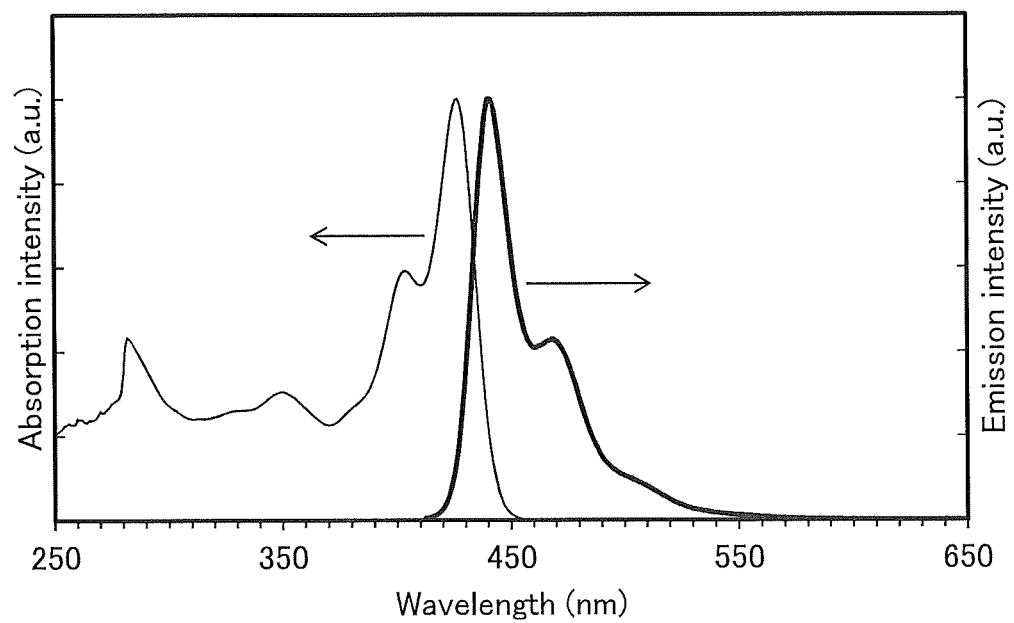

[FIG. 87]
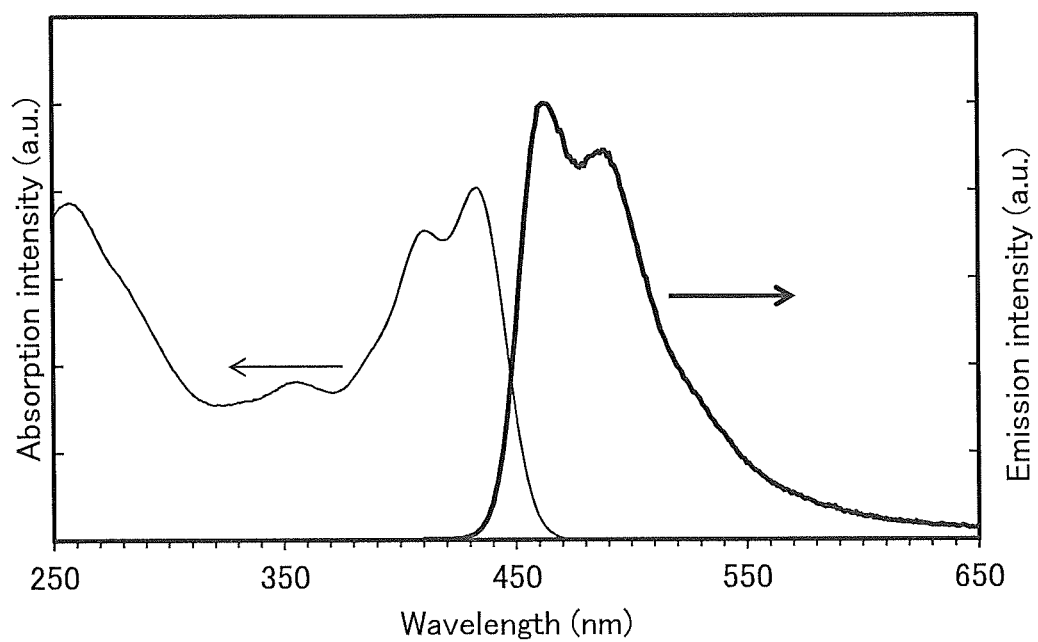

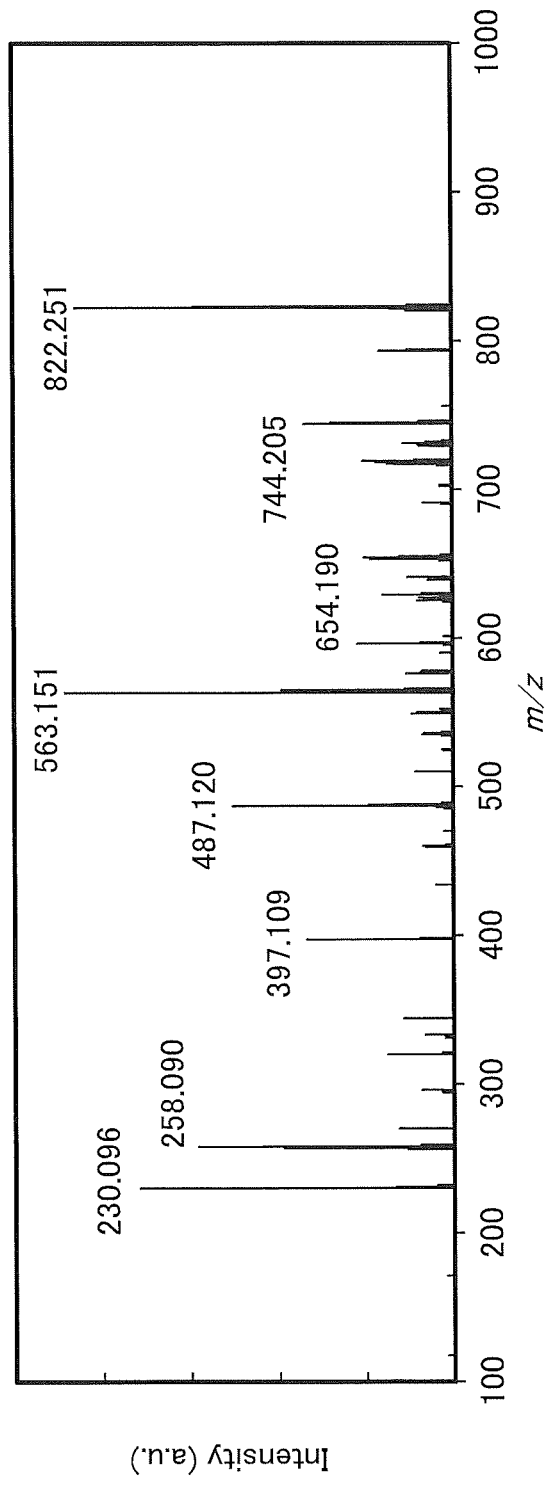
[FIG. 88]

[FIG. 89]
(A)
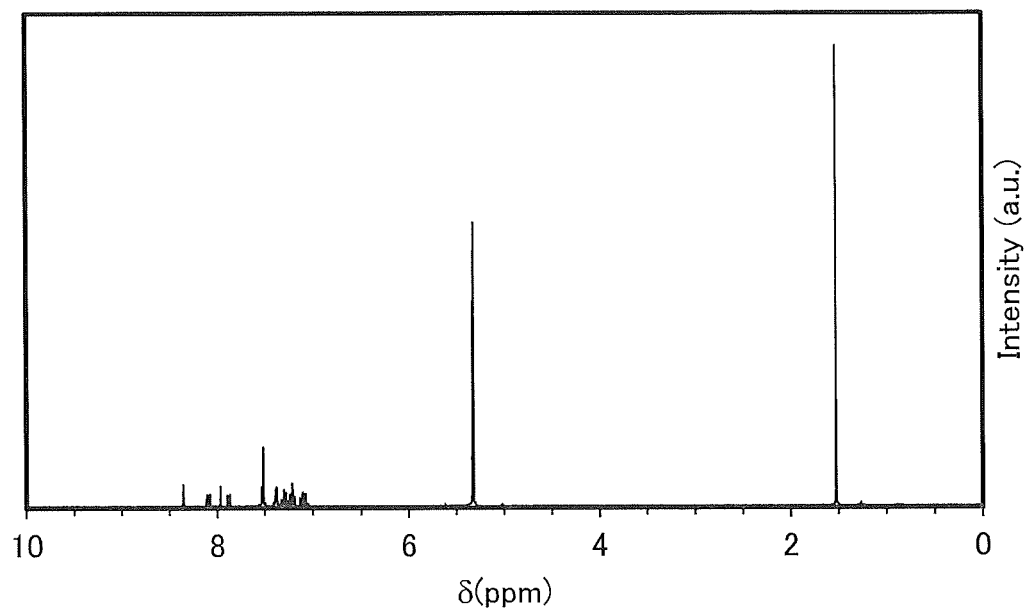
(B)
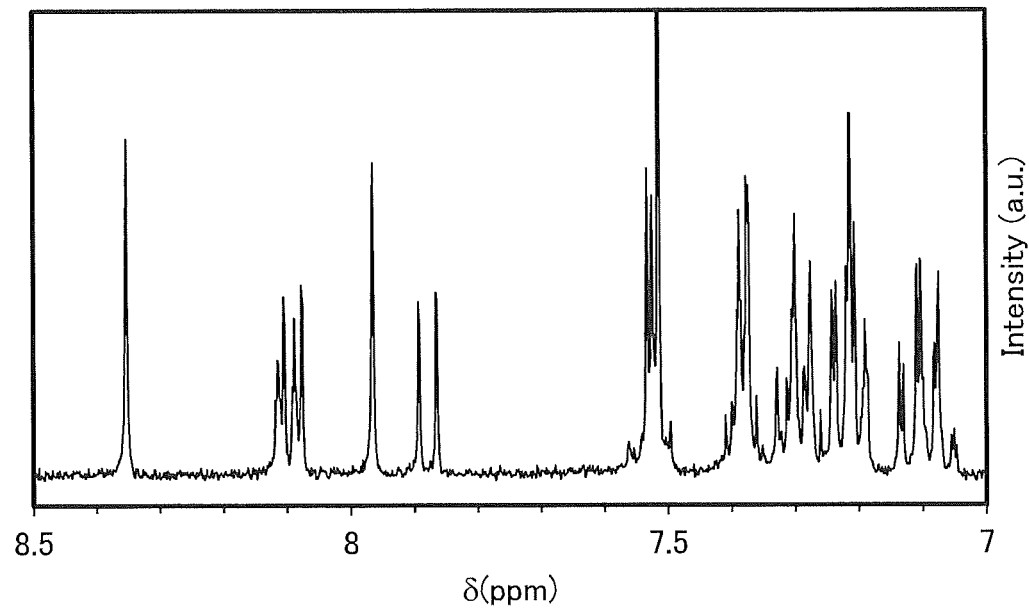

[FIG. 90]
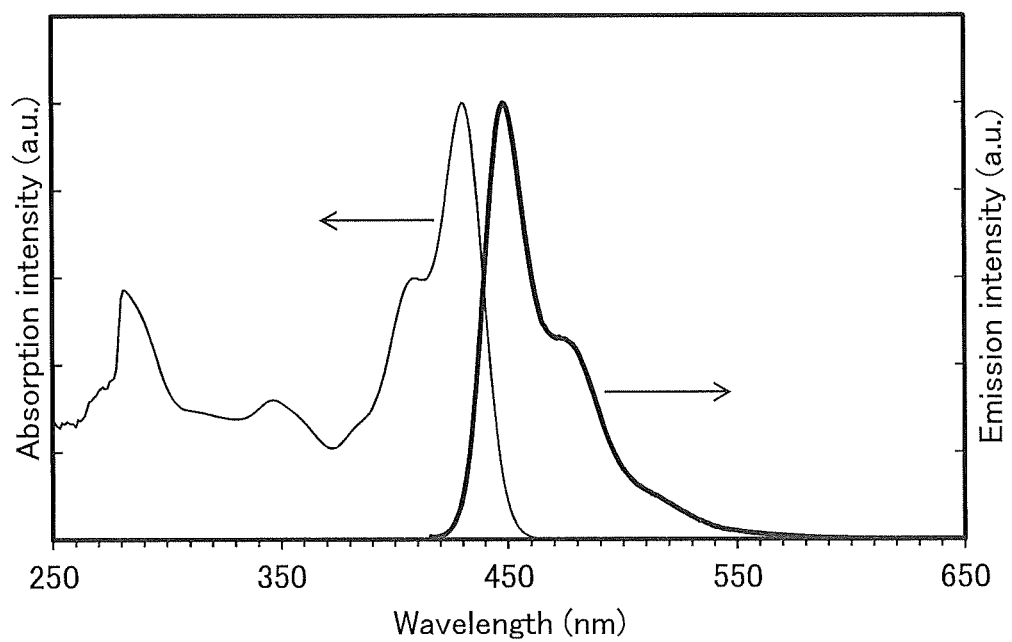

[FIG. 91]
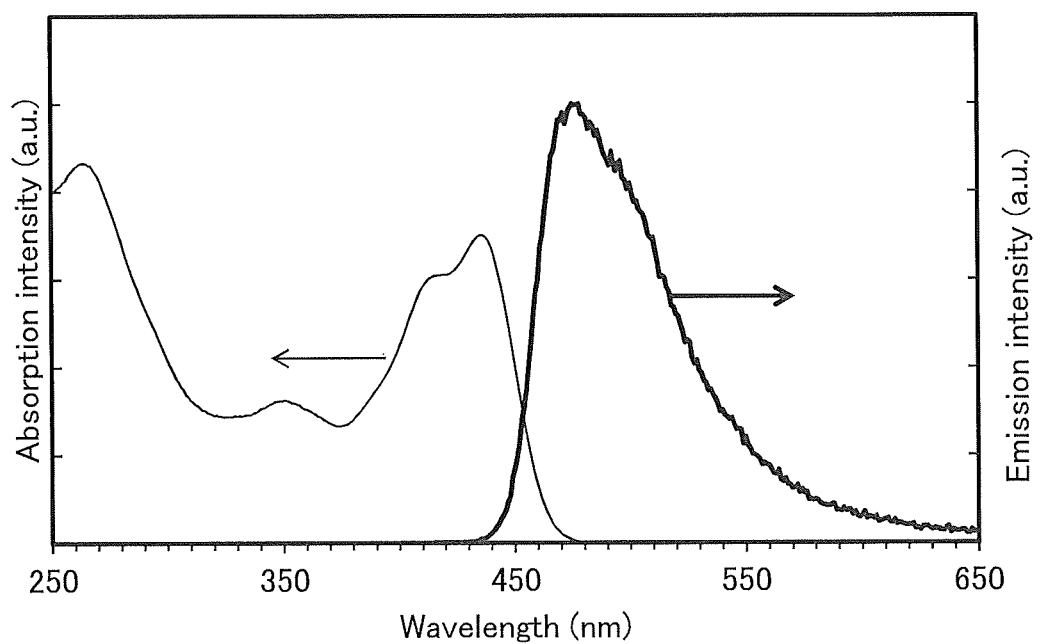

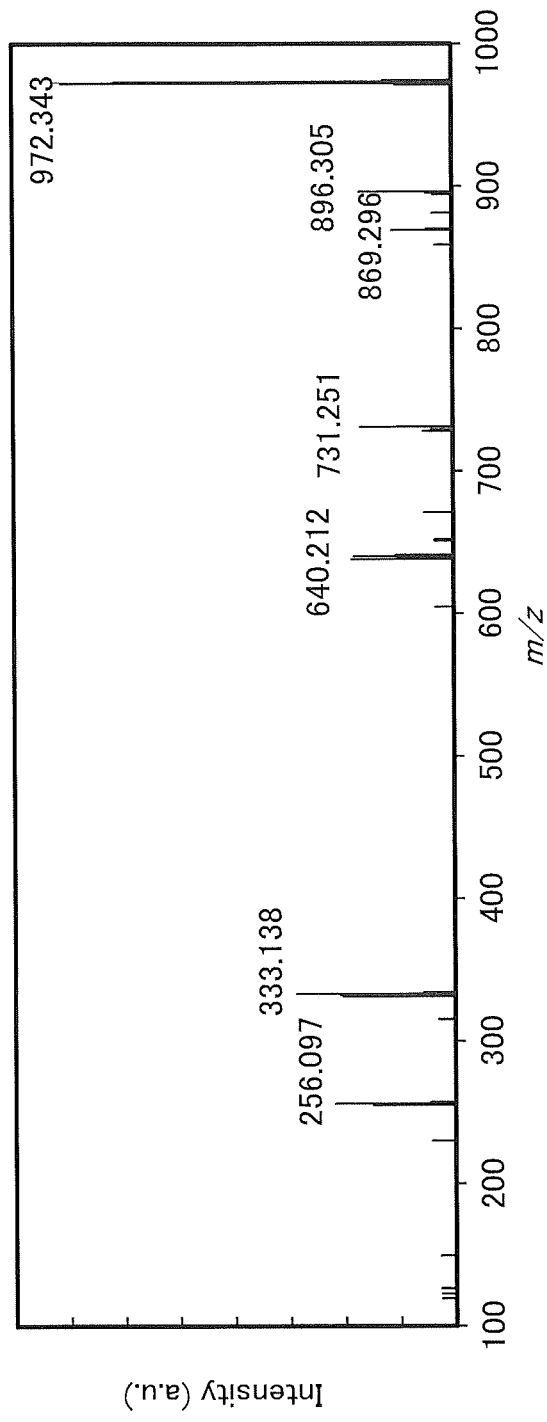
[FIG. 92]

[FIG. 93]
(A)
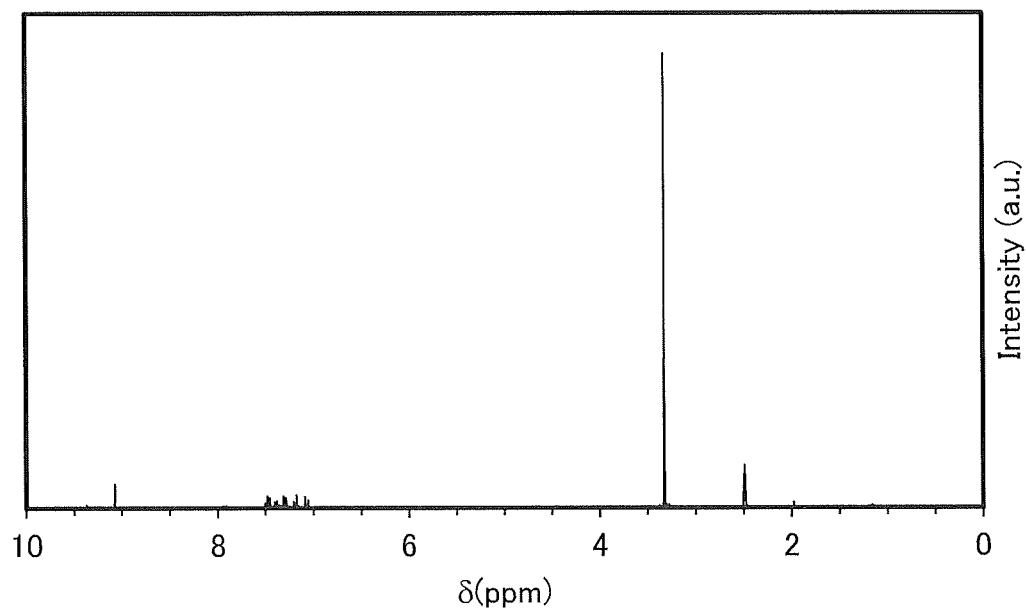
(B)
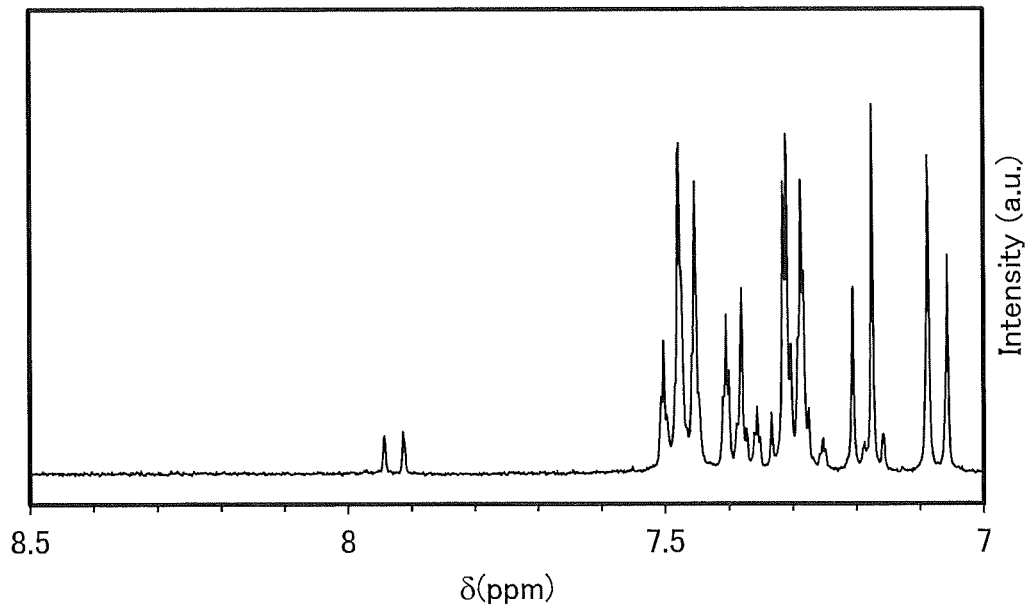

[FIG. 94]
(A)
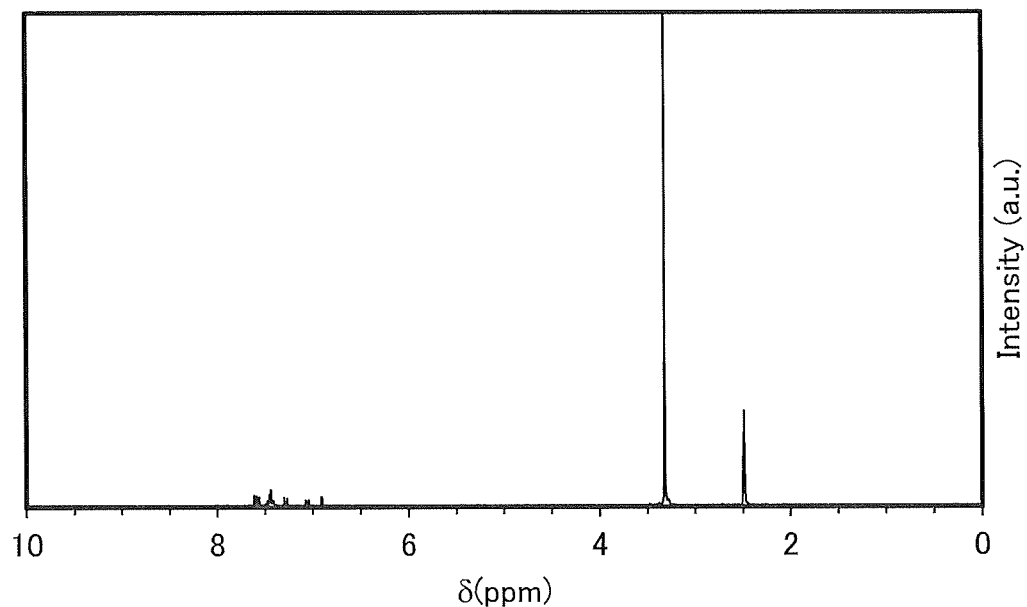
(B)
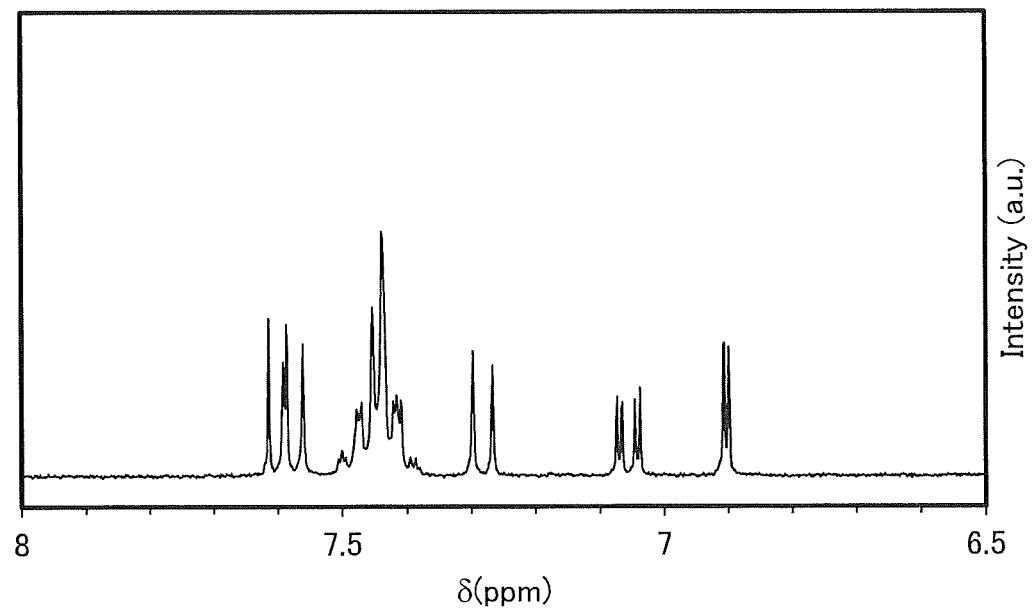

[FIG. 95]
(A)
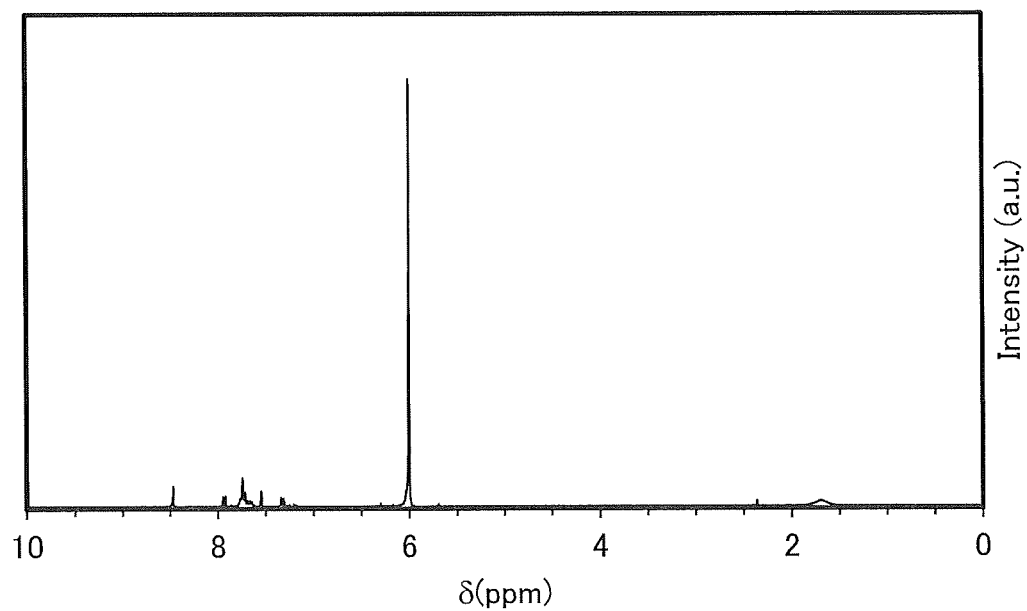
(B)
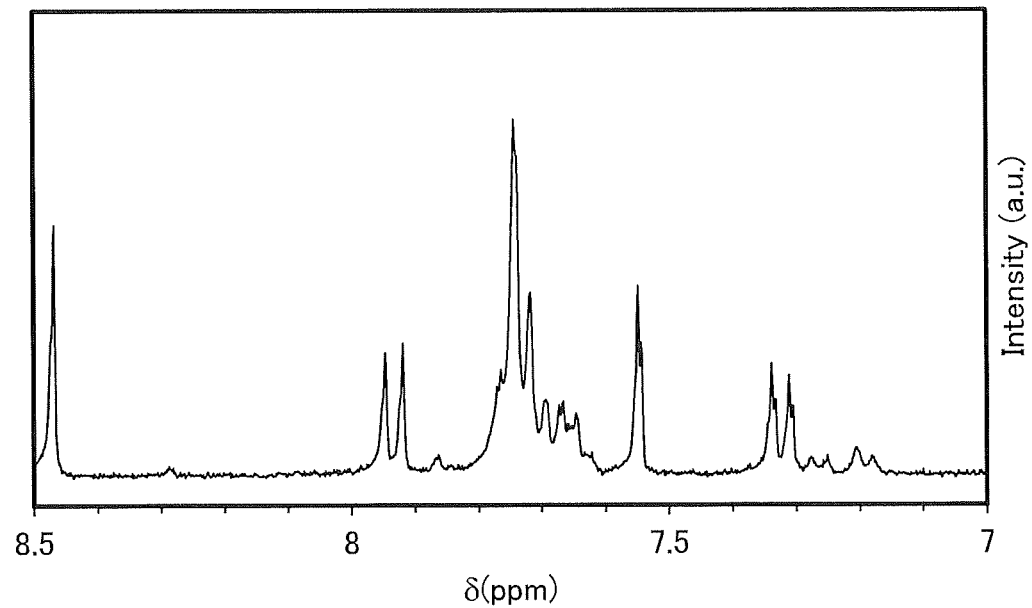

[FIG. 96]
(A)
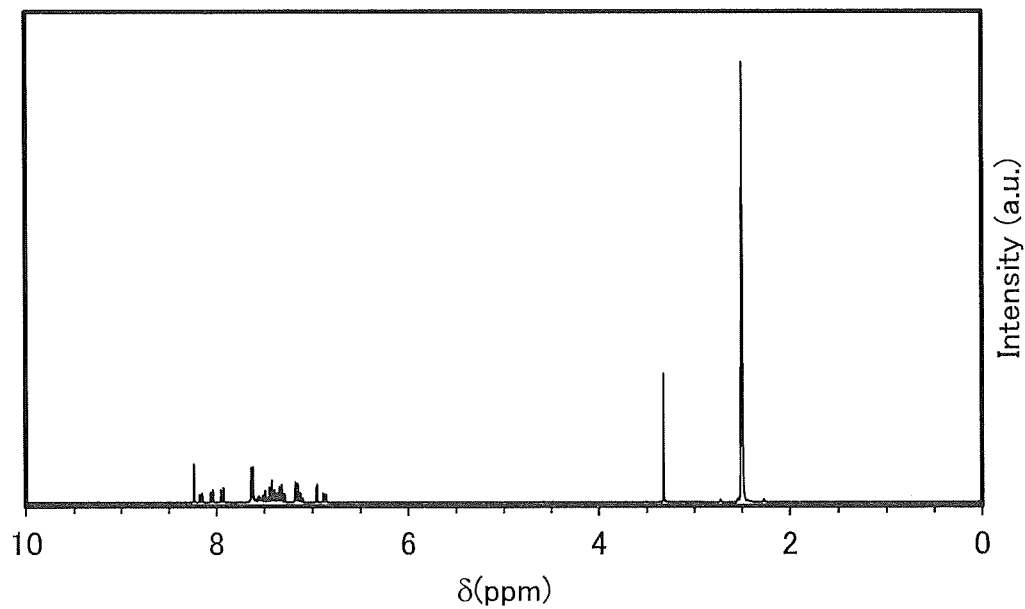
(B)
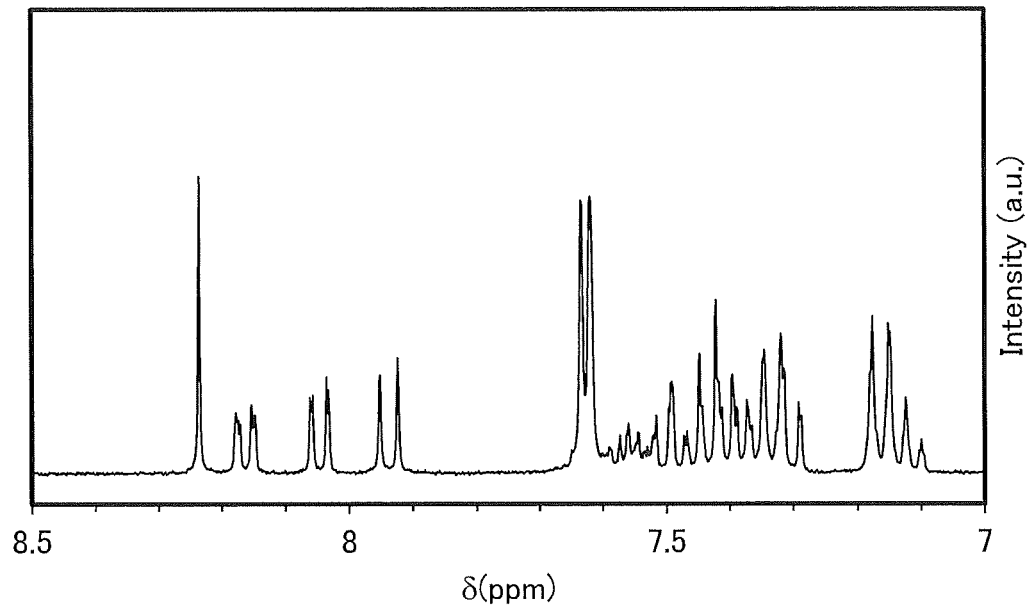

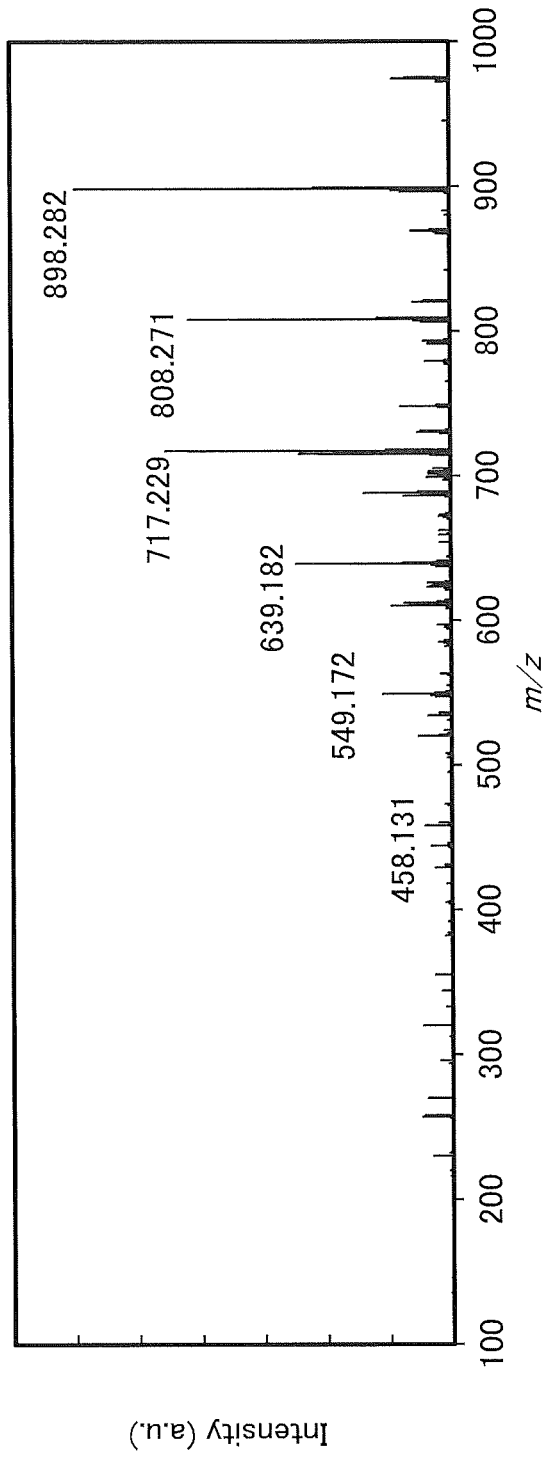
[FIG. 97]

[FIG. 98]
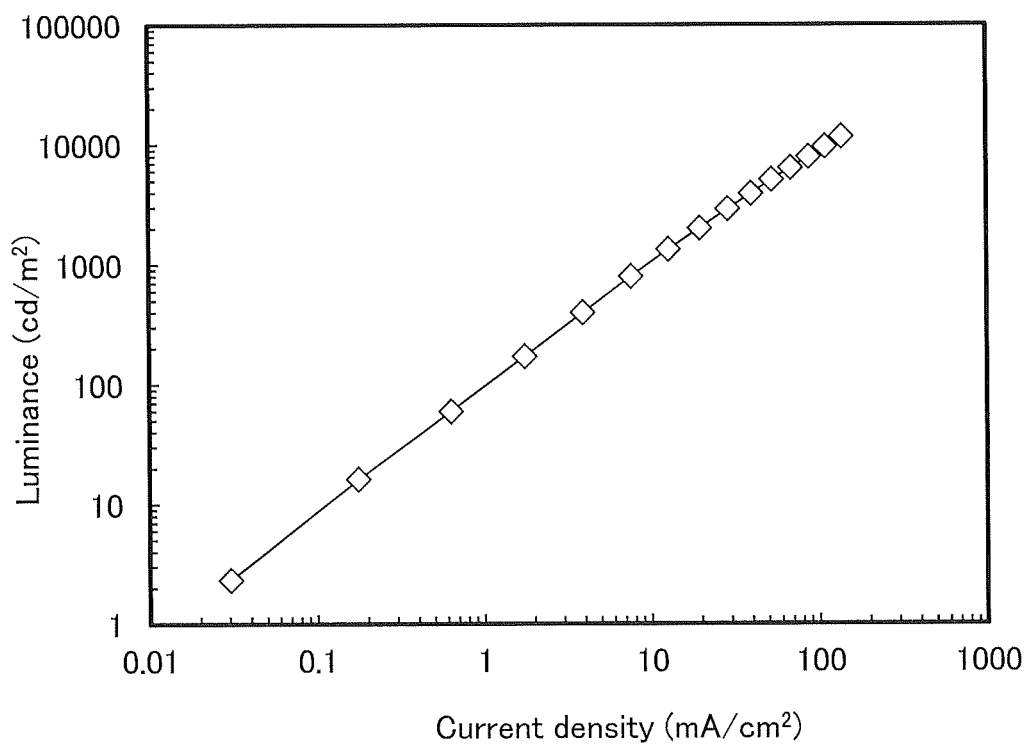
[FIG. 99]
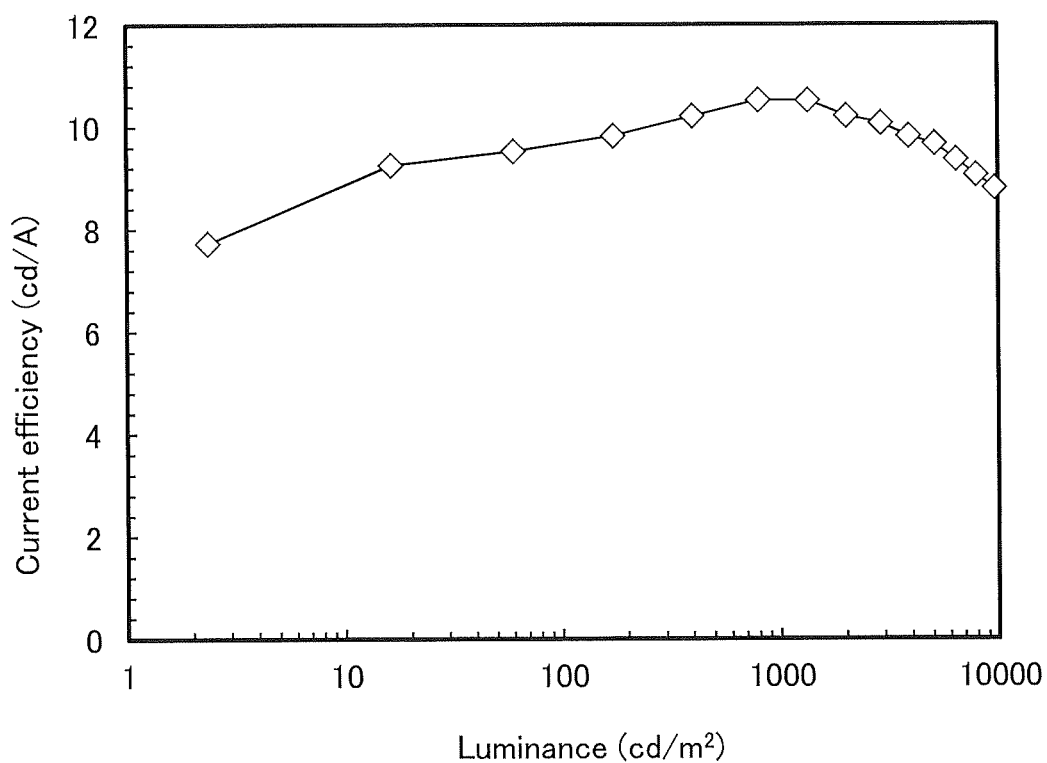

[FIG. 100]
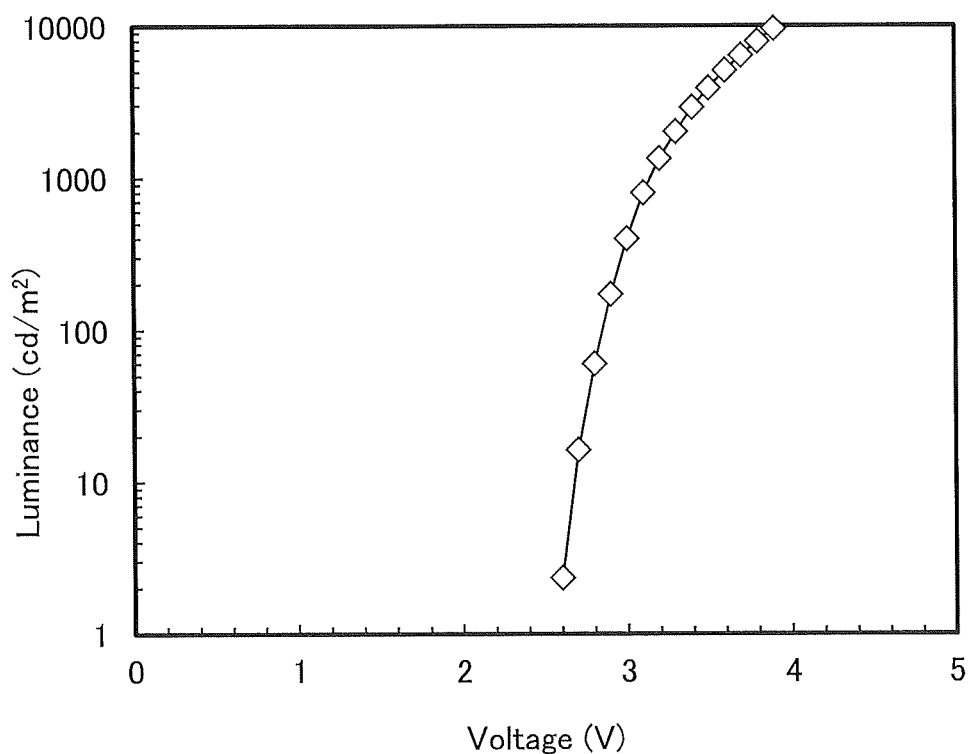
[FIG. 101]
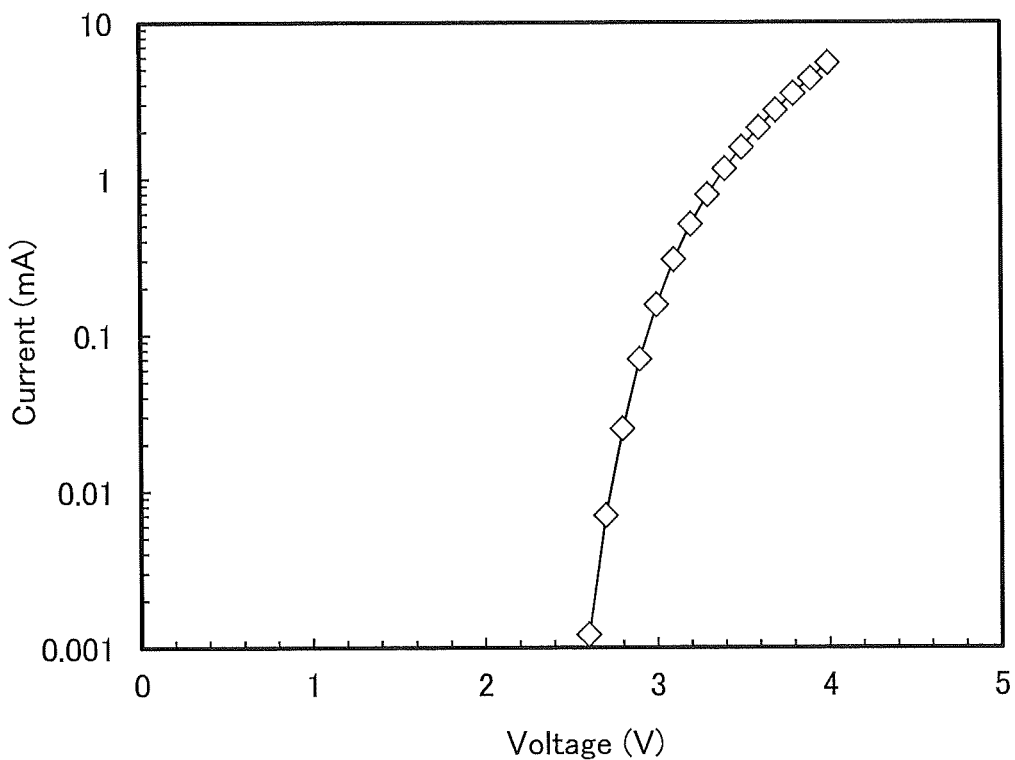

[FIG. 102]
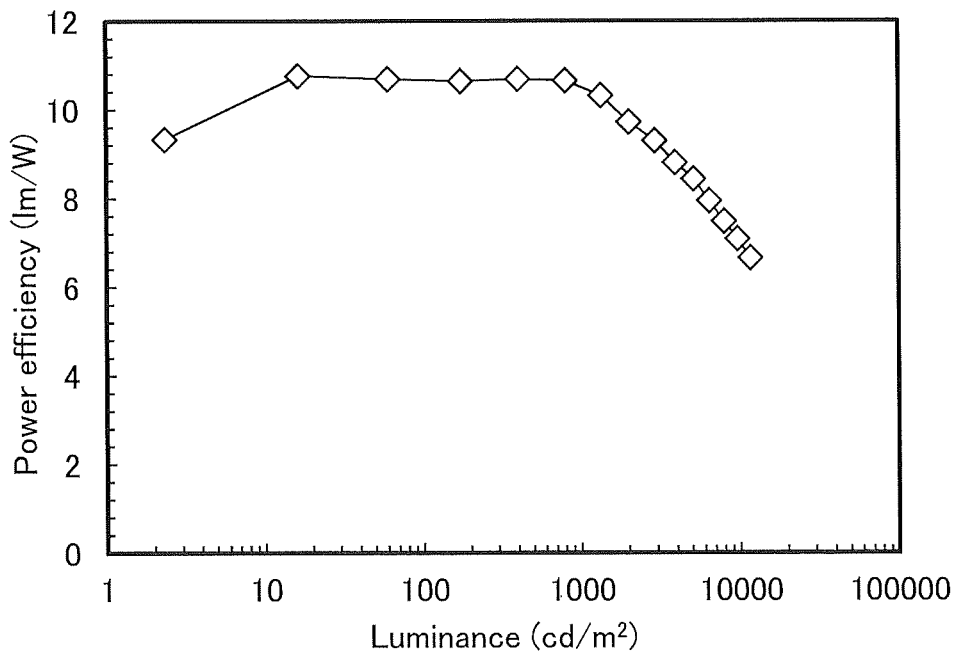
[FIG. 103]
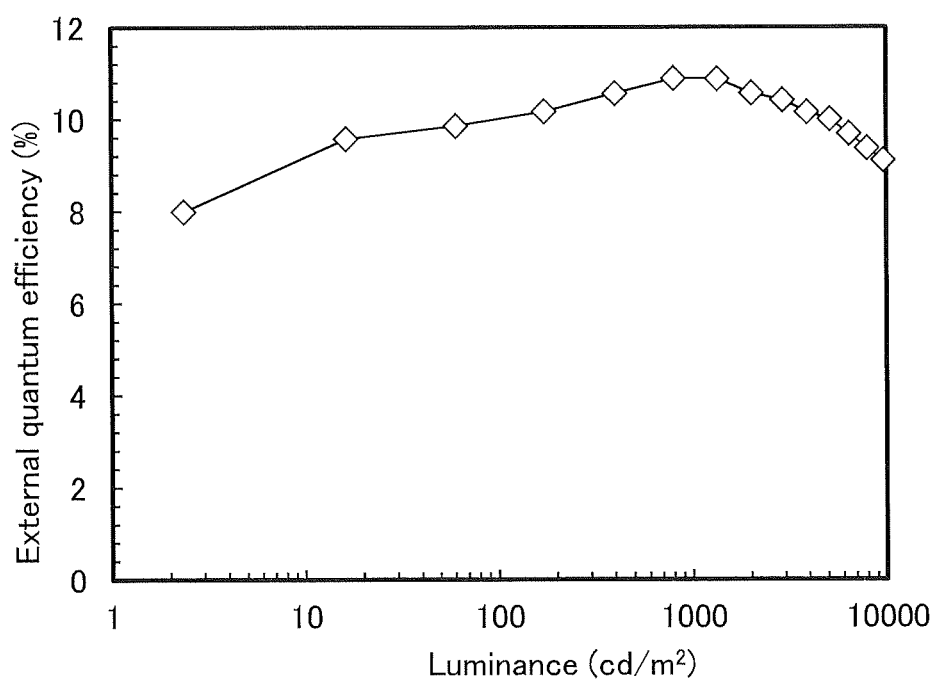

[FIG. 104]
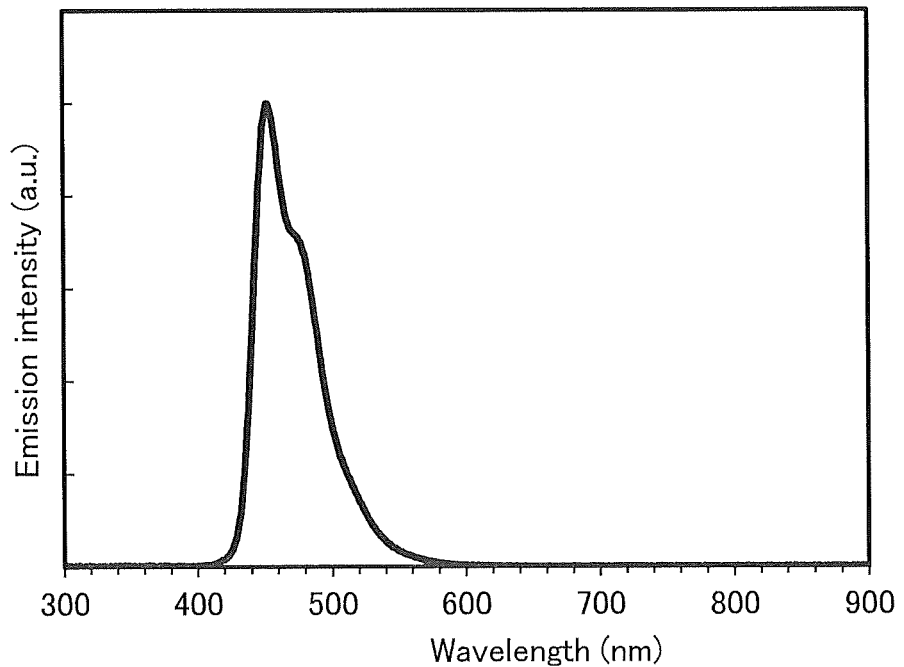
[FIG. 105]
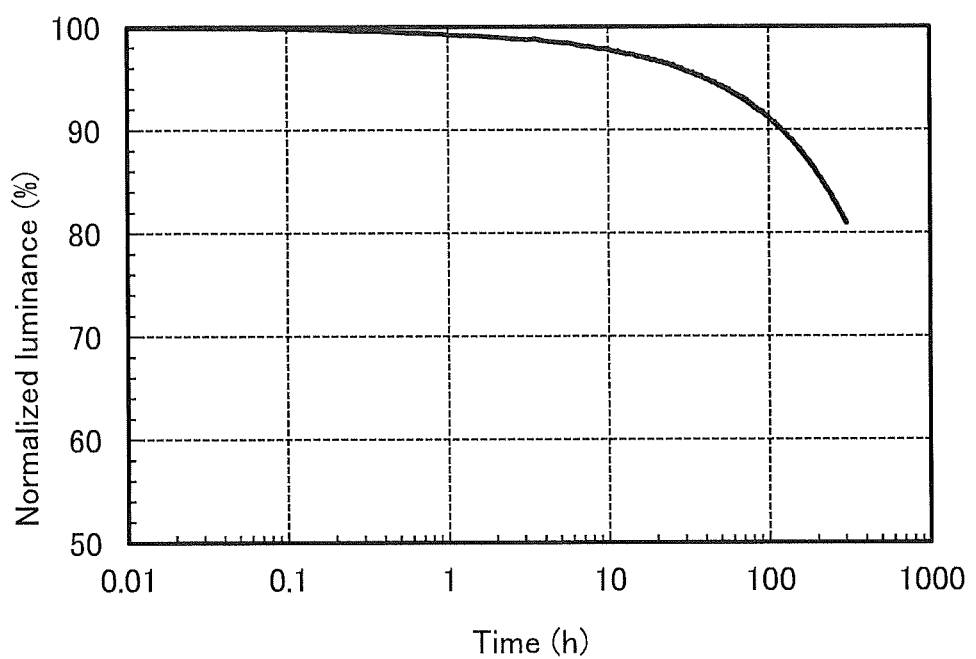

[FIG. 106]
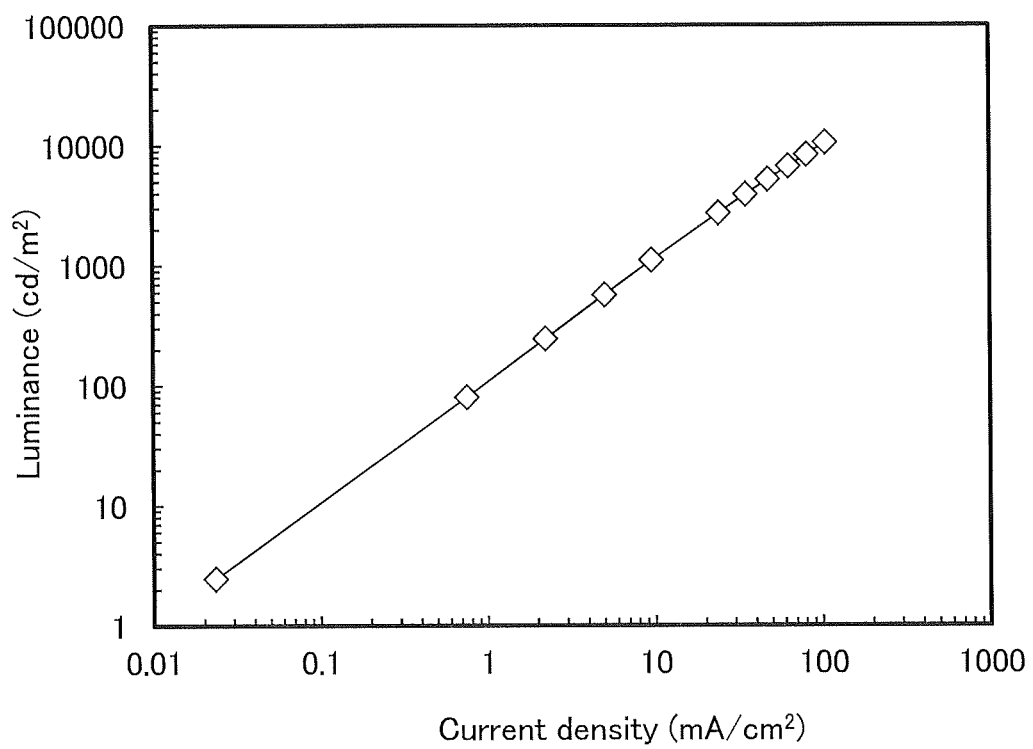
[FIG. 107]
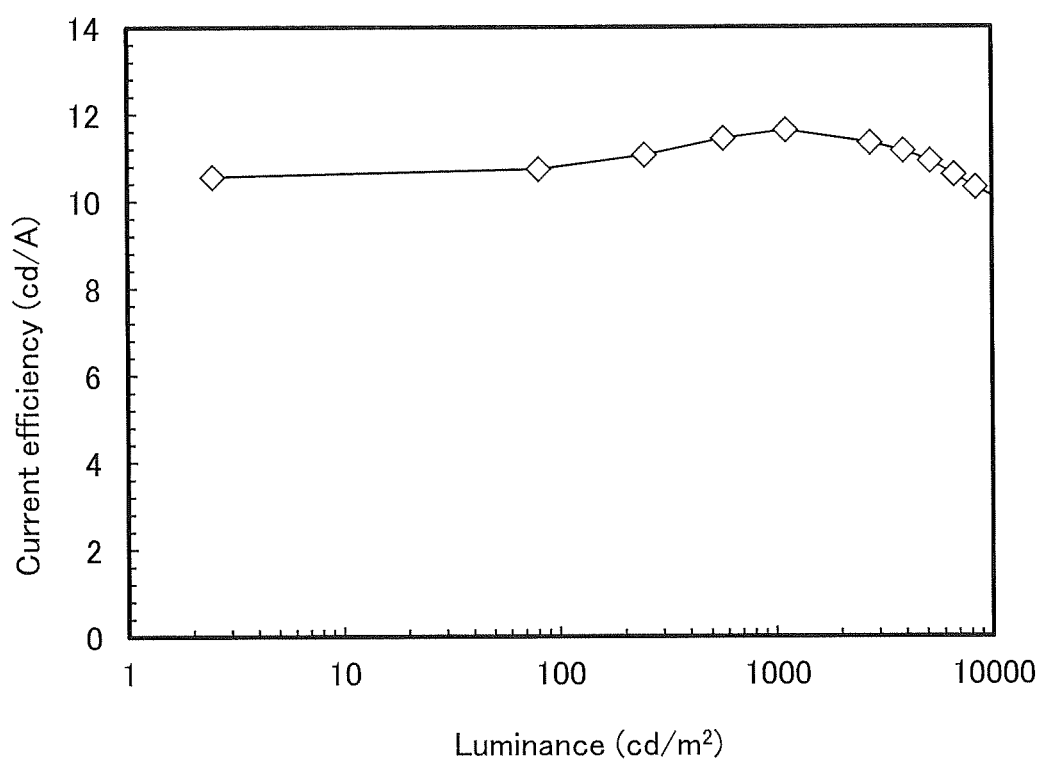

[FIG. 108]
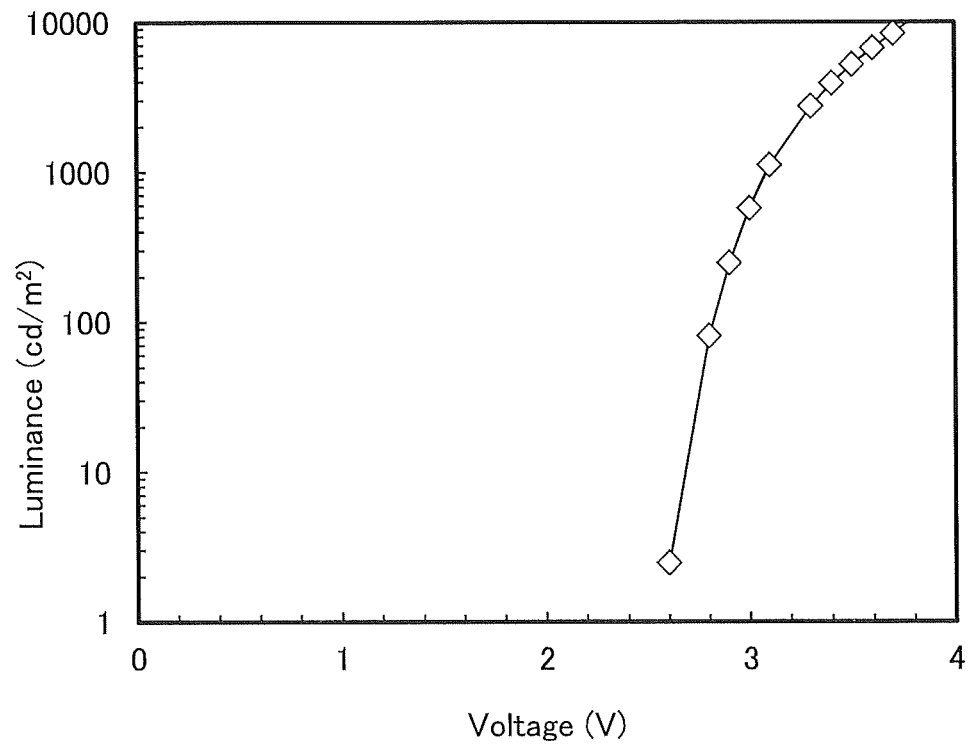
[FIG. 109]
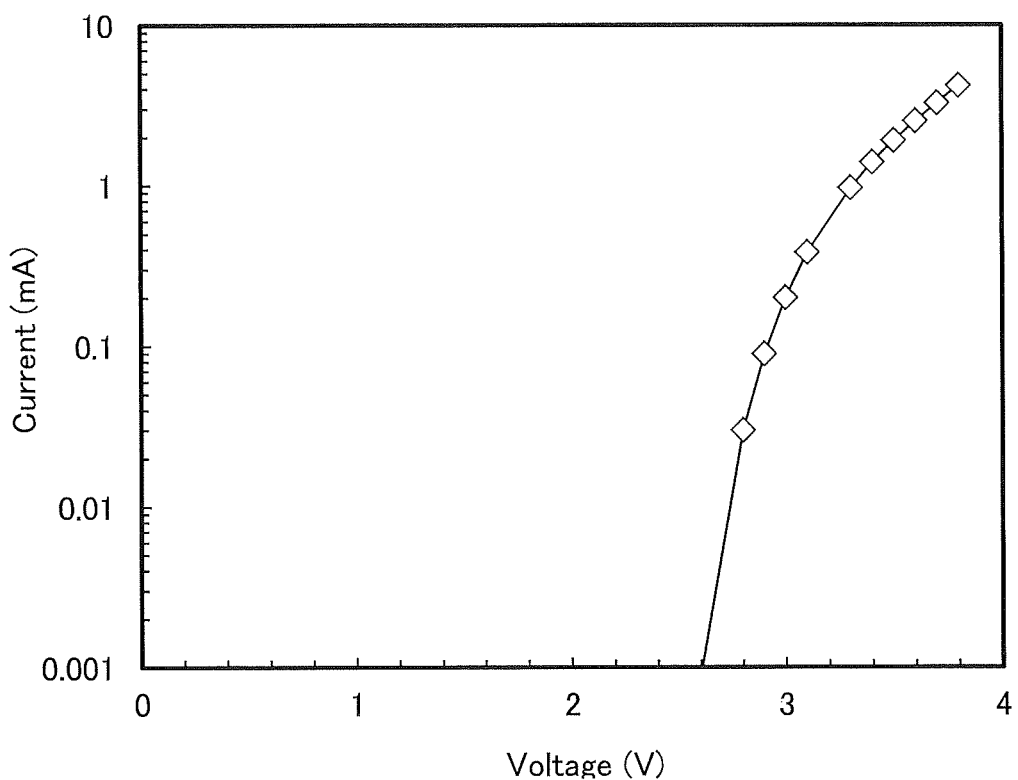

[FIG. 110]
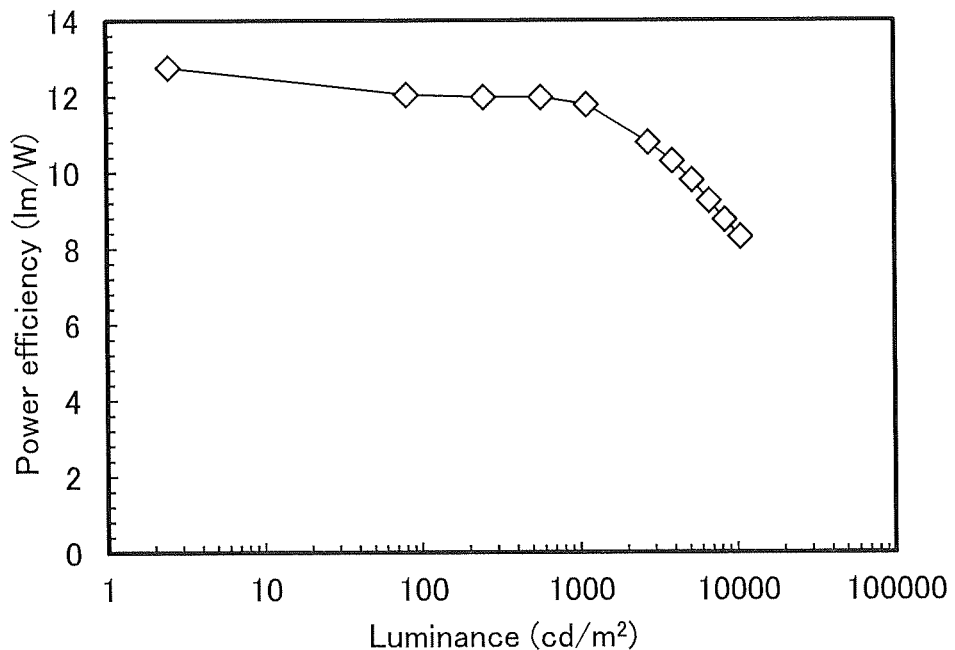
[FIG. 111]
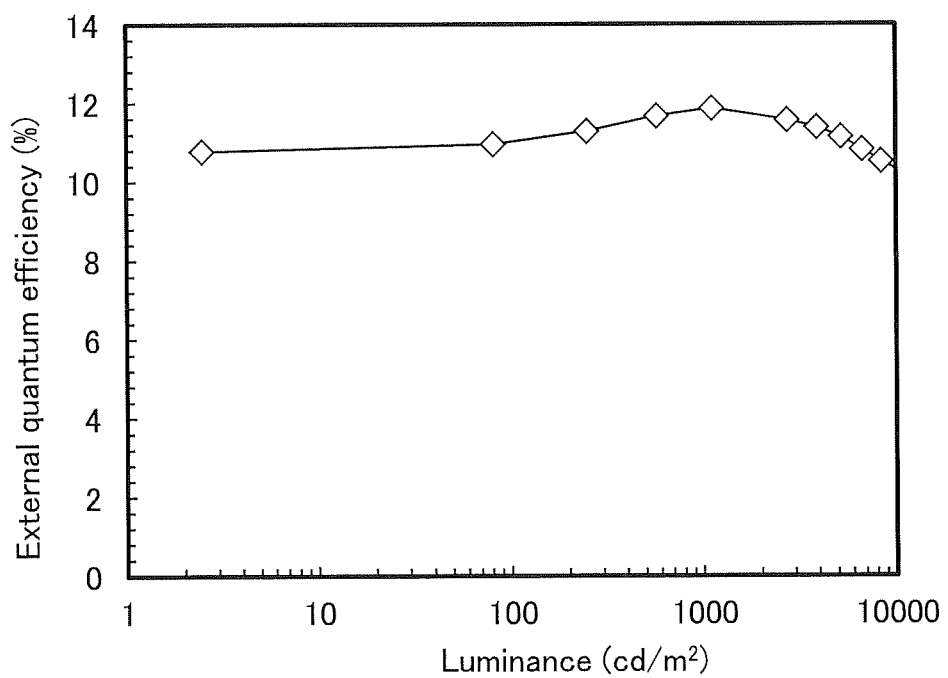

[FIG. 112]
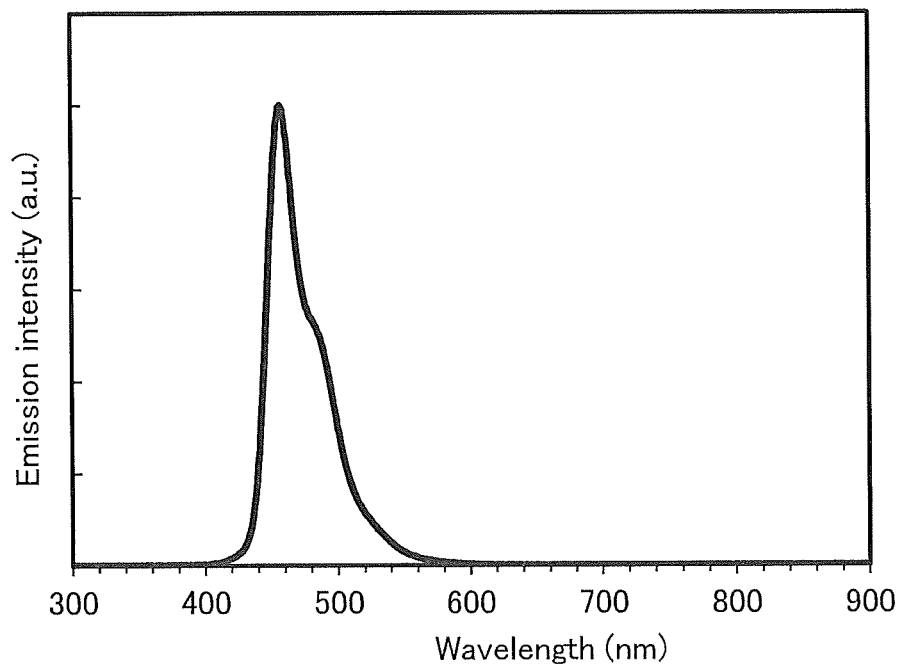
[FIG. 113]
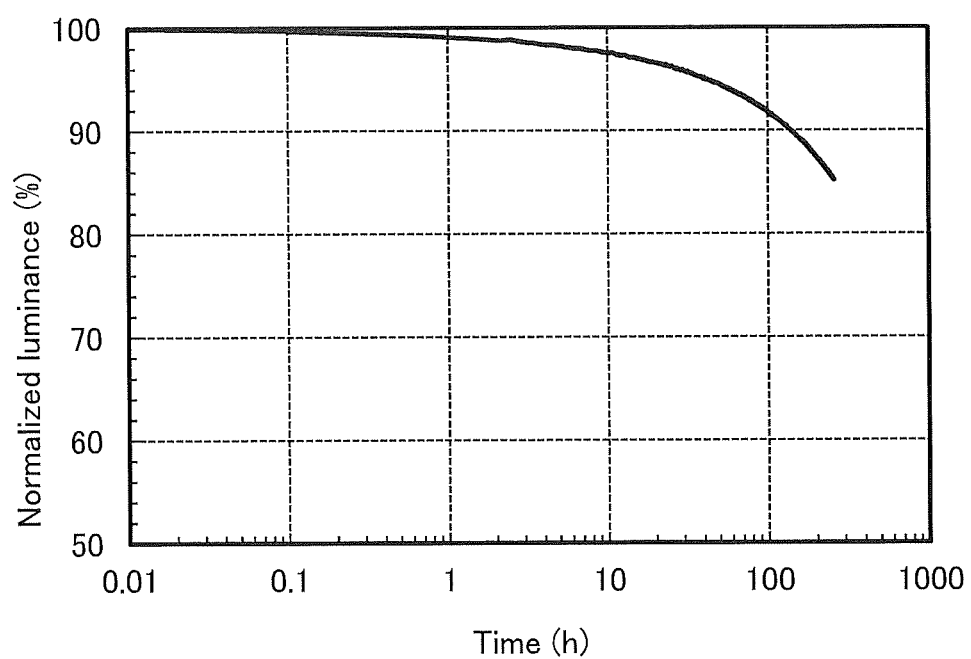

[FIG. 114]
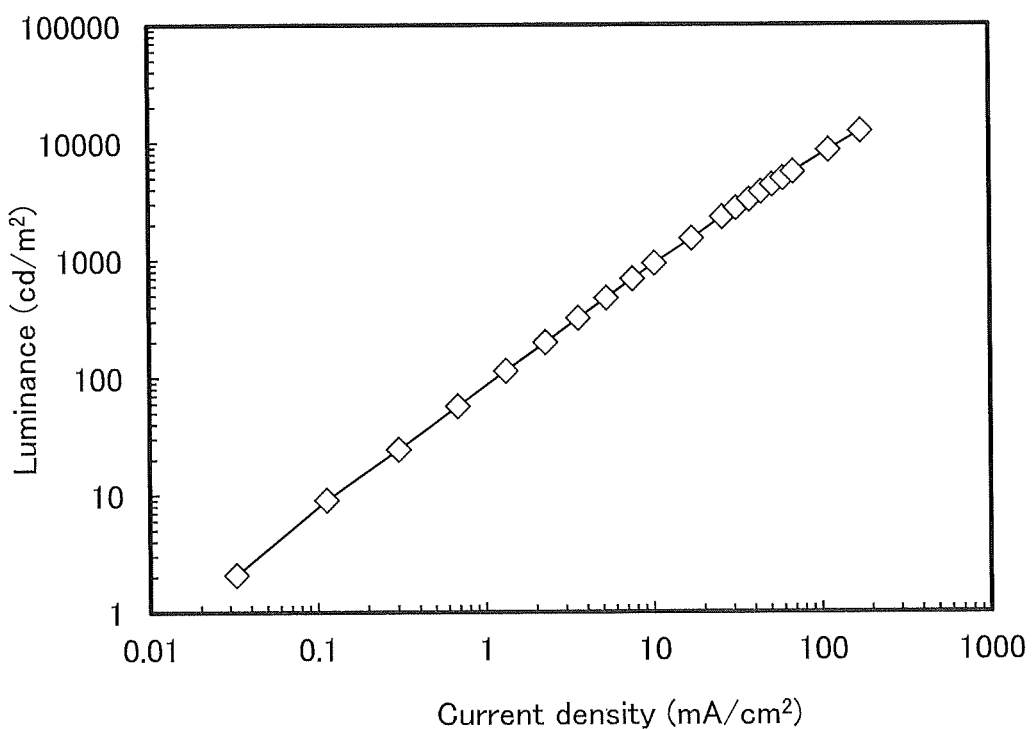
[FIG. 115]
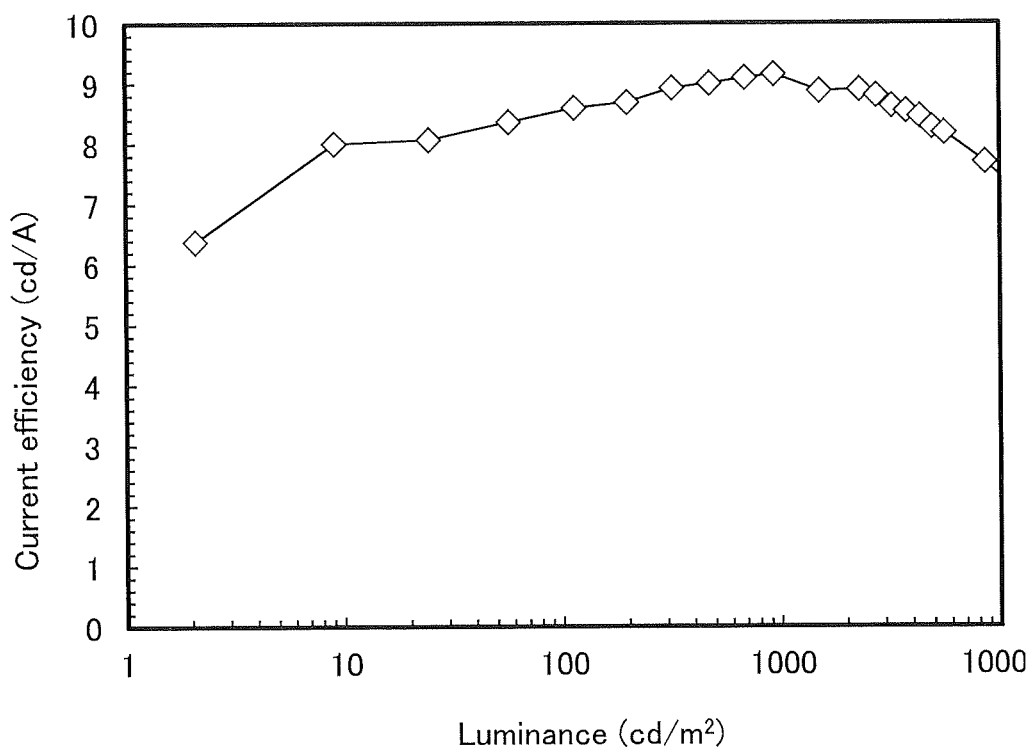

[FIG. 116]
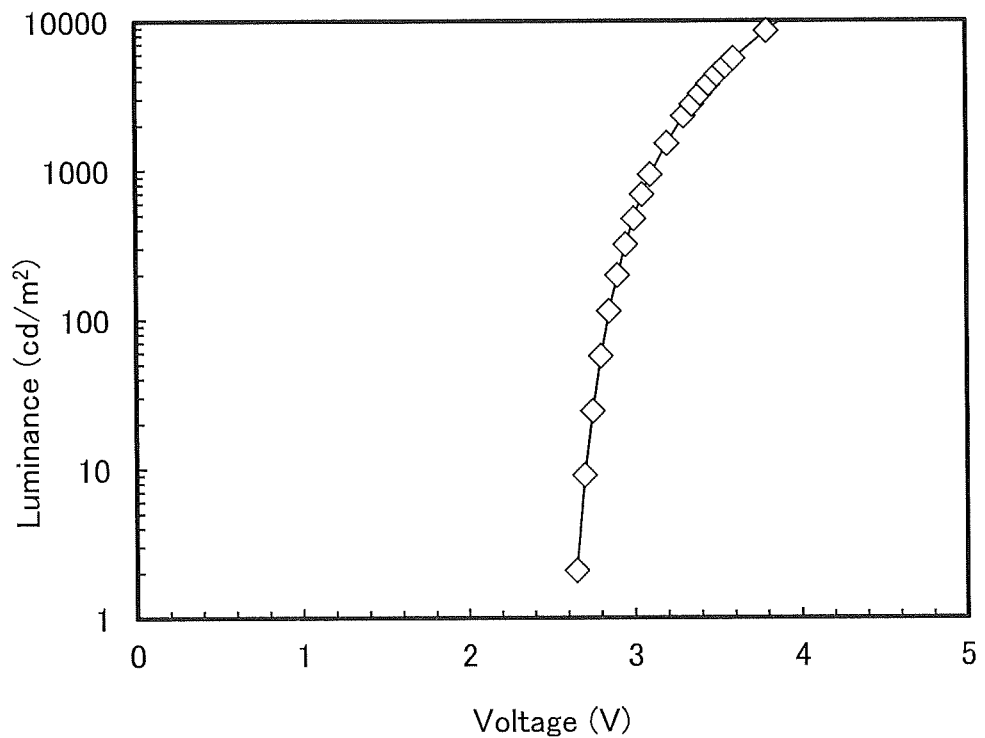
[FIG. 117]
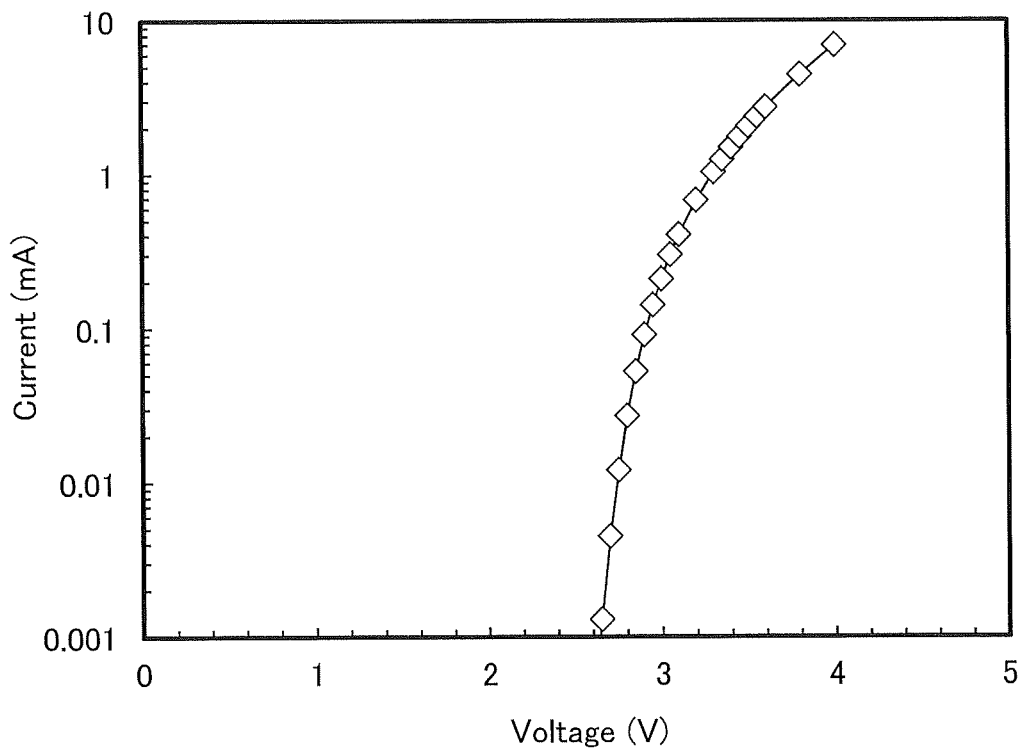

[FIG. 118]
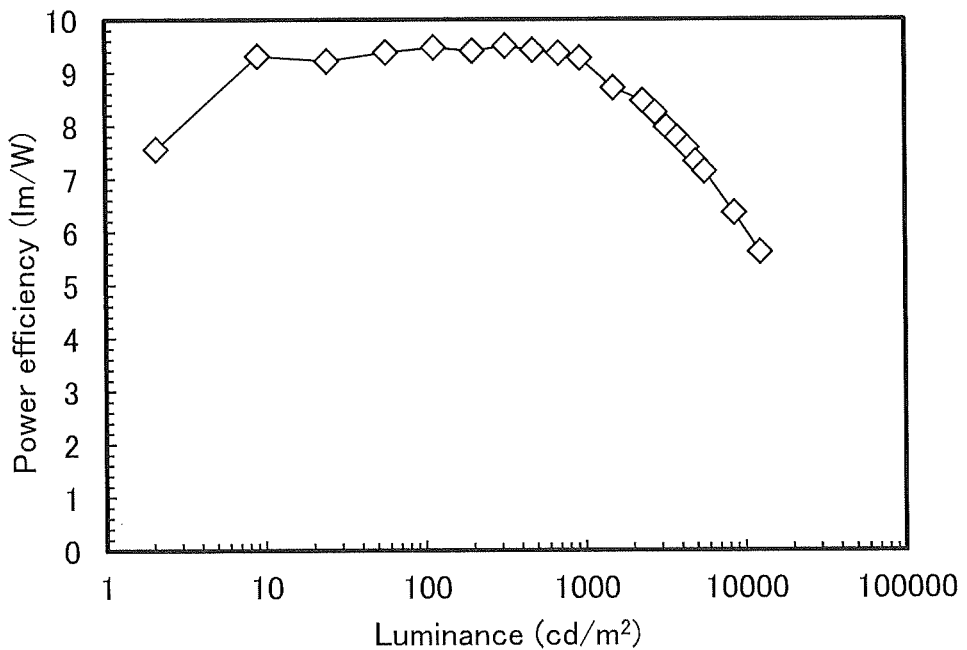
[FIG. 119]
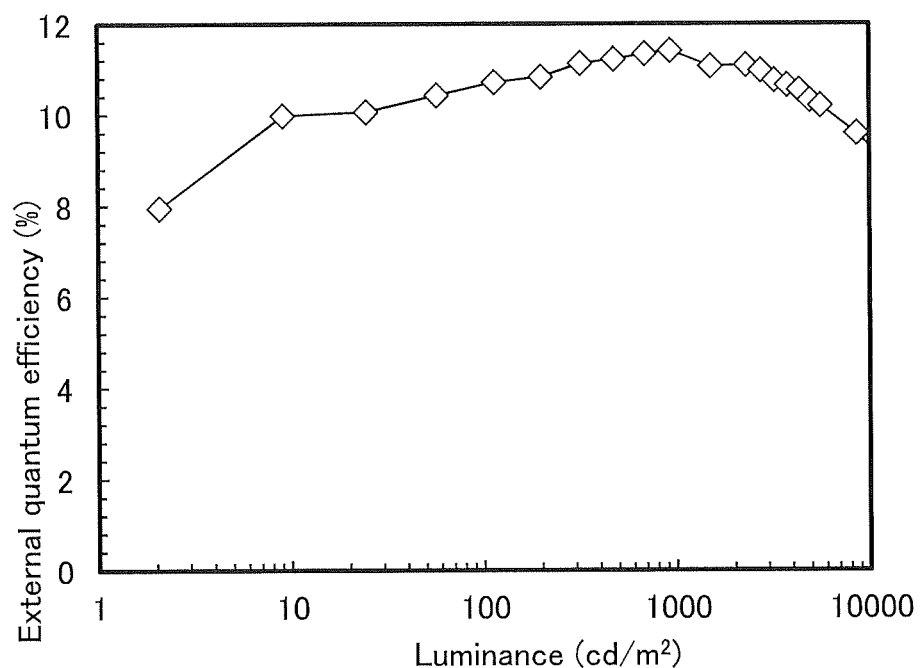

[FIG. 120]
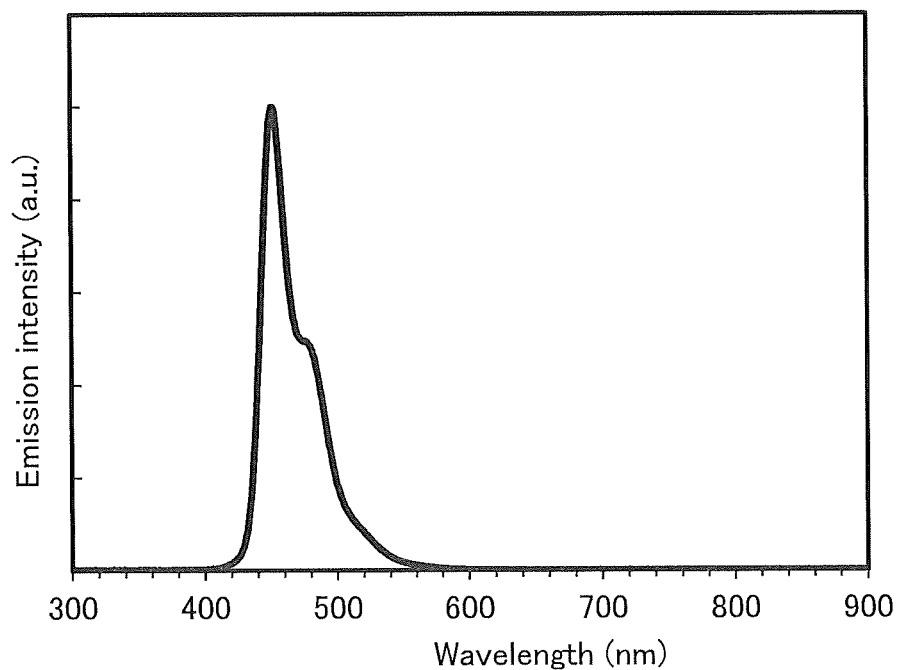
[FIG. 121]
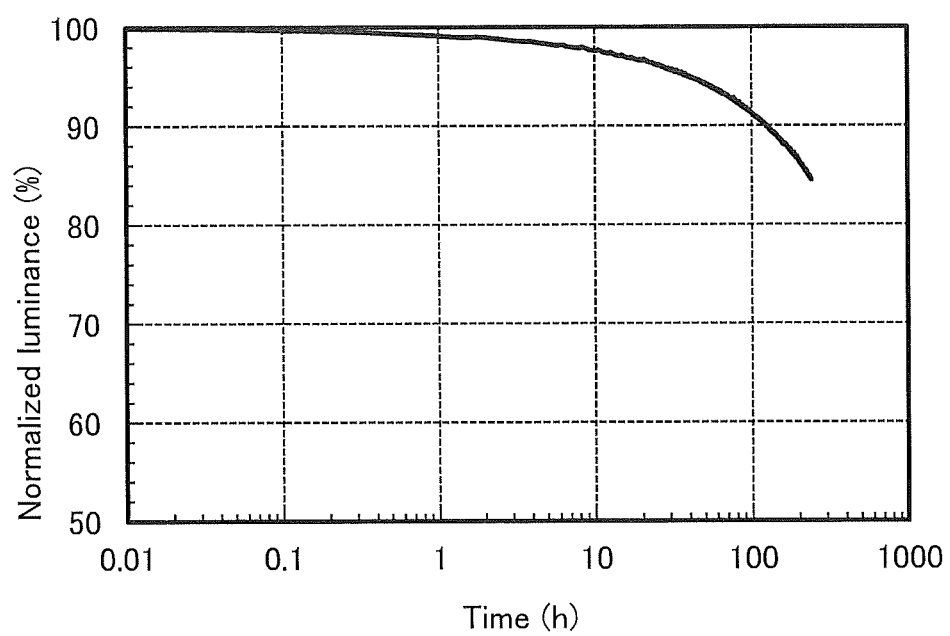

[FIG. 122]
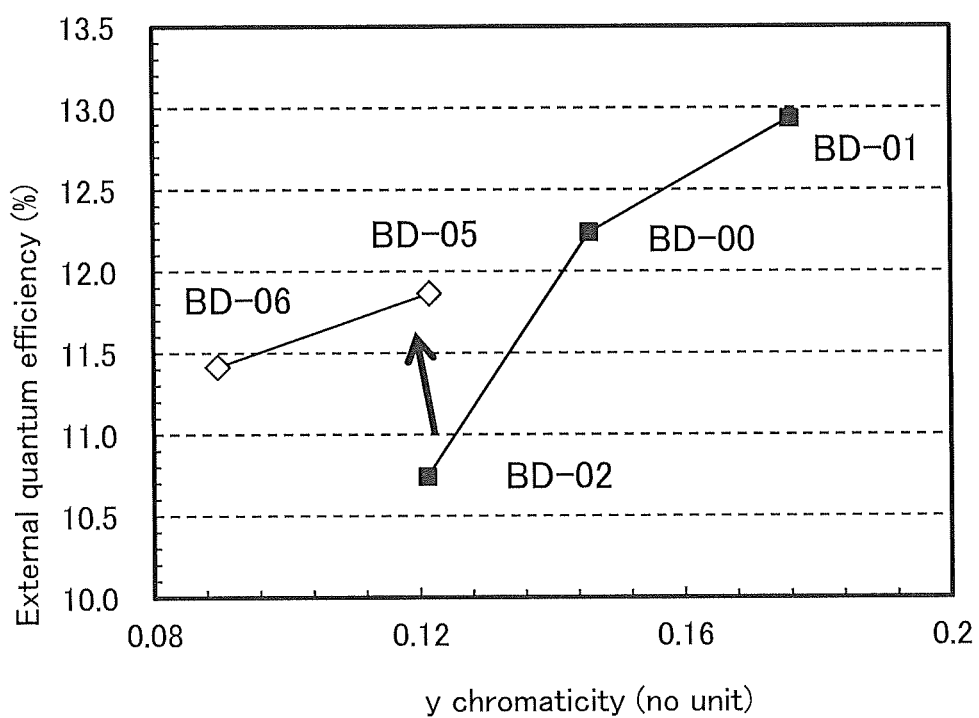

[FIG. 123]
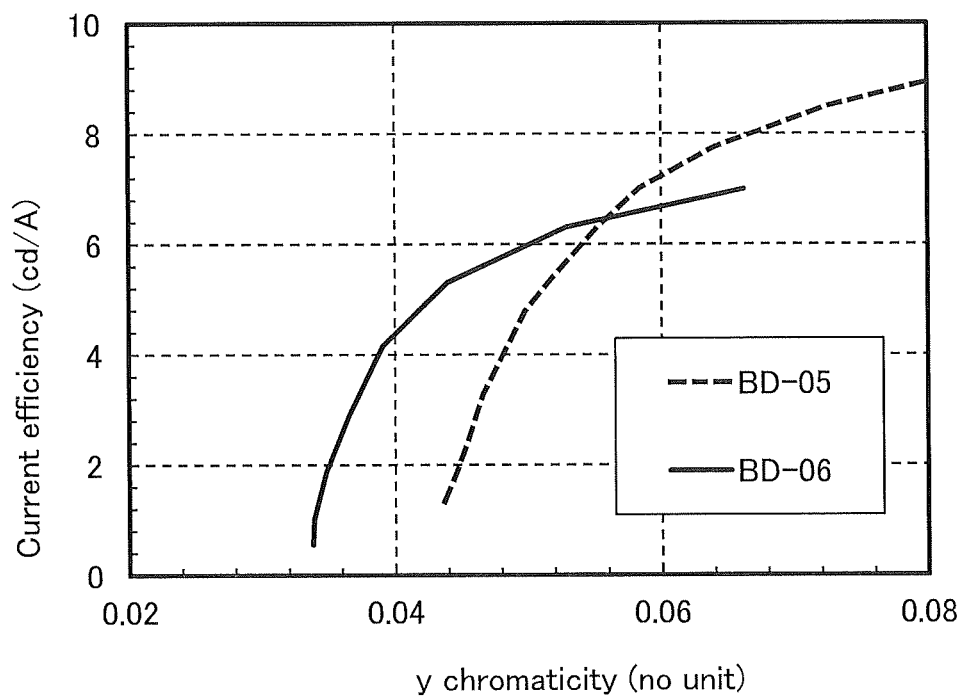

[FIG. 124]
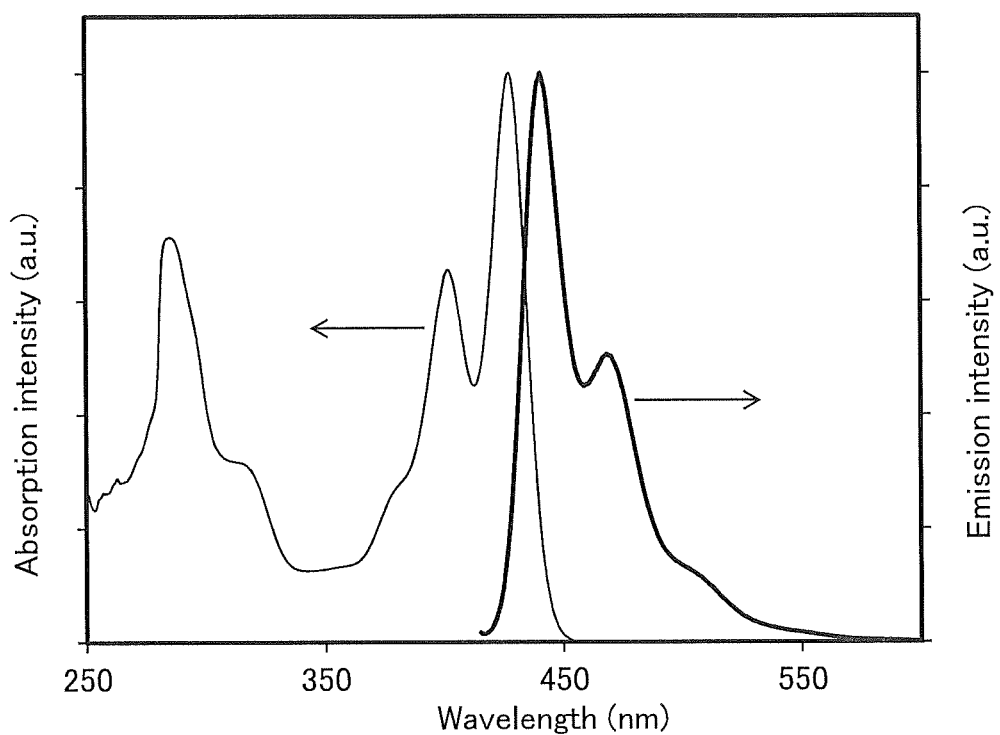

[FIG. 125]
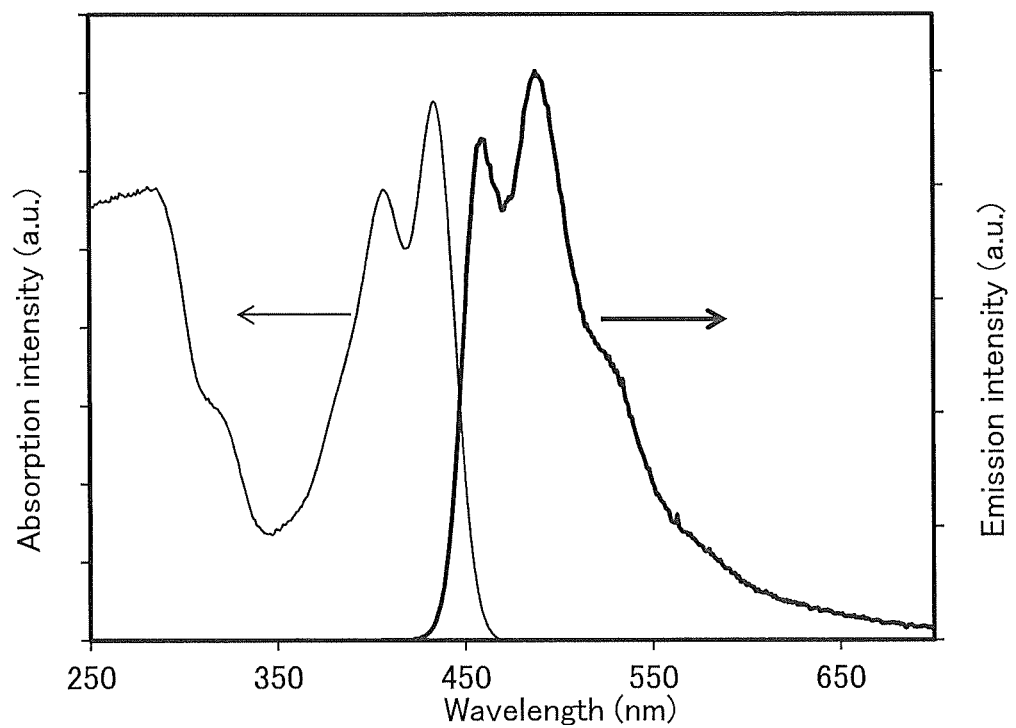

[FIG. 126]
(A)
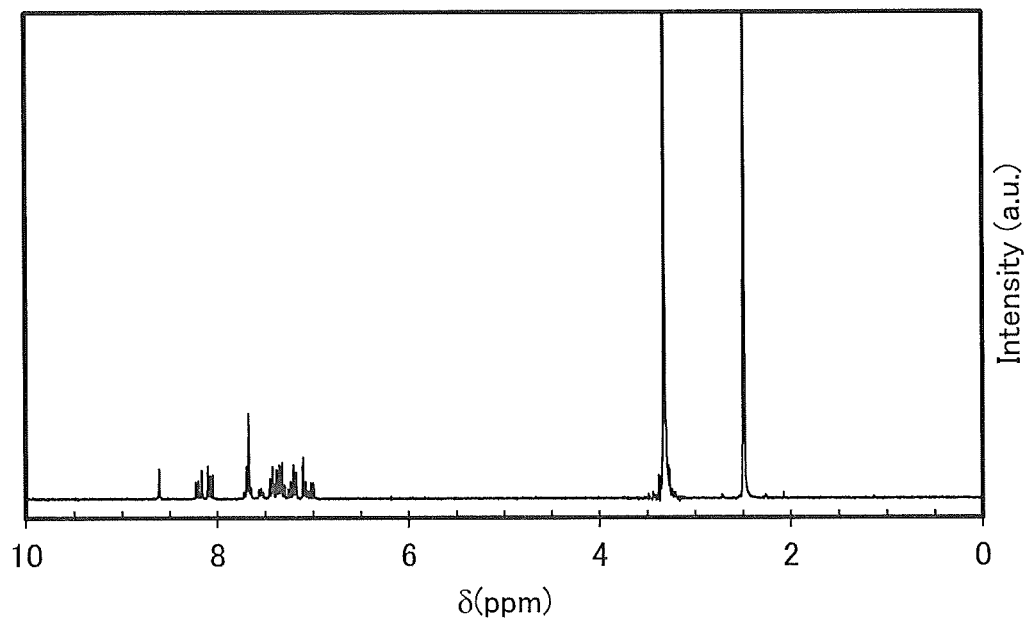
(B)
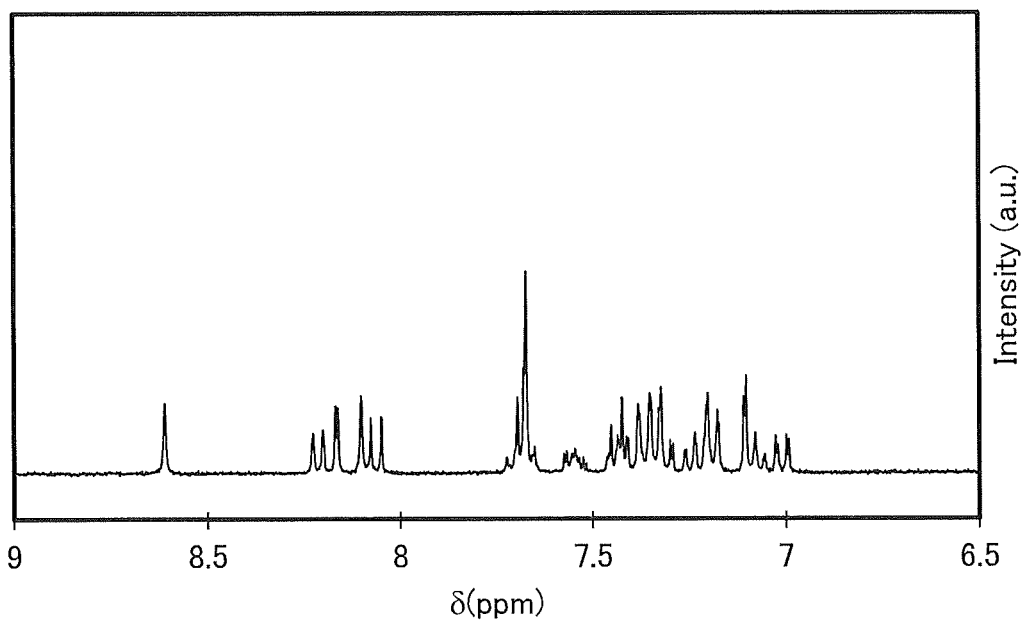

[FIG. 127]
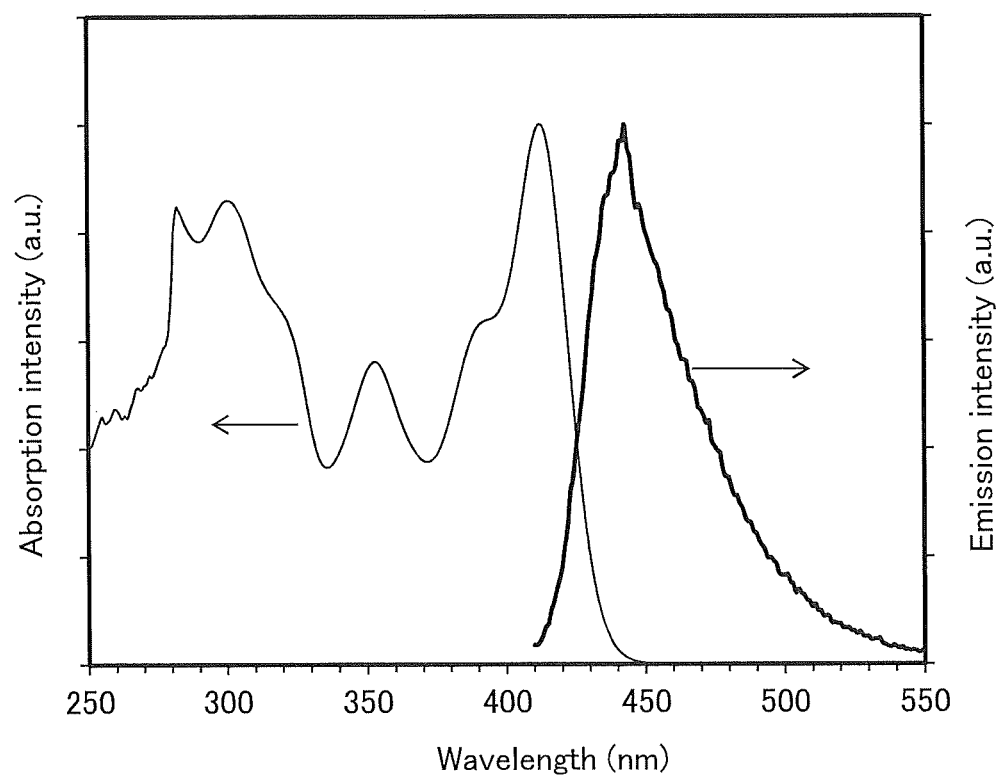

[FIG. 128]
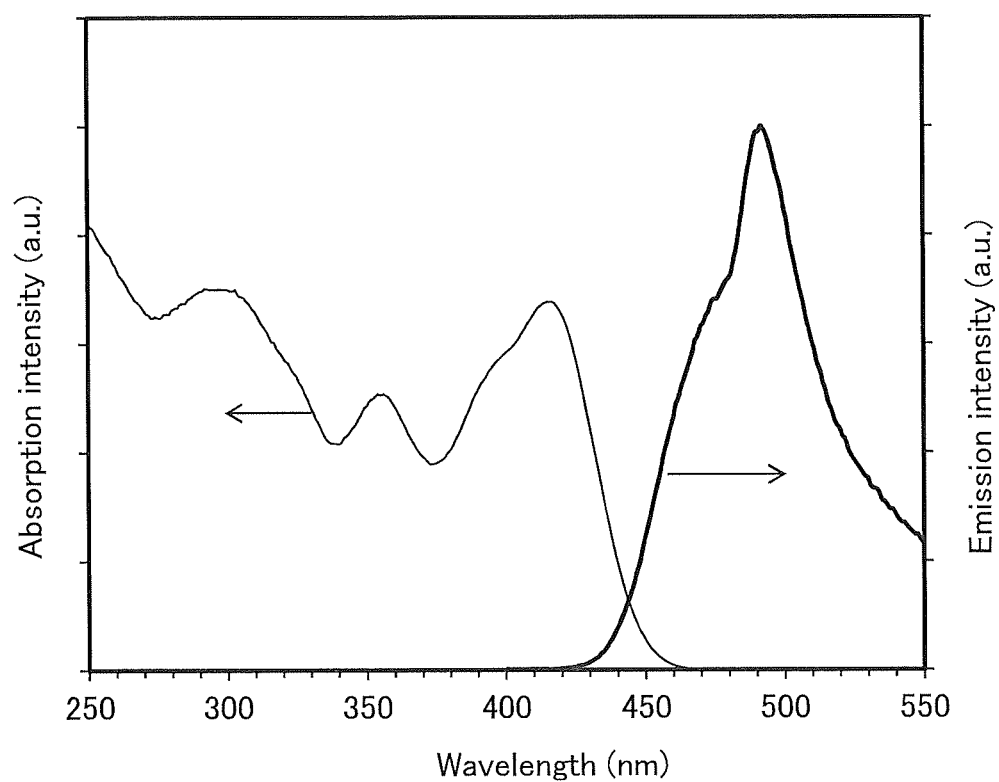

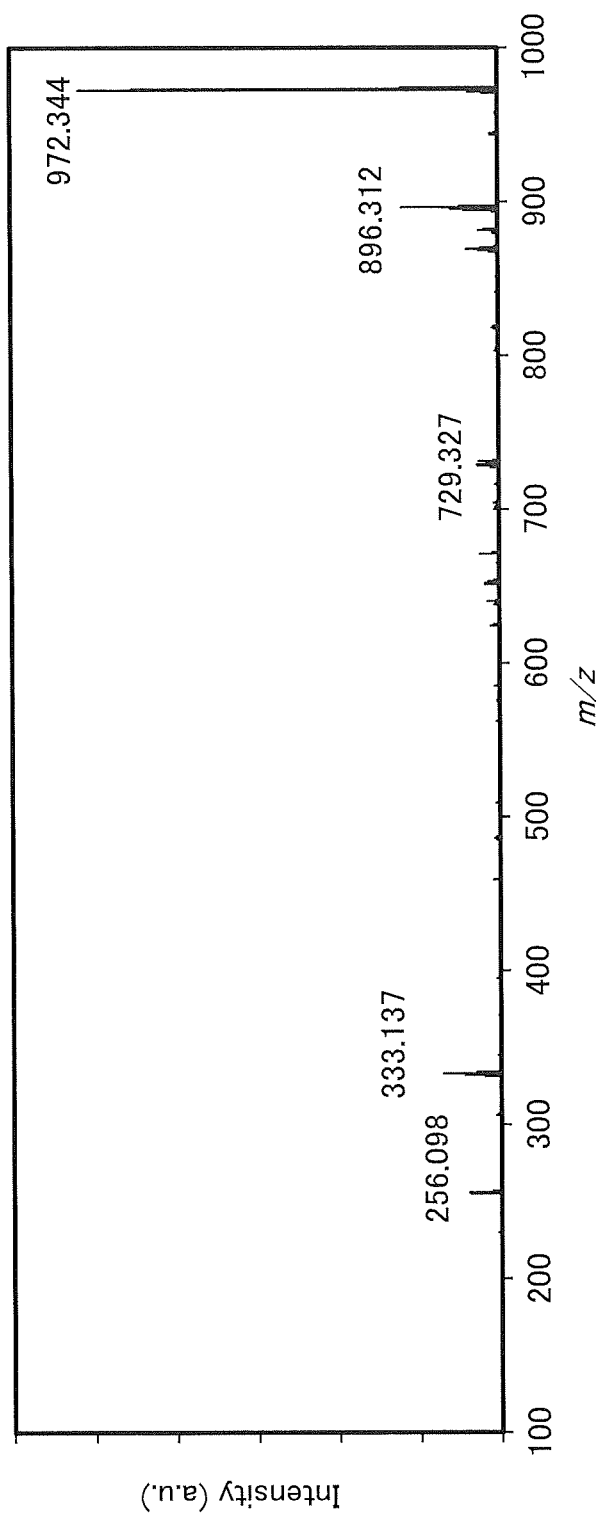
[FIG. 129]

[FIG. 130]
(A)
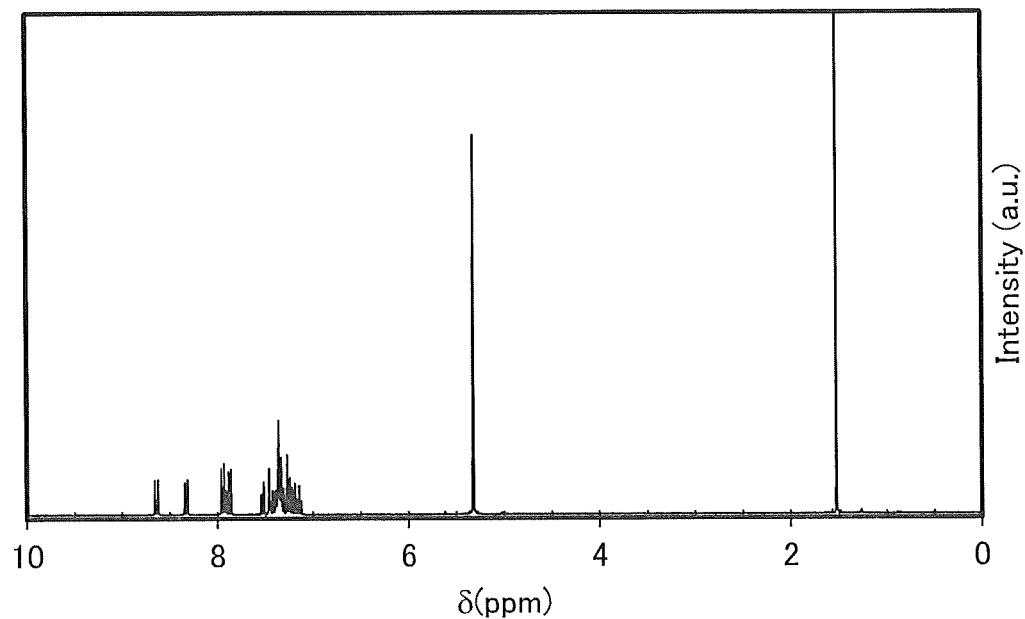
(B)
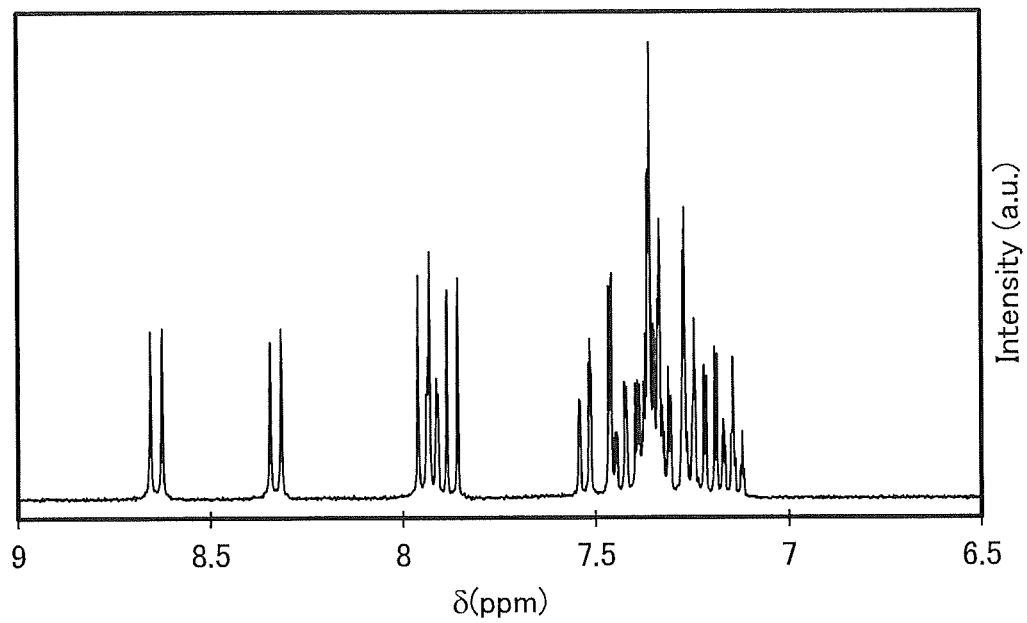

[FIG. 131]
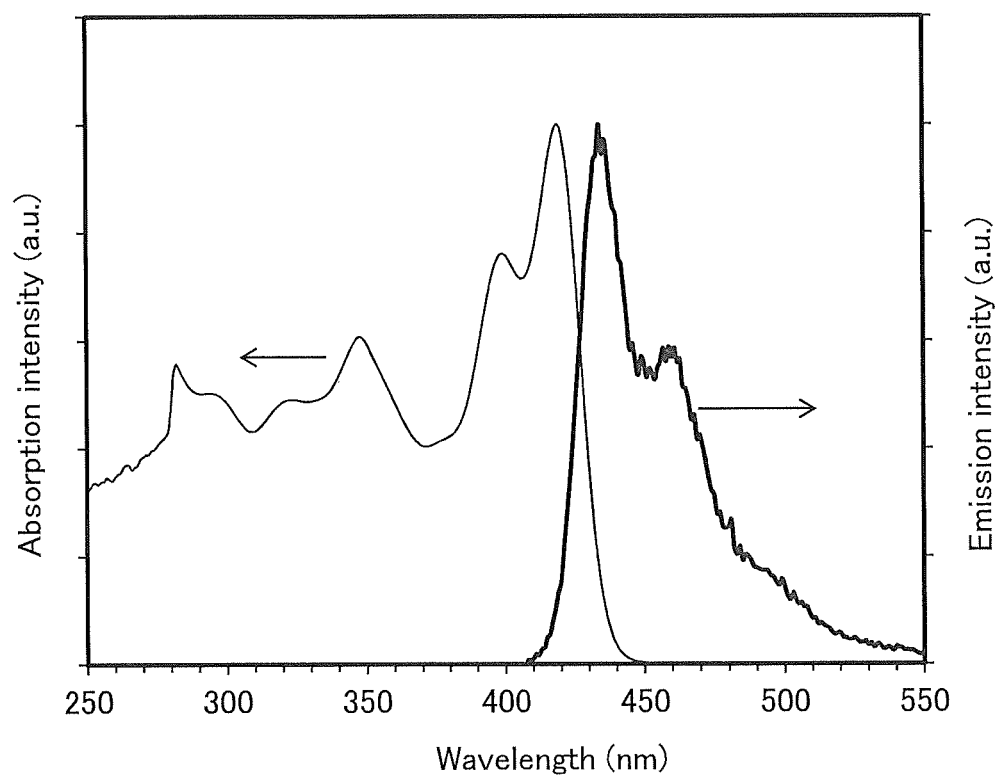

[FIG. 132]
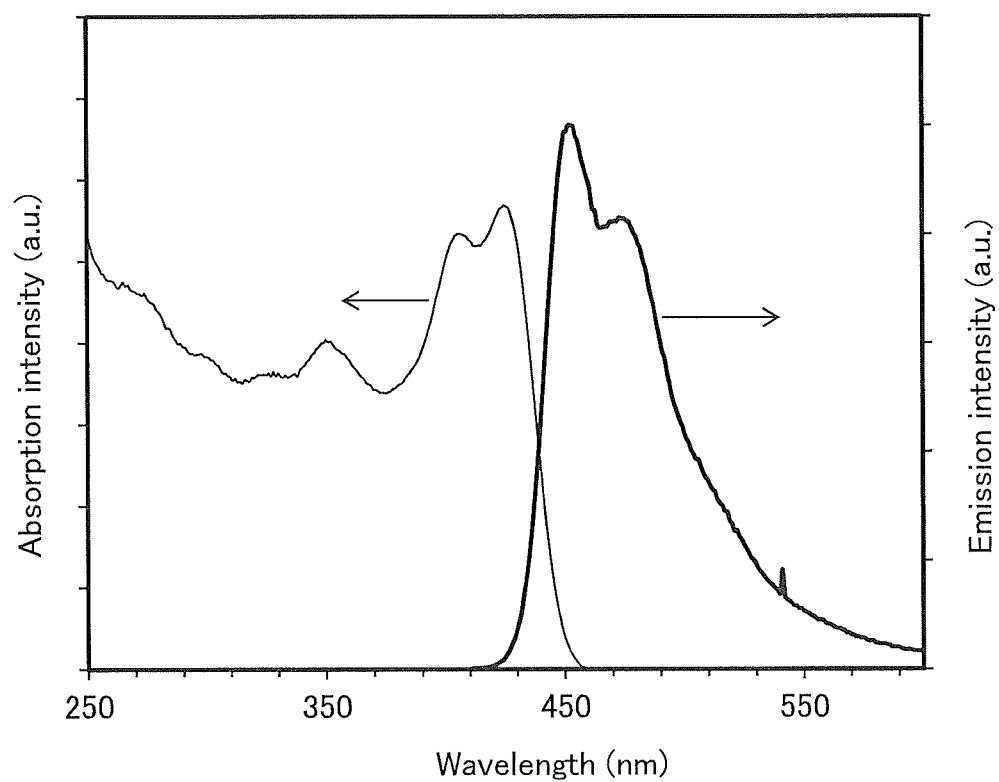

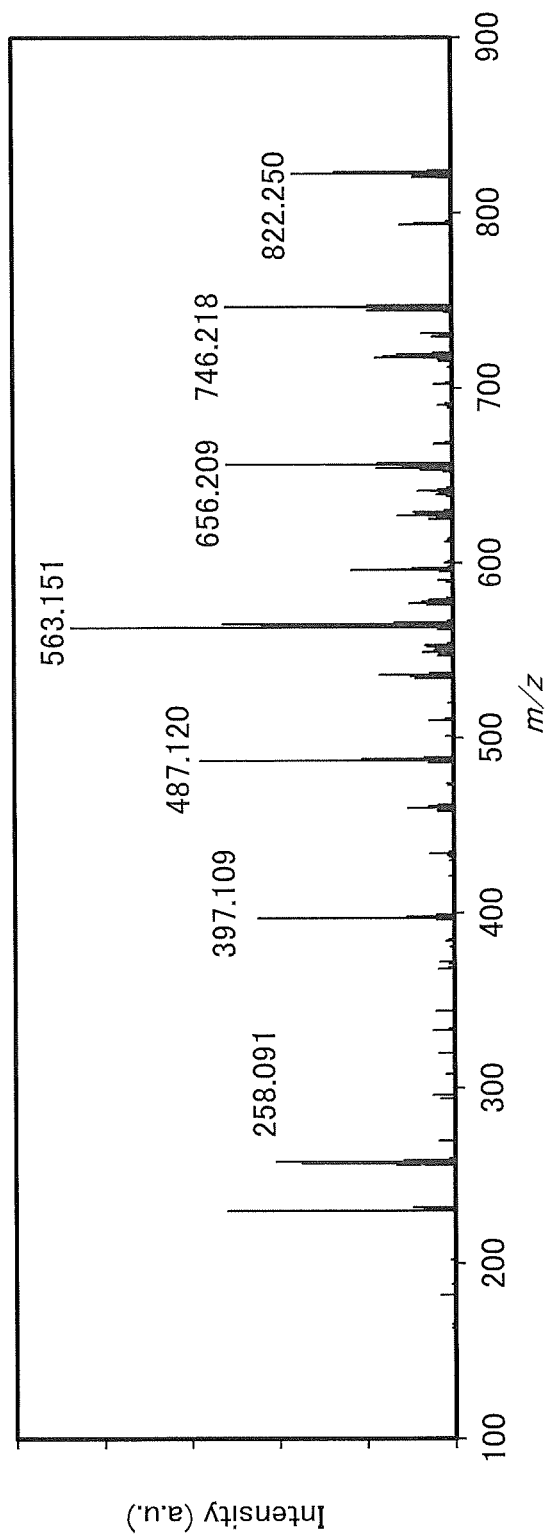
[FIG. 133]

[FIG. 134]
(A)
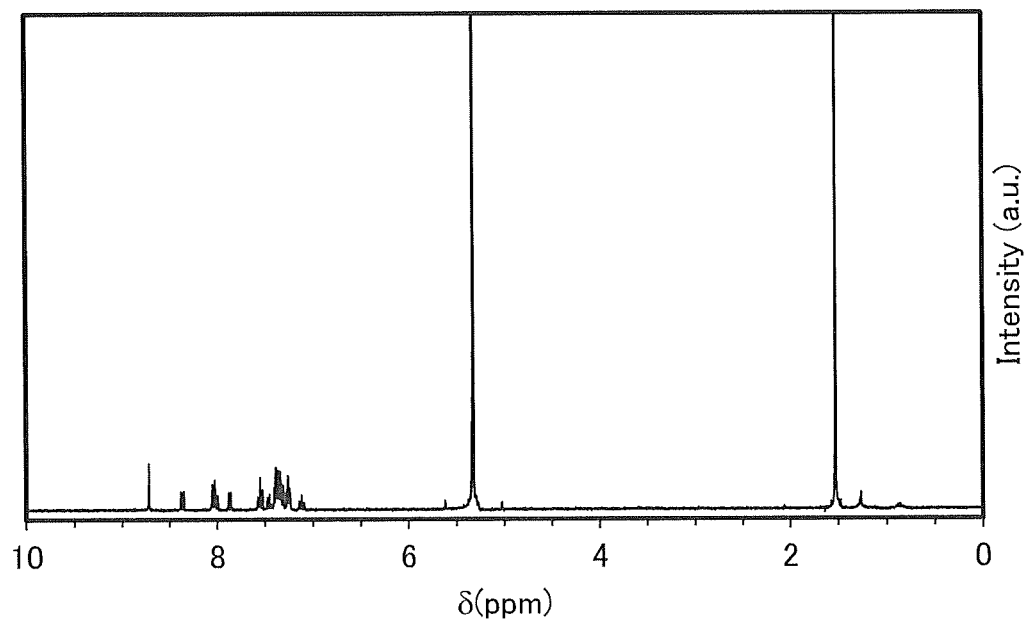
(B)
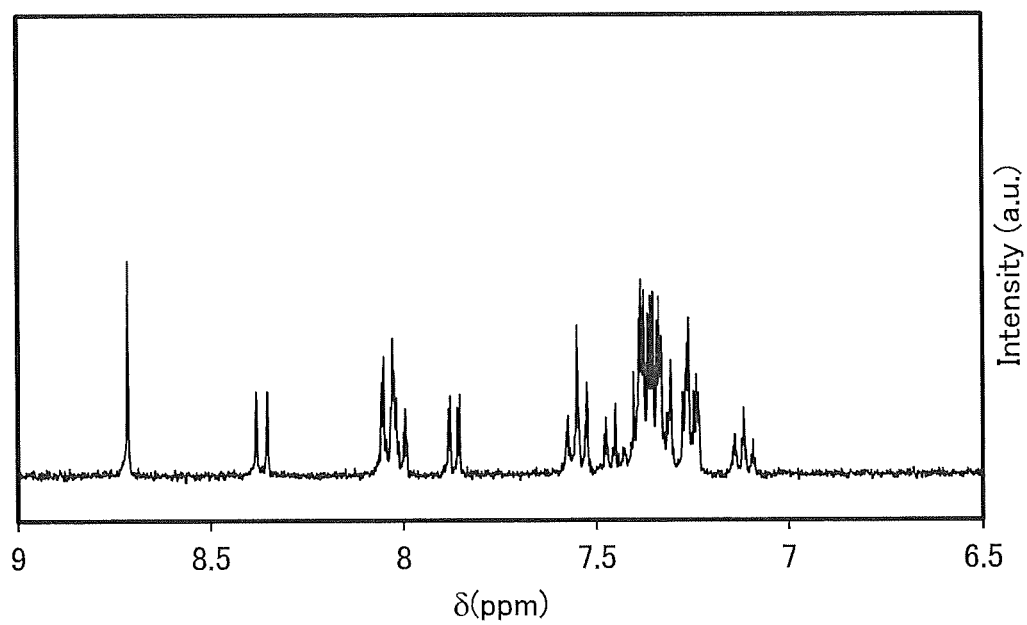

[FIG. 135]
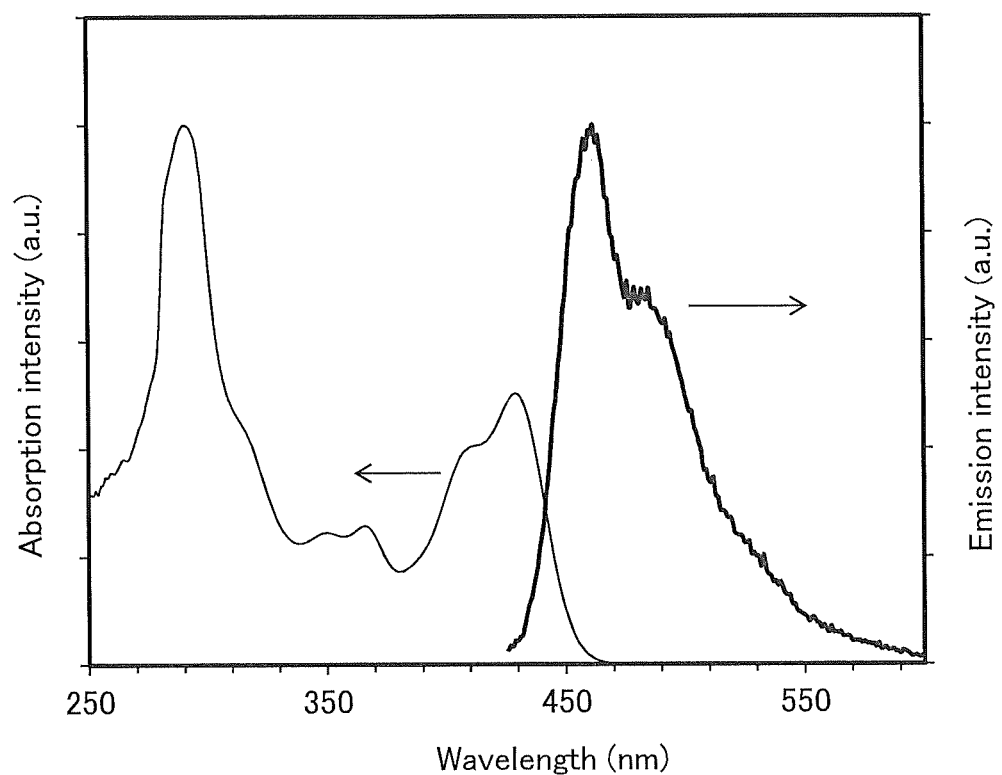

[FIG. 136]
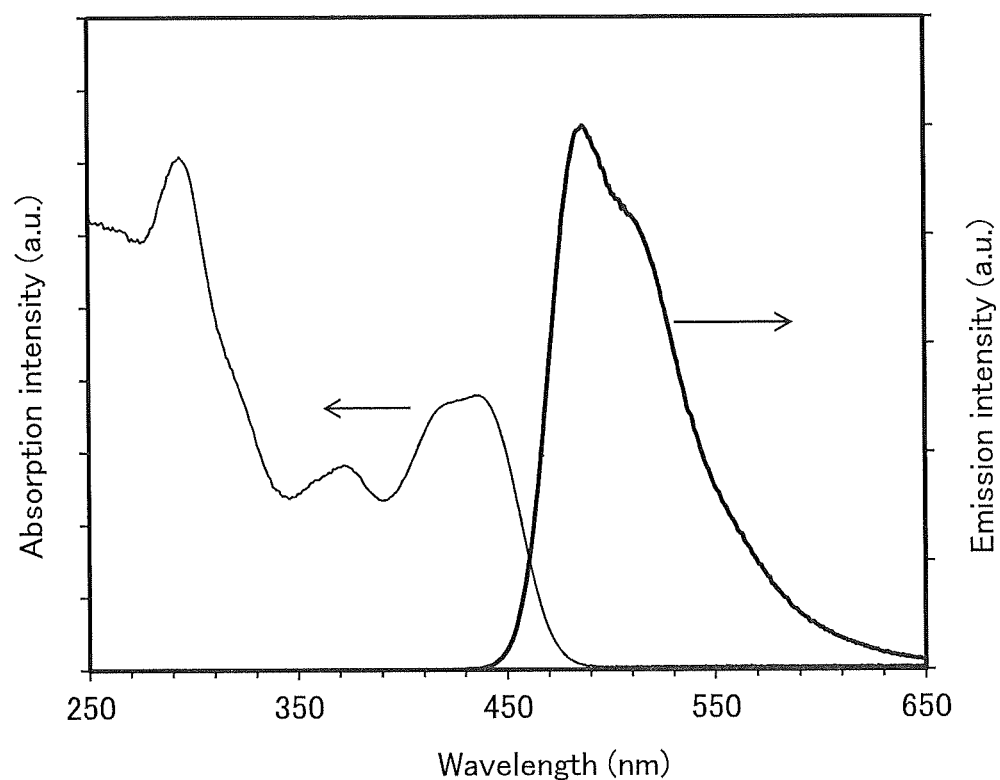

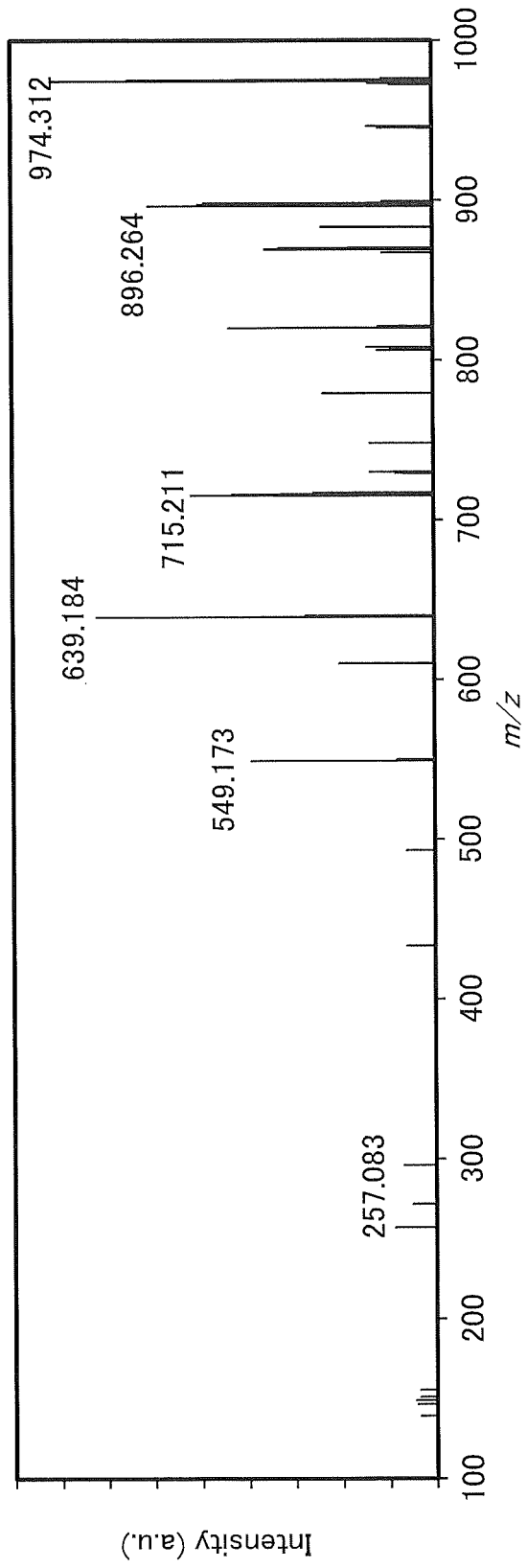
[FIG. 137]

[FIG. 138]
(A)
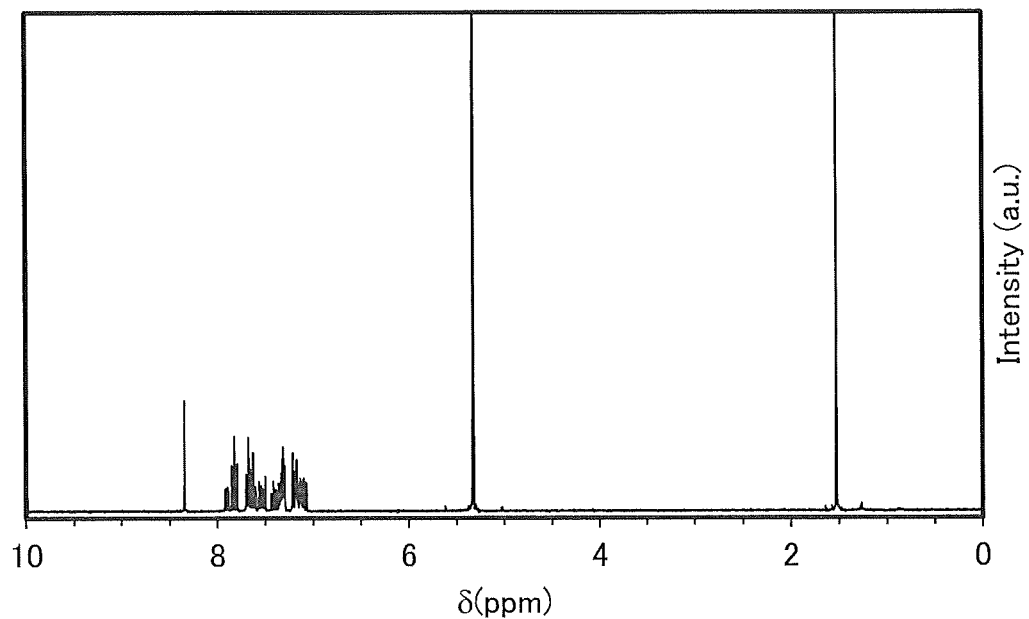
(B)
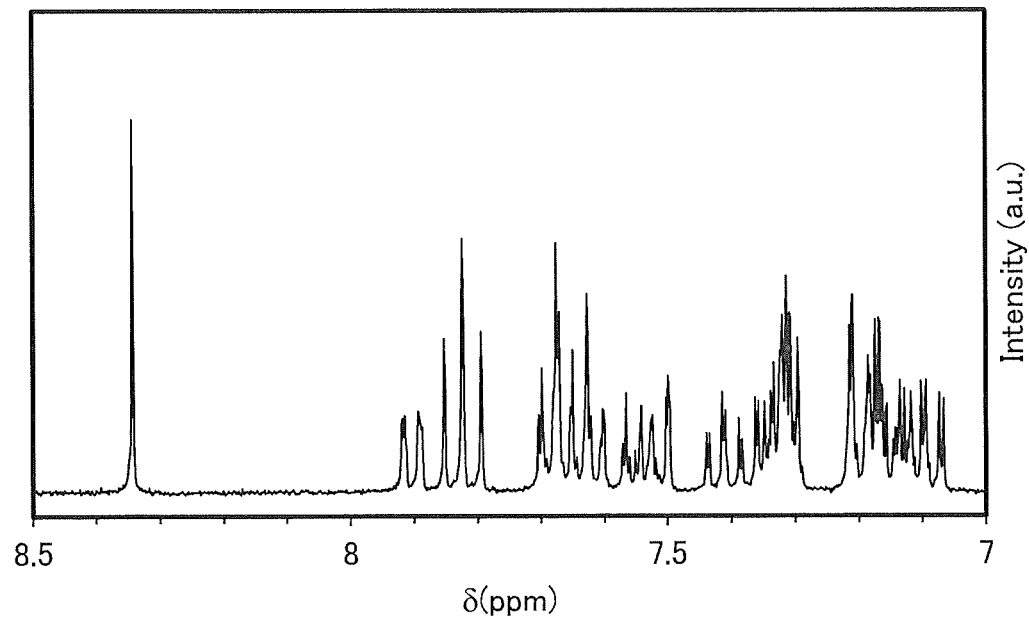

[FIG. 139]
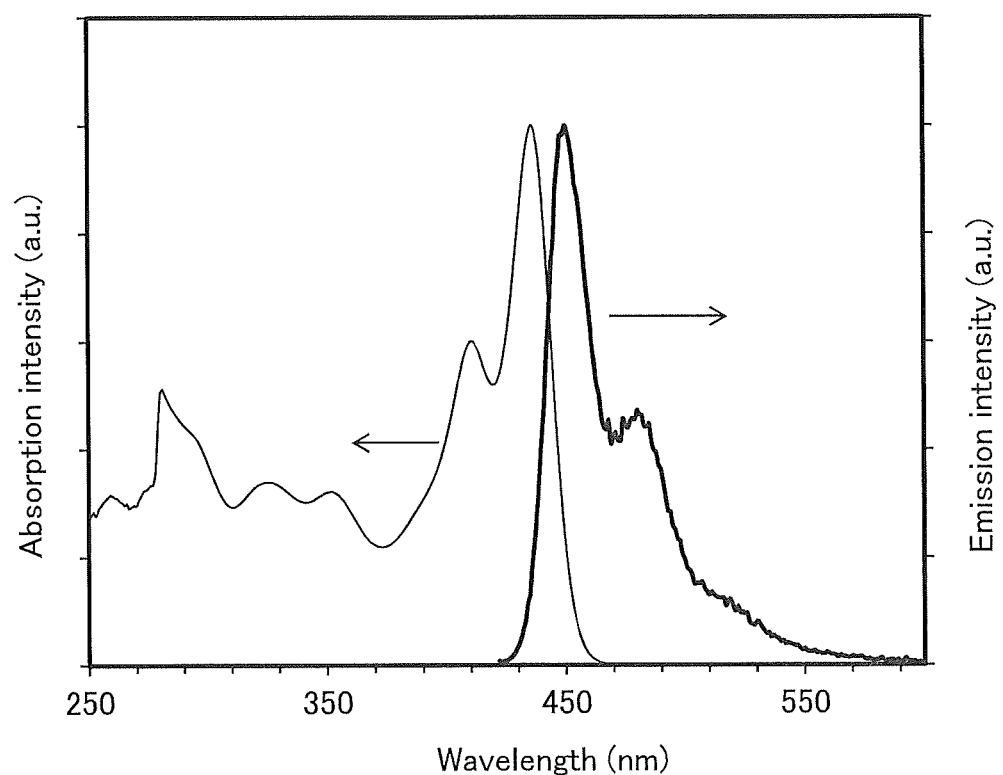

[FIG. 140]
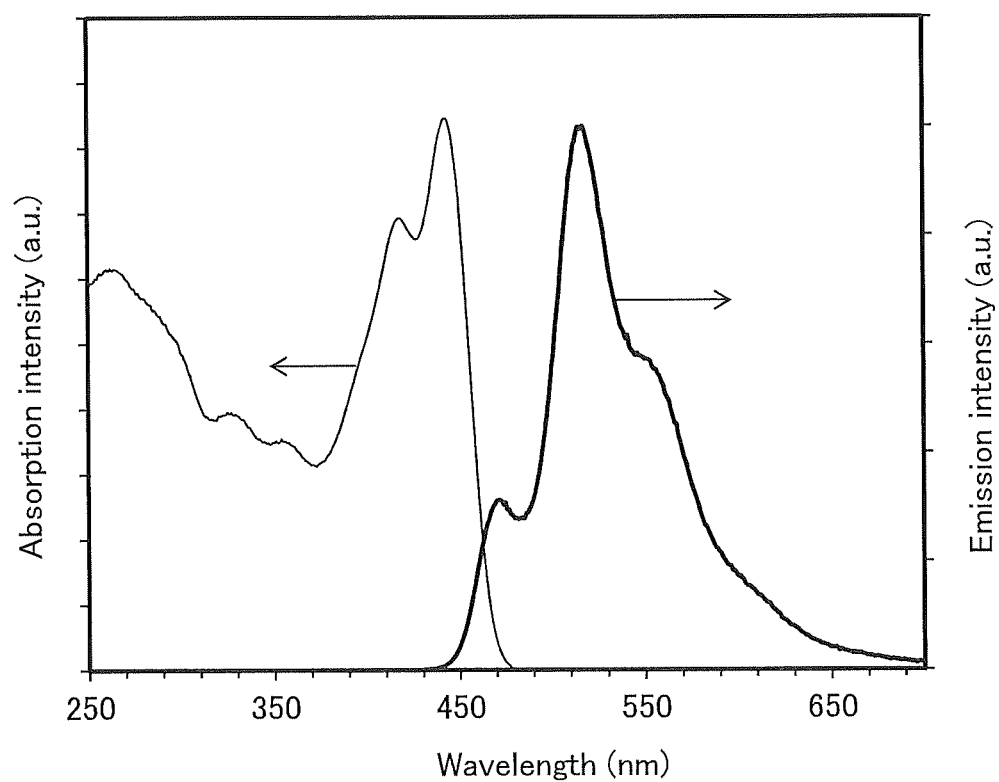

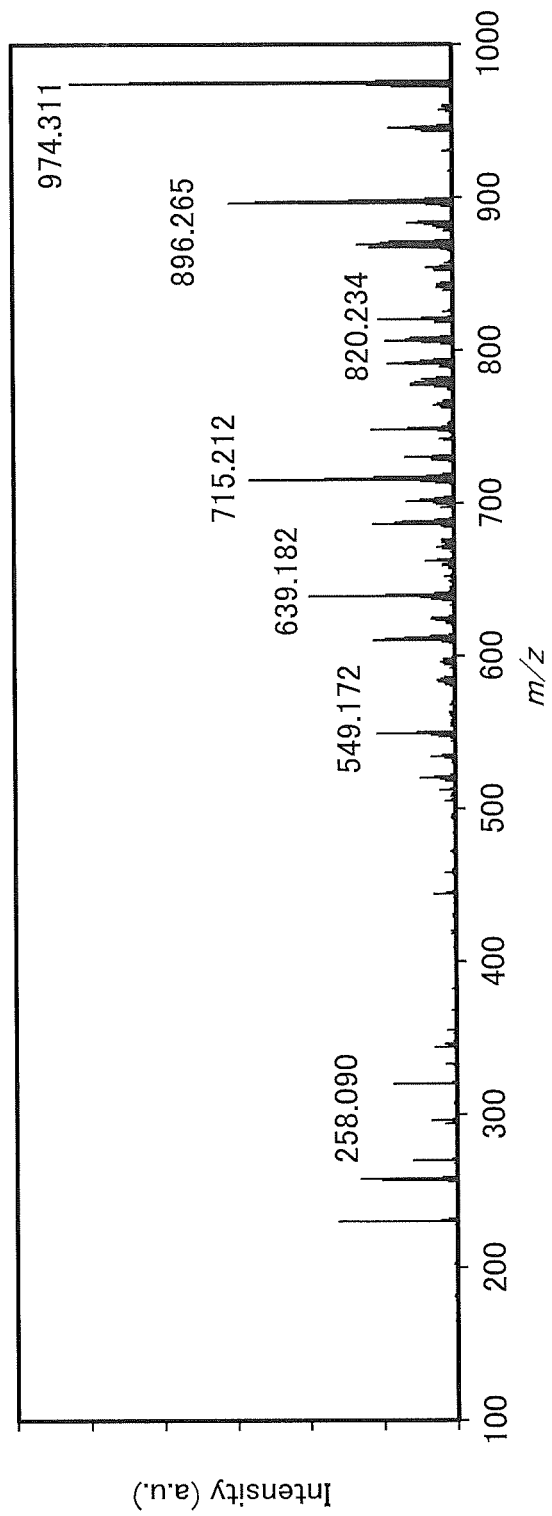
[FIG. 141]

[FIG. 142]
(A)
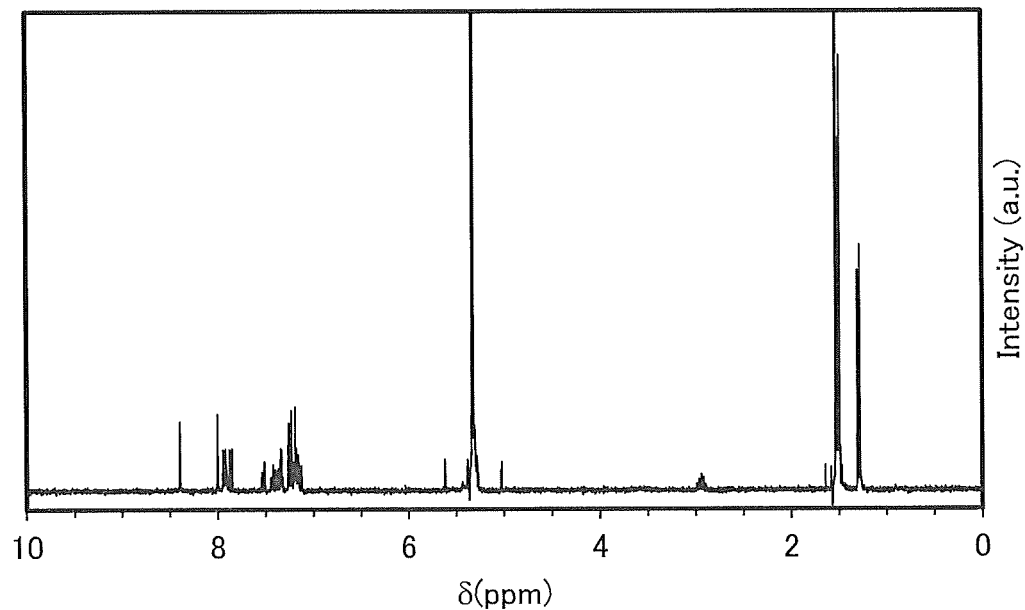
(B)
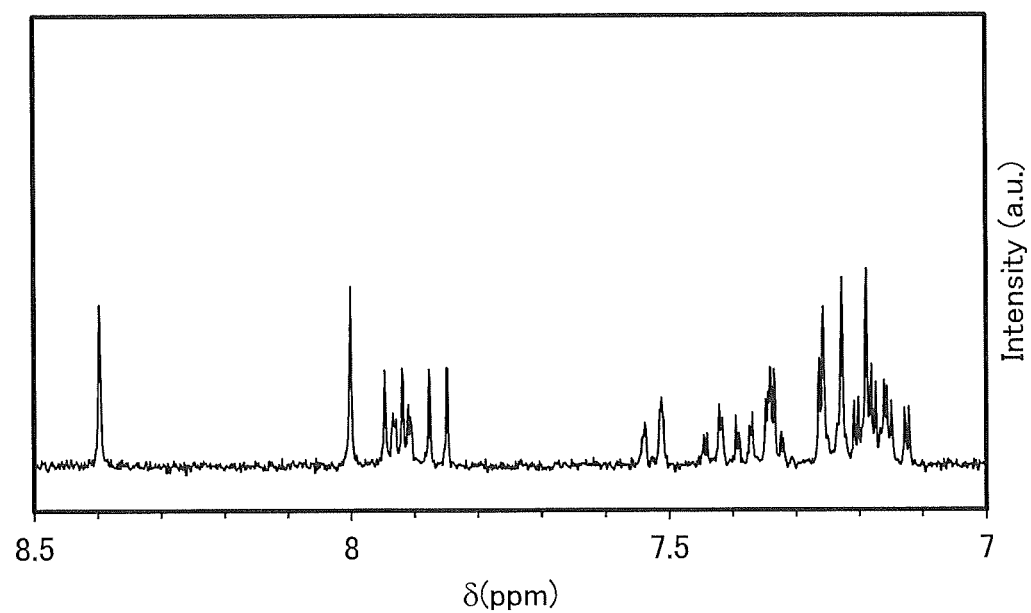

[FIG. 143]
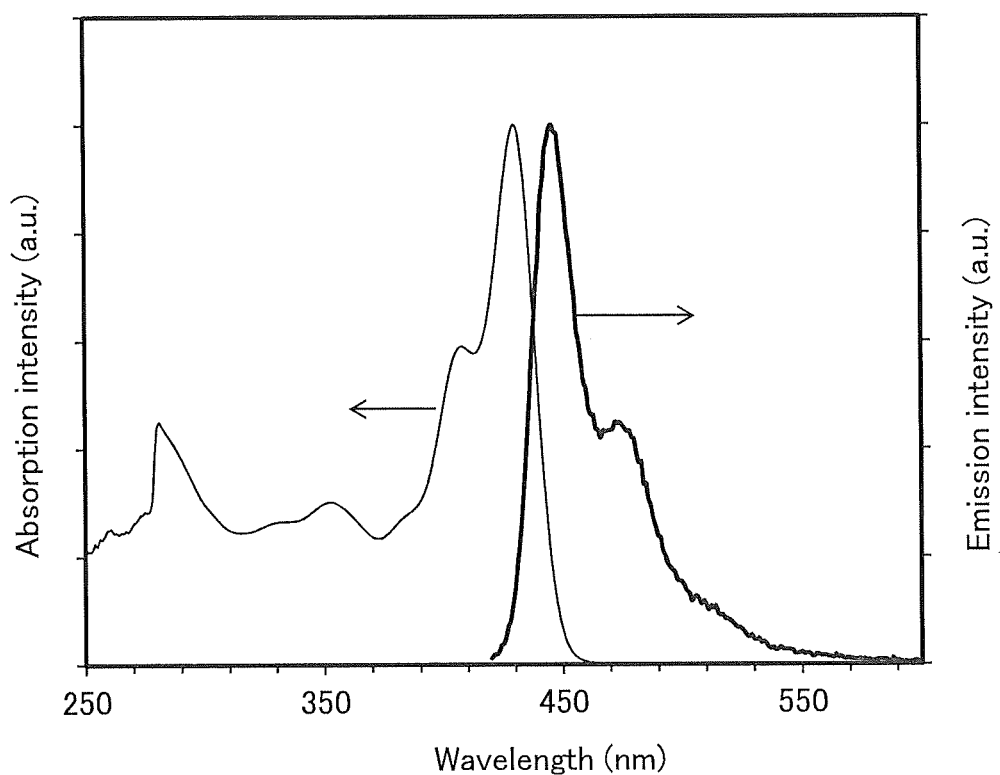

[FIG. 144]
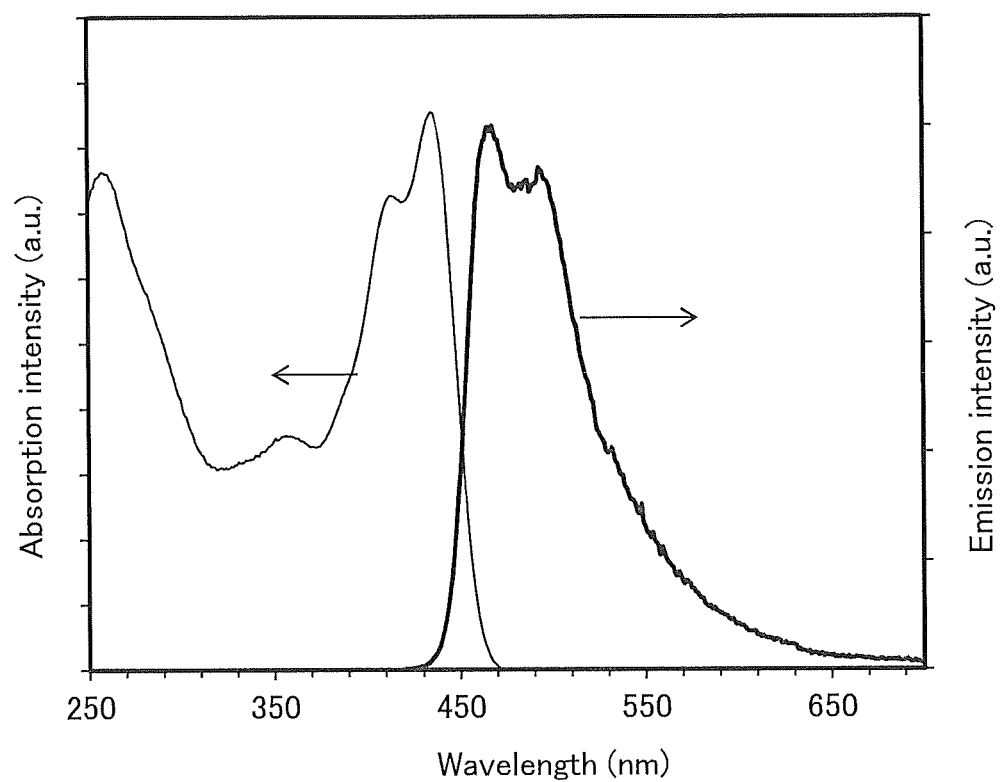

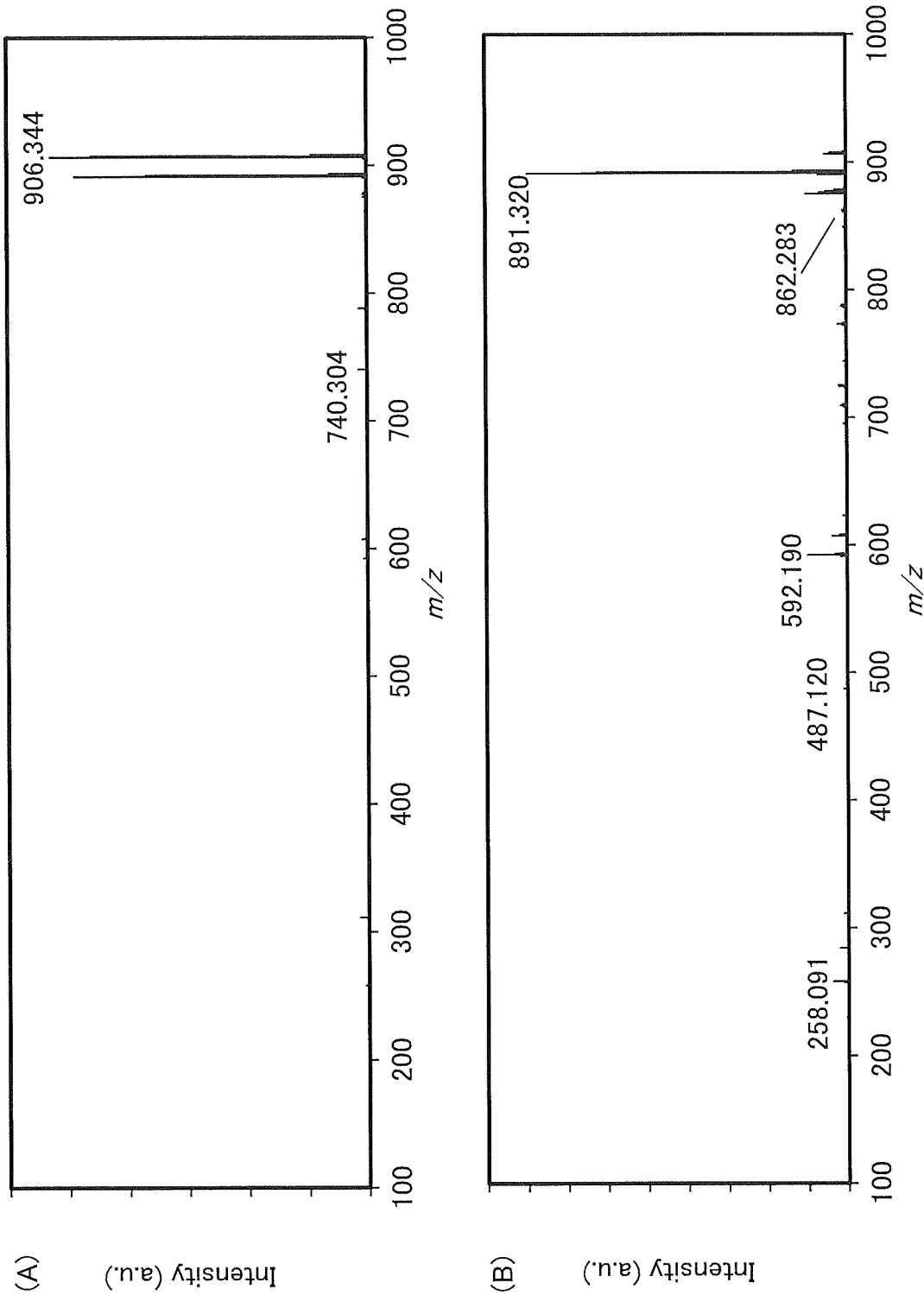
[FIG. 145]

[FIG. 146]
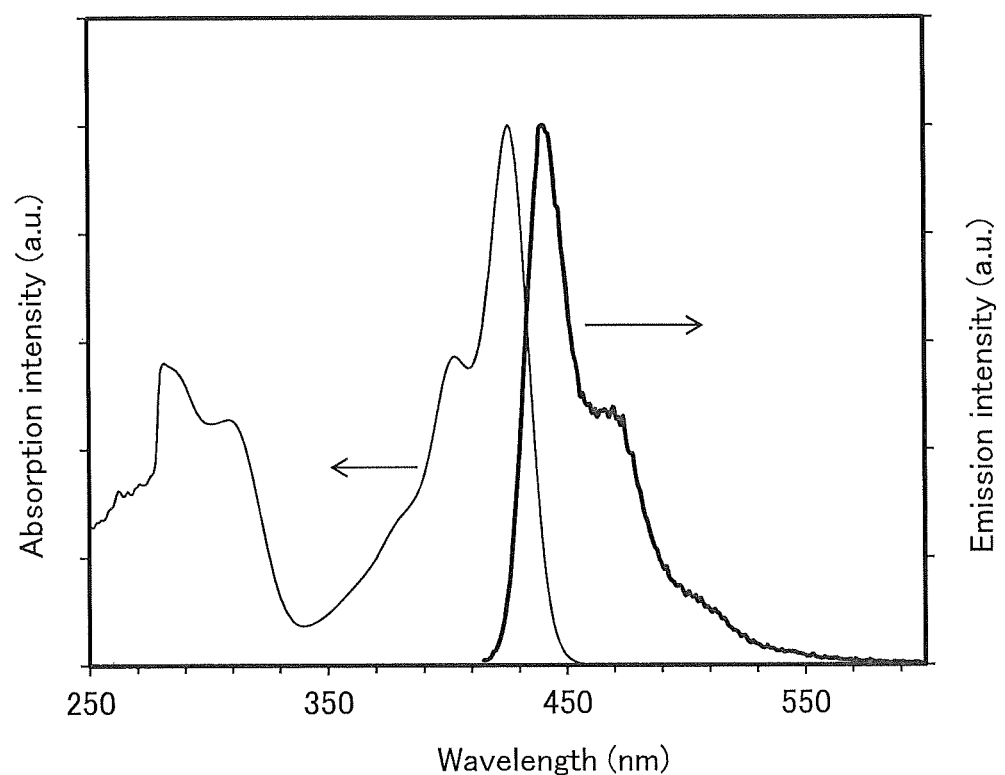

[FIG. 147]
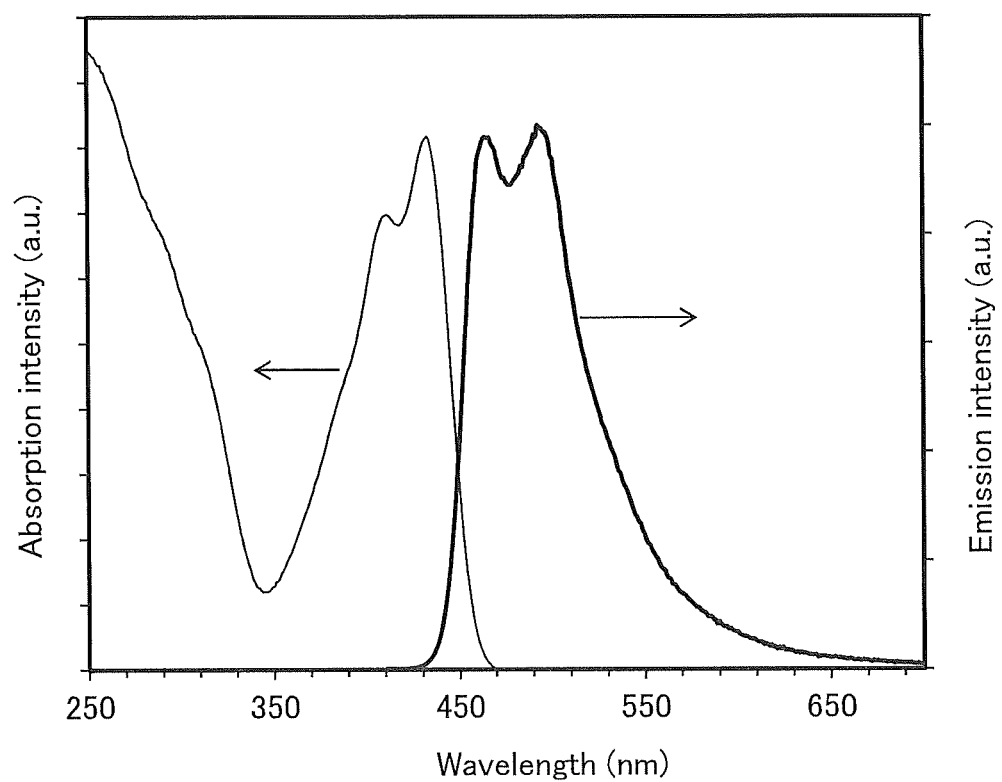

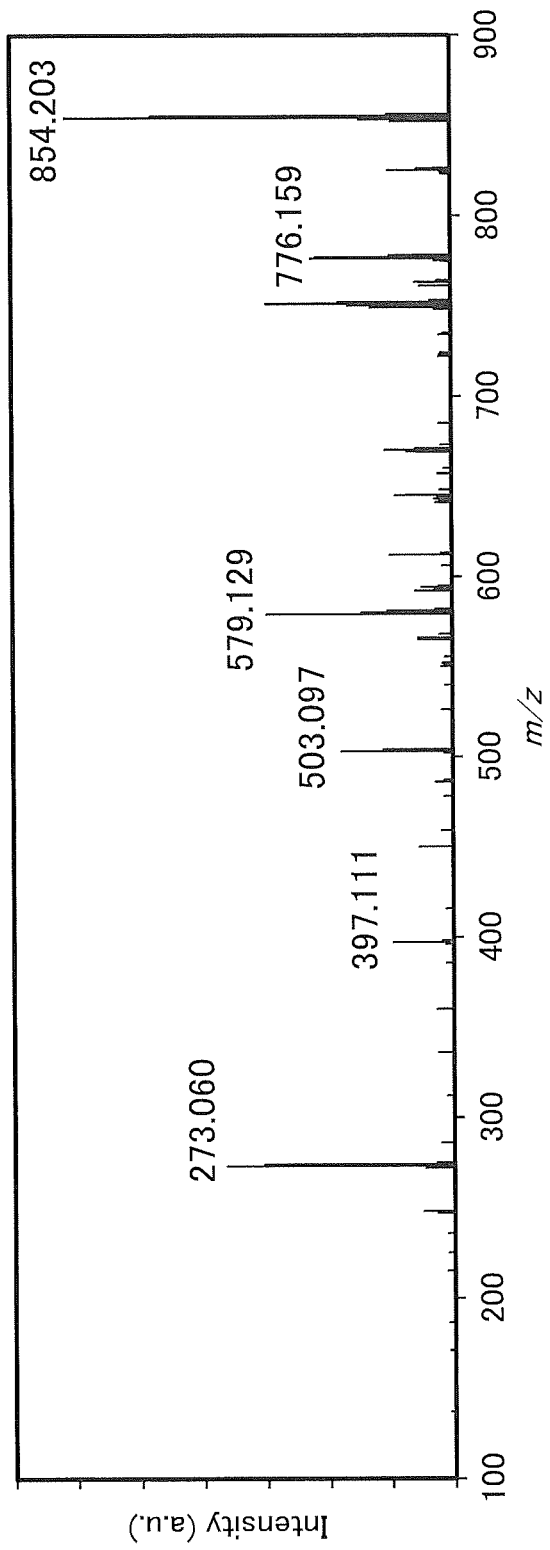
[FIG. 148]

[FIG. 149]
(A)
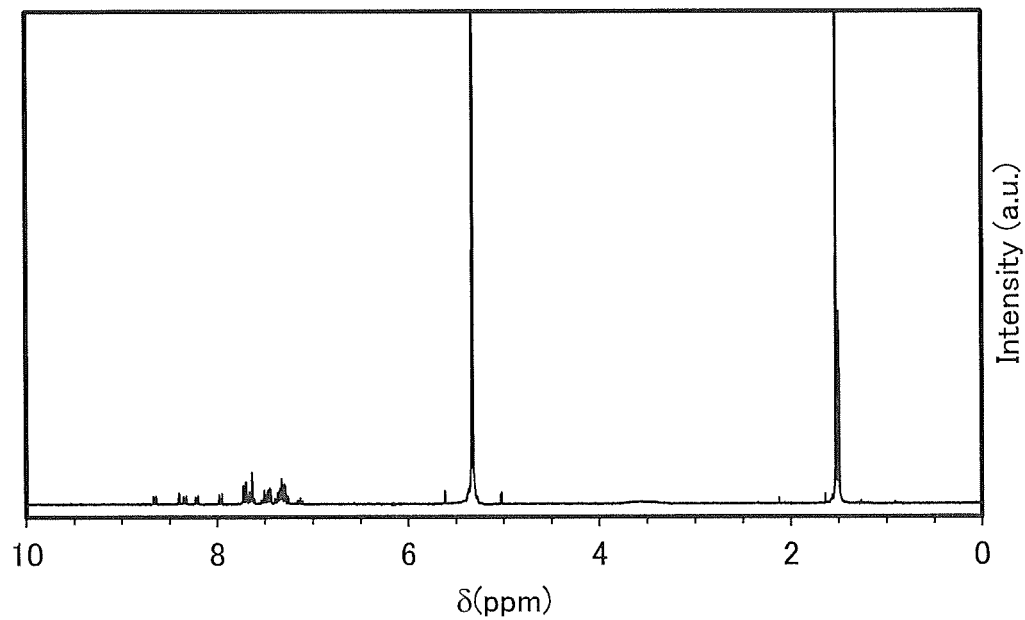
(B)
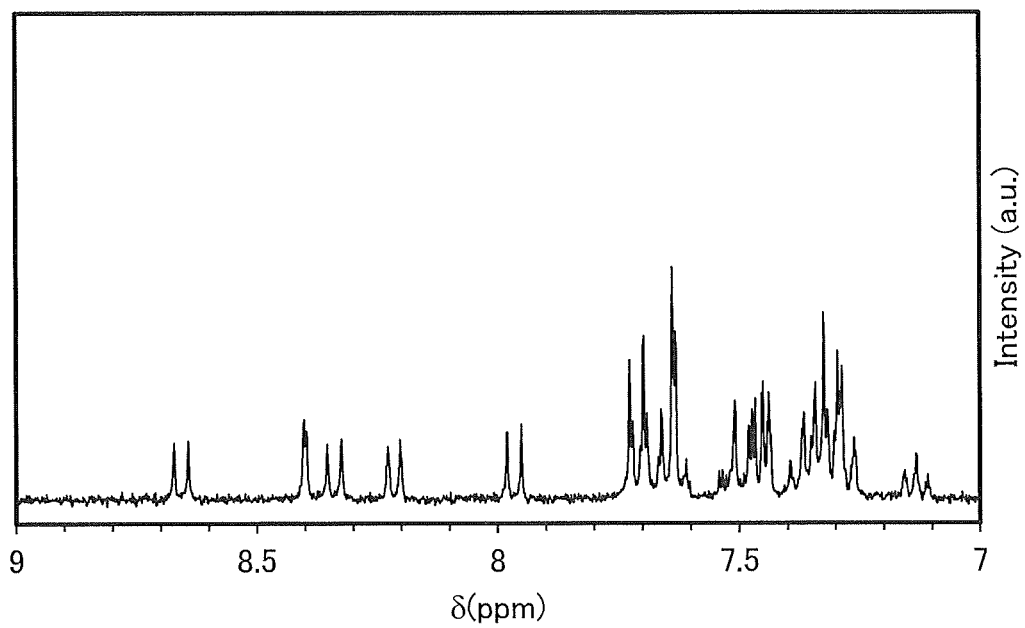

[FIG. 150]
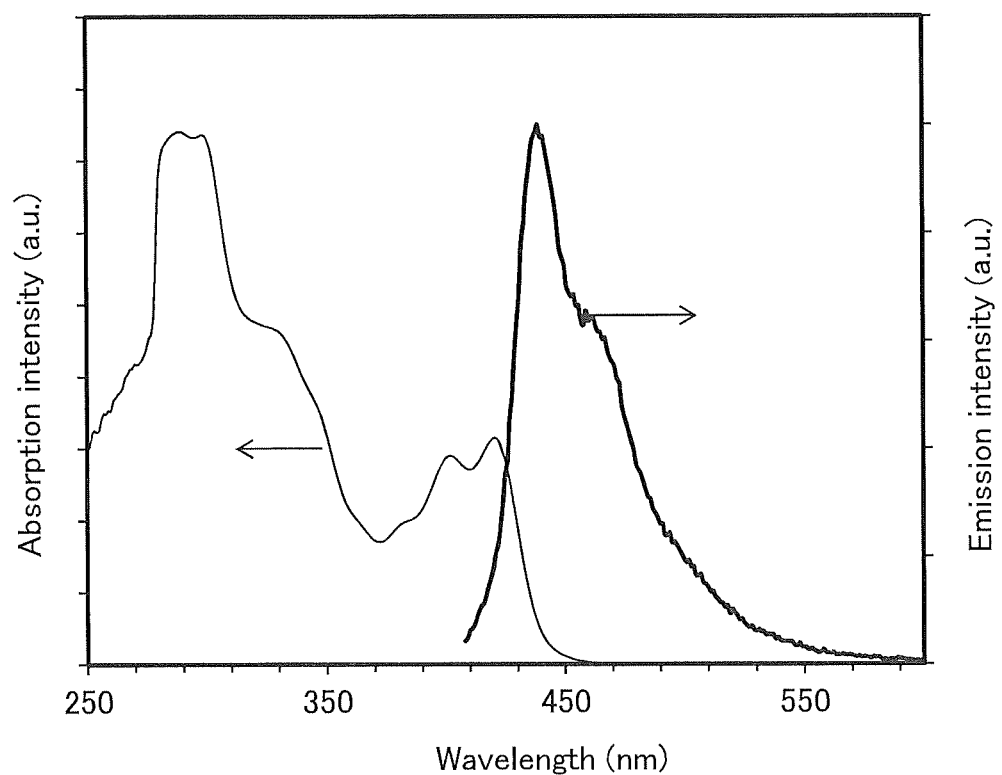

[FIG. 151]
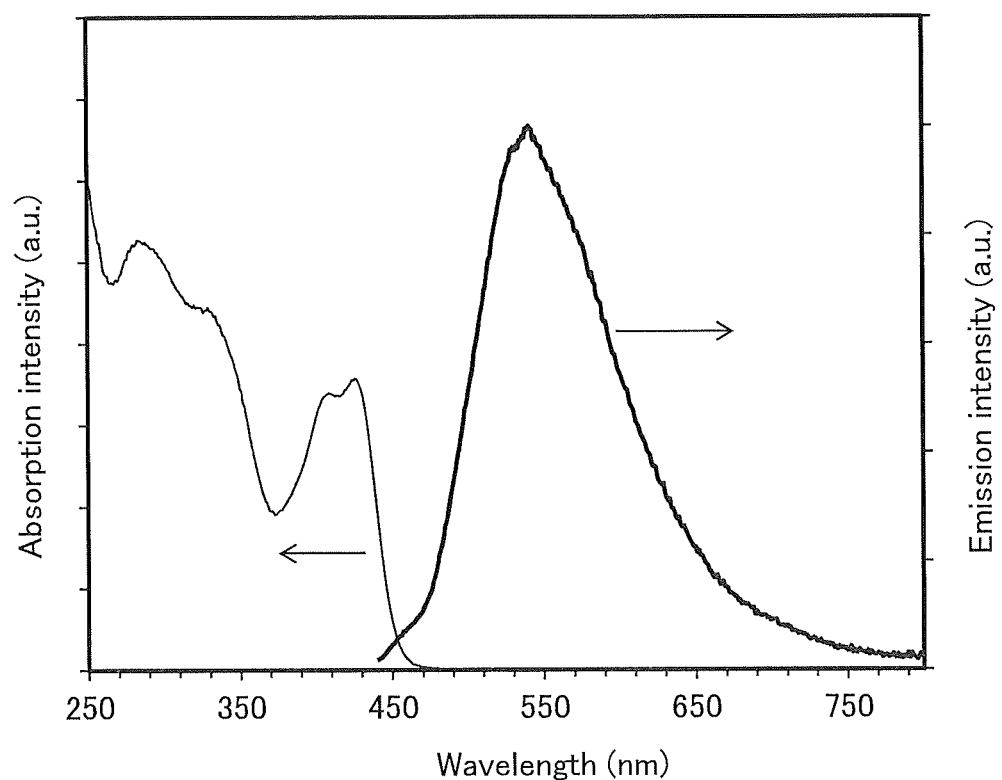

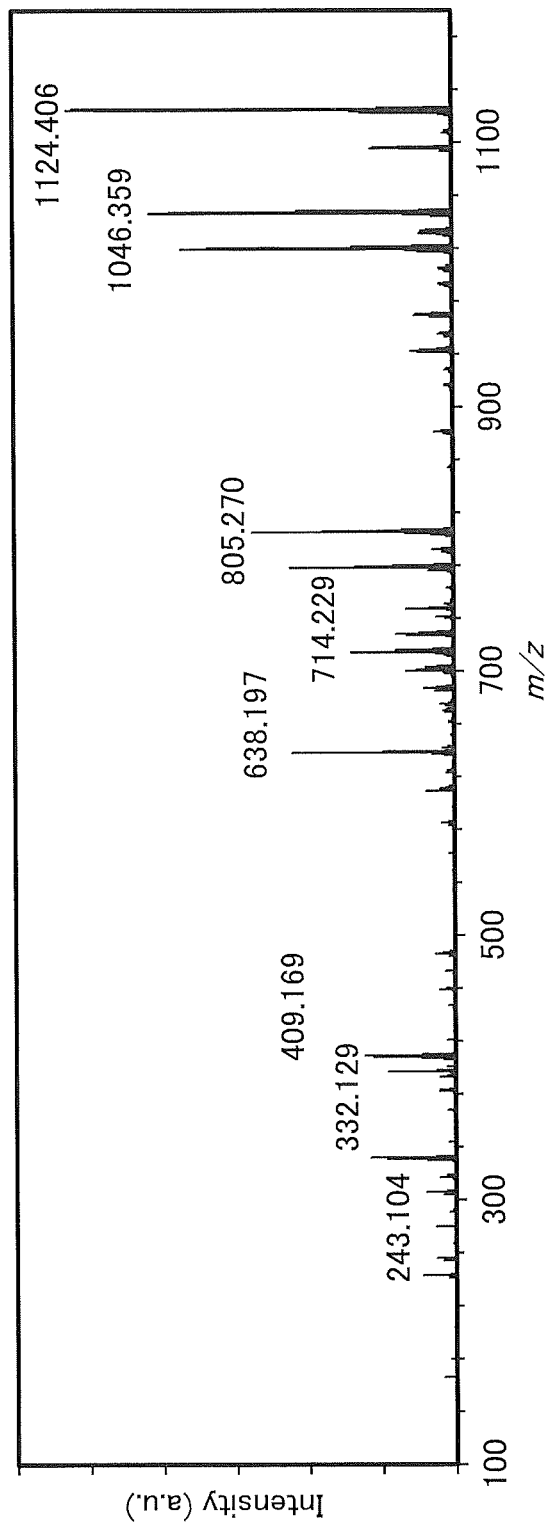
[FIG. 152]

[FIG. 153]
(A)
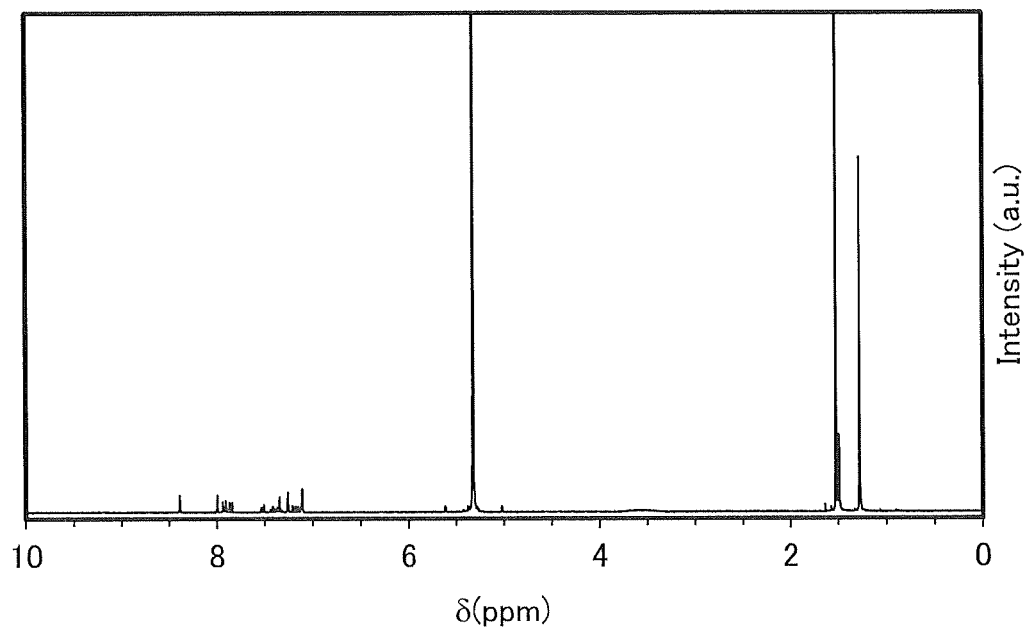
(B)
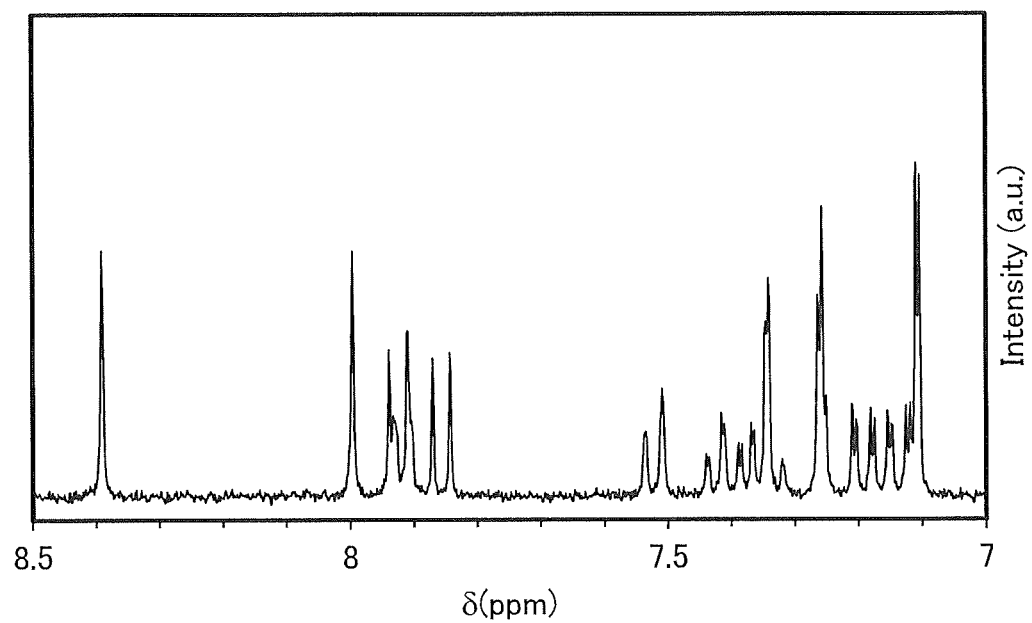

[FIG. 154]
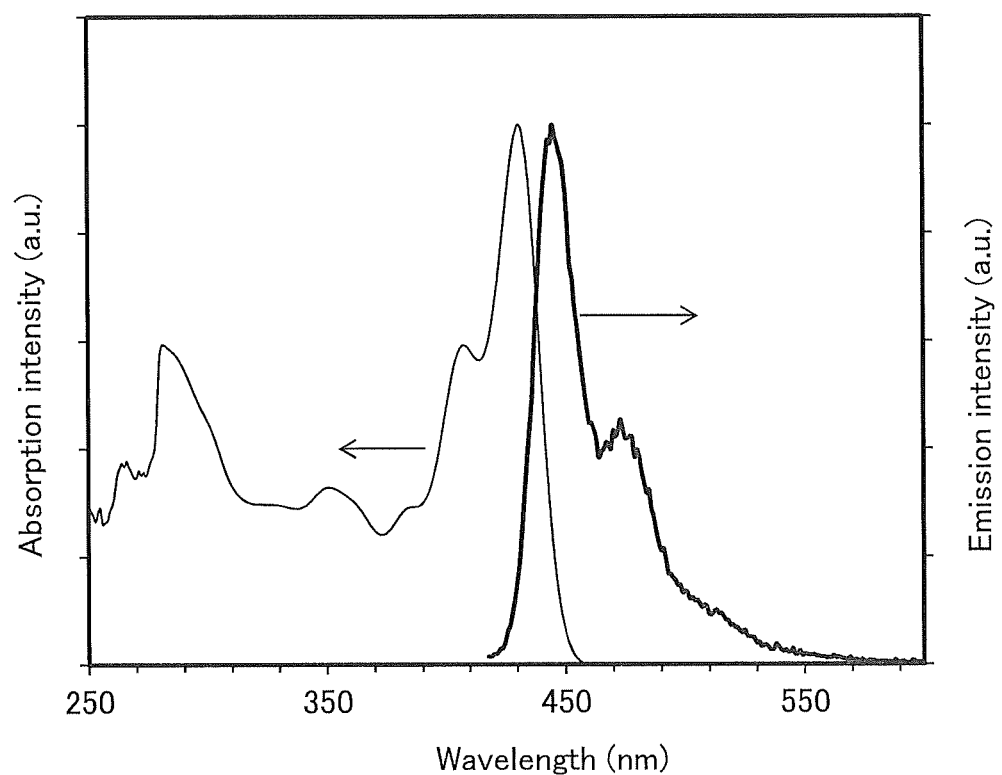

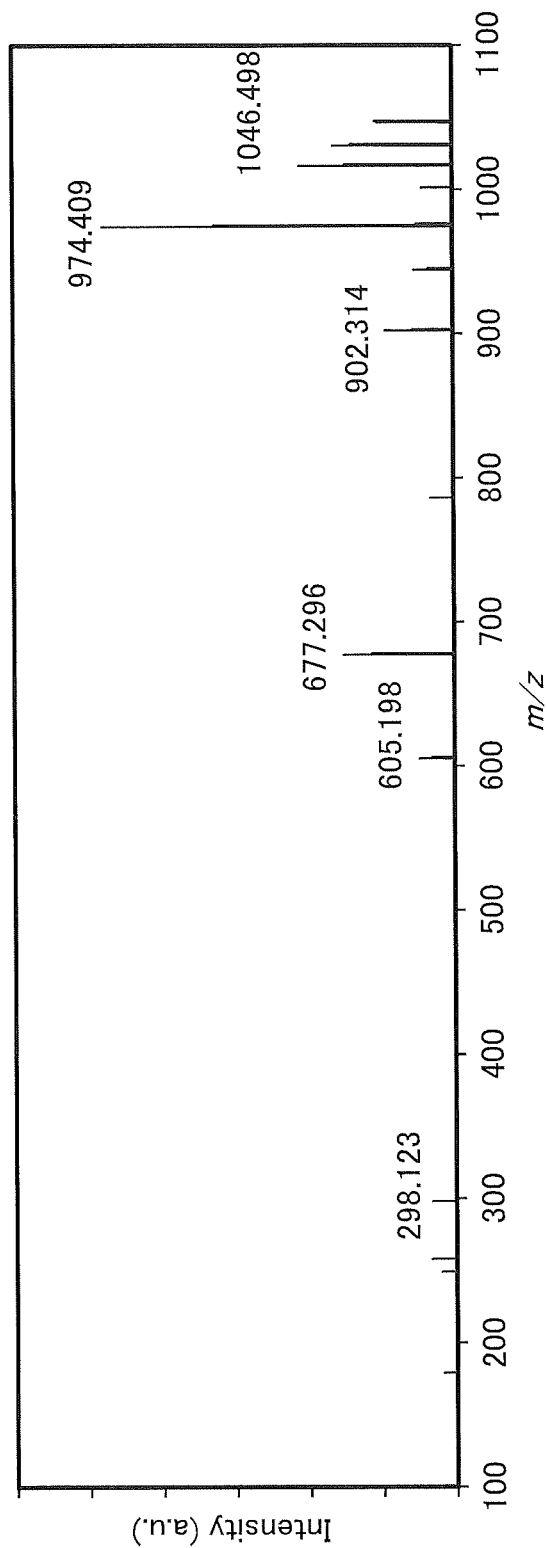
[FIG. 155]

[FIG. 156]
(A)
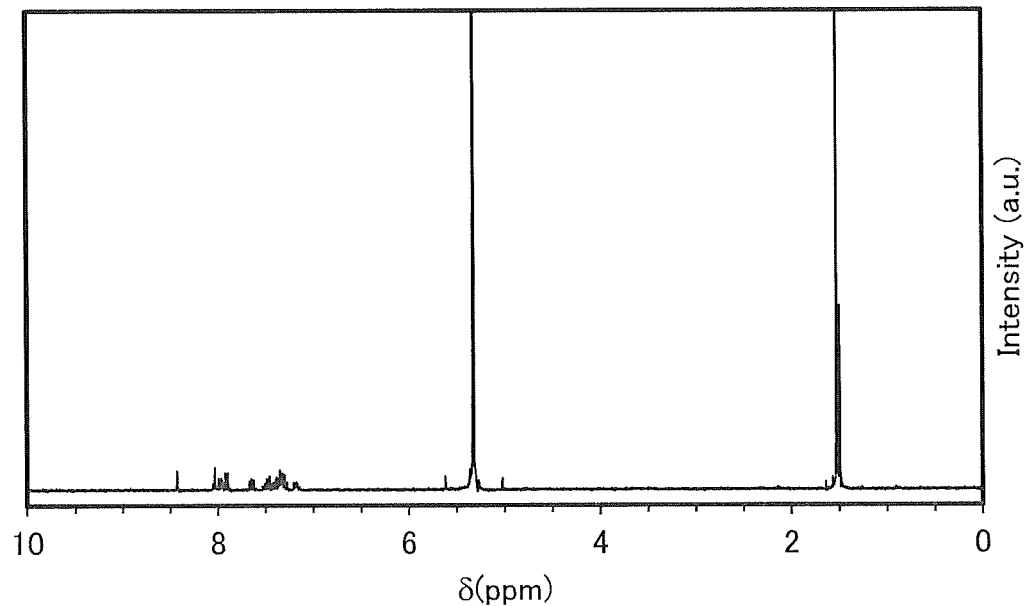
(B)
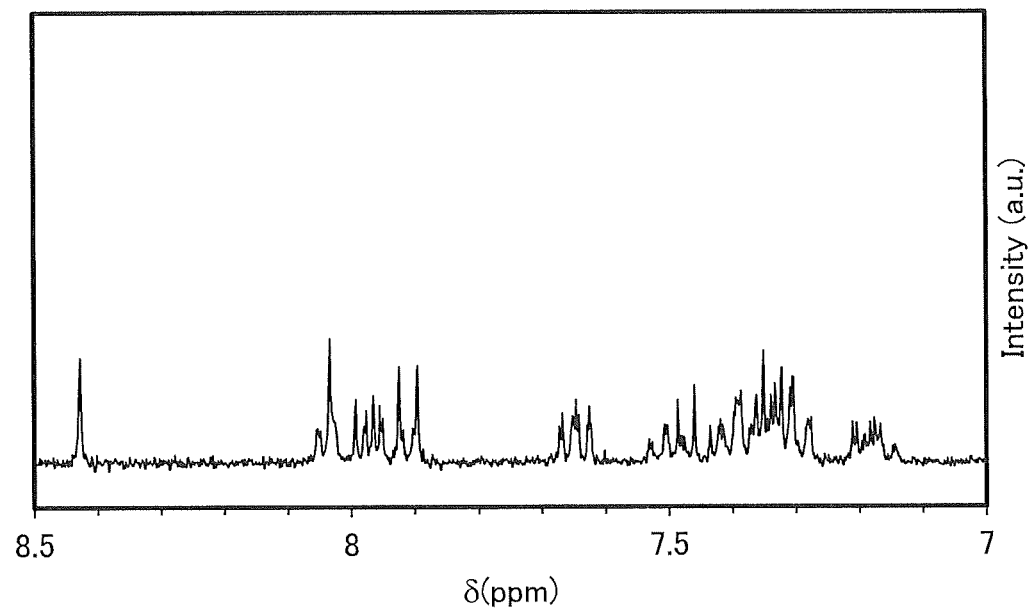

[FIG. 157]
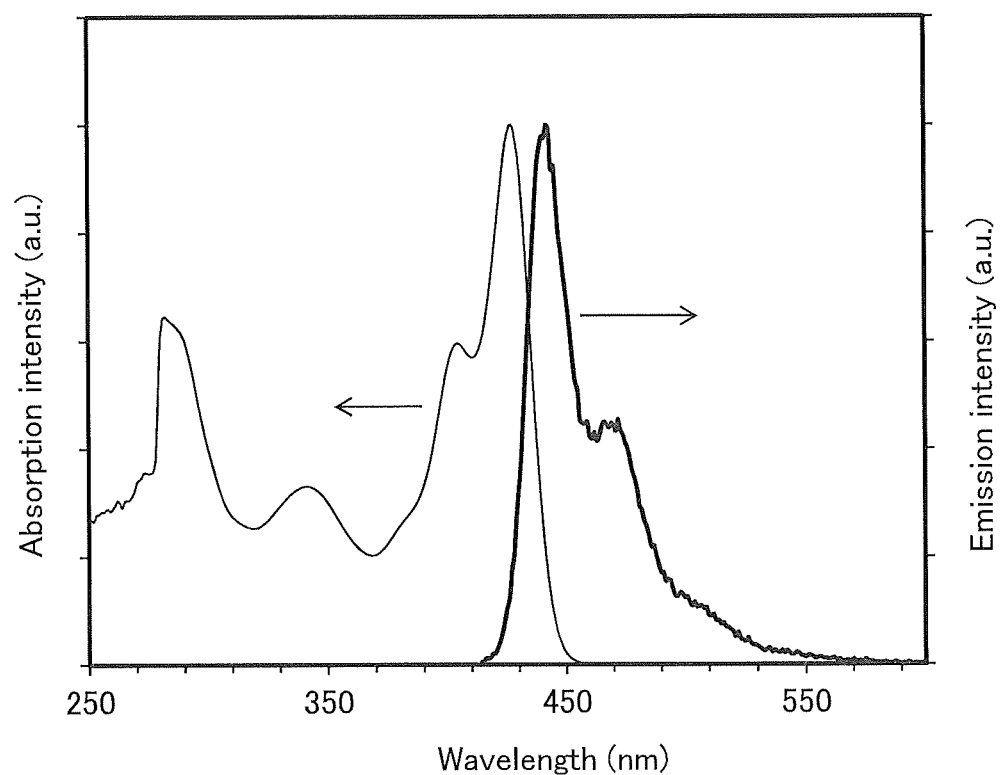

[FIG. 158]
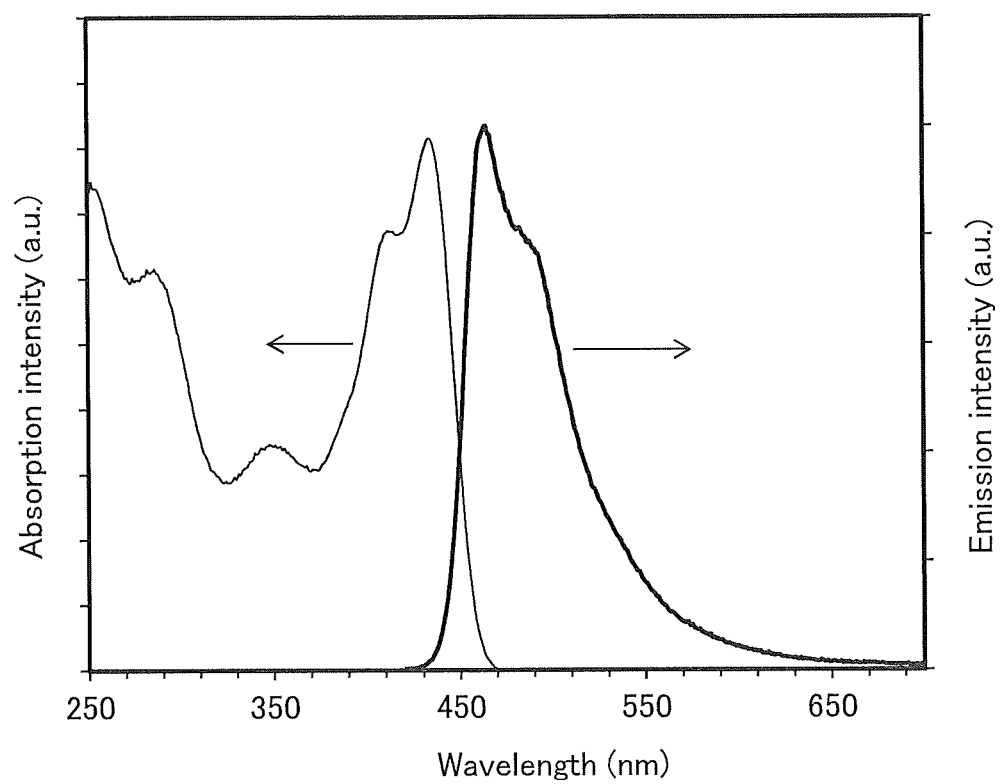

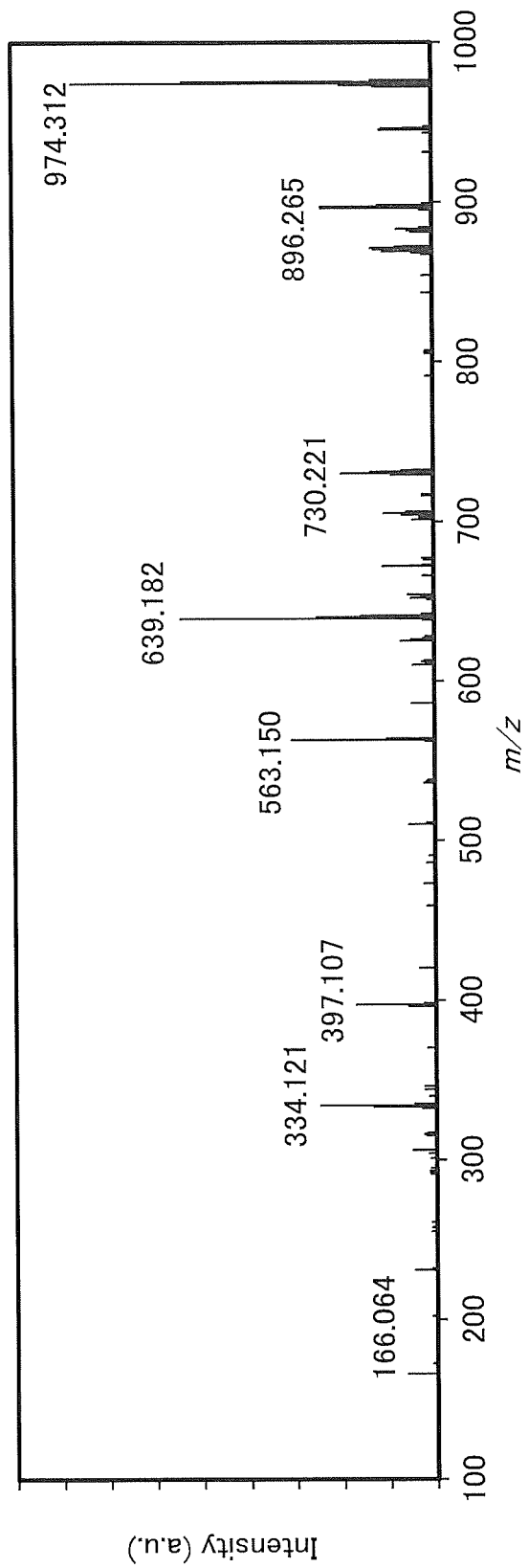
[FIG. 159]

[FIG. 160]
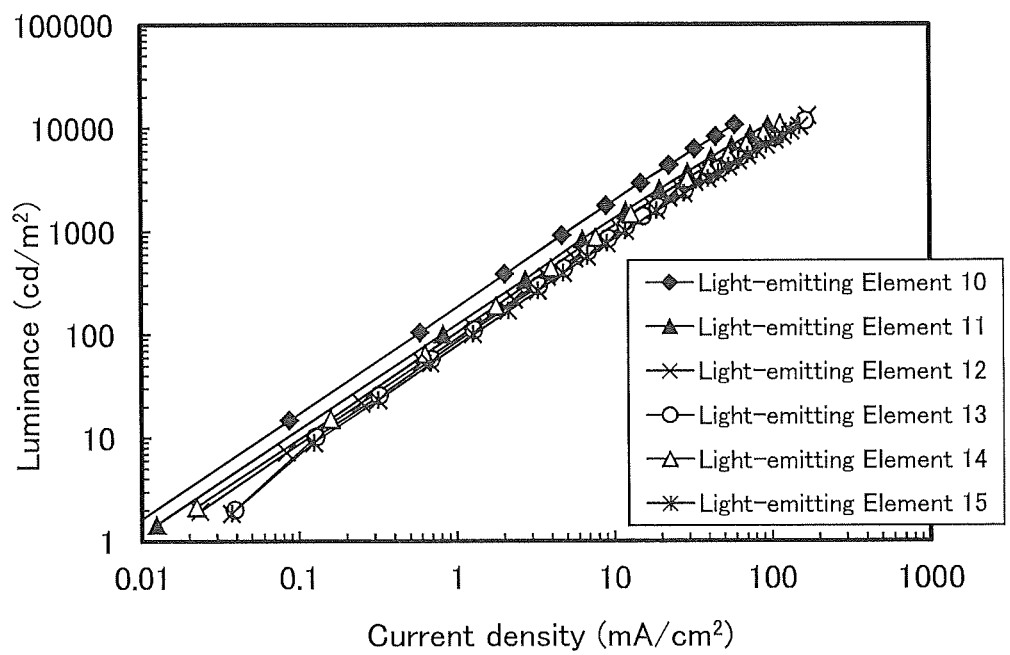
[FIG. 161]
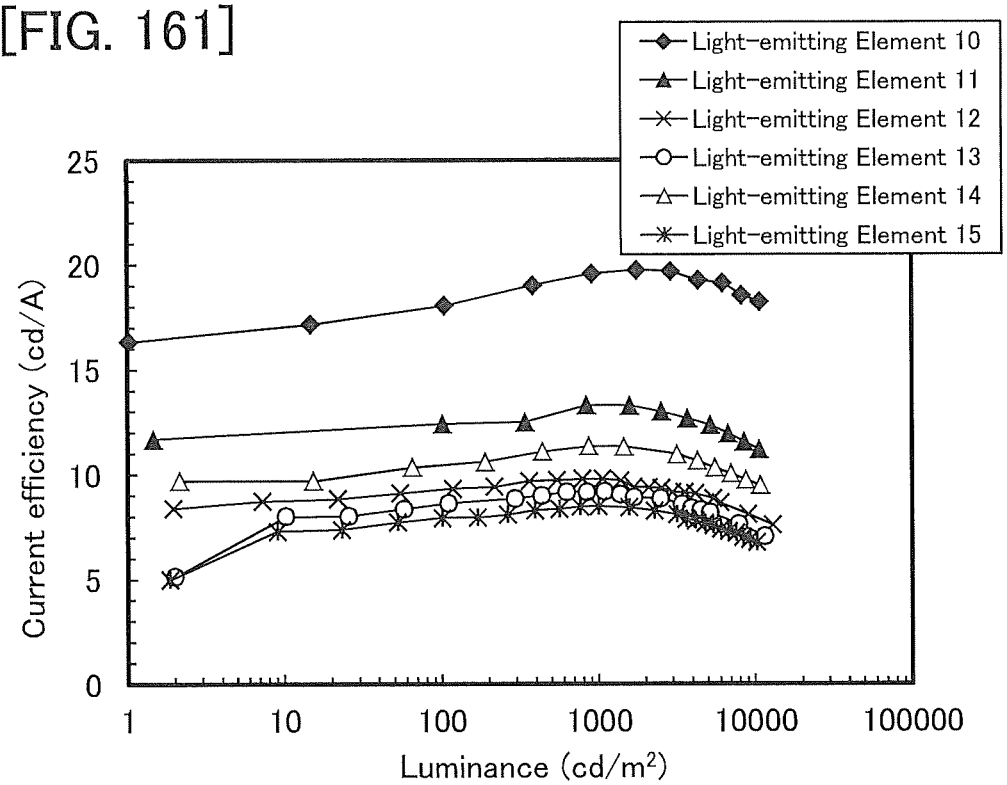

[FIG. 162]
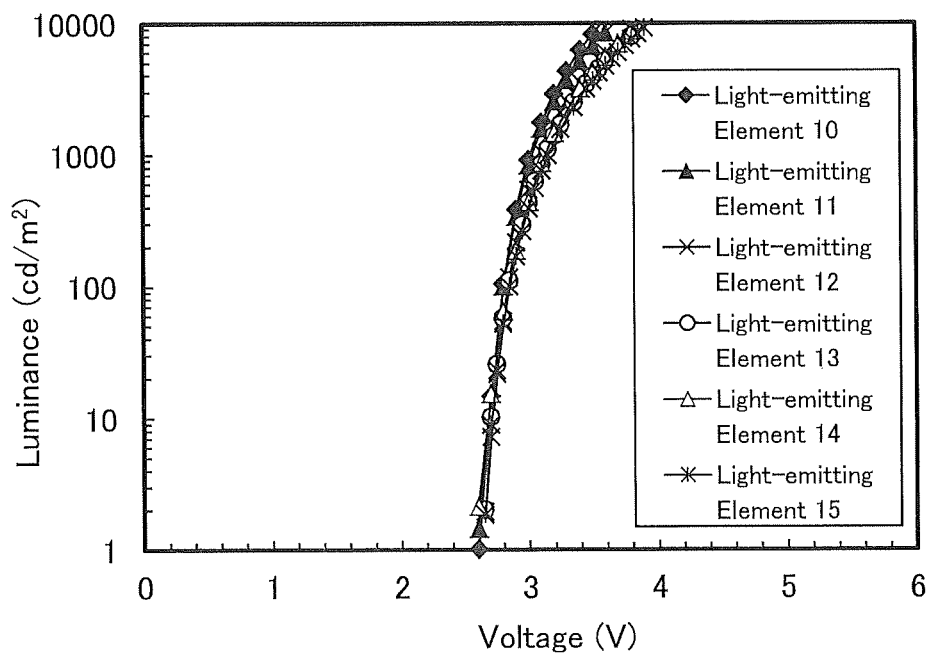
[FIG. 163]
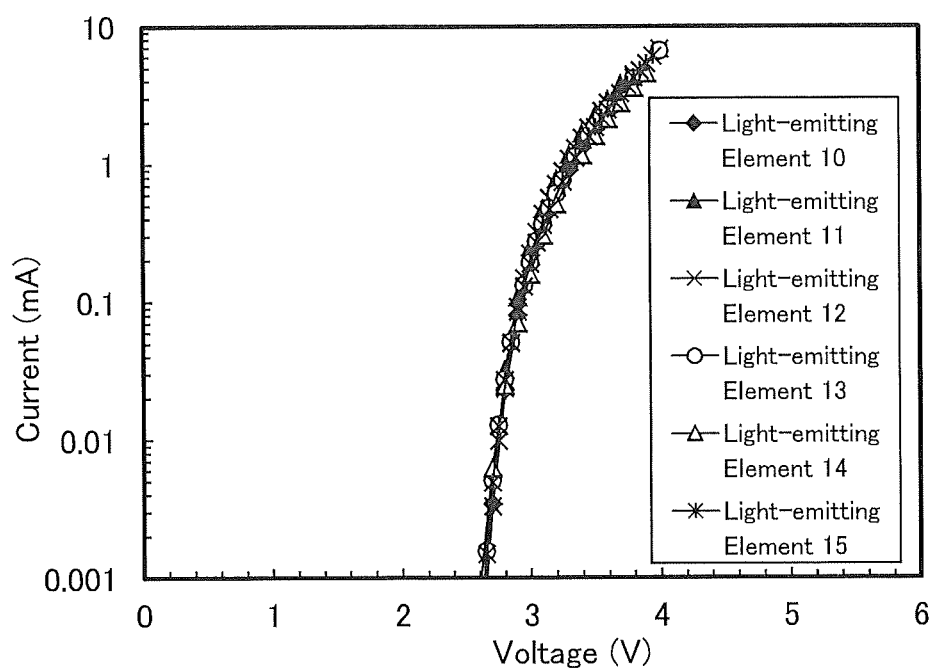

[FIG. 164]
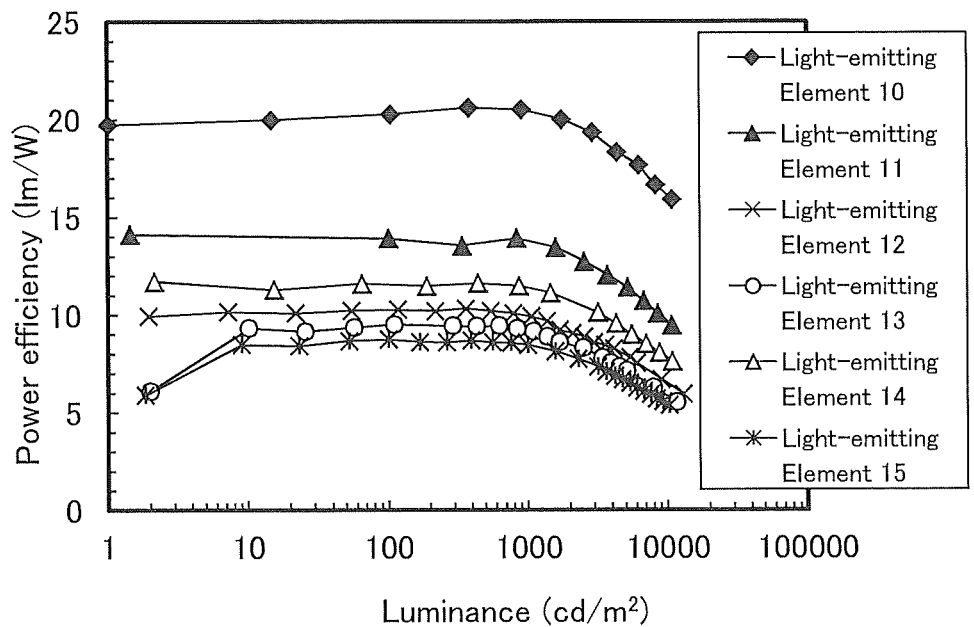
[FIG. 165]
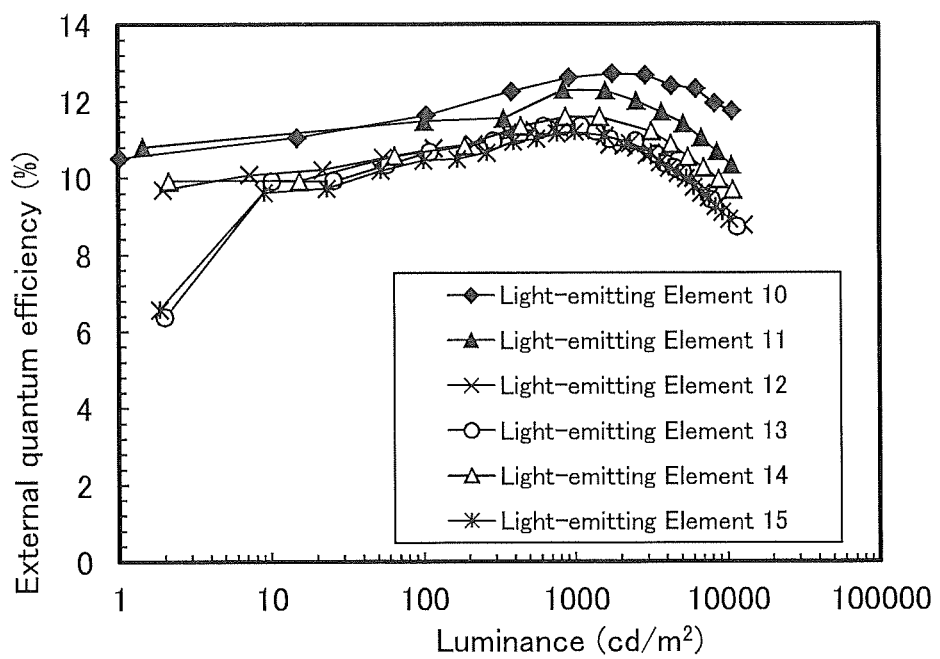

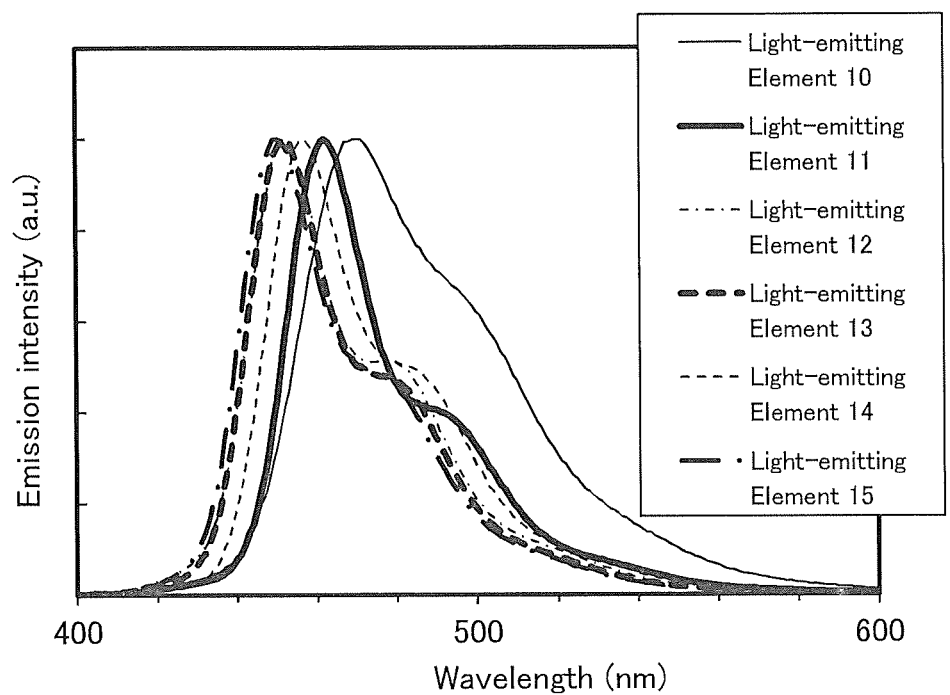
[FIG. 166]

[FIG. 167]
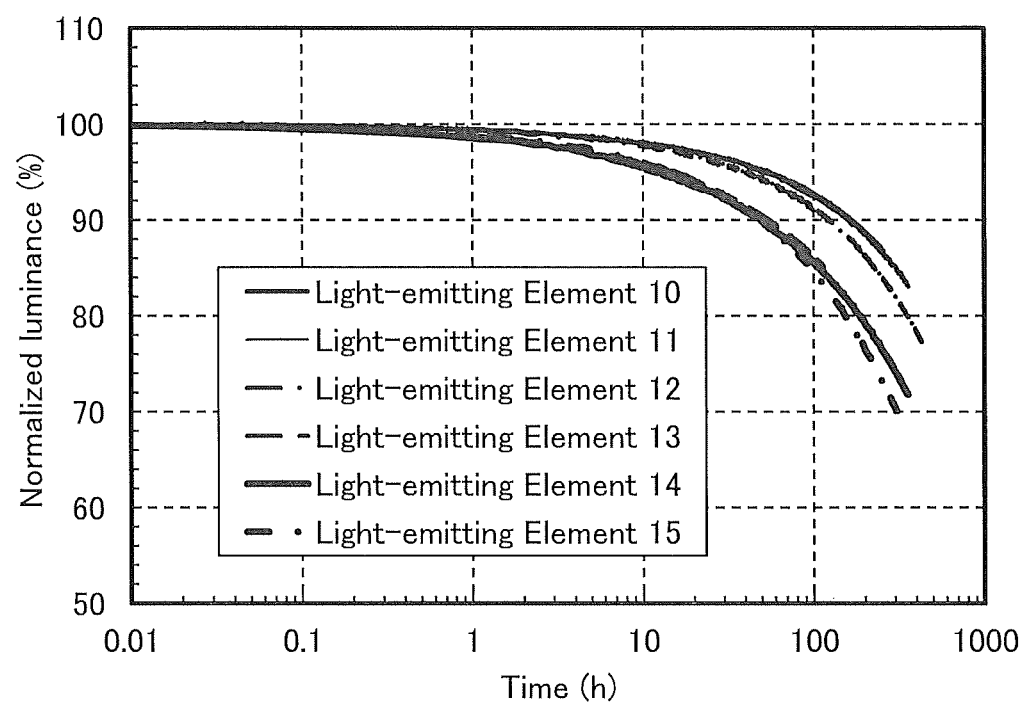

ORGANIC COMPOUND, LIGHT-EMITTING ELEMENT, LIGHT-EMITTING DEVICE, ELECTRONIC DEVICE, DISPLAY DEVICE, AND LIGHTING DEVICE

TECHNICAL FIELD

One embodiment of the present invention relates to an organic compound and a light-emitting element, a display module, a lighting module, a display device, a light-emitting device, an electronic device, and a lighting device in which the organic compound is used. Note that one embodiment of the present invention is not limited to the above technical field. The technical field of one embodiment of the invention disclosed in this specification and the like relates to an object, a method, or a manufacturing method. In addition, one embodiment of the present invention relates to a process, a machine, manufacture, or a composition (composition of matter). Therefore, specifically, examples of the technical field of one embodiment of the present invention disclosed in this specification include a semiconductor device, a display device, a liquid crystal display device, a light-emitting device, a lighting device, a power storage device, a memory device, an imaging device, a method for driving any of them, and a method for manufacturing any of them.

BACKGROUND ART

Some display devices and light-emitting devices using organic EL elements are practically used and the application thereof is gradually spreading. In recent years, liquid crystal displays have greatly progressed; organic EL displays, which are called next-generation displays, are naturally required to have high quality.

Although a variety of substances have been developed as materials for organic EL displays, not so many of them have high resistance enough for practical use. In consideration of diversity, affinity, and the like of combinations, it is obvious that, the larger the number of options is, the more convenient it is.

Organic EL elements have a function-separated-type structure in which a plurality of functions are given to different substances. Demands for light-emitting materials among them, in particular, emission efficiency, which affects power consumption, and emission colors for improving display quality, are high.

Patent Document 1 discloses an organic compound having a naphthobisbenzofuran skeleton.

REFERENCE

Patent Document

[Patent Document 1] Japanese Published Patent Application No. 2014-237682

SUMMARY OF THE INVENTION

Problems to be Solved by the Invention

An object of one embodiment of the present invention is to provide a novel organic compound. Alternatively, an object is to provide an organic compound that exhibits light emission with favorable chromaticity. Alternatively, an object is to provide an organic compound that exhibits blue light emission with favorable chromaticity. Alternatively, an object is to provide an organic compound with favorable emission efficiency. Alternatively, an object is to provide an organic compound having a high carrier-transport property. Alternatively, an object is to provide an organic compound with favorable reliability.

Furthermore, an object of one embodiment of the present invention is to provide a novel light-emitting element. Alternatively, an object is to provide a light-emitting element with favorable emission efficiency. Alternatively, an object is to provide a light-emitting element with favorable chromaticity. Alternatively, an object is to provide a light-emitting element that exhibits blue light emission with favorable chromaticity. Alternatively, an object is to provide a light-emitting element with a favorable lifetime. Alternatively, an object is to provide a light-emitting element with a low driving voltage.

Alternatively, an object of another embodiment of the present invention is to provide each of a light-emitting device, an electronic device, and a display device with low power consumption. Alternatively, an object of another embodiment of the present invention is to provide each of a light-emitting device, an electronic device, and a display device with high reliability. Alternatively, an object of another embodiment of the present invention is to provide each of a light-emitting device, an electronic device, and a display device with favorable display quality.

It is only necessary that at least one of the above-described objects be achieved in the present invention.

Means for Solving the Problems

One embodiment of the present invention is an organic compound represented by the following general formula (G1).

[Chemical Formula 1]

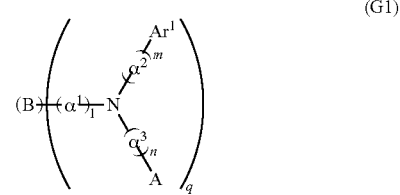

(G1)

Note that, in the formula, B represents any of a substituted or unsubstituted naphthobisbenzofuran skeleton, a substituted or unsubstituted naphthobisbenzothiophene skeleton, and a substituted or unsubstituted naphthobenzofuranobenzothiophene skeleton. Furthermore, $Ar^1$ is any of a substituted or unsubstituted aromatic hydrocarbon group having 6 to 25 carbon atoms, a substituted or unsubstituted dibenzofuranyl group, a substituted or unsubstituted dibenzothiophenyl group, and a substituted or unsubstituted carbazolyl group. A is any of a substituted or unsubstituted dibenzofuranyl group, a substituted or unsubstituted dibenzothiophenyl group, and a substituted or unsubstituted carbazolyl group, and $\alpha^1$ to $\alpha^3$ are each independently a substituted or unsubstituted bivalent aromatic hydrocarbon group having 6 to 25 carbon atoms. Furthermore, 1, m, and n each independently represent an integer of 0 to 2, and q is 1 or 2.

Alternatively, another embodiment of the present invention is an organic compound represented by the following general formula (G1).

[Chemical Formula 2]

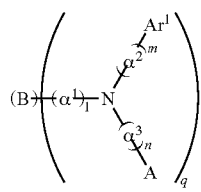
(G1)

Note that, in the formula, B represents any of a substituted or unsubstituted naphthobisbenzofuran skeleton, a substituted or unsubstituted naphthobisbenzothiophene skeleton, and a substituted or unsubstituted naphthobenzofuranobenzothiophene skeleton. Furthermore, $Ar^1$ is any one of a substituted or unsubstituted aromatic hydrocarbon group having 6 to 25 carbon atoms and groups represented by the following general formulae (g1) to (g3), and A is any of the groups represented by the following general formulae (g1) to (g3). Furthermore, $\alpha^1$ to $\alpha^3$ are each independently a substituted or unsubstituted bivalent aromatic hydrocarbon group having 6 to 25 carbon atoms. Furthermore, l, m, and n each independently represent an integer of 0 to 2, and q is 1 or 2.

[Chemical Formulae 3]

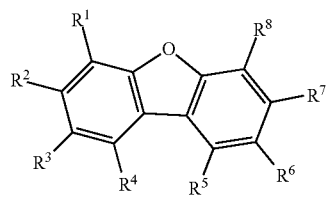
(g1)

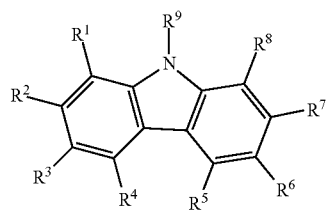
(g2)

(g3)

In the general formulae (g1) to (g3), any one of $R^1$ to $R^9$ represents a single bond and the others each independently represent any of hydrogen, a hydrocarbon group having 1 to 10 carbon atoms, a cyclic hydrocarbon group having 3 to 10 carbon atoms, and a substituted or unsubstituted aromatic hydrocarbon group having 6 to 14 carbon atoms. Note that in the case where A is the group represented by the general formula (g3) and $R^9$ in the group represented by the general formula (g3) represents a single bond, n is 1 or 2. Furthermore, in the case where $Ar^1$ is the group represented by the general formula (g3) and $R^9$ in (g3) represents a single bond, m is 1 or 2.

Alternatively, another embodiment of the present invention is the organic compound in which, in the above structure, in the case where A and/or $Ar^1$ are/is each independently the group represented by the above general formula (g1) or general formula (g2), any of $R^1$ to $R^3$ in the group represented by the general formula (g1) or general formula (g2) is a single bond; in the case where A and/or Ar are/is the group represented by the above general formula (g3), $R^2$ or $R^3$ in the group represented by the general formula (g3) is a single bond.

Alternatively, another embodiment of the present invention is the organic compound, in which, in the above structure, the A is the group represented by the general formula (g1) or the general formula (g3) and $R^2$ in the group represented by the general formula (g1) or the general formula (g3) represents a single bond.

Alternatively, another embodiment of the present invention is the organic compound in which, in the above structure, the n is 0.

Alternatively, another embodiment of the present invention is the organic compound in which, in the above structure, the $Ar^1$ is a substituted or unsubstituted aromatic hydrocarbon group having 6 to 25 carbon atoms.

Alternatively, another embodiment of the present invention is the organic compound in which, in the above structure, the l is 0.

Alternatively, another embodiment of the present invention is the organic compound in which, in the above structure, the B is any of skeletons represented by the following general formula (B1) to general formula (B4).

[Chemical Formulae 4]

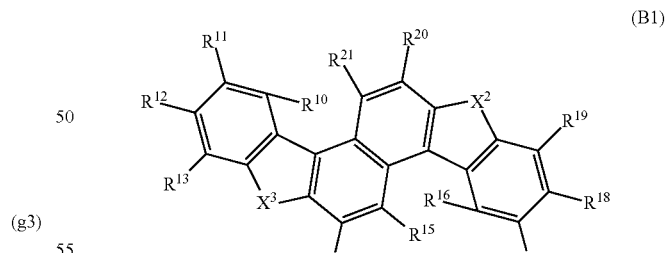
(B1)

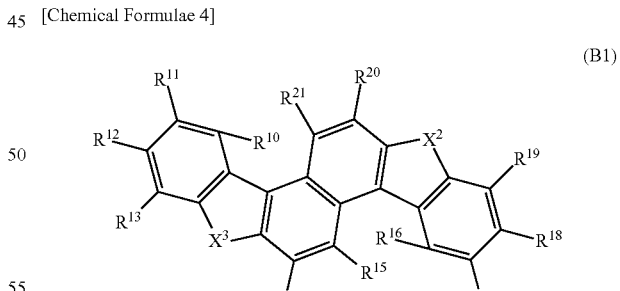
(B2)

-continued (B3)

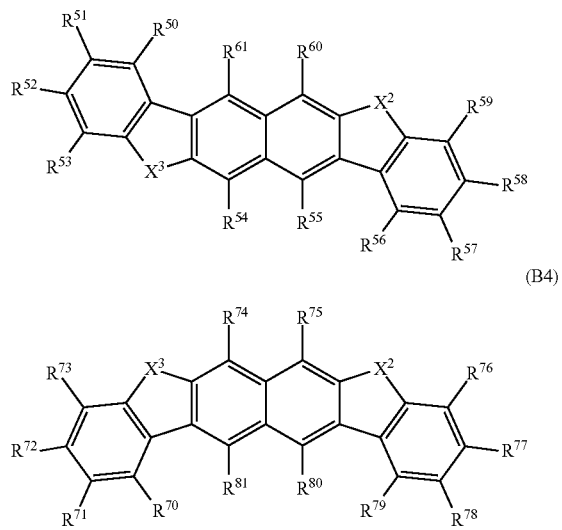

(B4)

Note that, in the above general formula (B1) to general formula (B4), $X^2$ and $X^3$ each independently represent an oxygen atom or a sulfur atom. Note that, in the above general formula (B1), any one or two of $R^{10}$ to $R^{21}$ represent a single bond and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms. Furthermore, in the above general formula (B2), any one or two of $R^{30}$ to $R^{41}$ represent a single bond and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms. Furthermore, in the above general formula (B3), any one or two of $R^{50}$ to $R^{61}$ represent a single bond and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms. Furthermore, in the above general formula (B4), any one or two of $R^{70}$ to $R^{81}$ represent a single bond and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms.

Alternatively, another embodiment of the present invention is the organic compound in which, in the above structure, the B is any of the skeletons represented by the above general formula (B1) to general formula (B3).

Alternatively, another embodiment of the present invention is the organic compound in which, in the above structure, the B is a skeleton represented by the following general formula (B1).

[Chemical Formula 5]

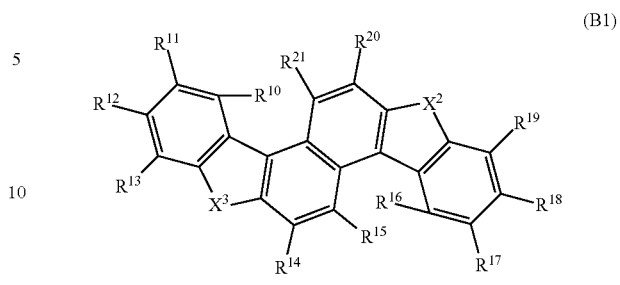

(B1)

Note that, in the formula, $X^2$ and $X^3$ each independently represent an oxygen atom or a sulfur atom. Furthermore, one or two of $R^{10}$ to $R^{21}$ represent a single bond and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms.

Alternatively, another embodiment of the present invention is the organic compound in which, in the above structure, any one or two of $R^{11}$, $R^{12}$, $R^{17}$, and $R^{18}$ in the above general formula (B1) represent a single bond.

Alternatively, another embodiment of the present invention is the organic compound in which, in the above structure, q in the above general formula (G1) is 2, and one of $R^{11}$ and $R^{12}$ is a single bond and one of $R^{17}$ and $R^{18}$ is a single bond in the above general formula (B1).

Alternatively, another embodiment of the present invention is the organic compound in which, in the above structure, q in the above general formula (G1) is 2, and $R^{11}$ and $R^{17}$ in the above general formula (B1) are a single bond.

Alternatively, another embodiment of the present invention is the organic compound in which, in the above structure, q in the above general formula (G1) is 2, and $R^{12}$ and $R^{18}$ in the above general formula (B1) are a single bond.

Alternatively, another embodiment of the present invention is the organic compound in which, in the above structure, the B is a skeleton represented by the following general formula (B2).

[Chemical Formula 6]

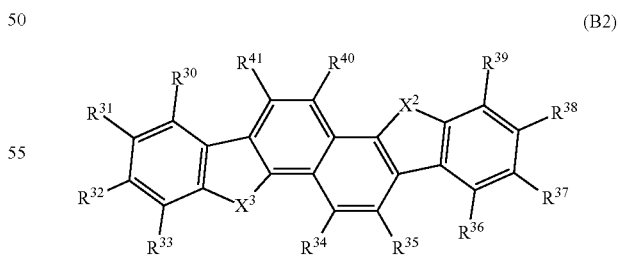

(B2)

Note that, in the formula, $X^2$ and $X^3$ each independently represent an oxygen atom or a sulfur atom. Furthermore, one or two of $R^{30}$ to $R^{41}$ represent a single bond and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms.

Alternatively, another embodiment of the present invention is the organic compound in which, in the above structure, any one or two of $R^{31}$, $R^{32}$, $R^{37}$, and $R^{38}$ in the above general formula (B2) represent a single bond.

Alternatively, another embodiment of the present invention is the organic compound in which, in the above structure, q in the above general formula (G1) is 2, and $R^{31}$ or $R^{32}$ and $R^{37}$ or $R^{38}$ in the above general formula (B2) are a single bond.

Alternatively, another embodiment of the present invention is the organic compound in which, in the above structure, q in the above general formula (G1) is 2, and $R^{31}$ and $R^{37}$ in the above general formula (B2) are a single bond.

Alternatively, another embodiment of the present invention is the organic compound in which, in the above structure, q in the above general formula (G1) is 2, and $R^{32}$ and $R^{38}$ in the above general formula (B2) are a single bond.

Alternatively, another embodiment of the present invention is the organic compound in which, in the above structure, the B is a skeleton represented by the following general formula (B3).

[Chemical Formula 7]

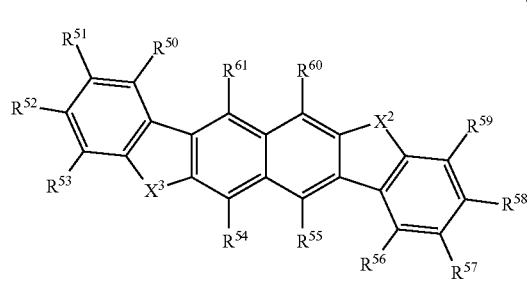

(B3)

Note that, in the formula, $X^2$ and $X^3$ each independently represent an oxygen atom or a sulfur atom. Furthermore, any one or two of $R^{50}$ to $R^{61}$ represent a single bond and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms.

Alternatively, another embodiment of the present invention is the organic compound in which, in the above structure, any one or two of $R^{51}$, $R^{52}$, $R^{57}$, and $R^{58}$ in the above general formula (B3) represent a single bond.

Alternatively, another embodiment of the present invention is the organic compound in which, in the above structure, q in the above general formula (G1) is 2, and $R^{51}$ or $R^{52}$ and $R^{57}$ or $R^{58}$ in the above general formula (B3) are a single bond.

Alternatively, another embodiment of the present invention is the organic compound in which, in the above structure, q in the above general formula (G1) is 2, and $R^{51}$ and $R^{57}$ in the above general formula (B3) are a single bond.

Alternatively, another embodiment of the present invention is the organic compound in which, in the above structure, q in the above general formula (G1) is 2, and $R^{52}$ and $R^{58}$ in the above general formula (B3) are a single bond.

Alternatively, another embodiment of the present invention is the organic compound in which, in the above structure, the $X^2$ and $X^3$ are each an oxygen atom.

Alternatively, another embodiment of the present invention is the organic compound in which, in the above structure, A is the group represented by the general formula (g1).

Alternatively, another embodiment of the present invention is an organic compound represented by the following general formula (G1-1).

[Chemical Formula 8]

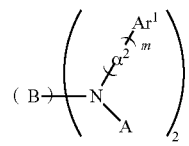

(G1-1)

Note that, in the above general formula (G1-1), B is a group represented by the following general formula (B1-1) or (B3-1). Furthermore, $Ar^1$ is a substituted or unsubstituted aromatic hydrocarbon group having 6 to 25 carbon atoms, and A is a group represented by the following general formula (g0). Furthermore, m represents an integer of 0 to 2. Furthermore, $\alpha^2$ is a substituted or unsubstituted bivalent aromatic hydrocarbon group having 6 to 14 carbon atoms.

[Chemical Formulae 9]

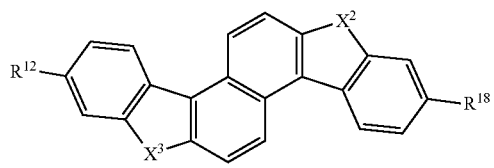

(B1-1)

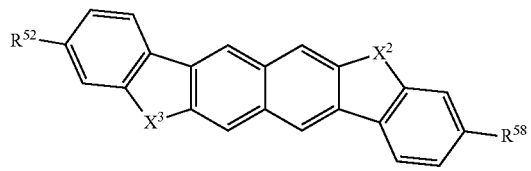

(B3-1)

Note that, in the above general formula (B1-1) or (B3-1), $X^2$ and $X^3$ each independently represent an oxygen atom or a sulfur atom. Furthermore, $R^{12}$, $R^{18}$, $R^{52}$, and $R^{58}$ represent a single bond.

[Chemical Formula 10]

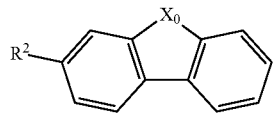

(g0)

Note that, in the above general formula (g0), $X_0$ is an oxygen atom or a nitrogen atom to which a substituted or unsubstituted phenyl group is bonded. Furthermore, $R^2$ represents a single bond.

Alternatively, another embodiment of the present invention is the organic compound in which, in the above structure, the molecular weight is 1300 or less.

Alternatively, another embodiment of the present invention is the organic compound in which, in the above structure, the molecular weight is 1000 or less.

Alternatively, another embodiment of the present invention is a light-emitting element containing the organic compound with the above structure.

Alternatively, another embodiment of the present invention is a light-emitting element containing an organic compound represented by any of the following structural formulae (iii), (vii), (ix), (x), (xi), (xiii), and (xv) to (XXiv).

[Chemical Formulae 11]

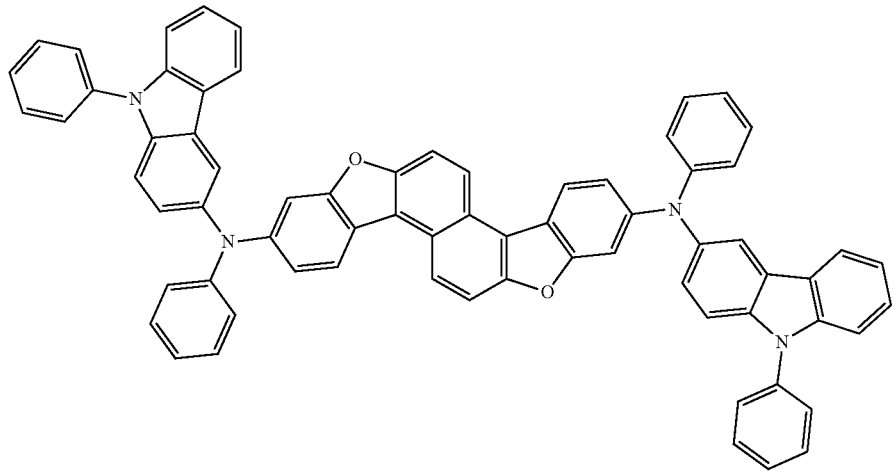

2,9PCA2Nbf(III)

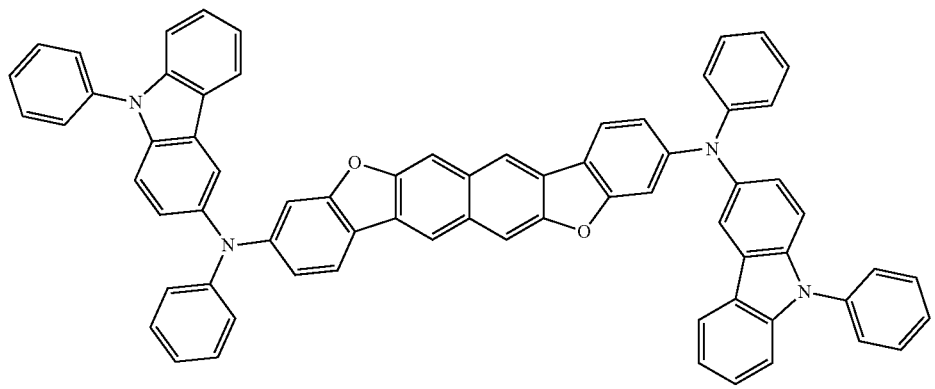

3,10PCA2Nbf(IV)

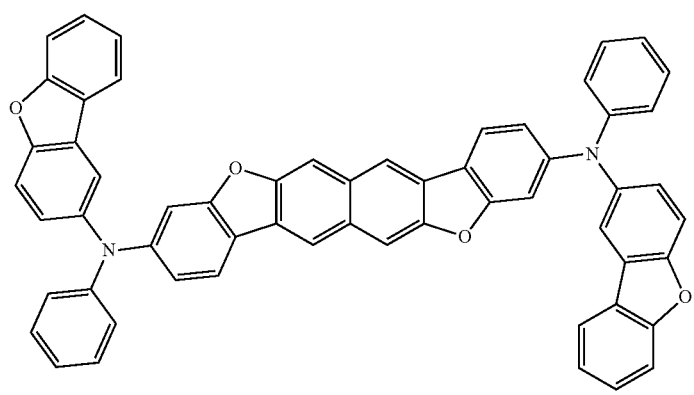

3,10FrA2Nbf(IV)

(x)
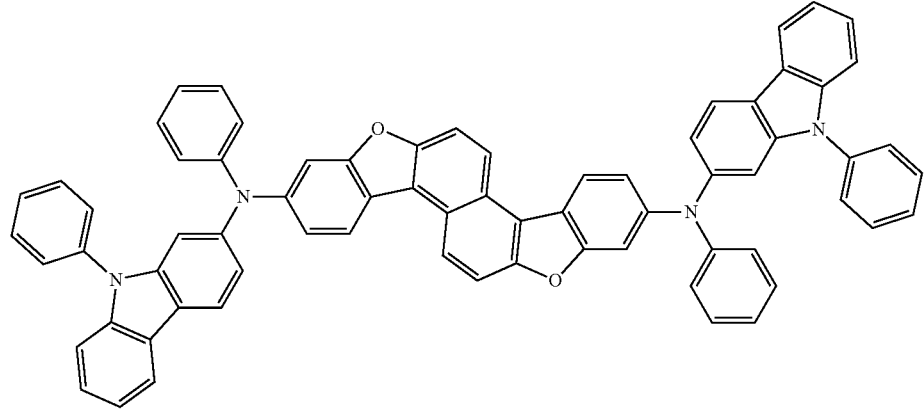
2,9PCA2Nbf (III)-02
(xi)
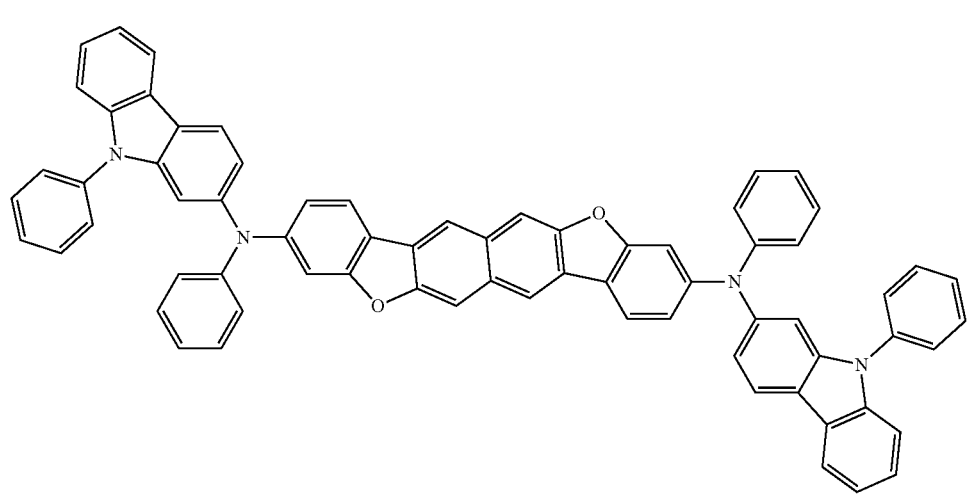
3,10PCA2Nbf (IV)-02
(xiii)
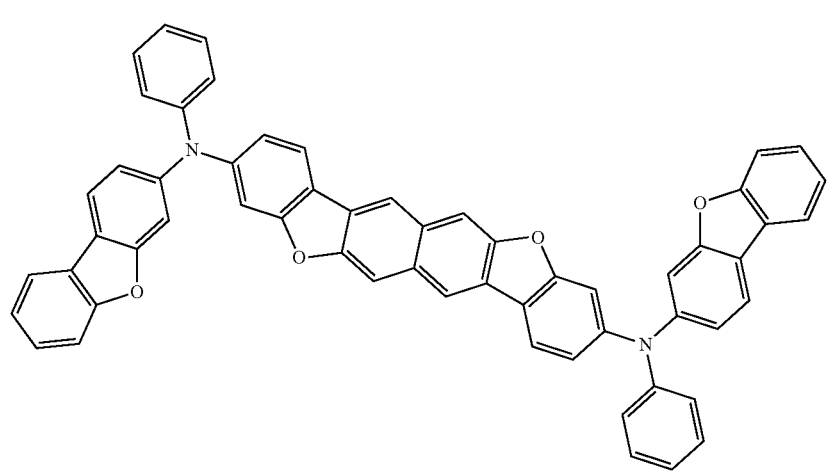
3,10FrA2Nbf (IV)-02

-continued
[Chemical Formulae 12]
(xv)
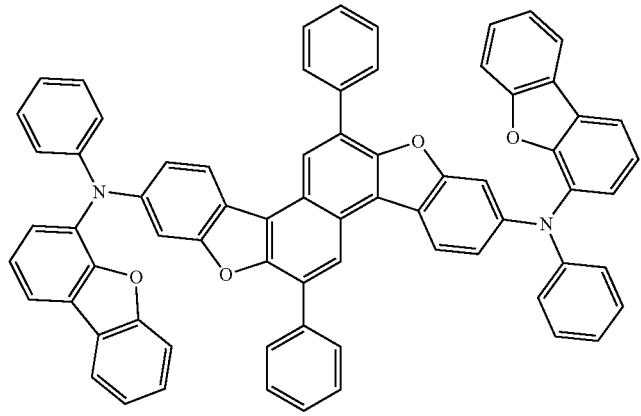
ph-2,9FrA2Nbf(III)-II
(xvi)
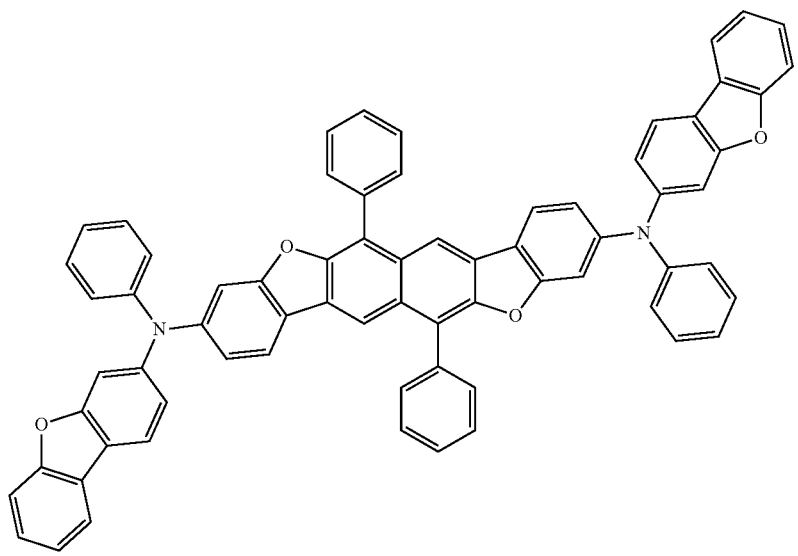
ph-3,10FrA2Nbf(IV)-02
(xvii)
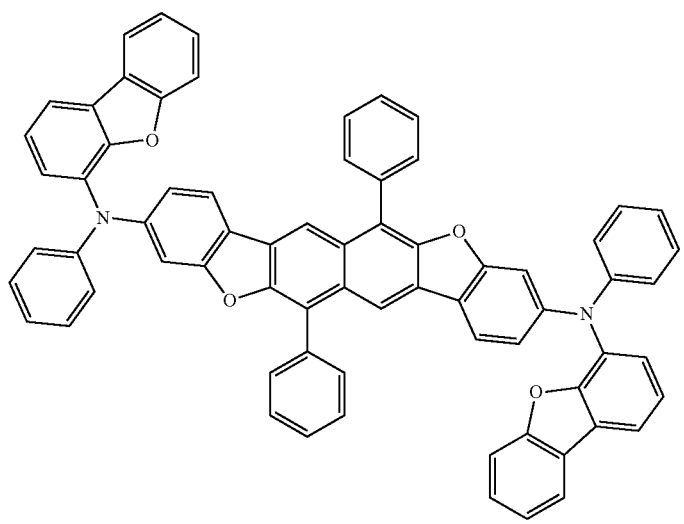
ph-3,10FrA2Nbf(IV)-II (xviii)
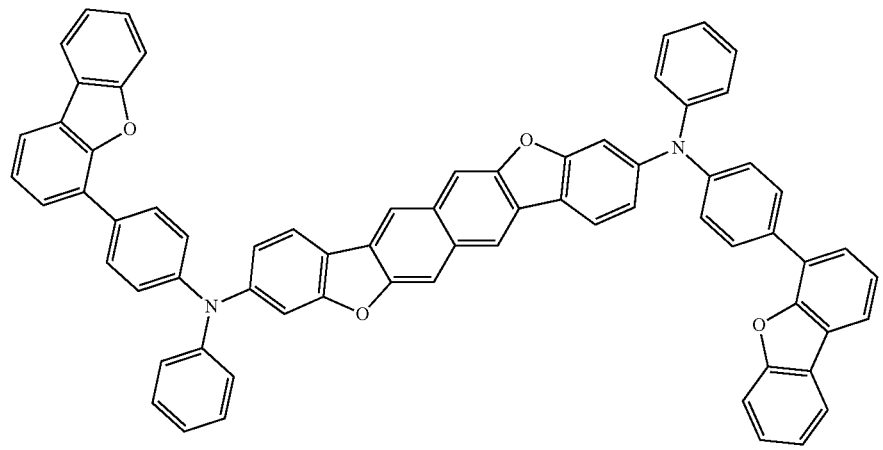
3,10FrBA2Nbf(IV)-II
(xix)
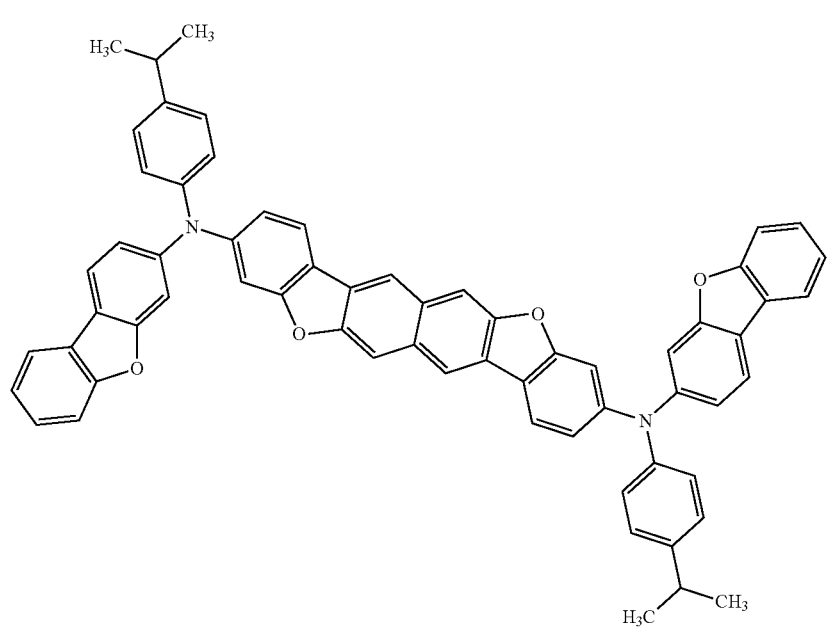
3,10iPrFrA2Nbf(IV)-02
[Chemical Formulae 13]
(xx)
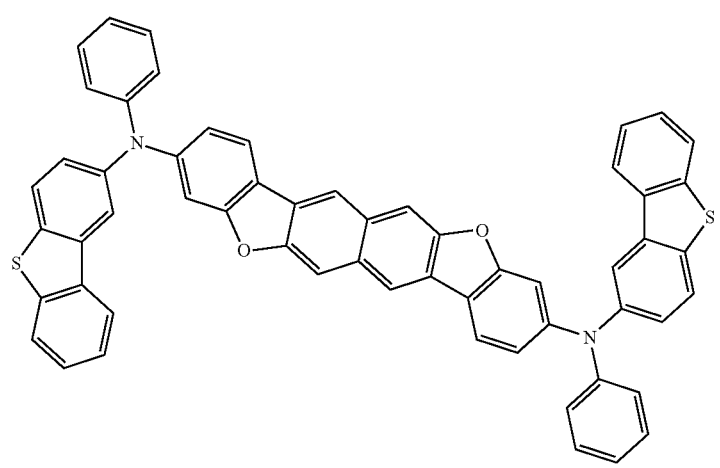
3,10ThA2Nbf(IV)

(xxi)
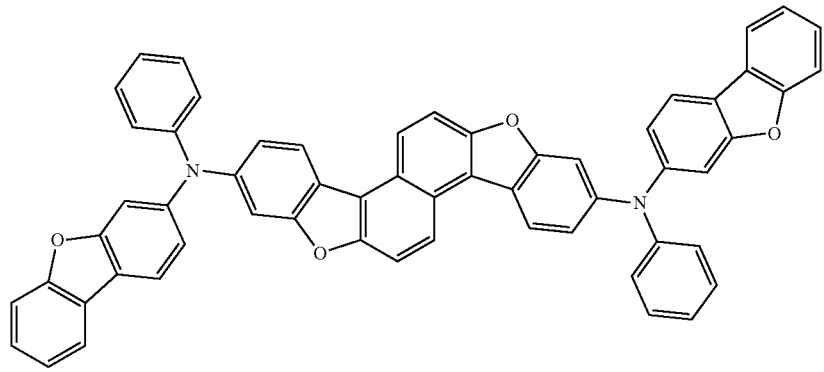
2,9FrA2Nbf(III)-02
(xxiv)
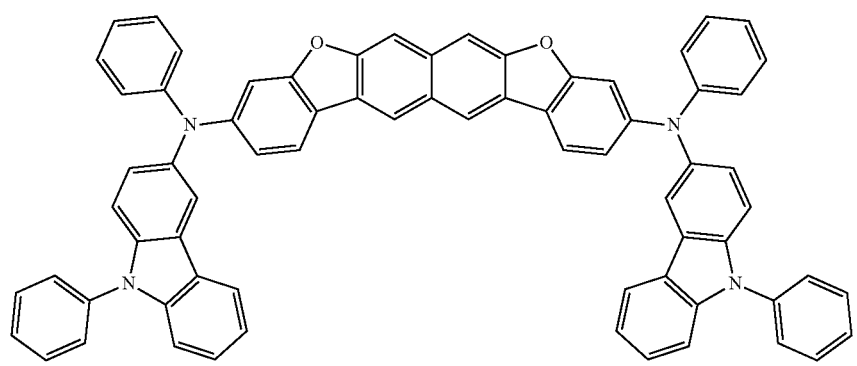
3,10PCA2Nbf(II)
(xxii)
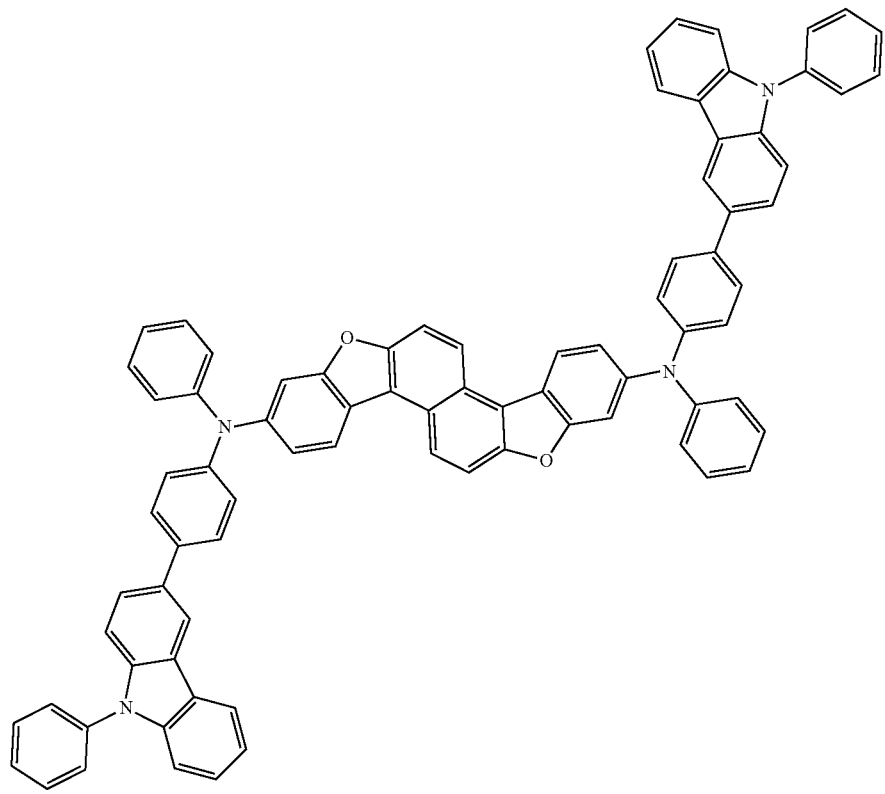
2,9PCBA2Nbf(III)

-continued

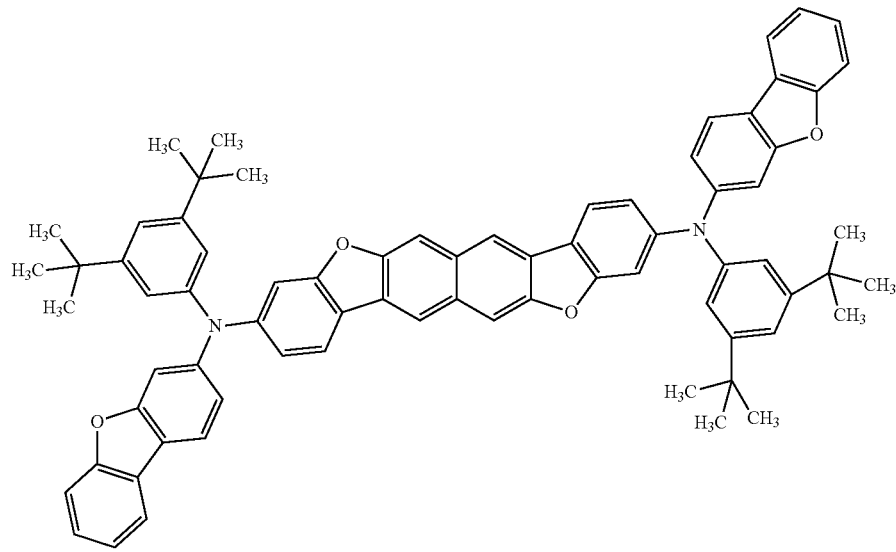

(xxiii)

3,10mmtBuFrA2Nbf(IV)-02

One embodiment of the present invention is a light-emitting device including the light-emitting element with the above structure, and a transistor or a substrate.

Another embodiment of the present invention is an electronic device including the light-emitting device with the above structure and a sensor, an operation button, a speaker, or a microphone.

Another embodiment of the present invention is a lighting device including the light-emitting device with the above structure and a housing.

Alternatively, another embodiment of the present invention is a light-emitting device including the light-emitting element with the above structure, a substrate, and a transistor.

Alternatively, another embodiment of the present invention is an electronic device including the light-emitting device with the above structure, and a sensor, an operation button, a speaker, or a microphone.

Alternatively, another embodiment of the present invention is a lighting device including the light-emitting device with the above structure and a housing.

Note that the light-emitting device in this specification includes an image display device using a light-emitting element. The light-emitting device includes, in some cases, a module in which a light-emitting element is provided with a connector such as an anisotropic conductive film or a TCP (Tape Carrier Package), a module in which a printed wiring board is provided at the end of a TCP, or a module in which an IC (integrated circuit) is directly mounted on a light-emitting element by a COG (Chip On Glass) method. Furthermore, in some cases, lighting equipment or the like includes the light-emitting device.

Effect of the Invention

In one embodiment of the present invention, a novel organic compound can be provided. Alternatively, an organic compound that exhibits light emission with favorable chromaticity can be provided. Alternatively, an organic compound that exhibits blue light emission with favorable chromaticity can be provided. Alternatively, an organic compound with favorable emission efficiency can be provided. Alternatively, an organic compound having a high carrier-transport property can be provided. Alternatively, an organic compound with favorable reliability can be provided.

Alternatively, in one embodiment of the present invention, a novel light-emitting element can be provided. Alternatively, a light-emitting element with favorable emission efficiency can be provided. Alternatively, a light-emitting element with favorable chromaticity can be provided. Alternatively, a light-emitting element that exhibits blue light emission with favorable chromaticity can be provided. Alternatively, a light-emitting element with a favorable lifetime can be provided. Alternatively, a light-emitting element with a low driving voltage can be provided.

Alternatively, in one embodiment of the present invention, a light-emitting device, an electronic device, and a display device with low power consumption can each be provided. Alternatively, in one embodiment of the present invention, a light-emitting device, an electronic device, and a display device with high reliability can each be provided. Alternatively, in one embodiment of the present invention, a light-emitting device, an electronic device, and a display device with favorable display quality can each be provided.

Note that the description of these effects does not preclude the existence of other effects. Note that one embodiment of the present invention does not necessarily have all the effects listed above. Effects other than these will be apparent from the description of the specification, the drawings, the claims, and the like and effects other than these can be derived from the description of the specification, the drawings, the claims, and the like.

BRIEF DESCRIPTION OF THE DRAWINGS

FIGS. 1(A)-1(C) are schematic diagrams of light-emitting elements.

FIGS. 2(A)-2(D) are drawings illustrating one example of a method for fabricating a light-emitting element.

FIG. 3 is a drawing illustrating one example of a method for fabricating a light-emitting element.

FIGS. 4(A) and 4(B) are schematic diagrams of an active-matrix-type light-emitting device.

FIGS. 5(A) and 5(B) are schematic diagrams of active-matrix-type light-emitting devices.

FIG. 6 is a schematic diagram of an active-matrix-type light-emitting device.

FIGS. 7(A) and 7(B) are schematic diagrams of a passive-matrix-type light-emitting device.

FIGS. 8(A) and 8(B) are drawings illustrating a lighting device.

FIGS. 9(A)-9(D) are drawings illustrating electronic devices.

FIG. 10 is a drawing illustrating a light source device.

FIG. 11 is a drawing illustrating a lighting device.

FIG. 12 is a drawing illustrating a lighting device.

FIG. 13 is a drawing illustrating car-mounted display devices and lighting devices.

FIGS. 14(A)-14(C) are drawings illustrating an electronic device.

FIGS. 15(A)-15(C) are drawings illustrating an electronic device.

FIGS. 16(A) and 16(B) is a $^1$H NMR spectrum of 3,10FrA2Nbf(IV).

FIG. 17 is an absorption spectrum and an emission spectrum of 3,10FrA2Nbf(IV) in a toluene solution.

FIG. 18 is an absorption spectrum and an emission spectrum of 3,10FrA2Nbf(IV) in a thin film state.

FIG. 19 is an MS spectrum of 3,10FrA2Nbf(IV).

FIGS. 20(A) and (B) is a $^1$H NMR spectrum of 2,9PCA2Nbf(III).

FIG. 21 is an absorption spectrum and an emission spectrum of 2,9PCA2Nbf(III) in a toluene solution.

FIG. 22 is an absorption spectrum and an emission spectrum of 2,9PCA2Nbf(III) in a thin film state.

FIG. 23 is an MS spectrum of 2,9PCA2Nbf(III).

FIGS. 24(A) and 24(B) is a $^1$H NMR spectrum of 3,10PCA2Nbf(IV).

FIG. 25 is an absorption spectrum and an emission spectrum of 3,10PCA2Nbf(IV) in a toluene solution.

FIG. 26 is an absorption spectrum and an emission spectrum of 3,10PCA2Nbf(IV) in a thin film state.

FIG. 27 is an MS spectrum of 3,10PCA2Nbf(IV).

FIG. 28 is a graph showing luminance-current density characteristics of a light-emitting element 1 and a comparative light-emitting element 1.

FIG. 29 is a graph showing current efficiency-luminance characteristics of the light-emitting element 1 and the comparative light-emitting element 1.

FIG. 30 is a graph showing luminance-voltage characteristics of the light-emitting element 1 and the comparative light-emitting element 1.

FIG. 31 is a graph showing current-voltage characteristics of the light-emitting element 1 and the comparative light-emitting element 1.

FIG. 32 is a graph showing power efficiency-luminance characteristics of the light-emitting element 1 and the comparative light-emitting element 1.

FIG. 33 is a graph showing external quantum efficiency-luminance characteristics of the light-emitting element 1 and the comparative light-emitting element 1.

FIG. 34 is emission spectra of the light-emitting element 1 and the comparative light-emitting element 1.

FIG. 35 is a graph showing normalized luminance-temporal change characteristics of the light-emitting element 1 and the comparative light-emitting element 1.

FIG. 36 is a graph showing luminance-current density characteristics of a light-emitting element 2 and a comparative light-emitting element 2.

FIG. 37 is a graph showing current efficiency-luminance characteristics of the light-emitting element 2 and the comparative light-emitting element 2.

FIG. 38 is a graph showing luminance-voltage characteristics of the light-emitting element 2 and the comparative light-emitting element 2.

FIG. 39 is a graph showing current-voltage characteristics of the light-emitting element 2 and the comparative light-emitting element 2.

FIG. 40 is a graph showing power efficiency-luminance characteristics of the light-emitting element 2 and the comparative light-emitting element 2.

FIG. 41 is a graph showing external quantum efficiency-luminance characteristics of the light-emitting element 2 and the comparative light-emitting element 2.

FIG. 42 is emission spectra of the light-emitting element 2 and the comparative light-emitting element 2.

FIG. 43 is a graph showing normalized luminance-temporal change characteristics of the light-emitting element 2 and the comparative light-emitting element 2.

FIG. 44 is a graph showing luminance-current density characteristics of a light-emitting element 3 and a comparative light-emitting element 3.

FIG. 45 is a graph showing current efficiency-luminance characteristics of the light-emitting element 3 and the comparative light-emitting element 3.

FIG. 46 is a graph showing luminance-voltage characteristics of the light-emitting element 3 and the comparative light-emitting element 3.

FIG. 47 is a graph showing current-voltage characteristics of the light-emitting element 3 and the comparative light-emitting element 3.

FIG. 48 is a graph showing power efficiency-luminance characteristics of the light-emitting element 3 and the comparative light-emitting element 3.

FIG. 49 is a graph showing external quantum efficiency-luminance characteristics of the light-emitting element 3 and the comparative light-emitting element 3.

FIG. 50 is emission spectra of the light-emitting element 3 and the comparative light-emitting element 3.

FIG. 51 is a graph showing normalized luminance-temporal change characteristics of the light-emitting element 3 and the comparative light-emitting element 3.

FIG. 52 is a graph showing luminance-current density characteristics of a light-emitting element 4 and a comparative light-emitting element 4.

FIG. 53 is a graph showing current efficiency-luminance characteristics of the light-emitting element 4 and the comparative light-emitting element 4.

FIG. 54 is a graph showing luminance-voltage characteristics of the light-emitting element 4 and the comparative light-emitting element 4.

FIG. 55 is a graph showing current-voltage characteristics of the light-emitting element 4 and the comparative light-emitting element 4.

FIG. 56 is a graph showing power efficiency-luminance characteristics of the light-emitting element 4 and the comparative light-emitting element 4.

FIG. 57 is a graph showing external quantum efficiency-luminance characteristics of the light-emitting element 4 and the comparative light-emitting element 4.

FIG. 58 is emission spectra of the light-emitting element 4 and the comparative light-emitting element 4.

FIG. 59 is a graph showing normalized luminance-temporal change characteristics of the light-emitting element 4 and the comparative light-emitting element 4.

FIG. 60 is a graph showing luminance-current density characteristics of a light-emitting element 5 and a comparative light-emitting element 5.

FIG. 61 is a graph showing current efficiency-luminance characteristics of the light-emitting element 5 and the comparative light-emitting element 5.

FIG. 62 is a graph showing luminance-voltage characteristics of the light-emitting element 5 and the comparative light-emitting element 5.

FIG. 63 is a graph showing current-voltage characteristics of the light-emitting element 5 and the comparative light-emitting element 5.

FIG. 64 is a graph showing power efficiency-luminance characteristics of the light-emitting element 5 and the comparative light-emitting element 5.

FIG. 65 is a graph showing external quantum efficiency-luminance characteristics of the light-emitting element 5 and the comparative light-emitting element 5.

FIG. 66 is emission spectra of the light-emitting element 5 and the comparative light-emitting element 5.

FIG. 67 is a graph showing normalized luminance-temporal change characteristics of the light-emitting element 5 and the comparative light-emitting element 5.

FIG. 68 is a graph showing luminance-current density characteristics of a light-emitting element 6 and a comparative light-emitting element 6.

FIG. 69 is a graph showing current efficiency-luminance characteristics of the light-emitting element 6 and the comparative light-emitting element 6.

FIG. 70 is a graph showing luminance-voltage characteristics of the light-emitting element 6 and the comparative light-emitting element 6.

FIG. 71 is a graph showing current-voltage characteristics of the light-emitting element 6 and the comparative light-emitting element 6.

FIG. 72 is a graph showing power efficiency-luminance characteristics of the light-emitting element 6 and the comparative light-emitting element 6.

FIG. 73 is a graph showing external quantum efficiency-luminance characteristics of the light-emitting element 6 and the comparative light-emitting element 6.

FIG. 74 is emission spectra of the light-emitting element 6 and the comparative light-emitting element 6.

FIG. 75 is a graph showing normalized luminance-temporal change characteristics of the light-emitting element 6 and the comparative light-emitting element 6.

FIGS. 76(A) and 76(B) is a $^1$H NMR spectrum of 3,7-bis(4-chloro-2-fluorophenyl)-2,6-dimethoxynaphthalene.

FIGS. 77(A) and 77(B) is a $^1$H NMR spectrum of 3,7-bis(4-chloro-2-fluorophenyl)-2,6-dihydroxynaphthalene.

FIGS. 78(A) and 78(B) is a $^1$H NMR spectrum of 3,10-dichloronaphtho[2,3-b;6,7-b']bisbenzofuran.

FIGS. 79(A) and 79(B) is a $^1$H NMR spectrum of 1,5-bis(4-chloro-2-fluorophenyl)-2,7-dihydroxynaphthalene.

FIGS. 80(A) and 80(B) is a $^1$H NMR spectrum of 2,9-dichloronaphtho[2,1-b;6,5-b']bisbenzofuran.

FIGS. 81(A) and 81(B) is a $^1$H NMR spectrum of 2,9PCA2Nbf(III)-02.

FIG. 82 is an absorption spectrum and an emission spectrum of 2,9PCA2Nbf(III)-02 in a toluene solution.

FIG. 83 is an absorption spectrum and an emission spectrum of 2,9PCA2Nbf(III)-02 in a thin film state.

FIG. 84 is an MS spectrum of 2,9PCA2Nbf(III)-02.

FIGS. 85(A) and 85(B) is a $^1$H NMR spectrum of 3,10FrA2Nbf(IV)-02.

FIG. 86 is an absorption spectrum and an emission spectrum of 3,10FrA2Nbf(IV)-02 in a toluene solution.

FIG. 87 is an absorption spectrum and an emission spectrum of 3,10FrA2Nbf(IV)-02 in a thin film state.

FIG. 88 is an MS spectrum of 3,10FrA2Nbf(IV)-02.

FIGS. 89(A) and 89(B) is a $^1$H NMR spectrum of 3,10PCA2Nbf(IV)-02.

FIG. 90 is an absorption spectrum and an emission spectrum of 3,10PCA2Nbf(IV)-02 in a toluene solution.

FIG. 91 is an absorption spectrum and an emission spectrum of 3,10PCA2Nbf(IV)-02 in a thin film state.

FIG. 92 is an MS spectrum of 3,10PCA2Nbf(IV)-02.

FIGS. 93(A) and 93(B) is a NMR spectrum of 2,6-dihydroxy-1,5-diphenylnaphthalene.

FIGS. 94(A) and 94(B) is a NMR spectrum of 2,6-bis(2-bromo-4-chlorophenoxy)-1,5-diphenylnaphthalene.

FIGS. 95(A) and 95(B) is a NMR spectrum of 3,10-dichloronaphtho[2,3-b;6,7-b']bisbenzofuran.

FIGS. 96(A) and 96(B) is a $^1$H NMR spectrum of ph-3,10FrA2Nbf(IV)-II.

FIG. 97 is an MS spectrum of ph-3,10FrA2Nbf(IV)-II.

FIG. 98 is a graph showing luminance-current density characteristics of a light-emitting element 7.

FIG. 99 is a graph showing current efficiency-luminance characteristics of the light-emitting element 7.

FIG. 100 is a graph showing luminance-voltage characteristics of the light-emitting element 7.

FIG. 101 is a graph showing current-voltage characteristics of the light-emitting element 7.

FIG. 102 is a graph showing power efficiency-luminance characteristics of the light-emitting element 7.

FIG. 103 is a graph showing external quantum efficiency-luminance characteristics of the light-emitting element 7.

FIG. 104 is an emission spectrum of the light-emitting element 7.

FIG. 105 is a graph showing normalized luminance-temporal change characteristics of the light-emitting element 7.

FIG. 106 is a graph showing luminance-current density characteristics of a light-emitting element 8.

FIG. 107 is a graph showing current efficiency-luminance characteristics of the light-emitting element 8.

FIG. 108 is a graph showing luminance-voltage characteristics of the light-emitting element 8.

FIG. 109 is a graph showing current-voltage characteristics of the light-emitting element 8.

FIG. 110 is a graph showing power efficiency-luminance characteristics of the light-emitting element 8.

FIG. 111 is a graph showing external quantum efficiency-luminance characteristics of the light-emitting element 8.

FIG. 112 is an emission spectrum of the light-emitting element 8.

FIG. 113 is a graph showing normalized luminance-temporal change characteristics of the light-emitting element 8.

FIG. 114 is a graph showing luminance-current density characteristics of a light-emitting element 9.

FIG. 115 is a graph showing current efficiency-luminance characteristics of the light-emitting element 9.

FIG. 116 is a graph showing luminance-voltage characteristics of the light-emitting element 9.

FIG. 117 is a graph showing current-voltage characteristics of the light-emitting element 9.

FIG. 118 is a graph showing power efficiency-luminance characteristics of the light-emitting element 9.

FIG. 119 is a graph showing external quantum efficiency-luminance characteristics of the light-emitting element 9.

FIG. 120 is an emission spectrum of the light-emitting element 9.

FIG. 121 is a graph showing normalized luminance-temporal change characteristics of the light-emitting element 9.

FIG. 122 is a graph showing a relation between a y chromaticity and an external quantum efficiency of bottom-emission elements using a variety of blue fluorescent dopants.

FIG. 123 is a graph showing a relation between a y chromaticity and a current efficiency of top-emission elements with different optical path lengths.

FIG. 124 is an absorption spectrum and an emission spectrum of ph-3,10FrA2Nbf(IV)-II in a toluene solution.

FIG. 125 is an absorption spectrum and an emission spectrum of ph-3,10FrA2Nbf(IV)-II in a thin film state.

FIGS. 126(A) and 126(B) is a $^1$H NMR spectrum of 3,10PCA2Nbf(II).

FIG. 127 is an absorption spectrum and an emission spectrum of 3,10PCA2Nbf(II) in a toluene solution.

FIG. 128 is an absorption spectrum and an emission spectrum of 3,10PCA2Nbf(II) in a thin film state.

FIG. 129 is an MS spectrum of 3,10PCA2Nbf(II).

FIGS. 130(A) and 130(B) is a $^1$H NMR spectrum of 2,9FrA2Nbf(III)-02.

FIG. 131 is an absorption spectrum and an emission spectrum of 2,9FrA2Nbf(III)-02 in a toluene solution.

FIG. 132 is an absorption spectrum and an emission spectrum of 2,9FrA2Nbf(III)-02 in a thin film state.

FIG. 133 is an MS spectrum of 2,9FrA2Nbf(III)-02.

FIGS. 134(A) and 134(B) is a $^1$H NMR spectrum of ph-2,9FrA2Nbf(III)-II.

FIG. 135 is an absorption spectrum and an emission spectrum of ph-2,9FrA2Nbf(III)-II in a toluene solution.

FIG. 136 is an absorption spectrum and an emission spectrum of ph-2,9FrA2Nbf(III)-II in a thin film state.

FIG. 137 is an MS spectrum of ph-2,9FrA2Nbf(III)-II.

FIGS. 138(A) and 138(B) is a $^1$H NMR spectrum of ph-3,10FrA2Nbf(IV)-02.

FIG. 139 is an absorption spectrum and an emission spectrum of ph-3,10FrA2Nbf(IV)-02 in a toluene solution.

FIG. 140 is an absorption spectrum and an emission spectrum of ph-3,10FrA2Nbf(IV)-02 in a thin film state.

FIG. 141 is an MS spectrum of ph-3,10FrA2Nbf(IV)-02.

FIGS. 142(A) and 142(B) is a $^1$H NMR spectrum of 3,10iPrFrA2Nbf(IV)-02.

FIG. 143 is an absorption spectrum and an emission spectrum of 3,10iPrFrA2Nbf(IV)-02 in a toluene solution.

FIG. 144 is an absorption spectrum and an emission spectrum of 3,10iPrFrA2Nbf(IV)-02 in a thin film state.

FIGS. 145(A) and 145(B) is an MS spectrum of 3,10iPrFrA2Nbf(IV)-02.

FIG. 146 is an absorption spectrum and an emission spectrum of 3,10ThA2Nbf(IV) in a toluene solution.

FIG. 147 is an absorption spectrum and an emission spectrum of 3,10ThA2Nbf(IV) in a thin film state.

FIG. 148 is an MS spectrum of 3,10ThA2Nbf(IV).

FIGS. 149(A) and 149(B) is a $^1$H NMR spectrum of 2,9PCBA2Nbf(III).

FIG. 150 is an absorption spectrum and an emission spectrum of 2,9PCBA2Nbf(III) in a toluene solution.

FIG. 151 is an absorption spectrum and an emission spectrum of 2,9PCBA2Nbf(III) in a thin film state.

FIG. 152 is an MS spectrum of 2,9PCBA2Nbf(III).

FIGS. 153(A) and 153(B) is a $^1$H NMR spectrum of 3,10mmtBuFrA2Nbf(IV)-02.

FIG. 154 is an absorption spectrum and an emission spectrum of 3,10mmtBuFrA2Nbf(IV)-02 in a toluene solution.

FIG. 155 is an MS spectrum of 3,10mmtBuFrA2Nbf(IV)-02.

FIGS. 156(A) and 156(B) is a $^1$H NMR spectrum of 3,10FrBA2Nbf(IV)-II.

FIG. 157 is an absorption spectrum and an emission spectrum of 3,10FrBA2Nbf(IV)-II in a toluene solution.

FIG. 158 is an absorption spectrum and an emission spectrum of 3,10FrBA2Nbf(IV)-II in a thin film state.

FIG. 159 is an MS spectrum of 3,10FrBA2Nbf(IV)-II.

FIG. 160 is a graph showing luminance-current density characteristics of a light-emitting element 10 to a light-emitting element 15.

FIG. 161 is a graph showing current efficiency-luminance characteristics of the light-emitting element 10 to the light-emitting element 15.

FIG. 162 is a graph showing luminance-voltage characteristics of the light-emitting element 10 to the light-emitting element 15.

FIG. 163 is a graph showing current-voltage characteristics of the light-emitting element 10 to the light-emitting element 15.

FIG. 164 is a graph showing power efficiency-luminance characteristics of the light-emitting element 10 to the light-emitting element 15.

FIG. 165 is a graph showing external quantum efficiency-luminance characteristics of the light-emitting element 10 to the light-emitting element 15.

FIG. 166 is emission spectra of the light-emitting element 10 to the light-emitting element 15.

FIG. 167 is a graph showing normalized luminance-temporal change characteristics of the light-emitting element 10 to the light-emitting element 15.

MODE FOR CARRYING OUT THE INVENTION

Embodiments of the present invention will be described below with reference to the drawings. Note that the present invention is not limited to the following description, and it will be readily appreciated by those skilled in the art that the modes and details can be changed in various ways without departing from the spirit and the scope of the present invention. Therefore, the present invention should not be construed as being limited to the description in the following embodiments.

Embodiment 1

An organic compound of one embodiment of the present invention is an organic compound represented by the following general formula (G1).

[Chemical Formula 14]

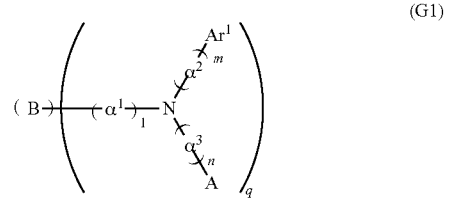

(G1)

In the above general formula (G1), B represents any of a substituted or unsubstituted naphthobisbenzofuran skeleton, a substituted or unsubstituted naphthobisbenzothiophene skeleton, and a substituted or unsubstituted naphthobenzofuranobenzothiophene skeleton. One or two substituted or unsubstituted arylamino groups are bonded to the skeleton B (that is, q is 1 or 2), and it is characterized that the arylamine is not amine including only a simple aryl group, e.g., only a phenyl group, but arylamine including at least one or more of a substituted or unsubstituted dibenzofuranyl group, a substituted or unsubstituted dibenzothiophenyl group, and a substituted or unsubstituted carbazolyl group.

In the above general formula (G1), A represents any of a substituted or unsubstituted dibenzofuranyl group, a substituted or unsubstituted dibenzothiophenyl group, and a substituted or unsubstituted carbazolyl group.

Furthermore, in the above general formula (G1), $Ar^1$ represents any of a substituted or unsubstituted aromatic hydrocarbon group having 6 to 25 carbon atoms, a substituted or unsubstituted dibenzofuranyl group, a substituted or unsubstituted dibenzothiophenyl group, and a substituted or unsubstituted carbazolyl group.

In the above general formula (G1), $\alpha^1$, $\alpha^2$, and $\alpha^3$ are each independently a substituted or unsubstituted bivalent aromatic hydrocarbon group having 6 to 25 carbon atoms, and 1, m, and n are each independently a numerical value of any of 0, 1, and 2.

A substituted or unsubstituted naphthobisbenzofuran skeleton, a substituted or unsubstituted naphthobisbenzothiophene skeleton, or a substituted or unsubstituted naphthobenzofuranobenzothiophene skeleton is a significantly useful skeleton as a luminophor of a light-emitting element. The organic compound has high emission efficiency and exhibits favorable blue light emission; thus, a light-emitting element using the organic compound can be a blue light-emitting element with favorable emission efficiency. A variety of substances have been developed as blue fluorescent materials, and this organic compound is a highly promising material as a blue light-emitting material for expressing a color gamut covering the ITU-R BT.2020 standard, which is an international standard for an ultra-wide color gamut based on an 8K display, because of its significantly favorable chromaticity of blue light emission.

The present inventors found that, in particular, a light-emitting element using an organic compound including special arylamine including, in addition to these skeletons, at least one or more of a substituted or unsubstituted dibenzofuranyl group, a substituted or unsubstituted dibenzothiophenyl group, and a substituted or unsubstituted carbazolyl group as described above is a light-emitting element having more favorable characteristics. Specifically, it has effects such as more favorable emission efficiency and more favorable color purity.

In the above general formula (G1), in some cases, one of or both $Ar^1$ and A represent any of a substituted or unsubstituted dibenzofuranyl group, a substituted or unsubstituted dibenzothiophenyl group, and a substituted or unsubstituted carbazolyl group; these are preferably groups represented by the following general formula (g1) to general formula (g3).

[Chemical Formulae 15]

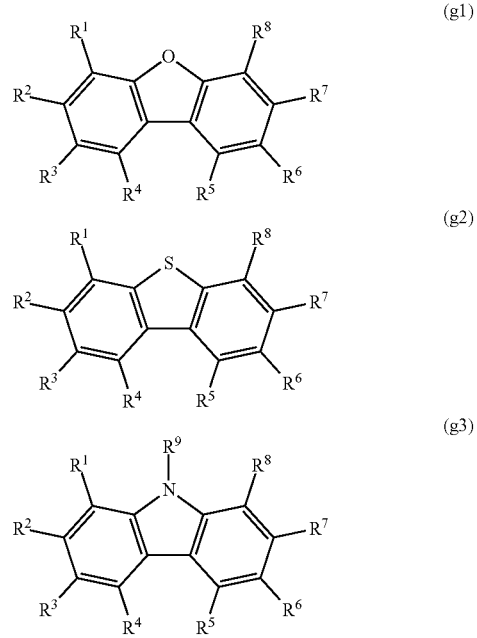

In the above general formula (g1) to general formula (g3), any one of $R^1$ to $R^9$ represents a single bond and the others each independently represent any of hydrogen, a hydrocarbon group having 1 to 10 carbon atoms, a cyclic hydrocarbon group having 3 to 10 carbon atoms, and a substituted or unsubstituted aromatic hydrocarbon group having 6 to 14 carbon atoms. Note that in the case where A is the group represented by the above general formula (g3) and $R^9$ in the group represented by the above general formula (g3) represents a single bond, n is 1 or 2. Furthermore, in the case where $Ar^1$ is the group represented by the above general formula (g3) and $R^9$ in the group represented by the above general formula (g3) represents a single bond, m is 1 or 2.

In the case where one of or both $Ar^1$ and A are the group represented by the above general formula (g1), any one of $R^1$ to $R^3$ is preferably a single bond. In the case where one of or both $Ar^1$ and A are the group represented by the above general formula (g2), any one of $R^1$ to $R^3$ is preferably a single bond. In the case where one of or both $Ar^1$ and A are the group represented by the above general formula (g3), $R^2$ or $R^3$ is preferably a single bond.

Note that a single bond here refers to an atomic bonding with $\alpha^2$, $\alpha^3$, or nitrogen (amine) in the above general formula (G1).

Unless A in the above general formula (G1) is the group represented by the above general formula (g3) and $R^9$ is a single bond, a structure where n is 0 is preferable because the number of synthesis steps is small and the sublimation temperature is low. Furthermore, 1 and n are each preferably 0 regardless of A because the number of synthesis steps is small and the sublimation temperature is low.

In the case where A in the above general formula (G1) is the group represented by the above general formula (g3) and $R^9$ is a single bond, a structure where n is 1 is preferable because it is easily synthesized and chemically stable. Also in the case where $Ar^1$ is the group represented by the above general formula (g3) and $R^9$ is a single bond, a structure where m is 1 is preferable for the same reason.

Furthermore, it is preferable that one of or both A and $Ar^1$ in the general formula (G1) be the group represented by the above general formula (g1) or the group represented by the above general formula (g2), preferably the group represented by the above general formula (g1), because the organic compound represented by the above general formula (G1) emits light with a short wavelength. In that case, the position of the single bond bonded to $\alpha^2$, $\alpha^3$, or nitrogen (amine) in the group represented by the above general formula (g1) or the group represented by the above general formula (g2) is preferably $R^1$ or $R^2$ because the organic compound represented by the above general formula (G1) emits light with a shorter wavelength. Furthermore, the position of the single bond bonded to $\alpha^2$, $\alpha^3$, or nitrogen (amine) in the group represented by the above general formula (g1) or the group represented by the above general formula (g2) is preferably $R^2$ or $R^3$ because the emission quantum yield becomes higher. Furthermore, the position of the single bond is preferably $R^2$ because the emission spectrum becomes narrower.

Furthermore, one of or both $Ar^1$ and A in the general formula (G1) are preferably the group represented by the above general formula (g3) because the reliability can be favorable.

Furthermore, $Ar^1$ is preferably a substituted or unsubstituted aromatic hydrocarbon group having 6 to 25 carbon atoms because the sublimation temperature can be low.

Furthermore, the emission quantum yield can be higher when q is 2, which is preferable. The sublimation temperature can be lower when q is 1, which is preferable.

Note that in this specification, the sublimation temperature also means an evaporation temperature.

Typical examples of a group represented by A in the above general formula (G1) are shown in the following structural formulae (Ar-50) to (Ar-66). Note that these may further have a substituent such as a hydrocarbon group having 1 to 10 carbon atoms, a cyclic hydrocarbon group having 3 to 10 carbon atoms, or a substituted or unsubstituted aromatic hydrocarbon group having 6 to 14 carbon atoms.

[Chemical Formulae 16]

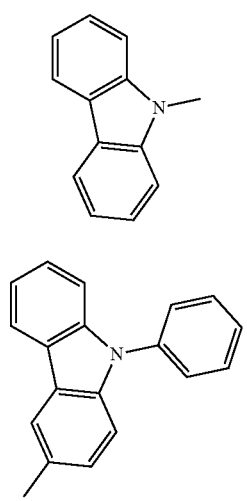

(Ar-50)

(Ar-51)

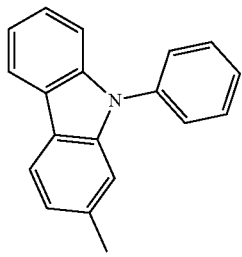

(Ar-52)

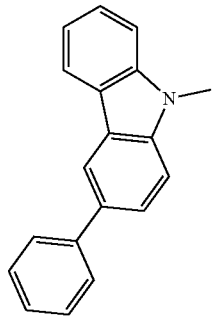

(Ar-53)

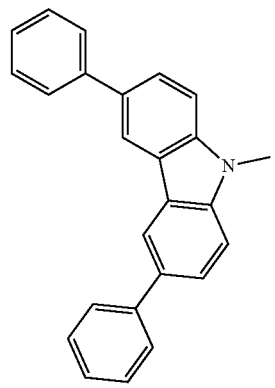

(Ar-54)

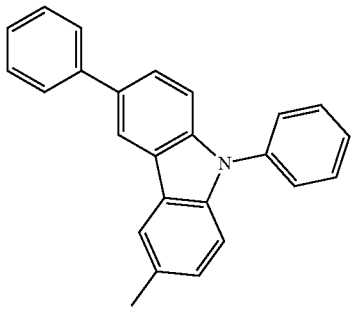

(Ar-55)

(Ar-56)
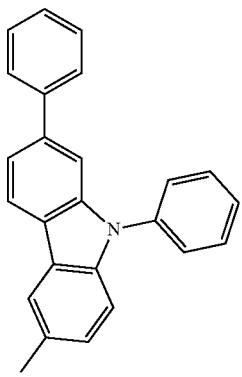

(Ar-57)
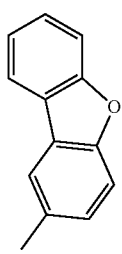

(Ar-58)
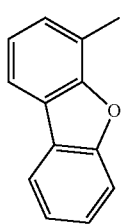

(Ar-59)
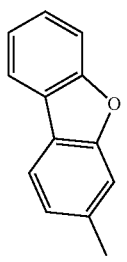

(Ar-60)
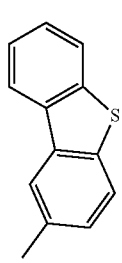

(Ar-61)
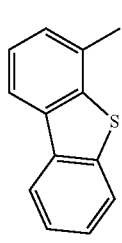

(Ar-62)
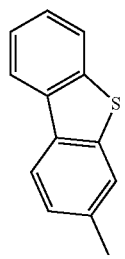

(Ar-63)
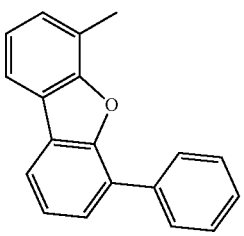

(Ar-64)

(Ar-65)

(Ar-66)

Furthermore, Ar$^1$ in the above general formula (G1) represents any of a substituted or unsubstituted aromatic hydrocarbon group having 6 to 25 carbon atoms, a substituted or unsubstituted dibenzofuranyl group, a substituted or unsubstituted dibenzothiophenyl group, and a substituted or unsubstituted carbazolyl group. As the substituted or unsubstituted aromatic hydrocarbon group having 6 to 25 carbon atoms, specifically, a phenyl group, a biphenyl group, a terphenyl group, a naphthyl group, a fluorenyl group, a dimethylfluorenyl group, a spirofluorenyl group, a diphenylfluorenyl group, a phenanthryl group, an anthryl group, a dihydroanthryl group, a triphenylenyl group, a pyrenyl group, and the like can be given. Typical examples of $Ar^1$ are shown in the following structural formulae (Ar-50) to (Ar-66), (Ar-100) to (Ar-119), and (Ar-130) to (Ar-140). Note that these may further have a substituent such as a hydrocarbon group having 1 to 10 carbon atoms, a cyclic hydrocarbon group having 3 to 10 carbon atoms, or a substituted or unsubstituted aromatic hydrocarbon group having 6 to 14 carbon atoms.

[Chemical Formulae 17]

(Ar-50)

(Ar-51)

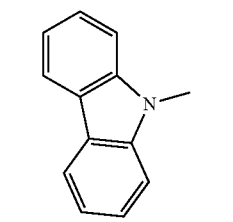

(Ar-52)

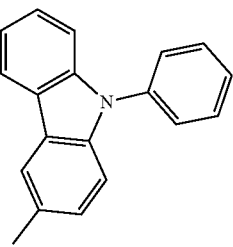

(Ar-53)

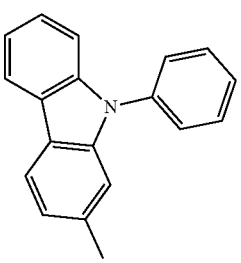

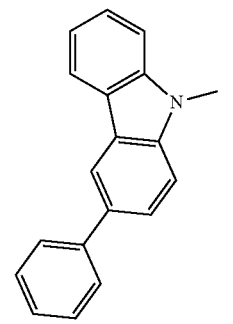

(Ar-54)

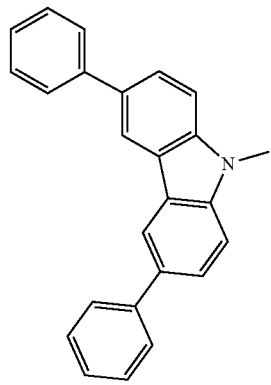

(Ar-55)

(Ar-56)

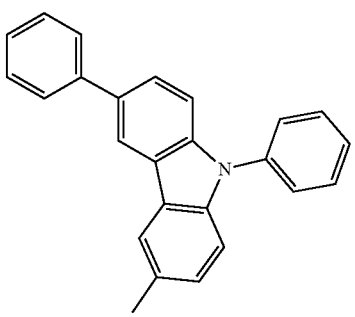

(Ar-57)

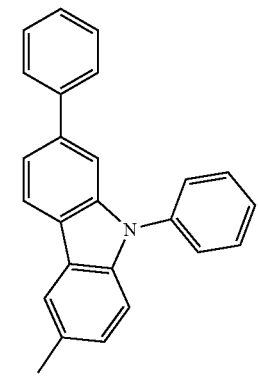

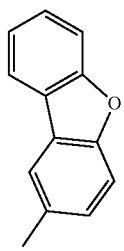

(Ar-58)

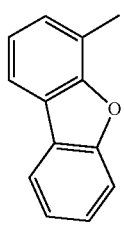

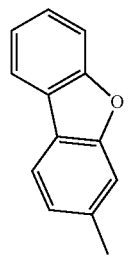 (Ar-59)
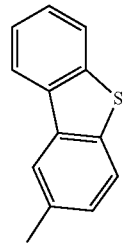 (Ar-60)
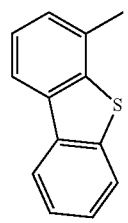 (Ar-61)
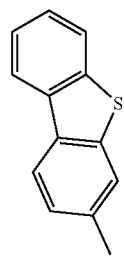 (Ar-62)
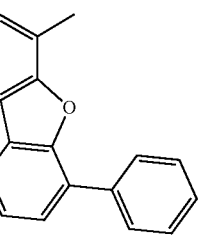 (Ar-63)
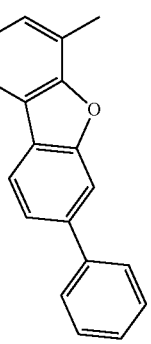 (Ar-64)
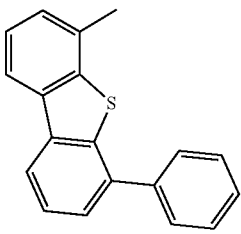 (Ar-65)
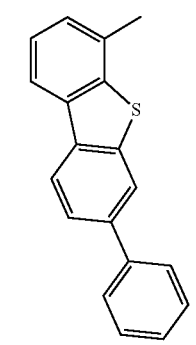 (Ar-66)
[Chemical Formulae 18]
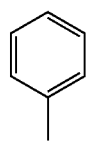 (Ar-100)
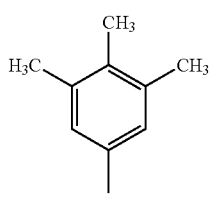 (Ar-101)
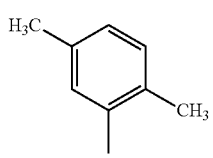 (Ar-102)
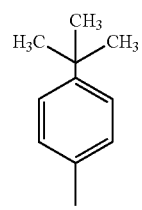 (Ar-103)
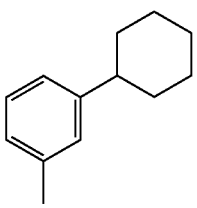 (Ar-104)

(Ar-105) 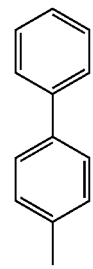
(Ar-106) 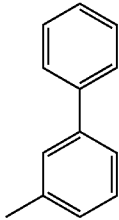
(Ar-107) 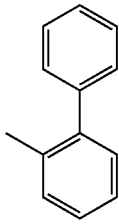
(Ar-108) 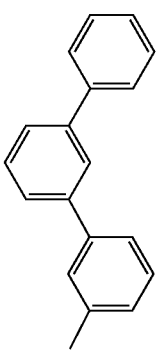
(Ar-109) 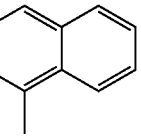
(Ar-110) 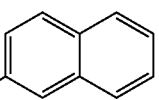
(Ar-111) 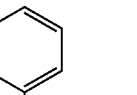
(Ar-112) 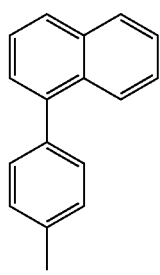
(Ar-113) 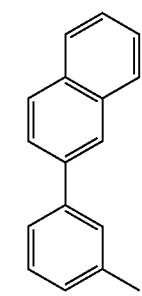
(Ar-114) 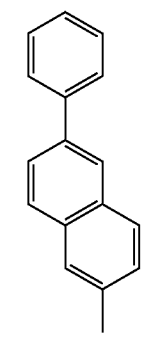
(Ar-115) 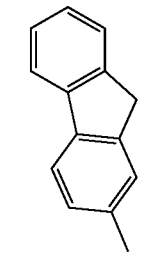
(Ar-116) 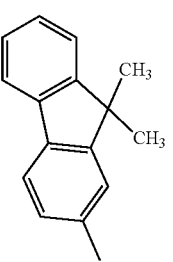

(Ar-117)
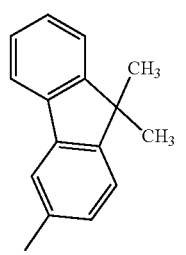
(Ar-118)
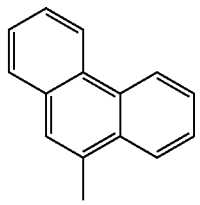
(Ar-119)
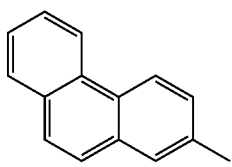
[Chemical Formulae 19]
(Ar-130)
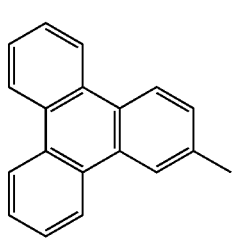
(Ar-131)
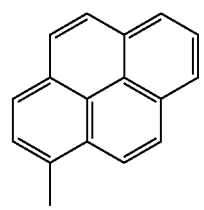
(Ar-132)
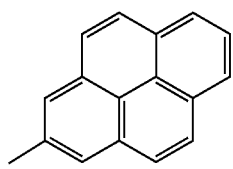
(Ar-133)
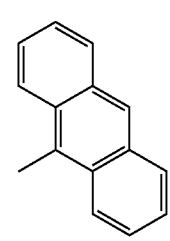
(Ar-134)
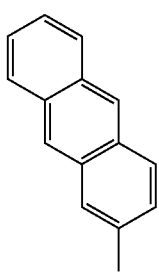
(Ar-135)
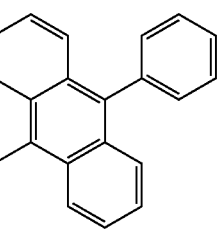
(Ar-136)
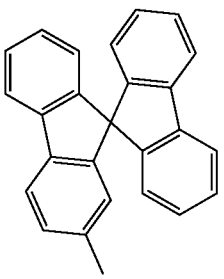
(Ar-137)
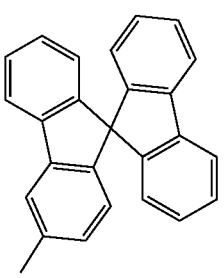
(Ar-138)
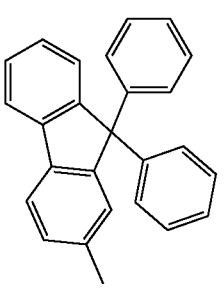
(Ar-139)
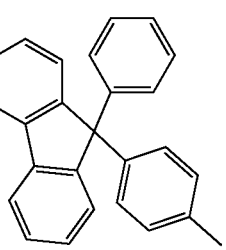

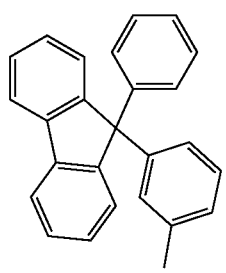
(Ar-140)

Note that an organic compound having a structure where a carbazolyl group is bonded to $\alpha^2$, $\alpha^3$, or nitrogen (amine) in the general formula (G1) at the 9-position, like (Ar-50), (Ar-53), and (Ar-54), is preferable because conjugation is less likely to extend and light emission with a short wavelength can be obtained.

Furthermore, an organic compound in which a carbazolyl group is bonded to $\alpha^2$, $\alpha^3$, or nitrogen (amine) in the general formula (G1) at the 3-position, an organic compound having a structure where a dibenzofuranyl group is bonded thereto at the 2-position, and an organic compound having a structure where a dibenzothiophenyl group is bonded thereto at the 2-position, like (Ar-51), (Ar-55), (Ar-56), (Ar-57), and (Ar-60), are preferable because they have effects in that conjugation is likely to extend, the hole-transport property is high, light emission with a long wavelength is obtained, and the reliability is favorable. In particular, those effects are prominent in the case of the carbazolyl group.

Furthermore, an organic compound having a structure where a carbazolyl group is bonded to $\alpha^2$, $\alpha^3$, or nitrogen (amine) in the general formula (G1) at the 2-position, an organic compound having a structure where a dibenzofuranyl group is bonded thereto at the 3-position, and an organic compound having a structure where a dibenzothiophenyl group is bonded thereto at the 3-position, like (Ar-52), (Ar-59), and (Ar-62), are preferable because the carrier-transport property is high and the driving voltage is expected to be reduced.

Furthermore, an aryl group is preferably bonded to the 9-position of a carbazolyl group, like in (Ar-51), (Ar-52), (Ar-55), and (Ar-56), because an effect such as favorable reliability can be obtained.

Furthermore, an organic compound having a structure where a dibenzofuranyl group is bonded to $\alpha^2$, $\alpha^3$, or nitrogen (amine) in the general formula (G1) at the 4-position, and an organic compound having a structure where a dibenzothiophenyl group is bonded thereto at the 4-position, like (Ar-58), (Ar-61), and (Ar-63) to (Ar-66), are preferable because conjugation is less likely to extend, light emission with a short wavelength is obtained, and the reliability is favorable.

Furthermore, the one to which a phenyl group is connected, like (Ar-100) to (Ar-108), is preferable because conjugation is less likely to extend and the emission wavelength is short.

Furthermore, like (Ar-100) to (Ar-119), the one in which the number of fusions of six-membered rings is two or less such as a benzene ring, a naphthalene ring, or a fluorene ring is preferable, or the one in which, to a six-membered ring, other six-membered rings are fused to only the a-face, the c-face, and the e-face even when the number of fusions of six-membered rings is three or more and which is formed with hydrocarbon, such as a phenanthrene ring, is preferable because conjugation is less likely to extend and the emission wavelength is short.

In the above general formula (G1), $\alpha^1$ to $\alpha^3$ each independently represent a substituted or unsubstituted bivalent aromatic hydrocarbon group having 6 to 25 carbon atoms; specifically, a phenylene group, a biphenylene group, a terphenylene group, a naphthylene group, a fluorenylene group, a dimethylfluorenyl group, and the like can be given. As typical examples of $\alpha^1$ to $\alpha^3$, groups represented by the following structural formulae (Ar-1) to (Ar-33) can be given. Note that these may further have a substituent such as a hydrocarbon group having 1 to 10 carbon atoms, a cyclic hydrocarbon group having 3 to 10 carbon atoms, or a substituted or unsubstituted aromatic hydrocarbon group having 6 to 14 carbon atoms.

[Chemical Formulae 20]

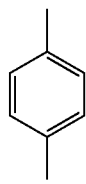
(Ar-1)

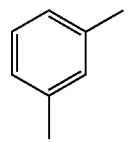
(Ar-2)

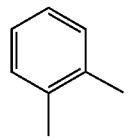
(Ar-3)

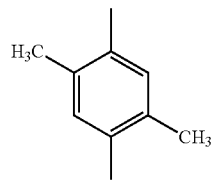
(Ar-4)

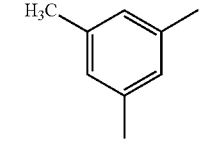
(Ar-5)

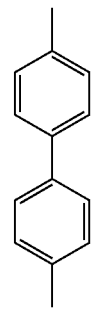
(Ar-6)

[Chemical Formulae 21]
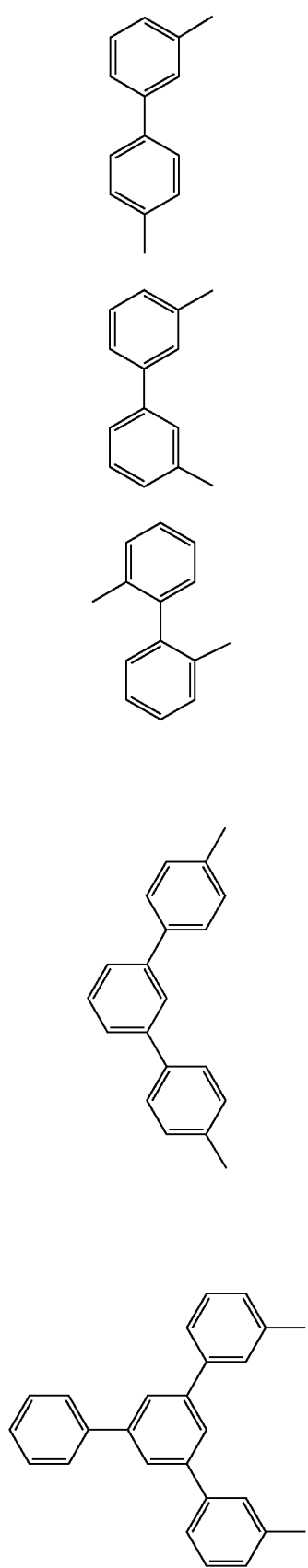
(Ar-7)
(Ar-8)
(Ar-9)
(Ar-10)
(Ar-11)
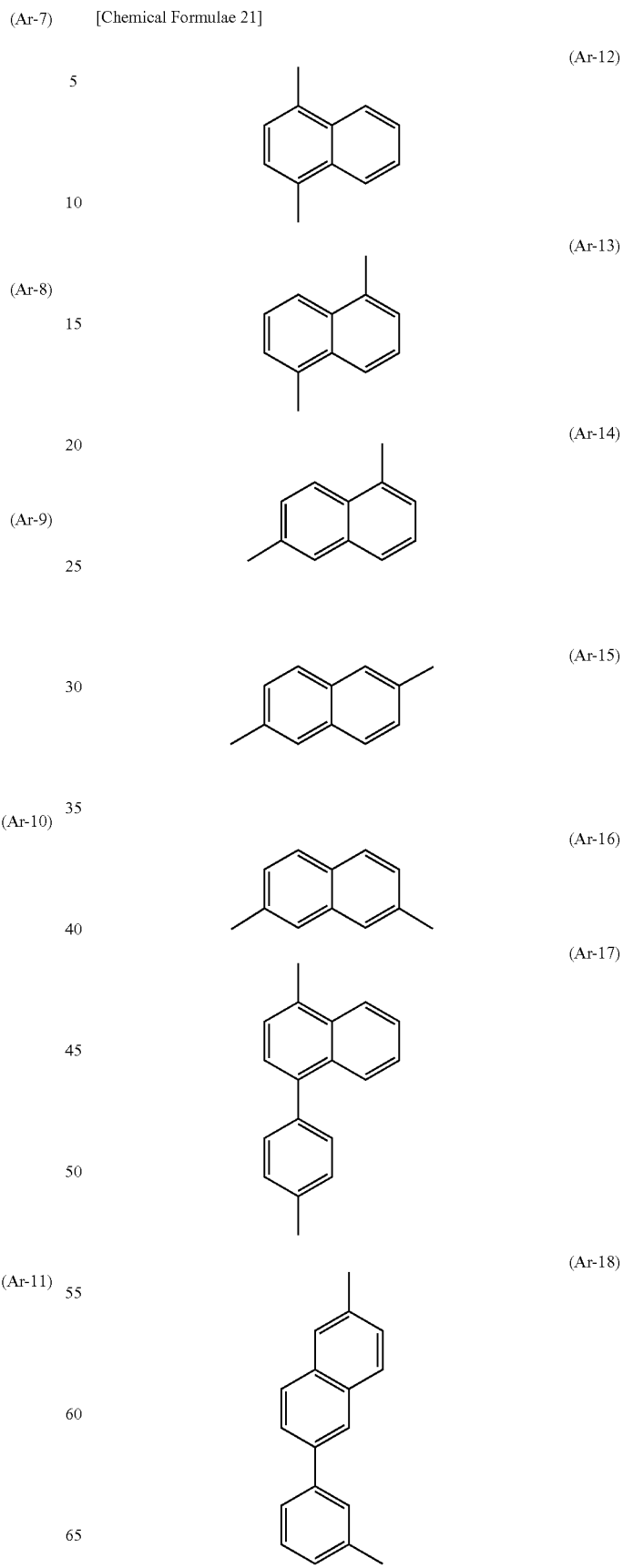
(Ar-12)
(Ar-13)
(Ar-14)
(Ar-15)
(Ar-16)
(Ar-17)
(Ar-18)

(Ar-19) 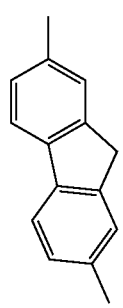

(Ar-20) 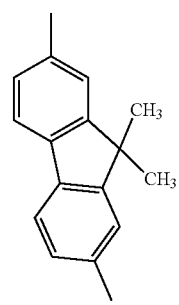

(Ar-21) 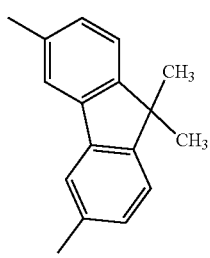

(Ar-22) 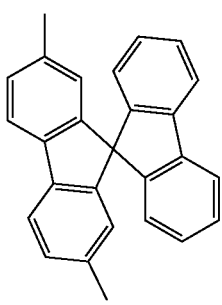

(Ar-23) 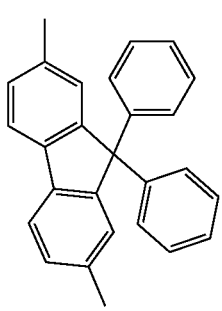

(Ar-24) 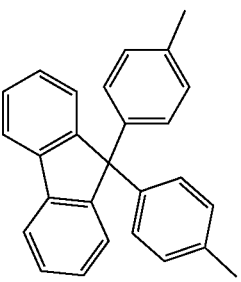

(Ar-25) 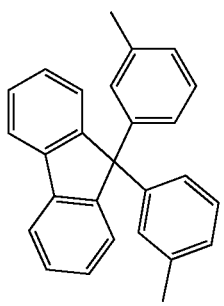

(Ar-26) 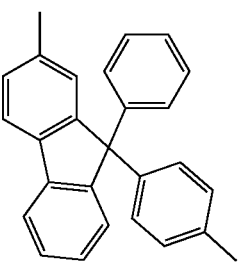

(Ar-27) 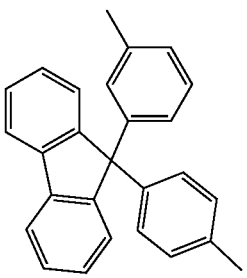

Note that, like (Ar-1) to (Ar-11), $\alpha^1$ to $\alpha^3$ are preferably a phenylene group or a group where some phenylene groups are connected because conjugation is less likely to extend and the singlet excitation level is kept high. In particular, a structure including a meta-phenylene group is preferable because those effects are prominent. Furthermore, a structure where $\alpha^1$ to $\alpha^3$ are para-phenylene groups is preferable because the reliability as a light-emitting material is high. Furthermore, like in (Ar-24) to (Ar-27), in the case where substituents are connected via carbon having a sigma bond at, for example, the 9-position of fluorene, conjugation is less likely to extend, the SI level is kept high, and thus the emission wavelength becomes shorter, which is preferable.

In the case where 1, m, and n are each 2, different substituents may be connected to each other in $\alpha^1$, $\alpha^2$, and $\alpha^3$. For example, in (Ar-17) and (Ar-18), naphthylene and phenylene are connected to each other.

In the organic compound represented by the above general formula (G1), a substituted or unsubstituted naphtho-bisbenzofuran skeleton, a substituted or unsubstituted naphthobisbenzothiophene skeleton, or a substituted or unsubstituted naphthobenzofuranobenzothiophene skeleton, which is represented by B, is preferably any of skeletons represented by the following general formulae (B1) to (B4).

[Chemical Formulae 22]

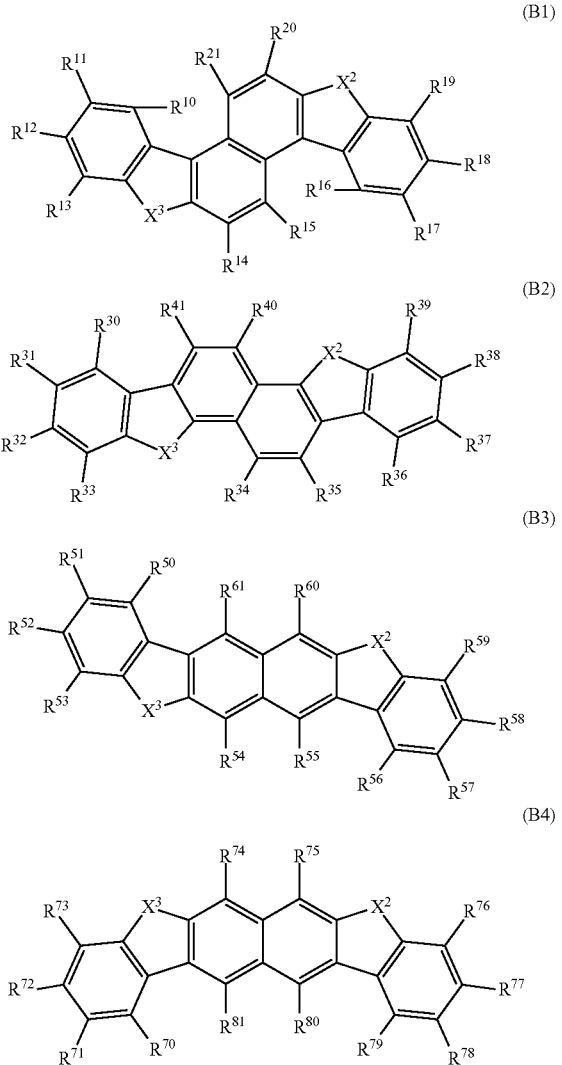

In the above general formula (B1) to general formula (B4), $X^2$ and $X^3$ each independently represent an oxygen atom or a sulfur atom. Note that these two are preferably the same atom for easy synthesis. A structure where both of them are oxygen atoms is preferable because there are effects in that the synthesis is easy, the singlet excitation level is high, light emission with a shorter wavelength is obtained, and high emission quantum yield is obtained. The larger the number of oxygen atoms of $X^2$ and $X^3$ is, the shorter the wavelength of exhibited light emission becomes. The larger the number of sulfur atoms of $X^2$ and $X^3$ is, the longer the wavelength of exhibited light emission becomes. Thus, they can be selected as appropriate according to an objective single excitation level and an objective emission wavelength.

The emission wavelength of the organic compound represented by the above general formula (G1) tends to be changed depending on the skeleton represented by B. The emission wavelength becomes longer in the order that B is a skeleton represented by the general formula (B2), a skeleton represented by the general formula (B4), a skeleton represented by the general formula (B1), and a skeleton represented by the general formula (B3). Therefore, the above skeleton may be selected in accordance with the objective emission color. In the case where blue emission with a shorter wavelength is desired, a compound represented by the general formula (B2) is preferable. In the case where blue emission with a relatively long wavelength is desired, a compound represented by the general formula (B3) is preferable.

In the organic compound represented by the above general formula (G1), the skeleton represented by B is preferably the skeleton represented by the general formula (B3) because the emission spectrum becomes narrower and light emission with high color purity can be obtained.

In the skeleton represented by the above general formula (B1), any one or two of $R^{10}$ to $R^{21}$ represent a single bond, and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms. Note that any one or two of $R^{11}$, $R^{12}$, $R^{17}$, and $R^{18}$ of $R^{10}$ to $R^{21}$ are preferably a single bond for easy synthesis.

Note that in the case where any two of $R^{10}$ to $R^{21}$ in the above general formula (B1) are a single bond (that is, in the case where q in the above general formula (G1) is 2), one of $R^{11}$ and $R^{12}$ and one of $R^{17}$ and $R^{18}$ are preferably a single bond for easy synthesis. In that case, in terms of obtaining light emission with a long wavelength, $R^{11}$ and $R^{17}$ are preferably a single bond; for obtaining light emission with a short wavelength, favorable light emission quantum efficiency, a high molar absorption coefficient, and favorable reliability at the time of light emission, $R^{12}$ and $R^{18}$ are preferably a single bond.

Furthermore, in the above general formula (B2), any one or two of $R^{30}$ to $R^{41}$ represent a single bond and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms. Note that any one or two of $R^{31}$, $R^{32}$, $R^{37}$, and $R^{38}$ of $R^{30}$ to $R^{41}$ are preferably a single bond for easy synthesis.

Note that in the case where any two of $R^{30}$ to $R^{41}$ in the above general formula (B2) are a single bond (that is, in the case where q in the above general formula (G1) is 2), one of $R^{31}$ and $R^{32}$ and one of $R^{37}$ and $R^{38}$ are preferably a single bond for easy synthesis. In that case, in terms of obtaining light emission with a long wavelength, $R^{31}$ and $R^{37}$ are preferably a single bond; for obtaining light emission with a short wavelength, favorable light emission quantum efficiency, a high molar absorption coefficient, and favorable reliability at the time of light emission, $R^{32}$ and $R^{38}$ are preferably a single bond.

Furthermore, in the above general formula (B3), any one or two of $R^{50}$ to $R^{61}$ represent a single bond and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group. Note that any one or two of $R^{51}$, $R^{52}$, $R^{57}$, and $R^{58}$ of $R^{50}$ to $R^{61}$ are preferably a single bond for easy synthesis.

Note that in the case where any two of $R^{50}$ to $R^{61}$ in the above general formula (B3) are a single bond (that is, in the case where q in the above general formula (G1) is 2), one of $R^{51}$ and $R^{52}$ and one of $R^{57}$ and $R^{58}$ are preferably a single bond for easy synthesis. In that case, in terms of obtaining light emission with a long wavelength, $R^{51}$ and $R^{57}$ are preferably a single bond; for obtaining light emission with a short wavelength, favorable light emission quantum efficiency, a high molar absorption coefficient, and favorable reliability at the time of light emission, $R^{52}$ and $R^{58}$ are preferably a single bond.

Furthermore, in the above general formula (B4), any one or two of $R^{70}$ to $R^{81}$ represent a single bond and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms. Note that any one or two of $R^{71}$, $R^{72}$, $R^{77}$, and $R^{78}$ of $R^{70}$ to $R^{81}$ are preferably a single bond for easy synthesis.

Note that in the case where any two of $R^{70}$ to $R^{81}$ in the above general formula (B4) are a single bond (that is, in the case where q in the above general formula (G1) is 2), one of R and $R^{72}$ and one of $R^{77}$ and $R^{78}$ are preferably a single bond for easy synthesis. In that case, in terms of obtaining light emission with a long wavelength, $R^{71}$ and $R^{78}$ are preferably a single bond; for obtaining light emission with a short wavelength, favorable light emission quantum efficiency, a high molar absorption coefficient, and favorable reliability at the time of light emission, $R^{72}$ and $R^{77}$ are preferably a single bond.

Note that a single bond here refers to an atomic bonding with $\alpha^1$ or nitrogen (amine) in the above general formula (G1).

In the above general formula (B1) to general formula (B4), the substituents represented by $R^{10}$ to $R^{21}$, $R^{30}$ to $R^{41}$, $R^{50}$ to $R^{61}$, and $R^{70}$ to $R^{81}$ other than the single bond are preferably hydrogen for easy synthesis and low sublimation temperature. However, with the use of substituents other than hydrogen, the heat resistance, the solubility in a solvent, and the like can be improved, and the emission wavelength can be shifted to a long wavelength.

Note that the organic compound represented by the above general formula (G1) is preferably an organic compound represented by the following general formula (G1-1).

[Chemical Formula 23]

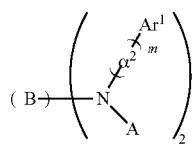

(G1-1)

Note that, in the above general formula (G1-1), B is a group represented by the following general formula (B1-1) or (B3-1). Furthermore, $Ar^1$ is a substituted or unsubstituted aromatic hydrocarbon group having 6 to 25 carbon atoms, and A is a group represented by the following general formula (g0). Furthermore, m represents an integer of 0 to 2. Furthermore, $\alpha^2$ is a substituted or unsubstituted bivalent aromatic hydrocarbon group having 6 to 14 carbon atoms.

[Chemical Formulae 24]

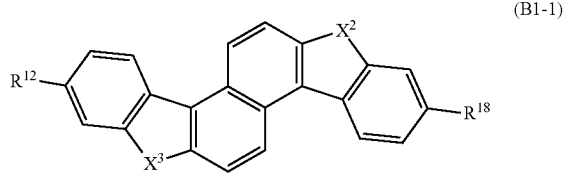

(B1-1)

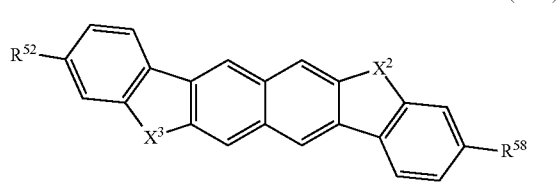

(B3-1)

Note that, in the above general formula (B1-1) or (B3-1), $X^2$ and $X^3$ each independently represent an oxygen atom or a sulfur atom. Furthermore, $R^{12}$, $R^{18}$, $R^{52}$, and $R^{58}$ represent a single bond.

[Chemical Formula 25]

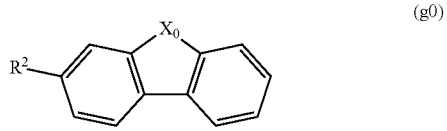

(g0)

Note that, in the above general formula (g0), $X_0$ is an oxygen atom or a nitrogen atom to which a substituted or unsubstituted phenyl group is bonded. Furthermore, $R^2$ represents a single bond.

Note that the molecular weight of the organic compound represented by the above general formula (G1) or (G1-1) may be 1300 or less, preferably 1000 or less in consideration of sublimation property. The molecular weight is preferably 650 or more in consideration of film quality.

Note that in the case where a skeleton or a group bonded to the above organic compound has a substituent, the substituent is preferably any of a hydrocarbon group having 1 to 10 carbon atoms, a cyclic hydrocarbon group having 3 to 10 carbon atoms, and an aromatic hydrocarbon group having 6 to 14 carbon atoms.

As the hydrocarbon group having 1 to 10 carbon atoms of the above substituent represented by R or a substituent further bonded to the substituent, a methyl group, an ethyl group, a propyl group, an isopropyl group, a butyl group, a tert-butyl group, a pentyl group, a hexyl group, a heptyl group, an octyl group, a nonyl group, a decyl group, an icosyl group, and the like can be given. As the cyclic hydrocarbon group having 3 to 10 carbon atoms, a cyclopropyl group, a cyclohexyl group, and the like can be given. As the aromatic hydrocarbon group having 6 to 14 carbon atoms, a phenyl group, a biphenyl group, a naphthyl group, a phenanthryl group, an anthryl group, a fluorenyl group, and the like can be given.

In the case where the above substituent represented by R is a diarylamino group having 12 to 32 carbon atoms, it is more preferable that two aryl groups included in the diarylamino group be each independently an aromatic hydrocarbon group having 6 to 16 carbon atoms. As the aromatic hydrocarbon group, a phenyl group, a biphenyl group, a naphthyl group, a phenanthryl group, an anthryl group, a fluorenyl group, a naphthyl phenyl group, and the like can be given.

Among them, the aromatic hydrocarbon group having 6 to 14 carbon atoms and the diarylamino group having 12 to 32 carbon atoms may further have, as a substituent, an aliphatic hydrocarbon group having 1 to 6 carbon atoms, an alicyclic hydrocarbon group having 3 to 6 carbon atoms, or the like.

Examples of the organic compound of the present invention with the above structure are shown below.

[Chemical Formulae 26]

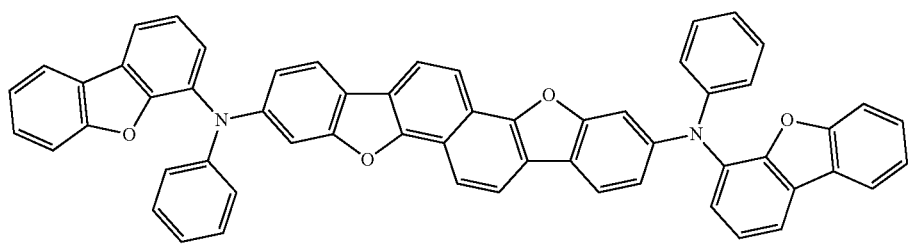

(100)

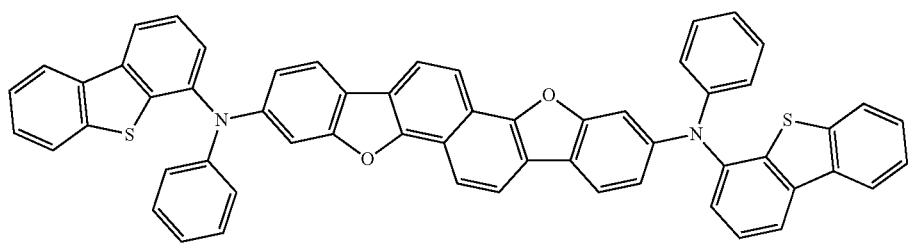

(101)

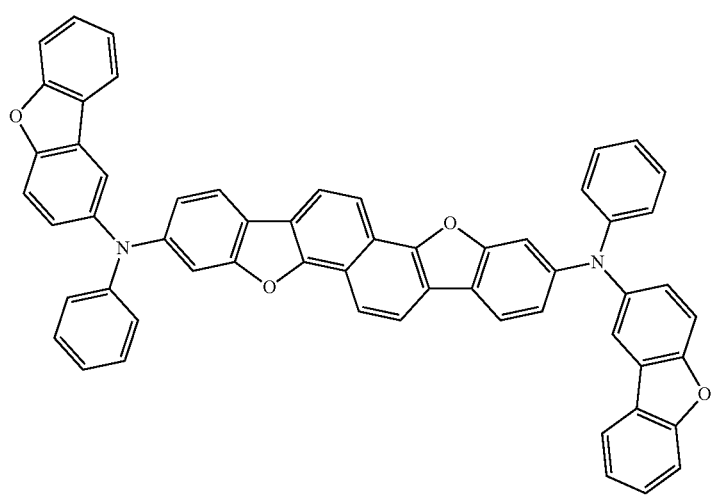

(102)

(103)
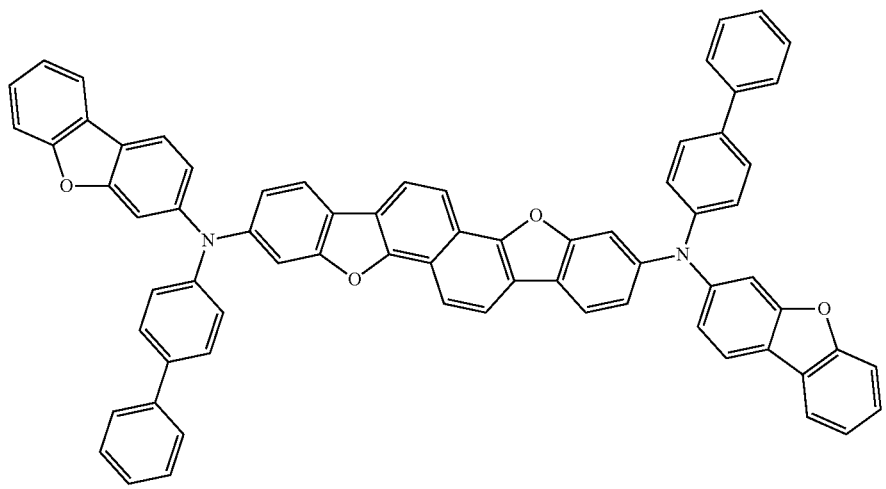
(104)
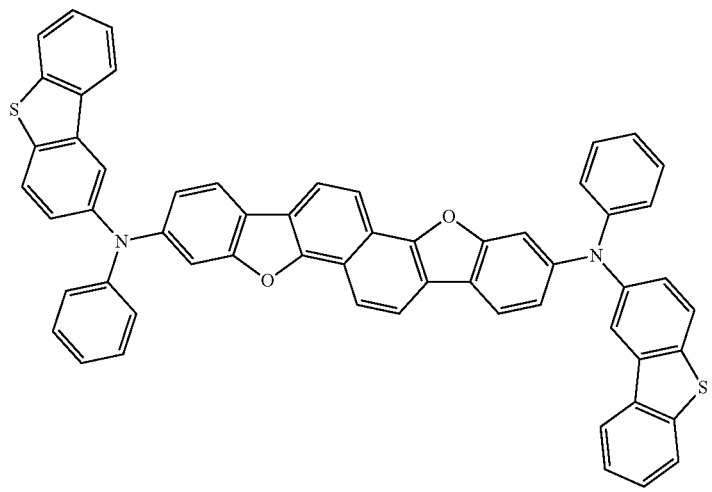
(105)
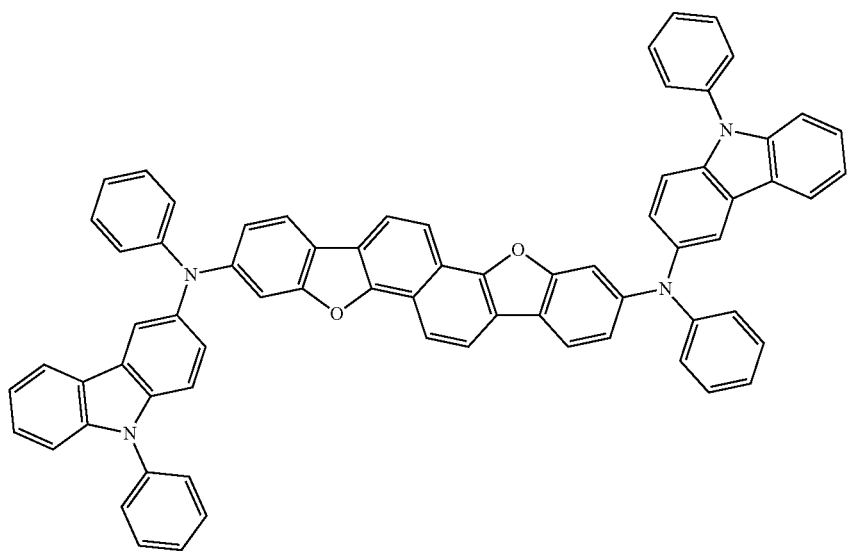

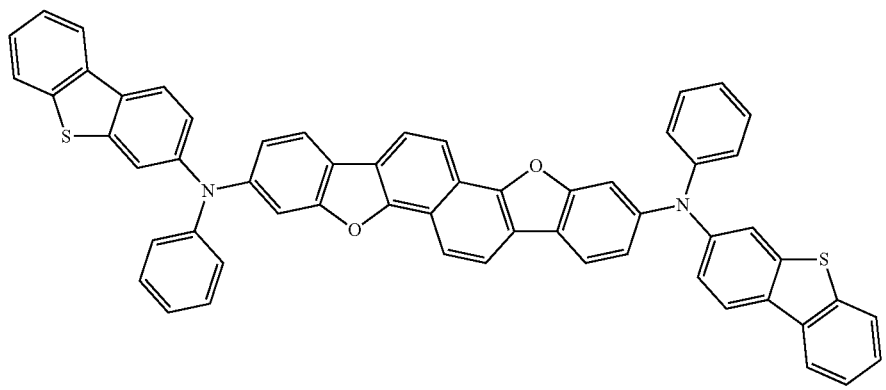
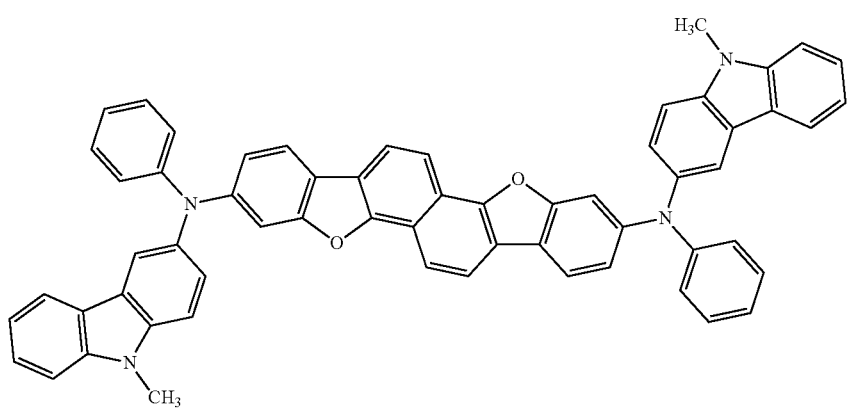
(106)
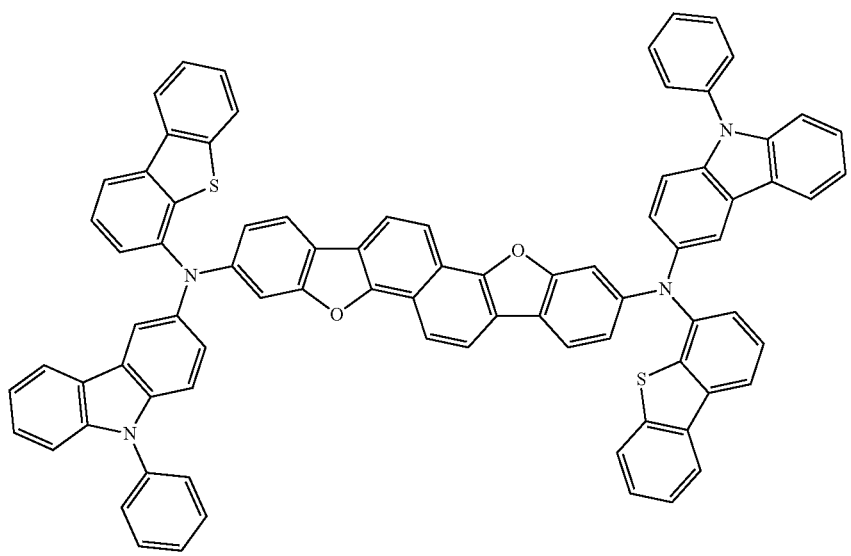
(107)

[Chemical Formulae 27]
(108)
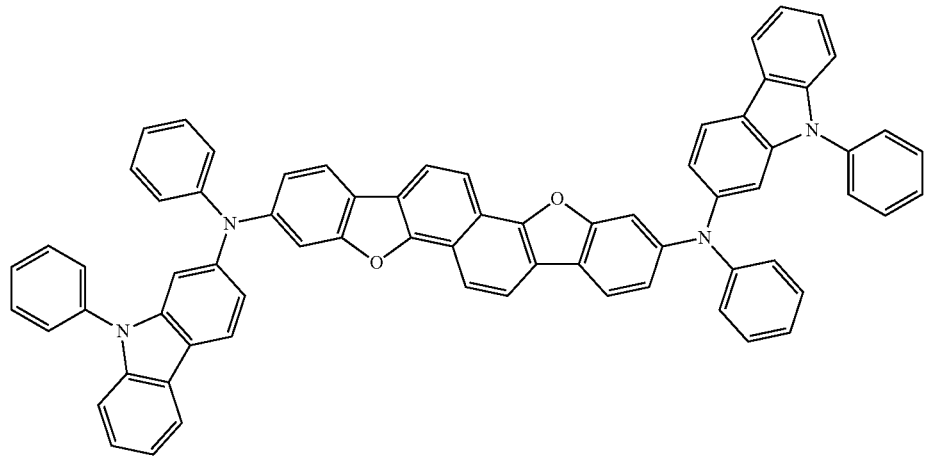
(109)
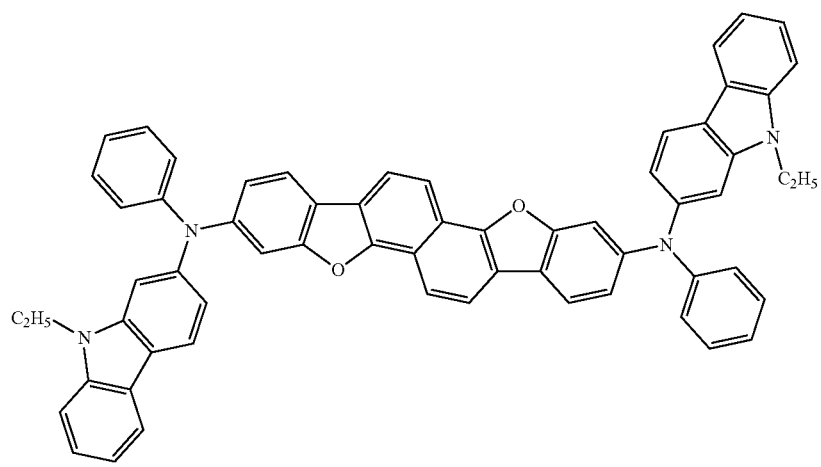
(110)
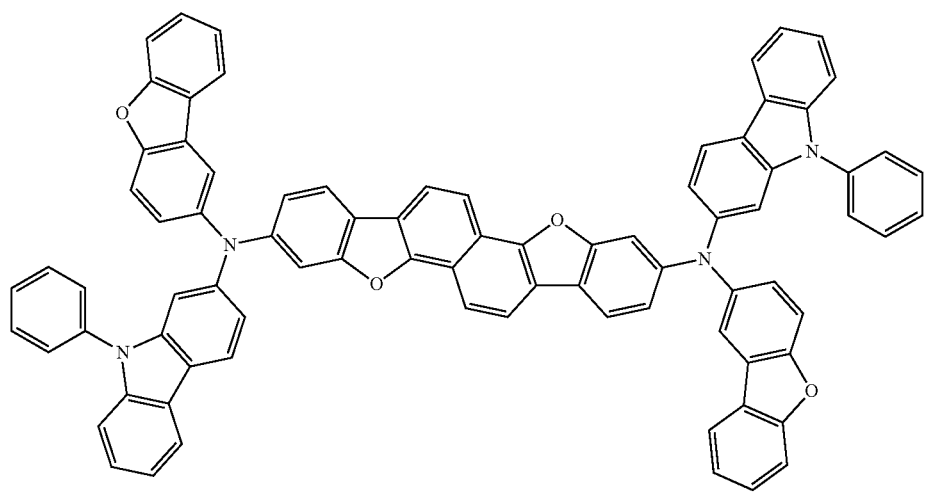

-continued
(111)
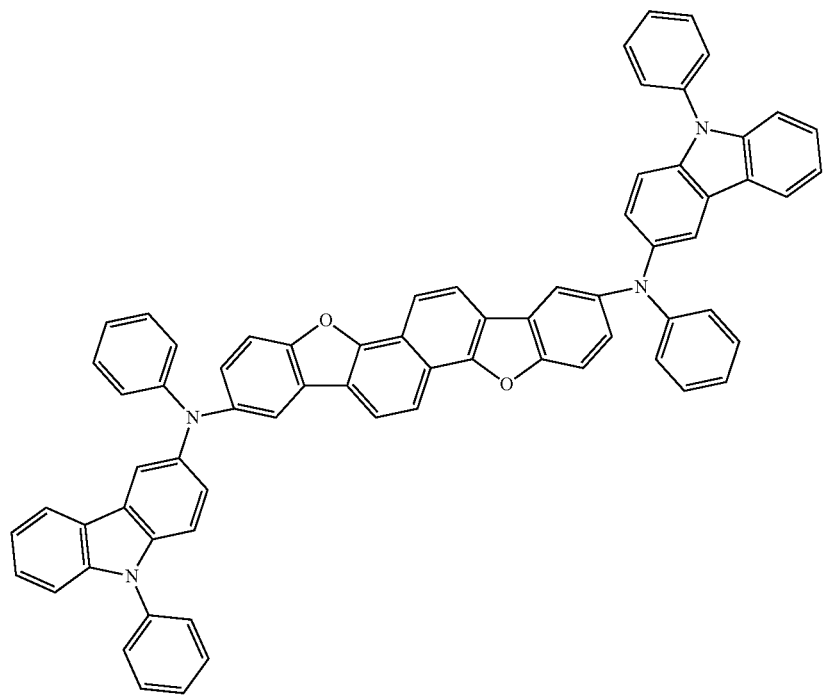
(112)
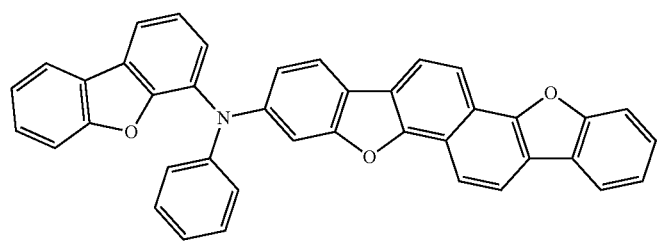
(113)
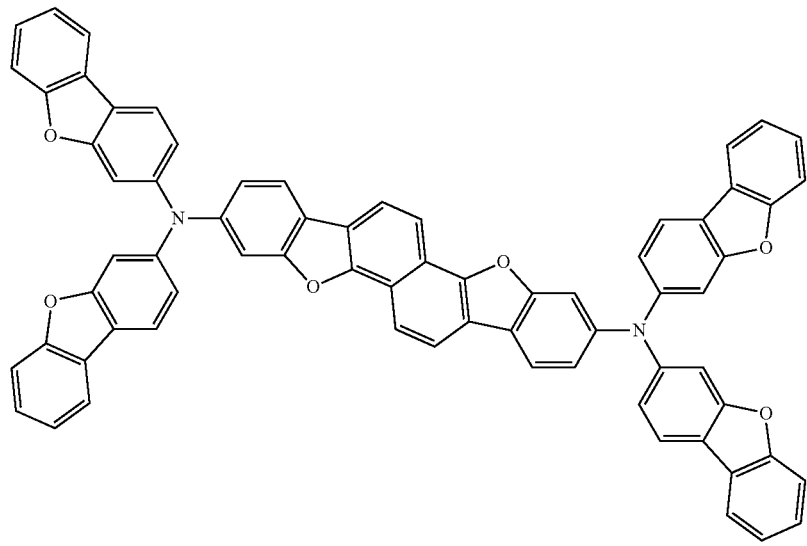

(114)
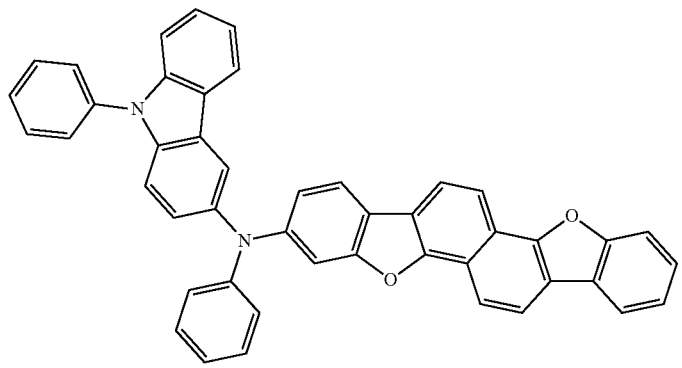
(115)
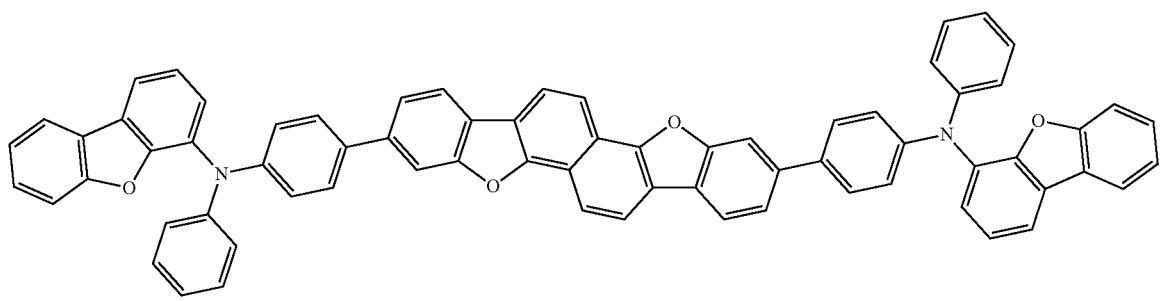
(116)
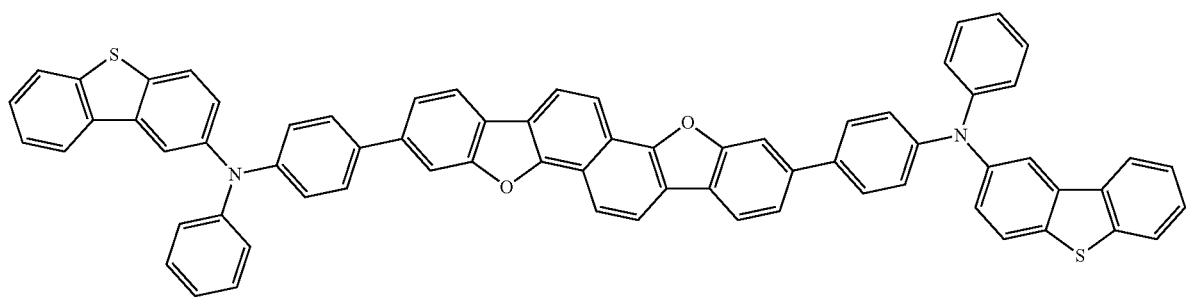
(117)
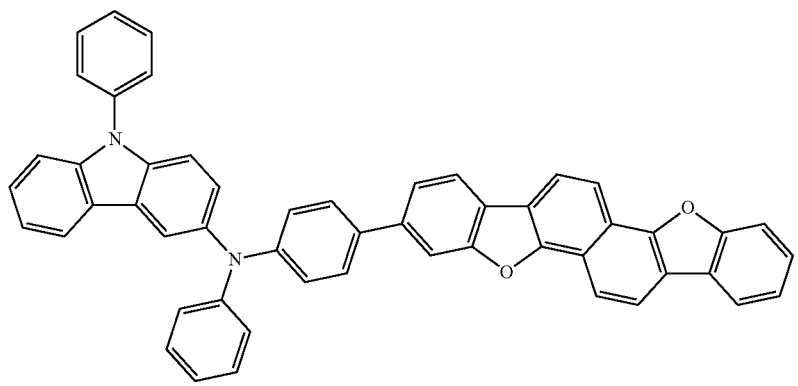

[Chemical Formulae 28]
(118)
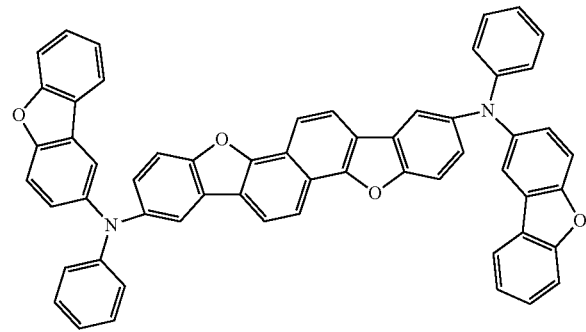
(119)
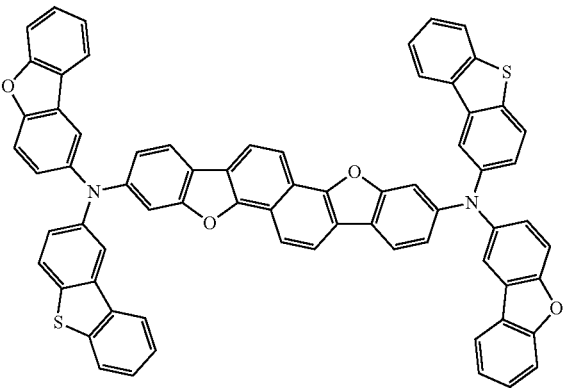
(120)
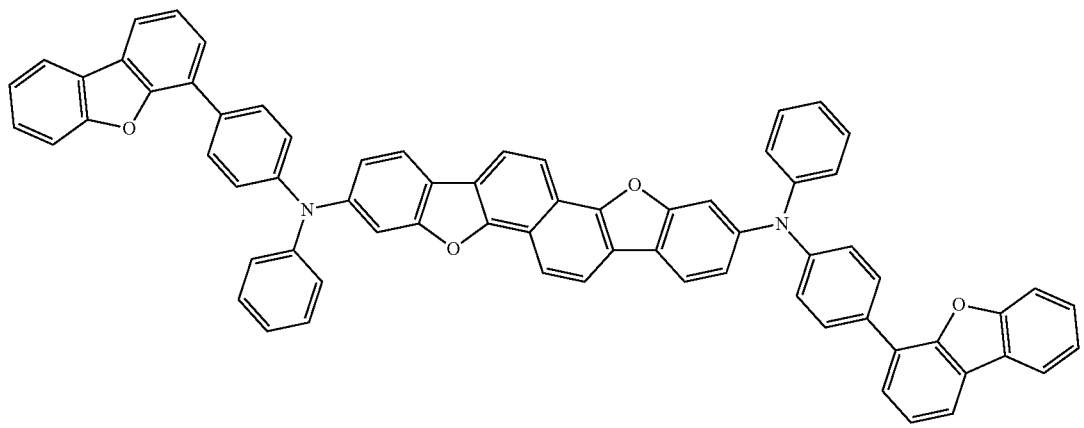
(121)
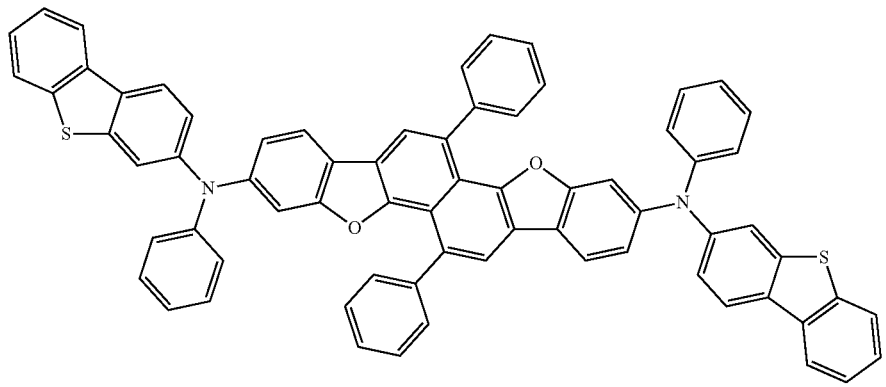

-continued
(122)
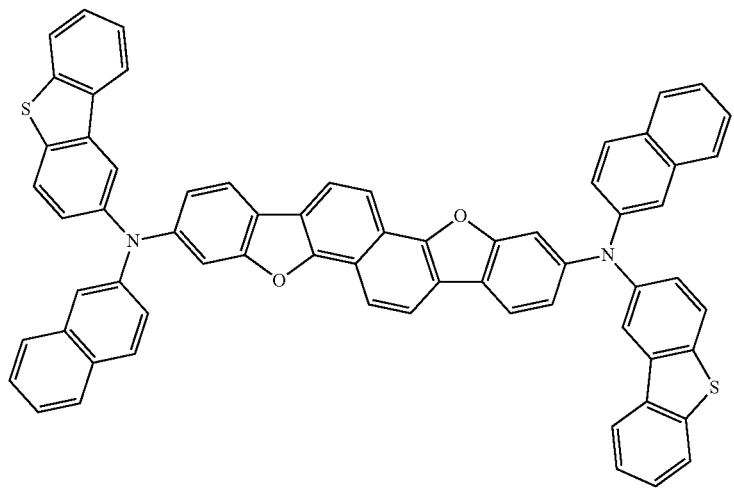
(123)
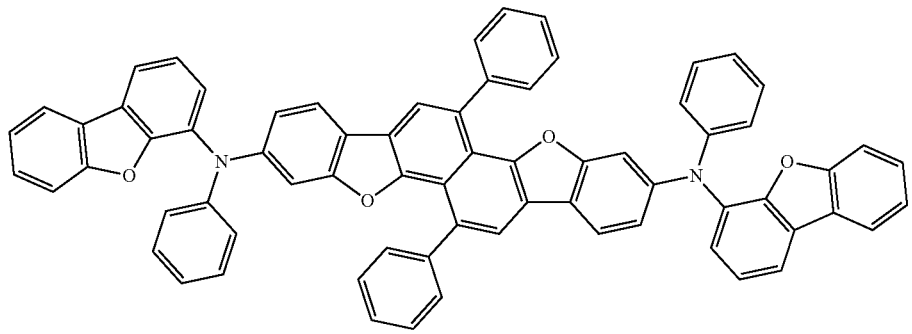
(124)
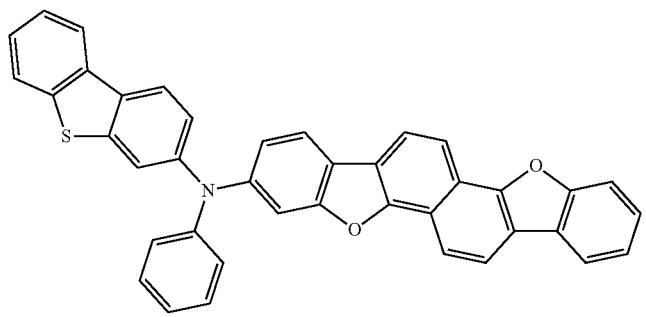
(125)
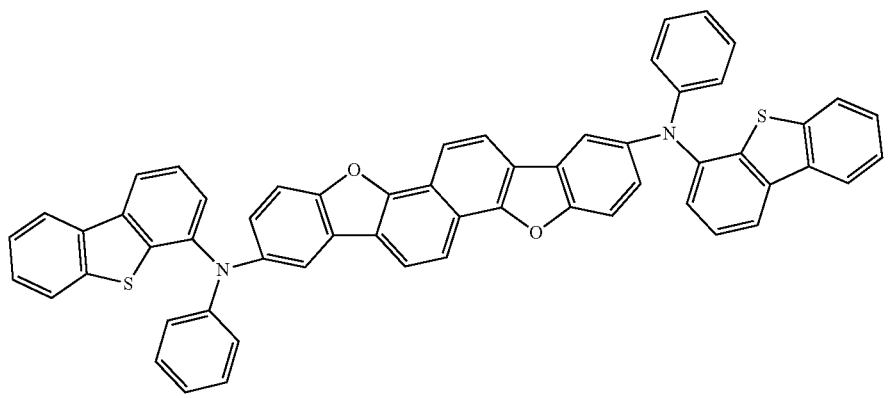

[Chemical Formulae 29]
(200)
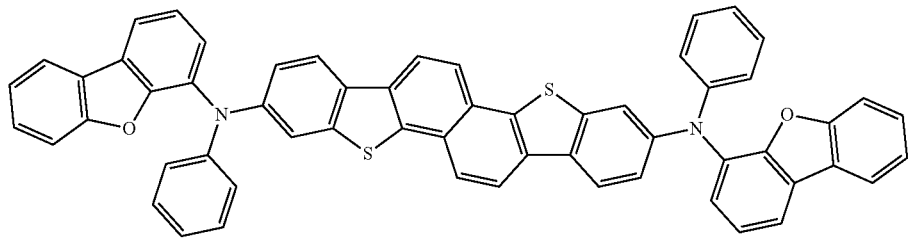
(201)
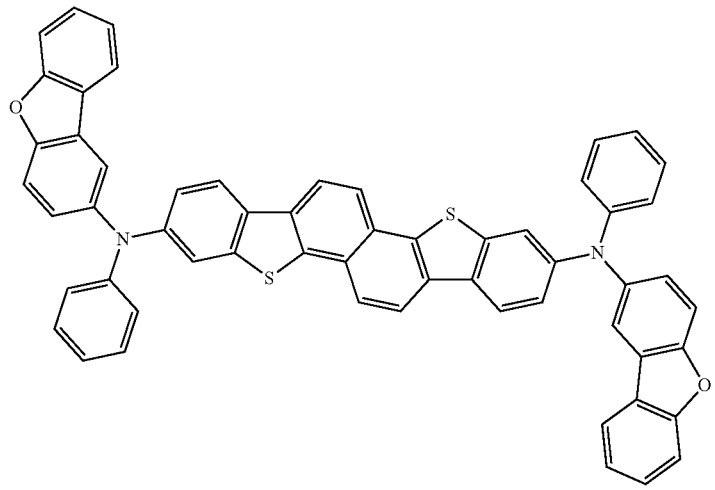
(202)
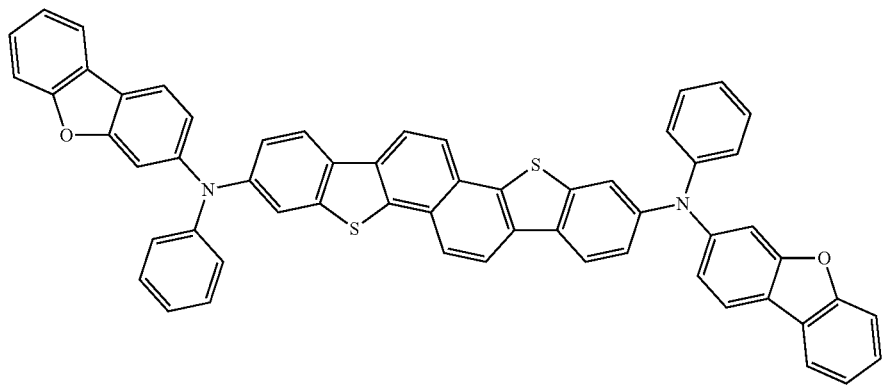
(203)
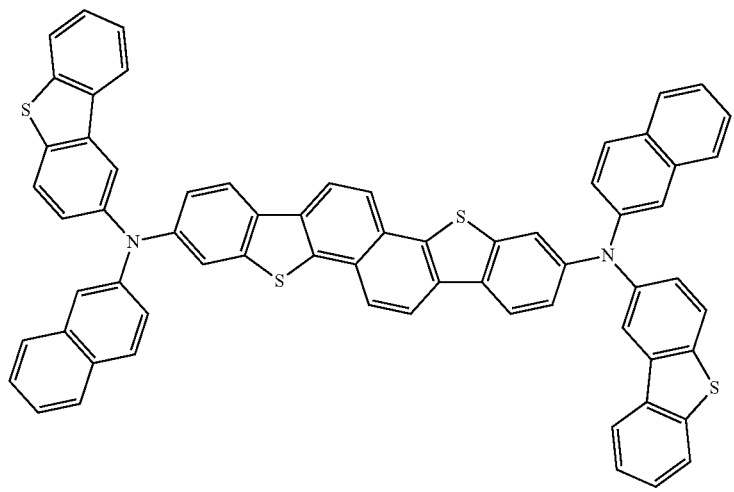

-continued
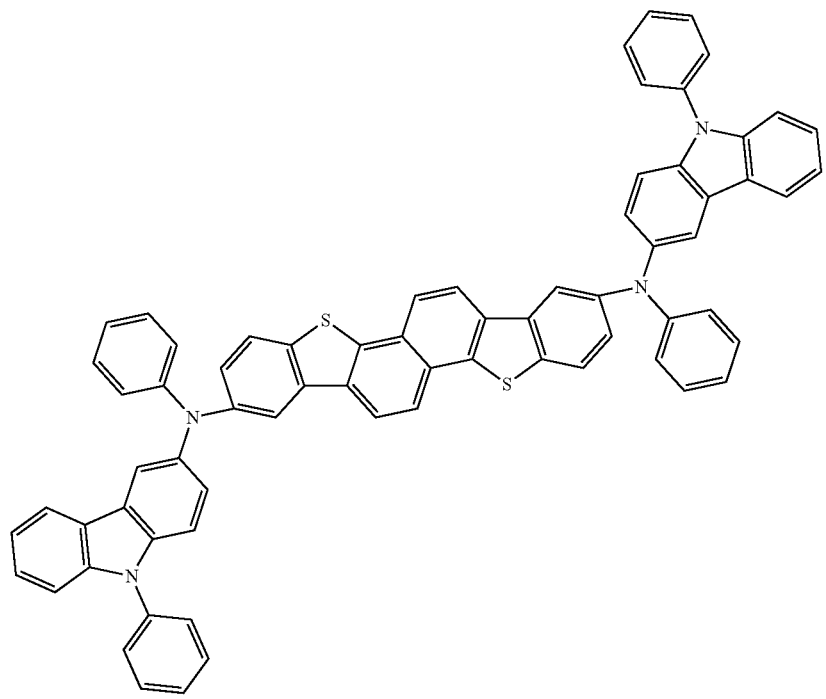
(204)
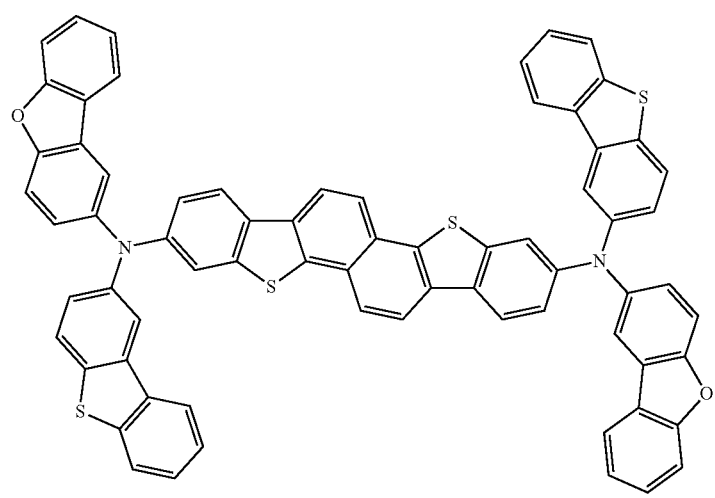
(205)

(206)
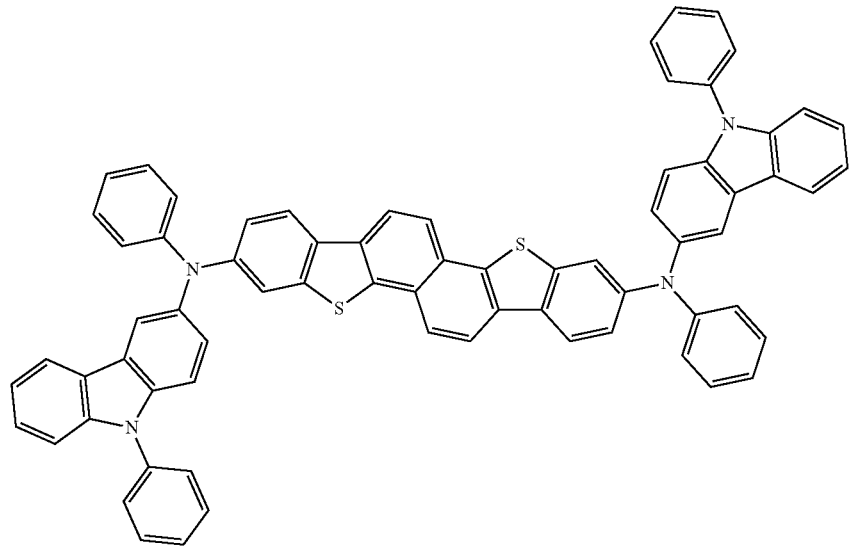
(207)
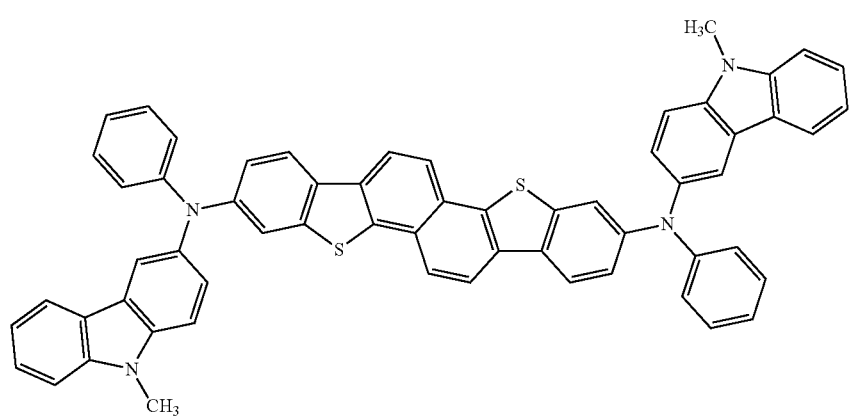
(208)
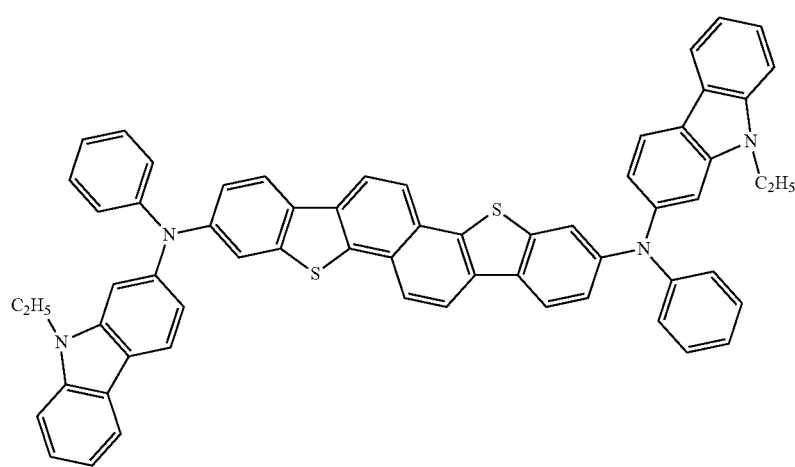

[Chemical Formulae 30]
(209)
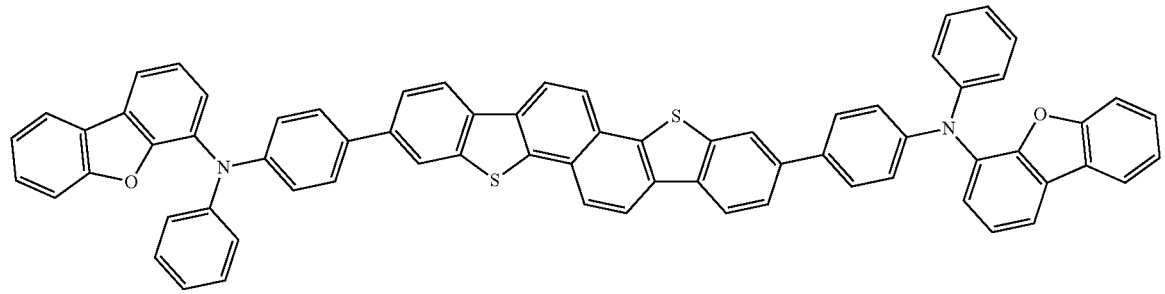
(210)
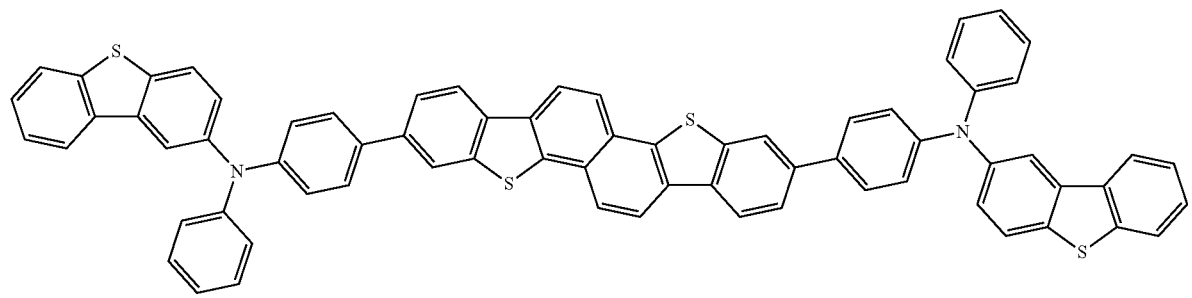
(211)
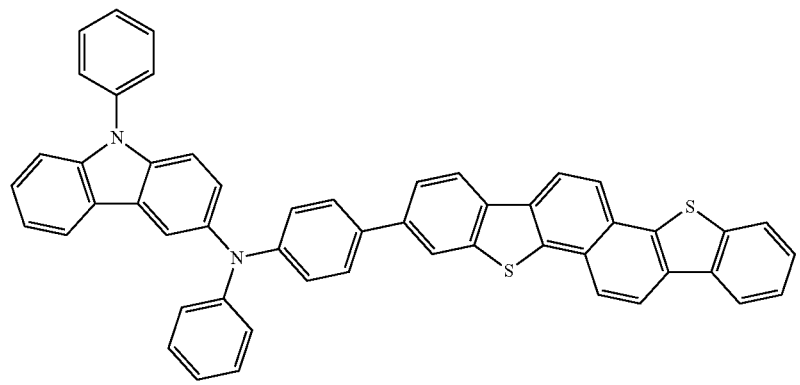
(212) (216)
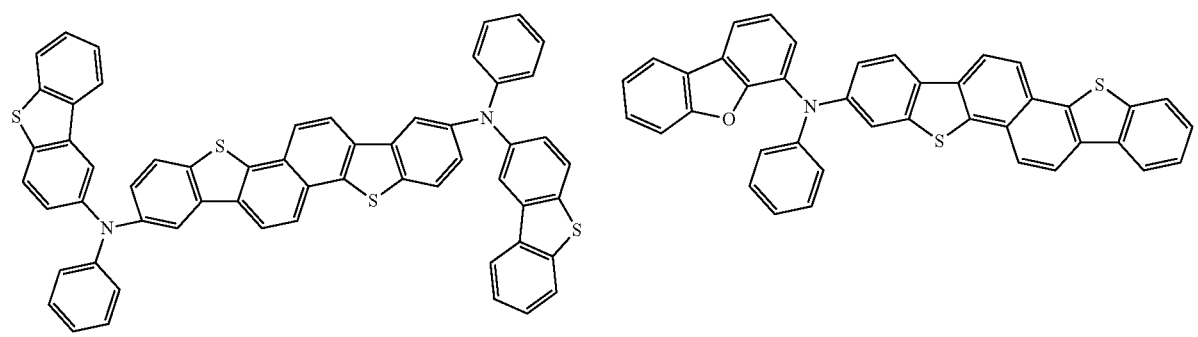

-continued
(214)
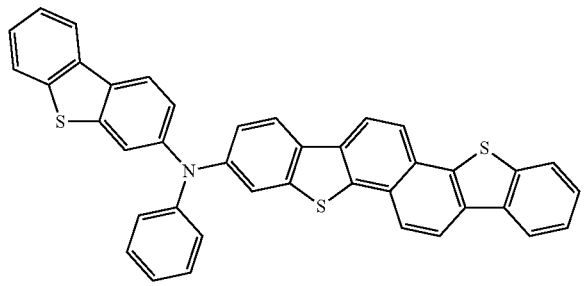
(215)
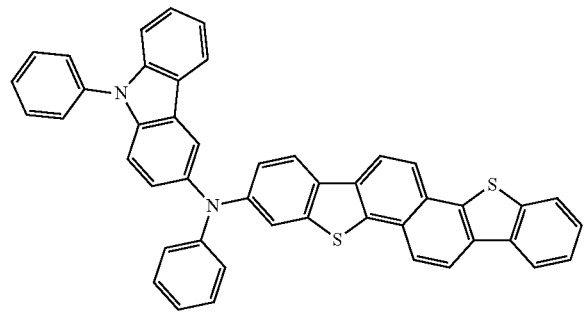
(216)
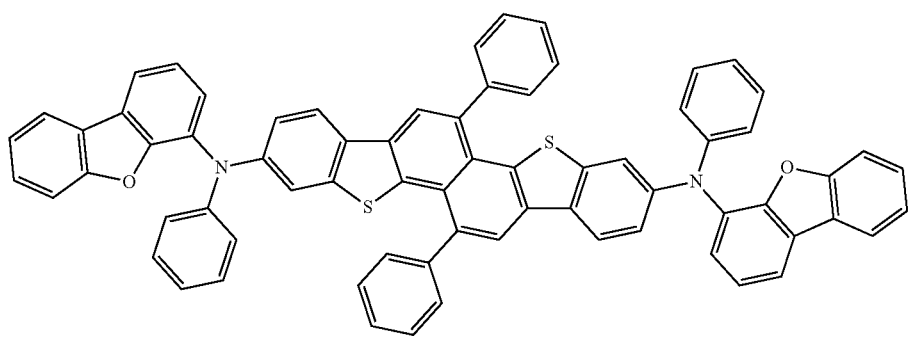
(217)
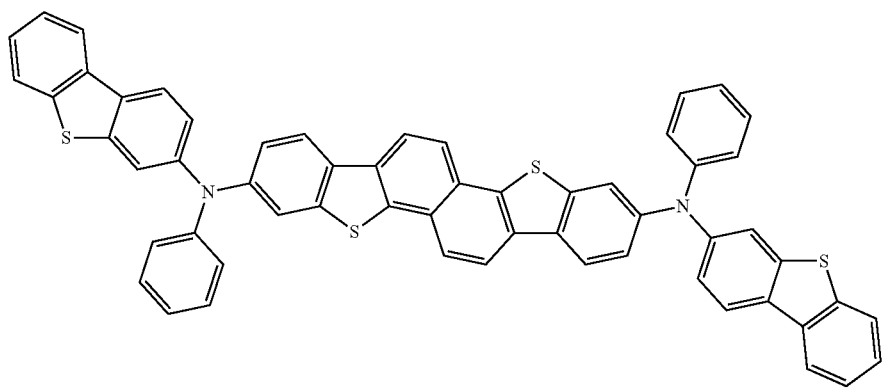
(218)
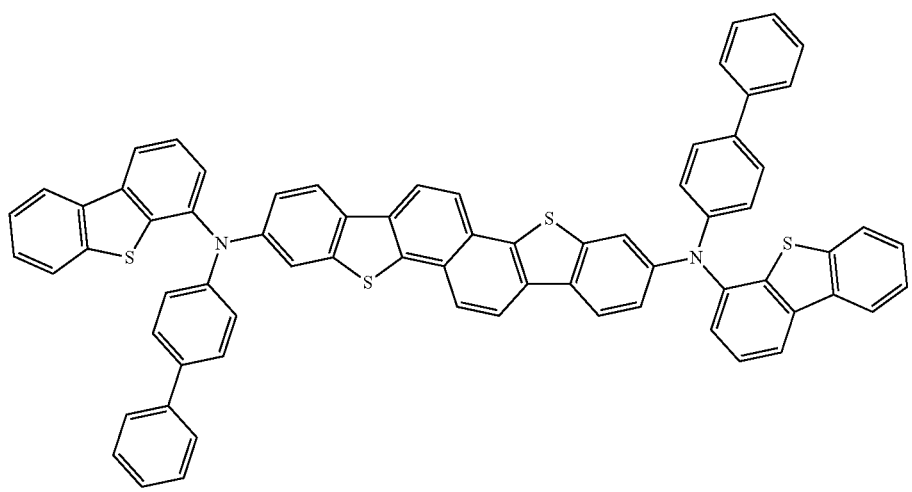

-continued
(219)
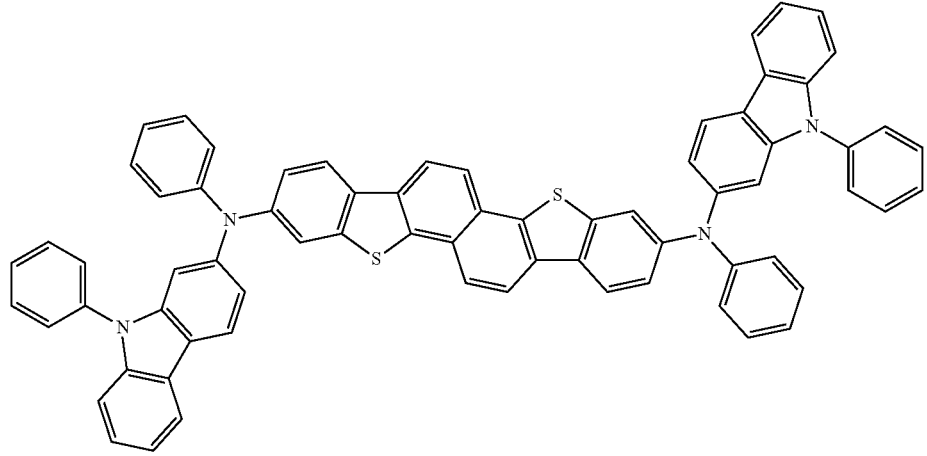
[Chemical Formulae 31]
(220)
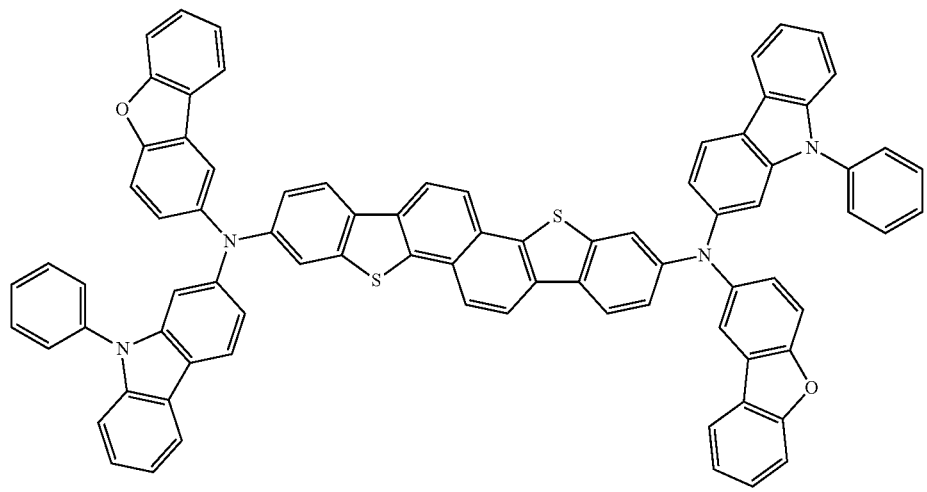
(221)
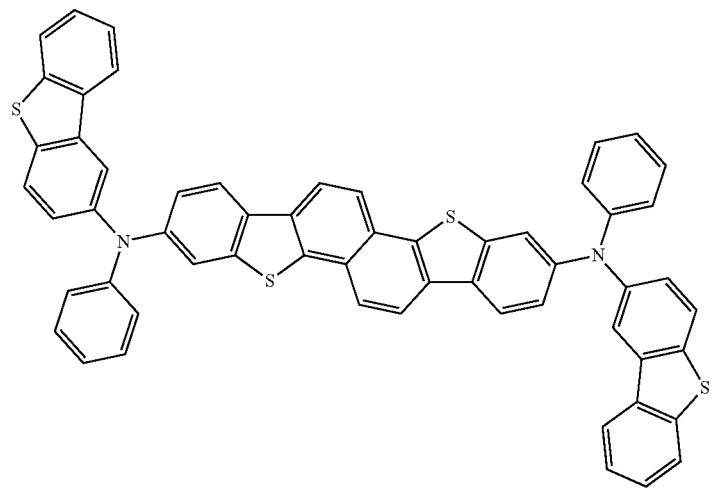

(222)
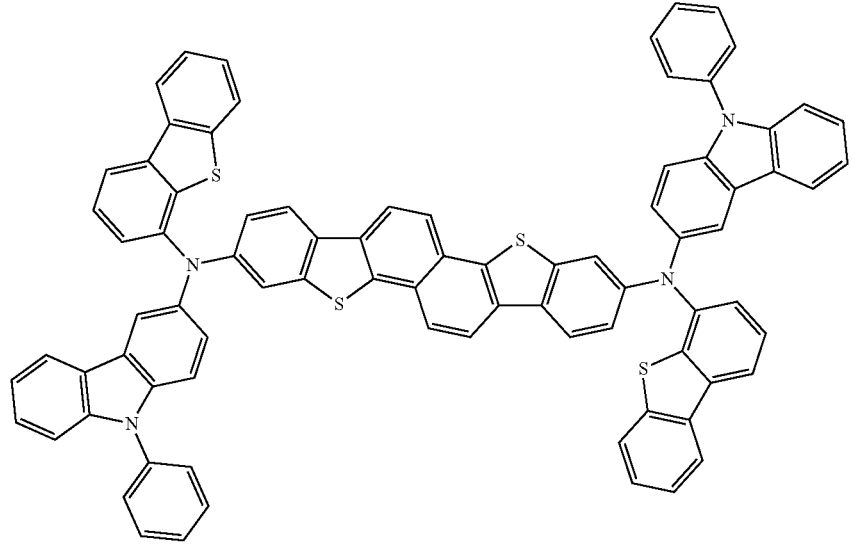
(223)
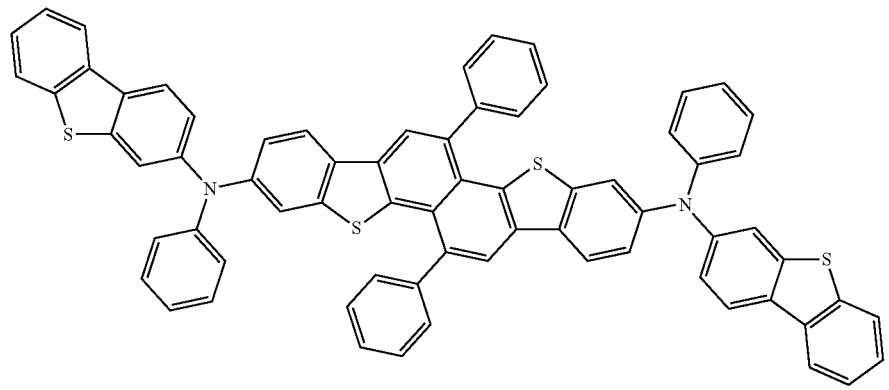
(224)
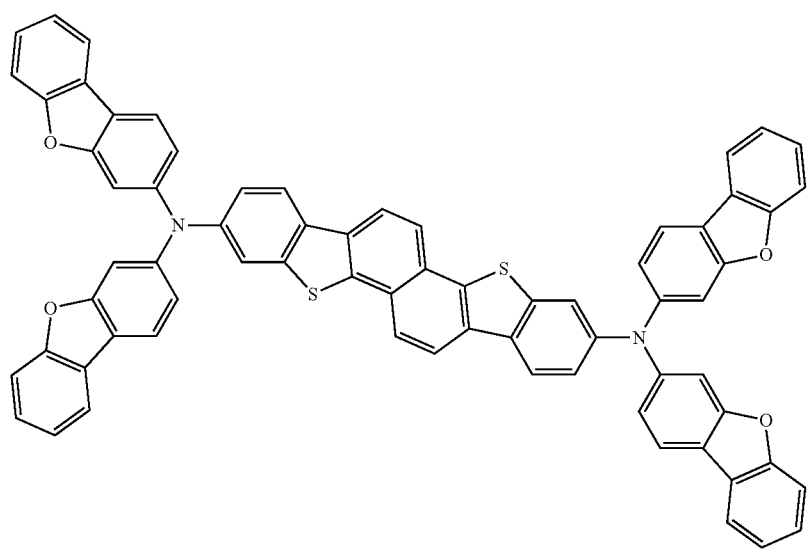

(225)
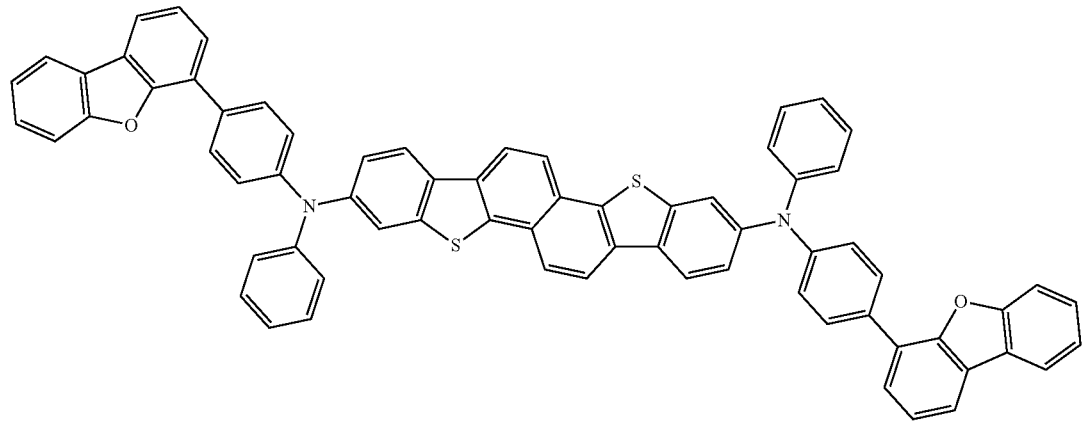
(226)
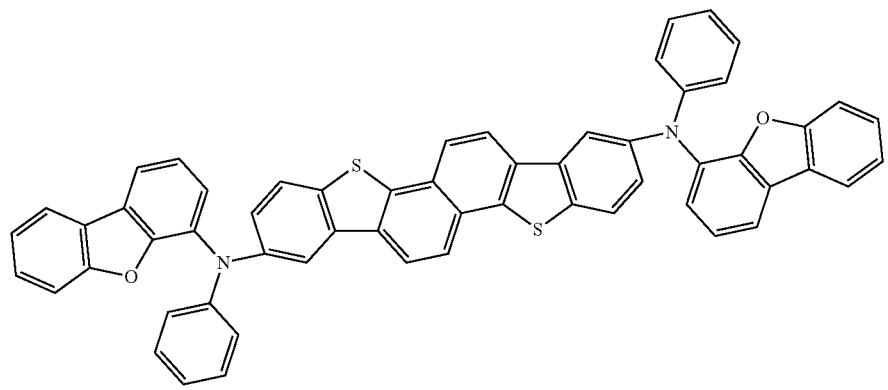
[Chemical Formulae 32]
(300)
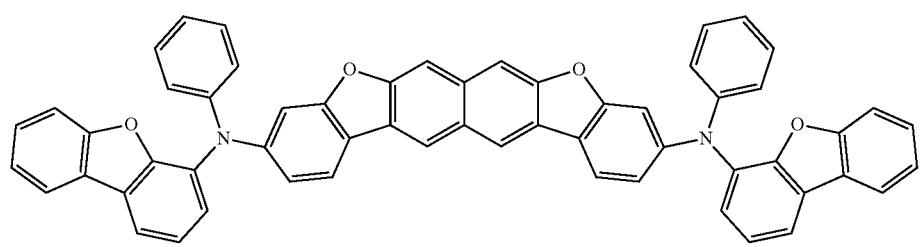
(301)
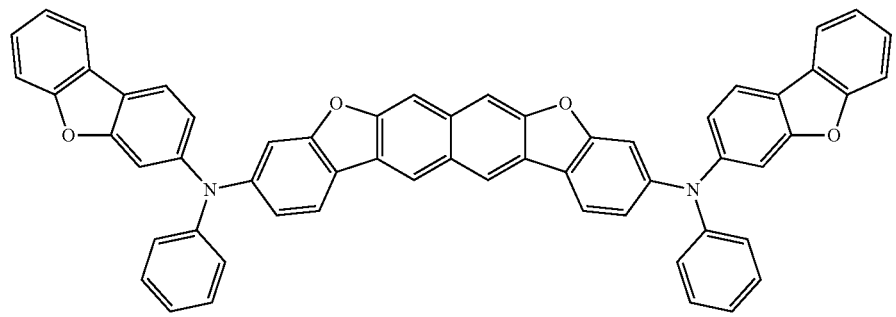

-continued
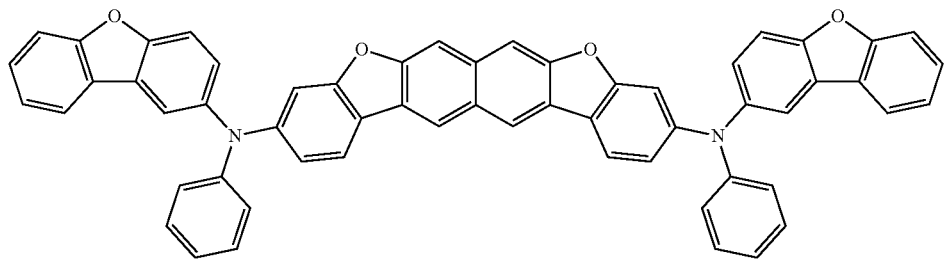
(302)
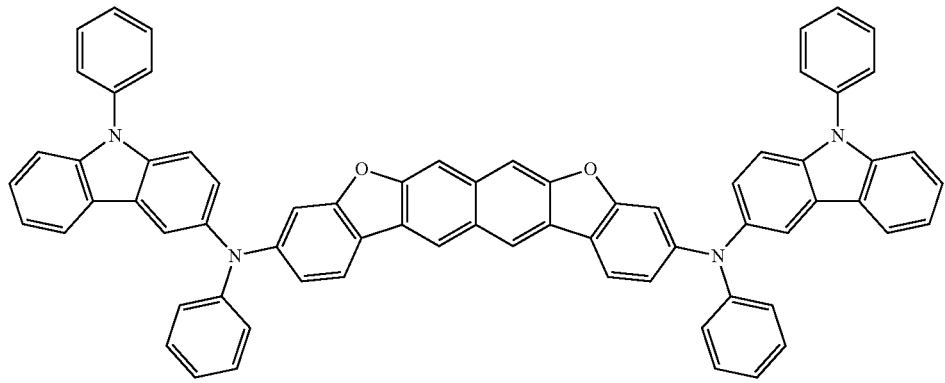
(303)
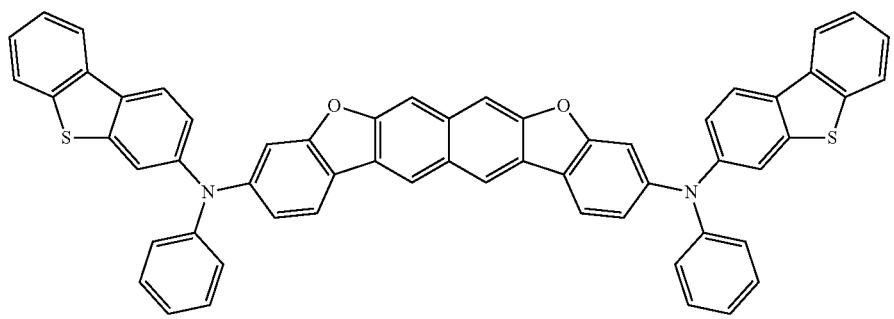
(304)
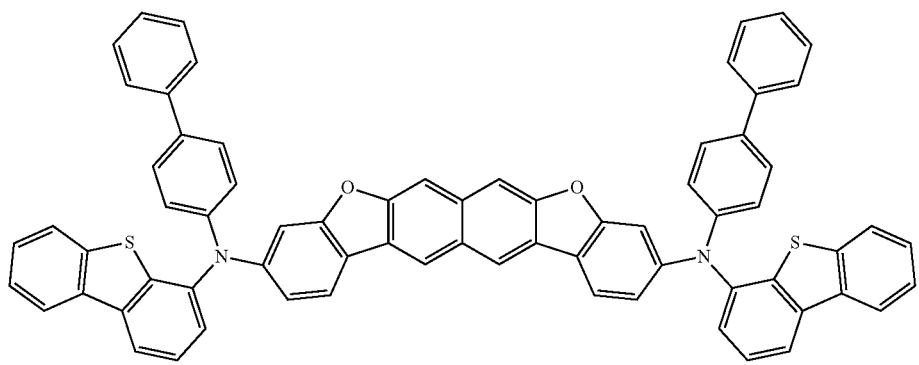
(305)
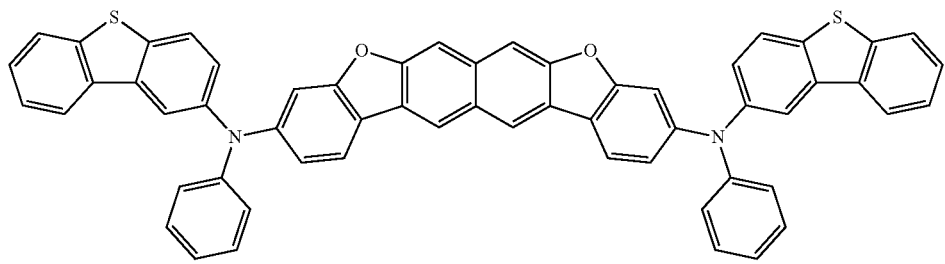
(306)

(307)
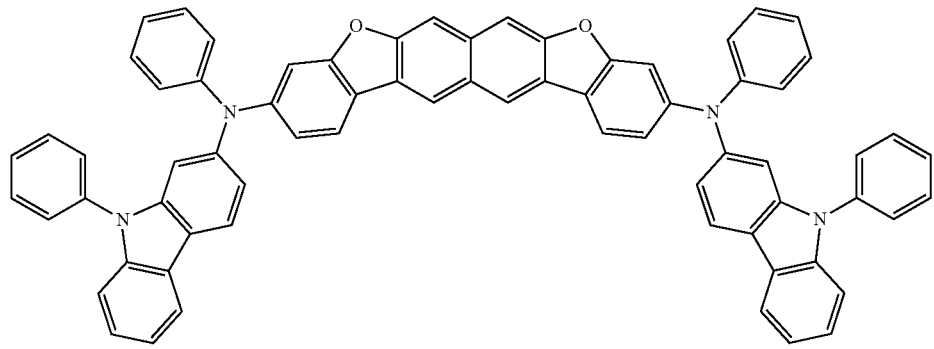
[Chemical Formulae 33]
(308)
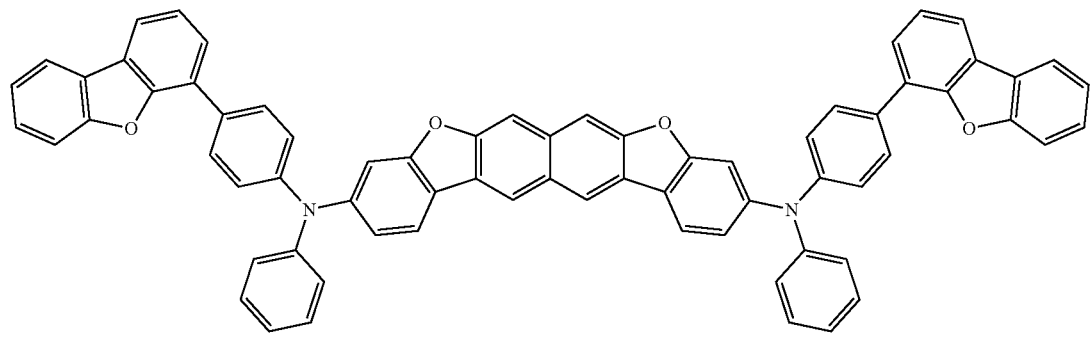
(309)
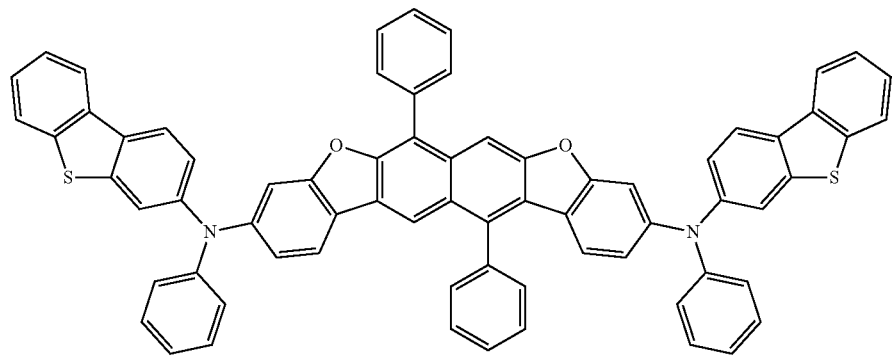
(310)
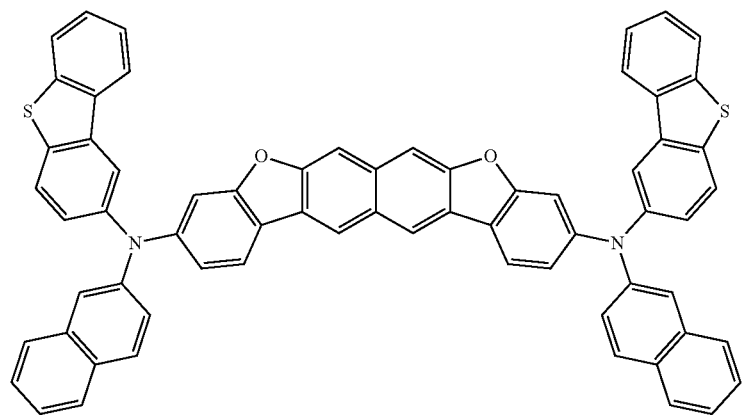

(311)
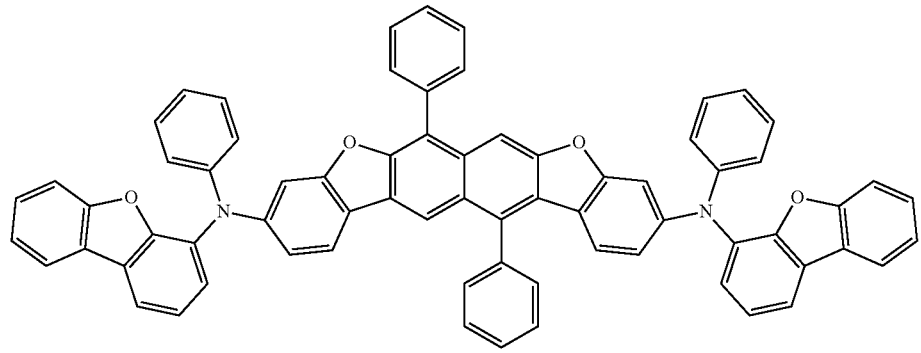
(312)
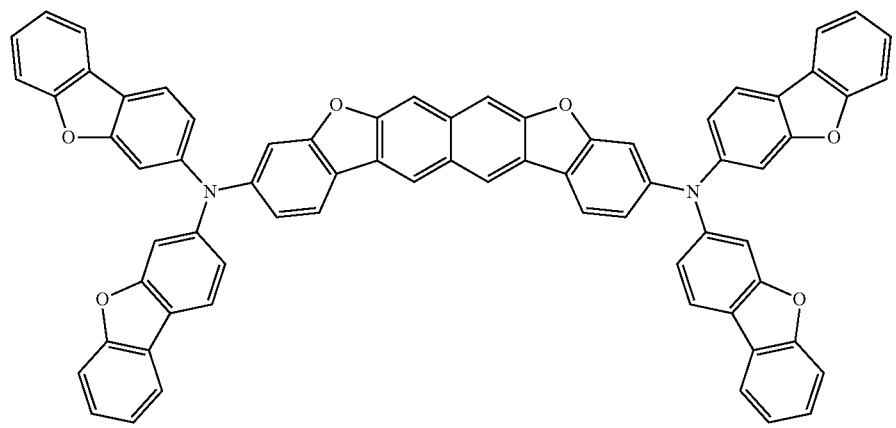
(313)
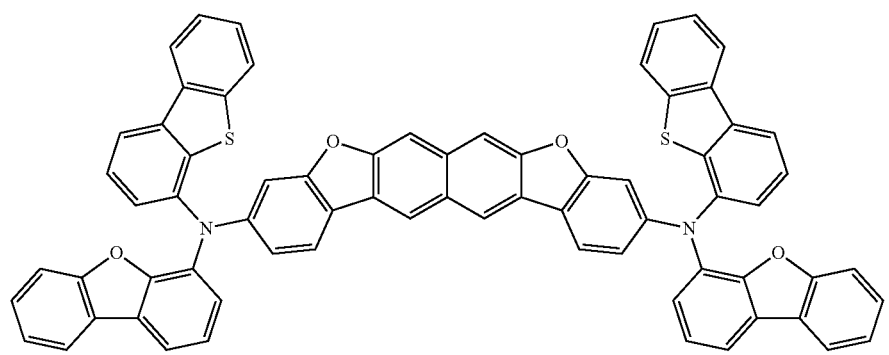
(314)
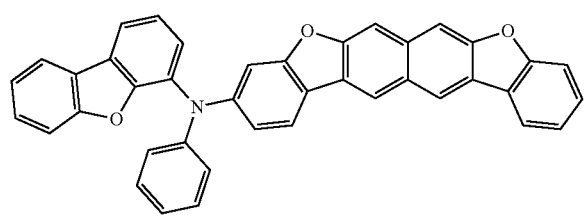
(315)
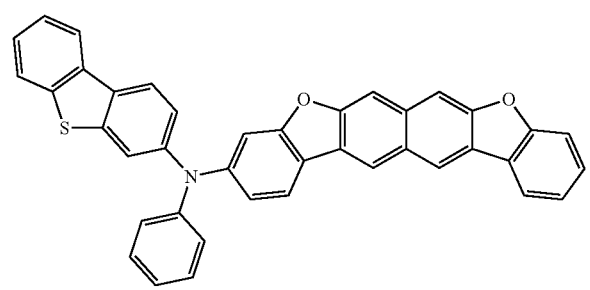

(316)
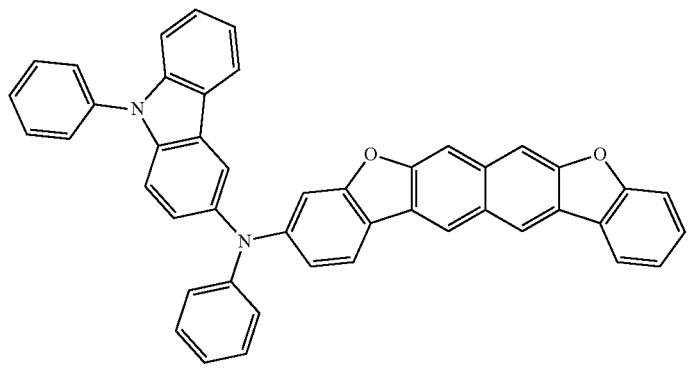
(317)
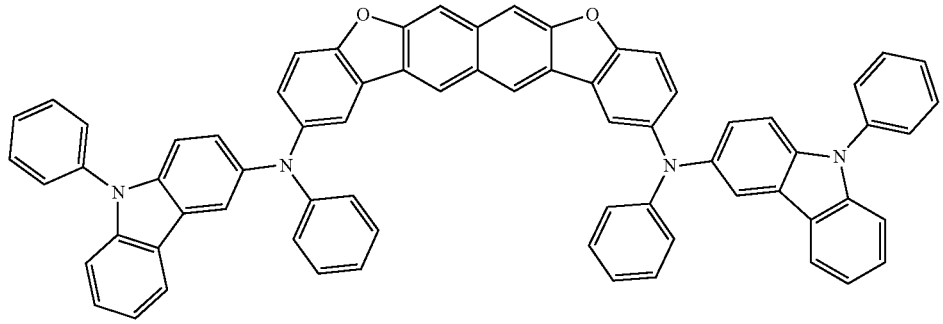
[Chemical Formulae 34]
(318)
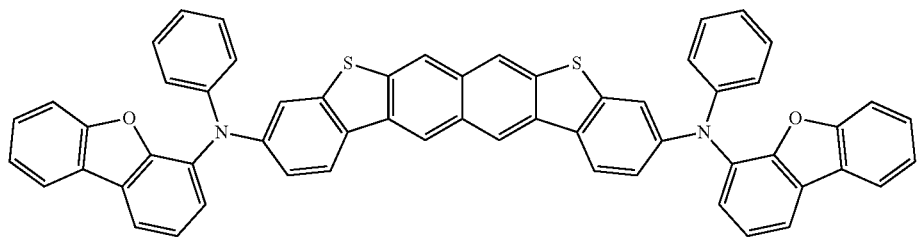
(319)
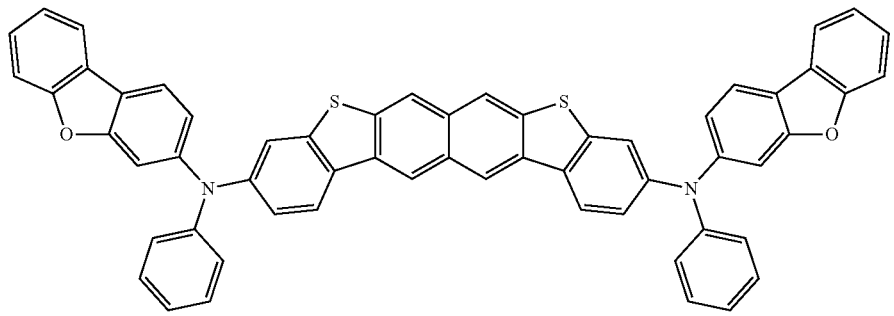
(320)
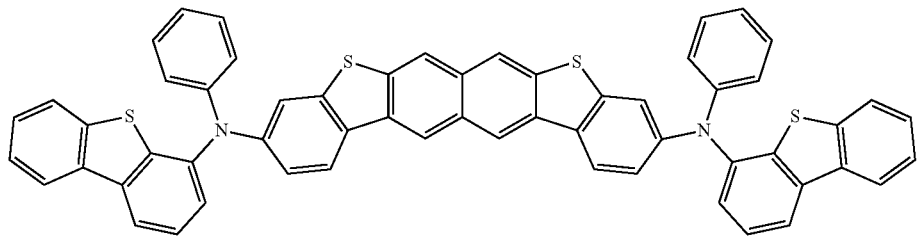

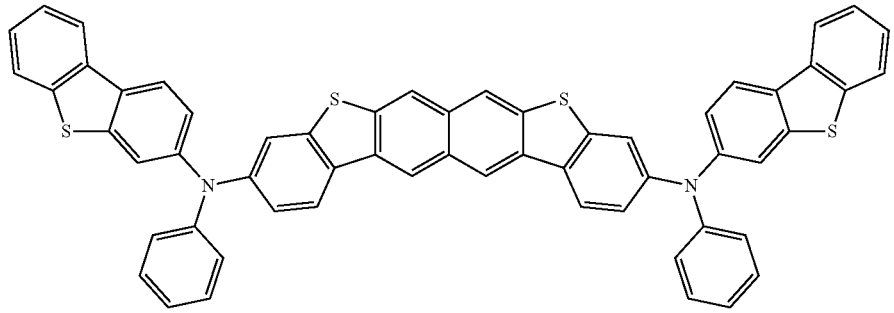
(321)
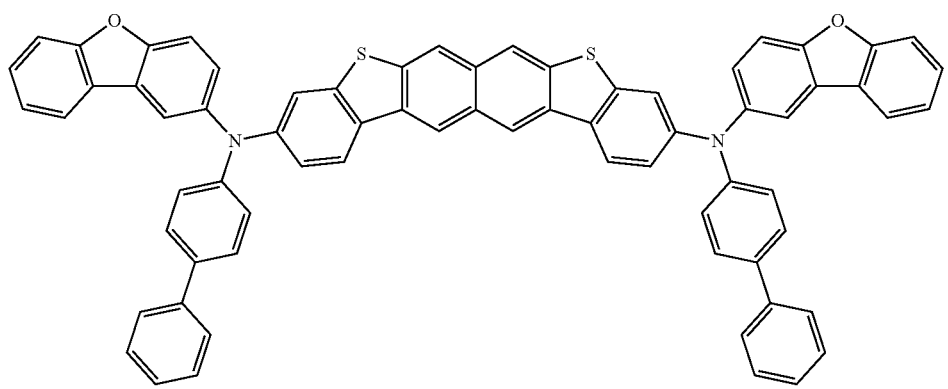
(322)
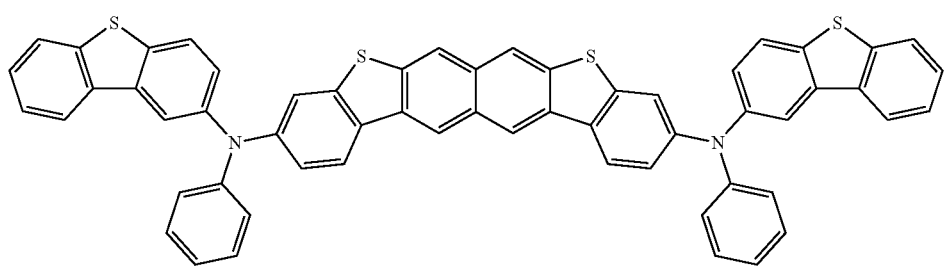
(323)
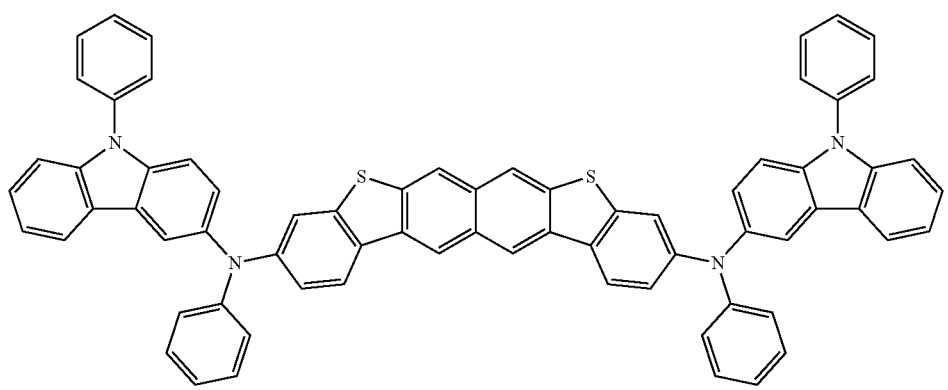
(324)

(325)
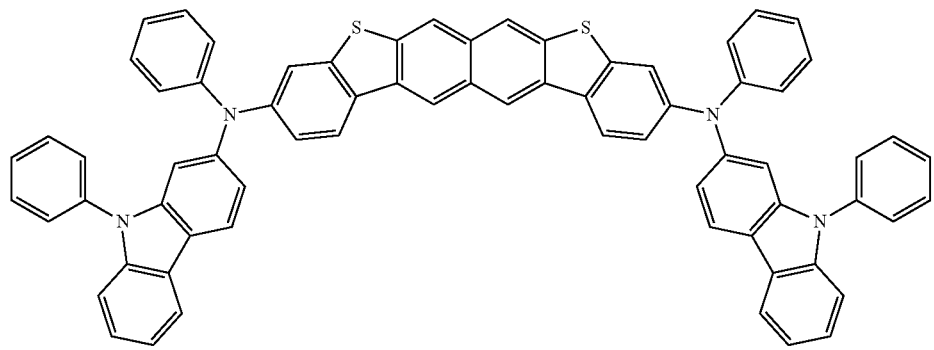
[Chemical Formulae 35]
(400)
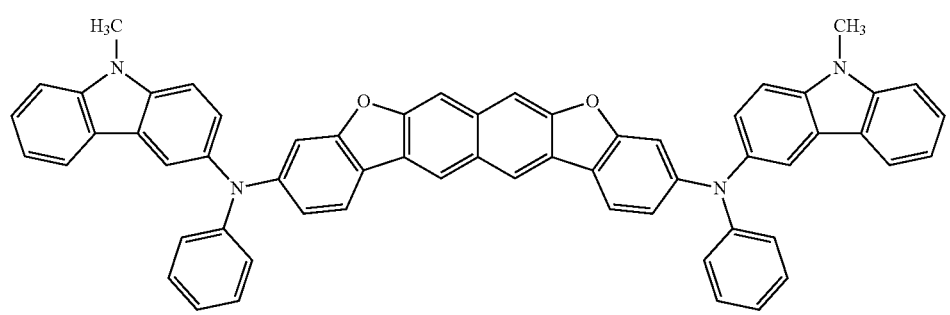
(401)
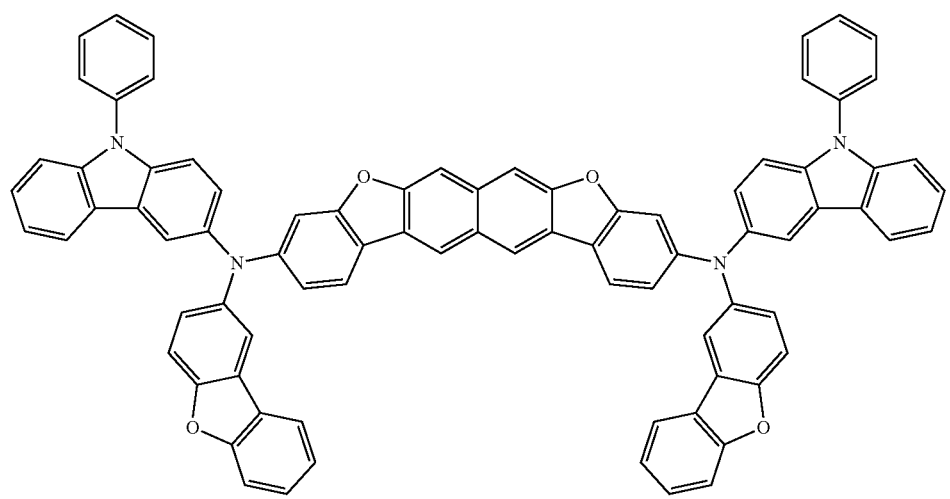
(402)
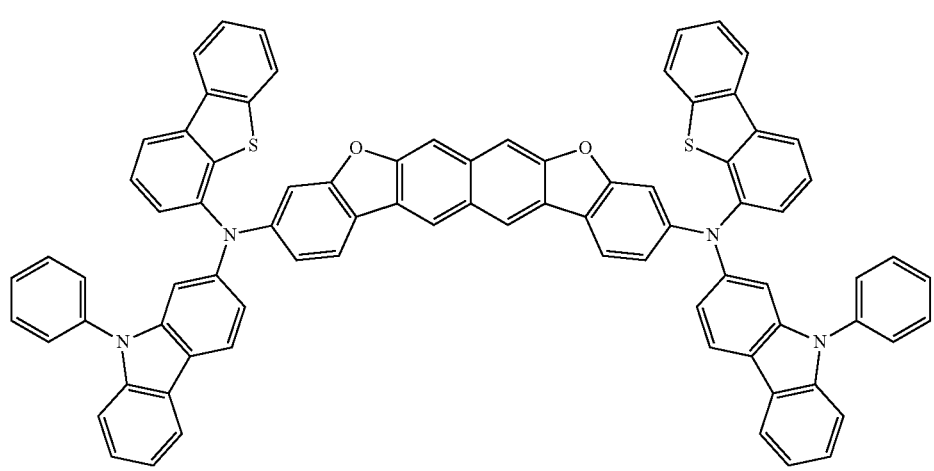

(403)
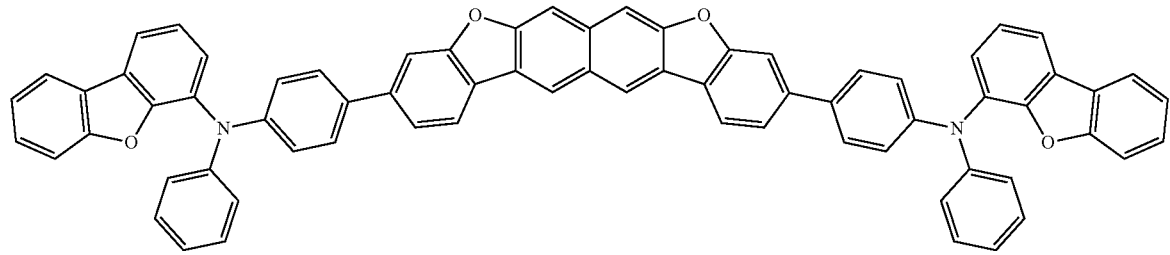
(404)
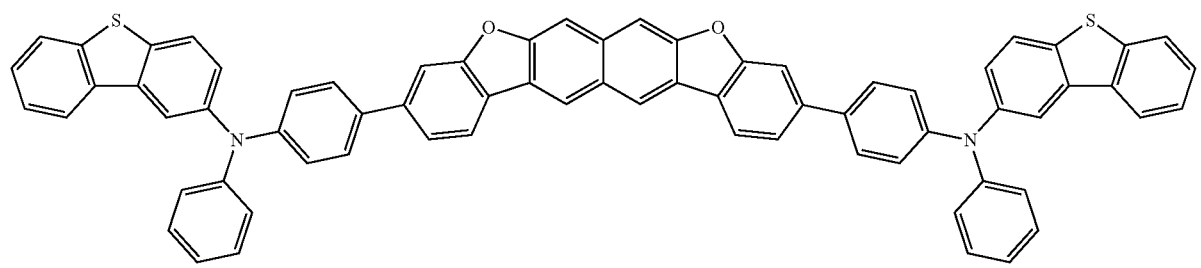
(405)
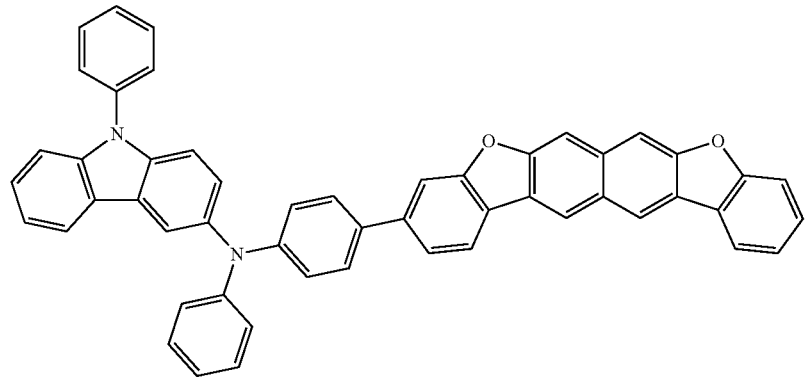
(406)
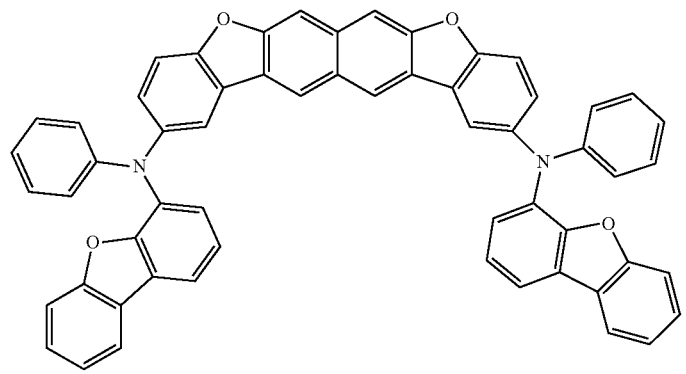
(407)
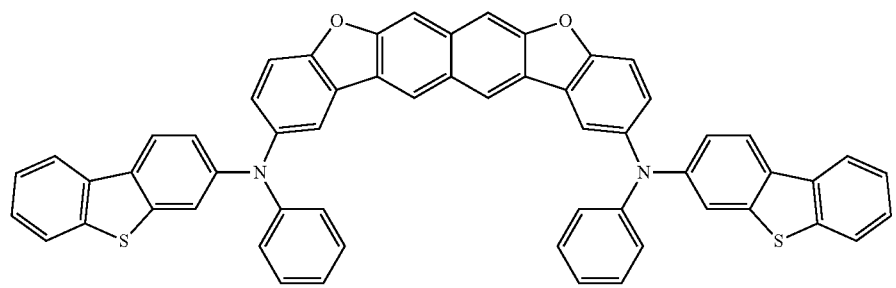

(408)
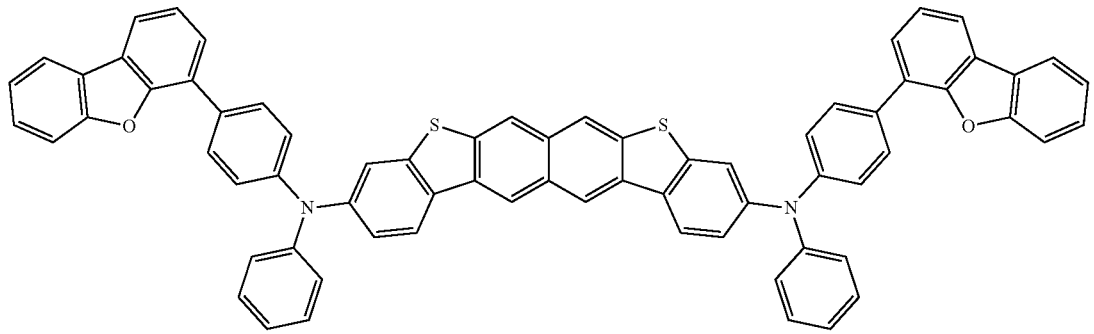
(409)
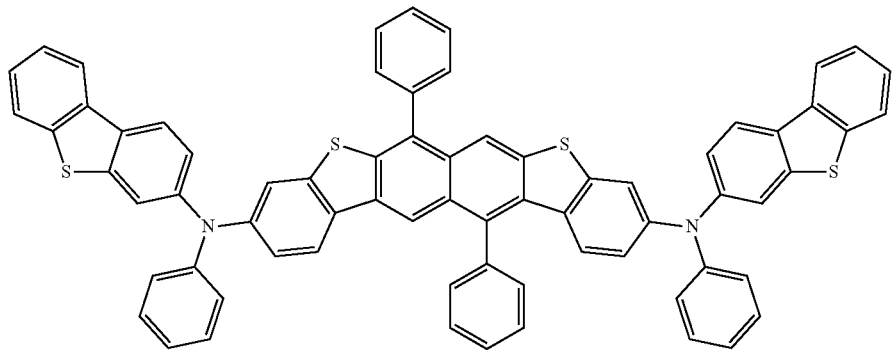
(410)
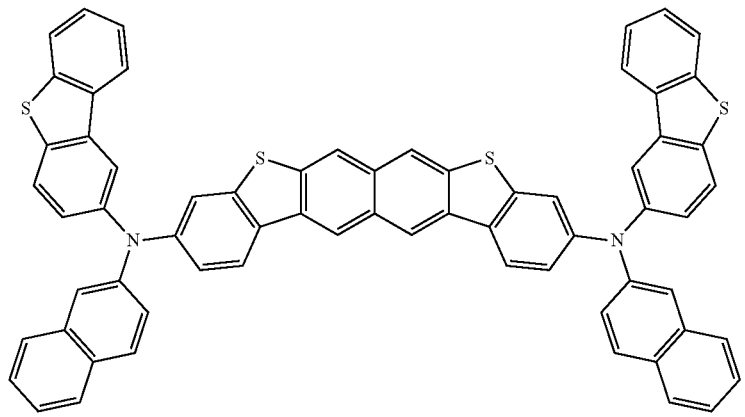
(411)
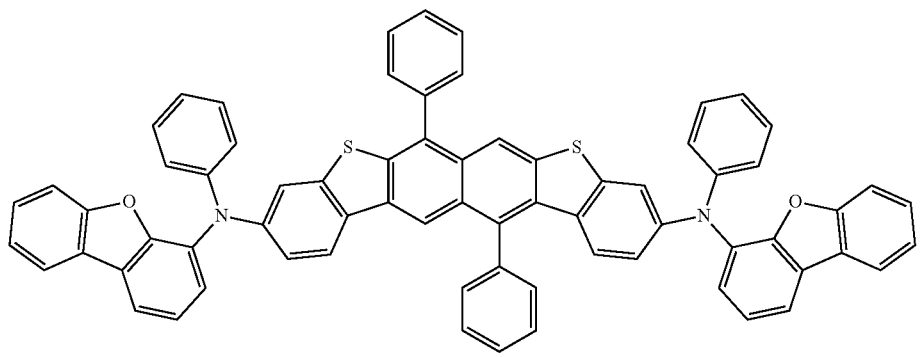

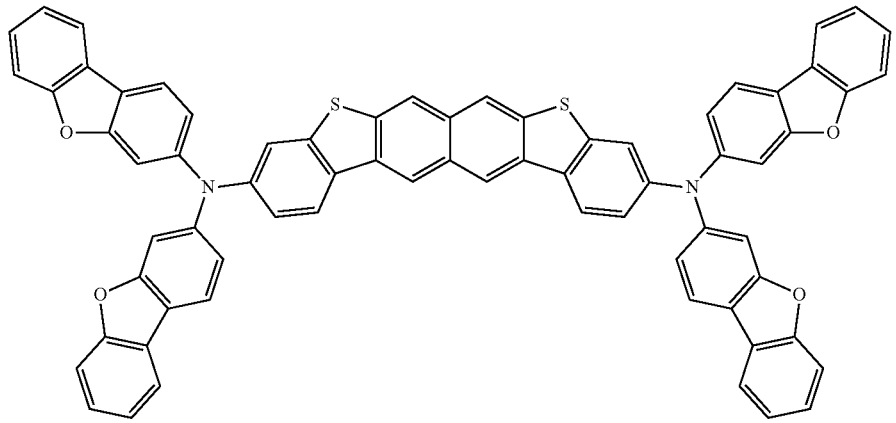
(412)
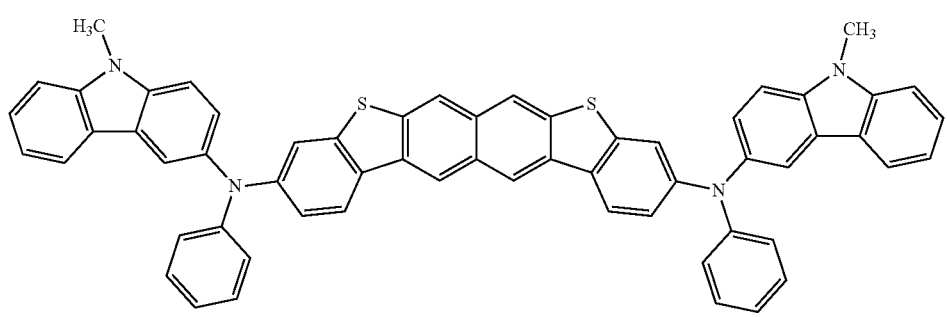
(413)
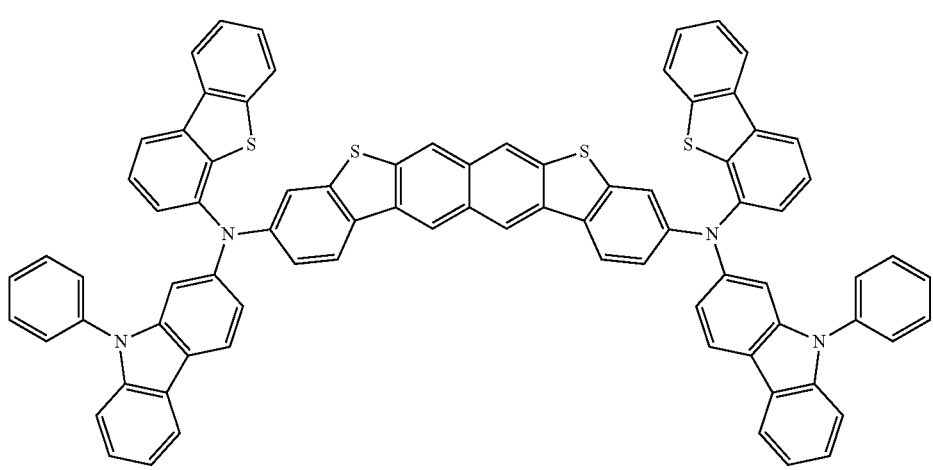
(414)

(415)
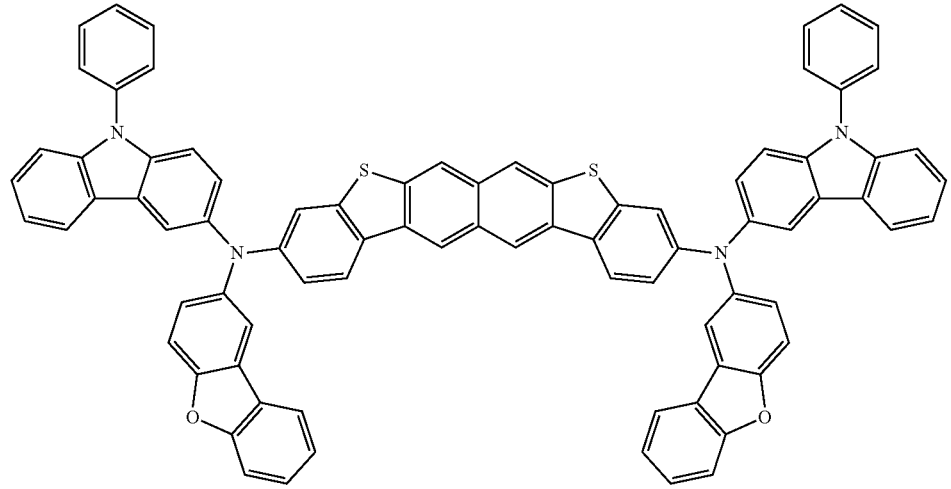
[Chemical Formulae 37]
(416)
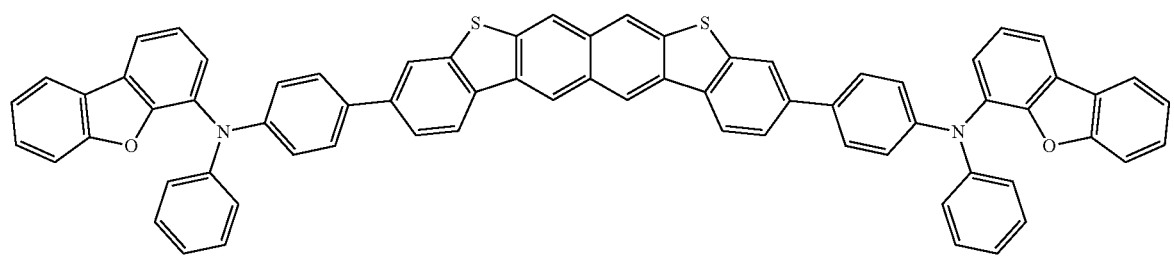
(417)
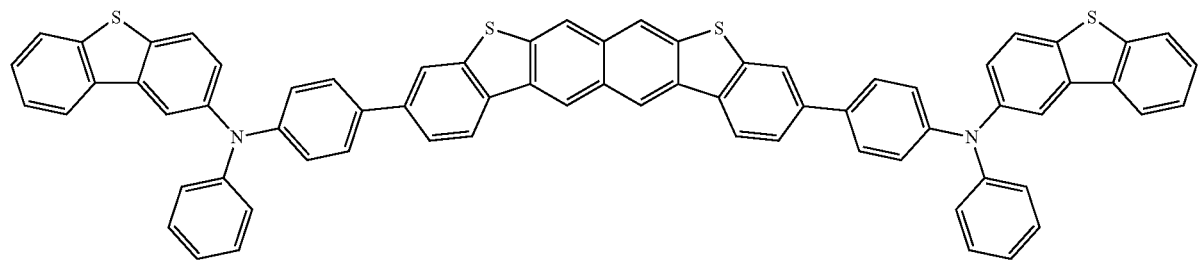
(418)
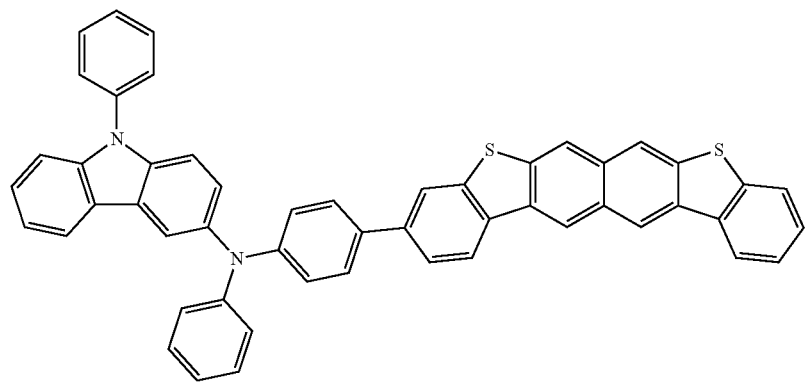

-continued
(419)
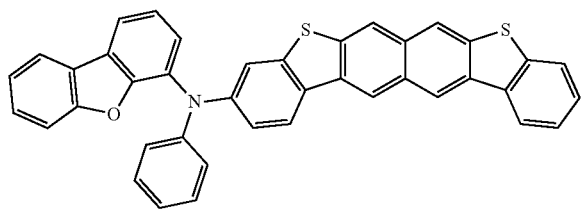
(420)
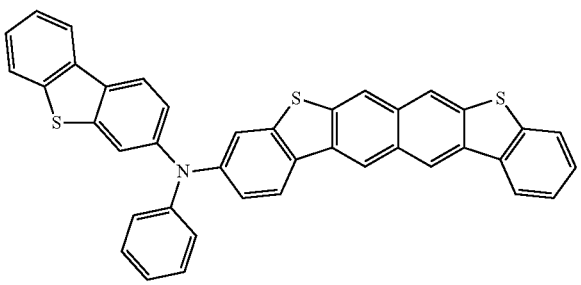
(421)
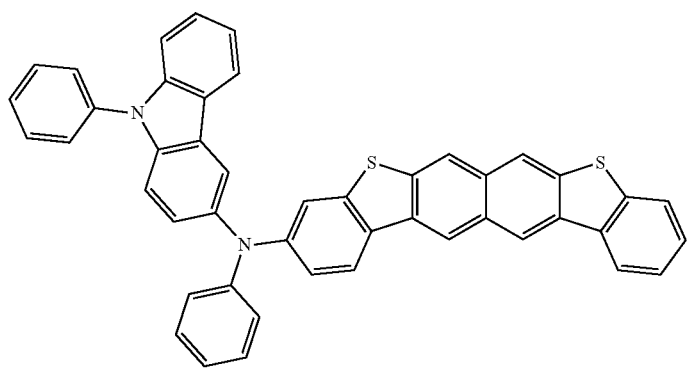
(422)
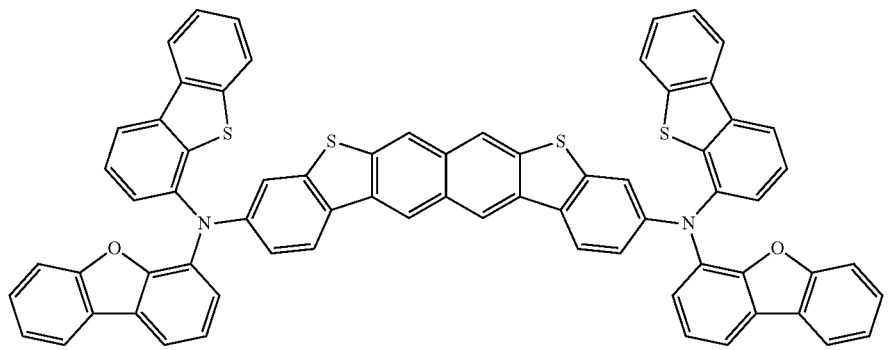
(423)
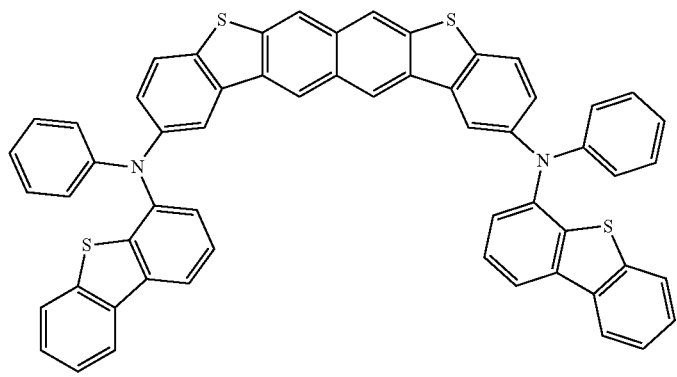

-continued
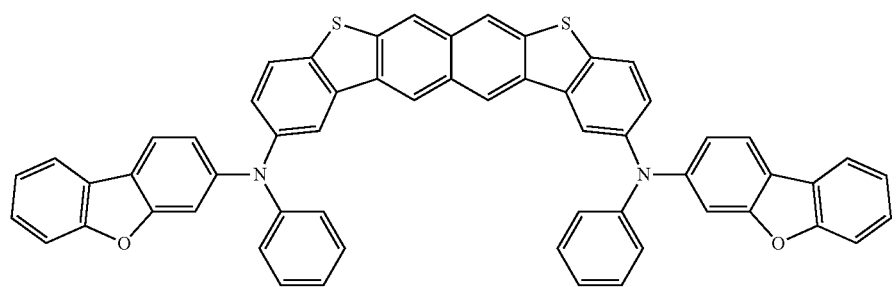
(424)
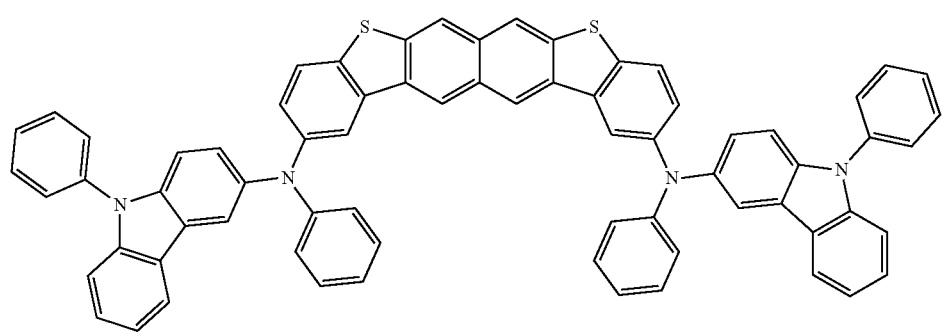
(425)
[Chemical Formulae 38]
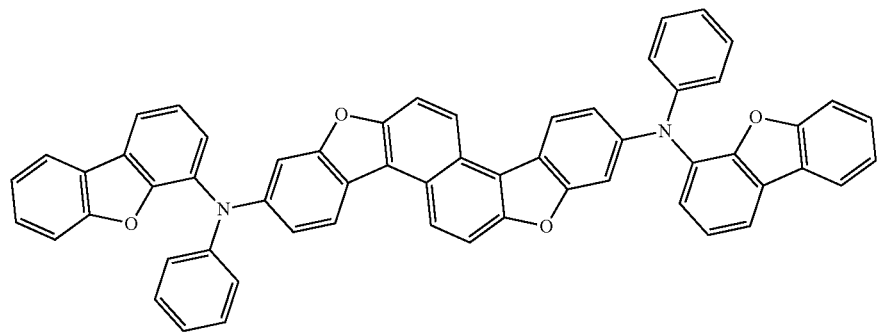
(500)
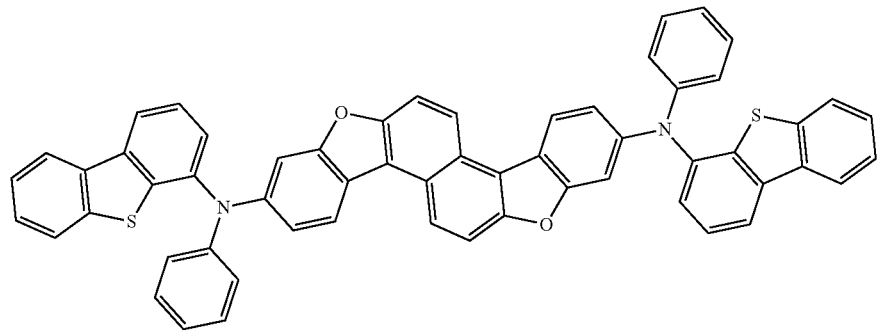
(501)

(502)
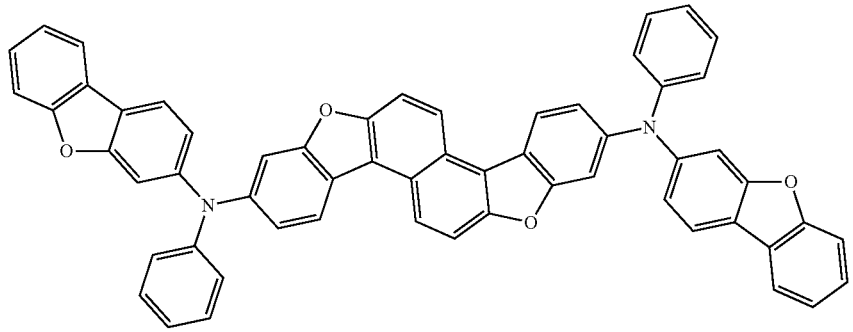
(503)
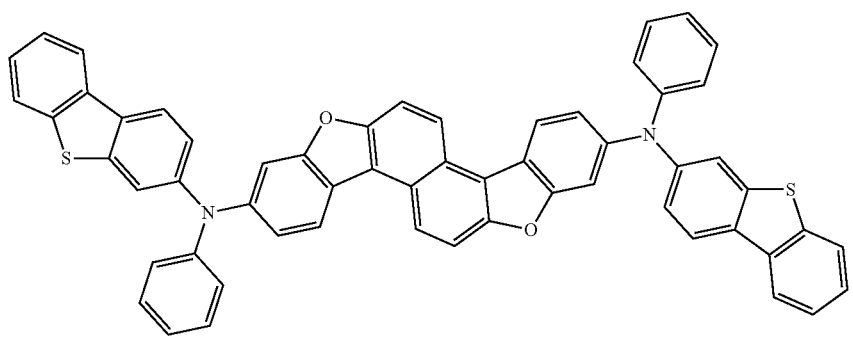
(504) (505)
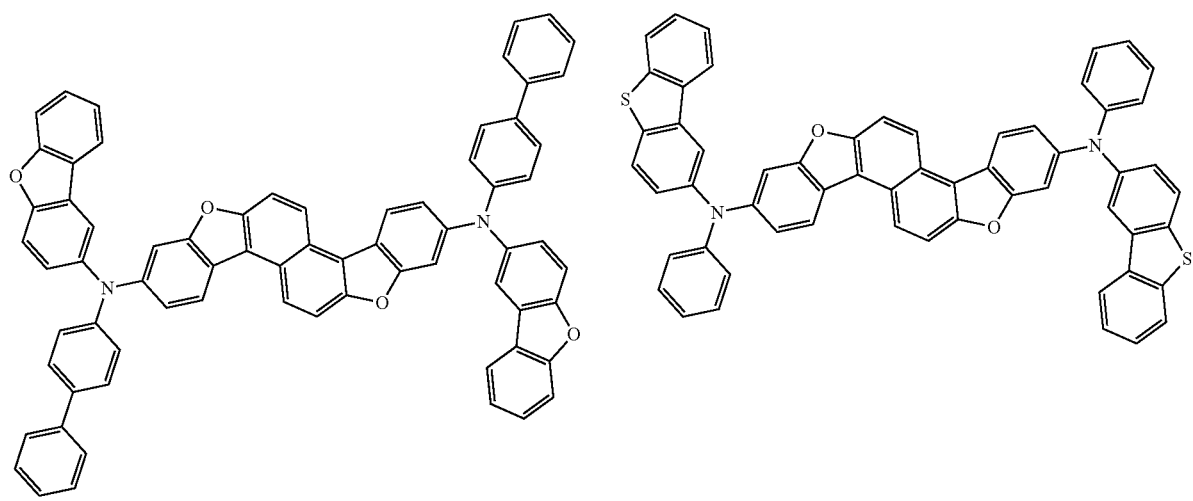
(506)
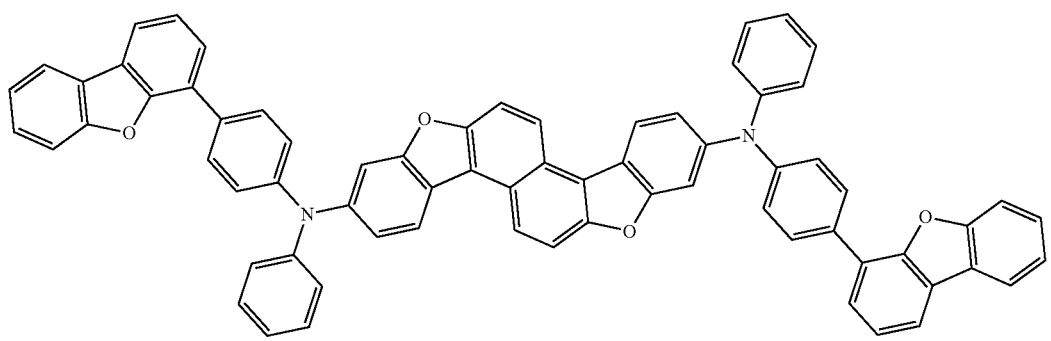

(507)
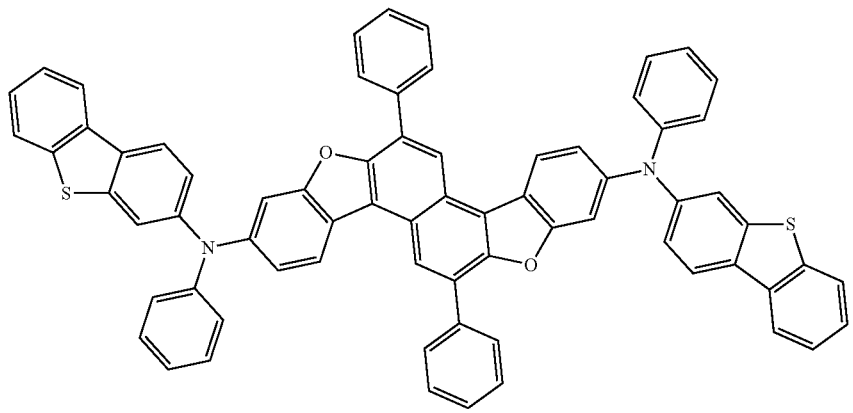
(508)
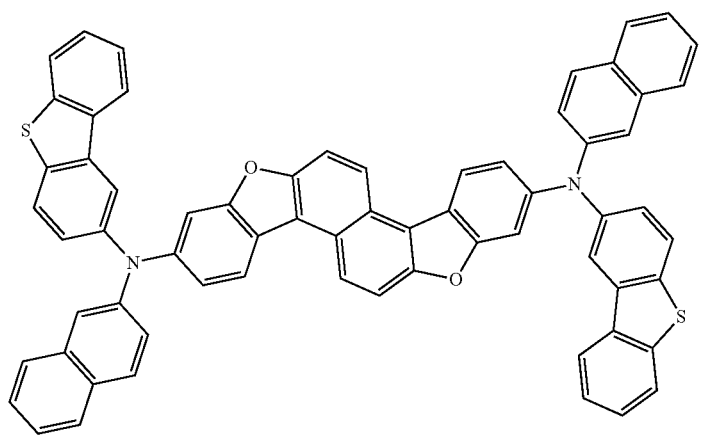
[Chemical Formulae 39]
(509)
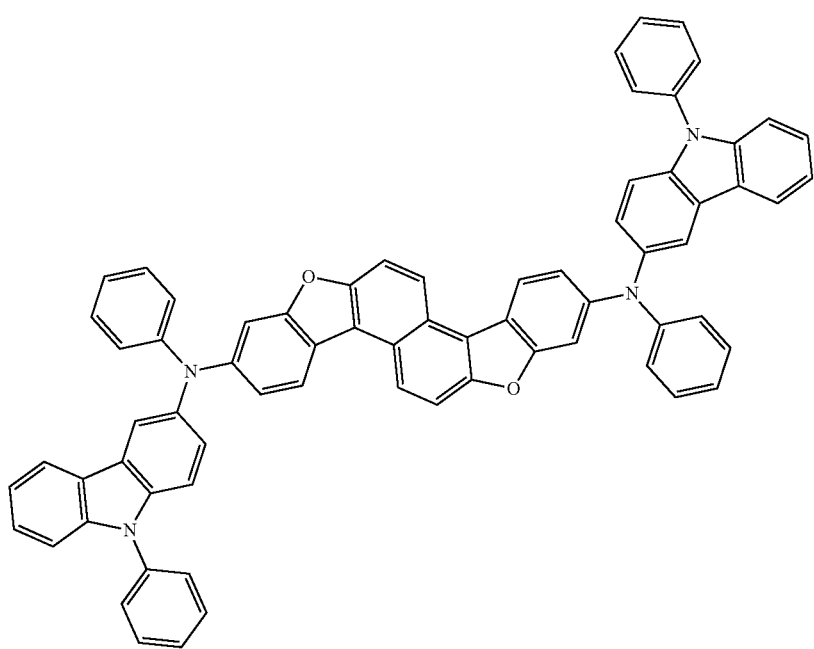

-continued
(510)
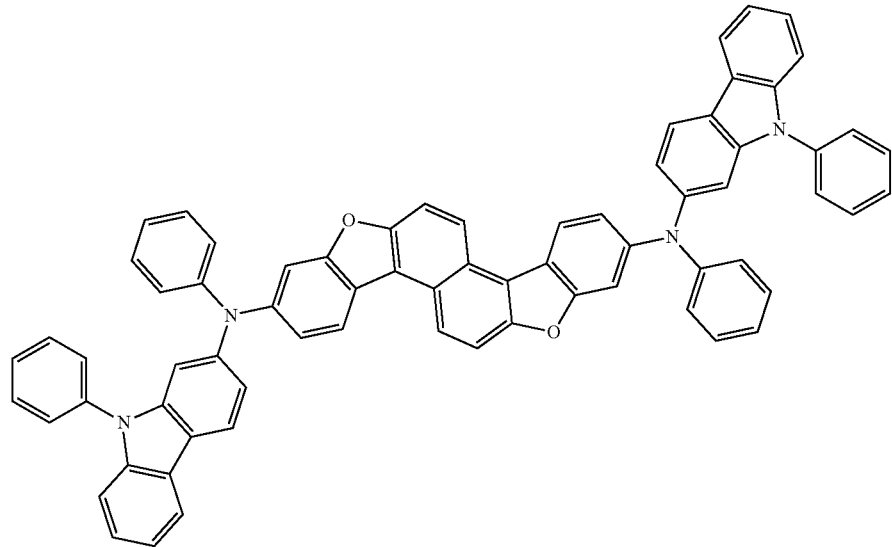
(511)
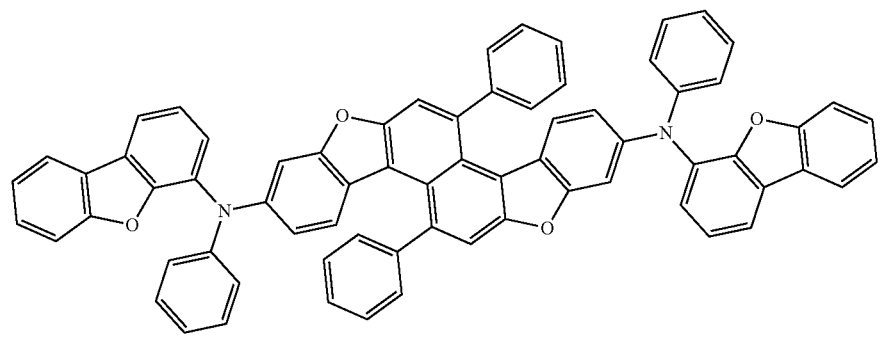
(512)
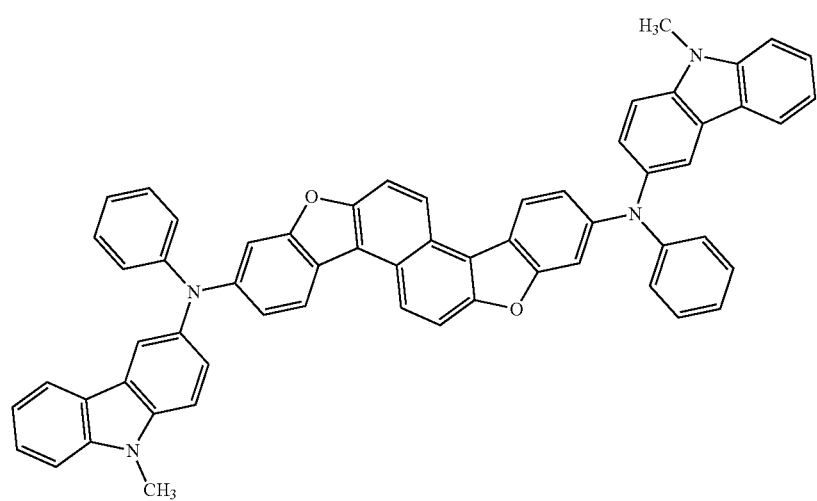

(513)
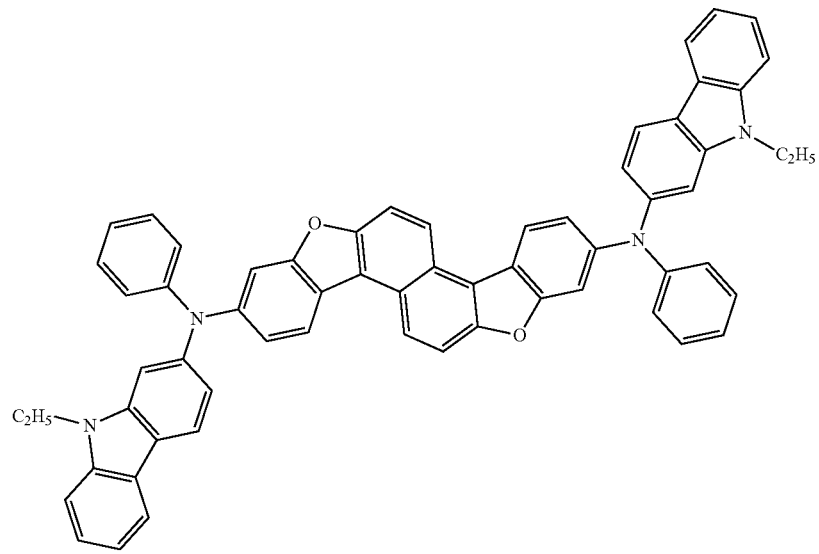
(514)
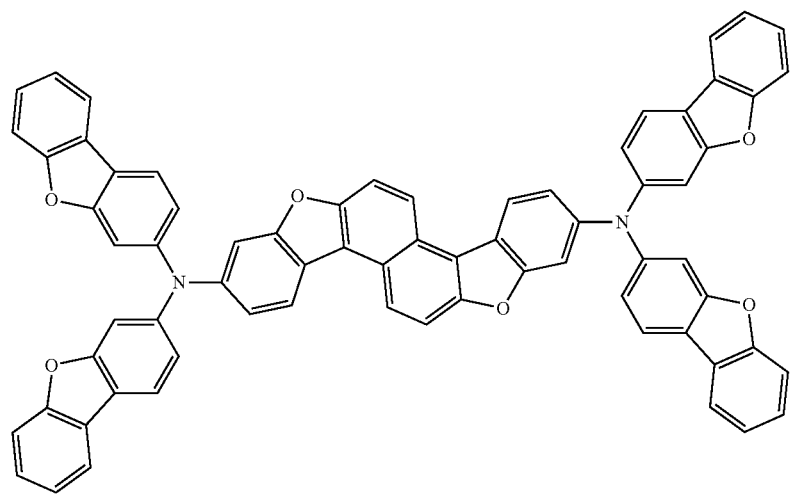
(515)
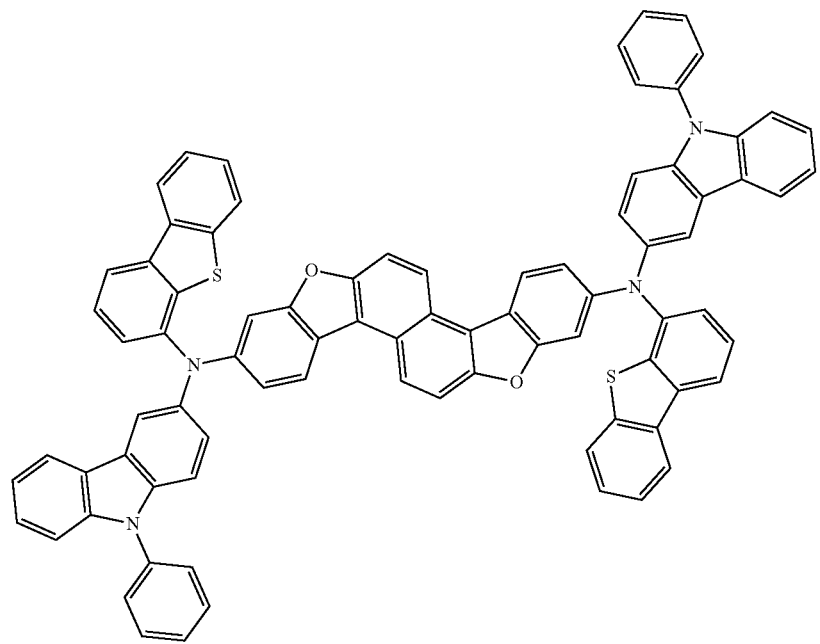

(516)
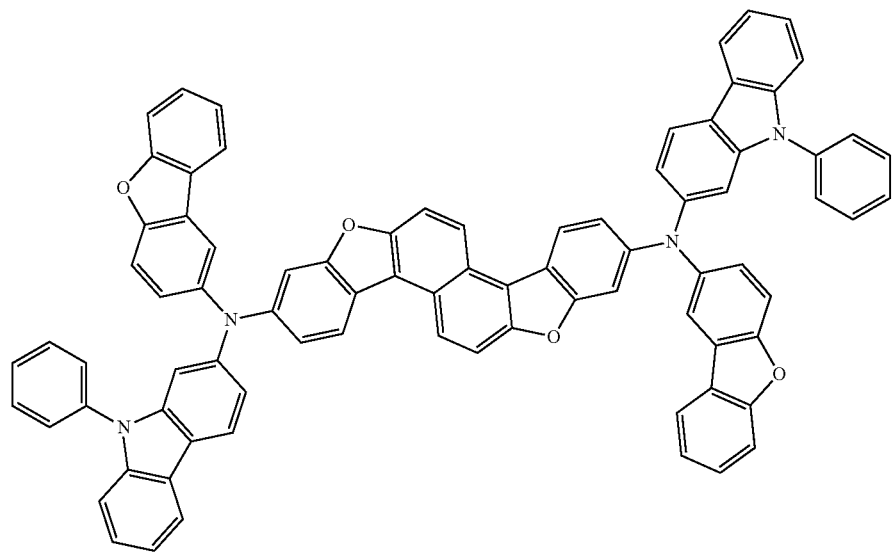
[Chemical Formulae 40]
(517)
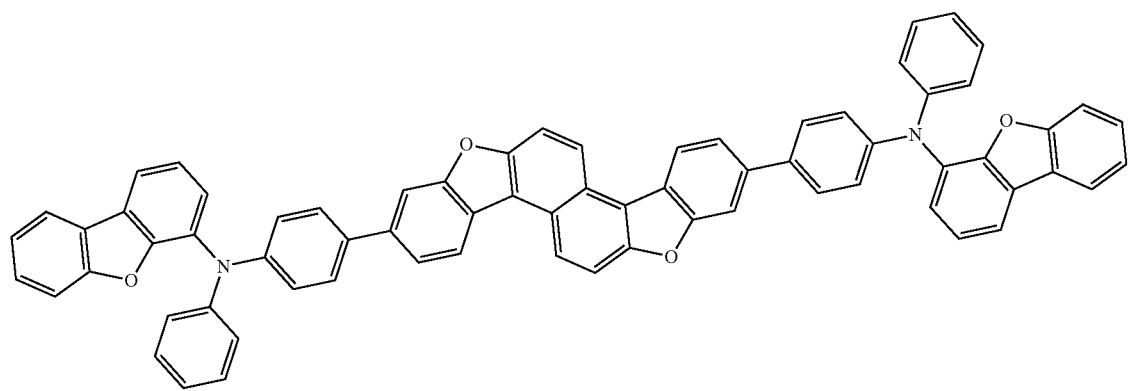
(518)
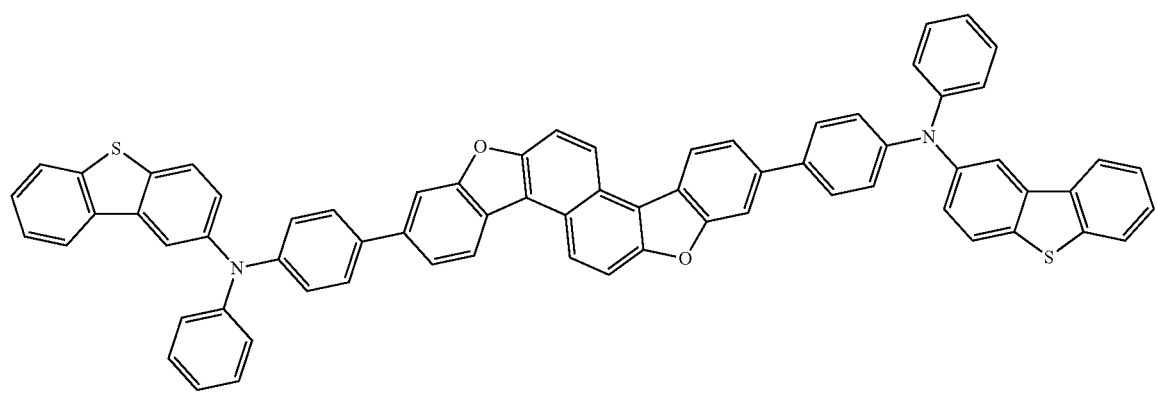

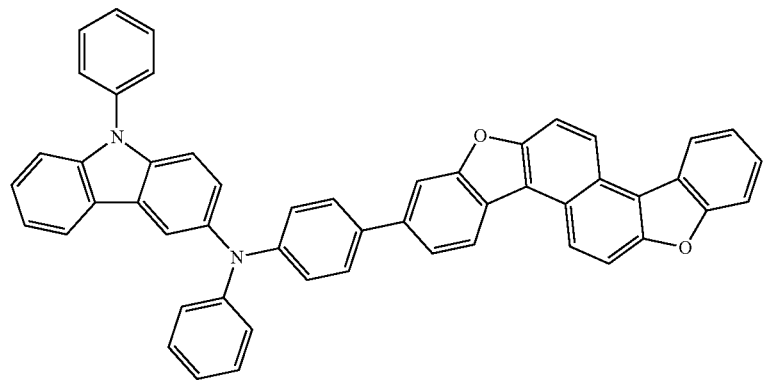
(519)
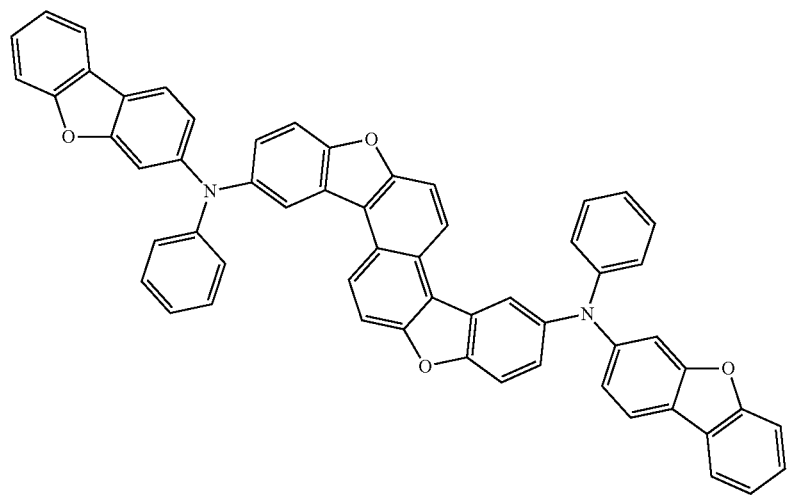
(520)
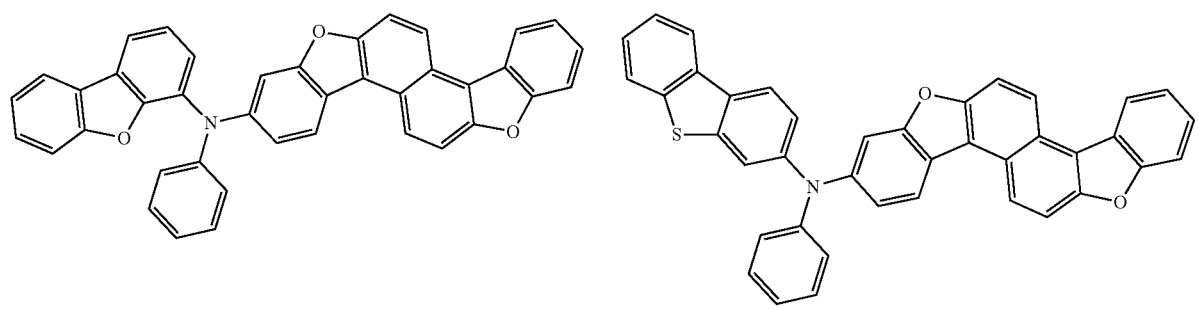
(521) (522)

(523)
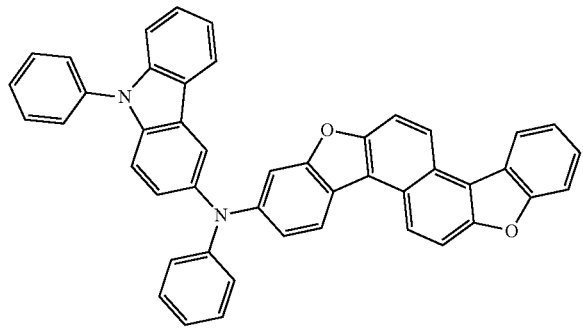
(524)
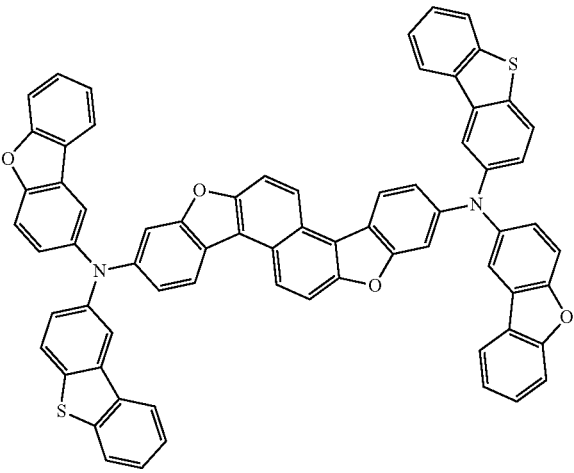
(525)
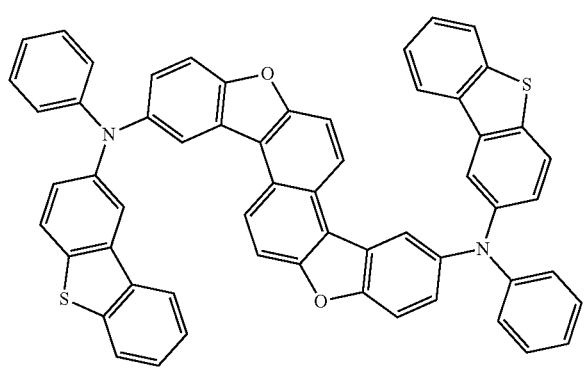
(526)
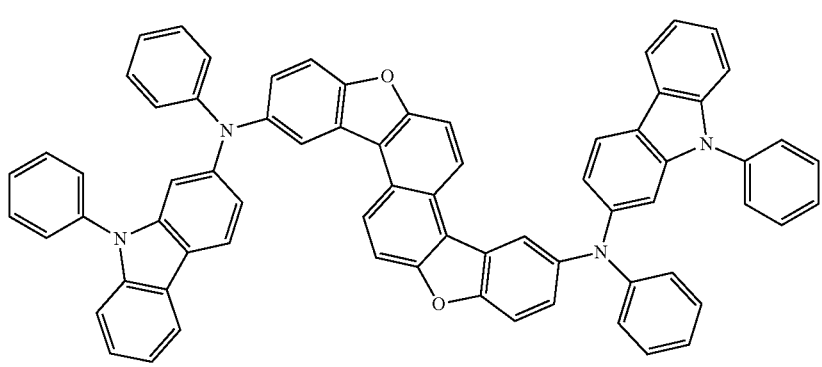

[Chemical Formulae 41]
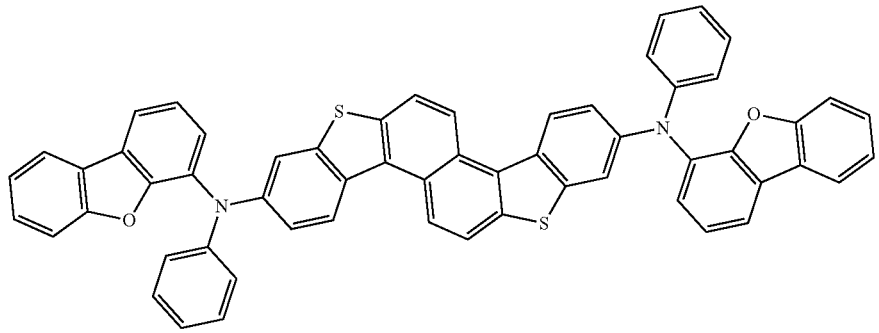
(600)
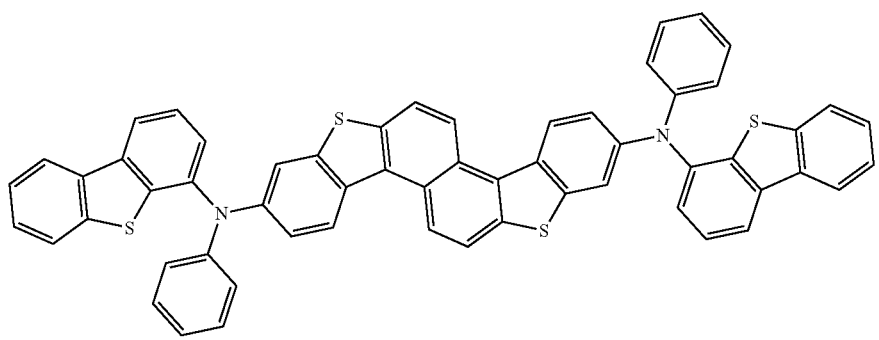
(601)
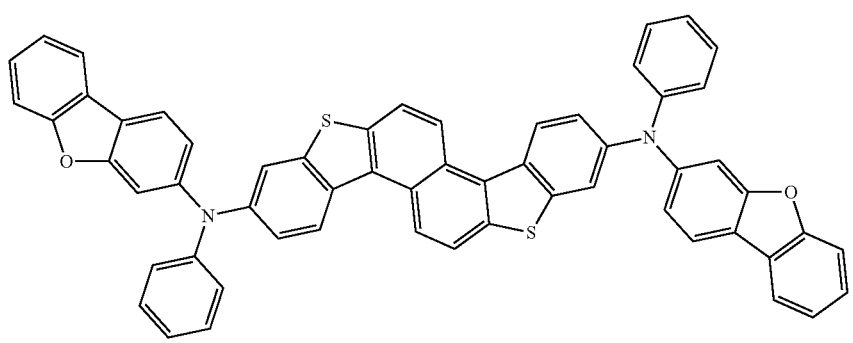
(502)
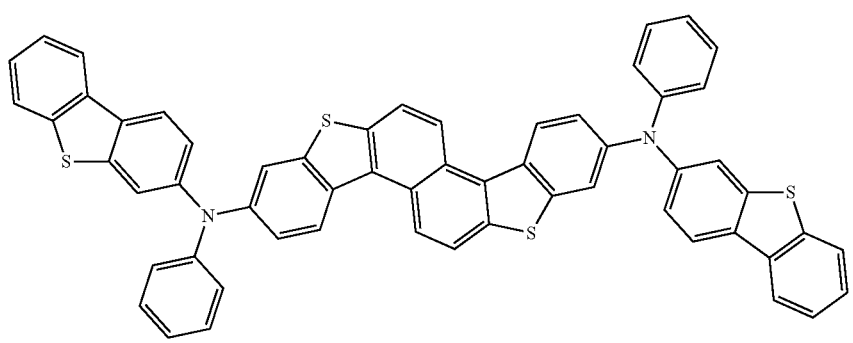
(603)

(604)
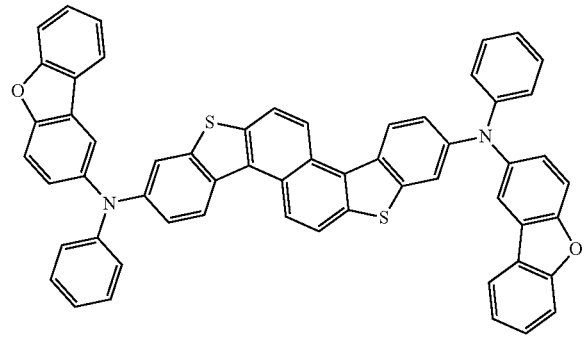
(605)
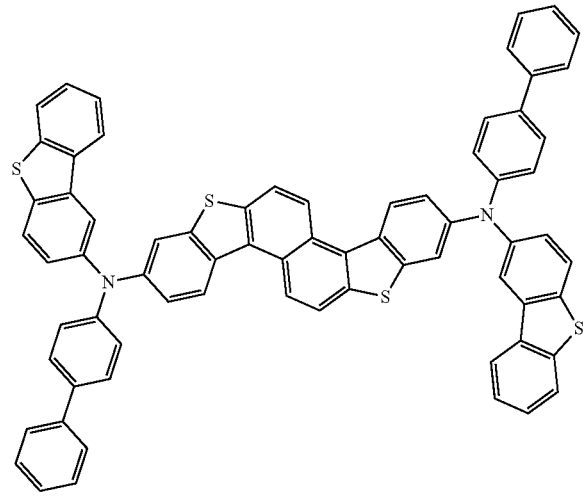
(606)
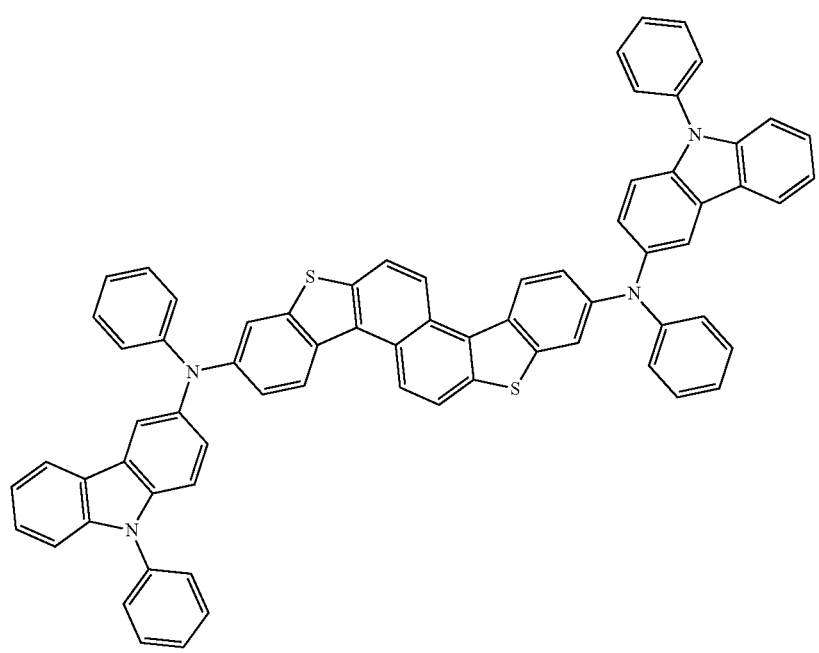

(607)
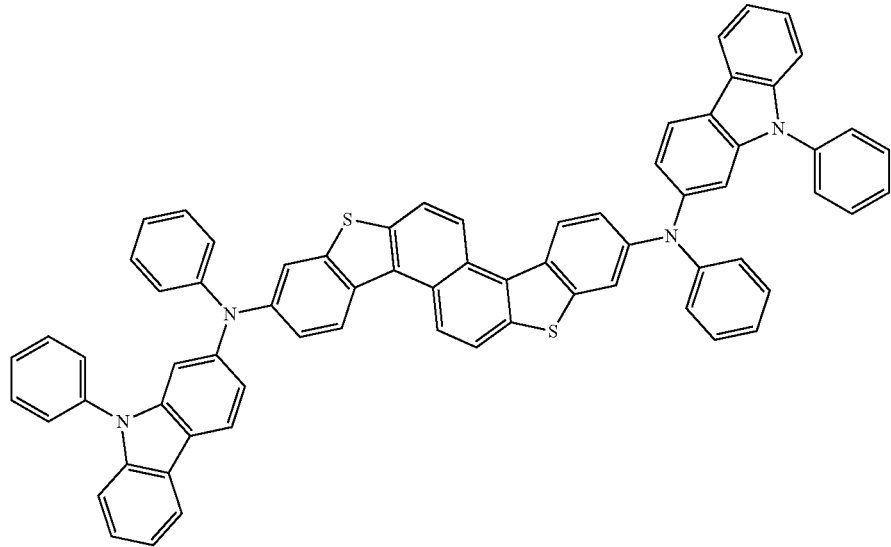
(608)
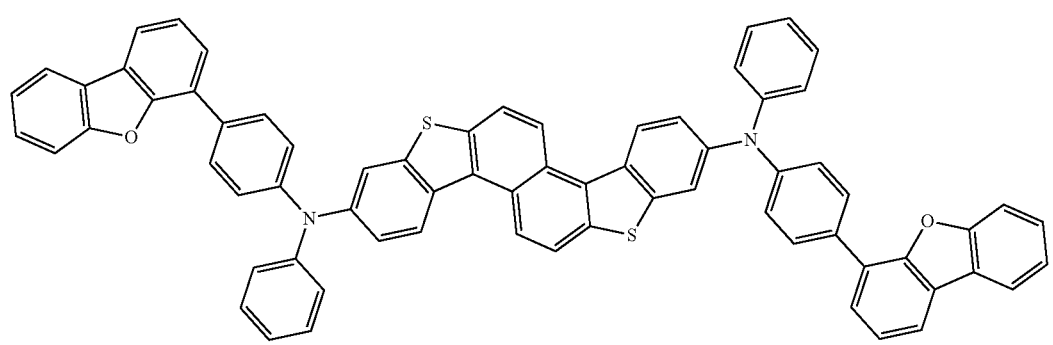
[Chemical Formulae 42]
(609)
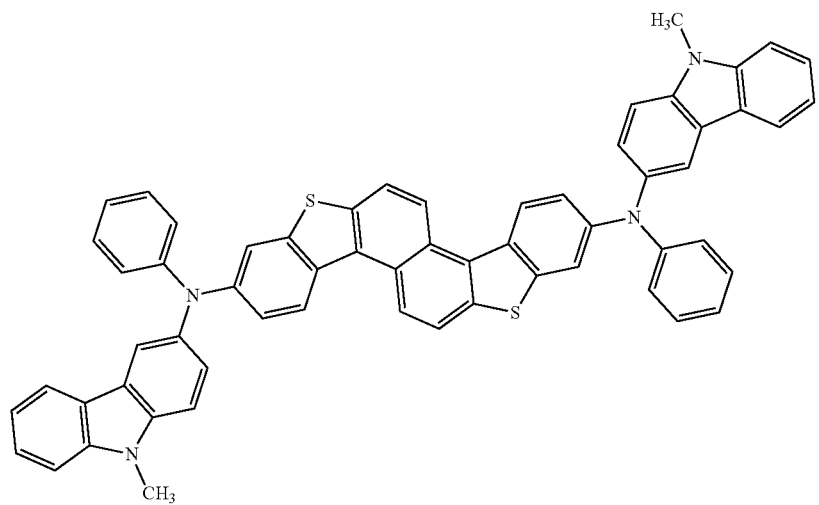

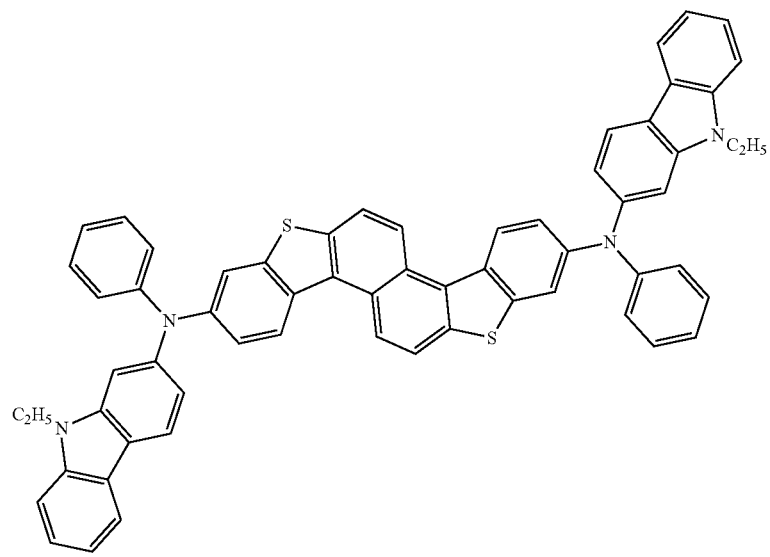
(610)
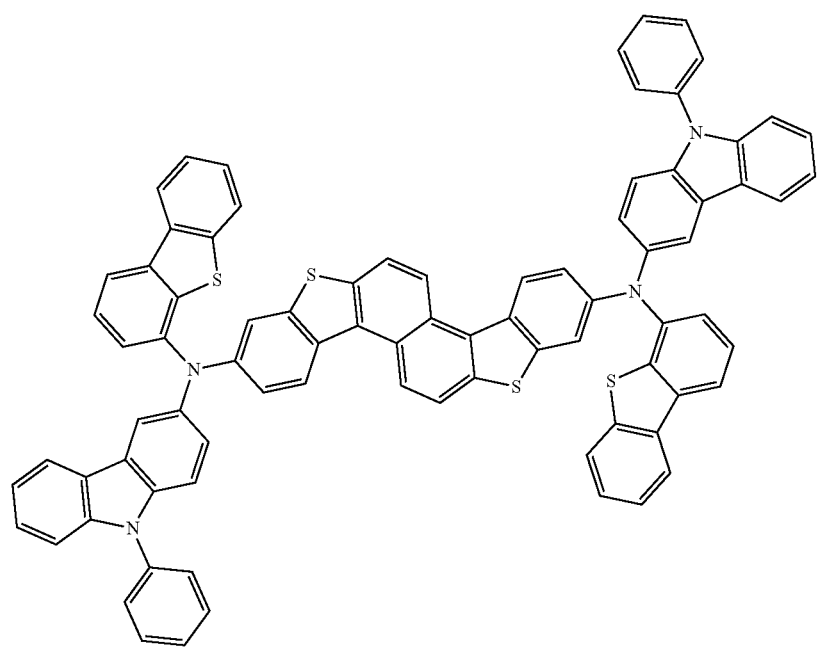
(611)

-continued
(612)
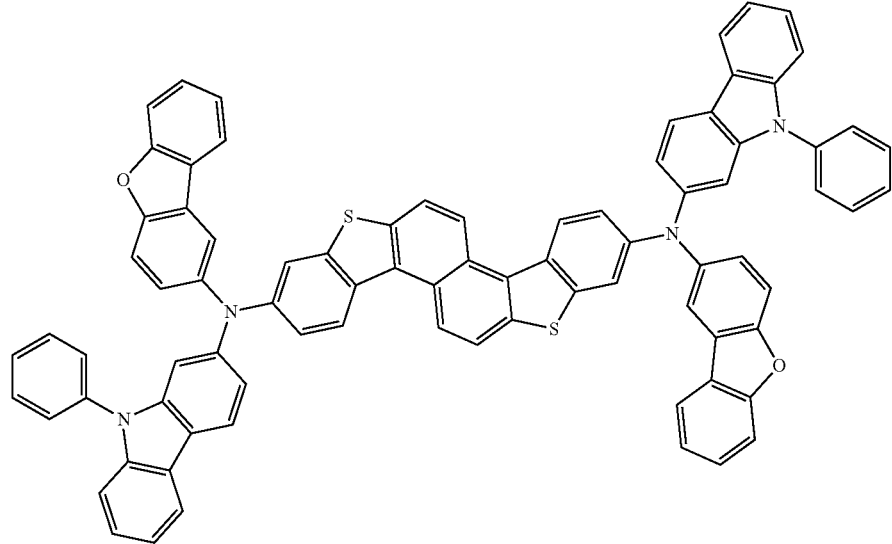
(613)
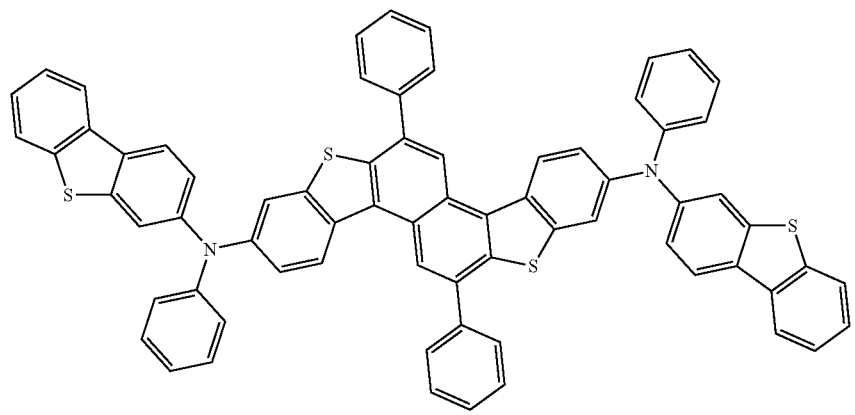
(614)
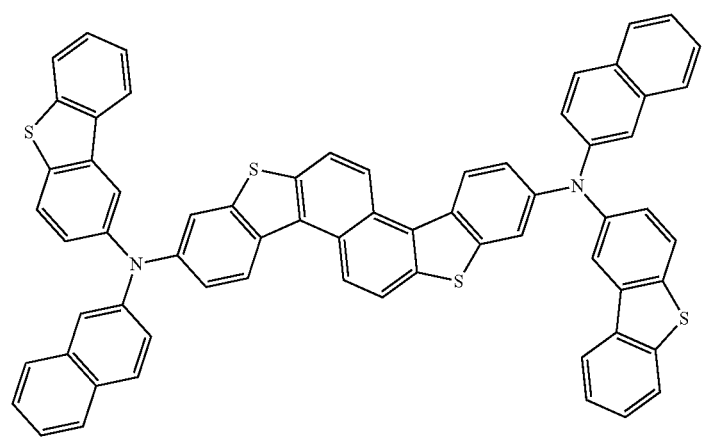

(615)
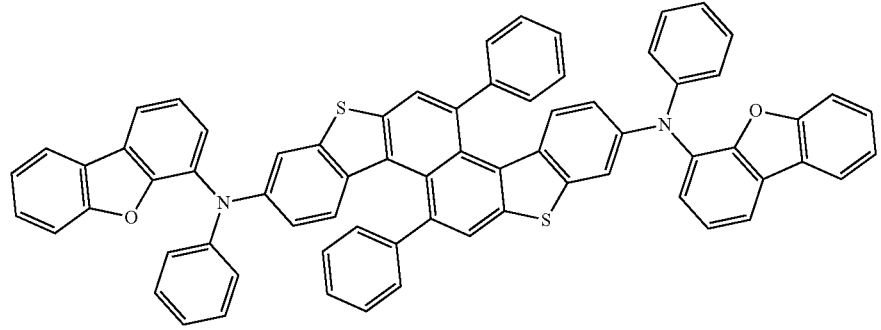
(616)
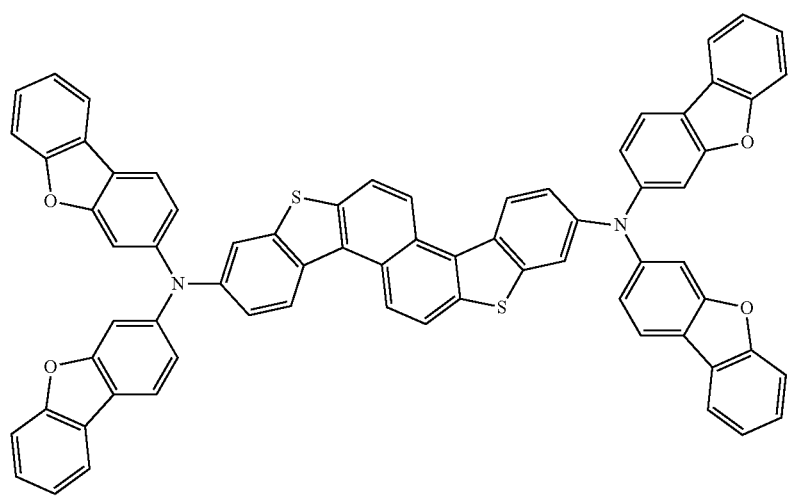
[Chemical Formulae 43]
(617)
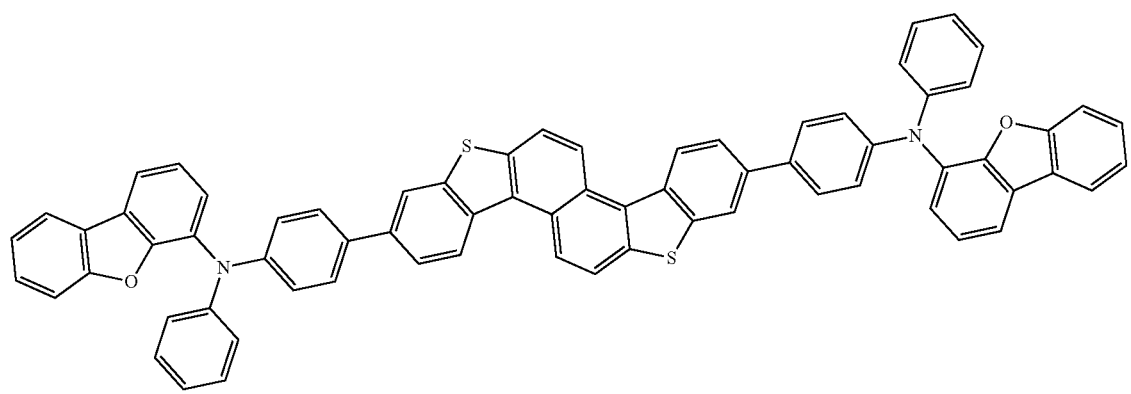

-continued
(618)
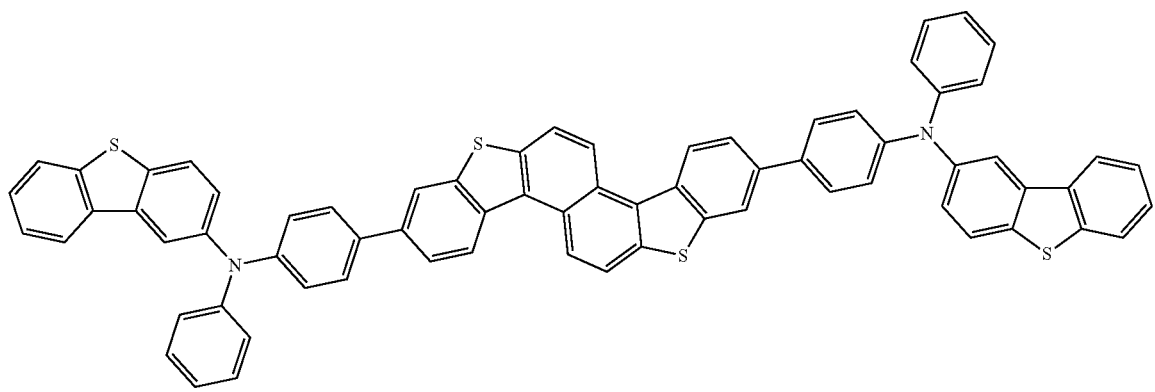
(619)
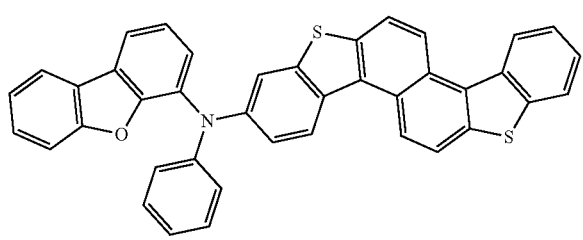
(620)
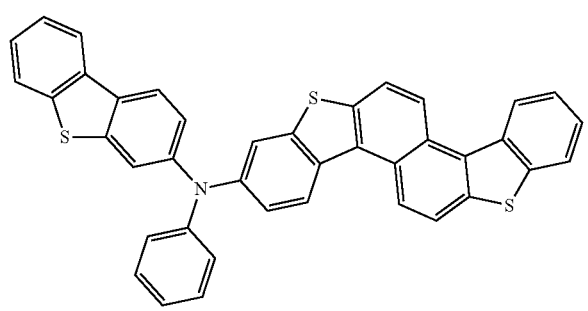
(621)
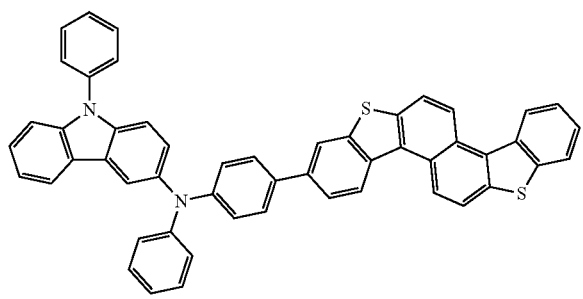
(622)
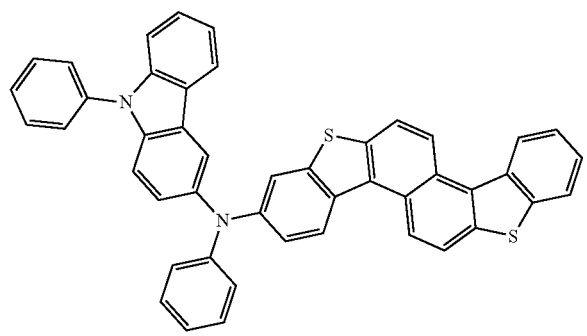
(623)
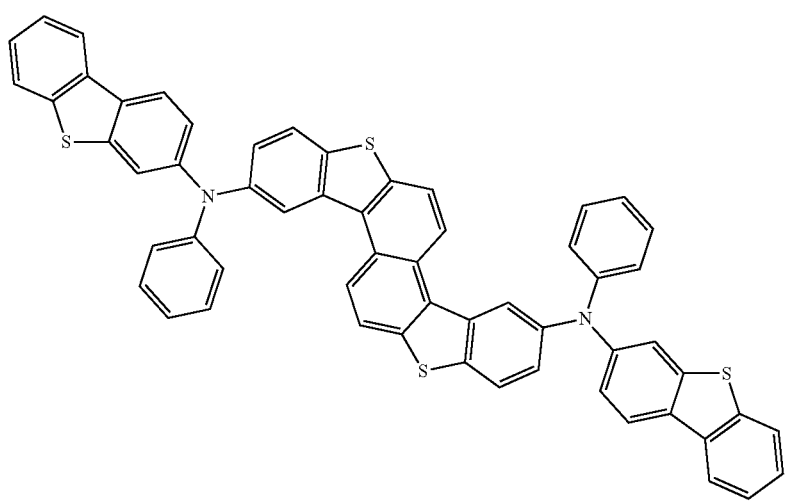

-continued
(624)
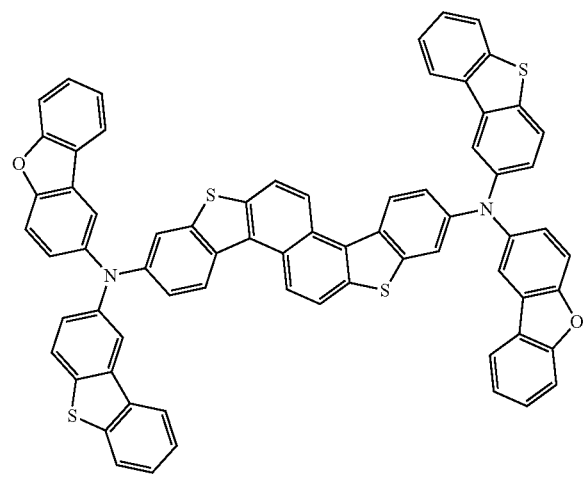
(625)
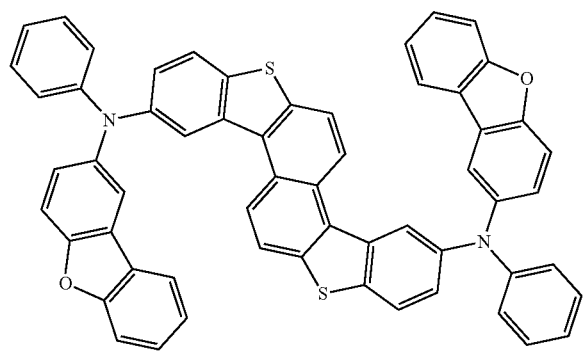
(626)
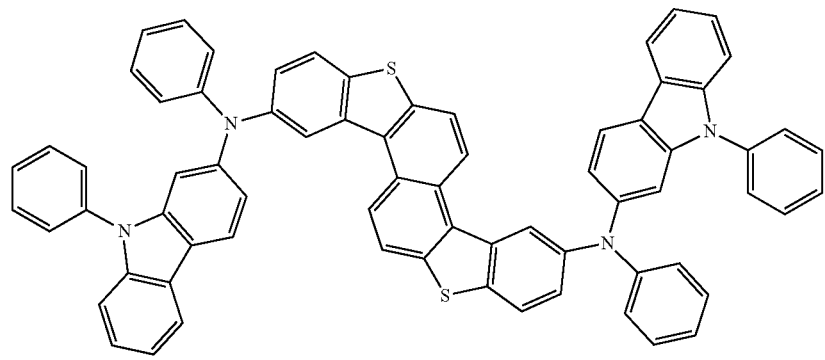
[Chemical Formulae 44]
(700)
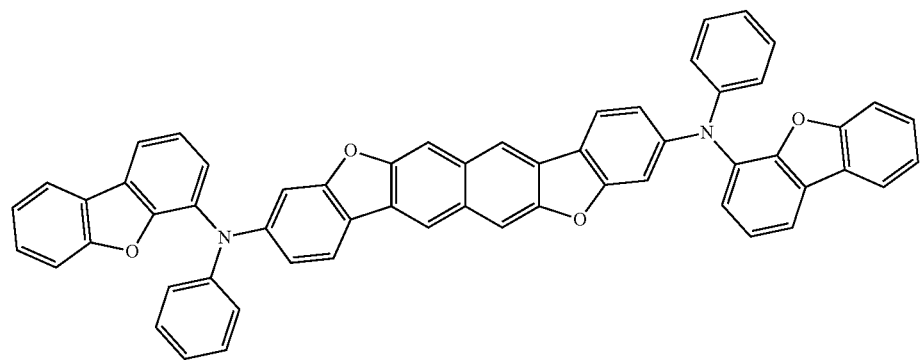
(701)
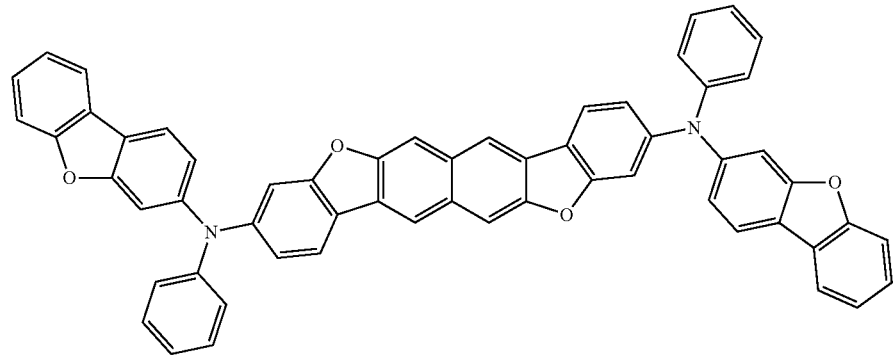

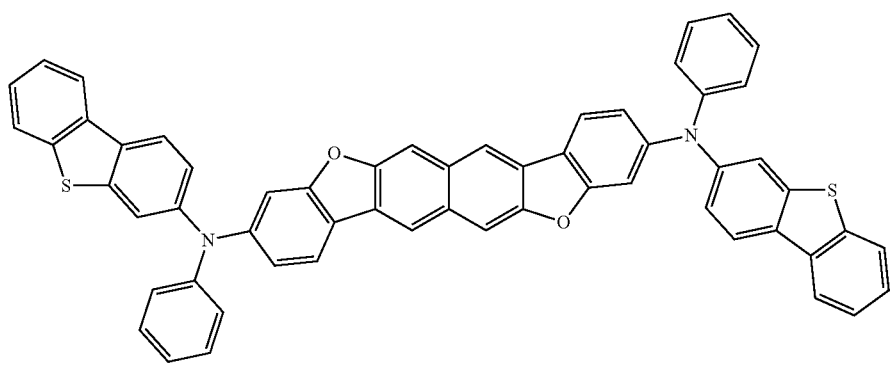
(702)
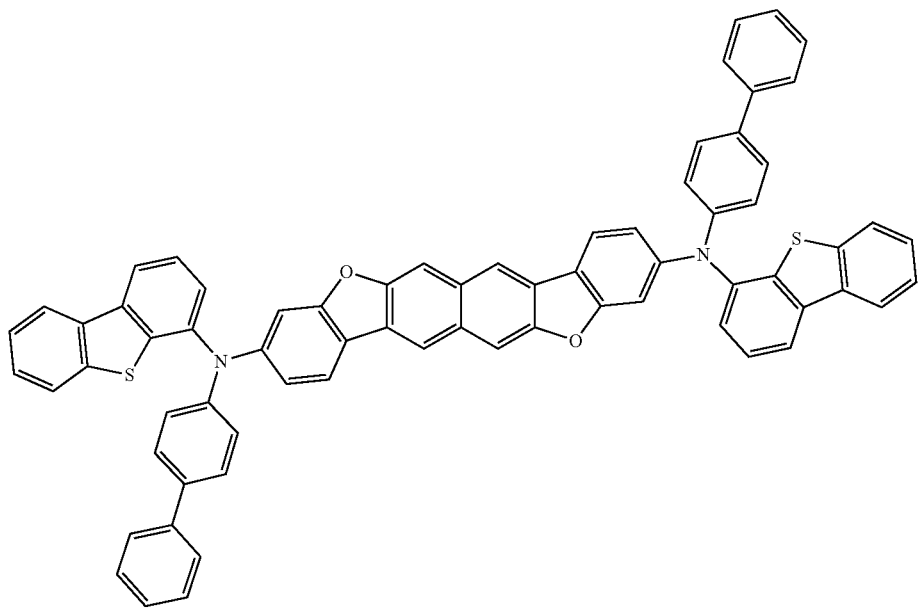
(703)
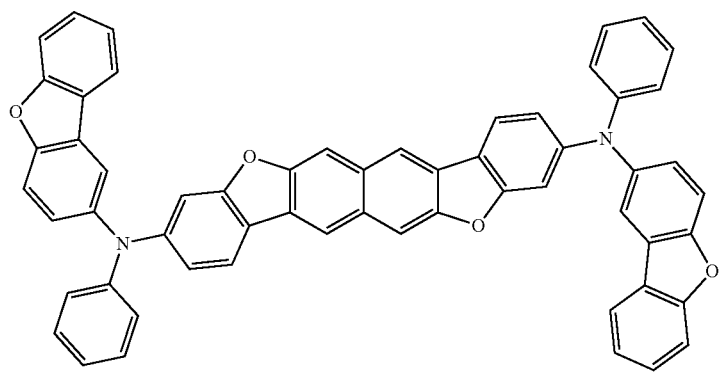
(704)

(705)
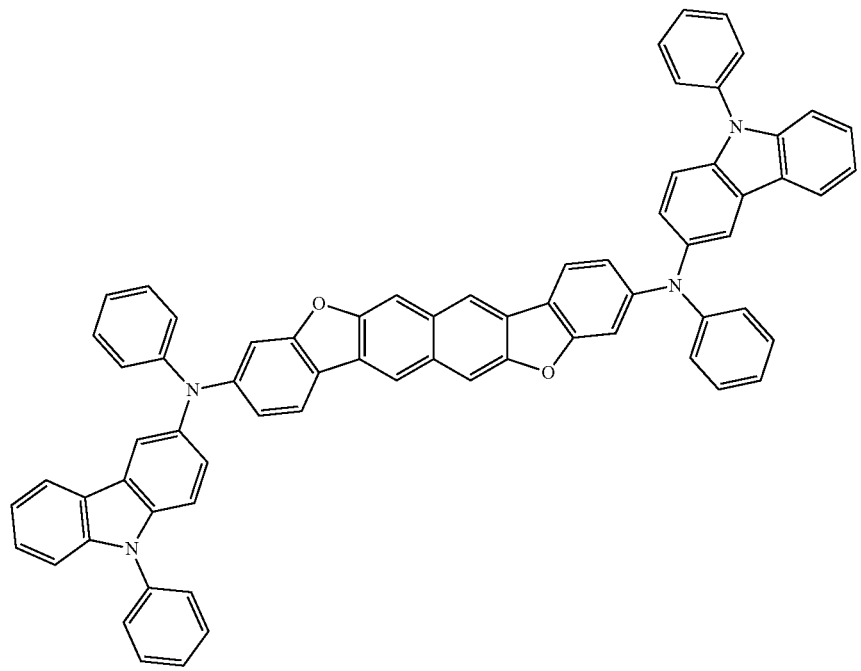
(706)
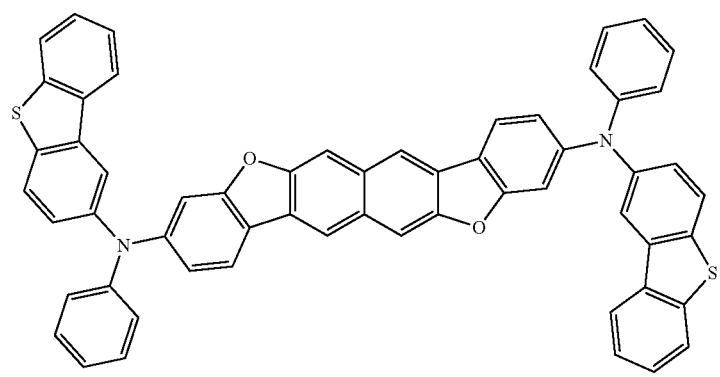
(707)
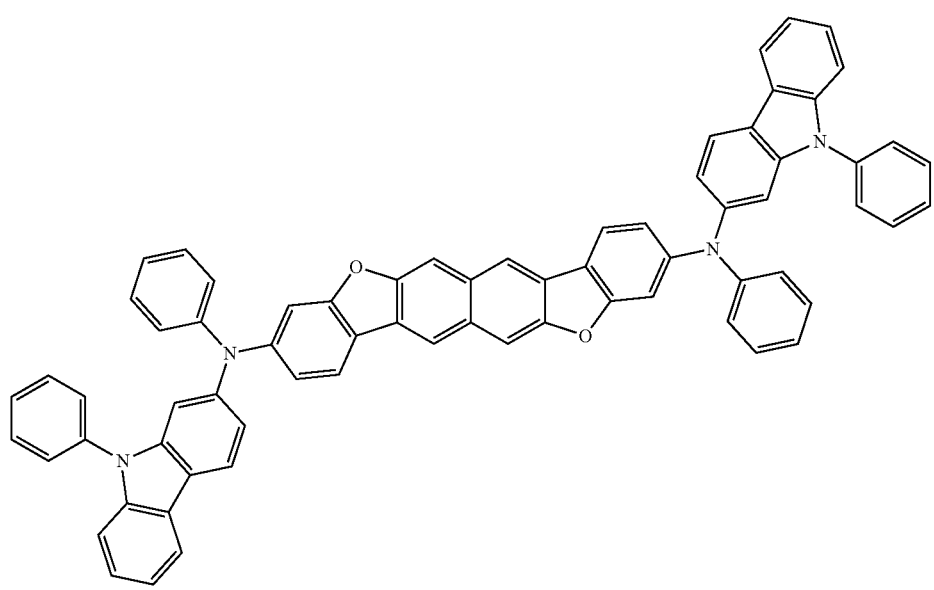

(708)
(709)
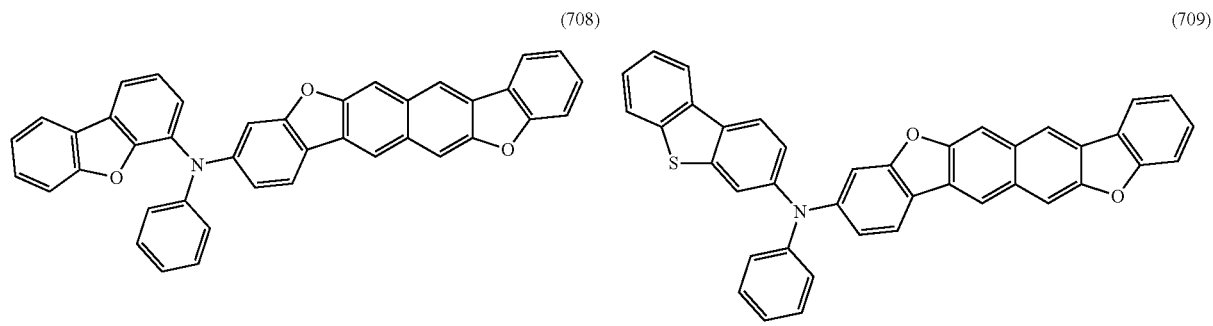
(710)
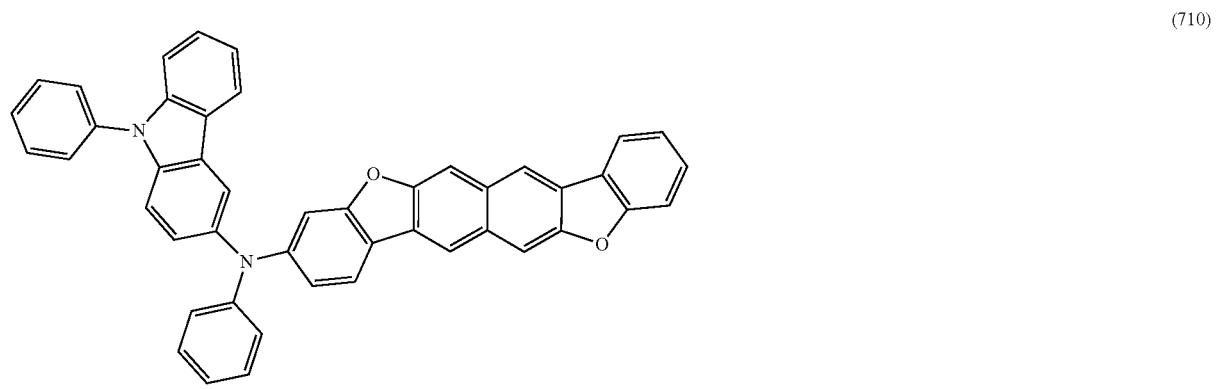
[Chemical Formulae 45]
(711)
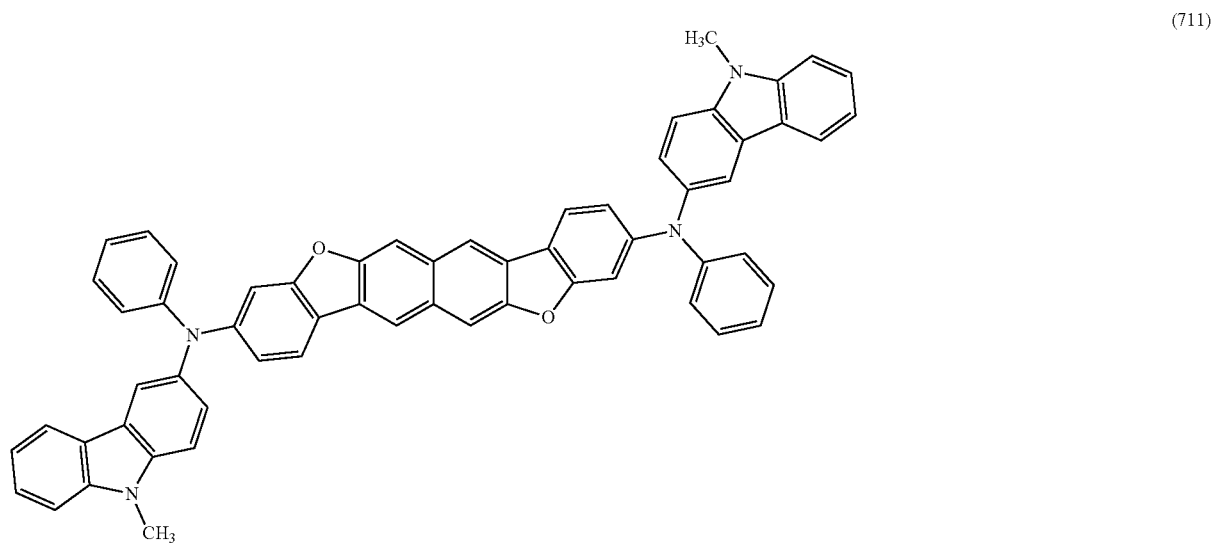 [SMILES: Cn1c2ccccc2c2cc(N(c3ccccc3)c3ccc4c(c3)sc3cc5cc6c(cc5cc34)sc3cc(N(c4ccccc4)c4ccc5c(c4)c4ccccc4n5C)ccc36)ccc21]

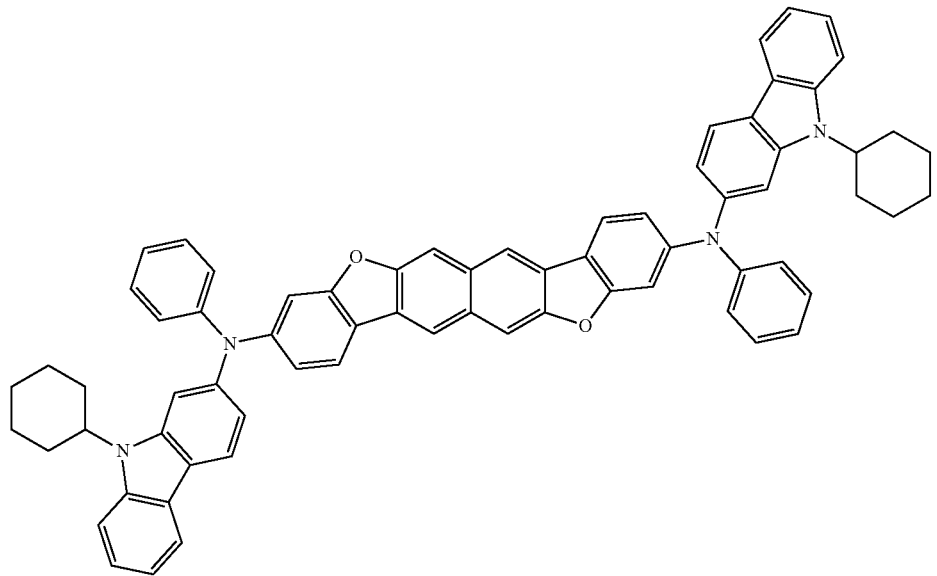
(712)
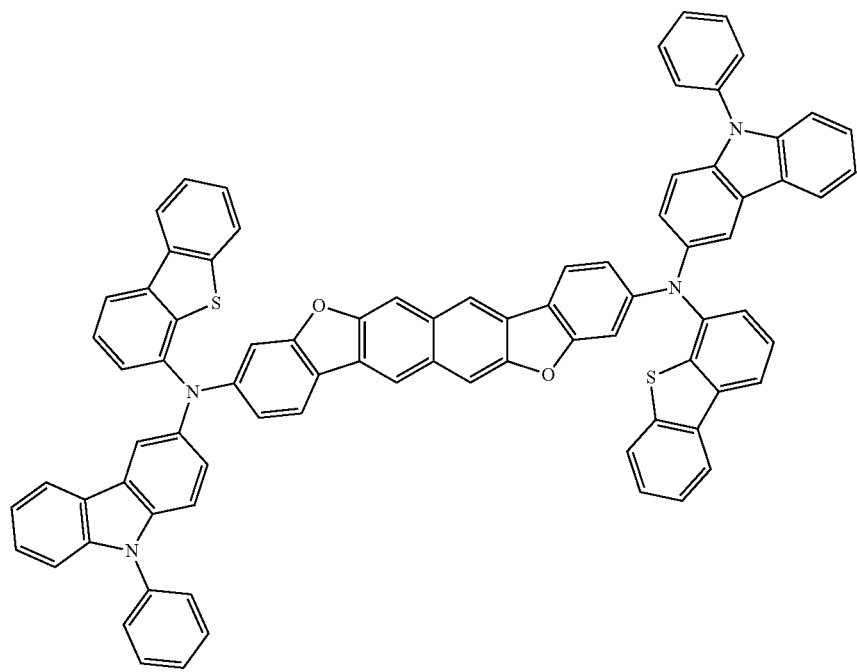
(713)

-continued
(714)
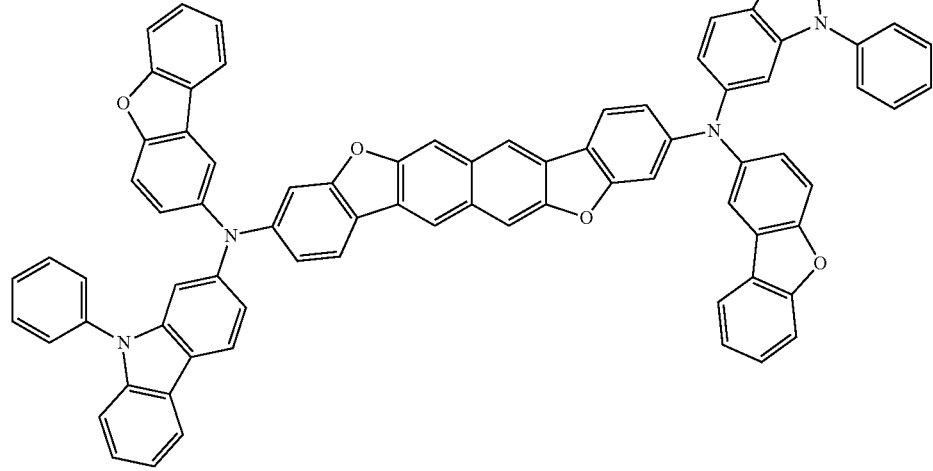
(715)
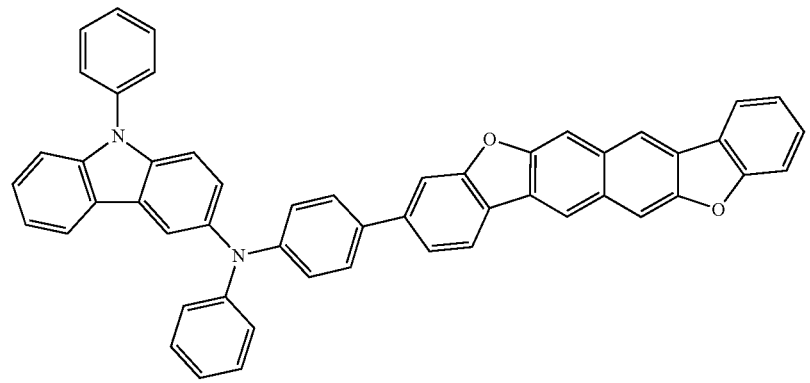
(716)
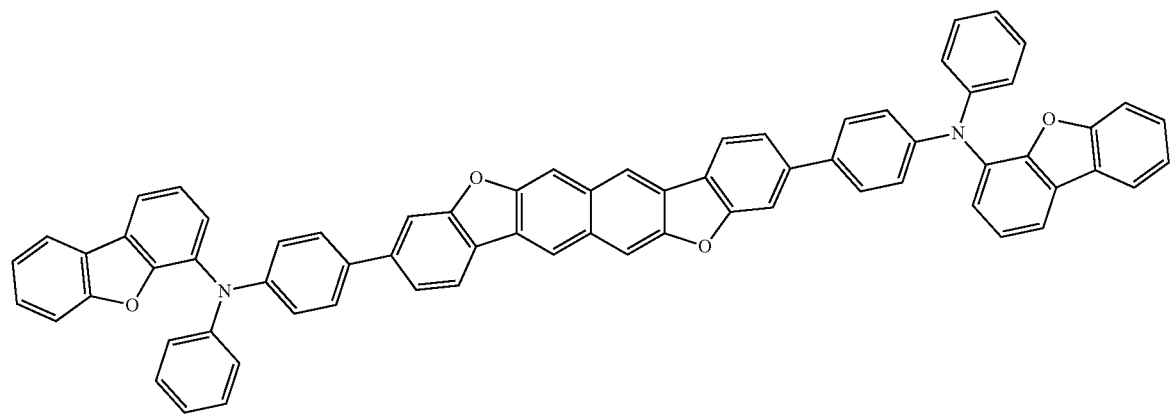

(717)

(718)

[Chemical Formulae 46]

(719)

-continued
(720)
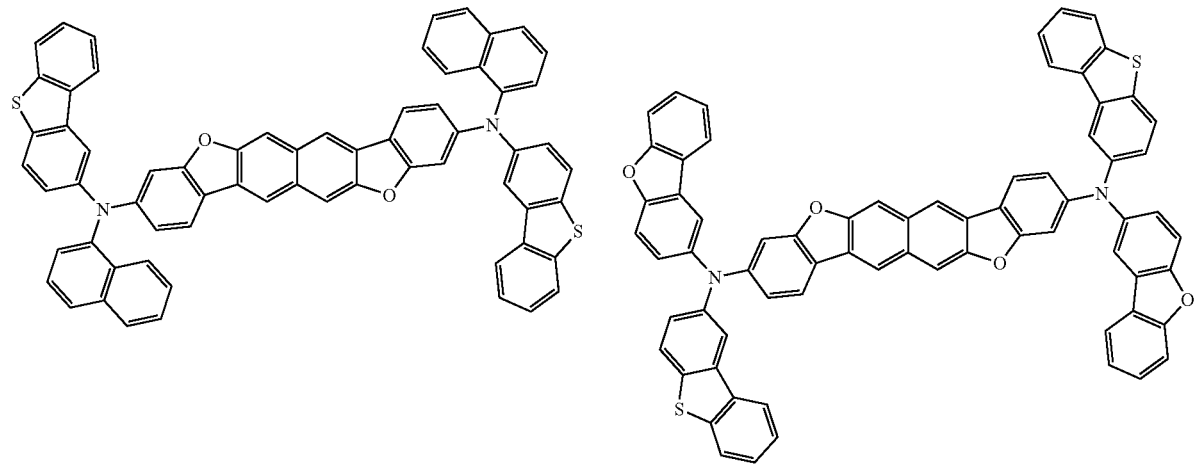
(721)
(722)
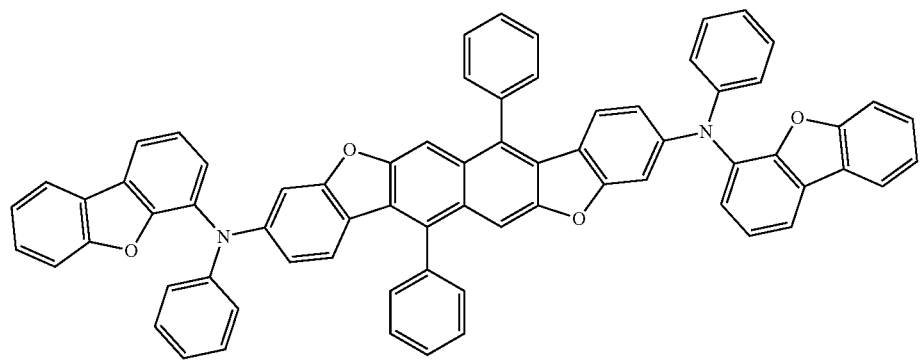
(723)
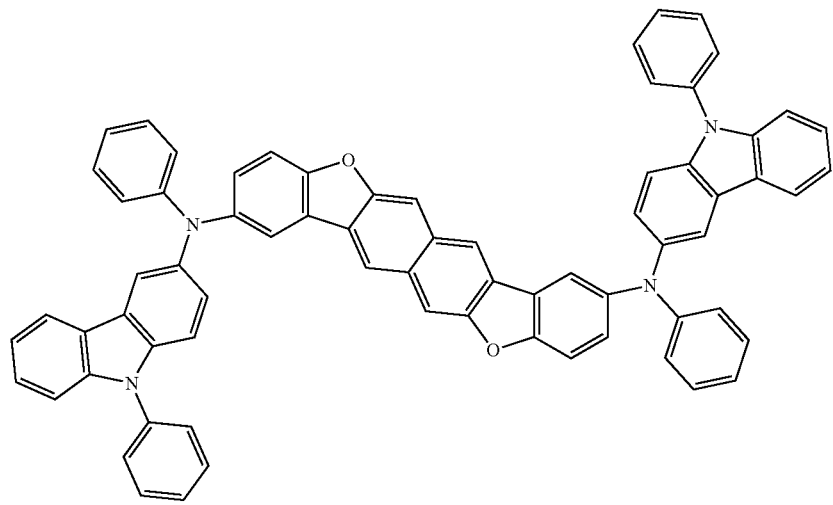
(724)
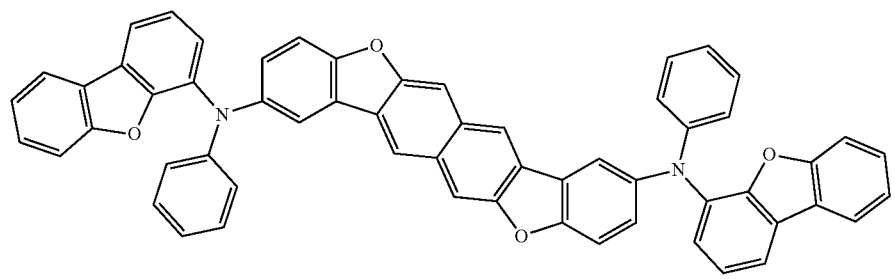

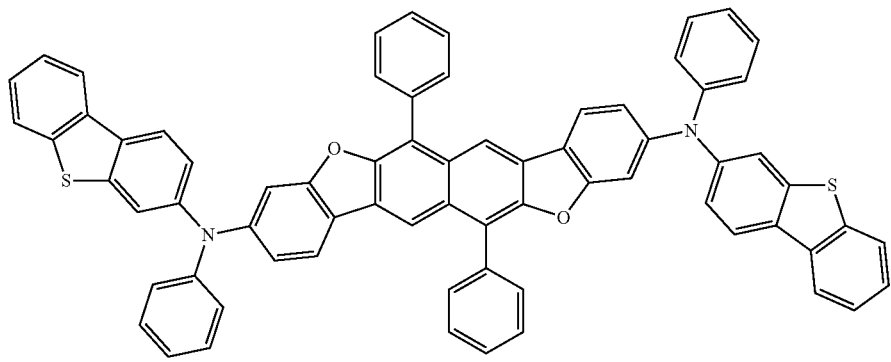
(725)
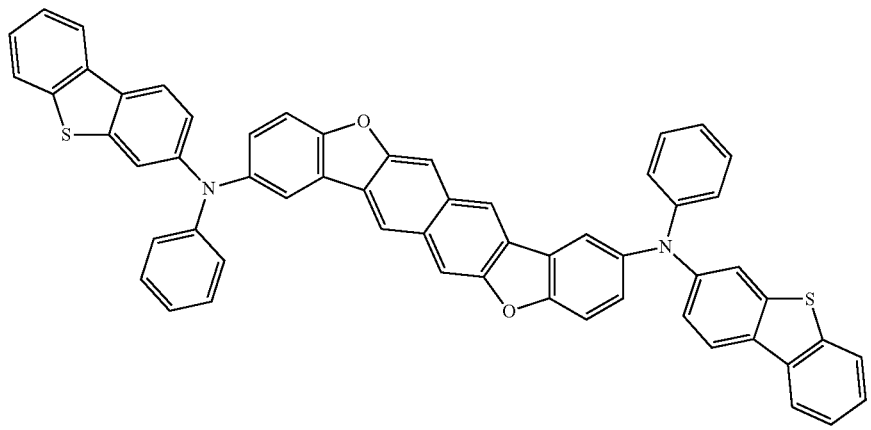
(726)
[Chemical Formulae 47]
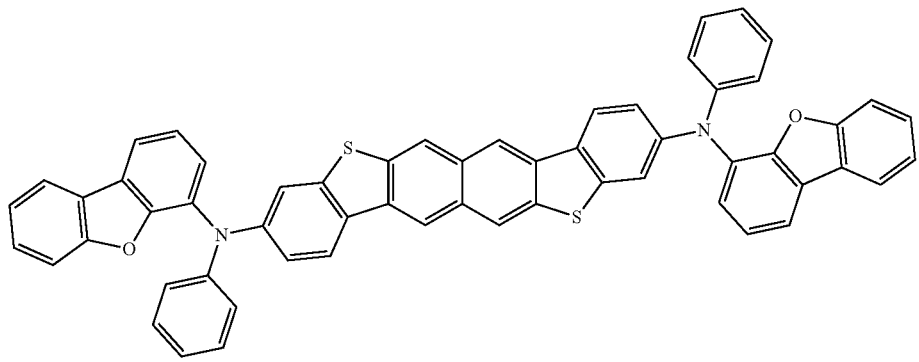
(800)
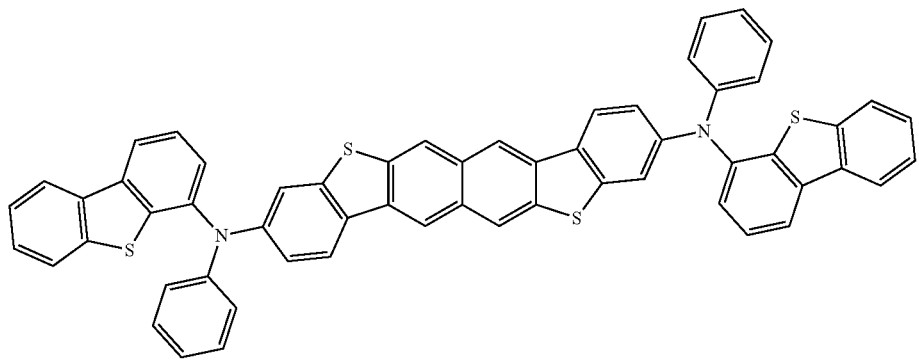
(801)

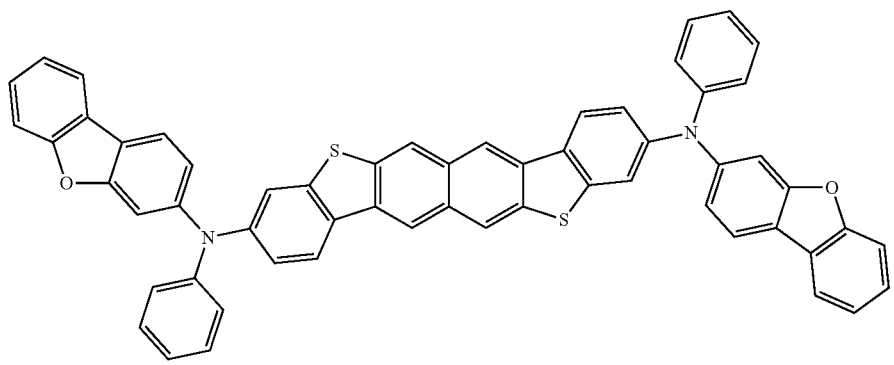
(802)
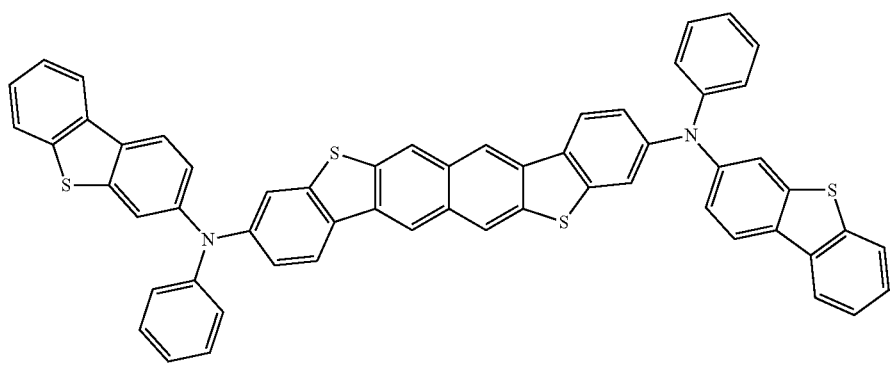
(803)
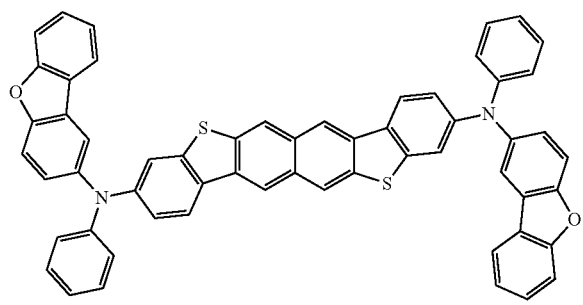
(804)
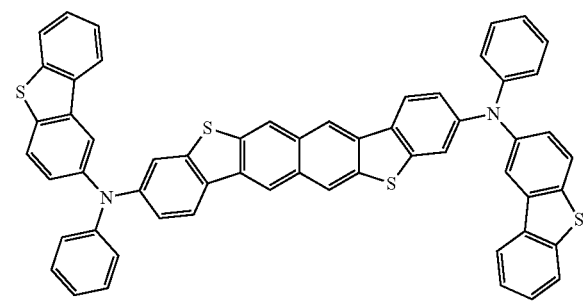
(805)

-continued
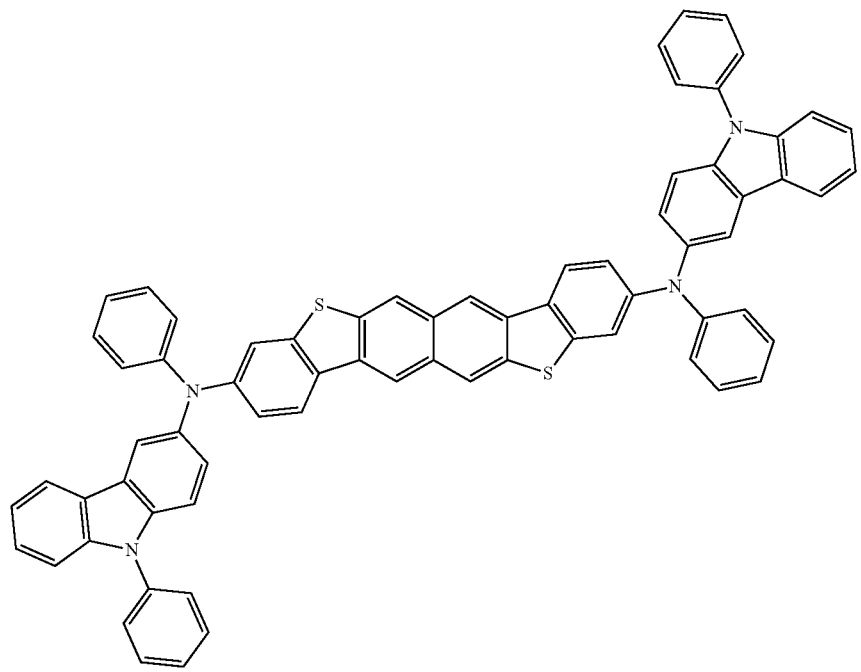
(806)
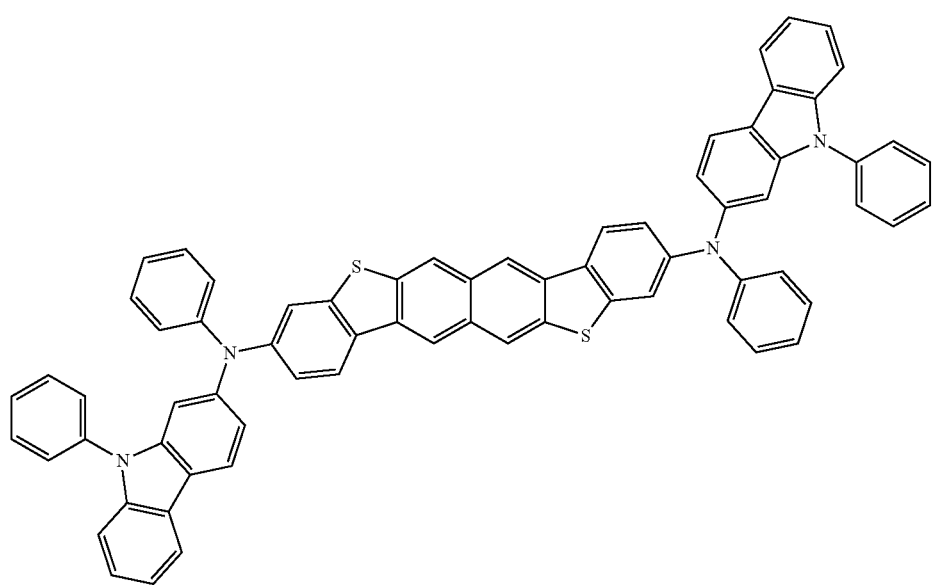
(807)

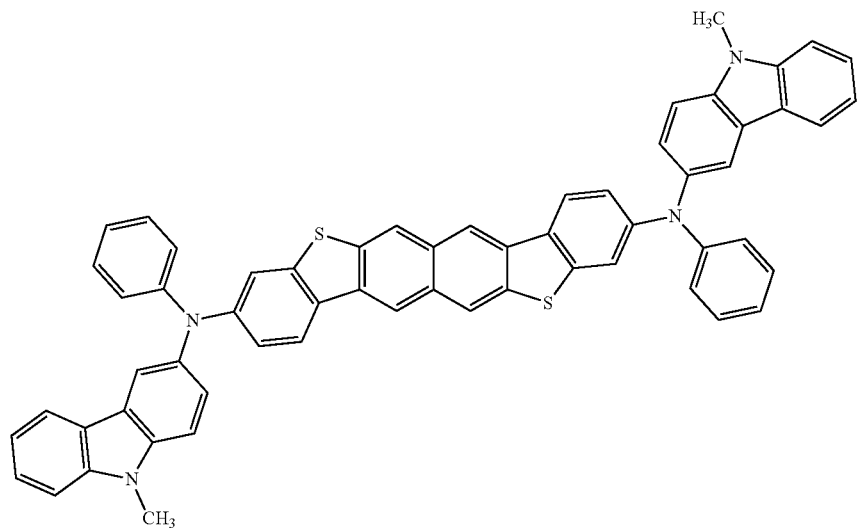
(808)
[Chemical Formulae 48]
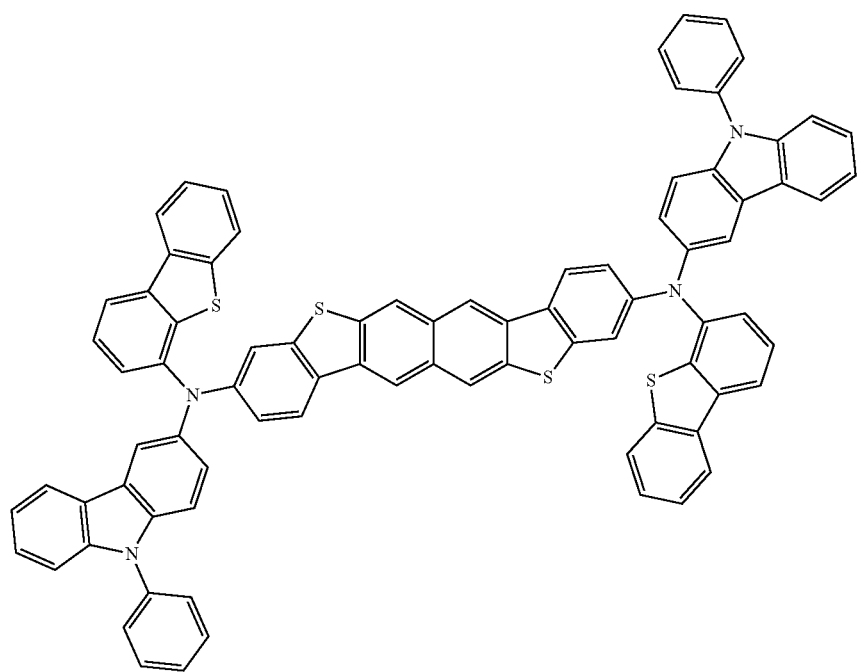
(809)

(810)
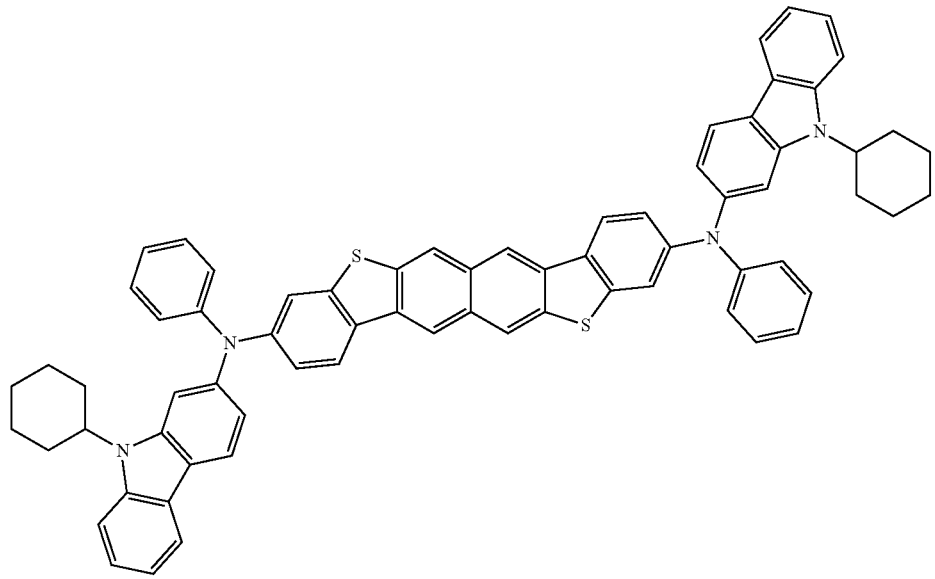
(811)
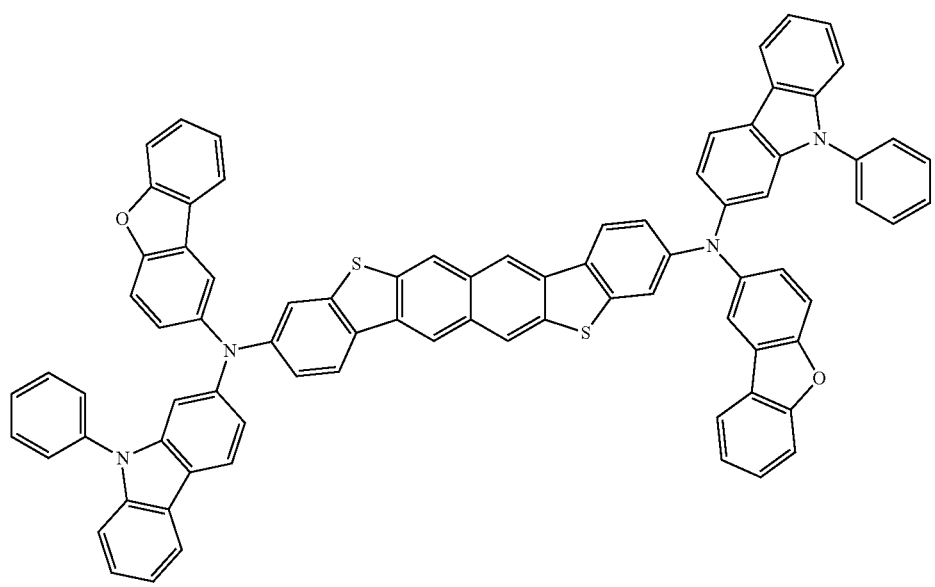
(812)
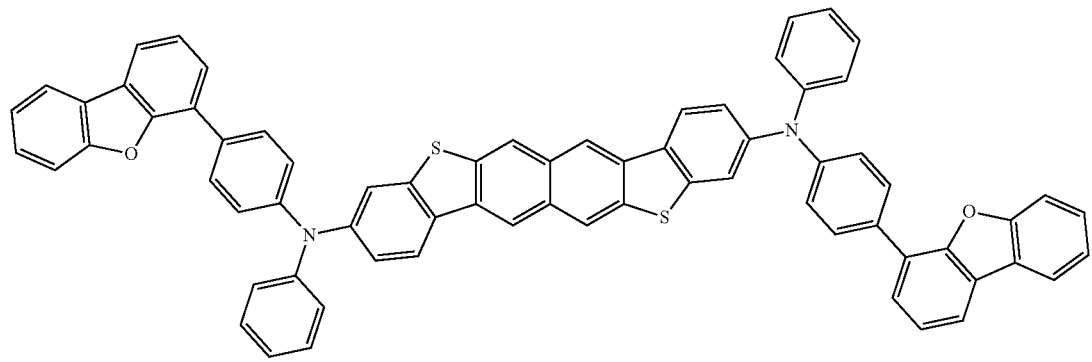

(813)
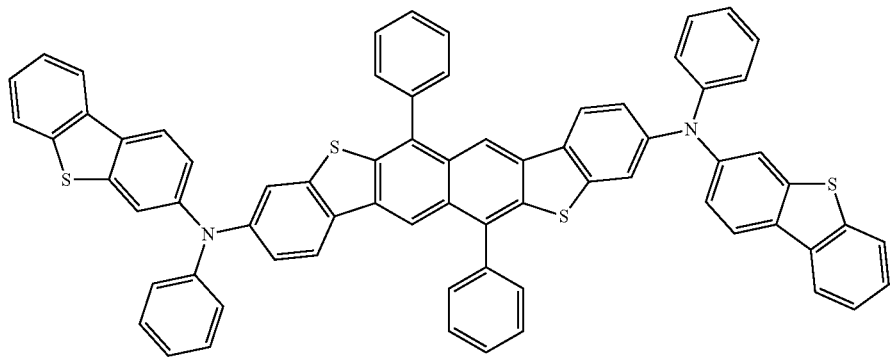
(814)
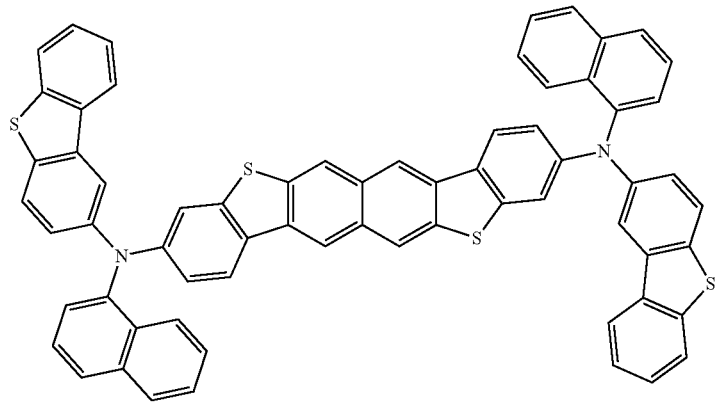
(815)
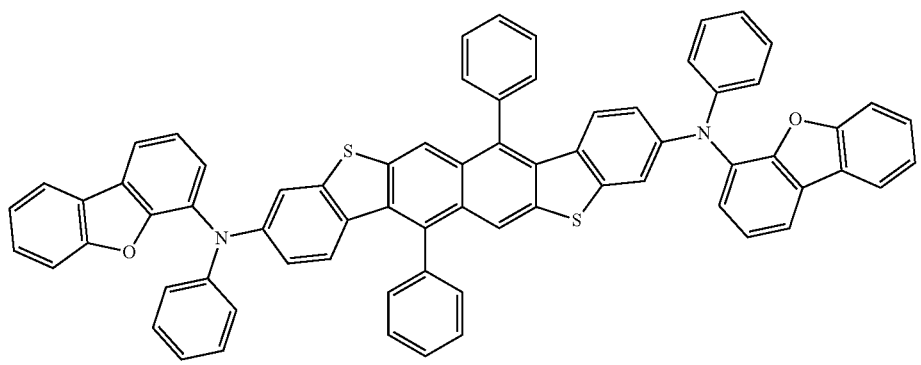
[Chemical Formulae 49]
(816)
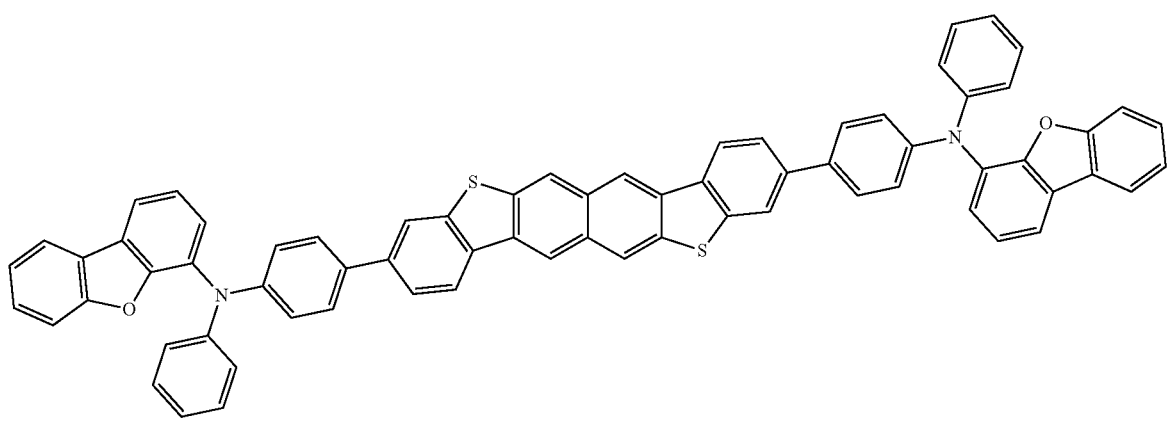

(817)
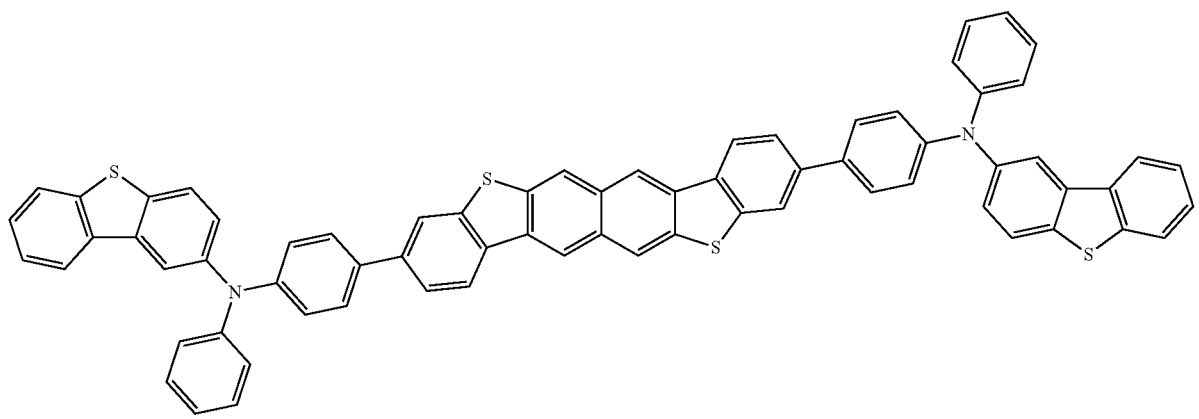
(818)
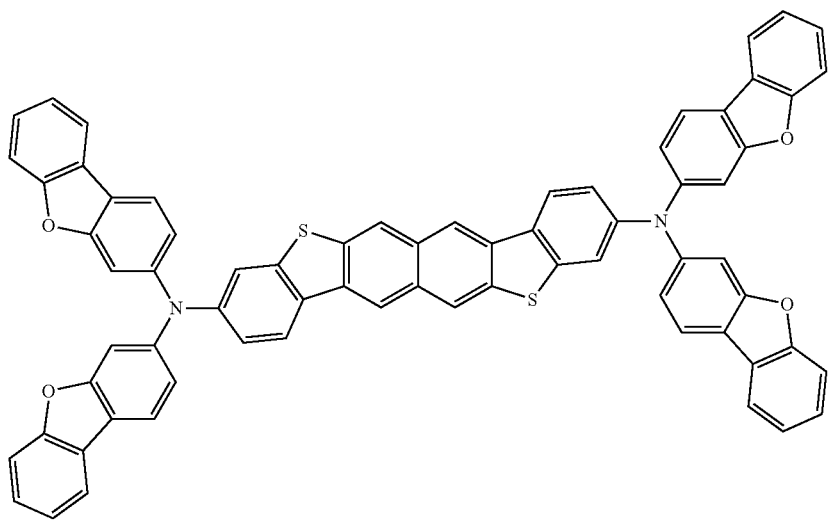
(819) (820)
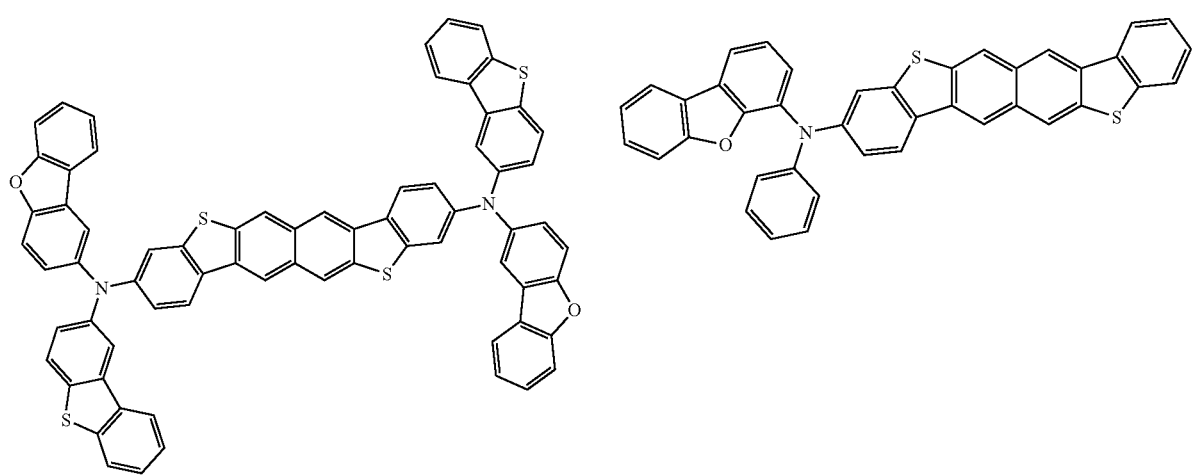

-continued
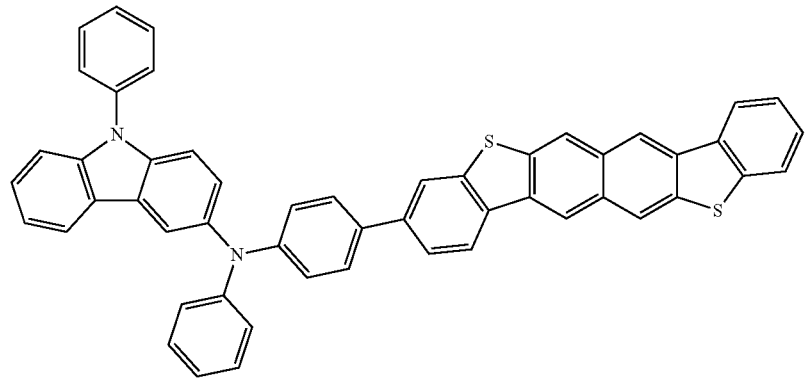
(821)
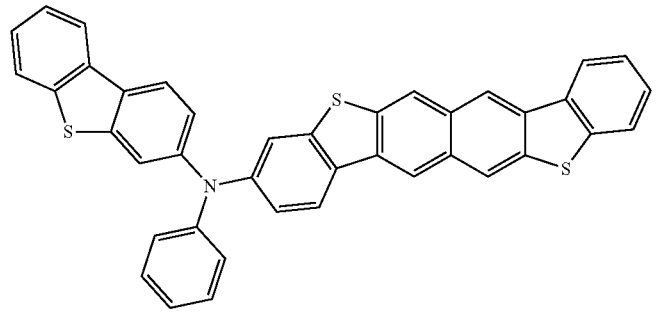
(822)
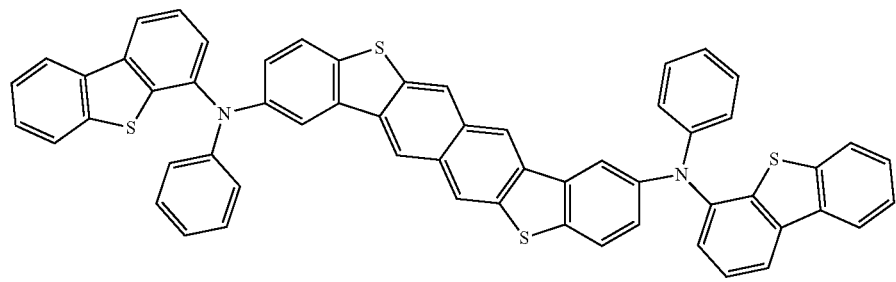
(823)
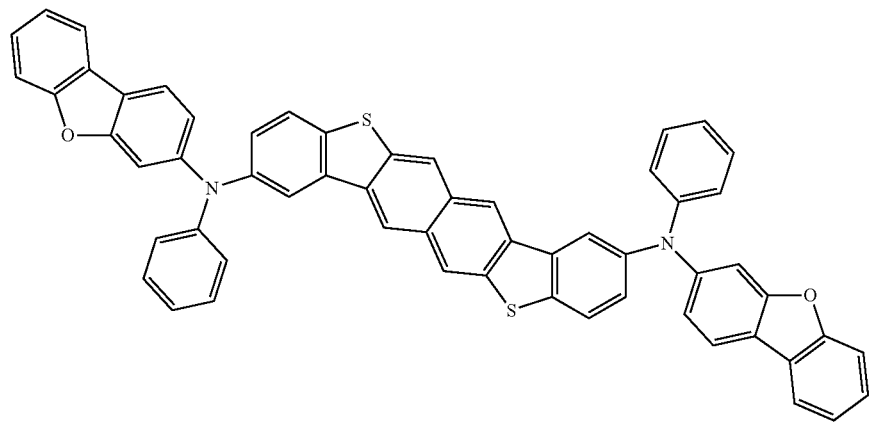
(824)

-continued
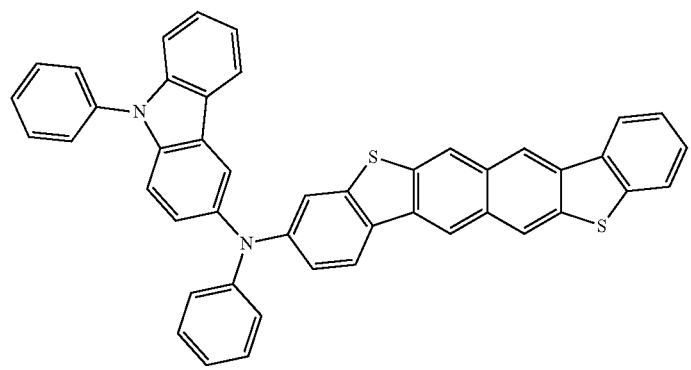
(825)
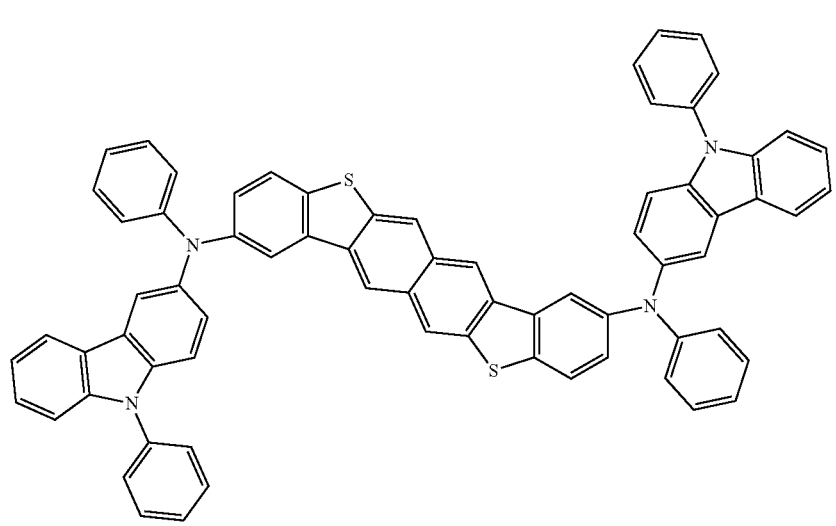
(826)
[Chemical Formulae 50]
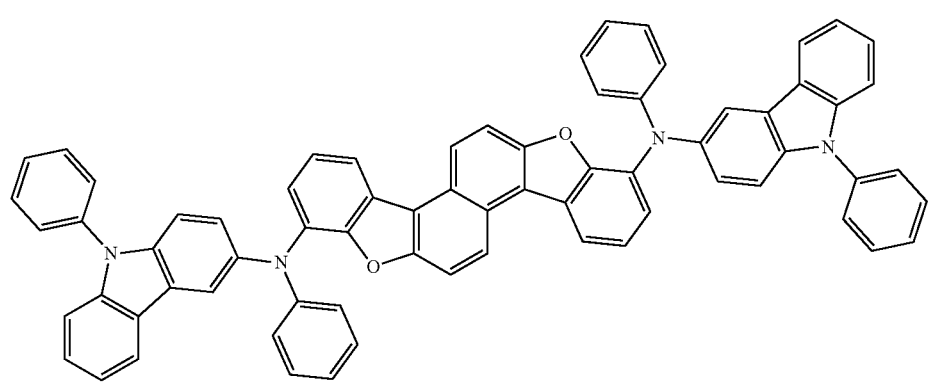
(900)

(901)
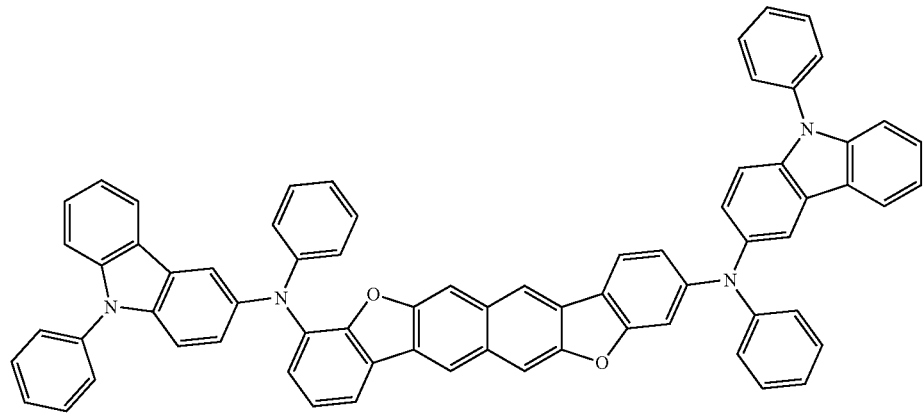
(902) (903)
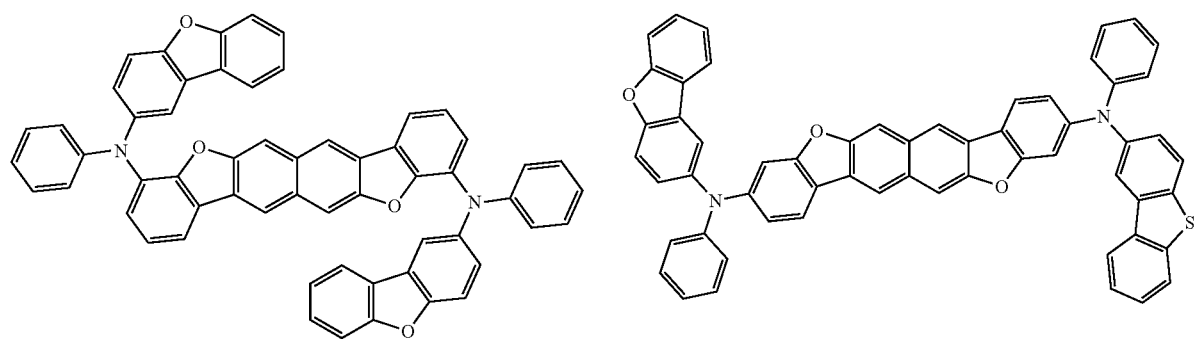
(904) (905)
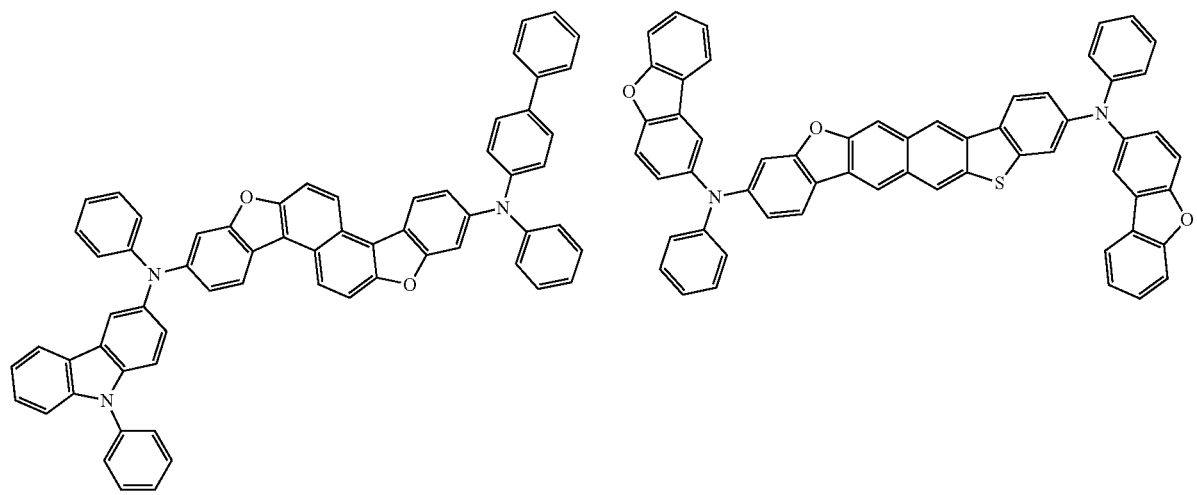

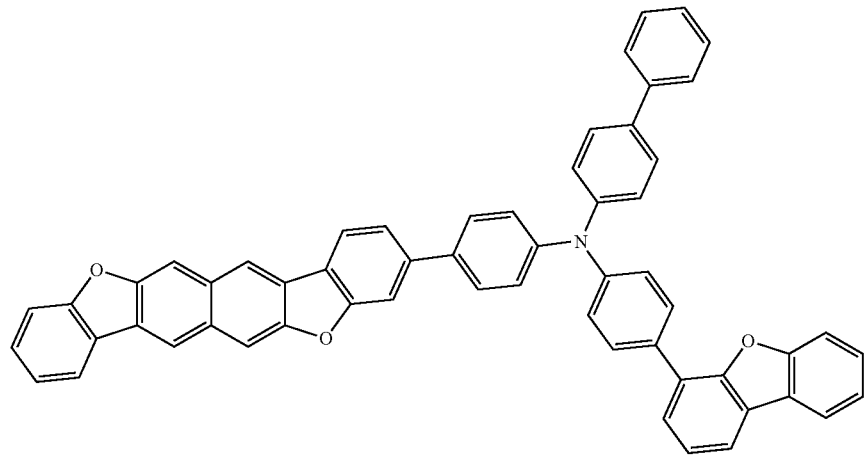

(906)

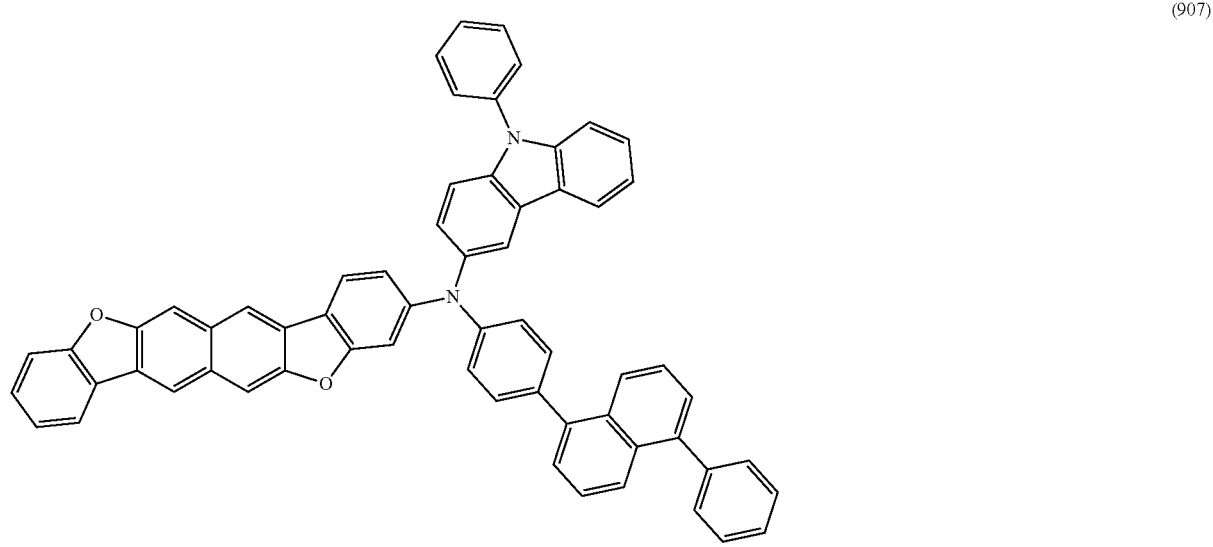

(907)

In the general formula (B1) to general formula (B4), $X^2$ and $X^3$ may be different as in a compound (905). However, they are preferably the same because the synthesis of the skeleton of B in the general formula (G1) is easier.

In the case where q in the general formula (G1) is 2, diarylamino groups do not need to have the same substituent like in a compound (903). However, they are preferably the same for easy synthesis.

In the case where q is 2 in the general formula (G1), that is, in the case where the number of diarylamino groups bonded to the skeleton B is two, the substituents may be bonded asymmetrically with respect to $X^2$ and $X^3$ in B like in a compound (901). Note that they are preferably symmetric like in a compound (100), a compound (200), a compound (300), a compound (400), a compound (500), a compound (600), a compound (700), a compound (800), a compound (900), and the like for easier synthesis of the skeleton of B.

In the general formula (G1), a structure where one of two arylamino groups is an arylamino group having any of a substituted or unsubstituted dibenzofuranyl group, a substituted or unsubstituted dibenzothiophenyl group, and a substituted or unsubstituted carbazolyl group and the other arylamino group is a diarylamino group, like in a compound (904), may be employed. Note that the two arylamino groups are preferably the same group for easier synthesis. Note that at least one of the two arylamino groups is preferably an arylamino group having any of a substituted or unsubstituted dibenzofuranyl group, a substituted or unsubstituted dibenzothiophenyl group, and a substituted or unsubstituted carbazolyl group because the reliability of a light-emitting element using the organic compound as a light-emitting material is favorable.

In the case where at least one or more of 1, m, and n in the general formula (G1) are 2, different skeletons may be connected to $\alpha^1$, $\alpha^2$, and $\alpha^3$ like in a compound (907).

Then, one example of a method for synthesizing an organic compound of the present invention as described above will be described. The organic compound represented by the general formula (G1) is shown below.

[Chemical Formula 51]

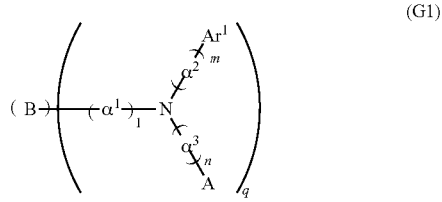

Note that, in the formula, B represents any of a substituted or unsubstituted naphthobisbenzofuran skeleton, a substituted or unsubstituted naphthobisbenzothiophene skeleton, and a substituted or unsubstituted naphthobenzofuranobenzothiophene skeleton. Furthermore, $Ar^1$ is any of a substituted or unsubstituted aromatic hydrocarbon group having 6 to 14 carbon atoms, a substituted or unsubstituted dibenzofuranyl group, a substituted or unsubstituted dibenzothiophenyl group, and a substituted or unsubstituted carbazolyl group. A is any of a substituted or unsubstituted dibenzofuranyl group, a substituted or unsubstituted dibenzothiophenyl group, and a substituted or unsubstituted carbazolyl group, and $\alpha^1$ to $\alpha^3$ each independently represent a substituted or unsubstituted bivalent aromatic hydrocarbon group having 6 to 14 carbon atoms. Furthermore, 1, m, and n each independently represent an integer of 0 to 2, and q is 1 or 2.

The organic compound represented by the above general formula (G1) can be obtained through a cross coupling reaction of a compound (a1) and an arylamine compound (a2) as shown in the following synthesis scheme. As examples of $X^1$, a halogen group such as chlorine, bromine, or iodine, a sulfonyl group, and the like can be given. $D^1$ represents hydrogen in the case where 1 is 0 (that is, the compound (a1) is secondary amine), and represents boronic acid, dialkoxyboronic acid, aryl aluminum, aryl zirconium, aryl zinc, aryl tin, or the like in the case where 1 is 1 or more (that is, the compound (a1) is tertiary amine).

[Chemical Formula 52]

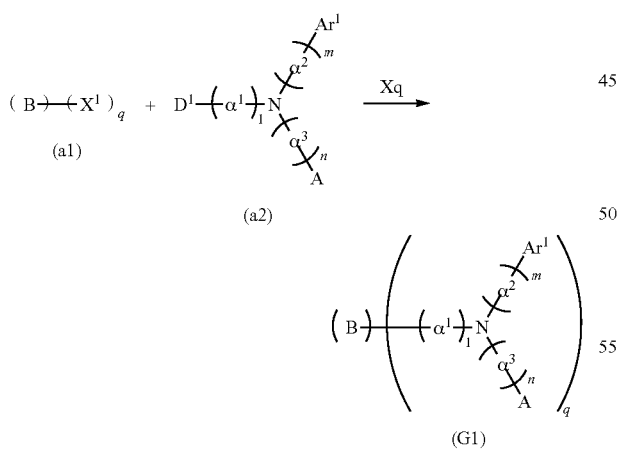

A variety of conditions can be employed for allowing this reaction to proceed; as one example thereof, a synthesis method using a metal catalyst in the presence of a base can be applied. For example, in the case where 1 is 0, Ullmann coupling or the Hartwig-Buchwald reaction can be used. In the case where 1 is 1 or more, the Suzuki-Miyaura reaction can be used.

Note that here, q equivalents of the compound (a2) are reacted with the compound (a1); however, in the case where q is 2 or more, that is, the number of substituents shown in parentheses of q with respect to B in the compound (G1) is two or more and the substituents are not the same, each kind of the compound (a2) may be reacted with the compound (a1).

The organic compound of one embodiment of the present invention can be synthesized in the above manner.

As the above compound (a1), the following general formula (B1-a1) to general formula (B4-a1) and the like can be given. These are effective compounds for synthesizing the compound of one embodiment of the present invention. Materials thereof are also effective. As for a synthesis method, it can be synthesized in a manner similar to that in the embodiments described below by changing the substitution site of a halogen as appropriate.

[Chemical Formulae 53]

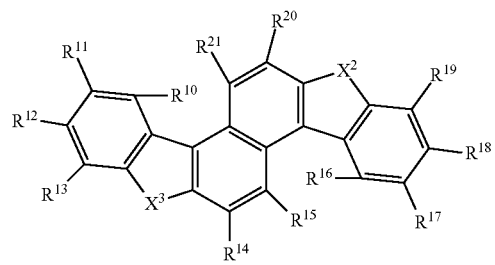

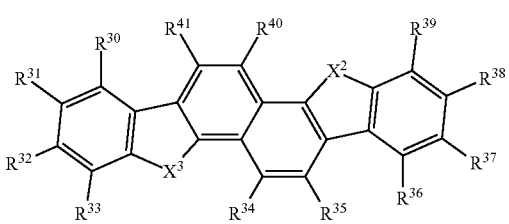

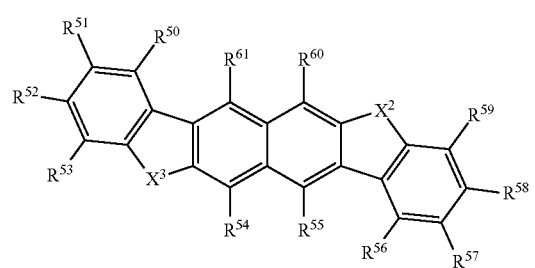

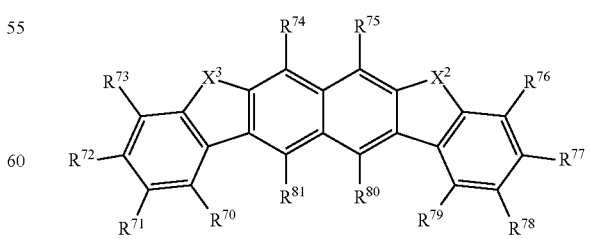

In the above general formula (B1-a1) to general formula (B4-a1), $X^2$ and $X^3$ each independently represent an oxygen atom or a sulfur atom.

In the above general formula (B1-a1), any one or two of $R^{10}$ to $R^{21}$ represent a halogen, and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms. Note that any one or two of $R^{11}$, $R^{12}$, $R^{17}$, and $R^{18}$ of $R^{10}$ to $R^{21}$ are preferably a halogen for easy synthesis.

Note that in the case where any two of $R^{10}$ to $R^{21}$ in the above general formula (B1-a1) are a halogen, one of $R^{11}$ and $R^{12}$ and one of $R^{17}$ and $R^{18}$ are preferably a halogen for easy synthesis. In that case, it is preferable that $R^{11}$ and $R^{17}$ be a halogen, or $R^{12}$ and $R^{18}$ be a halogen.

In the above general formula (B2-a1), any one or two of $R^{30}$ to $R^{41}$ represent a halogen and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms. Note that any one or two of $R^{31}$, $R^{32}$, $R^{37}$, and $R^{38}$ of $R^{30}$ to $R^{41}$ are preferably a halogen for easy synthesis.

Note that in the case where any two of $R^{30}$ to $R^{41}$ in the above general formula (B2-a1) are a halogen, one of $R^{31}$ and $R^{32}$ and one of $R^{37}$ and $R^{38}$ are preferably a halogen for easy synthesis. In that case, it is preferable that $R^{31}$ and $R^{37}$ be a halogen, or $R^{32}$ and $R^{38}$ be a halogen.

Furthermore, in the above general formula (B3-a1), any one or two of $R^{50}$ to $R^{61}$ represent a single bond and the others each independently represent any of hydrogen, a hydrocarbon group having 1 to 10 carbon atoms, a halogen hydrocarbon group having 3 to 10 carbon atoms, a substituted or unsubstituted aromatic hydrocarbon group having 6 to 14 carbon atoms, and a substituted or unsubstituted diarylamino group. Note that any one or two of $R^{51}$, $R^{52}$, $R^{57}$, and $R^{58}$ of $R^{50}$ to $R^{61}$ are preferably a halogen.

Note that in the case where any two of $R^{50}$ to $R^{61}$ in the above general formula (B3-a1) are a halogen, one of $R^{51}$ and $R^{52}$ and one of $R^{57}$ and $R^{58}$ are preferably a halogen for easy synthesis. In that case, it is preferable that R and R be a halogen, or R and R be a halogen.

Furthermore, in the above general formula (B4-a1), any one or two of $R^{70}$ to $R^{81}$ represent a halogen and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms. Note that any one or two of $R^{71}$, $R^{72}$, $R^{77}$, and $R^{78}$ of $R^{70}$ to $R^{81}$ are preferably a halogen.

Note that in the case where any two of $R^{70}$ to $R^{81}$ in the above general formula (B4-a1) are a halogen, one of $R^{71}$ and $R^{72}$ and one of $R^{77}$ and $R^{78}$ are preferably a halogen for easy synthesis. In that case, it is preferable that $R^{71}$ and $R^{78}$ be a halogen, or $R^{72}$ and $R^{77}$ be a halogen.

Then, a synthesis method of the organic compound represented by the above general formula (B1-a1) will be described. The general formula (B1-a1) is shown below. The substituents, $X^2$, and $X^3$ are the same as those described above.

[Chemical Formula 54]

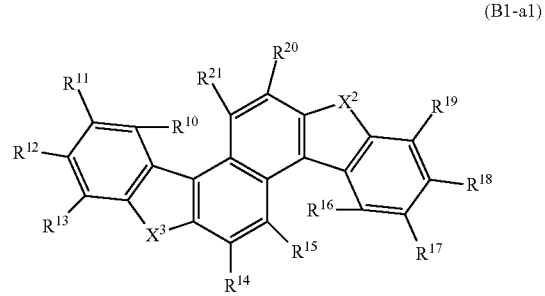

(B1-a1)

As shown in the following scheme, a naphthalene compound represented by (c1-14) can be obtained through a cross coupling reaction of a naphthalene compound (c1-11), an aryl compound (c1-12), and an aryl compound (c1-13). As each of $B^1$ and $B^2$, boronic acid, dialkoxyboronic acid, and the like can be given. $Y^3$ and $Y^4$ represent a halogen group such as chlorine or bromine or a sulfonyl group. Note that the sites of $Y^3$ and $Y^4$ are just examples, and an example in which $Y^3$ and $Y^4$ are introduced into the sites of $R^{12}$ and, $R^{18}$ in the above general formula (B1-a1) is shown in this synthesis example; however, $Y^3$ and $Y^4$ can be introduced into any sites of $R^{10}$ to $R^{21}$. Furthermore, an introduction of either $Y^3$ or $Y^4$ may be employed. By changing the introduction sites of $Y^3$ and $Y^4$, the substituent represented by the above (a2) can be introduced into various sites.

In the following scheme, $Y^1$ and $Y^2$ represent a halogen such as bromine or iodine or a sulfonyl group. $Y^1$ and $Y^2$ are preferably leaving groups having higher reactivity than $Y^3$ and $Y^4$.

[Chemical Formula 55]

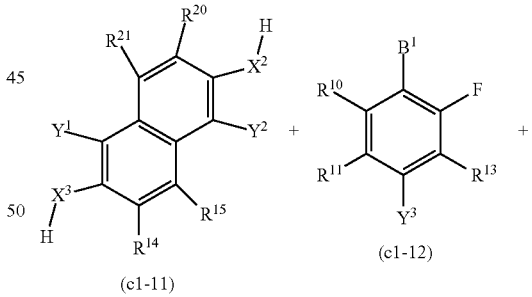

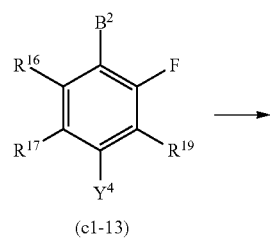

-continued

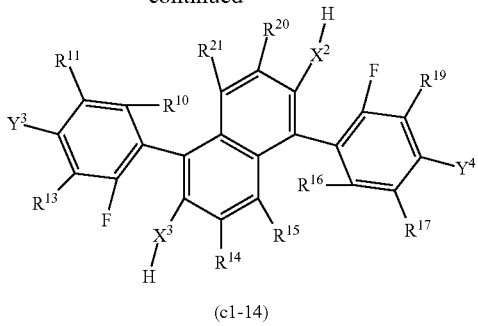

(c1-14)

A variety of conditions can be employed for causing this reaction; as one example thereof, there is a synthesis method using a metal catalyst in the presence of a base. As a specific example of the synthesis method, the Suzuki-Miyaura reaction can be given.

Note that here, the compound (c1-12) and the compound (c1-13) are made to react with the compound (c1-11) at the same time. However, in the case where the compound (c1-12) and the compound (c1-13) are compounds having different substituents, the compound (c1-11) and the compound (c1-12) may be reacted first and then a product thereof and the compound (c1-13) may be reacted; the yield and purity of the objective substance in that case become higher, which is preferable.

Next, as shown in the following scheme, a halogenated naphthobisbenzofuran compound or a halogenated naphthobisbenzothiophene compound represented by (c1-15) can be obtained from the naphthalene compound (c1-14). The halogenated naphthobisbenzofuran compound or the halogenated naphthobisbenzothiophene compound represented by the following general formula (c1-15) corresponds to an organic compound in which $R^{12}$ and $R^{18}$ in the organic compound represented by the above general formula (B1-a1) are a halogen or a sulfonyl group.

[Chemical Formula 56]

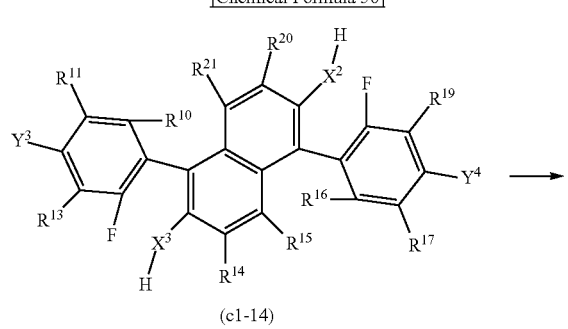

(c1-14)

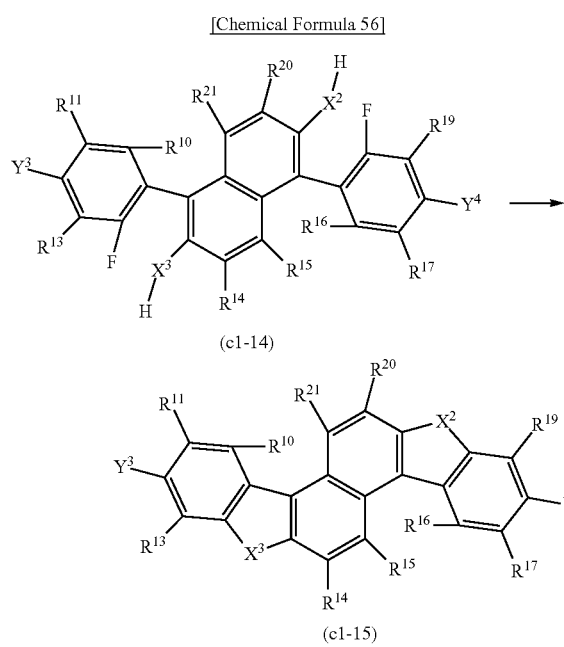

(c1-15)

A variety of conditions can be employed for causing this reaction. For example, the naphthalene compound (c1-14) is dissolved in A-methylpyrrolidone (abbreviation: NMP), dimethyl sulfoxide (abbreviation: DMSO), or the like, potassium carbonate or cesium carbonate is added to the solution, and heating is performed. Thus the reaction can be caused.

Then, another synthesis method of the organic compound represented by the above general formula (B1-a1) will be described. The general formula (B1-a1) is shown below. The substituents, $X^2$, and $X^3$ are the same as those described above. Note that this synthesis method is suitable for the case of a compound having substituents at the sites of $R^{14}$ and $R^{20}$. That is, it is preferable that $R^{14}$ and $R^{20}$ be each independently any one of a hydrocarbon group having 1 to 10 carbon atoms, a halogen hydrocarbon group having 3 to 10 carbon atoms, a substituted or unsubstituted aromatic hydrocarbon group having 6 to 14 carbon atoms, and a substituted or unsubstituted diarylamino group.

[Chemical Formula 57]

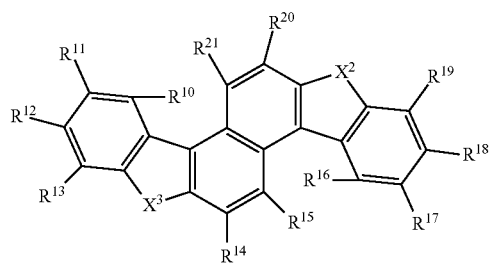

(B1-a1)

As shown in the following scheme, a naphthalene compound represented by (c1-24) can be obtained through a reaction of a naphthalene compound (c1-21), an aryl compound (c1-22), and an aryl compound (c1-23). $Y^3$ and $Y^4$ represent a halogen group such as chlorine or bromine or a sulfonyl group. Note that the sites of $Y^3$ and $Y^4$ are just examples, and an example in which $Y^3$ and $Y^4$ are introduced into the sites of $R^{12}$ and $R^{18}$ in the above general formula (B1-a1) is shown in this synthesis example; however, $Y^3$ and $Y^4$ can be introduced into any sites of $R^{10}$ to $R^{21}$. Furthermore, an introduction of either $Y^3$ or $Y^4$ may be employed. By changing the introduction sites of $Y^3$ and $Y^4$, the substituent represented by the above (a2) can be introduced into various sites.

Furthermore, $Y^1$ and $Y^2$ represent a halogen such as bromine or iodine or a sulfonyl group. $Y^1$ and $Y^2$ are preferably leaving groups having higher reactivity than $Y^3$ and $Y^4$.

Note that $R^{14}$ and $R^{20}$ are preferably substituents other than hydrogen in order that $Y^1$ and $Y^2$ are selectively reacted and cyclized at the alpha position of a naphthalene ring of the naphthalene compound in the subsequent reactions. Specifically, the naphthalene compound (c1-21) in the following scheme is preferably an organic compound having substituents at the sites of $R^{14}$ and $R^{20}$.

[Chemical Formula 58]

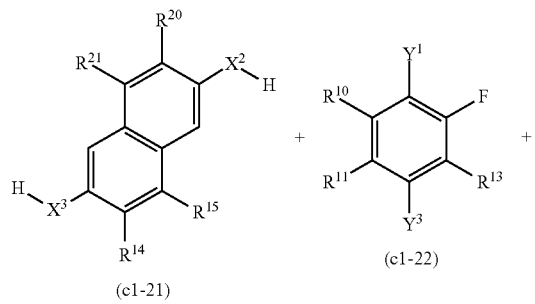

(c1-21)  (c1-22)

(c1-23)

(c1-24)

A variety of conditions can be employed for causing this reaction. For example, the naphthalene compound (c1-21), the aryl compound (c1-22), and the aryl compound (c1-23) are dissolved in IV-methylpyrrolidone (abbreviation: NMP), dimethyl sulfoxide (abbreviation: DMSO), or the like, potassium carbonate or cesium carbonate is added to the solution, and heating is performed. Thus the reaction can be caused.

Note that here, the compound (c1-22) and the compound (c1-23) are made to react with the compound (c1-21) at the same time. However, in the case where the compound (c1-22) and the compound (c1-23) are compounds having different substituents, the compound (c1-21) and the compound (c1-22) may be reacted first and then a product thereof and the compound (c1-23) may be reacted; the yield and purity of the objective substance in that case become higher, which is preferable.

Next, as shown in the following scheme, a halogenated naphthobisbenzofuran compound or a halogenated naphthobisbenzothiophene compound represented by (c1-15) can be obtained from the naphthalene compound (c1-24). The halogenated naphthobisbenzofuran compound or the halogenated naphthobisbenzothiophene compound represented by the following general formula (c1-15) corresponds to an organic compound in which $R^{12}$ and $R^{18}$ in the organic compound represented by the above general formula (B1-a1) are a halogen or a sulfonyl group.

[Chemical Formula 59]

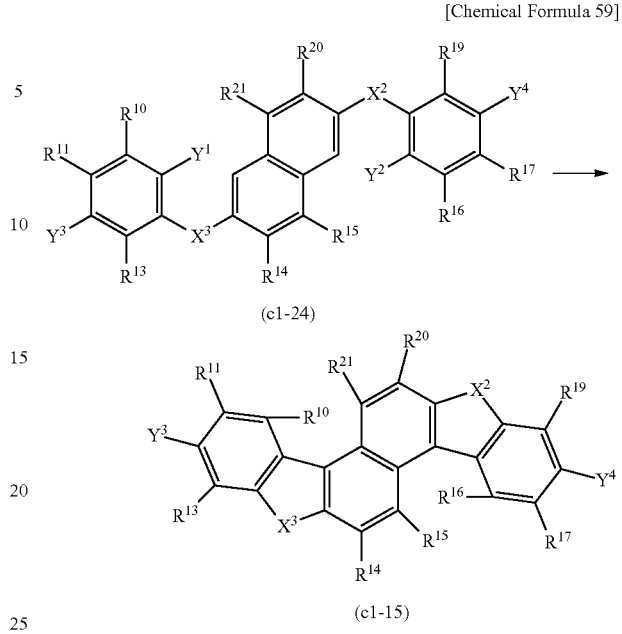

(c1-24)

(c1-15)

A variety of conditions can be employed for causing this reaction; as one example thereof, there is a synthesis method using a metal catalyst in the presence of a base. As a specific example of the synthesis method, the Suzuki-Miyaura reaction can be given.

Then, a synthesis method of the organic compound represented by the above general formula (B3-a1) will be described. The general formula (B3-a1) is shown below. The substituents, $X^2$, and $X^3$ are the same as those described above.

[Chemical Formula 60]

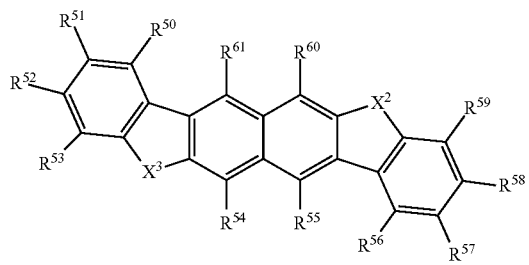

(B3-a1)

As shown in the following scheme, a naphthalene compound represented by (c3-14) can be obtained through a cross coupling reaction of a naphthalene compound (c3-11), an aryl compound (c3-12), and an aryl compound (c3-13). $R^{100}$ and $R^{101}$ each represent an alkyl group such as a methyl group. As each of $B^1$ and $B^2$, boronic acid, dialkoxyboronic acid, and the like can be given. $Y^3$ and $Y^4$ represent a halogen group such as chlorine or bromine or a sulfonyl group. Note that the sites of $Y^3$ and $Y^4$ are just examples, and an example in which $Y^3$ and $Y^4$ are introduced into the sites of $R^{52}$ and $R^{58}$ in the above general formula (B3-a1) is shown in this synthesis example; however, $Y^3$ and $Y^4$ can be introduced into any sites of $R^{50}$ to $R^{61}$. Furthermore, an introduction of either $Y^3$ or $Y^4$ may be employed. By changing the introduction sites of $Y^3$ and $Y^4$, the substituent represented by the above (a2) can be introduced into various sites.

Furthermore, $Y^1$ and $Y^2$ represent a halogen such as bromine or iodine or a sulfonyl group. $Y^1$ and $Y^2$ are preferably leaving groups having higher reactivity than $Y^3$ and $Y^4$.

[Chemical Formula 61]

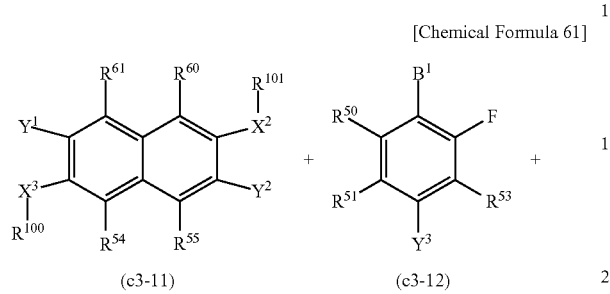

(c3-11)    (c3-12)

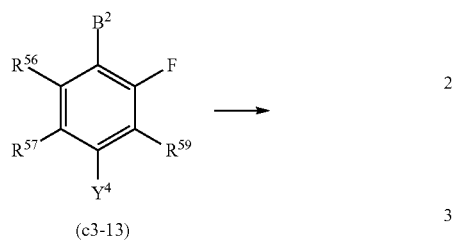

(c3-13)

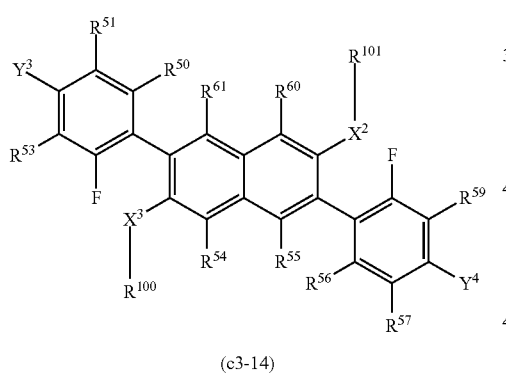

(c3-14)

A variety of conditions can be employed for causing this reaction; as one example thereof, there is a synthesis method using a metal catalyst in the presence of a base. As a specific example of the synthesis method, the Suzuki-Miyaura reaction can be given.

Note that here, the compound (c3-12) and the compound (c3-13) are made to react with the compound (c3-11) at the same time. However, in the case where the compound (c3-12) and the compound (c3-13) are compounds having different substituents, the compound (c3-11) and the compound (c3-12) may be reacted first and then a product thereof and the compound (c3-13) may be reacted; the yield and purity of the objective substance in that case become higher, which is preferable.

Next, as shown in the following scheme, a naphthalene compound represented by (c3-15) can be obtained through a dealkylation reaction of the naphthalene compound (c3-14).

[Chemical Formula 62]

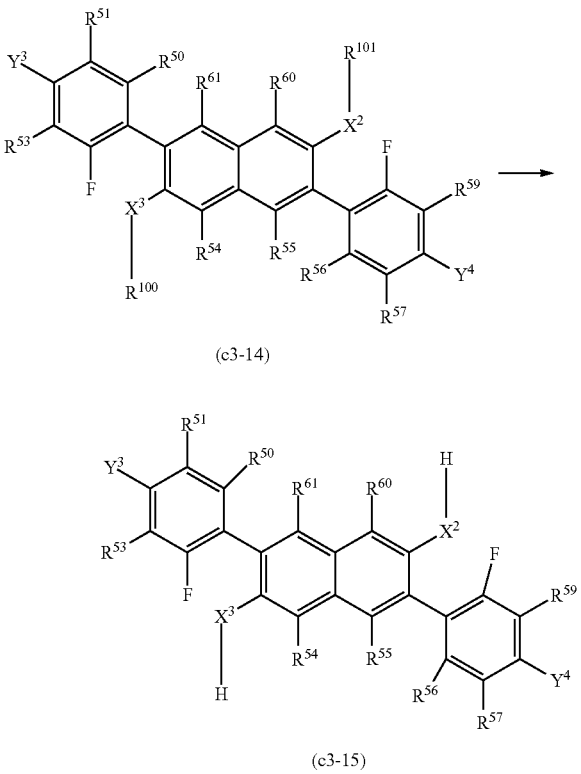

(c3-14)

(c3-15)

A variety of conditions can be employed for causing this reaction; for example, a reaction using Lewis acid such as boron tribromide in a solvent such as dichloromethane can be given.

Next, as shown in the following scheme, a halogenated naphthobisbenzofuran compound or a halogenated naphthobisbenzothiophene compound represented by (c3-16) can be obtained from the naphthalene compound (c3-15). The organic compound represented by the following general formula (c3-16) corresponds to an organic compound in which $R^{52}$ and $R^{58}$ in the organic compound represented by the above general formula (B3-a1) are a halogen or a sulfonyl group.

[Chemical Formula 63]

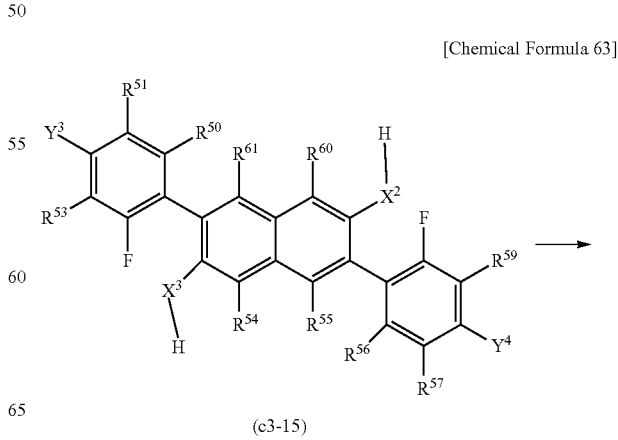

(c3-15)

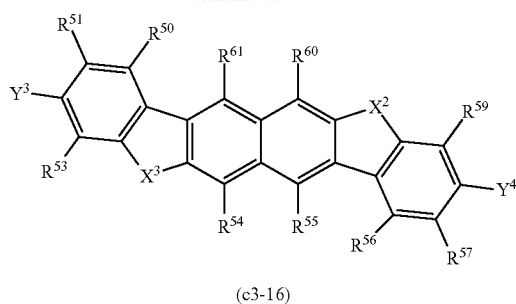

(c3-16)

A variety of conditions can be employed for causing this reaction. For example, the naphthalene compound (c3-15) is dissolved in N-methylpyrrolidone (abbreviation: NMP), dimethyl sulfoxide (abbreviation: DMSO), or the like, potassium carbonate or cesium carbonate is added to the solution, and heating is performed. Thus the reaction can be caused.

Then, another synthesis method of the organic compound represented by the above general formula (B3-a1) will be described. The general formula (B3-a1) is shown below. The substituents, $X^2$, and $X^3$ are the same as those described above. Note that this synthesis method is suitable for the case of a compound having substituents at the sites of $R^{54}$ and $R^{60}$. That is, it is preferable that $R^{54}$ and $R^{60}$ be each independently any one of a hydrocarbon group having 1 to 10 carbon atoms, a halogen hydrocarbon group having 3 to 10 carbon atoms, a substituted or unsubstituted aromatic hydrocarbon group having 6 to 14 carbon atoms, and a substituted or unsubstituted diarylamino group.

[Chemical Formula 64]

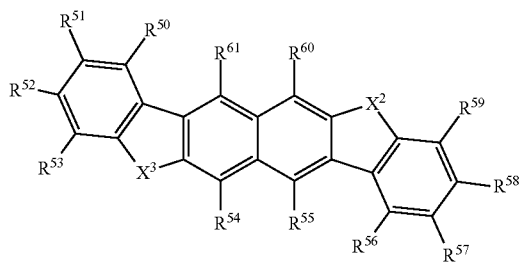

(B3-a1)

As shown in the following scheme, a naphthalene compound represented by (c3-22) can be obtained through a dealkylation reaction of a naphthalene compound (c3-21). $R^{100}$ and $R^{101}$ each represent an alkyl group such as a methyl group.

Note that $R^{54}$ and $R^{60}$ are preferably substituents other than hydrogen in order that $Y^1$ and $Y^2$ are selectively reacted and cyclized at the beta position of a naphthalene ring of the naphthalene compound in the subsequent reactions. Specifically, the naphthalene compound (c3-21) in the following scheme is preferably an organic compound having substituents at the sites of $R^{54}$ and $R^{60}$.

[Chemical Formula 65]

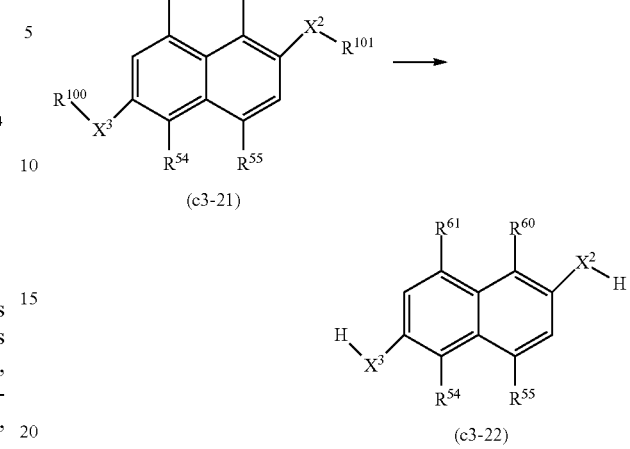

(c3-21)

(c3-22)

A variety of conditions can be employed for causing this reaction; for example, a reaction using Lewis acid such as boron tribromide in a solvent such as dichloromethane can be given.

Then, as shown in the following scheme, a naphthalene compound represented by (c3-25) can be obtained through a reaction of the naphthalene compound (c3-22), an aryl compound (c3-23), and an aryl compound (c3-24). $Y^3$ and $Y^4$ represent a halogen group such as chlorine or bromine or a sulfonyl group. Note that the sites of $Y^3$ and $Y^4$ are just examples, and an example in which $Y^3$ and $Y^4$ are introduced into the sites of $R^{52}$ and $R^{58}$ in the above general formula (B3-a1) is shown in this synthesis example; however, $Y^3$ and $Y^4$ can be introduced into any sites of $R^{50}$ to $R^{61}$. Furthermore, an introduction of either $Y^3$ or $Y^4$ may be employed. By changing the introduction sites of $Y^3$ and $Y^4$, the substituent represented by the above (a2) can be introduced into various sites.

Furthermore, $Y^1$ and $Y^2$ represent a halogen such as bromine or iodine or a sulfonyl group. $Y^1$ and $Y^2$ are preferably leaving groups having higher reactivity than $Y^3$ and $Y^4$.

[Chemical Formula 66]

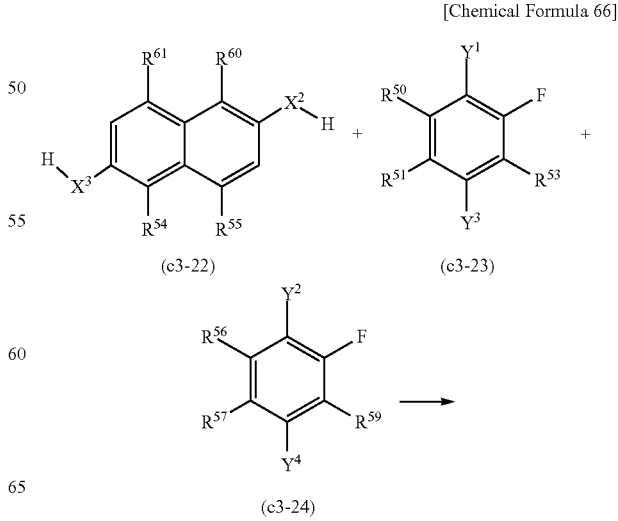

(c3-22)    (c3-23)

(c3-24)

185

-continued

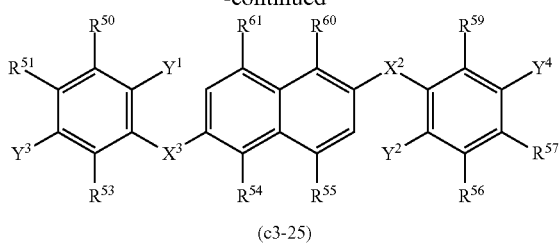

(c3-25)

A variety of conditions can be employed for causing this reaction. For example, in a solution of N-methylpyrrolidone (abbreviation: NMP), dimethyl sulfoxide (abbreviation: DMSO), or the like, potassium carbonate or cesium carbonate is added, and heating is performed. Thus the reaction can be caused.

Note that here, the compound (c3-23) and the compound (c3-24) are made to react with the compound (c3-22) at the same time. However, in the case where the compound (c3-23) and the compound (c3-24) are compounds having different substituents, the compound (c3-22) and the compound (c3-23) may be reacted first and then a product thereof and the compound (c3-24) may be reacted; the yield and purity of the objective substance in that case become higher, which is preferable.

Next, as shown in the following scheme, the halogenated naphthobisbenzofuran compound or the halogenated naphthobisbenzothiophene compound represented by (c3-16) can be obtained from the naphthalene compound (c3-25). The halogenated naphthobisbenzofuran compound or the halogenated naphthobisbenzothiophene compound represented by the following general formula (c3-16) corresponds to an organic compound in which R and R in the organic compound represented by the above general formula (B3-a1) are a halogen or a sulfonyl group.

[Chemical Formula 67]

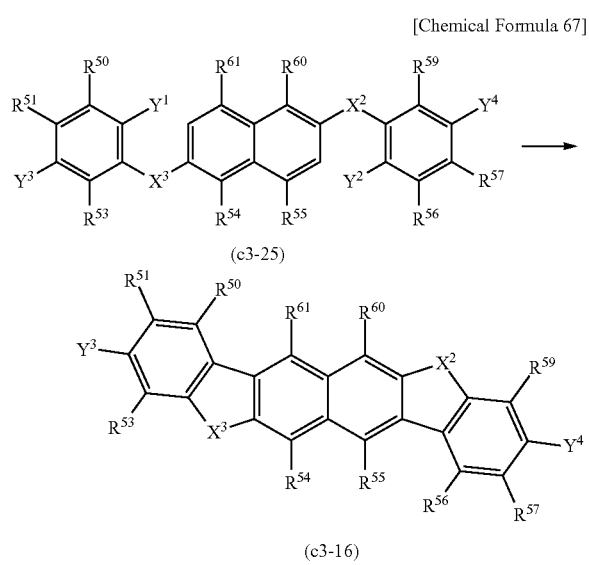

A variety of conditions can be employed for causing this reaction; as one example thereof, there is a synthesis method using a metal catalyst in the presence of a base. As a specific example of the synthesis method, the Suzuki-Miyaura reaction can be given.

186

Embodiment 2

Next, an example of a light-emitting element which is one embodiment of the present invention will be described in detail below with reference to FIG. 1(A).

The light-emitting element in this embodiment includes a pair of electrodes of an anode 101 and a cathode 102 and an EL layer 103 provided between the anode 101 and the cathode 102.

The anode 101 is preferably formed using a metal, an alloy, or a conductive compound having a high work function (specifically, 4.0 eV or more), a mixture thereof, or the like. Specifically, for example, indium oxide-tin oxide (ITO: Indium Tin Oxide), indium oxide-tin oxide containing silicon or silicon oxide, indium oxide-zinc oxide, indium oxide containing tungsten oxide and zinc oxide (IWZO), and the like can be given. Films of these conductive metal oxides are usually formed by a sputtering method but may also be formed by application of a sol-gel method or the like. As an example of the formation method, there is a method for forming indium oxide-zinc oxide by a sputtering method using a target in which zinc oxide is added to indium oxide at greater than or equal to 1 wt % and less than or equal to 20 wt %. Furthermore, indium oxide containing tungsten oxide and zinc oxide (IWZO) can be formed by a sputtering method using a target in which, to indium oxide, tungsten oxide is added at greater than or equal to 0.5 wt % and less than or equal to 5 wt % and zinc oxide is added at greater than or equal to 0.1 wt % and less than or equal to 1 wt %. Besides, gold (Au), platinum (Pt), nickel (Ni), tungsten (W), chromium (Cr), molybdenum (Mo), iron (Fe), cobalt (Co), copper (Cu), palladium (Pd), aluminum (Al), a nitride of a metal material (e.g., titanium nitride), and the like can be given. Graphene can also be used. In the case where a composite material containing a first substance and a second substance is used for a hole-injection layer 111, an electrode material other than the above can be selected regardless of the work function.

The hole-injection layer 111 may be formed using a first substance having a relatively high acceptor property. Preferably, the hole-injection layer 111 is formed using a composite material in which the first substance having an acceptor property and a second substance having a hole-transport property are mixed. In the case where the composite material is used as a material for the hole-injection layer 111, a substance having an acceptor property with respect to the second substance is used as the first substance. The first substance draws electrons from the second substance, so that electrons are generated in the first substance. In the second substance from which electrons are drawn, holes are generated. As for the drawn electrons and the generated holes, by an electric field, the electrons flow to the anode 101 and the holes are injected into a light-emitting layer 113 through a hole-transport layer 112. Thus, a light-emitting element having a low driving voltage can be obtained.

The first substance is preferably a transition metal oxide, an oxide of a metal belonging to any of Group 4 to Group 8 of the periodic table, an organic compound having an electron-withdrawing group (a halogen group or a cyano group), or the like.

As the transition metal oxide or the oxide of a metal belonging to any of Group 4 to Group 8 of the periodic table, vanadium oxide, niobium oxide, tantalum oxide, chromium oxide, molybdenum oxide, tungsten oxide, manganese oxide, rhenium oxide, titanium oxide, ruthenium oxide, zirconium oxide, hafnium oxide, or silver oxide is preferable because of its high acceptor property. Among them, molybdenum oxide is particularly preferable because of its high stability in the air, low hygroscopicity, and high handiness.

As the organic compound having an electron-withdrawing group (a halogen group or a cyano group), 7,7,8,8-tetracyano-2,3,5,6-tetrafluoroquinodimethane (abbreviation: $F_4$-TCNQ), chloranil, 2,3,6,7,10,11-hexacyano-1,4,5,8,9,12-hexaazatriphenylene (abbreviation: HAT-CN), 1,3,4,5,7,8-hexafluorotetracyano-naphthoquinodimethane (abbreviation: F6-TCNNQ), and the like can be given. A compound in which electron-withdrawing groups are bonded to a condensed aromatic ring having a plurality of hetero atoms, such as HAT-CN, is particularly preferable because it is thermally stable.

The second substance is a substance having a hole-transport property and preferably has a hole mobility of $10^{-6}$ $cm^2/Vs$ or higher. As a material that can be used as the second substance, aromatic amines such as N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B), carbazole derivatives such as 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), and 1,4-bis[4-(N-carbazolyl)phenyl]-2,3,5,6-tetraphenylbenzene, and aromatic hydrocarbons such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, pentacene, coronene, rubrene, perylene, and 2,5,8,11-tetra(tert-butyl)perylene can be given. The aromatic hydrocarbon may have a vinyl skeleton. As the aromatic hydrocarbon having a vinyl group, for example, 4,4'-bis(2,2-diphenylvinyl)biphenyl (abbreviation: DPVBi), 9,10-bis[4-(2,2-diphenylvinyl)phenyl]anthracene (abbreviation: DPVPA), and the like can be given. Alternatively, a compound having an aromatic amine skeleton, such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]-fluoren-2-amine (abbreviation: PCBAF), or N-phenyl-N-[4-(9-phenyl-9H-carbazol-3-yl)phenyl]-spiro-9,9'-bifluoren-2-amine (abbreviation: PCBASF), a compound having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), or 3,3'-bis(9-phenyl-9H-carbazole) (abbreviation: PCCP), a compound having a thiophene skeleton, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), or 4-[4-(9-phenyl-9H-fluoren-9-yl)phenyl]-6-phenyldibenzothiophene (abbreviation: DBTFLP-IV), or a compound having a furan skeleton, such as 4,4',4"-(benzene-1,3,5-triyl)tri(dibenzofuran) (abbreviation: DBF3P-II) or 4-{3-[3-(9-phenyl-9H-fluoren-9-yl)phenyl]phenyl}dibenzofuran (abbreviation: mmDBFFLBi-II), can be used. Among the above, the compound having an aromatic amine skeleton and the compound having a carbazole skeleton are preferred because these have favorable reliability, have high hole-transport properties, and contribute to a reduction in driving voltage.

The organic compound of one embodiment of the present invention is also a substance having a hole-transport property and thus can be used as the second substance.

The hole-injection layer 111 can also be formed by a wet process. In this case, a conductive high-molecular compound to which an acid is added, such as a poly(ethylenedioxythiophene)/poly(styrenesulfonic acid) aqueous solution (PEDOT/PSS), a polyaniline/camphor sulfonic acid aqueous solution (PANI/CSA), PTPDES, Et-PTPDEK, PPBA, or polyaniline/poly(styrenesulfonic acid) (PANI/PSS), can be used, for example.

The hole-transport layer 112 is a layer containing a material having a hole-transport property. As the material having a hole-transport property, a material which is the same as that for the second substance given as the substance for forming the hole-injection layer 111 can be used. The hole-transport layer 112 may be formed of either a single layer or a plurality of layers. In the case where the hole-transport layer 112 is formed of a plurality of layers, for easy hole injection, the HOMO levels thereof preferably become deeper stepwise from a layer on the hole-injection layer 111 side to a layer on the light-emitting layer 113 side. Such a structure is highly suitable for a blue fluorescence-emitting element in which a host material in the light-emitting layer 113 has a deep HOMO level.

The structure in which the hole-transport layer 112 is formed of a plurality of layers to have a HOMO level which becomes deeper stepwise toward the light-emitting layer 113 is particularly suitable for an element in which the hole-injection layer 111 is formed using an organic acceptor (an organic compound having the above-mentioned electron-withdrawing group (a halogen group or a cyano group)), and an element with significantly favorable characteristics in which the carrier-injection property is favorable and the driving voltage is low can be obtained.

The organic compound of one embodiment of the present invention is also a substance having a hole-transport property and thus can be used as the material having a hole-transport property.

Note that the hole-transport layer 112 can also be formed by a wet process. In the case where the hole-transport layer 112 is formed by a wet process, a high molecular compound such as poly(N-vinylcarbazole) (abbreviation: PVK), poly (4-vinyltriphenylamine) (abbreviation: PVTPA), poly[A-(4-{N'-[4-(4-diphenylamino)phenyl]phenyl-N'-phenylamino}phenyl)methacrylamide](abbreviation: PTPDMA), or poly[N,N'-bis(4-butylphenyl)-N,N'-bis(phenyl)benzidine](abbreviation: Poly-TPD) can be used.

The light-emitting layer 113 may be a layer containing any light-emitting substance, such as a layer containing a fluorescent substance, a layer containing a phosphorescent substance, a layer containing a substance that emits thermally activated delayed fluorescence (TADF), a layer containing quantum dots, or a layer containing metal halogen perovskites; however, the light-emitting layer 113 preferably contains the organic compound of one embodiment of the present invention described in Embodiment 1, as a light-emitting substance. With the use of the organic compound of one embodiment of the present invention as a light-emitting substance, a light-emitting element having favorable efficiency and significantly favorable chromaticity can be easily obtained.

Furthermore, the light-emitting layer 113 may be formed of a single layer or a plurality of layers. In the case where a light-emitting layer of a plurality of layers is formed, a layer containing a phosphorescent substance and a layer containing a fluorescent substance may be stacked. In this case, an exciplex described later is preferably utilized in the layer containing a phosphorescent substance.

The organic compound of one embodiment of the present invention is also a substance having a favorable quantum yield and thus can be used as a light-emitting substance.

As the fluorescent substance, the following substances can be used, for example. Fluorescent substances other than those given below can also be used. For example, 5,6-bis [4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-diphenyl-N,N'-bis[4-(9-phenyl-9H-fluoren-9-yl)phenyl] pyrene-1,6-diamine, N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N'-(2-tert-butylanthracene-9,10-diyldi-4,1-phenylene)bis [N,N',N'-triphenyl-1,4-phenylenediamine] (abbreviation: DPABPA), N,9-diphenyl-N-[4-(9,10-diphenyl-2-anthryl) phenyl]-9H-carbazol-3-amine (abbreviation: 2PCAPPA), N-[4-(9,10-diphenyl-2-anthryl)phenyl]-N,N',N'-triphenyl-1, 4-phenylenediamine (abbreviation: 2DPAPPA), N,N,N',N', N''',N''',N'''',N''''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9, 10-bis(1,1'-biphenyl-2-yl)-2-anthryl]-N,N',N'-triphenyl-1,4-phenylenediamine (abbreviation: 2DPABPhA), 9,10-bis(1, 1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl) tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2, 6-bis[2-(8-methoxy-1,1,7,7-tetramethyl-2,3,6,7-tetrahydro-1H,5H-benzo[ij]quinolizin-9-yl) ethenyl]-4H-pyran-4-ylidene}propanedinitrile (abbreviation: BisDCJTM) can be given. In particular, a condensed aromatic diamine compound typified by a pyrenediamine compound such as 1,6mMemFLPAPrn is preferred because of its high hole-trapping property, high emission efficiency, and high reliability.

Examples of a material that can be used as a phosphorescent substance in the light-emitting layer 113 are as follows. An organometallic iridium complex having a 4H-triazole skeleton, such as tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), or tris[4-(3-biphenyl)-5-isopropyl-3-phenyl-4H-1,2,4-triazolato]iridium(III) (abbreviation: [Ir(iPrptz-3b)$_3$]), an organometallic iridium complex having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) or tris(1-methyl-5-phenyl-3-propyl-1H-1,2,4-triazolato)iridium(III) (abbreviation: [Ir (Prptz1-Me)₃]), an organometallic iridium complex having an imidazole skeleton, such as fac-tris[1-(2,6-diisopropylphenyl)-2-phenyl-1H-imidazole]iridium(III) (abbreviation: [Ir(iPrpmi)₃]) or tris[3-(2,6-dimethylphenyl)-7-methylimidazo[1,2-f]phenanthridinato]iridium(III) (abbreviation: [Ir(dmpimpt-Me)₃]), and an organometallic iridium complex in which a phenylpyridine derivative having an electron-withdrawing group is a ligand, such as bis[2-(4',6'-difluorophenyl)pyridinato-N,C²']iridium(III) tetrakis(1-pyrazolyl)borate (abbreviation: FIr6), bis[2-(4',6'-difluorophenyl)pyridinato-N,C²']iridium(III) picolinate (abbreviation: FIrpic), bis{2-[3',5'-bis(trifluoromethyl)phenyl]pyridinato-N,C²'}iridium(III) picolinate (abbreviation: [Ir(CF₃ppy)₂(pic)]), or bis[2-(4',6'-difluorophenyl)pyridinato-N,C²']iridium(III) acetylacetonate (abbreviation: FIracac) can be given. These are compounds exhibiting blue phosphorescence, and are compounds having a peak of an emission spectrum at 440 nm to 520 nm.

Furthermore, an organometallic iridium complex having a pyrimidine skeleton, such as tris(4-methyl-6-phenylpyrimidinato)iridium(III) (abbreviation: [Ir(mppm)₃]), tris(4-t-butyl-6-phenylpyrimidinato)iridium(III) (abbreviation: [Ir(t-Buppm)₃]), (acetylacetonato)bis(6-methyl-4-phenylpyrimidinato)iridium(III) (abbreviation: [Ir(mppm)₂(acac)]), (acetylacetonato)bis(6-tert-butyl-4-phenylpyrimidinato)iridium(III) (abbreviation: [Ir(tBuppm)₂(acac)]), (acetylacetonato)bis[6-(2-norbornyl)-4-phenylpyrimidinato]iridium(III) (abbreviation: [Ir(nbppm)₂(acac)]), (acetylacetonato)bis[5-methyl-6-(2-methylphenyl)-4-phenylpyrimidinato]iridium(III) (abbreviation: [Ir(mpmppm)₂(acac)]), or (acetylacetonato)bis(4,6-diphenylpyrimidinato)iridium(III) (abbreviation: [Ir(dppm)₂(acac)]), an organometallic iridium complex having a pyrazine skeleton, such as (acetylacetonato)bis(3,5-dimethyl-2-phenylpyrazinato)iridium(III) (abbreviation: [Ir(mppr-Me)₂(acac)]) or (acetylacetonato)bis(5-isopropyl-3-methyl-2-phenylpyrazinato)iridium(III) (abbreviation: [Ir(mppr-iPr)₂(acac)]), an organometallic iridium complex having a pyridine skeleton, such as tris(2-phenylpyridinato-N,C²')iridium(III) (abbreviation: [Ir(ppy)₃]), bis(2-phenylpyridinato-N,C²')iridium(III) acetylacetonate (abbreviation: [Ir(ppy)₂(acac)]), bis(benzo[h]quinolinato)iridium(III) acetylacetonate (abbreviation: [Ir(bzq)₂(acac)]), tris(benzo[h]quinolinato)iridium(III) (abbreviation: [Ir(bzq)₃]), tris(2-phenylquinolinato-N,C²')iridium(III) (abbreviation: [Ir(pq)₃]), or bis(2-phenylquinolinato-N,C²')iridium(III) acetylacetonate (abbreviation: [Ir(pq)₂(acac)]), and a rare earth metal complex such as tris(acetylacetonato) (monophenanthroline)terbium(III) (abbreviation: [Tb(acac)₃(Phen)]) can be given. These are mainly compounds exhibiting green phosphorescence, and have a peak of an emission spectrum at 500 nm to 600 nm. Note that an organometallic iridium complex having a pyrimidine skeleton has distinctively high reliability and emission efficiency and is thus especially preferable.

Furthermore, an organometallic iridium complex having a pyrimidine skeleton, such as (diisobutyrylmethanato)bis[4,6-bis(3-methylphenyl)pyrimidinato]iridium(III) (abbreviation: [Ir(5mdppm)₂(dibm)]), bis[4,6-bis(3-methylphenyl)pyrimidinato](dipivaloylmethanato)iridium(III) (abbreviation: [Ir(5mdppm)₂(dpm)]), or bis[4,6-di(naphthalen-1-yl)pyrimidinato] (dipivaloylmethanato)iridium(III) (abbreviation: [Ir(d1npm)₂(dpm)]), an organometallic iridium complex having a pyrazine skeleton, such as (acetylacetonato)bis(2,3,5-triphenylpyrazinato)iridium(III) (abbreviation: [Ir(tppr)₂(acac)]), bis(2,3,5-triphenylpyrazinato)(dipivaloylmethanato)iridium(III) (abbreviation: [Ir(tppr)₂(dpm)]), or (acetylacetonato)bis[2,3-bis(4-fluorophenyl)quinoxalinato]iridium(III) (abbreviation: [Ir(Fdpq)₂(acac)]), an organometallic iridium complex having a pyridine skeleton, such as tris(1-phenylisoquinolinato-N,C²')iridium(III) (abbreviation: [Ir(piq)₃]) or bis(1-phenylisoquinolinato-N,C²')iridium(III) acetylacetonate (abbreviation: [Ir(piq)₂(acac)]), a platinum complex such as 2,3,7,8,12,13,17,18-octaethyl-21H,23H-porphyrin platinum(II) (abbreviation: PtOEP), and a rare earth metal complex such as tris(1,3-diphenyl-1,3-propanedionato) (monophenanthroline)europium(III) (abbreviation: [Eu(DBM)₃(Phen)]) or tris[1-(2-thenoyl)-3,3,3-trifluoroacetonato](monophenanthroline)europium(III) (abbreviation: [Eu(TTA)₃(Phen)]) can be given. These are compounds exhibiting red phosphorescence, and have a peak of an emission spectrum at 600 nm to 700 nm. Furthermore, the organometallic iridium complex having a pyrazine skeleton can provide red light emission with favorable chromaticity.

Besides the above phosphorescent compounds, a variety of phosphorescent materials may be selected and used.

As the TADF material, a fullerene, a derivative thereof, an acridine, a derivative thereof, an eosin derivative, or the like can be used. Furthermore, porphyrin containing a metal such as magnesium (Mg), zinc (Zn), cadmium (Cd), tin (Sn), platinum (Pt), indium (In), or palladium (Pd) can be used. As the metal-containing porphyrin, for example, a protoporphyrin-tin fluoride complex (SnF₂(Proto IX)), a mesoporphyrin-tin fluoride complex (SnF₂(Meso IX)), a hematoporphyrin-tin fluoride complex (SnF₂(Hemato IX)), a coproporphyrin tetramethyl ester-tin fluoride complex (SnF₂(Copro III-4Me)), an octaethylporphyrin-tin fluoride complex (SnF₂(OEP)), an etioporphyrin-tin fluoride complex (SnF₂(Etio I)), and an octaethylporphyrin-platinum chloride complex (PtCl₂(OEP)), which are represented by the following structural formulae, and the like can be given.

[Chemical Formulae 68]

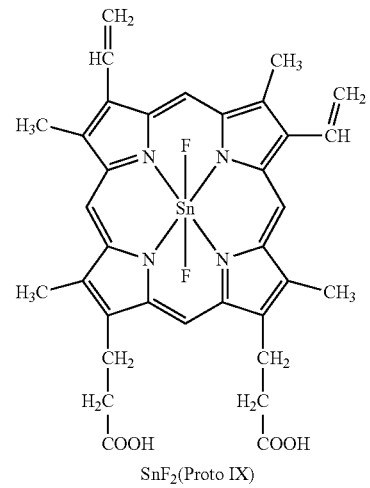

SnF₂(Proto IX)

-continued
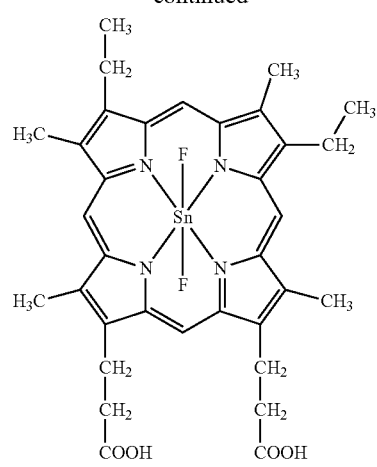
SnF₂(Meso IX)
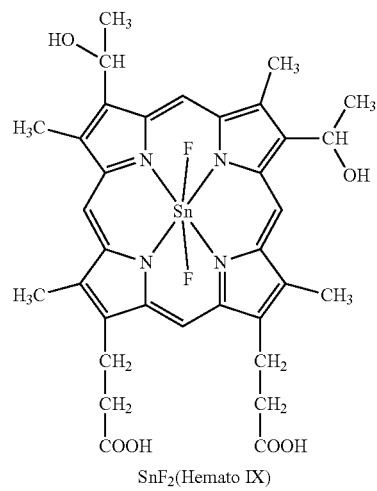
SnF₂(Hemato IX)
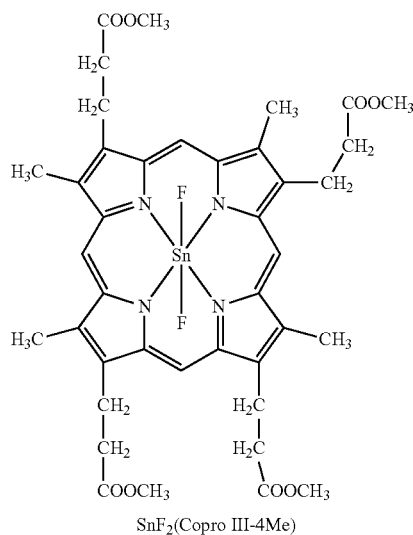
SnF₂(Copro III-4Me)
-continued
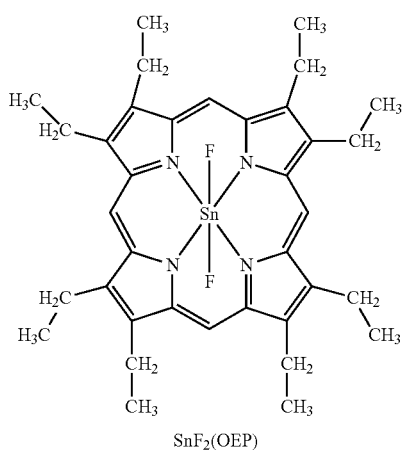
SnF₂(OEP)
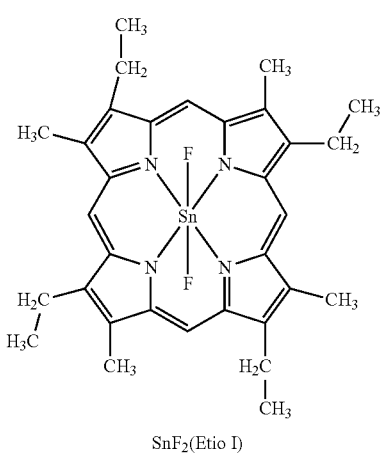
SnF₂(Etio I)
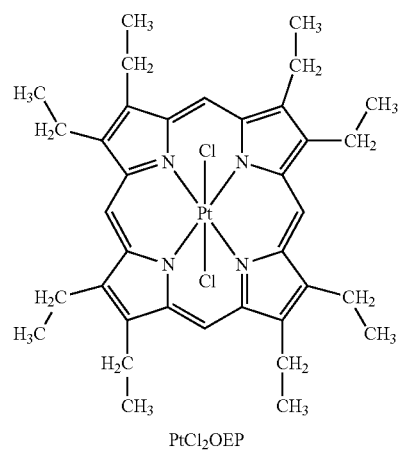
PtCl₂OEP Furthermore, a heterocyclic compound having both a n-electron rich heteroaromatic ring and a n-electron deficient heteroaromatic ring, such as 2-(biphenyl-4-yl)-4,6-bis(12-phenylindolo[2,3-a]carbazol-11-yl)-1,3,5-triazine (abbreviation: PIC-TRZ), 9-(4,6-diphenyl-1,3,5-triazin-2-yl)-9'-phenyl-9H,9'H-3,3'-bicarbazole (abbreviation: PCCzTzn), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazine-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA), which are represented by the following structural formulae, can also be used. The heterocyclic compound is preferable because of having high electron-transport and hole-transport properties owing to a n-electron rich heteroaromatic ring and a n-electron deficient heteroaromatic ring. Note that a substance in which the n-electron rich heteroaromatic ring and the n-electron deficient heteroaromatic ring are directly bonded to each other is particularly preferable because the donor property of the n-electron rich heteroaromatic ring and the acceptor property of the n-electron deficient heteroaromatic ring are both improved and the energy difference between the S1 level and the T1 level becomes small, so that thermally activated delayed fluorescence can be obtained with high efficiency. Note that an aromatic ring to which an electron-withdrawing group such as a cyano group is bonded may be used instead of the n-electron deficient heteroaromatic ring.

[Chemical Formulae 69]

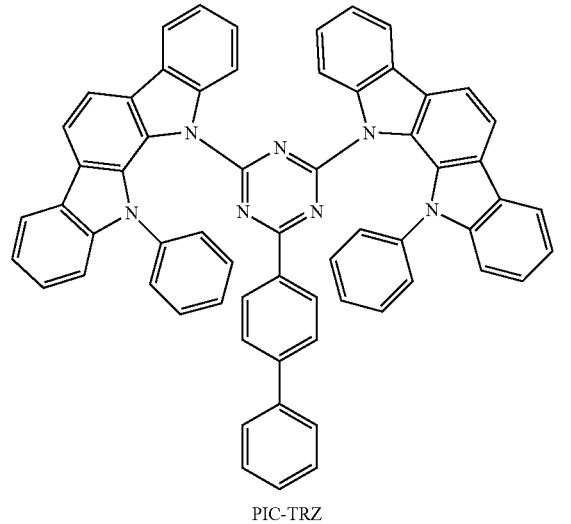

PIC-TRZ

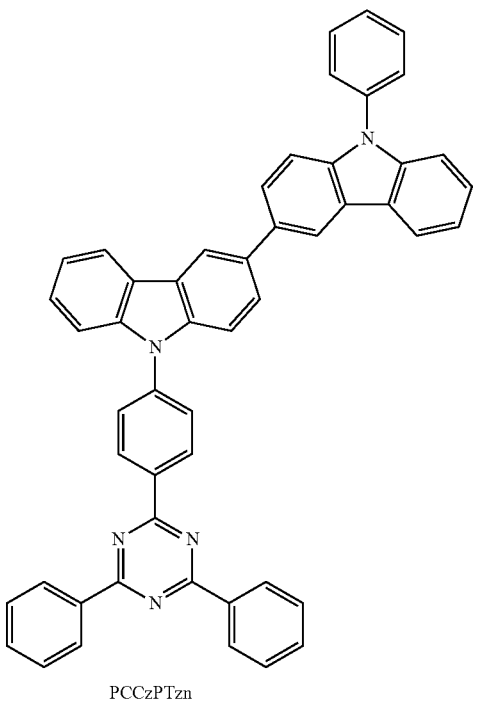

PCCzPTzn

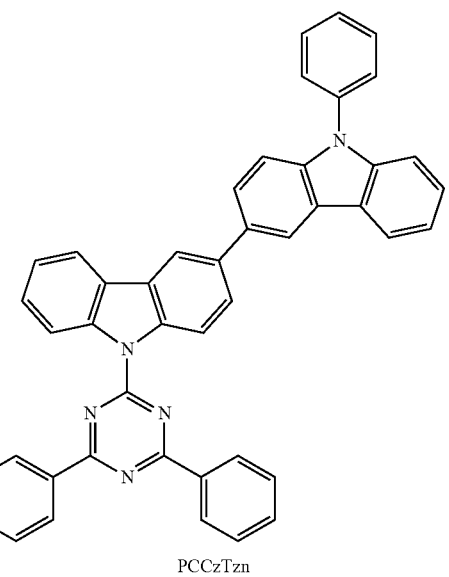

PCCzTzn

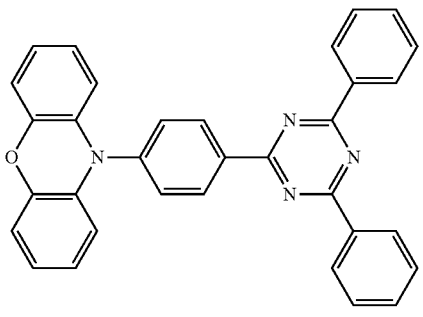

PXZ-TRZ

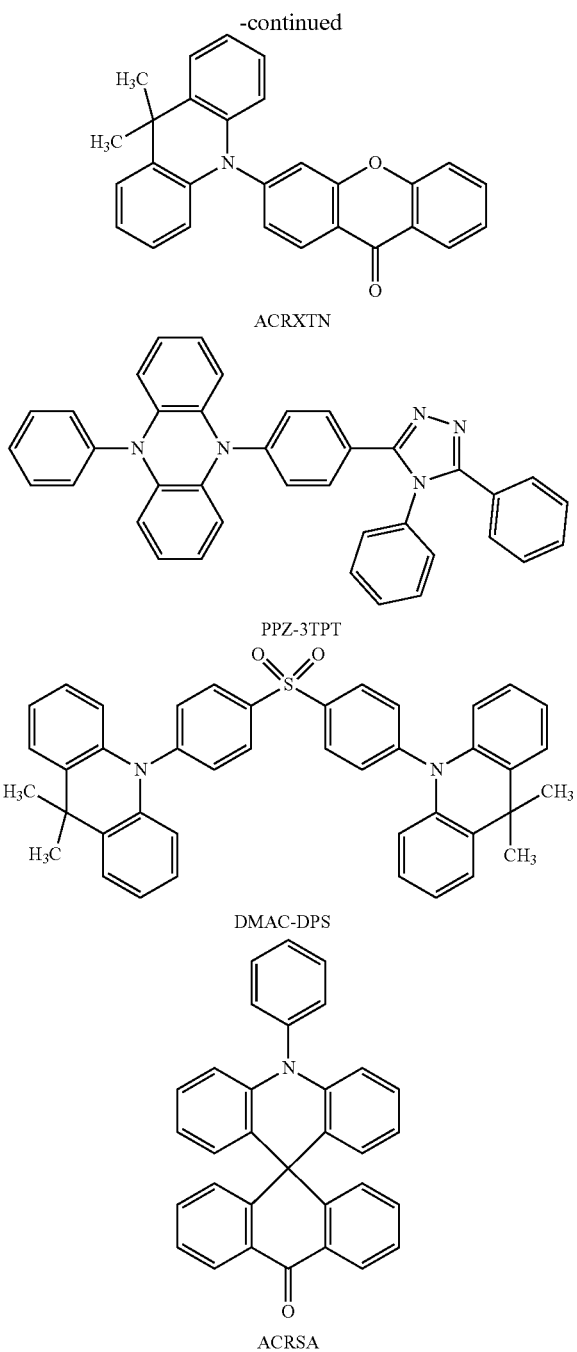

ACRXTN

PPZ-3TPT

DMAC-DPS

ACRSA

As the quantum dot, nano-sized particles of a Group 14 element, a Group 15 element, a Group 16 element, a compound of a plurality of Group 14 elements, a compound of an element belonging to Group 4 to Group 14 and a Group 16 element, a compound of a Group 2 element and a Group 16 element, a compound of a Group 13 element and a Group 15 element, a compound of a Group 13 element and a Group 17 element, a compound of a Group 14 element and a Group 15 element, a compound of a Group 11 element and a Group 17 element, iron oxides, titanium oxides, spinel chalcogenides, semiconductor clusters, metal halide perovskites, and the like can be given.

Specific examples include, but are not limited to, cadmium selenide (CdSe), cadmium sulfide (CdS), cadmium telluride (CdTe), zinc selenide (ZnSe), zinc oxide (ZnO), zinc sulfide (ZnS), zinc telluride (ZnTe), mercury sulfide (HgS), mercury selenide (HgSe), mercury telluride (HgTe), indium arsenide (InAs), indium phosphide (InP), gallium arsenide (GaAs), gallium phosphide (GaP), indium nitride (InN), gallium nitride (GaN), indium antimonide (InSb), gallium antimonide (GaSb), aluminum phosphide (AlP), aluminum arsenide (AlAs), aluminum antimonide (AlSb), lead(II) selenide (PbSe), lead(II) telluride (PbTe), lead(II) sulfide (PbS), indium selenide ($In_2Se_3$), indium telluride ($In_2Te_3$), indium sulfide ($In_2S_3$), gallium selenide ($Ga_2Se_3$), arsenic(III) sulfide ($As_2S_3$), arsenic(III) selenide ($As_2Se_3$), arsenic(III) telluride ($As_2Te_3$), antimony(III) sulfide ($Sb_2S_3$), antimony(III) selenide ($Sb_2Se_3$), antimony(III) telluride ($Sb_2Te_3$), bismuth(III) sulfide ($Bi_2S_3$), bismuth(III) selenide ($Bi_2Se_3$), bismuth(III) telluride ($Bi_2Te_3$), silicon (Si), silicon carbide (SiC), germanium (Ge), tin (Sn), selenium (Se), tellurium (Te), boron (B), carbon (C), phosphorus (P), boron nitride (BN), boron phosphide (BP), boron arsenide (BAs), aluminum nitride (AlN), aluminum sulfide ($Al_2S_3$), barium sulfide (BaS), barium selenide (BaSe), barium telluride (BaTe), calcium sulfide (CaS), calcium selenide (CaSe), calcium telluride (CaTe), beryllium sulfide (BeS), beryllium selenide (BeSe), beryllium telluride (BeTe), magnesium sulfide (MgS), magnesium selenide (MgSe), germanium sulfide (GeS), germanium selenide (GeSe), germanium telluride (GeTe), tin(IV) sulfide ($SnS_2$), tin(II) sulfide (SnS), tin(II) selenide (SnSe), tin(II) telluride (SnTe), lead(II) oxide (PbO), copper(I) fluoride (CuF), copper(I) chloride (CuCl), copper(I) bromide (CuBr), copper(I) iodide (CuI), copper(I) oxide ($Cu_2O$), copper(I) selenide ($Cu_2Se$), nickel(II) oxide (NiO), cobalt(II) oxide (CoO), cobalt(II) sulfide (CoS), triiron tetraoxide ($Fe_3O_4$), iron(II) sulfide (FeS), manganese(II) oxide (MnO), molybdenum (IV) sulfide ($MoS_2$), vanadium(II) oxide (VO), vanadium (IV) oxide ($VO_2$), tungsten(IV) oxide ($WO_2$), tantalum(V) oxide ($Ta_2O_5$), titanium oxide (e.g., $TiO_2$, $Ti_2O_5$, $Ti_2O_3$, or $Ti_5O_9$), zirconium oxide ($ZrO_2$), silicon nitride ($Si_3N_4$), germanium nitride ($Ge_3N_4$), aluminum oxide ($Al_2O_3$), barium titanate ($BaTiO_3$), a compound of selenium, zinc, and cadmium (CdZnSe), a compound of indium, arsenic, phosphorus (InAsP), a compound of cadmium, selenium, and sulfur (CdSeS), a compound of cadmium, selenium, and tellurium (CdSeTe), a compound of indium, gallium, and arsenic (InGaAs), a compound of indium, gallium, and selenium (InGaSe), a compound of indium, selenium, and sulfur (InSeS), a compound of copper, indium, and sulfur (e.g., $CuInS_2$), and combinations thereof. What is called an alloy-type quantum dot, whose composition is represented by a given ratio, may be used. For example, an alloy-type quantum dot represented by $CdS_xSe_{1-x}$ (x is a given number from 0 to 1) is an effective means for obtaining blue light emission because the emission wavelength can be changed by changing x.

As the structure of the quantum dot, a core type, a core-shell type, a core-multishell type, and the like can be given, and any of them may be used. When a core is covered with a shell formed of another inorganic material having a wider band gap, the influence of a defect or a dangling bond existing at the surface of a nanocrystal can be reduced. This can significantly improve the quantum efficiency of light emission, and thus it is preferable to use a core-shell-type or core-multishell-type quantum dot. As examples of the material for a shell, zinc sulfide (ZnS) and zinc oxide (ZnO) can be given.

Quantum dots have a high proportion of surface atoms and thus have high reactivity and easily cohere together. For this reason, it is preferable that a protective agent be attached to or a protective group be provided on the surfaces of the quantum dots. The attachment of the protective agent or the provision of the protective group can prevent cohesion and increase solubility in a solvent. It can also reduce reactivity and improve electrical stability. As the protective agent (or the protective group), for example, polyoxyethylene alkyl ethers such as polyoxyethylene lauryl ether, polyoxyethylene stearyl ether, and polyoxyethylene oleyl ether, trialkylphosphines such as tripropylphosphine, tributylphosphine, trihexylphosphine, and trioctylphoshine, polyoxyethylene alkylphenyl ethers such as polyoxyethylene n-octylphenyl ether and polyoxyethylene n-nonylphenyl ether, tertiary amines such as tri(n-hexyl)amine, tri(n-octyl) amine, and tri(n-decyl)amine, organophosphorus compounds such as tripropylphosphine oxide, tributylphosphine oxide, trihexylphosphine oxide, trioctylphosphine oxide, and tridecylphosphine oxide, polyethylene glycol diesters such as polyethylene glycol dilaurate and polyethylene glycol distearate, organic nitrogen compounds such as nitrogen-containing aromatic compounds, e.g., pyridines, lutidines, collidines, and quinolines, aminoalkanes such as hexylamine, octylamine, decylamine, dodecylamine, tetradecylamine, hexadecylamine, and octadecylamine, dialkylsulfides such as dibutylsulfide, dialkylsulfoxides such as dimethylsulfoxide and dibutylsulfoxide, organic sulfur compounds such as sulfur-containing aromatic compounds, e.g., thiophene, higher fatty acids such as a palmitin acid, a stearic acid, and an oleic acid, alcohols, sorbitan fatty acid esters, fatty acid modified polyesters, tertiary amine modified polyurethane, polyethyleneimines, and the like can be given.

The quantum dots may be quantum rods with rod-like shapes. A quantum rod exhibits directional light polarized in the c-axis direction; thus, when quantum rods are used as a light-emitting material, a light-emitting element with more favorable external quantum efficiency can be obtained.

To form a light-emitting layer in which the quantum dots are dispersed as a light-emitting material in a host material, the quantum dots are dispersed in the host material or the host material and the quantum dots are dissolved or dispersed in an appropriate liquid medium, a wet process (e.g., a spin coating method, a casting method, a die coating method, a blade coating method, a roll coating method, an inkjet method, a printing method, a spray coating method, a curtain coating method, or a Langmuir-Blodgett method) is performed to form a layer, and then, the liquid medium is removed or baking is performed.

As the liquid medium used for the wet process, organic solvents such as ketones, e.g., methyl ethyl ketone and cyclohexanone, fatty acid esters, e.g., ethyl acetate, halogenated hydrocarbons, e.g., dichlorobenzene, aromatic hydrocarbons, e.g., toluene, xylene, mesitylene, and cyclohexylbenzene, aliphatic hydrocarbons, e.g., cyclohexane, decalin, and dodecane, dimethylformamide (DMF), and dimethyl sulfoxide (DMSO) can be used.

In the case where a fluorescent substance is used, a host material suitable for the light-emitting layer is a material having an anthracene skeleton, such as 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), or 9-phenyl-10-{4-(9-phenyl-9H-fluoren-9-yl)-biphenyl-4'-yl}anthracene (abbreviation: FLPPA). The use of a substance having an anthracene skeleton as a host material for a fluorescent substance makes it possible to achieve a light-emitting layer with favorable emission efficiency and favorable durability. In particular, CzPA, cgDBCzPA, 2mBnfPPA, and PCzPA are preferably selected because they exhibit favorable characteristics.

In the case where a material other than the above materials is used as a host material, various carrier-transport materials, such as a material having an electron-transport property or a material having a hole-transport property, can be used.

As the material having an electron-transport property, for example, a metal complex such as bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), or bis[2-(2-benzothiazolyl)phenolato] zinc(II) (abbreviation: ZnBTZ), a heterocyclic compound having a polyazole skeleton, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2''-(1,3,5-benzenetriyl)tris(1-phenyl-1H-benzimidazole) (abbreviation: TPBI), or 2-[3-(dibenzothiophen-4-yl)phenyl]-1-phenyl-1H-benzimidazole (abbreviation: mDBTBIm-II), a heterocyclic compound having a diazine skeleton, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), or 4,6-bis[3-(4-dibenzothienyl)phenyl]pyrimidine (abbreviation: 4,6mDBTP2Pm-II), and a heterocyclic compound having a pyridine skeleton, such as 3,5-bis [3-(9H-carbazol-9-yl)phenyl]pyridine (abbreviation: 35DCzPPy) or 1,3,5-tri[3-(3-pyridyl)phenyl]benzene (abbreviation: TmPyPB) can be given. Among the above, the heterocyclic compound having a diazine skeleton and the heterocyclic compound having a pyridine skeleton have favorable reliability and thus are preferable. In particular, the heterocyclic compound having a diazine (pyrimidine or pyrazine) skeleton has a high electron-transport property and contributes to a reduction in driving voltage.

As a material having a hole-transport property, a compound having an aromatic amine skeleton, such as 4,4'-bis [N-(1-naphthyl)-N-phenylamino]biphenyl (abbreviation: NPB), N,N-bis(3-methylphenyl)-N,N-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 9,9-dimethyl-N-phenyl-N-[4-(9-phenyl-9H-carbazol-3-yl) phenyl]fluoren-2-amine (abbreviation: PCBAF), or N-phenyl-N-[4-(9-phenyl-9H-carbazol-3-yl)phenyl]spiro-9,9'-bifluoren-2-amine (abbreviation: PCBASF), a compound having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), or 3,3'-bis(9-phenyl-9H-carbazole) (abbreviation: PCCP), a compound having a thiophene skeleton, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), or 4-[4-(9-phenyl-9H-fluoren-9-yl)phenyl]-6-phenyldibenzothiophene (abbreviation: DBTFLP-IV), and a compound having a furan skeleton, such as 4,4',4"-(benzene-1,3,5-triyl)tri(dibenzofuran) (abbreviation: DBF3P-II) or 4-{3-[3-(9-phenyl-9H-fluoren-9-yl)phenyl]phenyl}dibenzofuran (abbreviation: mmDBFFLBi-II) can be given. Among the above, the compound having an aromatic amine skeleton and the compound having a carbazole skeleton are preferred because these have favorable reliability, have high hole-transport properties, and contribute to a reduction in driving voltage. The hole-transport material may be selected from a variety of substances as well as from the hole-transport materials given above and used.

In the case where a fluorescent substance is used as a light-emitting substance, a material having an anthracene skeleton, such as 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), or 9-phenyl-10-{4-(9-phenyl-9H-fluoren-9-yl)-biphenyl-4'-yl}-anthracene (abbreviation: FLPPA), is preferred. The use of a substance having an anthracene skeleton as a host material for a fluorescent substance makes it possible to achieve a light-emitting layer with favorable emission efficiency and favorable durability. In particular, CzPA, cgDBCzPA, 2mBnfPPA, and PCzPA are preferably selected because they exhibit significantly favorable characteristics.

Note that a host material may be a material of a mixture of a plurality of kinds of substances; in the case of using a mixed host material, it is preferable to mix a material having an electron-transport property with a material having a hole-transport property. By mixing the material having an electron-transport property with the material having a hole-transport property, the transport property of the light-emitting layer 113 can be easily adjusted and a recombination region can be easily controlled. The ratio of the content of the material having a hole-transport property to the content of the material having an electron-transport property may be the material having a hole-transport property:the material having an electron-transport property=1:9 to 9:1.

These mixed host materials may form an exciplex. When a combination is selected so as to form an exciplex that exhibits light emission whose wavelength overlaps with the wavelength of a lowest-energy-side absorption band of a fluorescent substance, a phosphorescent substance, and a TADF material, energy can be transferred smoothly and light emission can be efficiently obtained. Such a structure is preferred also in that driving voltage can be reduced.

The light-emitting layer 113 having the above-described structure can be formed using co-evaporation by a vacuum evaporation method, or a gravure printing method, an offset printing method, an inkjet method, a spin coating method, a dip coating method, or the like as a method using a mixed solution.

An electron-transport layer 114 is a layer containing a substance having an electron-transport property. As the substance having an electron-transport property, the material having an electron-transport property or the material having an anthracene skeleton, which are described above, can be used.

Between the electron-transport layer and the light-emitting layer, a layer that controls transport of electron carriers may be provided. This is a layer formed by addition of a small amount of a substance having a high electron-trapping property to the aforementioned material having a high electron-transport property and is capable of adjusting the carrier balance by retarding transport of electron carriers. Such a structure is very effective in preventing a problem (such as a reduction in element lifetime) caused when electrons pass through the light-emitting layer.

An electron-injection layer 115 may be provided between the electron-transport layer 114 and the cathode 102 and in contact with the cathode 102. As the electron-injection layer 115, an alkali metal, an alkaline earth metal, or a compound thereof, such as lithium fluoride (LiF), cesium fluoride (CsF), or calcium fluoride ($CaF_2$), can be used. For example, an alkali metal, an alkaline earth metal, or a compound thereof is contained in a layer of a substance having an electron-transport property, which can be used. In addition, an electride may be used for the electron-injection layer 115. As the electride, for example, a substance in which electrons are added at high concentration to a mixed oxide of calcium and aluminum, and the like can be given. Note that as the electron-injection layer 115, the one in which an alkali metal or an alkaline earth metal is contained in a layer of a substance having an electron-transport property is preferably used because electron injection from the cathode 102 is efficiently performed.

Instead of the electron-injection layer 115, a charge-generation layer 116 may be provided (FIG. 1(B)). The charge-generation layer 116 refers to a layer capable of injecting holes into a layer in contact with the cathode side of the charge-generation layer 116 and injecting electrons into a layer in contact with the anode side thereof when a potential is applied. The charge-generation layer 116 includes at least a P-type layer 117. The P-type layer 117 is preferably formed using the composite materials given above as the material that can form the hole-injection layer 111. The P-type layer 117 may be formed by stacking a film containing the above acceptor material as a material included in the composite material and a film containing the above hole-transport material. When a potential is applied to the P-type layer 117, electrons are injected into the electron-transport layer 114 and holes are injected into the cathode 102; thus, the light-emitting element operates. At this time, when a layer containing the organic compound of one embodiment of the present invention exists in the position of the electron-transport layer 114 in contact with the charge-generation layer 116, a luminance decrease over driving time of the light-emitting element can be suppressed, and thus, the light-emitting element with a long lifetime can be obtained.

Note that one of or both an electron-relay layer 118 and an electron-injection buffer layer 119 are preferably provided in the charge-generation layer 116 in addition to the P-type layer 117.

The electron-relay layer 118 contains at least a substance having an electron-transport property and has a function of preventing an interaction between the electron-injection buffer layer 119 and the P-type layer 117 to transfer electrons smoothly. The LUMO level of the substance having an electron-transport property contained in the electron-relay layer 118 is preferably between the LUMO level of an acceptor substance in the P-type layer 117 and the LUMO level of a substance contained in a layer of the electron-transport layer 114 in contact with the charge-generation layer 116. A specific energy level of the LUMO level of the substance having an electron-transport property used for the electron-relay layer 118 may be higher than or equal to −5.0 eV, preferably higher than or equal to −5.0 eV and lower than or equal to −3.0 eV. Note that as the substance having an electron-transport property used for the electron-relay layer 118, a phthalocyanine-based material or a metal complex having a metal-oxygen bond and an aromatic ligand is preferably used.

For the electron-injection buffer layer 119, a substance having a high electron-injection property, such as an alkali metal, an alkaline earth metal, a rare earth metal, or a compound thereof (an alkali metal compound (including an oxide such as lithium oxide, a halide, and a carbonate such as lithium carbonate or cesium carbonate), an alkaline earth metal compound (including an oxide, a halide, and a carbonate), or a rare earth metal compound (including an oxide, a halide, and a carbonate)), can be used.

In the case where the electron-injection buffer layer 119 is formed so as to contain the substance having an electron-transport property and a donor substance, an organic compound such as tetrathianaphthacene (abbreviation: TTN), nickelocene, or decamethylnickelocene can be used as the donor substance, as well as an alkali metal, an alkaline earth metal, a rare earth metal, a compound thereof (an alkali metal compound (including an oxide such as lithium oxide, a halide, and a carbonate such as lithium carbonate or cesium carbonate), an alkaline earth metal compound (including an oxide, a halide, and a carbonate), or a rare earth metal compound (including an oxide, a halide, and a carbonate)). Note that as the substance having an electron-transport property, a material similar to the above-described material forming the electron-transport layer 114 can be used for the formation.

As a substance forming the cathode 102, a metal, an alloy, an electrically conductive compound, or a mixture thereof having a low work function (specifically, 3.8 eV or less) or the like can be used. As specific examples of such a cathode material, elements belonging to Group 1 or Group 2 of the periodic table, such as alkali metals, e.g., lithium (Li) and cesium (Cs)), magnesium (Mg), calcium (Ca), and strontium (Sr), alloys containing these (MgAg and AlLi), rare earth metals such as europium (Eu) and ytterbium (Yb), alloys containing these rare earth metals, and the like can be given. However, when the electron-injection layer is provided between the cathode 102 and the electron-transport layer, as the cathode 102, a variety of conductive materials such as Al, Ag, ITO, or indium oxide-tin oxide containing silicon or silicon oxide can be used regardless of the work function. Films of these conductive materials can be formed by a dry process such as a vacuum evaporation method or a sputtering method, an inkjet method, a spin coating method, or the like. Alternatively, the films of these conductive materials may be formed by a wet process using a sol-gel method or a wet process using a paste of a metal material.

Various methods can be used as a method for forming the EL layer 103 regardless of whether it is a dry process or a wet process. For example, a vacuum evaporation method, a wet process (such as a spin coating method, a casting method, a die coating method, a blade coating method, a roll coating method, an inkjet method, a printing method (e.g., a gravure printing method, an offset printing method, or a screen printing method), a spray coating method, a curtain coating method, or a Langmuir-Blodgett method), or the like may be used.

Different deposition methods may be used to form the electrodes or the layers described above.

Here, a method for forming a layer 786 containing a light-emitting substance by a droplet discharge method will be described with reference to FIG. 2. FIG. 2(A) to FIG. 2(D) are cross-sectional views illustrating a method for forming the layer 786 containing a light-emitting substance.

First, a conductive film 772 is formed over a planarization insulating film 770, and an insulating film 730 is formed to cover part of the conductive film 772 (see FIG. 2(A)).

Then, a droplet 784 is discharged to an exposed portion of the conductive film 772, which is an opening of the insulating film 730, from a droplet discharge apparatus 783, so that a layer 785 containing a composition is formed. The droplet 784 is a composition containing a solvent and is attached to the conductive film 772 (see FIG. 2(B)).

Note that the step of discharging the droplet 784 may be performed under reduced pressure.

Next, the solvent is removed from the layer 785 containing a composition, which is subjected to solidification; thus, the layer 786 containing a light-emitting substance is formed (see FIG. 2(C)).

As a method for removing the solvent, a drying step or a heating step may be performed.

Next, a conductive film 788 is formed over the layer 786 containing a light-emitting substance; thus, a light-emitting element 782 is formed (see FIG. 2(D)).

When the layer 786 containing a light-emitting substance is formed by a droplet discharge method in this manner, the composition can be selectively discharged; accordingly, waste of material can be reduced. Furthermore, a lithography process or the like for processing a shape is not needed, and thus, the process can be simplified and cost reduction can be achieved.

The droplet discharge method described above is a general term for a means including a nozzle equipped with a composition discharge opening or a means to discharge droplets such as a head having one or a plurality of nozzles.

Next, a droplet discharge apparatus used for the droplet discharge method will be described with reference to FIG. 3. FIG. 3 is a conceptual diagram illustrating a droplet discharge apparatus 1400.

The droplet discharge apparatus 1400 includes a droplet discharge means 1403. The droplet discharge means 1403 includes a head 1405, a head 1412, and a head 1416.

The head 1405 and the head 1412 are connected to a control means 1407, which is controlled by a computer 1410; thus, a preprogrammed pattern can be drawn.

The drawing may be conducted at a timing, for example, based on a marker 1411 formed over a substrate 1402. Alternatively, the reference point may be determined on the basis of an outer edge of the substrate 1402. Here, the marker 1411 is detected by an imaging means 1404 and converted into a digital signal by an image processing means 1409. The computer 1410 recognizes the digital signal, generates a control signal, and transmits it to the control means 1407.

An image sensor or the like using a charge coupled device (CCD) or a complementary metal-oxide-semiconductor (CMOS) can be used as the imaging means 1404. Note that information on a pattern to be formed on the substrate 1402 is stored in a storage medium 1408, and a control signal is transmitted to the control means 1407 on the basis of the information, so that each of the head 1405, the head 1412, and the head 1416 of the droplet discharge means 1403 can be individually controlled. Materials to be discharged are supplied to the head 1405, the head 1412, and the head 1416 from a material supply source 1413, a material supply source 1414, and a material supply source 1415, respectively, through pipes.

Inside the head 1405, the head 1412, and the head 1416, a structure including a space to be filled with a liquid material, as indicated by a dotted line 1406, and a nozzle serving as a discharge outlet is employed. Although not illustrated, the inside structure of the head 1412 is similar to that of the head 1405. When the nozzles of the head 1405 and the head 1412 are provided so as to have different sizes, drawing can be performed using different materials simultaneously with different widths. Each head can discharge and draw a plurality of light-emitting materials. In the case of drawing over a large area, the same material can be simultaneously discharged to be drawn from a plurality of nozzles in order to improve throughput. When a large substrate is used, the head 1405, the head 1412, and the head 1416 can freely scan the substrate in the directions of arrows X, Y, and Z shown in FIG. 3, and a drawing region can be freely set. Thus, the same patterns can be drawn on one substrate.

Furthermore, the step of discharging the composition may be performed under reduced pressure. The substrate may be heated when the composition is discharged. After the composition is discharged, one of or both steps of drying and baking are performed. Both the steps of drying and baking are steps of heat treatment, but different in purpose, temperature, and time period. The step of drying and the step of baking are performed under normal pressure or reduced pressure by laser light irradiation, rapid thermal annealing, a heating furnace, or the like. Note that there is no particular limitation on the timing of performing the heat treatment and the number of times of the heat treatment. In order to favorably perform the steps of drying and baking, the temperature at that time depends on the material of the substrate and the properties of the composition.

In the above-described manner, the layer 786 containing a light-emitting substance can be formed using the droplet discharge apparatus.

In the case where the layer 786 containing a light-emitting substance is formed using the droplet discharge apparatus by a wet process using a composition in which a variety of organic materials and organic-inorganic halide perovskite materials are dissolved or dispersed in a solvent, a variety of organic solvents can be used as a coating composition. As an organic solvent that can be used for the composition, a variety of organic solvents such as benzene, toluene, xylene, mesitylene, tetrahydrofuran, dioxane, ethanol, methanol, n-propanol, isopropanol, n-butanol, 6-butanol, acetonitrile, dimethylsulfoxide, dimethylformamide, chloroform, methylene chloride, carbon tetrachloride, ethyl acetate, hexane, and cyclohexane can be used. In particular, a less polar benzene derivative such as benzene, toluene, xylene, or mesitylene is preferably used because a solution with a suitable concentration can be obtained and a material contained in ink can be prevented from deteriorating due to oxidation or the like. Furthermore, in consideration of the uniformity of a film after the formation, the uniformity of a film thickness, or the like, the boiling point is preferably 100° C. or higher, and toluene, xylene, or mesitylene is further preferable.

Note that the above-described structure can be combined with other structures in the other embodiments and this embodiment.

Next, an embodiment of a light-emitting element with a structure where a plurality of light-emitting units is stacked (also referred to as a stacked-type element) will be described with reference to FIG. 1(C). This light-emitting element is a light-emitting element including a plurality of light-emitting units between an anode and a cathode. One light-emitting unit has a structure similar to that of the EL layer 103, which is illustrated in FIG. 1(A). In other words, the light-emitting element illustrated in FIG. 1(A) or FIG. 1(B) can be called a light-emitting element including one light-emitting unit, and the light-emitting element illustrated in FIG. 1(C) can be called a light-emitting element including a plurality of light-emitting units.

In FIG. 1(C), a first light-emitting unit 511 and a second light-emitting unit 512 are stacked between a first electrode 501 and a second electrode 502, and a charge-generation layer 513 is provided between the first light-emitting unit 511 and the second light-emitting unit 512. The first electrode 501 and the second electrode 502 correspond to the anode 101 and the cathode 102, respectively, in FIG. 1(A), and the ones mentioned in the description for FIG. 1(A) can be applied. Furthermore, the first light-emitting unit 511 and the second light-emitting unit 512 may have the same structure or different structures.

The charge-generation layer 513 has a function of injecting electrons into one of the light-emitting units and injecting holes into the other light-emitting unit when a voltage is applied between the first electrode 501 and the second electrode 502. That is, in FIG. 1(C), any layer can be used as the charge generation layer 513 as long as the layer injects electrons into the first light-emitting unit 511 and injects holes into the second light-emitting unit 512 in the case where a voltage is applied such that the potential of the first electrode is higher than that of the second electrode.

The charge-generation layer 513 is preferably formed with a structure similar to that of the charge-generation layer 116 described with reference to FIG. 1(B). A composite material of an organic compound and a metal oxide has an excellent carrier-injection property and an excellent carrier-transport property; thus, low-voltage driving and low-current driving can be achieved. In the case where the anode-side surface of a light-emitting unit is in contact with the charge-generation layer 513, the charge-generation layer 513 can also serve as a hole-injection layer of the light-emitting unit; therefore, a hole-injection layer is not necessarily provided in the light-emitting unit.

In the case where the electron-injection buffer layer 119 is provided in the charge-generation layer 513, the electron-injection buffer layer 119 serves as an electron-injection layer in the light-emitting unit on the anode side; therefore, the light-emitting unit is not necessarily provided with an additional electron-injection layer.

The light-emitting element having two light-emitting units is described with reference to FIG. 1(C); however, the above structure can also be applied to a light-emitting element in which three or more light-emitting units are stacked. With a plurality of light-emitting units partitioned by the charge-generation layer 513 between a pair of electrodes as in the light-emitting element according to this embodiment, it is possible to achieve an element that can emit light with the current density kept low and has a longer lifetime. Moreover, a light-emitting device that can be driven at a low voltage and has low power consumption can be achieved.

Furthermore, when emission colors of the light-emitting units are different, light emission of a desired color can be obtained from the light-emitting element as a whole.

Embodiment 3

In this embodiment, a light-emitting device using the light-emitting element described in Embodiment 1 will be described.

A light-emitting device of one embodiment of the present invention will be described with reference to FIG. 4. Note that FIG. 4(A) is a top view illustrating the light-emitting device, and FIG. 4(B) is a cross-sectional view taken along A-B and C-D in FIG. 4(A). This light-emitting device includes a driver circuit portion (source line driver circuit) 601, a pixel portion 602, and a driver circuit portion (gate line driver circuit) 603, which are for controlling light emission of a light-emitting element and are illustrated with dotted lines. Furthermore, 604 denotes a sealing substrate, 605 denotes a sealant, and the inside surrounded by the sealant 605 is a space 607.

Note that a lead wiring 608 is a wiring for transmitting signals to be input to the source line driver circuit 601 and the gate line driver circuit 603 and receiving a video signal, a clock signal, a start signal, a reset signal, and the like from an FPC (flexible printed circuit) 609 serving as an external input terminal. Although only the FPC is illustrated here, a printed wiring board (PWB) may be attached to this FPC. The light-emitting device in this specification includes not only the light-emitting device itself but also the device provided with the FPC or the PWB.

Next, a cross-sectional structure will be described with reference to FIG. 4(B). The driver circuit portion and the pixel portion are formed over an element substrate 610. Here, the source line driver circuit 601, which is the driver circuit portion, and one pixel of the pixel portion 602 are illustrated.

In the source line driver circuit 601, a CMOS circuit in which an n-channel-type FET 623 and a p-channel-type FET 624 are combined is formed. The driver circuit may be formed using various circuits such as a CMOS circuit, a PMOS circuit, and an NMOS circuit. Although a driver-integrated type in which the driver circuit is formed over the substrate is described in this embodiment, the driver circuit is not necessarily formed over the substrate and may be formed outside.

The pixel portion 602 is formed with a plurality of pixels including an FET 611 for switching, an FET 612 for current control, and a first electrode 613 electrically connected to a drain of the FET 612 for current control; however, without being limited thereto, a pixel portion in which three or more FETs and a capacitor are combined may be employed.

There is no particular limitation on the kind and crystallinity of a semiconductor used for the FETs; an amorphous semiconductor or a crystalline semiconductor may be used. As examples of the semiconductor used for the FETs, Group 13 semiconductors, Group 14 semiconductors, compound semiconductors, oxide semiconductors, and organic semiconductor materials can be used. Oxide semiconductors are particularly preferable. As the oxide semiconductor, for example, an In—Ga oxide, an In-M-Zn oxide (M is Al, Ga, Y, Zr, La, Ce, or Nd), and the like can be given. Note that an oxide semiconductor material that has an energy gap of 2 eV or more, preferably 2.5 eV or more, further preferably 3 eV or more is preferably used, in which case the off-state current of the transistors can be reduced.

Note that an insulator 614 is formed to cover an end portion of the first electrode 613. The insulator 614 can be formed using a positive photosensitive acrylic resin film here.

In order to improve the coverage, the insulator 614 is formed so as to have a curved surface with curvature at its upper or lower end portion. For example, in the case where a positive photosensitive acrylic resin is used as a material of the insulator 614, only the upper end portion of the insulator 614 preferably has a curved surface with a curvature radius (0.2 μm to 3 μm). As the insulator 614, either a negative photosensitive resin or a positive photosensitive resin can be used.

Over the first electrode 613, an EL layer 616 and a second electrode 617 are formed. The first electrode 613, the EL layer 616, and the second electrode 617 respectively correspond to the anode 101, the EL layer 103, and the cathode 102 illustrated in FIGS. 1(A)(B), or to the first electrode 501, an EL layer 503, and the second electrode 502 illustrated in FIG. 1(C).

The EL layer 616 preferably contains an organometallic complex. The organometallic complex is preferably used as an emission center substance in the light-emitting layer.

The sealing substrate 604 and the element substrate 610 are attached to each other using the sealant 605, so that a structure in which a light-emitting element 618 is provided in the space 607 surrounded by the element substrate 610, the sealing substrate 604, and the sealant 605 is employed. The space 607 is filled with a filler; it is filled with an inert gas (e.g., nitrogen or argon) in some cases, and filled with the sealant 605 in some cases. It is preferable that the sealing substrate have a recessed portion provided with a desiccant, in which case deterioration due to moisture can be suppressed.

An epoxy-based resin or a glass frit is preferably used as the sealant 605. Furthermore, these materials are preferably materials that transmits moisture or oxygen as little as possible. As materials used for the element substrate 610 and the sealing substrate 604, a plastic substrate formed of FRP (Fiber Reinforced Plastics), PVF (polyvinyl fluoride), polyester, an acrylic resin, or the like can be used as well as a glass substrate or a quartz substrate.

In this specification and the like, a transistor or a light-emitting element can be formed using a variety of substrates, for example. The type of the substrate is not limited to a certain type. As examples of the substrate, a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, a base material film, and the like can be given. As examples of the glass substrate, barium borosilicate glass, aluminoborosilicate glass, soda lime glass, and the like can be given. As examples of the flexible substrate, the attachment film, the base material film, and the like, the following can be given. For example, plastic typified by polyethylene terephthalate (PET), polyethylene naphthalate (PEN), and polyether sulfone (PES) can be given. Furthermore, a synthetic resin such as an acrylic resin and the like can be given as examples. Furthermore, polytetrafluoroethylene (PTFE), polypropylene, polyester, polyvinyl fluoride, polyvinyl chloride, and the like can be given as examples. Furthermore, polyamide, polyimide, aramid, epoxy, an inorganic vapor deposition film, paper, and the like can be given as examples. In particular, the use of a semiconductor substrate, a single crystal substrate, an SOI substrate, or the like enables the manufacture of small-sized transistors with a small variation in characteristics, size, shape, or the like and with high current capability. When a circuit is formed with such transistors, lower power consumption of the circuit or higher integration of the circuit can be achieved.

Alternatively, a flexible substrate may be used as the substrate, and the transistor or the light-emitting element may be directly formed over the flexible substrate. Alternatively, a separation layer may be provided between the substrate and the transistor or between the substrate and the light-emitting element. After part or the whole of a semiconductor device is completed over the separation layer, the separation layer can be used for separation from the substrate and transfer to another substrate. In that case, the transistor can be transferred to even a substrate having low heat resistance or a flexible substrate. As the separation layer, a structure of a stacked structure of inorganic films of a tungsten film and a silicon oxide film, a structure in which an organic resin film of polyimide or the like is formed over a substrate, or the like can be used, for example.

In other words, the transistor or the light-emitting element may be formed using one substrate and then transferred to another substrate; thus, the transistor or the light-emitting may be positioned over another substrate. Examples of the substrate to which the transistor or the light-emitting element is transferred include, in addition to the above-described substrates over which the transistor can be formed, a paper substrate, a cellophane substrate, an aramid film substrate, a polyimide film substrate, a stone substrate, a wood substrate, a cloth substrate (including a natural fiber (silk, cotton, or hemp), a synthetic fiber (nylon, polyurethane, or polyester), a regenerated fiber (acetate, cupra, rayon, or regenerated polyester), or the like), a leather substrate, and a rubber substrate. When such a substrate is used, forming a transistor with excellent characteristics, forming a transistor with low power consumption, fabricating a device with high durability, providing high heat resistance, reducing weight, or reducing thickness can be achieved.

FIG. 5 illustrates examples of a light-emitting device in which full color display is achieved by forming a light-emitting element exhibiting white light emission and providing coloring layers (color filters) and the like. In FIG. 5(A), a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting elements, a partition 1025, an EL layer 1028, a cathode 1029 of the light-emitting elements, a sealing substrate 1031, a sealant 1032, and the like are illustrated.

In FIG. 5(A), coloring layers (a red coloring layer 1034R, a green coloring layer 1034G, and a blue coloring layer 1034B) are provided on a transparent base material 1033. A black layer (black matrix) 1035 may be additionally provided. The transparent base material 1033 provided with the coloring layers and the black layer is positioned and fixed to the substrate 1001. Note that the coloring layers and the black layer are covered with an overcoat layer 1036. In FIG. 5(A), a light-emitting layer from which light is emitted to the outside without passing through the coloring layer and light-emitting layers from which light is emitted to the outside, passing through the coloring layers of the respective colors are shown. Since light that does not pass through the coloring layer is white and light that passes through the coloring layer is red, blue, or green, an image can be expressed using pixels of the four colors.

FIG. 5(B) illustrates an example in which the coloring layers (the red coloring layer 1034R, the green coloring layer 1034G, and the blue coloring layer 1034B) are formed between the gate insulating film 1003 and the first interlayer insulating film 1020. The coloring layers may be provided between the substrate 1001 and the sealing substrate 1031 in this manner.

The above-described light-emitting device is a light-emitting device having a structure in which light is extracted to the substrate 1001 side where the FETs are formed (a bottom-mission type), but may be a light-emitting device having a structure in which light emission is extracted to the sealing substrate 1031 side (a top-emission type). FIG. 6 illustrates a cross-sectional view of a top-emission-type light-emitting device. In this case, a substrate that does not transmit light can be used as the substrate 1001. The top-emission-type light-emitting device is formed in a manner similar to that of the bottom-emission-type light-emitting device until a connection electrode which connects the FET and the anode of the light-emitting element is formed. Then, a third interlayer insulating film 1037 is formed to cover an electrode 1022. This insulating film may have a planarization function. The third interlayer insulating film 1037 can be formed using a material similar to that of the second interlayer insulating film or using any other various materials.

The first electrodes 1024W, 1024R, 1024G, and 1024B of the light-emitting elements are each an anode here, but may each be a cathode. Furthermore, in the case of the top-emission-type light-emitting device illustrated in FIG. 6, the first electrodes are preferably reflective electrodes. The structure of the EL layer 1028 is such a structure as is described as the EL layer 103 in FIGS. 1(A) and (B) or the EL layer 503 in FIG. 1(C), and an element structure with which white light emission can be obtained.

In the case of such a top-emission structure as in FIG. 6, sealing can be performed with the sealing substrate 1031 on which the coloring layers (the red coloring layer 1034R, the green coloring layer 1034G, and the blue coloring layer 1034B) are provided. The sealing substrate 1031 may be provided with the black layer (black matrix) 1035 which is positioned between pixels. The coloring layers (the red coloring layer 1034R, the green coloring layer 1034G, and the blue coloring layer 1034B) and the black layer may be covered with an overcoat layer. Note that a light-transmitting substrate is used as the sealing substrate 1031.

Although an example in which full color display is performed using four colors of red, green, blue, and white is shown here, there is no particular limitation and full color display may be performed using three colors of red, green, and blue or four colors of red, green, blue, and yellow.

FIG. 7 illustrates a passive-matrix-type light-emitting device which is one embodiment of the present invention. Note that FIG. 7(A) is a perspective view illustrating the light-emitting device, and FIG. 7(B) is a cross-sectional view taken along X-Y of FIG. 7(A). In FIG. 7, an EL layer 955 is provided between an electrode 952 and an electrode 956 over a substrate 951. An end portion of the electrode 952 is covered with an insulating layer 953. A partition layer 954 is provided over the insulating layer 953. Sidewalls of the partition layer 954 are aslope such that the distance between one sidewall and the other sidewall is gradually narrowed toward the surface of the substrate. That is, a cross section in the short side direction of the partition layer 954 is a trapezoidal shape, and the lower side (the side facing the same direction as the plane direction of the insulating layer 953 and touching the insulating layer 953) is shorter than the upper side (the side facing the same direction as the plane direction of the insulating layer 953, and not touching the insulating layer 953). By providing the partition layer 954 in this manner, defects of the light-emitting element due to static charge or the like can be prevented.

Since many minute light-emitting elements arranged in a matrix can each be controlled by the FETs formed in the pixel portion, the above-described light-emitting device is a light-emitting device that can be suitably used as a display device for expressing images.

<<Lighting Device>>

A lighting device which is one embodiment of the present invention will be described with reference to FIG. 8. FIG. 8(B) is a top view of the lighting device, and FIG. 8(A) is an e-f cross-sectional view in FIG. 8(B).

In the lighting device, a first electrode 401 is formed over a substrate 400 which is a support and has a light-transmitting property. The first electrode 401 corresponds to the anode 101 in FIGS. 1(A) and (B). When light emission is extracted from the first electrode 401 side, the first electrode 401 is formed using a material having a light-transmitting property.

A pad 412 for supplying a voltage to a second electrode 404 is formed over the substrate 400.

An EL layer 403 is formed over the first electrode 401. The EL layer 403 corresponds to, for example, the EL layer 103 in FIGS. 1(A) and (B) or the EL layer 503 in FIG. 1(C). For these structures, the corresponding description can be referred to.

The second electrode 404 is formed to cover the EL layer 403. The second electrode 404 corresponds to the cathode 102 in FIGS. 1(A) and (B). The second electrode 404 is formed so as to contain a material having high reflectivity when light emission is extracted from the first electrode 401 side. The second electrode 404 is connected to the pad 412, whereby a voltage is supplied thereto.

A light-emitting element is formed with the first electrode 401, the EL layer 403, and the second electrode 404. The light-emitting element and a sealing substrate 407 are fixed to each other using sealants 405 and 406 and sealing is performed, whereby the lighting device is completed. It is possible to use only either the sealant 405 or the sealant 406. In addition, the inner sealant 406 can be mixed with a desiccant, which enables moisture to be adsorbed, resulting in improved reliability.

When parts of the pad 412 and the first electrode 401 are extended to the outside of the sealants 405 and 406, those can serve as external input terminals. An IC chip 420 mounted with a converter or the like may be provided over the external input terminals.

<<Electronic Device>>

Examples of an electronic device which is one embodiment of the present invention will be described. As the electronic device, for example, a television device (also referred to as a television or a television receiver), a monitor for a computer or the like, a digital camera, a digital video camera, a digital photo frame, a mobile phone (also referred to as a cellular phone or a mobile phone device), a portable game console, a portable information terminal, an audio reproducing device, a large-sized game machine such as a pachinko machine, and the like can be given. Specific examples of these electronic devices are shown below.

FIG. 9(A) illustrates an example of a television device. In the television device, a display portion 7103 is incorporated in a housing 7101. Here, a structure in which the housing 7101 is supported by a stand 7105 is shown. Images can be displayed by the display portion 7103, and the display portion 7103 is formed in such a manner that light-emitting elements are arranged in a matrix.

The television device can be operated with an operation switch of the housing 7101 or a separate remote controller 7110. With operation keys 7109 of the remote controller 7110, channels and volume can be operated and images displayed on the display portion 7103 can be operated. Furthermore, a structure in which the remote controller 7110 is provided with a display portion 7107 for displaying data output from the remote controller 7110 may be employed.

Note that the television device has a structure of including a receiver, a modem, and the like. With the use of the receiver, a general television broadcast can be received. Moreover, when the television device is connected to a communication network with or without wires via the modem, one-way (from a sender to a receiver) or two-way (between a sender and a receiver or between receivers) data communication can be performed.

FIG. 9(B1) is a computer which includes a main body 7201, a housing 7202, a display portion 7203, a keyboard 7204, an external connection port 7205, a pointing device 7206, and the like. Note that this computer is manufactured by using light-emitting elements arranged in a matrix in the display portion 7203. The computer in FIG. 9(B1) may be such a mode as illustrated in in FIG. 9(B2). The computer in FIG. 9(B2) is provided with a second display portion 7210 instead of the keyboard 7204 and the pointing device 7206. The second display portion 7210 is of a touch-panel type, and input can be performed by operating display for input displayed on the second display portion 7210 with a finger or a dedicated pen. The second display portion 7210 can also display images other than the display for input. The display portion 7203 may also be a touch panel. Connecting the two screens with a hinge can prevent troubles such as a crack in or damage to the screens caused when the computer is stored or carried.

FIGS. 9(C)(D) illustrate examples of a portable information terminal. The portable information terminal is provided with a display portion 7402 incorporated in a housing 7401, operation buttons 7403, an external connection port 7404, a speaker 7405, a microphone 7406, and the like. Note that the portable information terminal includes the display portion 7402 which is formed by arranging light-emitting elements in a matrix.

The portable information terminals illustrated in FIGS. 9(C) and (D) may have a structure in which information can be input by touching the display portion 7402 with a finger or the like. In this case, operations such as making a call and creating an e-mail can be performed by touching the display portion 7402 with a finger or the like.

There are mainly three screen modes of the display portion 7402. The first one is a display mode mainly for displaying images. The second one is an input mode mainly for inputting data such as text. The third one is a display+input mode in which two modes of the display mode and the input mode are combined.

For example, in the case of making a call or creating an e-mail, a text input mode mainly for inputting text is selected for the display portion 7402 so that an operation of inputting text displayed on the screen may be performed. In this case, it is preferable to display a keyboard or number buttons on almost the entire screen of the display portion 7402.

When a sensing device including a sensor for sensing inclination, such as a gyroscope sensor or an acceleration sensor, is provided inside the portable information terminal, screen display of the display portion 7402 can be automatically changed by determining the orientation of the portable information terminal (vertically or horizontally).

The screen modes are changed by touching the display portion 7402 or operating the operation buttons 7403 of the housing 7401. Alternatively, the screen modes can be changed depending on the kind of image displayed on the display portion 7402. For example, when a signal of an image displayed on the display portion is moving image data, the screen mode is changed to the display mode. When the signal is text data, the screen mode is changed to the input mode.

Moreover, in the input mode, when input by the touch operation of the display portion 7402 is not performed for a certain period while a signal sensed by an optical sensor in the display portion 7402 is sensed, the screen mode may be controlled so as to be changed from the input mode to the display mode.

The display portion 7402 may also function as an image sensor. For example, an image of a palm print, a fingerprint, or the like is taken when the display portion 7402 is touched with the palm or the finger, whereby personal authentication can be performed. Furthermore, by using a backlight which emits near-infrared light or a sensing light source which emits near-infrared light in the display portion, an image of a finger vein, a palm vein, or the like can be taken.

Note that the above electronic devices can be used in combination with the structures described in this specification as appropriate.

A light-emitting element of one embodiment of the present invention is preferably used for the display portion. The light-emitting element can be a light-emitting element having high emission efficiency. In addition, the light-emitting element can be a light-emitting element with a low driving voltage. Thus, the electronic device including the light-emitting element of one embodiment of the present invention can be an electronic device with low power consumption.

FIG. 10 is an example of a liquid crystal display device in which a light-emitting element is used for a backlight. The liquid crystal display device illustrated in FIG. 10 includes a housing 901, a liquid crystal layer 902, a backlight unit 903, and a housing 904. The liquid crystal layer 902 is connected to a driver IC 905. The light-emitting element is used for the backlight unit 903, to which a current is supplied through a terminal 906.

For the light-emitting element, a light-emitting element of one embodiment of the present invention is preferably used. By using the light-emitting element for the backlight of the liquid crystal display device, a backlight with reduced power consumption can be obtained.

FIG. 11 is an example of a desk lamp which is one embodiment of the present invention. The desk lamp illustrated in FIG. 11 includes a housing 2001 and a light source 2002, and a lighting device using a light-emitting element is used as the light source 2002.

FIG. 12 is an example of an indoor lighting device 3001. A light-emitting element of one embodiment of the present invention is preferably used for the lighting device 3001.

An automobile which is one embodiment of the present invention is illustrated in FIG. 13. In the automobile, light-emitting elements are mounted on a windshield and a dashboard. A display region 5000 to a display region 5005 are display regions provided by using light-emitting elements. A light-emitting element of one embodiment of the present invention is preferably used, which can suppress the power consumption of the display region 5000 to the display region 5005, and thus is suitable for use in an automobile.

The display region 5000 and the display region 5001 are display devices which are provided in the automobile windshield and use the light-emitting elements. When these light-emitting elements are formed using electrodes having light-transmitting properties as a first electrode and a second electrode, what is called see-through display devices, through which the opposite side can be seen, can be obtained. See-through display devices can be provided without hindering the vision even when being provided in the automobile windshield. Note that in the case where a driving transistor or the like is provided, a transistor having a light-transmitting property, such as an organic transistor using an organic semiconductor material or a transistor using an oxide semiconductor, is preferably used.

The display region 5002 is a display device which is provided in a pillar portion and uses the light-emitting element. The display region 5002 can compensate for the view hindered by the pillar by displaying an image taken by an imaging means provided in the car body. Similarly, the display region 5003 provided in the dashboard portion can compensate for the view hindered by the car body by displaying an image taken by an imaging means provided on the outside of the automobile. Thus, blind areas can be compensated for and the safety can be enhanced. Showing an image so as to compensate for the area that cannot be seen makes it possible to confirm safety more naturally and comfortably.

The display region 5004 and the display region 5005 can provide a variety of other kinds of information such as navigation information, a speedometer, a rotational frequency, a mileage, a fuel quantity, a gear state, and air-condition setting. The content or layout of the display can be changed freely in accordance with the preference of a user. Note that such information can also be displayed on the display region 5000 to the display region 5003. The display region 5000 to the display region 5005 can also be used as lighting devices.

FIG. 14(A) and FIG. 14(B) are an example of a double-foldable tablet terminal. In FIG. 14(A), the tablet terminal is opened and includes a housing 9630, a display portion 9631*a*, a display portion 9631*b*, a switch 9034 for switching display modes, a power switch 9035, a switch 9036 for switching to power-saving mode, and a clasp 9033. Note that the tablet terminal is formed in such a manner that a light-emitting device including the light-emitting element of one embodiment of the present invention is used for one of or both the display portion 9631*a* and the display portion 9631*b*.

Part of the display portion 9631*a* can be a touch panel region 9632*a*, and data can be input when a displayed operation key 9637 is touched. The structure of the display portion 9631*a* is not limited to the illustrated structure in which a half region has only a display function and the other half region has a touch panel function. The whole region of the display portion 9631*a* may have a touch panel function. For example, the whole surface of the display portion 9631*a* can display keyboard buttons to serve as a touch panel, and the display portion 9631*b* can be used as a display screen.

Like the display portion 9631*a*, part of the display portion 9631*b* can be a touch panel region 9632*b*. When a position where a keyboard display switching button 9639 is displayed on the touch panel is touched with a finger, a stylus, or the like, keyboard buttons can be displayed on the display portion 9631*b*.

Touch input can be performed in the touch panel region 9632*a* and the touch panel region 9632*b* at the same time.

The switch 9034 for switching display modes can select the switching of the orientations of display such as portrait display or landscape display, the switching between monochrome display and color display, and the like. With the switch 9036 for switching to power-saving mode, the luminance of display can be optimized in accordance with the amount of external light in use which is sensed by an optical sensor incorporated in the tablet terminal. In addition to the optical sensor, another sensing device such as a sensor for sensing inclination, e.g., a gyroscope sensor or an acceleration sensor, may be incorporated in the tablet terminal.

Although an example in which the display portion 9631*a* and the display portion 9631*b* have the same display area is illustrated in FIG. 14(A), there is no particular limitation; the size of one of them may be different from the size of the other, and they may have different display qualities. For example, a display panel in which one of them can perform higher-definition display than the other may be employed.

The tablet terminal is closed in FIG. 14(B). An example in which the tablet terminal of this embodiment includes the housing 9630, a solar cell 9633, a charge and discharge control circuit 9634, a battery 9635, and a DCDC converter 9636 is described. In FIG. 14(B), a structure including the battery 9635 and the DCDC converter 9636 is illustrated as an example of the charge and discharge control circuit 9634.

Since the tablet terminal can be double-folded, the housing 9630 can be closed when the tablet terminal is not used. Thus, the display portion 9631*a* and the display portion 9631*b* can be protected; accordingly, a tablet terminal which has excellent durability and excellent reliability in terms of long-term use can be provided.

In addition, the tablet terminal illustrated in FIG. 14(A) and FIG. 14(B) can have a function of displaying a variety of kinds of information (e.g., a still image, a moving image, and a text image), a function of displaying a calendar, a date, the time, or the like on the display portion, a touch-input function of operating or editing information displayed on the display portion by touch input, a function of controlling processing by a variety of kinds of software (programs), and the like.

The solar cell 9633 provided on a surface of the tablet terminal can supply power to the touch panel, the display portion, a video signal processing portion, or the like. Note that the solar cell 9633 is preferably provided on one or two surfaces of the housing 9630, in which case a structure of efficiently charging the battery 9635 can be employed.

The structure and operation of the charge and discharge control circuit 9634 illustrated in FIG. 14(B) will be described with a block diagram illustrated in FIG. 14(C). FIG. 14(C) illustrates the solar cell 9633, the battery 9635, the DCDC converter 9636, a converter 9638, switches SW1 to SW3, and the display portion 9631. The battery 9635, the DCDC converter 9636, the converter 9638, and the switches SW1 to SW3 are portions corresponding to the charge and discharge control circuit 9634 illustrated in FIG. 14(B).

First, an example of the operation in the case where power is generated by the solar cell 9633 using external light is described. The voltage of power generated by the solar cell is raised or lowered by the DCDC converter 9636 so as to be a voltage for charging the battery 9635. Then, when the power charged by the solar cell 9633 is used for the operation of the display portion 9631, the switch SW1 is turned on and the voltage of the power is raised or lowered by the converter 9638 so as to be a voltage needed for the display portion 9631. When display on the display portion 9631 is not performed, SW1 is turned off and SW2 is turned on so that the battery 9635 may be charged.

Although the solar cell 9633 is described as an example of a power generation means, there is no particular limitation on the power generation means, and a structure may be employed in which the battery 9635 is charged by another power generation means such as a piezoelectric element (piezoelectric element) or a thermoelectric conversion element (Peltier element). A structure may be employed in which the battery 9635 is charged by a non-contact power transmission module performing charging by transmitting and receiving power wirelessly (without contact), or other charge means are used in combination; the power generation means is not necessarily provided.

A tablet terminal as an electronic device including the light-emitting element of one embodiment of the present invention is not limited to the tablet terminal having the shape illustrated in FIG. 14 as long as the display portion 9631 is included.

FIGS. 15(A) to (C) illustrate a foldable portable information terminal 9310. FIG. 15(A) illustrates the portable information terminal 9310 which is opened. FIG. 15(B) illustrates the portable information terminal 9310 which is in the state of being changed from one of an opened state and a folded state to the other. FIG. 15(C) illustrates the portable information terminal 9310 which is folded. The portable information terminal 9310 is highly portable when folded. The portable information terminal 9310 is excellent in display browsability when opened because of a seamless large display region.

A display panel 9311 is supported by three housings 9315 joined together by hinges 9313. Note that the display panel 9311 may be a touch panel (an input/output device) including a touch sensor (an input device). By folding the display panel 9311 at the hinges 9313 between two housings 9315, the portable information terminal 9310 can be reversibly changed in shape from the opened state to the folded state. A light-emitting device of one embodiment of the present invention can be used for the display panel 9311. A display region 9312 in the display panel 9311 is a display region that is positioned at a side surface of the portable information terminal 9310 which is folded. On the display region 9312, information icons, file shortcuts of frequently used applications or programs, and the like can be displayed, and confirmation of information and start of an application can be smoothly performed.

The organic compound of one embodiment of the present invention can be used for an electronic device such as an organic thin film solar cell. More specifically, the organic compound can be used in a carrier-transport layer or a carrier-injection layer since the organic compound has a carrier-transport property. In addition, a mixed film of the organic compound and an acceptor substance can be used as a charge generation layer. The organic compound is photo-excited and hence can be used as a power generation layer.

Example 1

Synthesis Example 1

In this synthesis example, a method for synthesizing 3,10-bis[N-(dibenzofuran-2-yl)-N-phenylamino]naphtho[2,3-b;6,7-b']bisbenzofuran (abbreviation: 3,10FrA2Nbf(IV)), which is represented as the structural formula (704) in Embodiment 1, will be described in detail. The structural formula of 3,10FrA2Nbf(IV) is shown below.

[Chemical Formula 70]

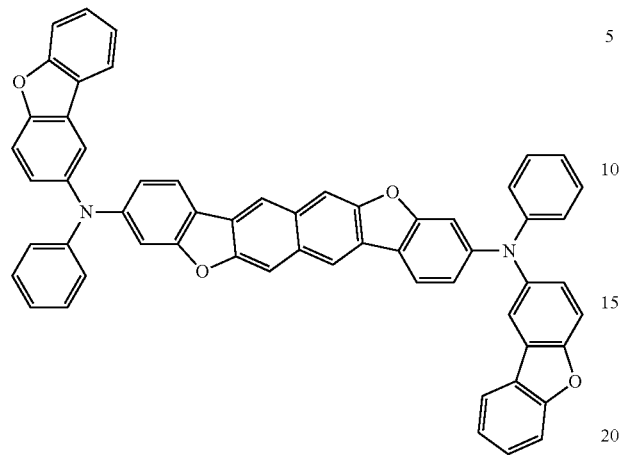

Step 1: Synthesis of 3,7-bis(4-chloro-2-fluorophenyl)-2,6-dimethoxynaphthalene

Into a 500 mL three-necked flask were put 11 g (24 mmol) of 3,7-diiodo-2,6-dimethoxynaphthalene, 14 g (78 mmol) of 4-chloro-2-fluorophenylboronic acid, 22 g (0.16 mol) of potassium carbonate, and 0.74 g (2.4 mmol) of tris(2-methylphenyl)phosphine. To this mixture was added 120 mL of toluene. This mixture was degassed by being stirred while the pressure was reduced. To this mixture was added 0.11 g (0.49 mmol) of palladium(II) acetate, and the mixture was stirred under a nitrogen stream at 110° C. for 50.5 hours.

After the stirring, toluene was added to the mixture, which was then subjected to suction filtration through Florisil (Wako Pure Chemical Industries, Ltd., Catalog Number: 540-00135), Celite (Wako Pure Chemical Industries, Ltd., Catalog Number: 531-16855), and alumina to give a filtrate. The filtrate was concentrated to give a solid.

The obtained solid was purified by silica gel column chromatography (developing solvent: toluene:hexane=1:1). The obtained solid was recrystallized with ethyl acetate to give 5.7 g of a white solid in a yield of 53%. The synthesis scheme of Step 1 is shown below.

[Chemical Formula 71]

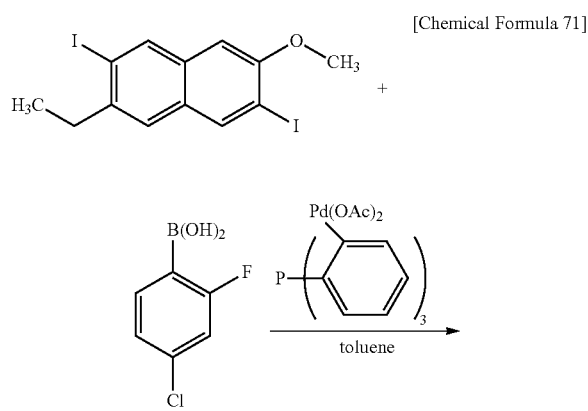

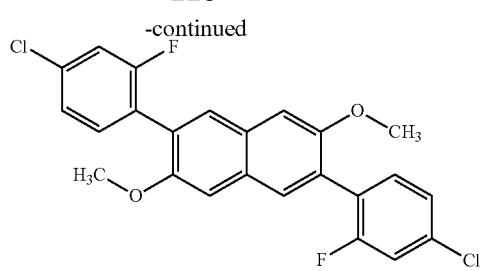

-continued

FIG. 76 shows $^1$H NMR data of the obtained solid, whose numerical data is given below.

$^1$H NMR (CDCl$_3$, 300 MHz): δ=3.88 (s, 6H), 7.18-7.24 (m, 6H), 7.37 (t, J1=7.2 Hz, 2H), 7.65 (s, 2H).

Step 2: Synthesis of 3,7-bis(4-chloro-2-fluorophenyl)-2,6-dihydroxynaphthalene

Into a 200 mL three-necked flask was put 5.7 g (13 mmol) of 3,7-bis(4-chloro-2-fluorophenyl)-2,6-dimethoxynaphthalene, and the air in the flask was replaced with nitrogen. Into this flask was added 32 mL of dichloromethane. Into this solution, 28 mL (28 mmol) of boron tribromide (approximately 1.0 mol/L of dichloromethane solution) and 20 mL of dichloromethane were dropped. After the dropping, this solution was stirred at room temperature.

After the stirring, approximately 20 mL of water was added to this solution and the solution was stirred while being cooled with ice. After the stirring, the mixture was separated into an organic layer and an aqueous layer, and the aqueous layer was subjected to extraction with dichloromethane and ethyl acetate. The solution of the extract and the organic layer were combined and washed with saturated saline solution and a saturated aqueous solution of sodium hydrogen carbonate. The organic layer was dried using magnesium sulfate, and after the drying, this mixture was subjected to gravity filtration. The obtained filtrate was concentrated to give 5.4 g of a white solid. The synthesis scheme of Step 2 is shown below.

[Chemical Formula 72]

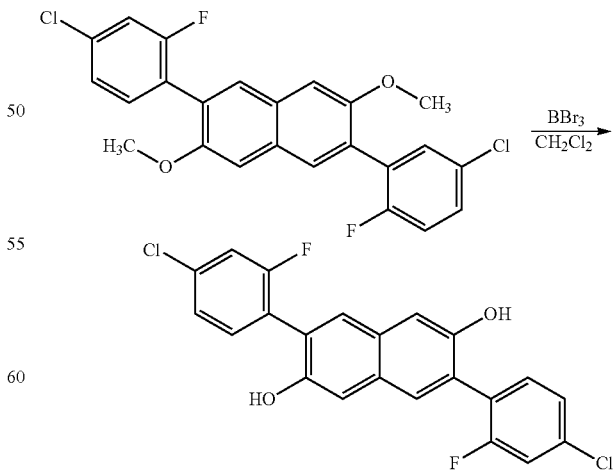

FIG. 77 shows H NMR data of the obtained solid, whose numerical data is given below.

$^1$H NMR (DMSO-d$_6$, 300 MHz): δ=7.20 (s, 2H), 7.37 (dd, J1=8.4 Hz, J2=1.8 Hz, 2H), 7.46-7.52 (m, 4H), 7.59 (s, 2H), 9.71 (s, 2H).

Step 3: Synthesis of 3,10-dichloronaphtho[2,3-b;6,7-b']bisbenzofuran

Into a 200 mL three-necked flask were put 5.4 g (13 mmol) of 3,7-bis(4-chloro-2-fluorophenyl)-2,6-dihydroxynaphthalene and 7.1 g (52 mmol) of potassium carbonate. To this mixture was added 130 mL of N-methyl-2-pyrrolidone, and this mixture was degassed by being stirred while the pressure was reduced. After the degassing, this mixture was stirred under a nitrogen stream at 120° C. for seven hours. After the stirring, water was added to this mixture, and a precipitated solid was collected by filtration. This solid was washed with water and ethanol. Ethanol was added to the obtained solid, which was then stirred while being heated and filtered to give a solid. Ethyl acetate was added to the obtained solid, which was then stirred while being heated and filtered to give 4.5 g of a pale yellow solid in a yield of 92%. The synthesis scheme of Step 3 is shown below.

[Chemical Formula 73]

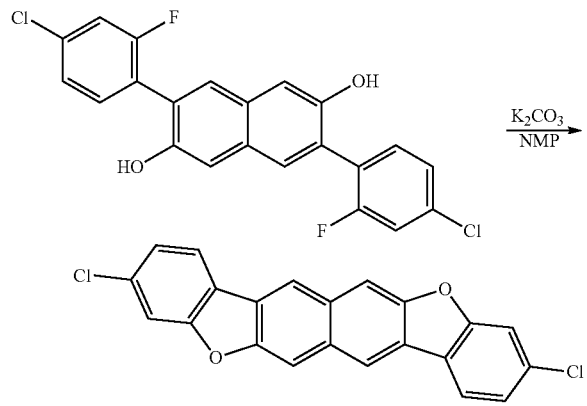

FIG. 78 shows H NMR data of the obtained solid, whose numerical data is given below.

$^1$H NMR (1,1,2,2-Tetrachloroethane-D2, 300 MHz): δ=7.44 (dd, J1=8.1 Hz, J2=1.5 Hz, 2H), 7.65 (d, J1=1.8 Hz, 2H), 8.05 (d, J1=8.4 Hz, 2H), 8.14 (s, 2H), 8.52 (s, 2H).

Step 4: Synthesis of 3,10-bis[N-(dibenzofuran-2-yl)-N-phenylamino]naphtho[2,3-b;6,7-b']bisbenzofuran (abbreviation: 3,10FrA2Nbf(IV))

Into a 200 mL three-necked flask were put 1.2 g (3.0 mmol) of 3,10-dichloronaphtho[2,3-b;6,7-b']bisbenzofuran, 2.4 g (9.1 mmol) of 2-anilinodibenzofuran, 0.11 g (0.30 mmol) of di(1-adamantyl)-n-butylphosphine, and 1.8 g (18 mmol) of sodium tert-butoxide. To this mixture was added 30 mL of xylene. This mixture was degassed by being stirred while the pressure was reduced. To this mixture was added 35 mg (61 μmol) of bis(dibenzylideneacetone)palladium(0), and the mixture was stirred under a nitrogen stream at 150° C. for 13 hours.

After the stirring, toluene was added to this mixture, which was then subjected to suction filtration through Florisil (Wako Pure Chemical Industries, Ltd., Catalog Number: 540-00135), Celite (Wako Pure Chemical Industries, Ltd., Catalog Number: 531-16855), and alumina to give a filtrate. The obtained filtrate was concentrated to give a solid. This solid was purified by silica gel column chromatography (developing solvent: toluene) to give a solid. The obtained solid was recrystallized with toluene three times, so that 1.8 g of a yellow solid was obtained in a yield of 72%.

By a train sublimation method, 1.1 g of the obtained solid was sublimated and purified. The sublimation purification was performed under the conditions where the pressure was 3.1 Pa and the argon flow rate was 15 mL/min, and the sample was heated at 390° C. After the sublimation purification, 0.93 g of a yellow solid was obtained at a collection rate of 87%. The synthesis scheme of Step 4 is shown below.

[Chemical Formula 74]

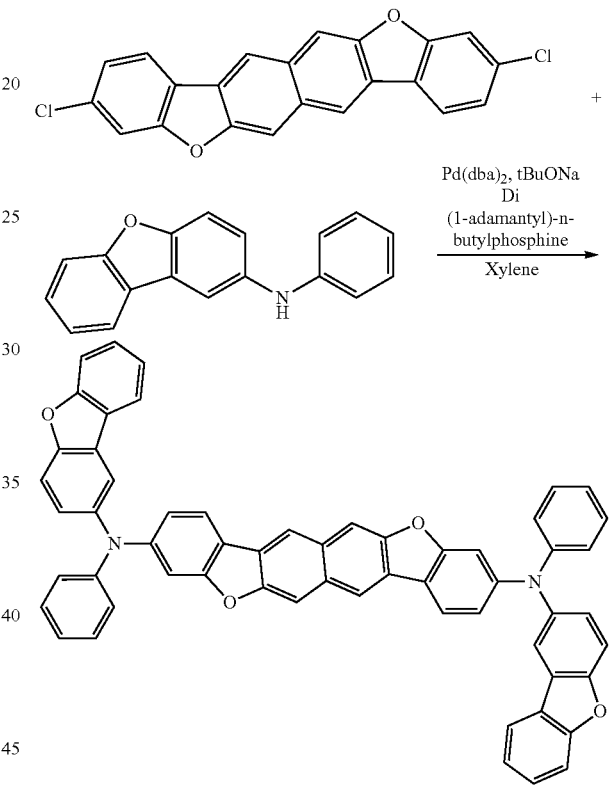

FIG. 16 shows $^1$H NMR data of the obtained solid, whose numerical data is given below. The data indicates that 3,10FrA2Nbf(IV), which is an organic compound of one embodiment of the present invention, was obtained in this synthesis example.

$^1$H NMR (1,1,2,2-Tetrachloroethane-D2, 300 MHz): δ=7.08-7.13 (m, 4H), 7.22-7.24 (m, 6H), 7.31-7.36 (m, 8H), 7.49 (t, J1=7.2 Hz, 2H), 7.56-7.62 (m, 4H), 7.83-7.90 (m, 6H), 7.98 (s, 2H), 8.35 (s, 2H).

Next, the measurement results of the absorption spectrum and emission spectrum of a toluene solution of 3,10FrA2Nbf(IV) are shown in FIG. 17. In addition, the absorption spectrum and emission spectrum of a thin film of 3,10FrA2Nbf(IV) are shown in FIG. 18. The solid thin film was formed over a quartz substrate by a vacuum evaporation method. The absorption spectrum of the toluene solution was measured using an ultraviolet-visible light spectrophotometer (V550 type manufactured by JASCO Corporation). The shown absorpotion spectrum is the one from which the spectrum of toluene alone in a quartz cell has been subtracted. The absorption spectrum of the thin film was measured using a spectrophotometer (U4100 Spectrophotometer, manufactured by Hitachi High-Technologies Corporation). The emission spectrum of the thin film was measured using a fluorescence spectrophotometer (FS920 manufactured by Hamamatsu Photonics K.K.). The emission spectrum and emission quantum yield of the solution were measured using an absolute PL quantum yield measurement system (Quantaurus-QY manufactured by Hamamatsu Photonics K.K.).

As can be seen from FIG. 17, the toluene solution of 3,10FrA2Nbf(IV) has absorption peaks at 424 nm, 401 nm, 300 nm, 289 nm, and 283 nm, and emission wavelength peaks at 440 nm and 465 nm (excitation wavelength 410 nm). In addition, as can be seen from FIG. 18, the thin film of 3,10FrA2Nbf(IV) has absorption peaks at 432 nm, 407 nm, 380 nm, 302 nm, 289 nm, and 251 nm, and emission wavelength peaks at 460 nm and 484 nm (excitation wavelength 390 nm). These results indicate that 3,10FrA2Nbf(IV) emits blue light and can be used as a host for a light-emitting substance or a host for a substance that emits fluorescence in the visible region.

Furthermore, in the emission spectrum of 3,10FrA2Nbf(IV) in the toluene solution, the intensity of the second peak at around 465 nm, which is on the long wavelength side, is small and the half width is 25 nm, which means that light with extremely narrow spectrum width is emitted.

Furthermore, the measured emission quantum yield in the toluene solution was as high as 86%, which indicates that 3,10FrA2Nbf(IV) is suitable as a light-emitting material.

Because of its narrow emission spectrum width and high emission quantum yield, 3,10FrA2Nbf(IV) of one embodiment of the present invention was found to be an organic compound that can emit light efficiently.

Next, 3,10FrA2Nbf(IV) obtained in this example was analyzed by liquid chromatography mass spectrometry (Liquid Chromatography Mass Spectrometry, abbreviation: LC/MS analysis).

In the LC/MS analysis, liquid chromatography (LC) separation was carried out with Ultimate 3000 produced by Thermo Fisher Scientific K.K., and the mass analysis (MS analysis) was carried out with Q Exactive produced by Thermo Fisher Scientific K.K.

In the LC separation, a given column was used and the column temperature was 40° C., and solution sending was performed under the conditions where an appropriate solvent was selected, the sample was prepared by dissolving 3,10FrA2Nbf(IV) in an organic solvent at an arbitrary concentration, and the injection amount was 5.0 μL.

A component with m/z=822.25, which is an ion derived from 3,10FrA2Nbf(IV), was subjected to the $MS^2$ measurement by a Targeted-$MS^2$ method. For setting of the Targeted-$MS^2$, the mass range of a target ion was set to m/z=822.25±2.0 (isolation window=4) and detection was performed in a positive mode. Measurement was performed with energy NCE (Normalized Collision Energy) for accelerating the target ion in a collision cell set to 50. The obtained MS spectrum is shown in FIG. 19.

From the results in FIG. 19, it was found that product ions from 3,10FrA2Nbf(IV) are detected mainly at around m/z=746, 656, 565, 487, 397, and 258. Note that the results shown in FIG. 19 exhibit characteristic results derived from 3,10FrA2Nbf(IV) and therefore are important data for identifying 3,10FrA2Nbf(IV) contained in a mixture.

Note that the product ion around m/z=746 is presumed to be a cation in the state where a phenyl group was eliminated from 3,10FrA2Nbf(IV), which suggests that 3,10FrA2Nbf(IV) contains a phenyl group. Furthermore, the product ion around n/z=656 is presumed to be a cation in the state where a dibenzofuranyl group was eliminated from 3,10FrA2Nbf(IV), which suggests that 3,10FrA2Nbf(IV) contains a dibenzofuranyl group. Furthermore, the product ion around m/z=565 is presumed to be a cation in the state where an N-(dibenzofuran-2-yl)-N-phenylamino group was eliminated from 3,10FrA2Nbf(IV), which suggests that 3,10FrA2Nbf(IV) contains an N-(dibenzofuran-2-yl)-N-phenylamino group.

Example 2

Synthesis Example 2

In this synthesis example, a method for synthesizing 2,9-bis[N-(9-phenyl-9H-carbazol-3-yl)-N-phenylamino] naphtho[2,1-b;6,5-b']bisbenzofuran (abbreviation: 2,9PCA2Nbf(III)), which is represented as the structural formula (509) in Embodiment 1, will be described in detail. The structural formula of 2,9PCA2Nbf(III) is shown below.

[Chemical Formula 75]

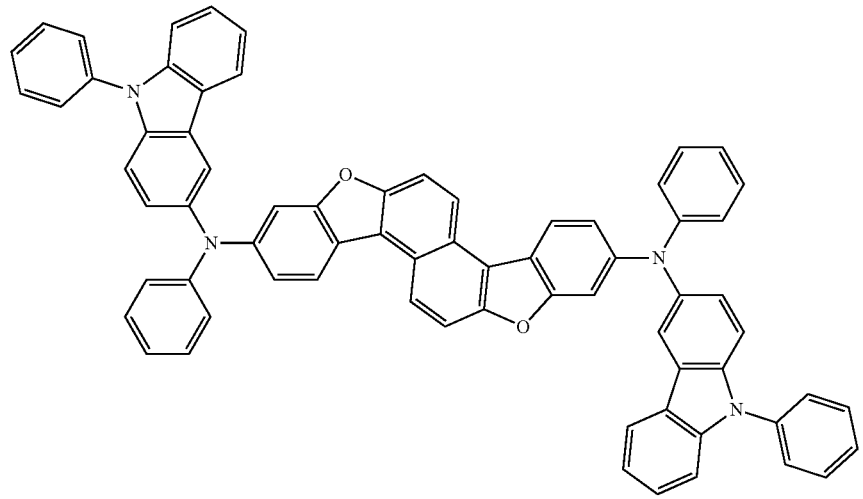

Step 1: Synthesis of 1,5-bis(4-chloro-2-fluorophenyl)-2,7-dihydroxynaphthalene Into a 500 mL three-necked flask were put 6.2 g (19 mmol) of 1.5-dibromo-2,6-dihydroxynaphthalene, 7.5 g (43 mmol) of 5-chloro-2-fluorophenylboronic acid, g (78 mmol) of cesium carbonate, and 0.80 g (1.9 mmol) of 2-dicyclohexylphosphino-2'-6'-dimethoxy-1,1'-biphenyl (abbreviation: Sphos). To this mixture was added 195 mL of toluene. This mixture was degassed by being stirred while the pressure was reduced. To this mixture was added 0.17 g (0.78 mmol) of palladium(II) acetate, and the mixture was stirred under a nitrogen stream at 110° C. for seven hours. After the stirring, toluene was added to the mixture, which was then subjected to suction filtration through Celite (Wako Pure Chemical Industries, Ltd., Catalog Number: 531-16855) to give a filtrate. The obtained filtrate was concentrated to give a solid. The obtained solid was purified by silica gel column chromatography (neutral silica gel, developing solvent: toluene) to give a solid.

The obtained solid was recrystallized with toluene to give 2.9 g of a white solid in a yield of 35%. The synthesis scheme of Step 1 is shown below.

[Chemical Formula 76]

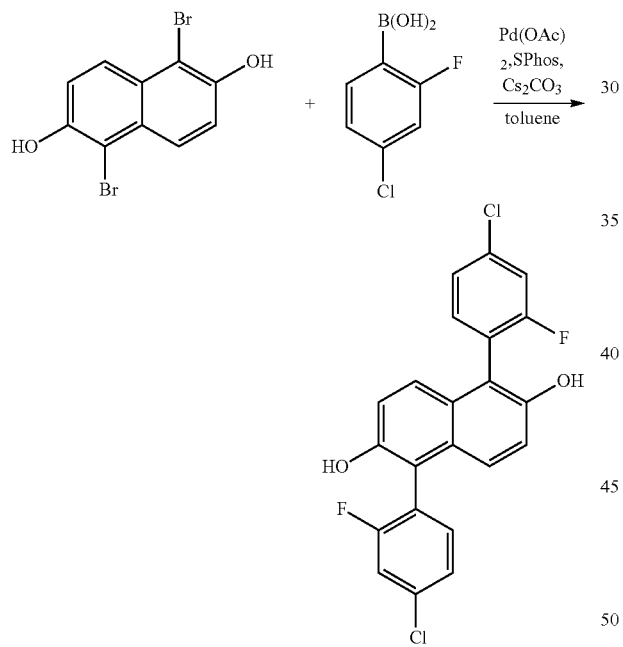

FIG. 79 shows $^1$H NMR data of the obtained solid, whose numerical data is given below.

$^1$H NMR (CDCl$_3$, 300 MHz): δ=4.78 (s, 2H), 7.15 (d, J1=9.3 Hz, 2H), 7.30-7.38 (m, 8H).

Step 2: Synthesis of 2,9-dichloronaphtho[2,1-b;6,5-b']bisbenzofuran

Into a 200 mL three-necked flask were put 2.8 g (6.8 mmol) of 1,5-bis(4-chloro-2-fluorophenyl)-2,7-dihydroxynaphthalene and 3.7 g (27 mmol) of potassium carbonate. To this mixture was added 70 mL of N-methyl-2-pyrrolidone, and this mixture was degassed by being stirred while the pressure was reduced. After the degassing, this mixture was stirred under a nitrogen stream at 120° C. for 7.5 hours. After the stirring, water was added to this mixture, and a precipitated solid was collected by filtration. This solid was washed with water and ethanol. Ethanol was added to the obtained solid, which was then stirred while being heated, and a solid was collected. Toluene was added to the obtained solid, which was then stirred while being heated, and a precipitated solid was collected, so that 2.3 g of a white solid was obtained in a yield of 91%. The synthesis scheme of Step 2 is shown below.

[Chemical Formula 77]

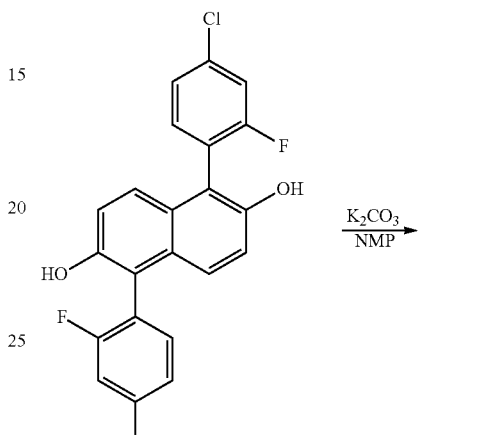

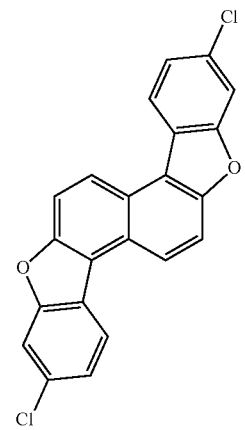

FIG. 80 shows H NMR data of the obtained solid, whose numerical data is given below.

$^1$H NMR (1,1,2,2-Tetrachloroethane-D2, 300 MHz): δ=7.56 (dd, J1=8.1 Hz, J2=1.5 Hz, 2H), 7.81 (d, J1=1.8 Hz, 2H), 8.06 (d, J1=8.7 Hz, 2H), 8.40 (d, J1=8.4 Hz, 2H), 8.73 (d, J1=8.7 Hz, 2H).

Step 3: Synthesis of 2,9-bis[N-(9-phenyl-9H-carbazol-3-yl)-N-phenylamino]naphtho[2,1-b;6,5-b']bisbenzofuran (abbreviation: 2,9PCA2Nbf(III))

Into a 200 mL three-necked flask were put 1.2 g (3.1 mmol) of 2,9-dichloronaphtho[2,1-b;6,5-b']bisbenzofuran, 3.1 g (9.2 mmol) of 3-anilino-9-phenyl-9H-carbazole, 0.11 g (0.31 mmol) of di(1-adamantyl)-n-butylphosphine, and 1.8 g (18 mmol) of sodium tert-butoxide. To this mixture was added 30 mL of xylene. This mixture was degassed by being stirred while the pressure was reduced. To this mixture was added 35 mg (62 μmol) of bis(dibenzylideneacetone)palladium(0), and the mixture was stirred under a nitrogen stream at 150° C. for 11 hours.

After the stirring, toluene was added to this mixture, which was then subjected to suction filtration through Florisil (Wako Pure Chemical Industries, Ltd., Catalog Number: 540-00135), Celite (Wako Pure Chemical Industries, Ltd., Catalog Number: 531-16855), and alumina to give a filtrate. The obtained filtrate was concentrated to give a solid. This solid was purified by silica gel column chromatography (neutral silica gel, developing solvent: toluene:hexane=1:1) to give a solid. The obtained solid was recrystallized with toluene, so that 2.0 g of a yellow solid was obtained in a yield of 66%.

By a train sublimation method, 1.2 g of the obtained solid was sublimated and purified. The sublimation purification was performed under the conditions where the pressure was $1.8 \times 10^{-2}$ Pa and the argon flow rate was 0 mL/min, and the sample was heated at 405° C. After the sublimation purification, 0.96 g of a yellow solid was obtained at a collection rate of 80%. The synthesis scheme of Step 3 is shown below.

[Chemical Formula 78]

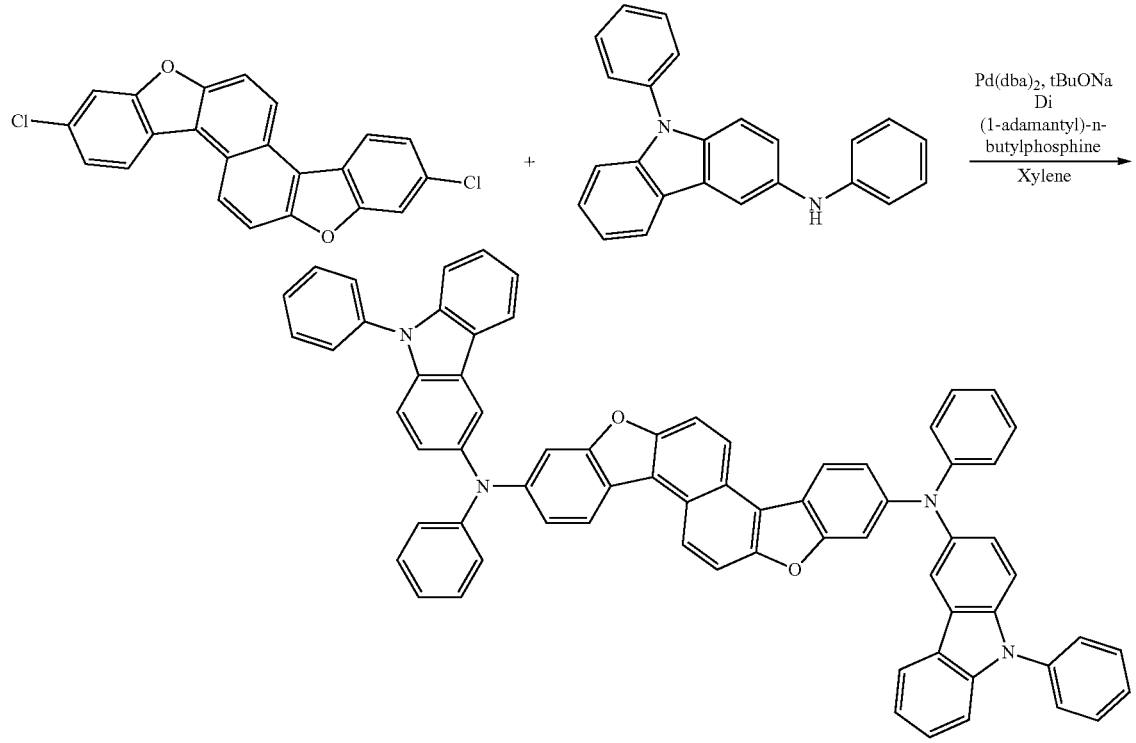

FIG. 20 shows $^1$H NMR data of the obtained solid, whose numerical data is given below. The data indicates that 2,9PCA2Nbf(III), which is an organic compound of one embodiment of the present invention, was obtained in this synthesis example.

$^1$H NMR (DMSO-d$_6$, 300 MHz): δ=7.08 (t, J1=7.2 Hz, 2H), 7.15-7.27 (m, 8H), 7.30-7.47 (m, 14H), 7.53-7.58 (m, 2H), 7.67-7.73 (m, 8H), 8.05 (d, J1=9.3 Hz, 2H), 8.18 (d, J1=2.1 Hz, 2H), 8.21 (d, J1=7.2 Hz, 2H), 8.50 (d, J1=8.7 Hz, 2H), 8.71 (d, J1=8.7 Hz, 2H).

Next, the measurement results of the absorption spectrum and emission spectrum of a toluene solution of 2,9PCA2Nbf (III) are shown in FIG. 21. In addition, the absorption spectrum and emission spectrum of a thin film of 2,9PCA2Nbf(III) are shown in FIG. 22. The solid thin film was formed over a quartz substrate by a vacuum evaporation method. The absorption spectrum of the toluene solution was measured using an ultraviolet-visible light spectrophotometer (V550 type manufactured by JASCO Corporation). The shown absorpotion spectrum is the one from which the spectrum of toluene alone in a quartz cell has been subtracted. The absorption spectrum of the thin film was measured using a spectrophotometer (U4100 Spectrophotometer, manufactured by Hitachi High-Technologies Corporation). The emission spectrum of the thin film was measured using a fluorescence spectrophotometer (FS920 manufactured by Hamamatsu Photonics K.K.). The emission spectrum and emission quantum yield of the solution were measured using an absolute PL quantum yield measurement system (Quantaurus-QY manufactured by Hamamatsu Photonics K.K.).

As can be seen from FIG. 21, the toluene solution of 2,9PCA2Nbf(III) has absorption peaks at around 424 nm, 405 nm, 381 nm, 346 nm, and 299 nm, and emission wavelength peaks at around 447 nm and 472 nm (excitation wavelength 400 nm). In addition, as can be seen from FIG. 22, the thin film of 2,9PCA2Nbf(III) has absorption peaks at around 431 nm, 409 nm, 383 nm, 350 nm, 300 nm, and 238 nm, and an emission wavelength peak at around 487 nm (excitation wavelength 405 nm). These results indicate that 2,9PCA2Nbf(III) emits blue light and can be used as a host for a light-emitting substance or a host for a substance that emits fluorescence in the visible region.

Furthermore, the half width of the emission spectrum of 2,9PCA2Nbf(III) in the toluene solution was found to be 47 nm.

Furthermore, the measured emission quantum yield of 2,9PCA2Nbf(III) in the toluene solution was as high as 87%, which indicates that 2,9PCA2Nbf(III) is suitable as a light-emitting material.

Next, 2,9PCA2Nbf(III) obtained in this example was analyzed by LC/MS analysis.

In the LC/MS analysis, LC (liquid chromatography) separation was carried out with Ultimate 3000 produced by Thermo Fisher Scientific K.K., and the MS analysis (mass analysis) was carried out with Q Exactive produced by Thermo Fisher Scientific K.K.

In the LC separation, a given column was used and the column temperature was 40° C., and solution sending was performed under the conditions where an appropriate solvent was selected, the sample was prepared by dissolving 2,9PCA2Nbf(III) in an organic solvent at an arbitrary concentration, and the injection amount was 5.0 μL.

A component with m/z=972.35, which is an ion derived from 2,9PCA2Nbf(III), was subjected to the MS$^2$ measurement by a Targeted-MS$^2$ method. For setting of the Targeted-MS$^2$, the mass range of a target ion was set to n/z=972.35±2.0 (isolation window=4) and detection was performed in a positive mode. Measurement was performed with energy NCE for accelerating the target ion in a collision cell set to 50. The obtained MS spectrum is shown in FIG. 23.

From the results in FIG. 23, it was found that product ions from 2,9PCA2Nbf(III) are detected mainly at around n/z=333 and 255. Note that the results shown in FIG. 23 exhibit characteristic results derived from 2,9PCA2Nbf(III) and therefore are important data for identifying 2,9PCA2Nbf(III) contained in a mixture.

Note that the product ion around m/z=333 is presumed to be a cation in the state where a 2-[N-(9-phenyl-9H-carbazol-3-yl)-N-phenylamino]naphtho[2,1-b;6,5-b']bisbenzofuranyl group was eliminated from 2,9PCA2Nbf(III), which suggests that 2,9PCA2Nbf(III) contains a 2-[N-(9-phenyl-9H-carbazol-3-yl)-N-phenylamino]naphtho[2,1-b;6,5-b']bisbenzofuranyl group.

Example 3

Synthesis Example 3

In this synthesis example, a method for synthesizing 3,10-bis[N-(9-phenyl-9H-carbazol-3-yl)-N-phenylamino]naphtho[2,3-b;6,7-b']bisbenzofuran (abbreviation: 3,10PCA2Nbf(IV)), which is represented as the structural formula (705) in Embodiment 1, will be described in detail. The structural formula of 3,10PCA2Nbf(IV) is shown below.

[Chemical Formula 79]

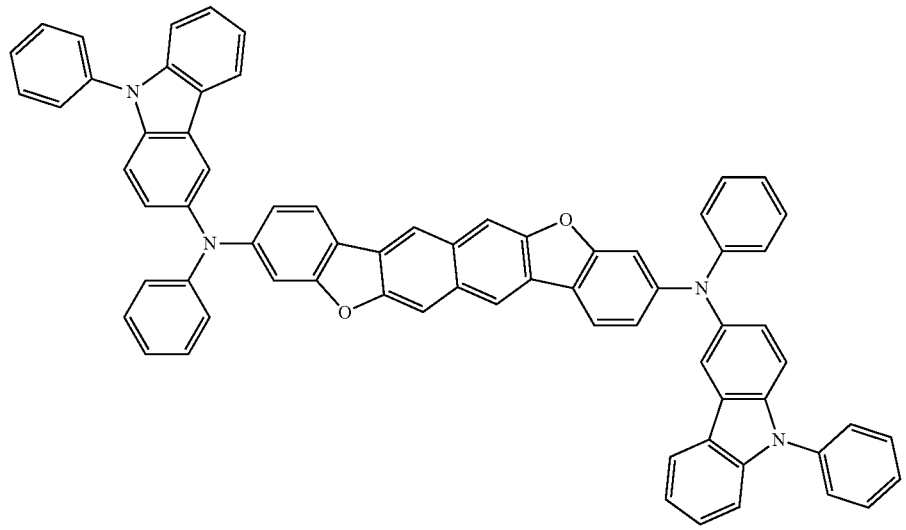

Step 1: Synthesis of 3,7-bis(4-chloro-2-fluorophenyl)-2,6-dimethoxynaphthalene

The synthesis was conducted in a similar manner to Step 1 of Synthesis Example 1 in Example 1.

Step 2: Synthesis of 3,7-bis(4-chloro-2-fluorophenyl)-2,6-dihydroxynaphthalene

The synthesis was conducted in a similar manner to Step 2 of Synthesis Example 1 in Example 1.

Step 3: Synthesis of 3,10-dichloronaphtho[2,3-b;6,7-b']bisbenzofuran

The synthesis was conducted in a similar manner to Step 3 of Synthesis Example 1 in Example 1.

Step 4: Synthesis of 3,10-bis[N-(9-phenyl-9H-carbazol-3-yl)-N-phenylamino]naphtho[2,3-b;6,7-b']bisbenzofuran (abbreviation: 3,10PCA2Nbf(IV))

Into a 200 mL three-necked flask were put 1.2 g (3.1 mmol) of 3,10-dichloronaphtho[2,3-b;6,7-b']bisbenzofuran, 3.1 g (9.2 mmol) of 3-anilino-9-phenyl-9H-carbazole, 0.11 g (0.31 mmol) of di(1-adamantyl)-n-butylphosphine, and 1.8 g (18 mmol) of sodium tert-butoxide. To this mixture was added 30 mL of xylene. This mixture was degassed by being stirred while the pressure was reduced. To this mixture was added 35 mg (62 μmol) of bis(dibenzylideneacetone)palladium(0), and the mixture was stirred under a nitrogen stream at 150° C. for six hours.

After the stirring, toluene was added to this mixture, which was then subjected to suction filtration through Florisil (Wako Pure Chemical Industries, Ltd., Catalog Number: 540-00135), Celite (Wako Pure Chemical Industries, Ltd., Catalog Number: 531-16855), and alumina to give a filtrate. The obtained filtrate was concentrated to give a solid. This solid was purified by silica gel column chromatography (developing solvent: toluene:hexane=1:2) to give a solid.

The obtained solid was recrystallized with toluene, so that 0.92 g of a yellow solid was obtained in a yield of 31%.

By a train sublimation method, 0.85 g of the obtained solid was sublimated and purified. The sublimation purification was performed under the conditions where the pressure was $3.2 \times 10^{-2}$ Pa and the argon flow rate was 0 mL/min, and the sample was heated at 375° C. After the sublimation purification, 0.55 g of a yellow solid was obtained at a collection rate of 65%. The synthesis scheme of Step 4 is shown below.

was formed over a quartz substrate by a vacuum evaporation method. The absorption spectrum of the toluene solution was measured using an ultraviolet-visible light spectrophotometer (V550 type manufactured by JASCO Corporation). The shown absorpotion spectrum is the one from which the spectrum of toluene alone in a quartz cell has been subtracted. The absorption spectrum of the thin film was measured using a spectrophotometer (U4100 Spectrophotometer, manufactured by Hitachi High-Technologies Corporation). The emission spectrum of the thin film was measured using a fluorescence spectrophotometer (FS920 manufactured by Hamamatsu Photonics K.K.). The emission spectrum and emission quantum yield of the solution were measured using an absolute PL quantum yield measurement system (Quantaurus-QY manufactured by Hamamatsu Photonics K.K.).

As can be seen from FIG. 25, the toluene solution of 3,10PCA2Nbf(IV) has absorption peaks at around 430 nm, 408 nm, 383 nm, 307 nm, 292 nm, and 283 nm, and an

[Chemical Formula 80]

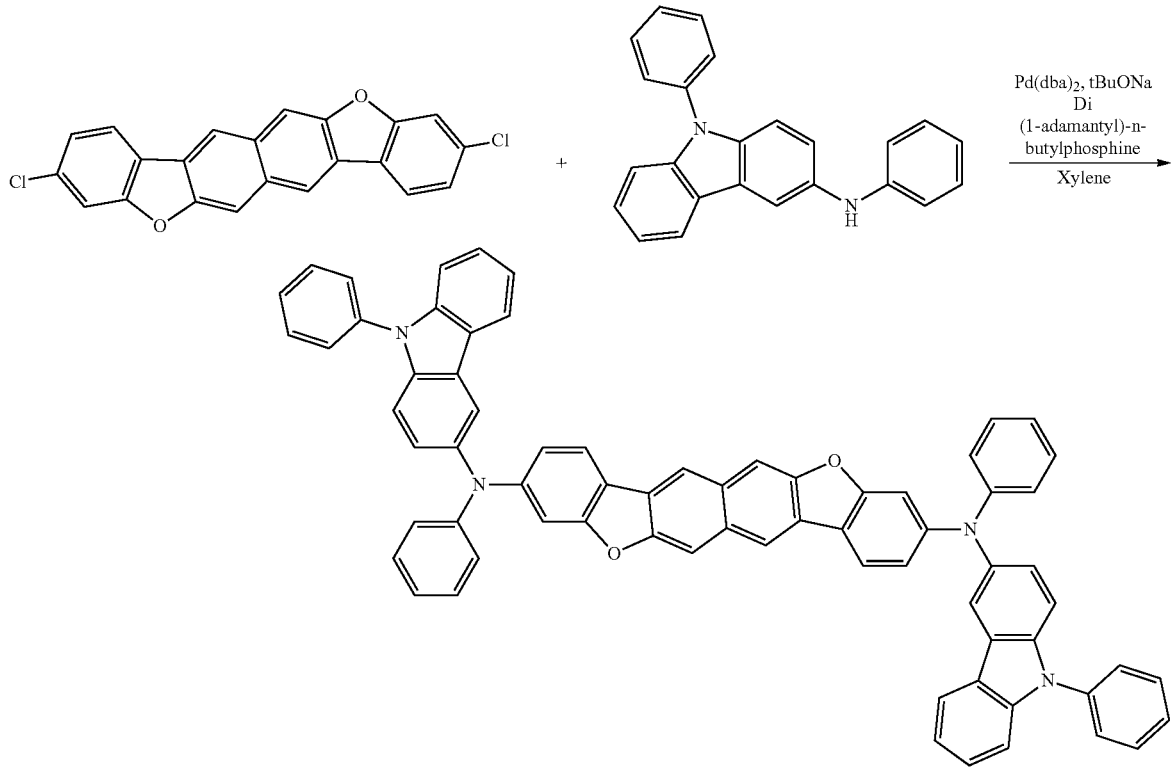

FIG. 24 shows H NMR data of the obtained solid, whose numerical data is given below. The data indicates that 3,10PCA2Nbf(IV), which is an organic compound of one embodiment of the present invention, was obtained in this synthesis example.

$^1$H NMR (DMSO-$d_6$, 300 MHz): δ=7.00-7.11 (m, 6H), 7.20-7.25 (m, 6H), 7.30-7.45 (m, 12H), 7.54 (t, J1=6.6 Hz, 2H), 7.61-7.71 (m, 8H), 8.00 (d, J1=8.7 Hz, 2H), 8.08-8.16 (m, 6H), 8.52 (s, 2H).

Next, the measurement results of the absorption spectrum and emission spectrum of a toluene solution of 3,10PCA2Nbf(IV) are shown in FIG. 25. In addition, the absorption spectrum and emission spectrum of a thin film of 3,10PCA2Nbf(IV) are shown in FIG. 26. The solid thin film emission wavelength peak at around 455 nm (excitation wavelength 410 nm). In addition, as can be seen from FIG. 26, the thin film of 3,10PCA2Nbf(IV) has absorption peaks at around 435 nm, 415 nm, 385 nm, 292 nm, and 244 nm, and an emission wavelength peak at around 494 nm (excitation wavelength 400 nm). These results indicate that 3,10PCA2Nbf(IV) emits blue light and can be used as a host for a light-emitting substance or a host for a substance that emits fluorescence in the visible region.

Furthermore, the half width of the emission spectrum of 3,10PCA2Nbf(IV) in the toluene solution was found to be 42 nm.

Furthermore, the measured emission quantum yield of 3,10PCA2Nbf(IV) in the toluene solution was as high as 88%, which indicates that 3,10PCA2Nbf(IV) is suitable as a light-emitting material.

Next, 3,10PCA2Nbf(IV) obtained in this example was analyzed by LC/MS analysis.

In the LC/MS analysis, LC (liquid chromatography) separation was carried out with Ultimate 3000 produced by Thermo Fisher Scientific K.K., and the MS analysis (mass analysis) was carried out with Q Exactive produced by Thermo Fisher Scientific K.K.

In the LC separation, a given column was used and the column temperature was 40° C., and solution sending was performed under the conditions where an appropriate solvent was selected, the sample was prepared by dissolving 3,10PCA2Nbf(IV) in an organic solvent at an arbitrary concentration, and the injection amount was 5.0 μL.

A component with nm/z=972.35, which is an ion derived from 3,10PCA2Nbf(IV), was subjected to the $MS^2$ measurement by a Targeted-$MS^2$ method. For setting of the Targeted-$MS^2$, the mass range of a target ion was set to m/z=972.35±2.0 (isolation window=4) and detection was performed in a positive mode. Measurement was performed with energy NCE for accelerating the target ion in a collision cell set to 60. The obtained MS spectrum is shown in FIG. 27.

From the results in FIG. 27, it was found that product ions from 3,10PCA2Nbf(IV) are detected mainly at around m/z=894, 728, 652, 332, and 255. Note that the results shown in FIG. 27 exhibit characteristic results derived from 3,10PCA2Nbf(IV) and therefore are important data for identifying 3,10PCA2Nbf(IV) contained in a mixture.

Note that the product ion around m/z=894 is presumed to be a cation in the state where a phenyl group was eliminated from 3,10PCA2Nbf(IV), which suggests that 3,10PCA2Nbf (IV) contains a phenyl group. Furthermore, the product ion around m/z=728 is presumed to be a cation in the state where a 9-phenylcarbazolyl group was eliminated from 3,10PCA2Nbf(IV), which suggests that 3,10PCA2Nbf(IV) contains a 9-phenylcarbazolyl group. Furthermore, the product ion around m/z=332 is presumed to be a cation in the state where a 3-[N-(9-phenyl-9H-carbazol-3-yl)-N-phenylamino]naphtho[2,1-b;6,5-b']bisbenzofuranyl group was eliminated from 3,10PCA2Nbf(IV), which suggests that 3,10PCA2Nbf(IV) contains a 3-[N-(9-phenyl-9H-carbazol-3-yl)-N-phenylamino]naphtho[2,1-b;6,5-b']bisbenzofuranyl group.

Example 4

In this example, a light-emitting element 1, which is a light-emitting element of one embodiment of the present invention described in Embodiments, and a comparative light-emitting element 1, which is a light-emitting element of a comparative example, will be described in detail. The structural formulae of organic compounds used in the light-emitting element 1 and the comparative light-emitting element 1 are shown below.

[Chemical Formulae 8]

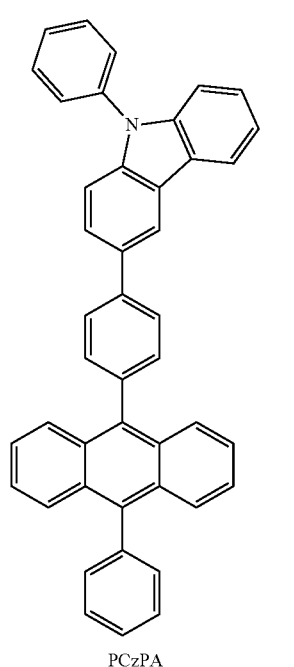

(i)

PCzPA

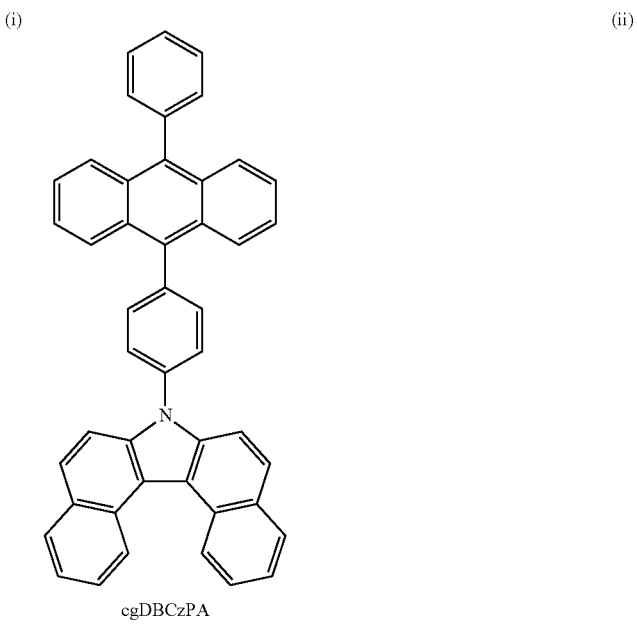

(ii)

cgDBCzPA

-continued

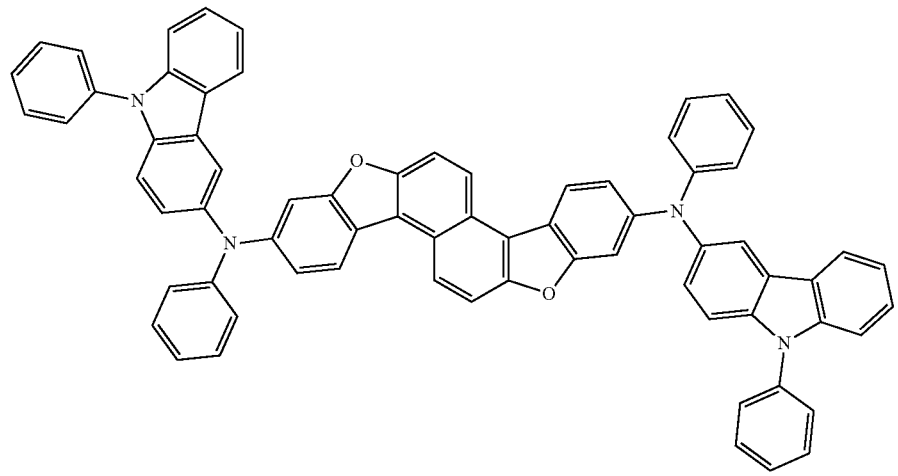

2,9PCA2Nbf(III)

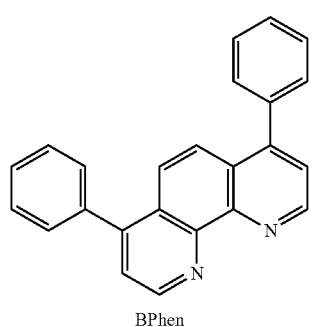

BPhen

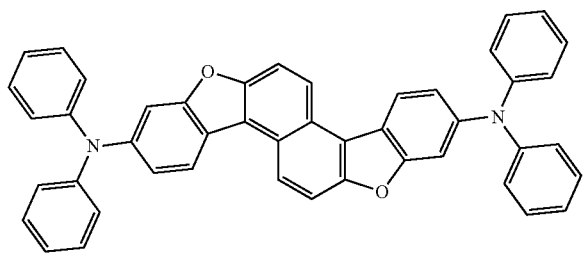

2,9DPhA2Nbf(III)

(Fabrication Method of Light-Emitting Element 1)

First, a film of indium tin oxide containing silicon oxide (ITSO) was formed on a glass substrate by a sputtering method, so that the anode 101 was formed. Note that the thickness was 70 nm and the area of the electrode was 4 mm² (2 mm×2 mm).

Next, in pretreatment for forming the light-emitting element over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to about $10^{-4}$ Pa, vacuum baking at 170° C. for 30 minutes was performed in a heating chamber in the vacuum evaporation apparatus, and then the substrate was naturally cooled down for about 30 minutes.

Next, the substrate on which the anode 101 was formed was fixed to a substrate holder provided in the vacuum evaporation apparatus such that the side on which the anode 101 was formed faced downward, and 9-phenyl-3-[4-(10-phenyl-9-anthryl)phenyl]-9H-carbazole (abbreviation: PCzPA) represented as the above structural formula (i) and molybdenum(VI) oxide were deposited by co-evaporation on the anode 101 to have a weight ratio of 4:2 (=PCzPA: molybdenum oxide) to a thickness of 10 nm by an evaporation method using resistance heating, whereby the hole-injection layer 111 was formed.

Next, on the hole-injection layer 111, PCzPA was deposited by evaporation to a thickness of 30 nm to form the hole-transport layer 112.

Subsequently, 7-[4-(10-phenyl-9-anthryl)phenyl]-7H-dibenzo[c,g]carbazole (abbreviation: cgDBCzPA) represented as the above structural formula (ii) and 2,9-bis[N-(9-phenyl-9H-carbazol-3-yl)-N-phenylamino]naphtho[2,1-b;6,5-b']bisbenzofuran (abbreviation: 2,9PCA2Nbf(III)) represented as the above structural formula (iii) were deposited by co-evaporation to have a weight ratio of 1:0.03 (=cgDBCzPA: 2,9PCA2Nbf(III)) to a thickness of 25 nm, whereby the light-emitting layer 113 was formed.

After that, on the light-emitting layer 113, cgDBCzPA was deposited by evaporation to a thickness of 15 nm, and bathophenanthroline (abbreviation: BPhen) represented as the above structural formula (iv) was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115, and aluminum was deposited by evaporation to a thickness of 200 nm to form the cathode 102. Thus, the light-emitting element 1 was fabricated.

(Fabrication Method of Comparative Light-Emitting Element 1)

The comparative light-emitting element 1 was fabricated in such a manner that the light-emitting layer 113 was formed using 2,9-bis(diphenylamino)naphtho[2,1-b;6,5-b']bisbenzofuran (abbreviation: 2,9DPhA2Ndf(III)) represented as the above structural formula (v) instead of 2,9PCA2Nbf(III) used for the light-emitting layer 113 in the light-emitting element 1, and the electron-transport layer 114 was formed by depositing cgDBCzPA by evaporation to a thickness of 10 nm and then depositing BPhen by evaporation to a thickness of 15 nm. Although 2,9DPhA2Ndf(III) used in the comparative light-emitting element 1 and 2,9PCA2Nbf(III) used in the light-emitting element 1 have the same structure of naphthobisbenzofuran, which is a main skeleton, they are different in the structure of amine connected thereto.

The element structures of the light-emitting element 1 and the comparative light-emitting element 1 are listed in the following table.

TABLE 1

| | Hole-injection layer | Hole-transport layer | Light-emitting layer | Electron-transport layer | | Electron-injection layer |
|---|---|---|---|---|---|---|
| | 10 nm | 30 nm | 25 nm | *1 | *2 | 1 nm |
| Light-emitting element 1 Comparative light-emitting element 1 | PCzPA:MoOx (4:2) | PCzPA | *3 | cgDBCzPA | BPhen | LiF |

Light-emitting element 1 *1: 15 nm, *2: 10 nm, *3: cgDBCzPA:2,9PCA2Nbf(III) (1:0.03)
Comparative light-emitting element 1 *1: 10 nm, *2: 15 nm, *3: cgDBCzPA:2,9DPhA2Nbf(III) (1:0.03)

Each of the light-emitting element 1 and the comparative light-emitting element 1 was subjected to sealing with a glass substrate (a sealing material was applied to surround the element, followed by UV treatment and one-hour heat treatment at 80° C. at the time of sealing) in a glove box containing a nitrogen atmosphere so that the light-emitting element is not exposed to the air. Then, initial characteristics of these light-emitting elements were measured. Note that the measurement was carried out at room temperature (an atmosphere maintained at 25° C.).

Luminance-current density characteristics of the light-emitting element 1 and the comparative light-emitting element 1 are shown in FIG. 28, current efficiency-luminance characteristics thereof are shown in FIG. 29, luminance-voltage characteristics thereof are shown in FIG. 30, current-voltage characteristics thereof are shown in FIG. 31, power efficiency-luminance characteristics thereof are shown in FIG. 32, external quantum efficiency-luminance characteristics thereof are shown in FIG. 33, and emission spectra thereof are shown in FIG. 34. In addition, their element characteristics at around a luminance of 1000 cd/m$^2$ are listed in Table 2.

TABLE 2

| | Voltage (V) | Current (mA) | Current density (mA/cm$^2$) | Chromaticity x | Chromaticity y | Current efficiency (cd/A) | Power efficiency (lm/W) | External quantum efficiency (%) |
|---|---|---|---|---|---|---|---|---|
| Light-emitting element 1 | 3.1 | 0.59 | 14.7 | 0.14 | 0.17 | 9.0 | 9.2 | 7.4 |
| Comparative light-emitting element 1 | 3.0 | 0.54 | 13.5 | 0.14 | 0.08 | 5.3 | 5.5 | 6.9 |

As can be seen from FIG. 28 to FIG. 33 and Table 2, the light-emitting element 1 exhibited favorable results, the external quantum efficiency at 1000 cd/m² being 7.4%. The light-emitting element 1 was also found to be a light-emitting element with more favorable efficiency than the comparative light-emitting element 1.

In addition, a graph of a change in luminance with driving time under the conditions where the current value was 2 mA and the current density was constant is shown in FIG. 35. As can be seen from FIG. 35, the light-emitting element 1 maintains 90% or higher of the initial luminance even after 100 hours of driving, which indicates that the light-emitting element 1 has a favorable lifetime. Furthermore, the light-emitting element 1 was found to be a light-emitting element with a more favorable lifetime than the comparative light-emitting element 1.

Example 5

In this example, a light-emitting element 2, which is a light-emitting element of one embodiment of the present invention described in Embodiments, and a comparative light-emitting element 2, which is a light-emitting element of a comparative example, will be described in detail. The structural formulae of organic compounds used in the light-emitting element 2 and the comparative light-emitting element 2 are shown below.

[Chemical Formulae 82]

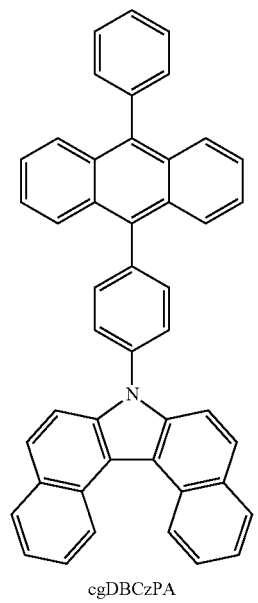

cgDBCzPA (ii)

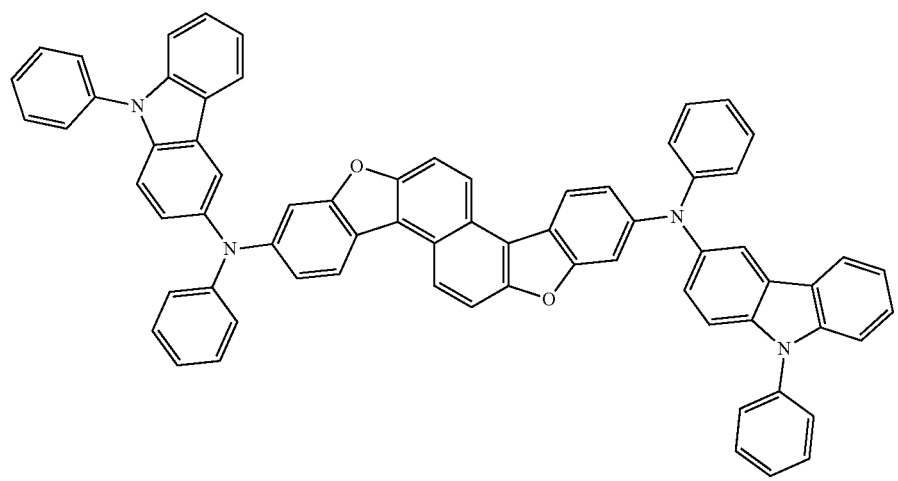

2,9PCA2Nbf(III)

(iii)

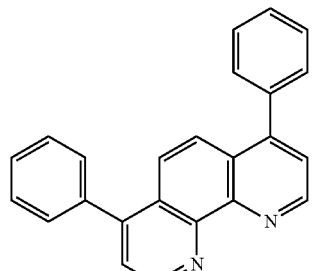

BPhen

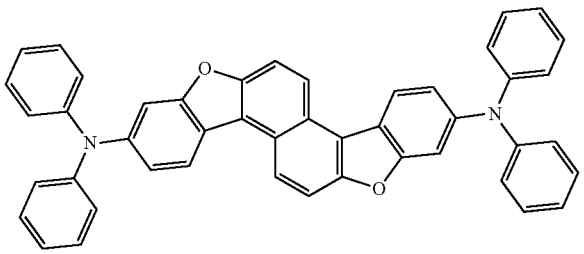

2,9DPhA2Nbf(III)

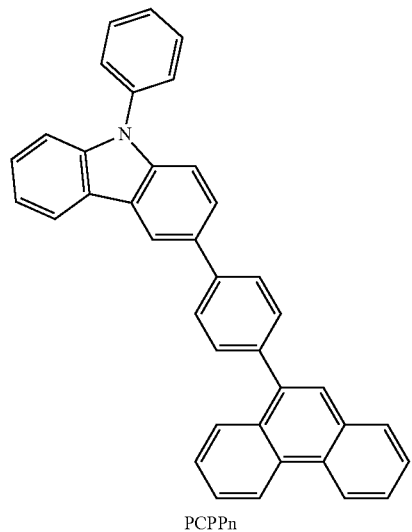

PCPPn (Fabrication Method of Light-Emitting Element 2)

First, a film of indium tin oxide containing silicon oxide (ITSO) was formed on a glass substrate by a sputtering method, so that the anode 101 was formed. Note that the thickness was 70 nm and the area of the electrode was 4 mm² (2 mm×2 mm).

Next, in pretreatment for forming the light-emitting element over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to about $10^{-4}$ Pa, vacuum baking at 170° C. for 30 minutes was performed in a heating chamber in the vacuum evaporation apparatus, and then the substrate was naturally cooled down for about 30 minutes.

Next, the substrate on which the anode 101 was formed was fixed to a substrate holder provided in the vacuum evaporation apparatus such that the side on which the anode 101 was formed faced downward, and 3-[4-(9-phenanthryl)-phenyl]-9-phenyl-9H-carbazole (abbreviation: PCPPn) represented as the above structural formula (vi) and molybdenum(VI) oxide were deposited by co-evaporation on the anode 101 to have a weight ratio of 4:2 (=PCPPn:molybdenum oxide) to a thickness of 10 nm by an evaporation method using resistance heating, whereby the hole-injection layer 111 was formed.

Next, on the hole-injection layer 111, PCPPn was deposited by evaporation to a thickness of 30 nm to form the hole-transport layer 112.

Subsequently, 7-[4-(10-phenyl-9-anthryl)phenyl]-7H-dibenzo[c,g]carbazole (abbreviation: cgDBCzPA) represented as the above structural formula (ii) and 2,9-bis[N-(9-phenyl-9H-carbazol-3-yl)-N-phenylamino]naphtho[2,1-b;6,5-b']bisbenzofuran (abbreviation: 2,9PCA2Nbf(III)) represented as the above structural formula (iii) were deposited by co-evaporation to have a weight ratio of 1:0.03 (=cgDBCzPA: 2,9PCA2Nbf(III)) to a thickness of 25 nm, whereby the light-emitting layer 113 was formed.

After that, on the light-emitting layer 113, cgDBCzPA was deposited by evaporation to a thickness of 15 nm, and bathophenanthroline (abbreviation: BPhen) represented as the above structural formula (iv) was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115, and aluminum was deposited by evaporation to a thickness of 200 nm to form the cathode 102. Thus, the light-emitting element 2 of this example was fabricated.

(Fabrication Method of Comparative Light-Emitting Element 2)

The comparative light-emitting element 2 was fabricated in such a manner that the light-emitting layer 113 was formed using 2,9-bis(diphenylamino)naphtho[2,1-b;6,5-b'] bisbenzofuran (abbreviation: 2,9DPhA2Ndf(III)) represented as the above structural formula (v) instead of 2,9PCA2Nbf(III) used for the light-emitting layer 113 in the light-emitting element 2, and the electron-transport layer 114 was formed by depositing cgDBCzPA by evaporation to a thickness of 10 nm and then depositing BPhen by evaporation to a thickness of 15 nm. Although 2,9DPhA2Ndf(III) used in the comparative light-emitting element 2 and 2,9PCA2Nbf(III) used in the light-emitting element 2 have the same structure of naphthobisbenzofuran, which is a main skeleton, they are different in the structure of amine connected thereto.

The element structures of the light-emitting element 2 and the comparative light-emitting element 2 are listed in the following table.

TABLE 3

|  | Hole-injection layer | Hole-transport layer | Light-emitting layer | Electron-transport layer | | Electron-injection layer |
|---|---|---|---|---|---|---|
|  | 10 nm | 30 nm | 25 nm | *1 | *2 | 1 nm |
| Light-emitting element 2 Comparative light-emitting element 2 | PCPPn:MoOx (42) | PCPPn | *3 | cgDBCzPA | BPhen | LiF |

Light-emitting element 2 *1: 15 nm, *2: 10 nm, *3: cgDBCzPA:2,9PCA2Nbf(III) (1:0.03)
Comparative light-emitting element 2 *1: 10 nm, *2: 15 nm, *3: cgDBCzPA:2,9DPhA2Nbf(III) (1:0.03)

Each of the light-emitting element 2 and the comparative light-emitting element 2 was subjected to sealing with a glass substrate (a sealing material was applied to surround the element, followed by UV treatment and one-hour heat treatment at 80° C. at the time of sealing) in a glove box containing a nitrogen atmosphere so that the light-emitting element is not exposed to the air. Then, initial characteristics of these light-emitting elements were measured. Note that the measurement was carried out at room temperature (under an atmosphere maintained at 25° C.).

Luminance-current density characteristics of the light-emitting element 2 and the comparative light-emitting element 2 are shown in FIG. 36, current efficiency-luminance characteristics thereof are shown in FIG. 37, luminance-voltage characteristics thereof are shown in FIG. 38, current-voltage characteristics thereof are shown in FIG. 39, power efficiency-luminance characteristics thereof are shown in FIG. 40, external quantum efficiency-luminance characteristics thereof are shown in FIG. 41, and emission spectra thereof are shown in FIG. 42. In addition, their element characteristics at around a luminance of 1000 cd/m$^2$ are listed in Table 4.

As can be seen from FIG. 36 to FIG. 41 and Table 4, the light-emitting element 2 was found to be a light-emitting element exhibiting favorable characteristics, the external quantum efficiency at 1000 cd/m$^2$ being 10.0%. The light-emitting element 2 was also found to be an element that emits light with more favorable efficiency than the comparative light-emitting element 2.

In addition, a graph of a change in luminance with driving time under the conditions where the current value was 2 mA and the current density was constant is shown in FIG. 43. As can be seen from FIG. 43, the light-emitting element 2 maintains 90% or higher of the initial luminance even after 100 hours of driving, which indicates that the light-emitting element 2 has a significantly favorable lifetime. Furthermore, the light-emitting element 2 was found to be a light-emitting element with a more favorable lifetime than the comparative light-emitting element 2.

From the above, the naphthobisbenzofuran compound of one embodiment of the present invention, which has as a substituent an amino group containing a carbazolyl group, was found to be a material with a favorable lifetime.

Example 6

In this example, a light-emitting element 3, which is a light-emitting element of one embodiment of the present invention described in Embodiments, and a comparative light-emitting element 3, which is a light-emitting element of a comparative example, will be described in detail. The structural formulae of organic compounds used in the light-emitting element 3 and the comparative light-emitting element 3 are shown below.

TABLE 4

|  | Voltage (V) | Current (mA) | Current density (mA/cm$^2$) | Chromaticity x | Chromaticity y | Current efficiency (cd/A) | Power efficiency (lm/W) | External quantum efficiency (%) |
|---|---|---|---|---|---|---|---|---|
| Light-emitting element 2 | 3.1 | 0.34 | 8.4 | 0.14 | 0.16 | 12.2 | 12.4 | 10.0 |
| Comprative light-emitting element 2 | 3.2 | 0.74 | 18.5 | 0.14 | 0.08 | 6.5 | 6.4 | 8.6 |

[Chemical Formulae 83]
(i)
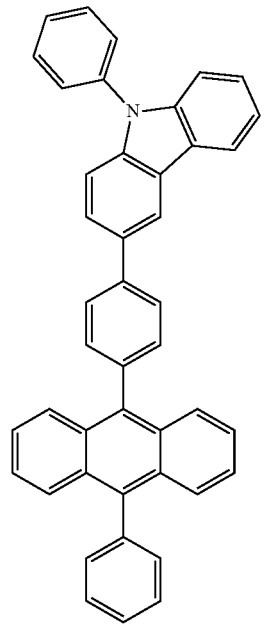
PCzPA
(ii)
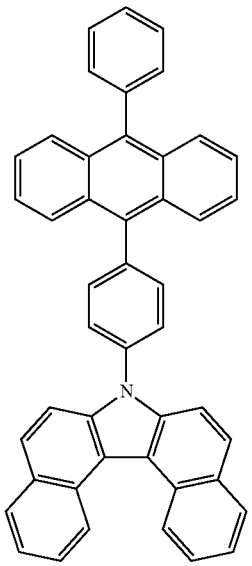
cgDBCzPA
(iv)
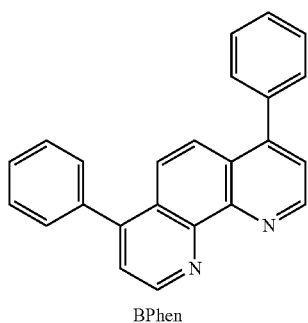
BPhen
(vii)
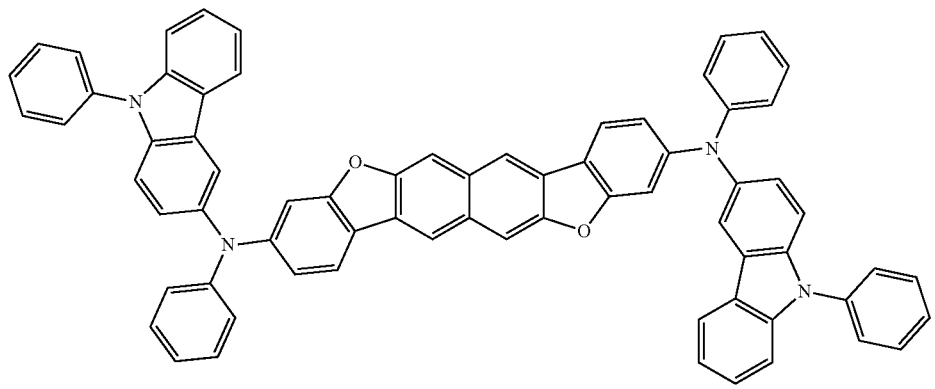
3,10PCA2Nbf(IV)

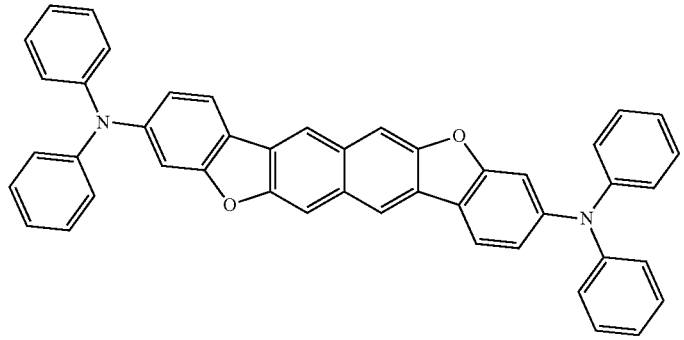

3,10DPhA2Nbf(IV)            (viii)

(Fabrication Method of Light-Emitting Element 3)

First, a film of indium tin oxide containing silicon oxide (ITSO) was formed on a glass substrate by a sputtering method, so that the anode 101 was formed. Note that the thickness was 70 nm and the area of the electrode was 4 mm$^2$ (2 mm×2 mm).

Next, in pretreatment for forming the light-emitting element over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to about $10^{-4}$ Pa, vacuum baking at 170° C. for 30 minutes was performed in a heating chamber in the vacuum evaporation apparatus, and then the substrate was naturally cooled down for about 30 minutes.

Next, the substrate on which the anode 101 was formed was fixed to a substrate holder provided in the vacuum evaporation apparatus such that the side on which the anode 101 was formed faced downward, and 9-phenyl-3-[4-(10-phenyl-9-anthryl)phenyl]-9H-carbazole (abbreviation: PCzPA) represented as the above structural formula (i) and molybdenum(VI) oxide were deposited by co-evaporation on the anode 101 to have a weight ratio of 4:2 (=PCzPA: molybdenum oxide) to a thickness of 10 nm by an evaporation method using resistance heating, whereby the hole-injection layer 111 was formed.

Next, on the hole-injection layer 111, PCzPA was deposited by evaporation to a thickness of 30 nm to form the hole-transport layer 112.

Subsequently, 7-[4-(10-phenyl-9-anthryl)phenyl]-7H-dibenzo[c,g]carbazole (abbreviation: cgDBCzPA) represented as the above structural formula (ii) and 3,10-bis[N-(9-phenyl-9H-carbazol-3-yl)-N-phenylamino]naphtho[2,3-b;6,7-b']bisbenzofuran (abbreviation: 3,10PCA2Nbf(IV)) represented as the above structural formula (vii) were deposited by co-evaporation to have a weight ratio of 1:0.03 (=cgDBCzPA: 3,10PCA2Nbf(IV)) to a thickness of 25 nm, whereby the light-emitting layer 113 was formed.

After that, on the light-emitting layer 113, cgDBCzPA was deposited by evaporation to a thickness of 15 nm, and bathophenanthroline (abbreviation: BPhen) represented as the above structural formula (iv) was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115, and aluminum was deposited by evaporation to a thickness of 200 nm to form the cathode 102. Thus, the light-emitting element 3 was fabricated.

(Fabrication Method of Comparative Light-Emitting Element 3)

The comparative light-emitting element 3 was fabricated in such a manner that the light-emitting layer 113 was formed using 3,10-bis(diphenylamino)naphtho[2,3-b;6,7-b'] bisbenzofuran (abbreviation: 3,10DPhA2Ndf(IV)) represented as the above structural formula (viii) instead of 3,10PCA2Nbf(IV) used for the light-emitting layer 113 in the light-emitting element 3. Although 3,10DPhA2Ndf(IV) used in the comparative light-emitting element 3 and 3,10PCA2Nbf(IV) used in the light-emitting element 3 have the same structure of naphthobisbenzofuran, which is a main skeleton, they are different in the structure of amine connected thereto.

The element structures of the light-emitting element 3 and the comparative light-emitting element 3 are listed in the following table.

TABLE 5

|  | Hole-injection layer | Hole-transport layer | Light-emitting layer | Electron-transport layer | | Electron-injection layer |
| --- | --- | --- | --- | --- | --- | --- |
|  | 10 nm | 30 nm | 25 nm | 15 nm | 10 nm | 1 nm |
| Light-emitting element 3 | PCzPA:MoOx (4:2) | PCzPA | *3 | cgDBCzPA | BPhen | LiF |
| Comparative light-emitting element 3 |  |  |  |  |  |  |

Light-emitting element 3 *3: cgDBCzPA:3,10PCA2Nbf(IV) (1:0.03)
Comparative light-emitting element 3 *3: cgDBCzPA:3,10DPhA2Nbf(IV) (1:0.03)

Each of the light-emitting element 3 and the comparative light-emitting element 3 was subjected to sealing with a glass substrate (a sealing material was applied to surround the element, followed by UV treatment and one-hour heat treatment at 80° C. at the time of sealing) in a glove box containing a nitrogen atmosphere so that the light-emitting element is not exposed to the air. Then, initial characteristics of these light-emitting elements were measured. Note that the measurement was carried out at room temperature (an atmosphere maintained at 25° C.).

Luminance-current density characteristics of the light-emitting element 3 and the comparative light-emitting element 3 are shown in FIG. 44, current efficiency-luminance characteristics thereof are shown in FIG. 45, luminance-voltage characteristics thereof are shown in FIG. 46, current-voltage characteristics thereof are shown in FIG. 47, power efficiency-luminance characteristics thereof are shown in FIG. 48, external quantum efficiency-luminance characteristics thereof are shown in FIG. 49, and emission spectra thereof are shown in FIG. 50. In addition, their element characteristics at around a luminance of 1000 cd/m$^2$ are listed in Table 6.

As can be seen from FIG. 44 to FIG. 49 and Table 6, the light-emitting element 3 exhibited favorable results, the external quantum efficiency at 1000 cd/m$^2$ being 8.7%. Furthermore, the light-emitting element 3 was found to be a light-emitting element with more favorable efficiency than the comparative light-emitting element 3.

In addition, a graph of a change in luminance with driving time under the conditions where the current value was 2 mA and the current density was constant is shown in FIG. 51. As can be seen from FIG. 51, the light-emitting element 3 maintains 90% or higher of the initial luminance even after 100 hours of driving, which indicates that the light-emitting element 3 has a favorable lifetime. Furthermore, the light-emitting element 3 was found to be a light-emitting element with a more favorable lifetime than the comparative light-emitting element 3.

Example 7

In this example, a light-emitting element 4, which is a light-emitting element of one embodiment of the present

TABLE 6

| | Voltage (V) | Current (mA) | Current density (mA/cm$^2$) | Chromaticity x | Chromaticity y | Current efficiency (cd/A) | Power efficiency (lm/W) | External quantum efficiency (%) |
| --- | --- | --- | --- | --- | --- | --- | --- | --- |
| Light-emitting element 3 | 3.0 | 0.34 | 8.5 | 0.14 | 0.21 | 12.0 | 12.6 | 8.7 |
| Comparative light-emitting element 3 | 3.1 | 0.90 | 22.6 | 0.14 | 0.12 | 4.6 | 4.7 | 4.6 | invention described in Embodiments, and a comparative light-emitting element 4, which is a light-emitting element of a comparative example, will be described in detail. The structural formulae of organic compounds used in the light-emitting element 4 and the comparative light-emitting element 4 are shown below.
[Chemical Formulae 84]
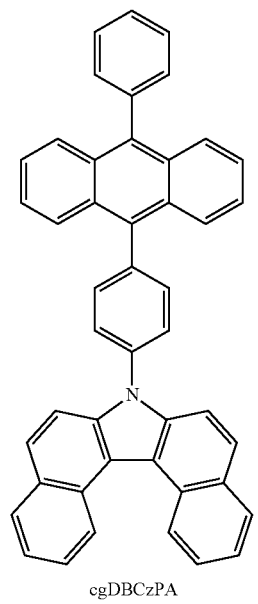
cgDBCzPA
(ii)
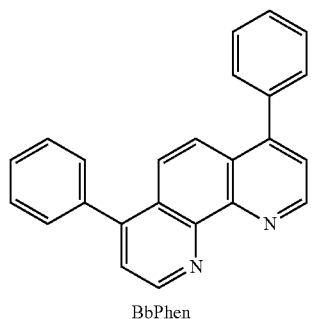
BbPhen
(iv)
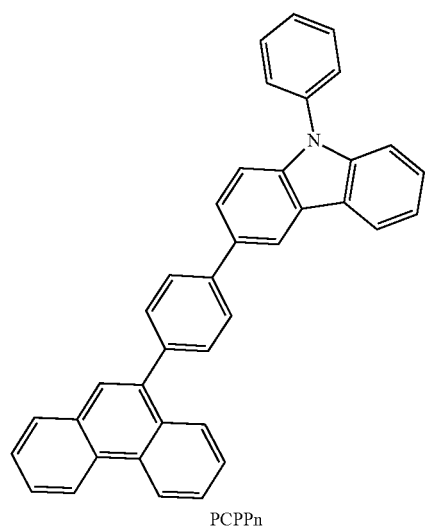
PCPPn
(vi)

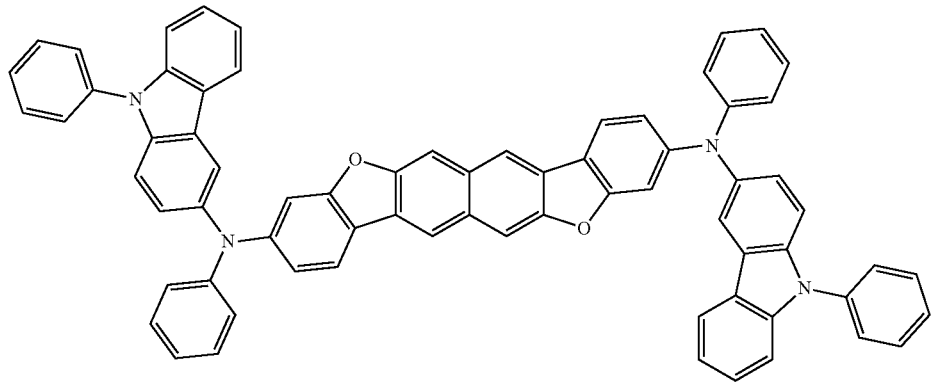

3,10PCA2Nbf(IV)

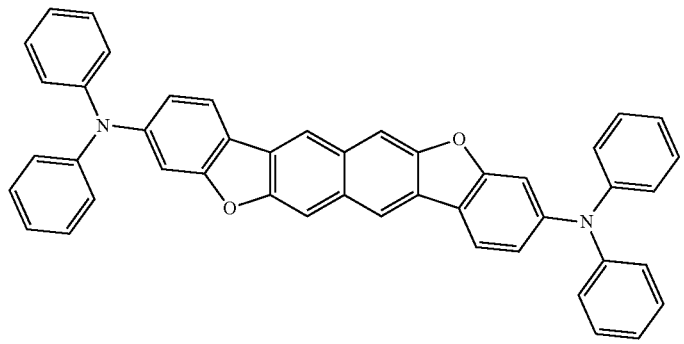

3,10DPhA2Nbf(IV)

(Fabrication Method of Light-Emitting Element 4)

First, a film of indium tin oxide containing silicon oxide (ITSO) was formed on a glass substrate by a sputtering method, so that the anode 101 was formed. Note that the thickness was 70 nm and the area of the electrode was 4 mm$^2$ (2 mm×2 mm).

Next, in pretreatment for forming the light-emitting element over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to about 10$^{-4}$ Pa, vacuum baking at 170° C. for 30 minutes was performed in a heating chamber in the vacuum evaporation apparatus, and then the substrate was naturally cooled down for about 30 minutes.

Next, the substrate on which the anode 101 was formed was fixed to a substrate holder provided in the vacuum evaporation apparatus such that the side on which the anode 101 was formed faced downward, and 3-[4-(9-phenanthryl)-phenyl]-9-phenyl-9H-carbazole (abbreviation: PCPPn) represented as the above structural formula (vi) and molybdenum(VI) oxide were deposited by co-evaporation on the anode 101 to have a weight ratio of 4:2 (=PCPPn:molybdenum oxide) to a thickness of 10 nm by an evaporation method using resistance heating, whereby the hole-injection layer 111 was formed.

Next, on the hole-injection layer 111, PCPPn was deposited by evaporation to a thickness of 30 nm to form the hole-transport layer 112.

Subsequently, 7-[4-(10-phenyl-9-anthryl)phenyl]-7H-dibenzo[c,g]carbazole (abbreviation: cgDBCzPA) represented as the above structural formula (ii) and 3,10-bis[N-(9-phenyl-9H-carbazol-3-yl)-N-phenylamino]naphtho[2,3-b;6,7-b']bisbenzofuran (abbreviation: 3,10PCA2Nbf(IV)) represented as the above structural formula (vii) were deposited by co-evaporation to have a weight ratio of 1:0.03 (=cgDBCzPA: 3,10PCA2Nbf(IV)) to a thickness of 25 nm, whereby the light-emitting layer 113 was formed.

After that, on the light-emitting layer 113, cgDBCzPA was deposited by evaporation to a thickness of 15 nm, and bathophenanthroline (abbreviation: BPhen) represented as the above structural formula (iv) was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115, and aluminum was deposited by evaporation to a thickness of 200 nm to form the cathode 102. Thus, the light-emitting element 4 of this example was fabricated.

(Fabrication Method of Comparative Light-Emitting Element 4)

The comparative light-emitting element 4 was fabricated in such a manner that the light-emitting layer 113 was formed using 3,10-bis(diphenylamino)naphtho[2,3-b;6,7-b'] bisbenzofuran (abbreviation: 3,10DPhA2Ndf(IV)) represented as the above structural formula (viii) instead of 3,10PCA2Nbf(IV) used for the light-emitting layer 113 in the light-emitting element 4. Although 3,10DPhA2Ndf(IV) used in the comparative light-emitting element 4 and 3,10PCA2Nbf(IV) used in the light-emitting element 4 have the same structure of naphthobisbenzofuran, which is a main skeleton, they are different in the structure of amine connected thereto.

The element structures of the light-emitting element 4 and the comparative light-emitting element 4 are listed in the following table.

TABLE 7

|  | Hole-injection layer | Hole-transport layer | Light-emitting layer | Electron-transport layer | | Electron-injection layer |
| --- | --- | --- | --- | --- | --- | --- |
|  | 10 nm | 30 nm | 25 nm | 15 nm | 10 nm | 1 nm |
| Light-emitting element 4 Comparative light-emitting element 4 | PCPPn: MoOx (4:2) | PCPPn | *3 | cgDBCzPA | BPhen | LiF |

Light-emitting element 4 *3: cgDBCzPA:3,10PCA2Nbf(IV) (1:0.03)
Comparative light-emitting element 4 *3: cgDBCzPA:3,10DPhA2Nbf(IV) (1:0.03)

Each of the light-emitting element 4 and the comparative light-emitting element 4 was subjected to sealing with a glass substrate (a sealing material was applied to surround the element, followed by UV treatment and one-hour heat treatment at 80° C. at the time of sealing) in a glove box containing a nitrogen atmosphere so that the light-emitting element is not exposed to the air. Then, initial characteristics of these light-emitting elements were measured. Note that the measurement was carried out at room temperature (an atmosphere maintained at 25° C.).

Luminance-current density characteristics of the light-emitting element 4 and the comparative light-emitting element 4 are shown in FIG. 52, current efficiency-luminance characteristics thereof are shown in FIG. 53, luminance-voltage characteristics thereof are shown in FIG. 54, current-voltage characteristics thereof are shown in FIG. 55, power efficiency-luminance characteristics thereof are shown in FIG. 56, external quantum efficiency-luminance characteristics thereof are shown in FIG. 57, and emission spectra thereof are shown in FIG. 58. In addition, their element characteristics at around a luminance of 1000 cd/m$^2$ are listed in Table 8.

As can be seen from FIG. 52 to FIG. 57 and Table 8, the light-emitting element 4 was found to be a light-emitting element exhibiting favorable characteristics, the external quantum efficiency at 1000 cd/m$^2$ being 11.8%. The light-emitting element 4 was also found to be an element that emits light with more favorable efficiency than the comparative light-emitting element 4.

In addition, a graph of a change in luminance with driving time under the conditions where the current value was 2 mA and the current density was constant is shown in FIG. 59. As can be seen from FIG. 59, the light-emitting element 4 maintains 85% or higher of the initial luminance even after 100 hours of driving, which indicates that the light-emitting element 4 has a significantly favorable lifetime. Furthermore, the light-emitting element 4 was found to be a light-emitting element with a more favorable lifetime than the comparative light-emitting element 4.

From the above, the naphthobisbenzofuran compound of one embodiment of the present invention, which has as a substituent an amino group containing a carbazolyl group, was found to be a material with a favorable lifetime.

Example 8

In this example, a light-emitting element 5, which is a light-emitting element of one embodiment of the present invention described in Embodiments, and a comparative light-emitting element 5, which is a light-emitting element of a comparative example, will be described in detail. The structural formulae of organic compounds used in the light-emitting element 5 and the comparative light-emitting element 5 are shown below.

TABLE 8

| | Voltage (V) | Current (mA) | Current density (mA/cm$^2$) | Chromaticity x | Chromaticity y | Current efficiency (cd/A) | Power efficiency (lm/W) | External quantum efficiency (%) |
| --- | --- | --- | --- | --- | --- | --- | --- | --- |
| Light-emitting element 4 | 3.0 | 0.19 | 4.7 | 0.14 | 0.19 | 15.7 | 16.5 | 11.8 |
| Comparative light-emitting element 4 | 3.2 | 0.66 | 16.6 | 0.14 | 0.11 | 6.5 | 6.3 | 6.8 |

[Chemical Formulae 85]
(i)
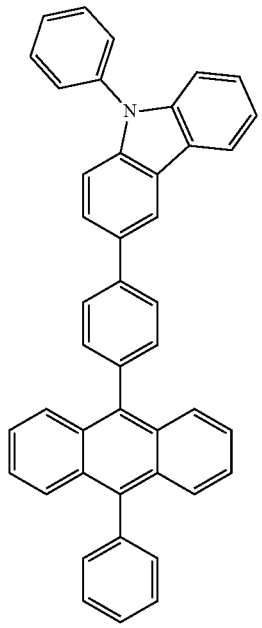
PCzPA
(ii)
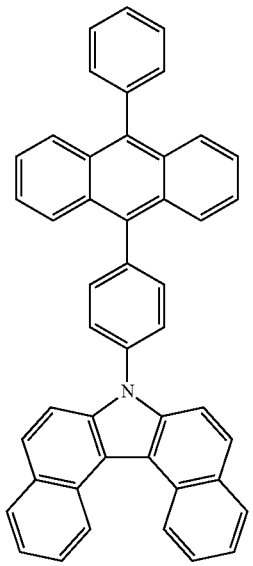
cgDBCzPA
(iv)
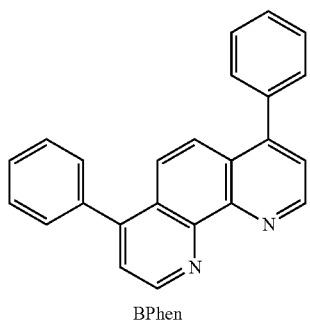
BPhen
(viii)
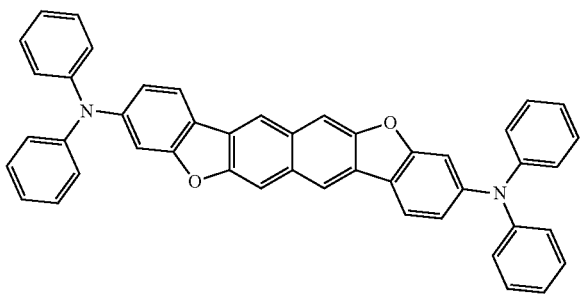
3,10DPhA2Nbf(IV)
(ix)
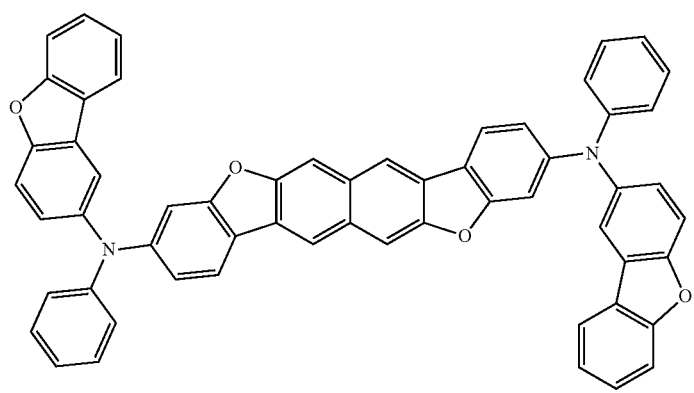
3,10FrA2Nbf(IV)

(Fabrication Method of Light-Emitting Element 5)

First, a film of indium tin oxide containing silicon oxide (ITSO) was formed on a glass substrate by a sputtering method, so that the anode 101 was formed. Note that the thickness was 70 nm and the area of the electrode was 4 mm$^2$ (2 mm×2 mm).

Next, in pretreatment for forming the light-emitting element over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to about $10^{-4}$ Pa, vacuum baking at 170° C. for 30 minutes was performed in a heating chamber in the vacuum evaporation apparatus, and then the substrate was naturally cooled down for about 30 minutes.

Next, the substrate on which the anode 101 was formed was fixed to a substrate holder provided in the vacuum evaporation apparatus such that the side on which the anode 101 was formed faced downward, and 9-phenyl-3-[4-(10-phenyl-9-anthryl)phenyl]-9H-carbazole (abbreviation: PCzPA) represented as the above structural formula (i) and molybdenum(VI) oxide were deposited by co-evaporation on the anode 101 to have a weight ratio of 4:2 (=PCzPA: molybdenum oxide) to a thickness of 10 nm by an evaporation method using resistance heating, whereby the hole-injection layer 111 was formed.

Next, on the hole-injection layer 111, PCzPA was deposited by evaporation to a thickness of 30 nm to form the hole-transport layer 112.

Subsequently, 7-[4-(10-phenyl-9-anthryl)phenyl]-7H-dibenzo[c,g]carbazole (abbreviation: cgDBCzPA) represented as the above structural formula (ii) and 3,10-bis[N-(dibenzofuran-2-yl)-N-phenylamino]naphtho[2,3-b;6,7-b'] bisbenzofuran (abbreviation: 3,10FrA2Nbf(IV)) represented as the above structural formula (ix) were deposited by co-evaporation to have a weight ratio of 1:0.03 (=cgDBCzPA: 3,10FrA2Nbf(IV)) to a thickness of 25 nm, whereby the light-emitting layer 113 was formed.

After that, on the light-emitting layer 113, cgDBCzPA was deposited by evaporation to a thickness of 15 nm, and bathophenanthroline (abbreviation: BPhen) represented as the above structural formula (iv) was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115, and aluminum was deposited by evaporation to a thickness of 200 nm to form the cathode 102. Thus, the light-emitting element 5 was fabricated.

(Fabrication Method of Comparative Light-Emitting Element 5)

The comparative light-emitting element 5 was fabricated in such a manner that the light-emitting layer 113 was formed using 3,10-bis(diphenylamino)naphtho[2,3-b;6,7-b'] bisbenzofuran (abbreviation: 3,10DPhA2Ndf(IV)) represented as the above structural formula (viii) instead of 3,10FrA2Nbf(IV) used for the light-emitting layer 113 in the light-emitting element 5. Although 3,10DPhA2Ndf(IV) used in the comparative light-emitting element 5 and 3,10FrA2Nbf(IV) used in the light-emitting element 5 have the same structure of naphthobisbenzofuran, which is a main skeleton, they are different in the structure of amine connected thereto.

The element structures of the light-emitting element 5 and the comparative light-emitting element 5 are listed in the following table.

TABLE 9

| | Hole-injection layer | Hole-transport layer | Light-emitting layer | Electron-transport layer | | Electron-injection layer |
|---|---|---|---|---|---|---|
| | 10 nm | 30 nm | 25 nm | 15 nm | 10 nm | 1 nm |
| Light-emitting element 5 Comparative light-emitting element 5 | PCzPA: MoOx (4:2) | PCzPA | *3 | cgDBCzPA | BPhen | LiF |

Light-emitting element 5 *3: cgDBCzPA:3,10FrA2Nbf(IV) (1:0.03)

Comparative light-emitting element 5 *3: cgDBCzPA:3,10DPhA2Nbf(IV) (1:0.03)

Each of the light-emitting element 5 and the comparative light-emitting element 5 was subjected to sealing with a glass substrate (a sealing material was applied to surround the element, followed by UV treatment and one-hour heat treatment at 80° C. at the time of sealing) in a glove box containing a nitrogen atmosphere so that the light-emitting element is not exposed to the air. Then, initial characteristics of these light-emitting elements were measured. Note that the measurement was carried out at room temperature (an atmosphere maintained at 25° C.).

Luminance-current density characteristics of the light-emitting element 5 and the comparative light-emitting element 5 are shown in FIG. 60, current efficiency-luminance characteristics thereof are shown in FIG. 61, luminance-voltage characteristics thereof are shown in FIG. 62, current-voltage characteristics thereof are shown in FIG. 63, power efficiency-luminance characteristics thereof are shown in FIG. 64, external quantum efficiency-luminance characteristics thereof are shown in FIG. 65, and emission spectra thereof are shown in FIG. 66. In addition, their element characteristics at around a luminance of 1000 cd/m$^2$ are listed in Table 10.

TABLE 10

|  | Voltage (V) | Current (mA) | Current density (mA/cm²) | Chromaticity x | Chromaticity y | Current efficiency (cd/A) | Power efficiency (lm/W) | External quantum efficiency (%) |
|---|---|---|---|---|---|---|---|---|
| Light-emitting element 5 | 3.0 | 0.44 | 11.1 | 0.14 | 0.12 | 7.1 | 7.4 | 6.9 |
| Comparative light-emitting element 5 | 3.1 | 0.90 | 22.6 | 0.14 | 0.12 | 4.6 | 4.7 | 4.6 |

As can be seen from FIG. 60 to FIG. 66 and Table 10, the light-emitting element 5 exhibited favorable results, the external quantum efficiency at 1000 cd/m² being 6.9%. The light-emitting element 5 was also found to be a light-emitting element with more favorable efficincy than the comparative light-emitting element 5.

In addition, a graph of a change in luminance with driving time under the conditions where the current value was 2 mA and the current density was constant is shown in FIG. 67. As can be seen from FIG. 67, the light-emitting element 5 maintains 85% or higher of the initial luminance even after 100 hours of driving, which indicates that the light-emitting element 5 has a favorable lifetime. Furthermore, the light-emitting element 5 was found to be a light-emitting element with a more favorable lifetime than the comparative light-emitting element 5.

From the above, the naphthobisbenzofuran compound of one embodiment of the present invention, which has as a substituent an amino group containing a dibenzofuranyl group, was found to be a material with a favorable lifetime.

Example 9

In this example, a light-emitting element 6, which is a light-emitting element of one embodiment of the present invention described in Embodiments, and a comparative light-emitting element 6, which is a light-emitting element of a comparative example, will be described in detail. The structural formulae of organic compounds used in the light-emitting element 6 and the comparative light-emitting element 6 are shown below.

[Chemical Formulae 86]

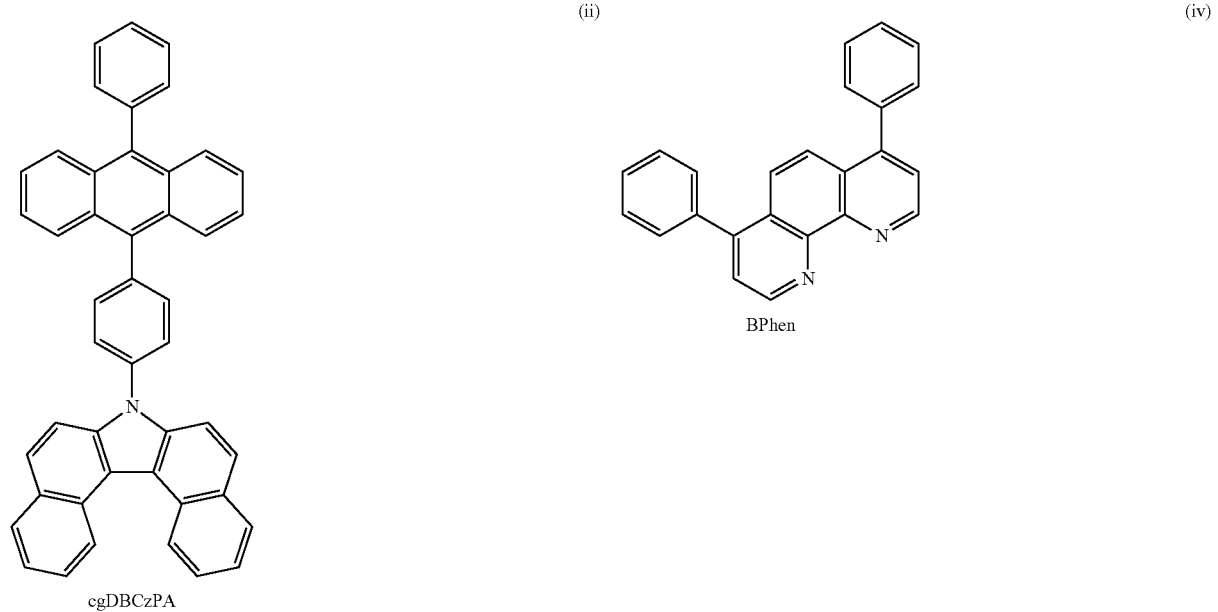

(vi)

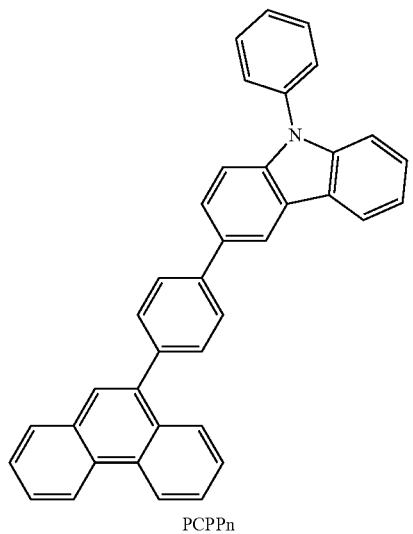

PCPPn (viii)

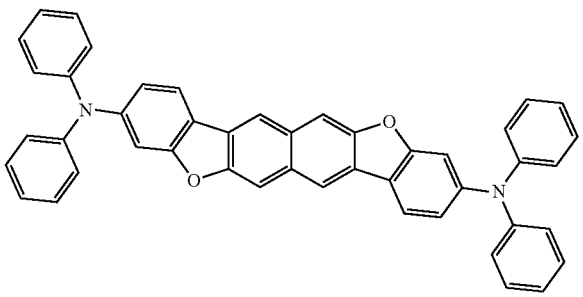

3,10DPhA2Nbf(IV)

(ix)

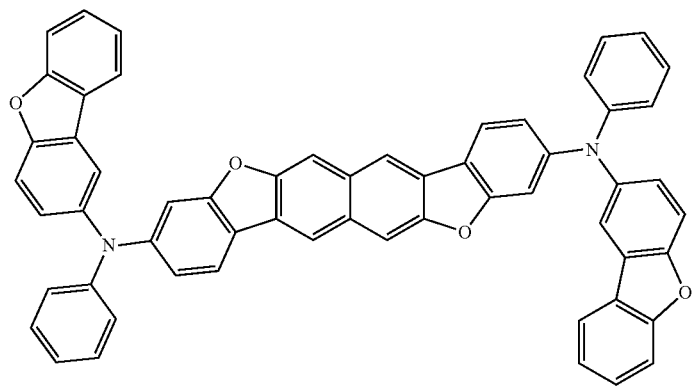

3,10FrA2Nbf(IV)

(Fabrication Method of Light-Emitting Element 6)

First, a film of indium tin oxide containing silicon oxide (ITSO) was formed on a glass substrate by a sputtering method, so that the anode 101 was formed. Note that the thickness was 70 nm and the area of the electrode was 4 mm² (2 mm×2 mm).

Next, in pretreatment for forming the light-emitting element over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to about $10^{-4}$ Pa, vacuum baking at 170° C. for 30 minutes was performed in a heating chamber in the vacuum evaporation apparatus, and then the substrate was naturally cooled down for about 30 minutes.

Next, the substrate on which the anode 101 was formed was fixed to a substrate holder provided in the vacuum evaporation apparatus such that the side on which the anode 101 was formed faced downward, and 3-[4-(9-phenanthryl)-phenyl]-9-phenyl-9H-carbazole (abbreviation: PCPPn) represented as the above structural formula (vi) and molybdenum(VI) oxide were deposited by co-evaporation on the anode 101 to have a weight ratio of 4:2 (=PCPPn:molybdenum oxide) to a thickness of 10 nm by an evaporation method using resistance heating, whereby the hole-injection layer 111 was formed.

Next, on the hole-injection layer 111, PCPPn was deposited by evaporation to a thickness of 30 nm to form the hole-transport layer 112.

Subsequently, 7-[4-(10-phenyl-9-anthryl)phenyl]-7H-dibenzo[c,g]carbazole (abbreviation: cgDBCzPA) represented as the above structural formula (ii) and 3,10-bis[N-(dibenzofuran-2-yl)-N-phenylamino]naphtho[2,3-b;6,7-b'] bisbenzofuran (abbreviation: 3,10FrA2Nbf(IV)) represented as the above structural formula (ix) were deposited by co-evaporation to have a weight ratio of 1:0.03 (=cgDBCzPA: 3,10FrA2Nbf(IV)) to a thickness of 25 nm, whereby the light-emitting layer 113 was formed.

After that, on the light-emitting layer 113, cgDBCzPA was deposited by evaporation to a thickness of 15 nm, and bathophenanthroline (abbreviation: BPhen) represented as the above structural formula (iv) was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115, and aluminum was deposited by evaporation to a thickness of 200 nm to form the cathode 102. Thus, the light-emitting element 6 of this example was fabricated.

(Fabrication method of comparative light-emitting element 6) The comparative light-emitting element 6 was fabricated in such a manner that the light-emitting layer 113 was formed using 3,10-bis(diphenylamino)naphtho[2,3-b;6,7-b']bisbenzofuran (abbreviation: 3,10DPhA2Ndf(IV)) represented as the above structural formula (viii) instead of 3,10FrA2Nbf(IV) used for the light-emitting layer 113 in the light-emitting element 6. Although 3,10DPhA2Ndf(IV) used in the comparative light-emitting element 6 and 3,10FrA2Nbf(IV) used in the light-emitting element 6 have the same structure of naphthobisbenzofuran, which is a main skeleton, they are different in the structure of amine connected thereto.

The element structures of the light-emitting element 6 and the comparative light-emitting element 6 are listed in the following table.

TABLE 11

|  | Hole-injection layer | Hole-transport layer | Light-emitting layer | Electron-transport layer | | Electron-injection layer |
| --- | --- | --- | --- | --- | --- | --- |
|  | 10 nm | 30 nm | 25 nm | 15 nm | 10 nm | 1 nm |
| Light-emitting element 6 Comparative light-emitting element 6 | PCPPn: MoOx (4:2) | PCPPn | *3 | cgDBCzPA | BPhen | LiF |

Light-emitting element 6 *3: cgDBCzPA:3,10FrA2Nbf(IV) (1:0.03)
Comparative light-emitting element 6 *3: cgDBCzPA:3,10DPhA2Nbf(IV) (1:0.03)

Each of the light-emitting element 6 and the comparative light-emitting element 6 was subjected to sealing with a glass substrate (a sealing material was applied to surround the element, followed by UV treatment and one-hour heat treatment at 80° C. at the time of sealing) in a glove box containing a nitrogen atmosphere so that the light-emitting element is not exposed to the air. Then, initial characteristics of these light-emitting elements were measured. Note that the measurement was carried out at room temperature (an atmosphere maintained at 25° C.).

Luminance-current density characteristics of the light-emitting element 6 and the comparative light-emitting element 6 are shown in FIG. 68, current efficiency-luminance characteristics thereof are shown in FIG. 69, luminance-voltage characteristics thereof are shown in FIG. 70, current-voltage characteristics thereof are shown in FIG. 71, power efficiency-luminance characteristics thereof are shown in FIG. 72, external quantum efficiency-luminance characteristics thereof are shown in FIG. 73, and emission spectra thereof are shown in FIG. 74. In addition, their element characteristics at around a luminance of 1000 cd/m² are listed in Table 12.

As can be seen from FIG. 68 to FIG. 74 and Table 12, the light-emitting element 6 was found to be a light-emitting element exhibiting favorable characteristics, the external quantum efficiency at 1000 cd/m² being 9.4%. The light-emitting element 6 was also found to be an element that emits light with more favorable efficiency than the comparative light-emitting element 6.

In addition, a graph of a change in luminance with driving time under the conditions where the current value was 2 mA and the current density was constant is shown in FIG. 75. As can be seen from FIG. 75, the light-emitting element 6 maintains 75% or higher of the initial luminance even after 100 hours of driving, which indicates that the light-emitting element 6 has a favorable lifetime. Furthermore, the light-emitting element 6 was found to be a light-emitting element with a more favorable lifetime than the comparative light-emitting element 6.

From the above, the naphthobisbenzofuran compound of one embodiment of the present invention, which has as a substituent an amino group containing a dibenzofuranyl group, was found to be a material with a favorable lifetime.

Example 10

Synthesis Example 4

In this synthesis example, a method for synthesizing 2,9-bis[N-(9-phenyl-9H-carbazol-3-yl)-N-phenylamino]naphtho[2,1-b;6,5-b']bisbenzofuran (abbreviation: 2,9PCA2Nbf(III)-02), which is represented as the structural formula (510) in Embodiment 1, will be described in detail. The structural formula of 2,9PCA2Nbf(III)-02 is shown below.

TABLE 12

|  | Voltage (V) | Current (mA) | Current density (mA/cm²) | Chromaticity x | Chromaticity y | Current efficiency (cd/A) | Power efficiency (lm/W) | External quantum efficiency (%) |
| --- | --- | --- | --- | --- | --- | --- | --- | --- |
| Light-emitting element 6 | 3.1 | 0.44 | 10.9 | 0.14 | 0.11 | 9.2 | 9.3 | 9.4 |
| Comparative light-emitting element 6 | 3.2 | 0.66 | 16.6 | 0.14 | 0.11 | 6.5 | 6.3 | 6.8 |

[Chemical Formula 87]

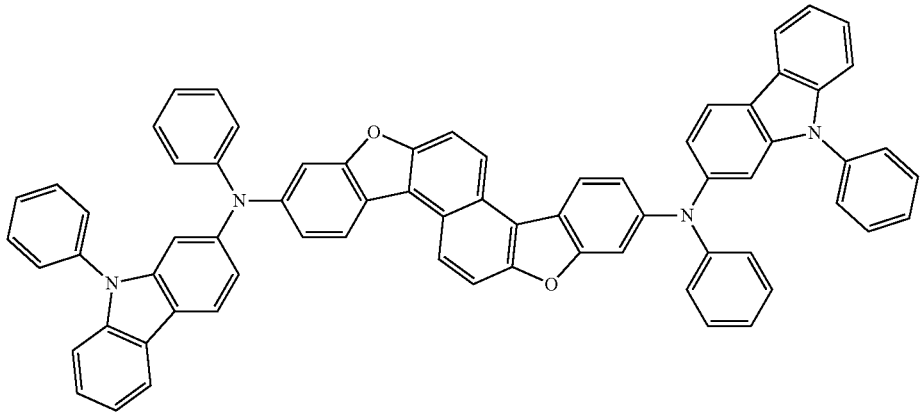

Step 1: Synthesis of 1,5-bis(4-chloro-2-fluorophenyl)-2,7-dihydoroxynaphthalene

The synthesis was conducted in a similar manner to Step 1 of Synthesis Example 2 in Example 2.

Step 2: Synthesis of 2,9-dichloronaphtho[2,1-b;6,5-b']bisbenzofuran

The synthesis was conducted in a similar manner to Step 2 of Synthesis Example 2 in Example 2.

Step 3: Synthesis of 2,9-bis[N-(9-phenyl-9H-carbazol-3-yl)-N-phenylamino]naphtho[2,1-b;6,5-b']bisbenzofuran (abbreviation: 2,9PCA2Nbf(III)-02)

Into a 200 mL three-necked flask were put 0.90 g (2.4 mmol) of 2,9-dichloronaphtho[2,1-b;6,5-b']bisbenzofuran, 2.0 g (6.0 mmol) of 2-anilino-9-phenyl-9H-carbazole, 86 mg (0.24 mmol) of di(1-adamantyl)-n-butylphosphine, and 1.4 g (14 mmol) of sodium tert-butoxide. To this mixture was added 25 mL of xylene. This mixture was degassed by being stirred while the pressure was reduced. To this mixture was added 28 mg (48 μmol) of bis(dibenzylideneacetone)palladium(0), and the mixture was stirred under a nitrogen stream at 150° C. for 11 hours. After the stirring, toluene was added to this mixture, which was then subjected to suction filtration through Florisil, Celite, and alumina to give a filtrate. The obtained filtrate was concentrated to give a solid. This solid was purified by silica gel column chromatography (developing solvent: toluene), so that a solid was obtained. The obtained solid was recrystallized with toluene three times, so that 0.76 g of a yellow solid was obtained in a yield of 33%.

By a train sublimation method, 0.76 g of the obtained solid was sublimated and purified. The sublimation purification was performed by heating at 380° C. under the conditions where the pressure was $1.7 \times 10^{-2}$ Pa and the argon flow rate was 0 mL/min. After the sublimation purification, 0.63 g of a yellow solid was obtained at a collection rate of 83%. The synthesis scheme of Step 3 is shown below.

[Chemical Formula 88]

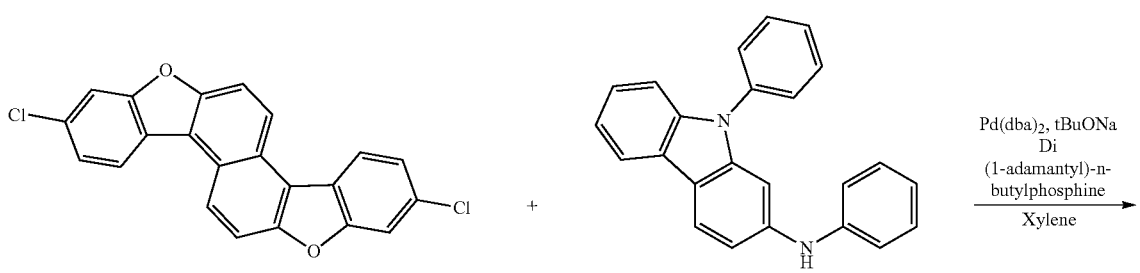

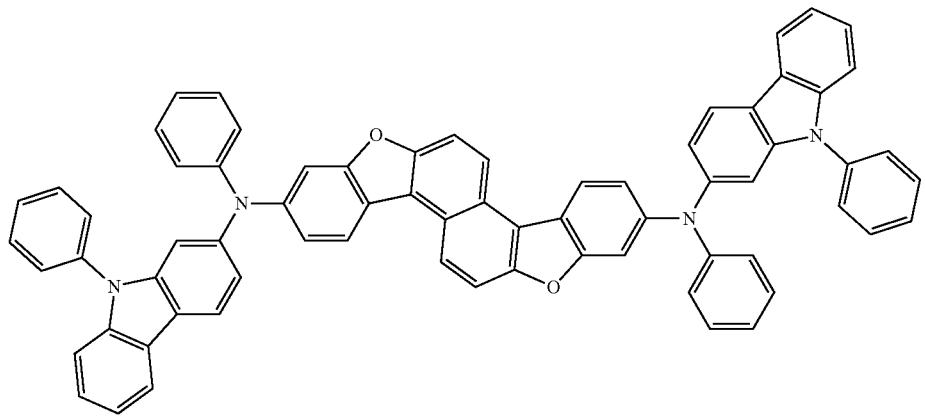

FIG. 81 shows $^1$H NMR data of the obtained solid, whose numerical data is given below. The data indicates that 2,9PCA2Nbf(III)-02, which is an organic compound of one embodiment of the present invention, was obtained in this synthesis example.

$^1$H NMR (CD$_2$Cl$_2$, 300 MHz): δ=7.07 (tt, J1=7.5 Hz, J2=1.5 Hz, 2H), 7.13 (dd, J1=8.1 Hz, J2=1.8 Hz, 2H), 7.19-7.33 (m, 14H), 7.35-7.40 (m, 8H), 7.51-7.53 (m, 8H), 7.91 (d, J1=8.7 Hz, 2H), 8.07-8.11 (m, 4H), 8.26 (d, J1=8.7 Hz, 2H), 8.60 (d, J1=8.7 Hz, 2H).

Next, the measurement results of the absorption spectrum and emission spectrum of a toluene solution of 2,9PCA2Nbf (III)-02 are shown in FIG. 82. In addition, the absorption spectrum and emission spectrum of a thin film of 2,9PCA2Nbf(III)-02 are shown in FIG. 83. The fabrication method of the sample and the measurement method were similar to those of Synthesis Example 3.

As can be seen from FIG. 82, the toluene solution of 2,9PCA2Nbf(III)-02 has absorption peaks at around 423 nm, 403 nm, 347 nm, 317 nm, and 281 nm, and emission wavelength peaks at around 441 nm and 463 nm (excitation wavelength 410 nm). In addition, as can be seen from FIG. 83, the thin film of 2,9PCA2Nbf(III)-02 has absorption peaks at around 428 nm, 408 nm, 347 nm, 265 nm, and 235 nm, and emission wavelength peaks at around 460 nm and 481 nm (excitation wavelength 410 nm). These results indicate that 2,9PCA2Nbf(III)-02 emits blue light and can be used as a host for a light-emitting substance or a host for a substance that emits fluorescence in the visible region.

Furthermore, the half width of the emission spectrum of 2,9PCA2Nbf(III)-02 in the toluene solution was found to be 43 nm.

Furthermore, the measured emission quantum yield of 2,9PCA2Nbf(III)-02 in the toluene solution was as high as 89%, which indicates that 2,9PCA2Nbf(III)-02 is suitable as a light-emitting material.

Next, 2,9PCA2Nbf(III)-02 obtained in this example was analyzed by LC/MS analysis. The fabrication method of the sample, and the measurement method and conditions were similar to those of Synthesis Example 3 in Example 3.

A component with m/z=972.35, which is an ion derived from 2,9PCA2Nbf(III)-02, was subjected to the MS$^2$ measurement by a Targeted-MS$^2$ method. For setting of the Targeted-MS$^2$, the mass range of a target ion was set to n/z=972.35±2.0 (isolation window=4) and detection was performed in a positive mode. Measurement was performed with energy NCE for accelerating the target ion in a collision cell set to 50. The obtained MS spectrum is shown in FIG. 84.

From the results in FIG. 84, it was found that product ions from 2,9PCA2Nbf(III)-02 are detected mainly at around m/z=896, 731, 640, 333, and 256. Note that the results shown in FIG. 84 exhibit characteristic results derived from 2,9PCA2Nbf(III)-02 and therefore are important data for identifying 2,9PCA2Nbf(III)-02 contained in a mixture.

Note that the product ion around m/z=896 is presumed to be a cation in the state where a phenyl group was eliminated from 2,9PCA2Nbf(III)-02, which suggests that 2,9PCA2Nbf(III)-02 contains a phenyl group. Furthermore, the product ion around m/z=731 is presumed to be a cation in the state where a 9-phenylcarbazolyl group was eliminated from 2,9PCA2Nbf(III)-02, which suggests that 2,9PCA2Nbf(III)-02 contains a 9-phenyl-9H-carbazolyl group.

Note that the product ion around n/z=640 is presumed to be a cation in the state where an N-(9-phenyl-9H-carbazol-2-yl)-N-phenylamino group was eliminated from 2,9PCA2Nbf(III)-02, which suggests that 2,9PCA2Nbf(III)-02 contains an N-(9-phenyl-9H-carbazol-2-yl)-N-phenylamino group.

In addition, the product ion around m/z=333 is presumed to be a cation in the state where a 2-[N-(9-phenyl-9H-carbazol-2-yl)-N-phenylamino]naphtho[2,1-b;6,5-b']bisbenzofuranyl group was eliminated from 2,9PCA2Nbf(III)-02, which suggests that 2,9PCA2Nbf(III)-02 contains a 2-[N-(9-phenyl-9H-carbazol-2-yl)-N-phenylamino]naphtho[2,1-b;6,5-b']bisbenzofuranyl group.

Example 11

Synthesis Example 5

In this synthesis example, a method for synthesizing 3,10-bis[N-(dibenzofuran-3-yl)-N-phenylamino]naphtho[2,3-b;6,7-b']bisbenzofuran (abbreviation: 3,10FrA2Nbf(IV)-02), which is represented as the structural formula (701) in Embodiment 1, will be described in detail. The structural formula of 3,10FrA2Nbf(IV)-02 is shown below.

[Chemical Formula 89]

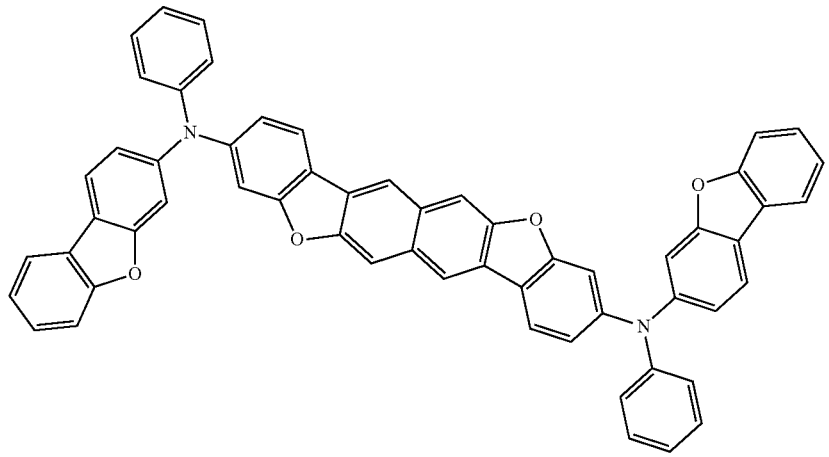

Step 1: Synthesis of 3,7-bis(4-chloro-2-fluorophenyl)-2,6-dimethoxynaphthalene

The synthesis was conducted in a similar manner to Step 1 of Synthesis Example 1 in Example 1.

Step 2: Synthesis of 3,7-bis(4-chloro-2-fluorophenyl)-2,6-dihydroxynaphthalene

The synthesis was conducted in a similar manner to Step 2 of Synthesis Example 1 in Example 1.

Step 3: Synthesis of 3,10-dichloronaphtho[2,3-b;6,7-b']bisbenzofuran

The synthesis was conducted in a similar manner to Step 3 of Synthesis Example 1 in Example 1.

Step 4: Synthesis of 3,10-bis[N-(dibenzofuran-3-yl)-N-phenylamino]naphtho[2,3-b;6,7-b']bisbenzofuran (abbreviation: 3,10FrA2Nbf(IV)-02)

Into a 200 mL three-necked flask were put 1.2 g (3.0 mmol) of 3,10-dichloronaphtho[2,3-b;6,7-b']bisbenzofuran, 2.0 g (7.7 mmol) of N-(dibenzofuran-3-yl)-N-phenylamine, 0.11 g (0.30 mmol) of di(1-adamantyl)-n-butylphosphine, and 1.8 g (18 mmol) of sodium tert-butoxide. To this mixture was added 30 mL of xylene. This mixture was degassed by being stirred while the pressure was reduced. To this mixture was added 35 mg (61 μmol) of bis(dibenzylideneacetone)palladium(0), and the mixture was stirred under a nitrogen stream at 150° C. for 32 hours.

After the stirring, toluene and water were added to this mixture, which was then subjected to suction filtration to give a solid. Toluene was added to the obtained solid, and suction filtration through Florisil, Celite, and alumina was conducted to give a filtrate. The obtained filtrate was concentrated to give a solid. This solid was purified by silica gel column chromatography (developing solvent: toluene), so that a solid was obtained. The obtained solid was recrystallized with toluene three times, so that 1.8 g of a yellow solid was obtained in a yield of 71%.

By a train sublimation method, 1.2 g of the obtained solid was sublimated and purified. The sublimation purification was performed by heating at 380° C. under the conditions where the pressure was $2.3 \times 10^{-2}$ Pa and the argon flow rate was 0 mL/min. After the sublimation purification, 1.0 g of a yellow solid was obtained at a collection rate of 88%. The synthesis scheme of Step 4 is shown below.

[Chemical Formula 90]

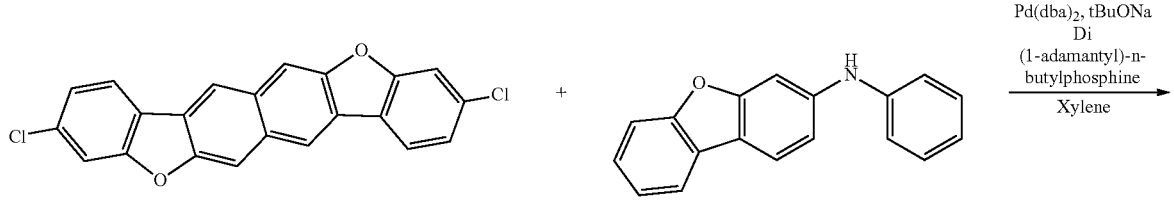

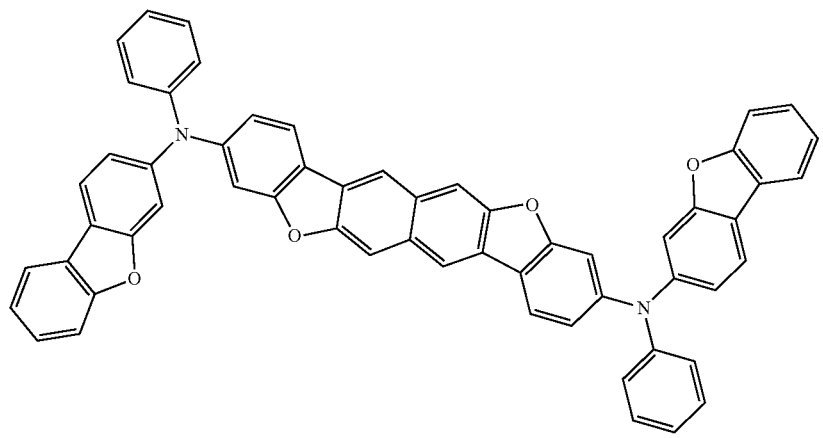
-continued

FIG. 85 shows $^1$H NMR data of the obtained solid, whose numerical data is given below. The data indicates that 3,10FrA2Nbf(IV)-02, which is an organic compound of one embodiment of the present invention, was obtained in this synthesis example.

$^1$H NMR (CD$_2$Cl$_2$, 300 MHz): δ=7.12-7.21 (m, 6H), 7.23-7.26 (m, 4H), 7.28 (d, J1=2.1 Hz, 2H), 7.32-7.40 (m, 8H), 7.44 (dd, J1=7.5 Hz, J2=1.2 Hz, 2H), 7.53 (d, J1=7.8 Hz, 2H), 7.88 (d, J1=8.1 Hz, 2H), 7.91-7.96 (m, 4H), 8.01 (s, 2H), 8.41 (s, 2H).

Next, the measurement results of the absorption spectrum and emission spectrum of a toluene solution of 3,10FrA2Nbf (IV)-02 are shown in FIG. 86. In addition, the absorption spectrum and emission spectrum of a thin film of 3,10FrA2Nbf(IV)-02 are shown in FIG. 87. The fabrication method of the sample and the measurement method were similar to those of Synthesis Example 3.

As can be seen from FIG. 86, the toluene solution of 3,10FrA2Nbf(IV)-02 has absorption peaks at 427 nm, 404 nm, 350 nm, and 282 nm, and emission wavelength peaks at 441 nm and 468 nm (excitation wavelength 400 nm). In addition, as can be seen from FIG. 87, the thin film of 3,10FrA2Nbf(IV)-02 has absorption peaks at 432 nm, 412 nm, 353 nm, and 257 nm, and emission wavelength peaks at 462 nm and 488 nm (excitation wavelength 400 nm). These results indicate that 3,10FrA2Nbf(IV)-02 emits blue light and can be used as a host for a light-emitting substance or a host for a substance that emits fluorescence in the visible region.

Furthermore, in the emission spectrum of 3,10FrA2Nbf (IV)-02 in the toluene solution, the intensity of the second peak at around 468 nm, which is on the long wavelength side, is small and the half width is 22 nm, which means that light with extremely narrow spectrum width is emitted.

Furthermore, the measured emission quantum yield in the toluene solution was as high as 97%, which indicates that 3,10FrA2Nbf(IV)-02 is suitable as a light-emitting material.

Note that, from the toluene solution of 3,10FrA2Nbf(IV)-02, the molar absorption coefficient ε was found to be as high as 120,000 [M-1·cm-1] at 427 nm. This indicates that, in the case where 3,10FrA2Nbf(IV)-02 of one embodiment of the present invention is dispersed as a light-emitting material (guest material) in a host material, energy transfer from the host material is carried out efficiently. In other words, the compound of one embodiment of the present invention has a property that is advantageous as a guest material in obtaining high emission efficiency in a host-guest-type light-emitting element.

Because of its narrow emission spectrum width and high emission quantum yield, 3,10FrA2Nbf(IV)-02 of one embodiment of the present invention was found to be an organic compound that can emit light efficiently.

Next, 3,10FrA2Nbf(IV)-02 obtained in this example was analyzed by LC/MS analysis. The fabrication method of the sample, and the measurement method and conditions were similar to those of Synthesis Example 3 in Example 3.

A component with m/z=822.25, which is an ion derived from 3,10FrA2Nbf(IV)-02, was subjected to the MS$^2$ measurement by a Targeted-MS$^2$ method. For setting of the Targeted-MS$^2$, the mass range of a target ion was set to m/z=822.25±2.0 (isolation window=4) and detection was performed in a positive mode. Measurement was performed with energy NCE for accelerating the target ion in a collision cell set to 60. The obtained MS spectrum is shown in FIG. 88.

From the results in FIG. 88, it was found that product ions from 3,10FrA2Nbf(IV)-02 are detected mainly at around m/z=744, 654, 563, 487, 397, 258, and 230. Note that the results shown in FIG. 88 exhibit characteristic results derived from 3,10FrA2Nbf(IV)-02 and therefore are important data for identifying 3,10FrA2Nbf(IV)-02 contained in a mixture.

Note that the product ion around m/z=744 is presumed to be a cation in the state where a phenyl group was eliminated from 3,10FrA2Nbf(IV)-02, which suggests that 3,10FrA2Nbf(IV)-02 contains a phenyl group. Furthermore, the product ion around m/z=654 is presumed to be a cation in the state where a dibenzofuranyl group was eliminated from 3,10FrA2Nbf(IV)-02, which suggests that 3,10FrA2Nbf(IV)-02 contains a dibenzofuranyl group.

Note that the product ion around m/z=563 is presumed to be a cation in the state where an N-(dibenzofuran-3-yl)-N-phenylamino group was eliminated from 3,10FrA2Nbf(IV)-02, which suggests that 3,10FrA2Nbf(IV)-02 contains an N-(dibenzofuran-3-yl)-N-phenylamino group. Furthermore, the product ion around m/z=258 is presumed to be a cation in the state where a 3-[N-(dibenzofuran-3-yl)-N-phenylamino]naphtho[2,3-b;6,7-b']bisbenzofuranyl group was eliminated from 3,10FrA2Nbf(IV)-02, which suggests that 3,10FrA2Nbf(IV)-02 contains a 3-[N-(dibenzofuran-3-yl)-N-phenylamino]naphtho[2,3-b;6,7-b']bisbenzofuranyl group.

Example 12

Synthesis Example 6

In this synthesis example, a method for synthesizing 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02) represented as the structural formula (707) in Embodiment 1 will be described in detail. The structural formula of 3,10PCA2Nbf(IV)-02 is shown below.

[Chemical Formula 91]

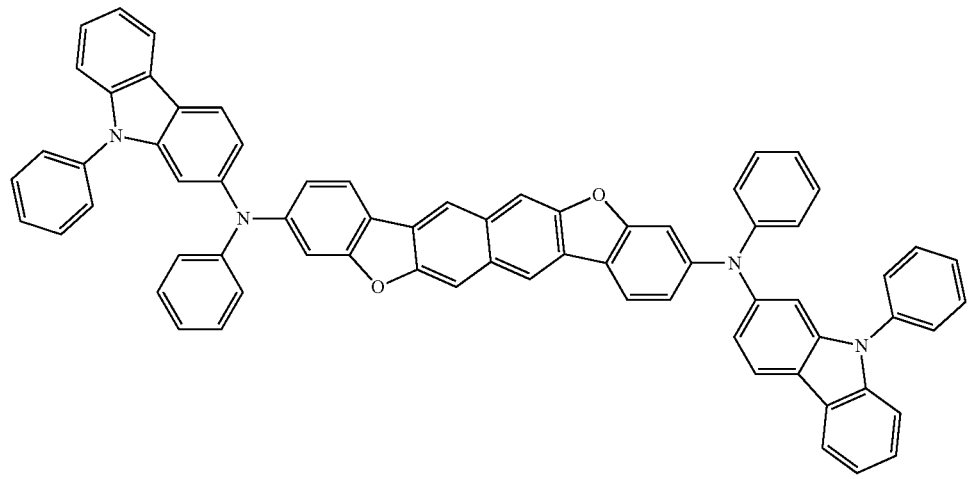

Step 1: Synthesis of 3,7-bis(4-chloro-2-fluorophenyl)-2,6-dimethoxynaphthalene The synthesis was conducted in a similar manner to Step 1 of Synthesis Example 1 in Example 1.

Step 2: Synthesis of 3,7-bis(4-chloro-2-fluorophenyl)-2,6-dihydroxynaphthalene The synthesis was conducted in a similar manner to Step 2 of Synthesis Example 1 in Example 1.

Step 3: Synthesis of 3,10-dichloronaphtho[2,3-b;6,7-b']bisbenzofuran

The synthesis was conducted in a similar manner to Step 3 of Synthesis Example 1 in Example 1.

Step 4: Synthesis of 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02)

Into a 200 mL three-necked flask were put 0.97 g (2.6 mmol) of 3,10-dichloronaphtho[2,3-b;6,7-b']bisbenzofuran, 2.6 g (7.7 mmol) of 2-anilino-9-phenyl-9H-carbazole, 92 mg (0.26 mmol) of di(1-adamantyl)-n-butylphosphine, and 1.5 g (15 mmol) of sodium tert-butoxide. To this mixture was added 26 mL of xylene. This mixture was degassed by being stirred while the pressure was reduced. To this mixture was added 30 mg (51 μmol) of bis(dibenzylideneacetone)palladium(0), and the mixture was stirred under a nitrogen stream at 150° C. for seven hours. After the stirring, toluene was added to this mixture, which was then subjected to suction filtration through Florisil, Celite, and alumina to give a filtrate. The obtained filtrate was concentrated to give a solid. This solid was purified by silica gel column chromatography (developing solvent: toluene), so that a solid was obtained. The obtained solid was recrystallized with toluene twice, so that 1.6 g of a yellow solid was obtained in a yield of 62%.

By a train sublimation method, 1.1 g of the obtained solid was sublimated and purified. The sublimation purification was performed by heating at 375° C. under the conditions where the pressure was $1.7 \times 10^{-2}$ Pa and the argon flow rate was 0 mL/min. After the sublimation purification, 0.57 g of a yellow solid was obtained at a collection rate of 51%. The synthesis scheme of Step 4 is shown below.

[Chemical Formula 92]

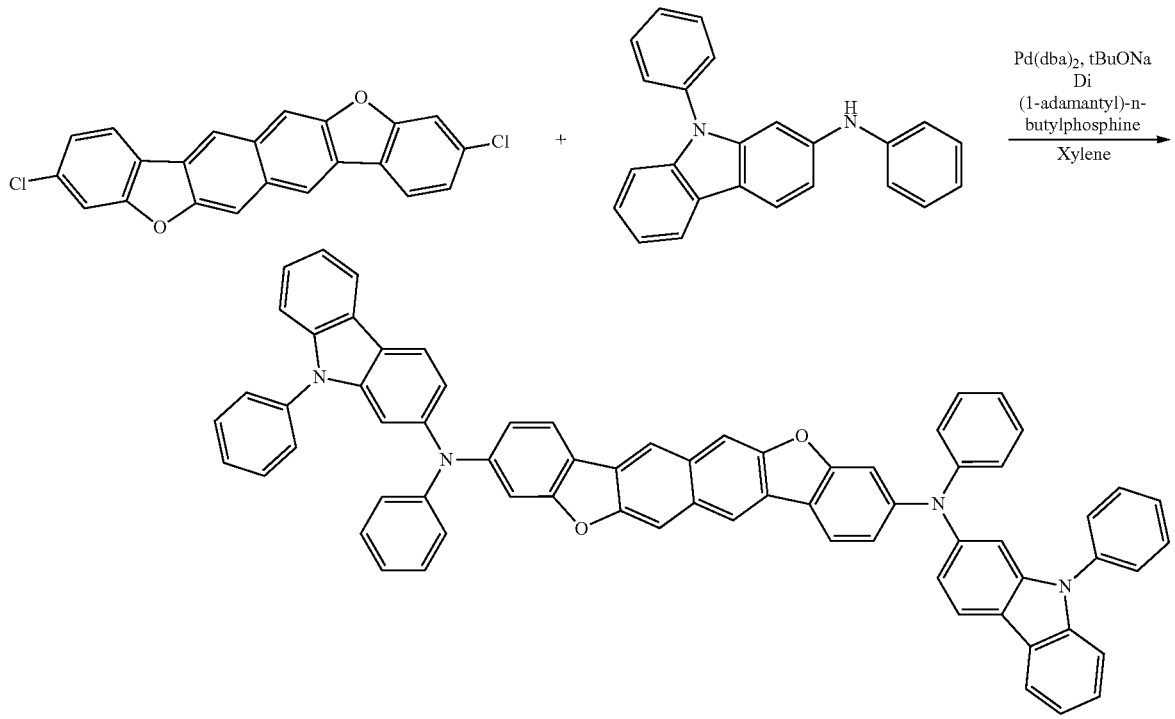

FIG. 89 shows ¹H NMR data of the obtained solid, whose numerical data is given below. The data indicates that 3,10PCA2Nbf(IV)-02, which is an organic compound of one embodiment of the present invention, was obtained in this synthesis example.

¹H NMR (CD$_2$Cl$_2$, 300 MHz): δ=7.05-7.14 (m, 6H), 7.19-7.24 (m, 8H), 7.26-7.33 (m, 6H), 7.36-7.41 (m, 6H), 7.50-7.56 (m, 8H), 7.88 (d, J1=8.4 Hz, 2H), 7.97 (s, 2H), 8.08-8.12 (m, 4H), 8.35 (s, 2H).

Next, the measurement results of the absorption spectrum and emission spectrum of a toluene solution of 3,10PCA2Nbf(IV)-02 are shown in FIG. 90. In addition, the absorption spectrum and emission spectrum of a thin film of 3,10PCA2Nbf(IV)-02 are shown in FIG. 91. The fabrication method of the sample and the measurement method were similar to those of Synthesis Example 3.

As can be seen from FIG. 90, the toluene solution of 3,10PCA2Nbf(IV)-02 has absorption peaks at 430 nm, 408 nm, 346 nm, and 282 nm, and emission wavelength peaks at 448 nm and 476 nm (excitation wavelength 410 nm). In addition, as can be seen from FIG. 91, the thin film of 3,10PCA2Nbf(IV)-02 has absorption peaks at 436 nm, 415 nm, 350 nm, 264 nm, and 236 nm, and an emission wavelength peak at 476 nm (excitation wavelength 410 nm). These results indicate that 3,10PCA2Nbf(IV)-02 emits blue light and can be used as a host for a light-emitting substance or a host for a substance that emits fluorescence in the visible region.

Furthermore, in the emission spectrum of 3,10PCA2Nbf(IV)-02 in the toluene solution, the intensity of the second peak at around 476 nm, which is on the long wavelength side, is small and the half width is 26 nm, which means that light with extremely narrow spectrum width is emitted.

Furthermore, the measured emission quantum yield in the toluene solution was as high as 93%, which indicates that 3,10PCA2Nbf(IV)-02 is suitable as a light-emitting material.

Note that, from the toluene solution of 3,10PCA2Nbf(IV)-02, the molar absorption coefficient ε was found to be as high as 110,000 [M-1·cm-1] at 430 nm. This indicates that, in the case where 3,10PCA2Nbf(IV)-02 of one embodiment of the present invention is dispersed as a light-emitting material (guest material) in a host material, energy transfer from the host material is carried out efficiently. In other words, the compound of one embodiment of the present invention has a property that is advantageous as a guest material in obtaining high emission efficiency in a host-guest-type light-emitting element.

Because of its narrow emission spectrum width and high emission quantum yield, 3,10PCA2Nbf(IV)-02 of one embodiment of the present invention was found to be an organic compound that can emit light efficiently.

Next, 3,10PCA2Nbf(IV)-02 obtained in this example was analyzed by LC/MS analysis. The fabrication method of the sample, and the measurement method and conditions were similar to those of Synthesis Example 3 in Example 3.

A component with m/z=972.35, which is an ion derived from 3,10PCA2Nbf(IV)-02, was subjected to the MS² measurement by a Targeted-MS² method. For setting of the Targeted-MS², the mass range of a target ion was set to m/z=972.35±2.0 (isolation window=4) and detection was performed in a positive mode. Measurement was performed with energy NCE for accelerating the target ion in a collision cell set to 50. The obtained MS spectrum is shown in FIG. 92.

From the results in FIG. 92, it was found that product ions from 3,10PCA2Nbf(IV)-02 are detected mainly at around m/z=896, 869, 731, 640, 333, and 256. Note that the results shown in FIG. 92 exhibit characteristic results derived from 3,10PCA2Nbf(IV)-02 and therefore are important data for identifying 3,10PCA2Nbf(IV)-02 contained in a mixture.

Note that the product ion around m/z=896 is presumed to be a cation in the state where a phenyl group was eliminated from 3,10PCA2Nbf(IV)-02, which suggests that 3,10PCA2Nbf(IV)-02 contains a phenyl group. Furthermore, the product ion around m/z=731 is presumed to be a cation in the state where a 9-phenylcarbazolyl group was eliminated from 3,10PCA2Nbf(IV)-02, which suggests that 3,10PCA2Nbf(IV)-02 contains a 9-phenylcarbazolyl group.

Furthermore, the product ion around m/z=640 is presumed to be a cation in the state where an N-(9-phenyl-9H-carbazol-2-yl)-N-phenylamino group was eliminated from 3,10PCA2Nbf(IV)-02, which suggests that 3,10PCA2Nbf(IV)-02 contains an N-(9-phenyl-9H-carbazol-2-yl)-N-phenylamino group. Furthermore, the product ion around n/z=333 is presumed to be a cation in the state where a 3-[N-(9-phenyl-9H-carbazol-2-yl)-N-phenylamino]naphtho[2,3-b;6,7-b']bisbenzofuranyl group was eliminated from 3,10PCA2Nbf(IV)-02, which suggests that 3,10PCA2Nbf(IV)-02 contains a 3-[N-(9-phenyl-9H-carbazol-2-yl)-N-phenylamino]naphtho[2,3-b;6,7-b']bisbenzofuranyl group.

Example 13

Synthesis Example 7

In this synthesis example, a method for synthesizing 3,10-bis[N-(dibenzofuran-4-yl)-N-phenylamino]-6,13-diphenylnaphtho[2,3-b;6,7-b']bisbenzofuran (abbreviation: ph-3,10FrA2Nbf(IV)-II) will be described in detail. The structural formula of ph-3,10FrA2Nbf(IV)-II is shown below.

[Chemical Formula 93]

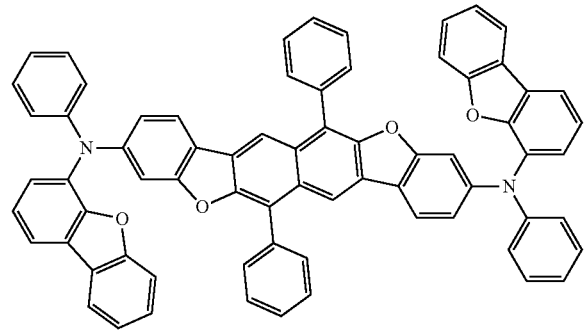

Step 1: Synthesis of
2,6-dihydroxy-1,5-diphenylnaphthalene

Into a 1 L three-necked flask were put 9.5 g (30 mmol) of 1,5-dibromo-2,6-dihydroxynaphthalene, 8.0 g (66 mmol) of phenylboronic acid, 37 g (120 mmol) of cesium carbonate, and 1.2 g (3.0 mmol) of SPhos. To this mixture was added 300 mL of toluene. This mixture was degassed by being stirred while the pressure was reduced. To this mixture was added 0.27 g (1.2 mmol) of palladium(II) acetate, and the mixture was stirred under a nitrogen stream at 110° C. for seven hours. After the stirring, toluene was added to the mixture, which was then subjected to suction filtration through Celite to give a filtrate. The obtained filtrate was concentrated to give a solid. The obtained solid was purified by silica gel column chromatography (neutral silica gel, developing solvent: toluene) to give 4.3 g (crude) of a yellow solid. The synthesis scheme of Step 1 is shown below.

[Chemical Formula 94]

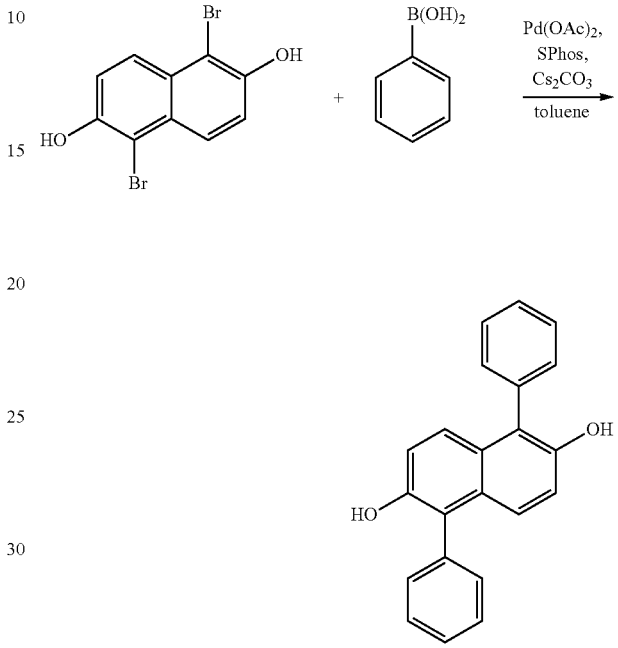

FIG. 93 shows $^1$H NMR data of the obtained solid, whose numerical data is given below. The data indicates that 2,6-dihydroxy-1,5-diphenylnaphthalene, which is an organic compound of one embodiment of the present invention, was obtained in this synthesis example.

$^1$H NMR (DMSO-d$_6$, 300 MHz): δ=7.07 (d, J1=9.3 Hz, 2H), 7.19 (d, J1=8.7 Hz, 2H), 7.25-7.41 (m, 6H), 7.45-7.51 (m, 4H), 9.07 (s, 2H).

Step 2: Synthesis of 2,6-bis(2-bromo-4-chlorophenoxy)-1,5-diphenylnaphthalene

Into a 200 mL three-necked flask were put 4.3 g (crude) of 2,6-dihydroxy-1,5-diphenylnaphthalene, 8.6 g (0.42 mol) of 1-bromo-4-chloro-2-fluorobenzene, and 13 g (41 mmol) of cesium carbonate. To this mixture was added 70 mL of N-methyl-2-pyrrolidone, and this mixture was degassed by being stirred while the pressure was reduced. After the degassing, this mixture was stirred under a nitrogen stream at 120° C. for 13.5 hours. After the stirring, 2.9 g (14 mmol) of 1-bromo-4-chloro-2-fluorobenzene was added, and the mixture was stirred under a nitrogen stream at 120° C. for 13.5 hours.

After the stirring, water was added to this mixture, and after the irradiation with ultrasonic waves, the mixture was filtered to give a solid. The obtained solid was washed with water and ethanol. This solid was purified by silica gel column chromatography (developing solvent: toluene). This solid was recrystallized with a mixed solvent of toluene and ethanol to give 6.3 g of a pale yellow solid in a yield of 66%. The synthesis scheme of Step 2 is shown below.

[Chemical Formula 95]

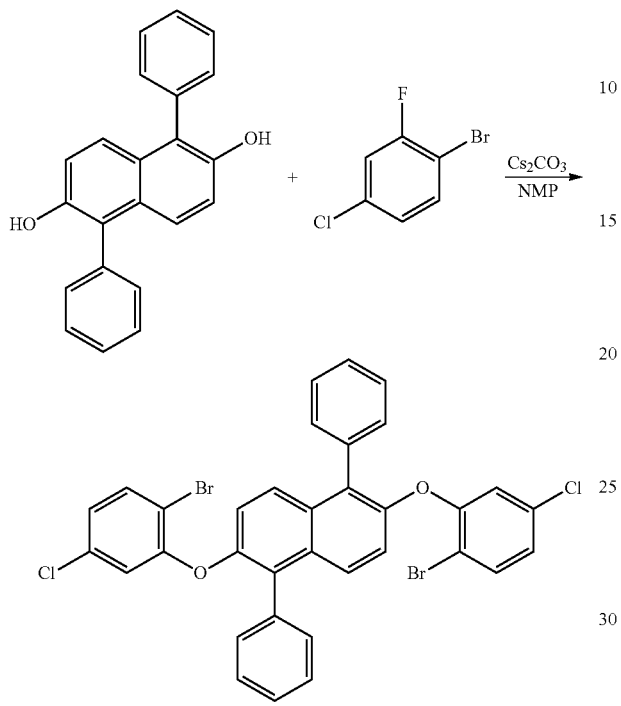

FIG. 94 shows ¹H NMR data of the obtained solid, whose numerical data is given below. The data indicates that 2,6-bis(2-bromo-4-chlorophenoxy)-1,5-diphenylnaphthalene, which is an organic compound of one embodiment of the present invention, was obtained in this synthesis example.

¹H NMR (DMSO-$d_6$, 300 MHz): δ=6.90 (d, J1=1.8 Hz, 2H), 7.06 (dd, J1=8.1 Hz, J2=2.4 Hz, 2H), 7.28 (d, J1=9.3 Hz, 2H), 7.39-7.51 (m, 10H), 7.56-7.61 (m, 4H).

Step 3: Synthesis of 3,10-dichloro-6,13-diphenylnaphtho[2,3-b;6,7-b']bisbenzofuran Into a 200 mL three-necked flask were put 6.2 g (9.0 mmol) of 2,6-bis(2-bromo-4-chlorophenoxy)-1,5-diphenylnaphthalene, 0.47 g (1.8 mmol) of triphenylphosphine, and 7.1 g (22 mmol) of cesium carbonate. To this mixture was added 45 mL of N-methyl-2-pyrrolidone, and this mixture was degassed by being stirred while the pressure was reduced. After the degassing, this mixture was stirred under a nitrogen stream at 120° C. for 15 hours.

After the stirring, water was added to this mixture, and after the irradiation with ultrasonic waves, the mixture was filtered to give a solid. The obtained solid was dissolved in toluene, and the solution was subjected to suction filtration through Florisil, Celite, and alumina to give a filtrate. The obtained filtrate was concentrated to give a solid. The obtained solid was recrystallized with toluene, so that 3.2 g of a yellow solid was obtained in a yield of 67%. The synthesis scheme of Step 3 is shown below.

[Chemical Formula 96]

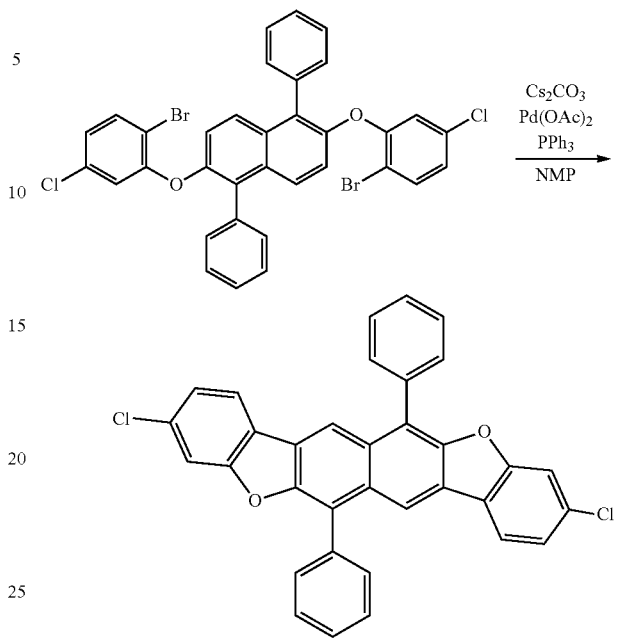

FIG. 95 shows ¹H NMR data of the obtained solid, whose numerical data is given below. The data indicates that 3,10-dichloro-6,13-diphenylnaphtho[2,3-b;6,7-b']bisbenzofuran, which is an organic compound of one embodiment of the present invention, was obtained in this synthesis example.

¹H NMR (1,1,2,2-Tetrachloroethane-D2, 300 MHz): δ=7.32 (dd, J1=8.4 Hz, J2=1.5 Hz, 2H), 7.55 (d, J1=1.5 Hz, 2H), 7.65-7.76 (m, 10H), 7.93 (d, J1=8.1 Hz, 2H), 8.47 (s, 2H).

Step 4: Synthesis of 3,10-bis[N-(dibenzofuran-4-yl)-N-phenylamino]-6,13-diphenylnaphtho[2,3-b;6,7-b']bisbenzofuran (abbreviation: ph-3,10FrA2Nbf (IV)-II)

Into a 200 mL three-necked flask were put 1.4 g (2.6 mmol) of 3,10-dichloro-6,13-diphenylnaphtho[2,3-b;6,7-b'] bisbenzofuran, 1.7 g (6.4 mmol) of N-(dibenzofuran-4-yl)-N-phenylamine, 92 mg (0.26 mmol) of di(1-adamantyl)-n-butylphosphine, and 1.5 g (15 mmol) of sodium tert-butoxide. To this mixture was added 25 mL of xylene. This mixture was degassed by being stirred while the pressure was reduced. To this mixture was added 29 mg (51 μmol) of bis(dibenzylideneacetone)palladium(0), and the mixture was stirred under a nitrogen stream at 150° C. for 15 hours.

After the stirring, toluene was added to the mixture, which was then subjected to suction filtration through Florisil, Celite, and alumina to give a filtrate. The obtained filtrate was concentrated to give a solid. This solid was purified by silica gel column chromatography (developing solvent: toluene:hexane=1:2 and then toluene:hexane=2:3). The obtained solid was recrystallized with a mixed solvent of toluene and ethyl acetate to give 2.0 g of a yellow solid in a yield of 80%. By a train sublimation method, 1.1 g of the obtained solid was sublimated and purified. The sublimation purification was performed by heating at 380° C. under the conditions where the pressure was $2.7 \times 10^{-2}$ Pa and the argon flow rate was 0 mL/min. After the sublimation purification, 0.94 g of a yellow solid was obtained at a collection rate of 84%. The synthesis scheme of Step 4 is shown below.

[Chemical Formula 97]

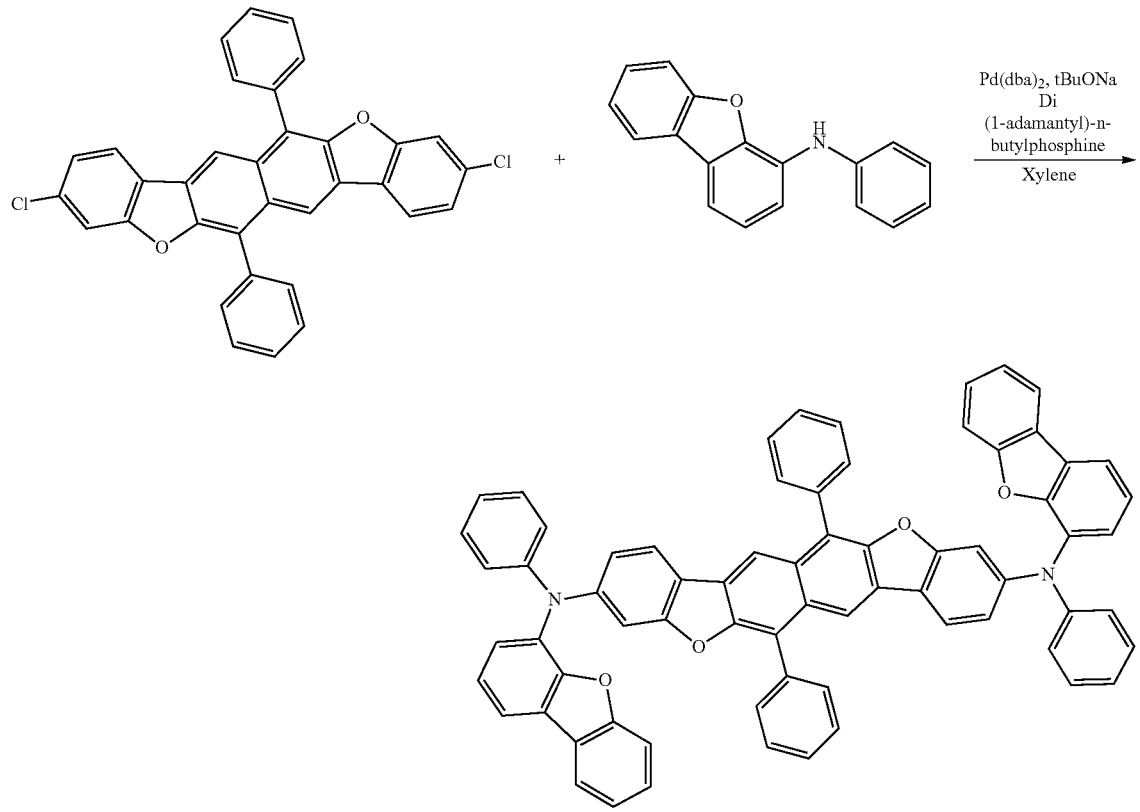

FIG. 96 shows $^1$H NMR data of the obtained solid, whose numerical data is given below. The data indicates that ph-3,10FrA2Nbf(IV)-II, which is an organic compound of one embodiment of the present invention, was obtained in this synthesis example.

$^1$H NMR (DMSO-d$_6$, 300 MHz): δ=6.87 (dd, J1=8.7 Hz, J2=2.4 Hz, 2H), 6.96 (d, J1=2.4 Hz, 2H), 7.10-7.18 (m, 6H), 7.28-7.64 (m, 24H), 7.94 (d, J1=8.1 Hz, 2H), 8.05 (d, J1=7.8 Hz, J2=1.5 Hz, 2H), 8.16 (dd, J1=6.9 Hz, J2=1.5 Hz, 2H), 8.24 (s, 2H).

Next, ph-3,10FrA2Nbf(IV)-II obtained in this example was analyzed by LC/MS analysis. The fabrication method of the sample, and the measurement method and conditions were similar to those of Synthesis Example 3 in Example 3.

A component with m/z=974.31, which is an ion derived from ph-3,10FrA2Nbf(IV)-II, was subjected to the MS$^2$ measurement by a Targeted-MS$^2$ method. For setting of the Targeted-MS$^2$, the mass range of a target ion was set to m/z=974.31±2.0 (isolation window=4) and detection was performed in a positive mode. Measurement was performed with energy NCE for accelerating the target ion in a collision cell set to 60. The obtained MS spectrum is shown in FIG. 97.

From the results in FIG. 97, it was found that product ions from ph-3,10FrA2Nbf(IV)-II are detected mainly at around m/z=898, 808, 717, 639, 549, 520, and 458. Note that the results shown in FIG. 97 exhibit characteristic results derived from ph-3,10FrA2Nbf(IV)-II and therefore are important data for identifying ph-3,10FrA2Nbf(IV)-II contained in a mixture.

Note that the product ion around m/z=898 is presumed to be a cation in the state where a phenyl group was eliminated from ph-3,10FrA2Nbf(IV)-II, which suggests that ph-3,10FrA2Nbf(IV)-II contains a phenyl group. Furthermore, the product ion around m/z=808 is presumed to be a cation in the state where a dibenzofuranyl group was eliminated from ph-3,10FrA2Nbf(IV)-II, which suggests that ph-3,10FrA2Nbf(IV)-II contains a dibenzofuranyl group.

Note that the product ion around m/z=717 is presumed to be a cation in the state where an N-(dibenzofuran-4-yl)-N-phenylamino group was eliminated from ph-3,10FrA2Nbf(IV)-II, which suggests that ph-3,10FrA2Nbf(IV)-II contains an N-(dibenzofuran-4-yl)-N-phenylamino group. Furthermore, the product ion around m/z=458 is presumed to be a cation in the state where two N-(dibenzofuran-4-yl)-N-phenylamino groups were eliminated from ph-3,10FrA2Nbf(IV)-II, which suggests that ph-3,10FrA2Nbf(IV)-II contains two N-(dibenzofuran-4-yl)-N-phenylamino groups.

Furthermore, the product ion around m/z=257 is presumed to be a cation in the state where a 3-[N-(dibenzofuran-4-yl)-N-phenylamino]-6,13-diphenylnaphtho[2,3-b;6,7-b']bisbenzofuranyl group was eliminated from ph-3,10FrA2Nbf(IV)-II, which suggests that ph-3,10FrA2Nbf(IV)-II contains a 3-[N-(dibenzofuran-4-yl)-N-phenylamino]-6,13-diphenylnaphtho[2,3-b;6,7-b']bisbenzofuranyl group.

Next, the measurement results of the absorption spectrum and emission spectrum of a toluene solution of ph-3,10FrA2Nbf(IV)-II are shown in FIG. 124. In addition, the absorption spectrum and emission spectrum of a thin film of ph-3,10FrA2Nbf(IV)-II are shown in FIG. 125. The solid thin film was formed over a quartz substrate by a vacuum evaporation method. The absorption spectrum of the toluene solution was measured using an ultraviolet-visible light spectrophotometer (V550 type manufactured by JASCO Corporation). The shown absorpotion spectrum is the one from which the spectrum of toluene alone in a quartz cell has been subtracted. The absorption spectrum of the thin film was measured using a spectrophotometer (U4100 Spectrophotometer, manufactured by Hitachi High-Technologies Corporation). The emission spectrum of the thin film was measured using a fluorescence spectrophotometer (FS920 manufactured by Hamamatsu Photonics K.K.). The emission spectrum and emission quantum yield of the solution were measured using an absolute PL quantum yield measurement system (Quantaurus-QY manufactured by Hamamatsu Photonics K.K.).

As can be seen from FIG. 124, the toluene solution of ph-3,10FrA2Nbf(IV)-II has absorption peaks at 428 nm, 402 nm, 317 nm, and 285 nm, and emission wavelength peaks at 441 nm and 469 nm (excitation wavelength 400 nm). In addition, as can be seen from FIG. 125, the thin film of ph-3,10FrA2Nbf(IV)-II has absorption peaks at 434 nm, 408 nm, 380 nm, 322 nm, and 286 nm, and emission wavelength peaks at 459 nm, 488 nm, and 531 nm (excitation wavelength 400 nm). These results indicate that ph-3,10FrA2Nbf (IV)-II emits blue light and can be used as a host for a light-emitting substance or a host for a substance that emits fluorescence in the visible region.

Furthermore, the measured emission quantum yield in the toluene solution was as high as 86%, which indicates that ph-3,10FrA2Nbf(IV)-II is suitable as a light-emitting material.

Example 14

In this example, a light-emitting element 7, which is a light-emitting element of one embodiment of the present invention described in Embodiments, will be described in detail. The structural formulae of organic compounds used in the light-emitting element 7 are shown below.

[Chemical Formulae 98]

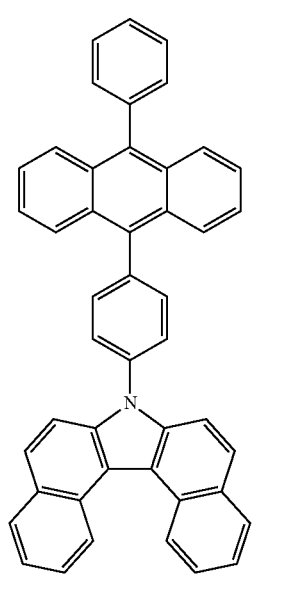

cgDBCzPA (ii)

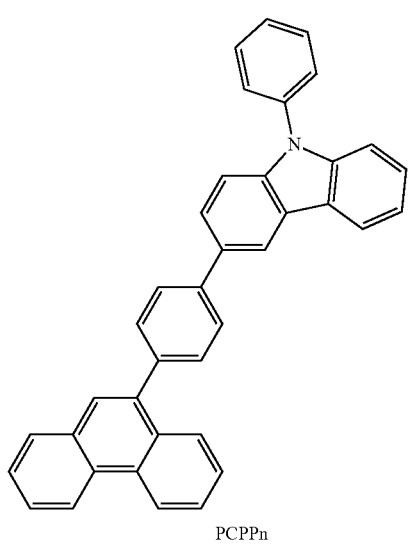

PCPPn (vi)

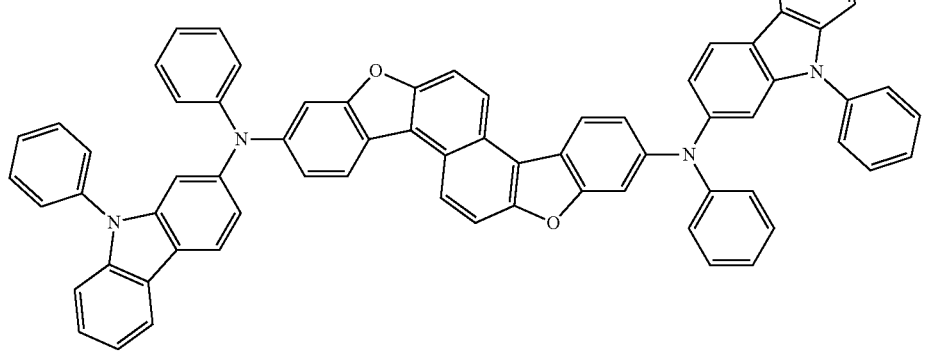

2,9PCA2Nbf(III)-02 (x)

-continued

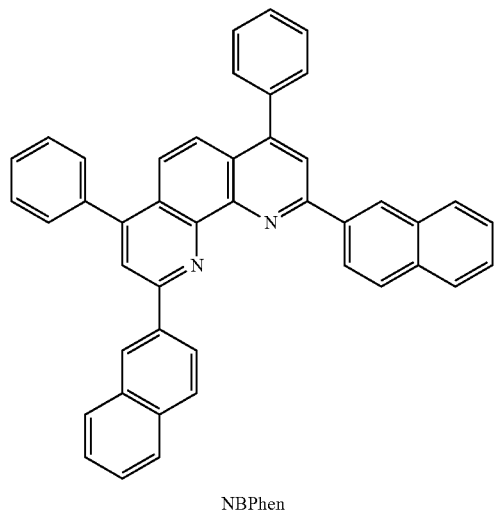

NBPhen (xii)

(Fabrication Method of Light-Emitting Element 7)

First, a film of indium tin oxide containing silicon oxide (ITSO) was formed on a glass substrate by a sputtering method, so that the anode 101 was formed. Note that the thickness was 70 nm and the area of the electrode was 4 mm$^2$ (2 mm×2 mm).

Next, in pretreatment for forming the light-emitting element over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to about $10^{-4}$ Pa, vacuum baking at 170° C. for 30 minutes was performed in a heating chamber in the vacuum evaporation apparatus, and then the substrate was naturally cooled down for about 30 minutes.

Next, the substrate on which the anode 101 was formed was fixed to a substrate holder provided in the vacuum evaporation apparatus such that the side on which the anode 101 was formed faced downward, and 3-[4-(9-phenanthryl)-phenyl]-9-phenyl-9H-carbazole (abbreviation: PCPPn) represented as the above structural formula (vi) and molybdenum(VI) oxide were deposited by co-evaporation on the anode 101 to have a weight ratio of 4:2 (=PCPPn:molybdenum oxide) to a thickness of 10 nm by an evaporation method using resistance heating, whereby the hole-injection layer 111 was formed.

Next, on the hole-injection layer 111, PCPPn was deposited by evaporation to a thickness of 30 nm to form the hole-transport layer 112.

Subsequently, 7-[4-(10-phenyl-9-anthryl)phenyl]-7H-dibenzo[c,g]carbazole (abbreviation: cgDBCzPA) represented as the above structural formula (ii) and 2,9-bis[N-(9-phenyl-9H-carbazol-2-yl)-N-phenylamino]naphtho[2,1-b;6,5-b']bisbenzofuran (abbreviation: 2,9PCA2Nbf(III)-02) represented as the above structural formula (x) were deposited by co-evaporation to have a weight ratio of 1:0.03 (=cgDBCzPA: 2,9PCA2Nbf(III)-02) to a thickness of 25 nm, whereby the light-emitting layer 113 was formed.

After that, on the light-emitting layer 113, cgDBCzPA was deposited by evaporation to a thickness of 15 nm, and 2,9-bis(naphthalen-2-yl)-4,7-diphenyl-1,10-phenanthroline (abbreviation: NBPhen) represented as the above structural formula (xii) was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115, and aluminum was deposited by evaporation to a thickness of 200 nm to form the cathode 102. Thus, the light-emitting element 7 of this example was fabricated.

The element structure of the light-emitting element 7 is listed in the following table.

TABLE 13

| | Hole-injection layer | Hole-transport layer | Light-emitting layer | Electron-transport layer | | Electron-injection layer |
|---|---|---|---|---|---|---|
| | 10 nm | 30 nm | 25 nm | 15 nm | 10 nm | 1 nm |
| Light-emitting element 7 | PCPPn: MoOx (4:2) | PCPPn | cgDBCzPA: 2,9PCA2Nbf(III)-02 (1:0.03) | cgDBCzPA | NBPhen | LiF |

The light-emitting element 7 was subjected to sealing with a glass substrate (a sealing material was applied to surround the element, followed by UV treatment and one-hour heat treatment at 80° C. at the time of sealing) in a glove box containing a nitrogen atmosphere so that the light-emitting element is not exposed to the air. Then, initial characteristics of this light-emitting element were measured. Note that the measurement was carried out at room temperature.

Luminance-current density characteristics of the light-emitting element 7 are shown in FIG. 98, current efficiency-luminance characteristics thereof are shown in FIG. 99, luminance-voltage characteristics thereof are shown in FIG. 100, current-voltage characteristics thereof are shown in FIG. 101, power efficiency-luminance characteristics thereof are shown in FIG. 102, external quantum efficiency-luminance characteristics thereof are shown in FIG. 103, and emission spectrum thereof is shown in FIG. 104. In addition, the element characteristics at around a luminance of 1000 cd/m² are listed in Table 14.

TABLE 14

|  | Voltage (V) | Current (mA) | Current density (mA/cm²) | Chromaticity x | Chromaticity y | Current efficiency (cd/A) | Power efficiency (lm/W) | External quantum efficiency (%) |
| --- | --- | --- | --- | --- | --- | --- | --- | --- |
| Light-emitting element 7 | 3.1 | 0.30 | 7.6 | 0.14 | 0.12 | 10.5 | 10.7 | 10.9 |

As can be seen from FIG. 98 to FIG. 104 and Table 14, the light-emitting element 7 was found to be a light-emitting element exhibiting favorable characteristics, the external quantum efficiency at 1000 cd/m² being 10.9%.

From the above, the naphthobisbenzofuran compound of one embodiment of the present invention, which has as a substituent an amino group containing a phenylcarbazolyl group, was found to be a material with high efficiency.

In addition, a graph of a change in luminance with driving time under the conditions where the current value was 2 mA and the current density was constant is shown in FIG. 105. As can be seen from FIG. 105, the light-emitting element 7 maintains 80% or higher of the initial luminance even after 300 hours of driving, which indicates that the light-emitting element 7 has a favorable lifetime.

Example 15

In this example, a light-emitting element 8, which is a light-emitting element of one embodiment of the present invention described in Embodiments, will be described in detail. The structural formulae of organic compounds used in the light-emitting element 8 are shown below.

[Chemical Formulae 99]

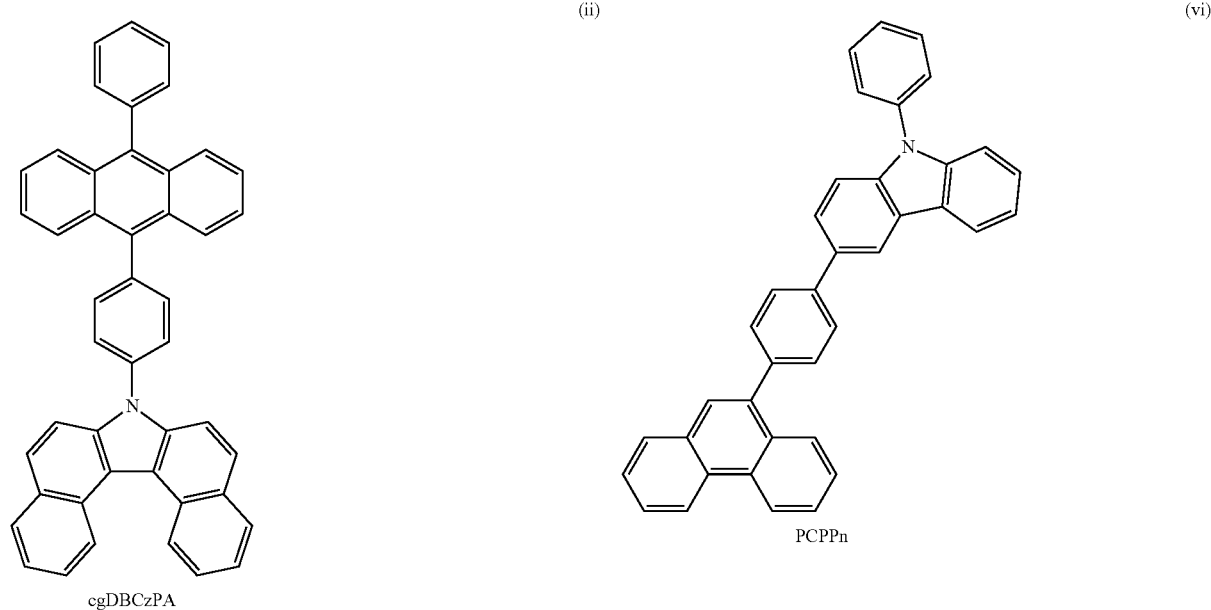

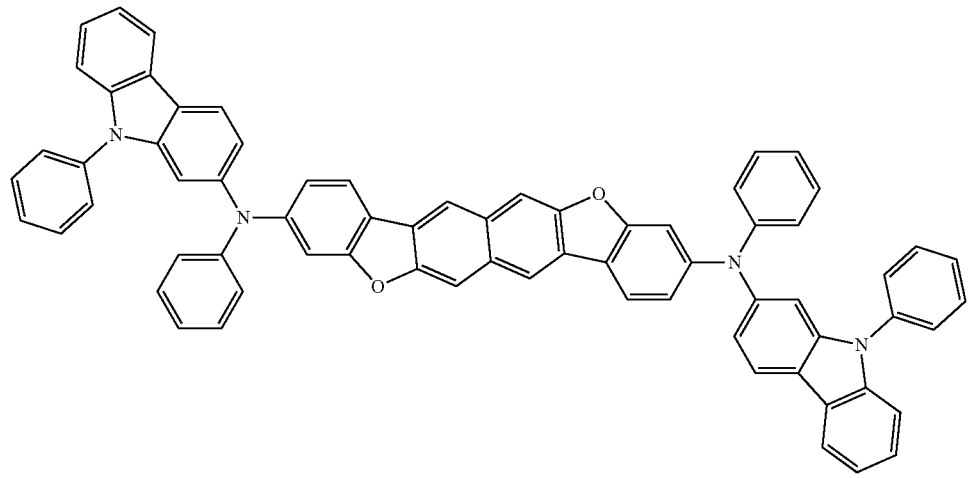

3,10PCA2Nbf (IV)-02

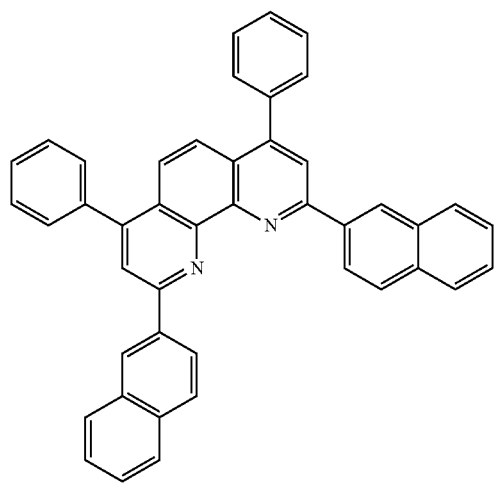

NBPhen (Fabrication Method of Light-Emitting Element 8)

First, a film of indium tin oxide containing silicon oxide (ITSO) was formed on a glass substrate by a sputtering method, so that the anode 101 was formed. Note that the thickness was 70 nm and the area of the electrode was 4 mm² (2 mm×2 mm).

Next, in pretreatment for forming the light-emitting element over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to about $10^{-4}$ Pa, vacuum baking at 170° C. for 30 minutes was performed in a heating chamber in the vacuum evaporation apparatus, and then the substrate was naturally cooled down for about 30 minutes.

Next, the substrate on which the anode 101 was formed was fixed to a substrate holder provided in the vacuum evaporation apparatus such that the side on which the anode 101 was formed faced downward, and 3-[4-(9-phenanthryl)-phenyl]-9-phenyl-9H-carbazole (abbreviation: PCPPn) represented as the above structural formula (vi) and molybdenum(VI) oxide were deposited by co-evaporation on the anode 101 to have a weight ratio of 4:2 (=PCPPn:molybdenum oxide) to a thickness of 10 nm by an evaporation method using resistance heating, whereby the hole-injection layer 111 was formed.

Next, on the hole-injection layer 111, PCPPn was deposited by evaporation to a thickness of 30 nm to form the hole-transport layer 112.

Subsequently, 7-[4-(10-phenyl-9-anthryl)phenyl]-7H-dibenzo[c,g]carbazole (abbreviation: cgDBCzPA) represented as the above structural formula (ii) and 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02) represented as the above structural formula (xi) were deposited by co-evaporation to have a weight ratio of 1:0.01 (=cgDBCzPA: 3,10PCA2Nbf(IV)-02) to a thickness of 25 nm, whereby the light-emitting layer 113 was formed.

After that, on the light-emitting layer 113, cgDBCzPA was deposited by evaporation to a thickness of 15 nm, and 2,9-bis(naphthalen-2-yl)-4,7-diphenyl-1,10-phenanthroline (abbreviation: NBPhen) represented as the above structural formula (xii) was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115, and aluminum was deposited by evaporation to a thickness of 200 nm to form the cathode 102. Thus, the light-emitting element 8 of this example was fabricated.

The element structure of the light-emitting element 8 is listed in the following table.

TABLE 15

|  | Hole-injection layer | Hole-transport layer | Light-emitting layer | Electron-transport layer | | Electron-injection layer |
| --- | --- | --- | --- | --- | --- | --- |
|  | 10 nm | 30 nm | 25 nm | 15 nm | 10 nm | 1 nm |
| Light-emitting element 8 | PCPPn: MoOx (4:2) | PCPPn | cgDBCzPA: 3,10PCA2Nbf(IV)-02 (1:0.01) | cgDBCzPA | NBPhen | LiF |

The light-emitting element 8 was subjected to sealing with a glass substrate (a sealing material was applied to surround the element, followed by UV treatment and one-hour heat treatment at 80° C. at the time of sealing) in a glove box containing a nitrogen atmosphere so that the light-emitting element is not exposed to the air. Then, initial characteristics of this light-emitting element were measured. Note that the measurement was carried out at room temperature.

Luminance-current density characteristics of the light-emitting element 8 are shown in FIG. 106, current efficiency-luminance characteristics thereof are shown in FIG. 107, luminance-voltage characteristics thereof are shown in FIG. 108, current-voltage characteristics thereof are shown in FIG. 109, power efficiency-luminance characteristics thereof are shown in FIG. 110, external quantum efficiency-luminance characteristics thereof are shown in FIG. 111, and emission spectrum thereof is shown in FIG. 112. In addition, the element characteristics at around a luminance of 1000 cd/m$^2$ are listed in Table 16.

TABLE 16

|  | Voltage (V) | Current (mA) | Current density (mA/cm$^2$) | Chromaticity x | Chromaticity y | Current efficiency (cd/A) | Power efficiency (lm/W) | External quantum efficiency (%) |
| --- | --- | --- | --- | --- | --- | --- | --- | --- |
| Light-emitting element 8 | 3.1 | 0.38 | 9.6 | 0.14 | 0.12 | 11.6 | 11.8 | 11.9 |

As can be seen from FIG. 106 to FIG. 112 and Table 16, the light-emitting element 8 was found to be a light-emitting element exhibiting favorable characteristics, the external quantum efficiency at 1000 cd/m² being 11.9%.

In addition, a graph of a change in luminance with driving time under the conditions where the current value was 2 mA and the current density was constant is shown in FIG. 113. As can be seen from FIG. 113, the light-emitting element 8 maintains 85% or higher of the initial luminance even after 250 hours of driving, which indicates that the light-emitting element 8 has a favorable lifetime.

Example 16

In this example, a light-emitting element 9, which is a light-emitting element of one embodiment of the present invention described in Embodiments, will be described in detail. The structural formulae of organic compounds used in the light-emitting element 9 are shown below.

[Chemical Formulae 100]

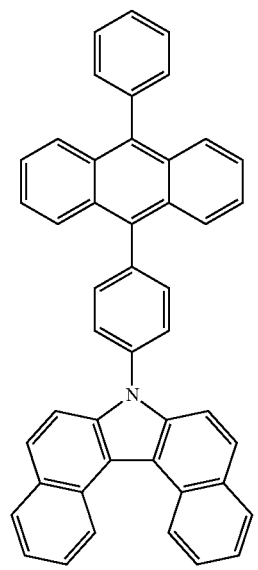

cgDBCzPA (ii)

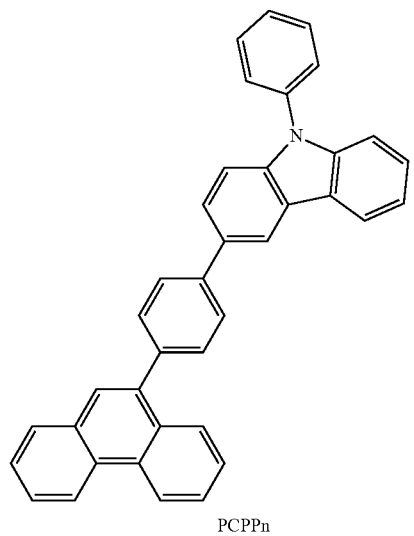

PCPPn (vi)

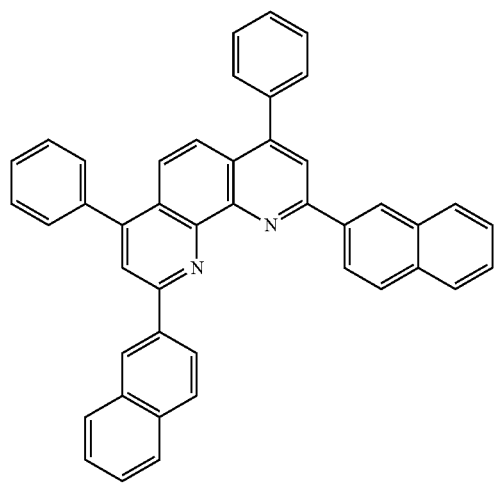

NBPhen (xii)

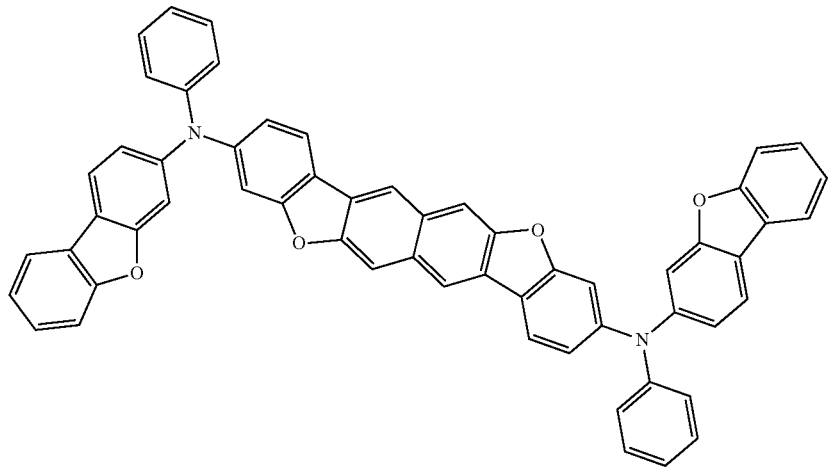

3,10FrA2Nbf(IV)-02

(Fabrication Method of Light-Emitting Element 9)

First, a film of indium tin oxide containing silicon oxide (ITSO) was formed on a glass substrate by a sputtering method, so that the anode 101 was formed. Note that the thickness was 70 nm and the area of the electrode was 4 mm² (2 mm×2 mm).

Next, in pretreatment for forming the light-emitting element over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to about $10^{-4}$ Pa, vacuum baking at 170° C. for 30 minutes was performed in a heating chamber in the vacuum evaporation apparatus, and then the substrate was naturally cooled down for about 30 minutes.

Next, the substrate on which the anode 101 was formed was fixed to a substrate holder provided in the vacuum evaporation apparatus such that the side on which the anode 101 was formed faced downward, and 3-[4-(9-phenanthryl)-phenyl]-9-phenyl-9H-carbazole (abbreviation: PCPPn) represented as the above structural formula (vi) and molybdenum(VI) oxide were deposited by co-evaporation on the anode 101 to have a weight ratio of 4:2 (=PCPPn:molybdenum oxide) to a thickness of 10 nm by an evaporation method using resistance heating, whereby the hole-injection layer 111 was formed.

Next, on the hole-injection layer 111, PCPPn was deposited by evaporation to a thickness of 30 nm to form the hole-transport layer 112.

Subsequently, 7-[4-(10-phenyl-9-anthryl)phenyl]-7H-dibenzo[c,g]carbazole (abbreviation: cgDBCzPA) represented as the above structural formula (ii) and 3,10-bis[N-(dibenzofuran-3-yl)-N-phenylamino]naphtho[2,3-b;6,7-b'] bisbenzofuran (abbreviation: 3,10FrA2Nbf(IV)-02) represented as the above structural formula (xiii) were deposited by co-evaporation to have a weight ratio of 1:0.01 (=cgDBCzPA: 3,10FrA2Nbf(IV)-02) to a thickness of 25 nm, whereby the light-emitting layer 113 was formed.

After that, on the light-emitting layer 113, cgDBCzPA was deposited by evaporation to a thickness of 15 nm, and 2,9-bis(naphthalen-2-yl)-4,7-diphenyl-1,10-phenanthroline (abbreviation: NBPhen) represented as the above structural formula (xii) was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115, and aluminum was deposited by evaporation to a thickness of 200 nm to form the cathode 102. Thus, the light-emitting element 9 of this example was fabricated.

The element structure of the light-emitting element 9 is listed in the following table.

TABLE 17

| | Hole-injection layer | Hole-transport layer | Light-emitting layer | Electron-transport layer | | Electron-injection layer |
|---|---|---|---|---|---|---|
| | 10 nm | 30 nm | 25 nm | 15 nm | 10 nm | 1 nm |
| Light-emitting element 9 | PCPPn:MoOx (4:2) | PCPPn | cgDBCzPA:3,10FrA2Nbf(IV)-02 (1:0.01) | cgDBCzPA | NBPhen | LiF |

The light-emitting element 9 was subjected to sealing with a glass substrate (a sealing material was applied to surround the element, followed by UV treatment and one-hour heat treatment at 80° C. at the time of sealing) in a glove box containing a nitrogen atmosphere so that the light-emitting element is not exposed to the air. Then, initial characteristics of this light-emitting element were measured. Note that the measurement was carried out at room temperature.

Luminance-current density characteristics of the light-emitting element 9 are shown in FIG. 114, current efficiency-luminance characteristics thereof are shown in FIG. 115, luminance-voltage characteristics thereof are shown in FIG. 116, current-voltage characteristics thereof are shown in FIG. 117, power efficiency-luminance characteristics thereof are shown in FIG. 118, external quantum efficiency-luminance characteristics thereof are shown in FIG. 119, and emission spectrum thereof is shown in FIG. 120. In addition, the element characteristics at around a luminance of 1000 cd/m$^2$ are listed in Table 18.

Example 17

FIG. 122 is a graph showing the relation between y chromaticity and external quantum efficiency at around 1000 cd/m$^2$ of light-emitting elements using pyrene-based blue fluorescent dopants and having substantially the same element structure and light-emitting elements using blue fluorescent dopants with a naphthobenzofuran skeleton of one embodiment of the present invention.

In the graph, BD-00, BD-01, and BD-02 correspond to plots of light-emitting elements using pyrene-based dopants which are different from each other, and BD-05 and BD-06 correspond to plots of light-emitting elements using 3,10PCA2Nbf(IV)-02 and 3,10FrA2Nbf(IV)-02 as dopants, respectively.

A tendency for the external quantum efficiency to decrease as the y chromaticity becomes deeper was seen for BD-00, BD-01, and BD-02, which are conventional pyrene-based dopants, and the efficiency considerably decreased for

TABLE 18

| | Voltage (V) | Current (mA) | Current density (mA/cm$^2$) | Chromaticity x | Chromaticity y | Current efficiency (cd/A) | Power efficiency (lm/W) | External quantum efficiency (%) |
|---|---|---|---|---|---|---|---|---|
| Light-emitting element 9 | 3.1 | 0.41 | 10.2 | 0.14 | 0.09 | 9.2 | 9.3 | 11.4 |

As can be seen from FIG. 114 to FIG. 120 and Table 18, the light-emitting element 9 was found to be a light-emitting element exhibiting favorable characteristics, the external quantum efficiency at 1000 cd/m$^2$ being 11.4%.

In addition, a graph of a change in luminance with driving time under the conditions where the current value was 2 mA and the current density was constant is shown in FIG. 121. As can be seen from FIG. 121, the light-emitting element 9 maintains 90% or higher of the initial luminance even after 100 hours of driving, which indicates that the light-emitting element 9 has a favorable lifetime.

a deep blue dopant such as BD-02. By contrast, for BD-05 and BD-06, which have deep y chromaticity, considerable decrease in efficiency like BD-02 was not seen, and the high efficiency was maintained.

Example 18

In this example, a plurality of top-emission elements in which the thickness of hole-injection layers is varied so as to change the optical path length were fabricated, and the result of studying the relation between the obtained y chromaticity and current efficiency is described. The structural formulae of organic compounds used in the light-emitting elements fabricated in this example are shown below.

[Chemical Formulae 101]
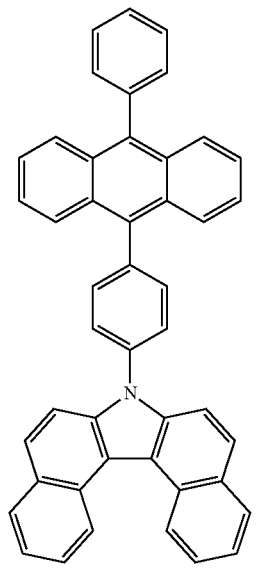
cgDBCzPA (ii)
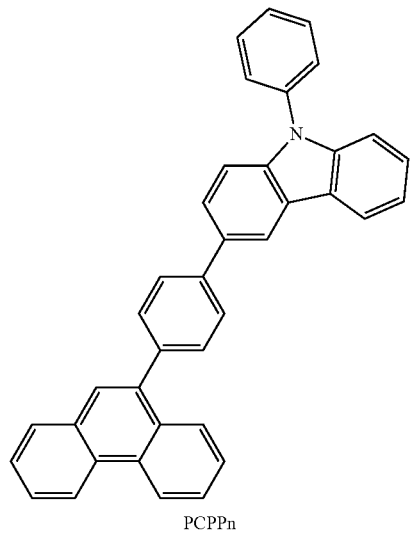
PCPPn (vi)
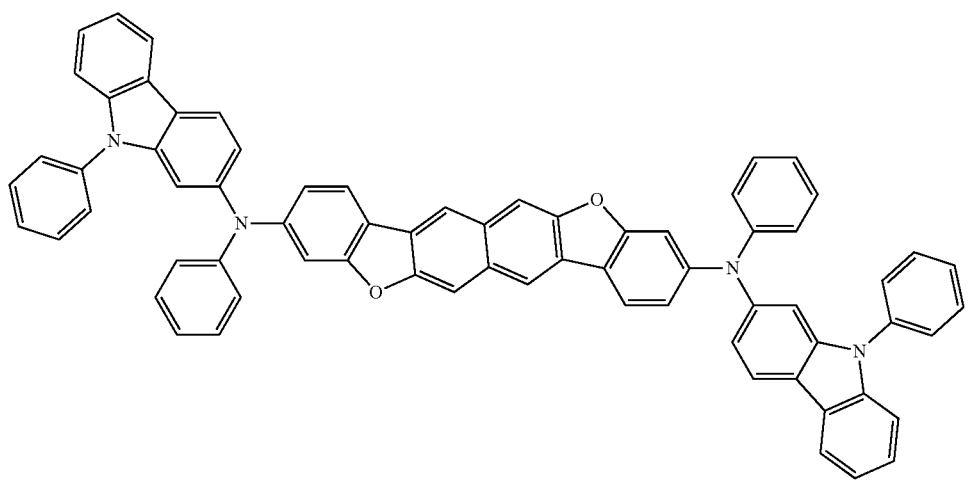
3,10PCA2Nbf (IV)-02 (xi)
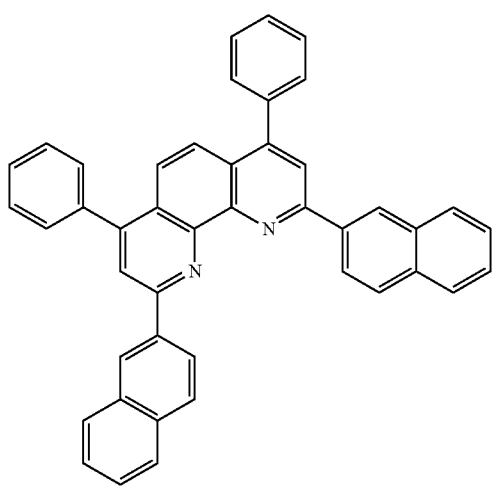
NBPhen (xii)

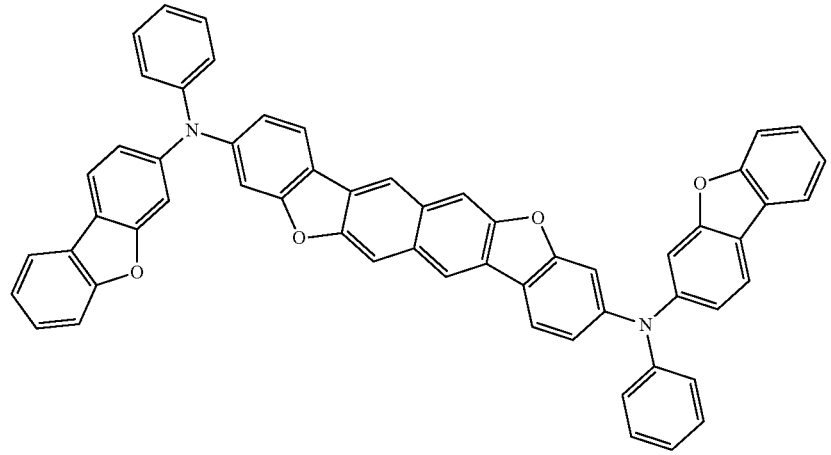

3,10FrA2Nbf (IV)-02

(xiii)

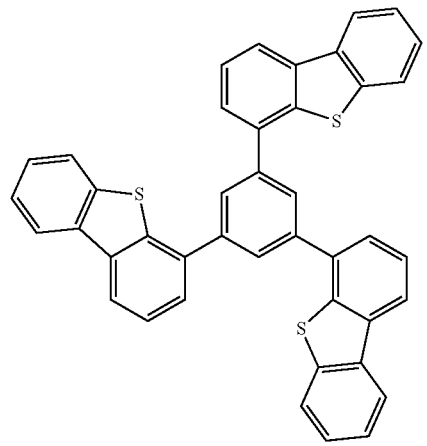

DBT3P-II (xiv)

(Fabrication Method of Top-Emission Light-Emitting Element)

First, over a glass substrate, an alloy film of silver (Ag), palladium (Pd), and copper (Cu) (an Ag—Pd—Cu (APC) film) was formed to a thickness of 100 nm by a sputtering method, and a film of indium tin oxide containing silicon oxide (ITSO) was formed to a thickness of 85 nm by a sputtering method, so that the anode 101 was formed. Note that the area of the electrode was 4 mm$^2$ (2 mm×2 mm).

Next, in pretreatment for forming the light-emitting element over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to about 10$^{-4}$ Pa, vacuum baking at 170° C. for 30 minutes was performed in a heating chamber in the vacuum evaporation apparatus, and then the substrate was naturally cooled down for about 30 minutes.

Next, the substrate on which the anode 101 was formed was fixed to a substrate holder provided in the vacuum evaporation apparatus such that the side on which the anode 101 was formed faced downward, and 3-[4-(9-phenanthryl)-phenyl]-9-phenyl-9H-carbazole (abbreviation: PCPPn) represented as the above structural formula (vi) and molybdenum(VI) oxide were deposited by co-evaporation on the anode 101 to have a weight ratio of 4:2 (=PCPPn:molybdenum oxide) by an evaporation method, whereby the hole-injection layer 111 was formed.

The optical path lengths of the light-emitting elements were changed by varying the thickness of the hole-injection layer 111, and 16 light-emitting elements using 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02) in which the thicknesses of the hole-injection layers 111 were 5 nm, 7.5 nm, 10 nm, 12.5 nm, 15 nm, 17.5 nm, 20 nm, 22.5 nm, 25 nm, 27.5 nm, 30 nm, 32.5 nm, 35 nm, 37.5 nm, 40 nm and 42.5 nm, respectively, and eight light-emitting elements using 3,10-bis[N-(dibenzofuran-3-yl)-N-phenylamino]naphtho[2,3-b;6,7-b']bisbenzofuran (abbreviation: 3,10FrA2Nbf(IV)-02) in which the thicknesses of the hole-injection layers 111 were 10 nm, 15 nm, 20 nm, 25 nm, 30 nm, 35 nm, 40 nm, and 45 nm, respectively, were fabricated.

Next, on the hole-injection layer 111, PCPPn was deposited by evaporation to a thickness of 15 nm to form the hole-transport layer 112.

Subsequently, 7-[4-(10-phenyl-9-anthryl)phenyl]-7H-dibenzo[c,g]carbazole (abbreviation: cgDBCzPA) represented as the above structural formula (ii) and 3,10PCA2Nbf (IV)-02 were deposited by co-evaporation to have a weight ratio of 1:0.01 (=cgDBCzPA: 3,10PCA2Nbf(IV)-02) to a thickness of 25 nm, or cgDBCzPA and 3,10FrA2Nbf(IV)-02 were deposited by co-evaporation to have a weight ratio of 1:0.01 (=cgDBCzPA: 3,10FrA2Nbf(IV)-02) to a thickness of 25 nm, whereby the light-emitting layer 113 was formed.

After that, on the light-emitting layer 113, cgDBCzPA was deposited by evaporation to a thickness of 5 nm, and 2,9-bis(naphthalen-2-yl)-4,7-diphenyl-1,10-phenanthroline (abbreviation: NBPhen) represented as the above structural formula (xii) was deposited by evaporation to a thickness of 15 nm, whereby the electron-transport layer 114 was formed.

After the formation of the electron-transport layer 114, lithium fluoride (LiF) was deposited by evaporation to a thickness of 1 nm to form the electron-injection layer 115, and silver (Ag) and magnesium (Mg) in a volume ratio of 1:0.1 were deposited by evaporation to a thickness of 10 nm to form the cathode 102, whereby the light-emitting elements were fabricated. Note that the cathode 102 is a semi-transmissive and semi-reflective electrode having a function of reflecting light and a function of transmitting light, and the light-emitting elements of this example are top-emission elements from which light is extracted through the cathode 102. In addition, 1,3,5-tri(dibenzothiophen-4-yl)-benzene (abbreviation: DBT3P-II) represented as the above structural formula (xiv) was deposited by evaporation to a thickness of 70 nm on the cathode 102, whereby the extraction efficiency was improved.

Each of the fabricated light-emitting elements was sealed using a glass substrate (a sealing material was applied to surround the element, followed by UV treatment and one-hour heat treatment at 80° C. at the time of sealing) in a glove box containing a nitrogen atmosphere so that the light-emitting element is not exposed to the air, and then measurements were carried out. Note that the measurements were carried out at room temperature.

The relation between y chromaticity and current efficiency at around 1000 cd/m² is shown in FIG. 123. BD-05 and BD-06 correspond to light-emitting elements using 3,10PCA2Nbf(IV)-02 and 3,10FrA2Nbf(IV)-02 as dopants, respectively. The light-emitting elements using 3,10PCA2Nbf(IV)-02 as a dopant obtain high current efficiency in a pure blue region like the chromaticity of NTSC standard. The major factors of this are probably the fluorescent quantum yield and molar absorption coefficient of 3,10PCA2Nbf(IV)-02 being significantly high. Meanwhile, devices using 3,10FrA2Nbf(IV)-02 are excellent in current efficiency in a region with deep y chromaticity, and obtain high current efficiency even in blue-color chromaticity of BT.2020 standard. Since 3,10FrA2Nbf(IV)-02 has a short emission wavelength, it is a material advantageous in obtaining deep blue light emission like blue of BT.2020 standard. From the above, it is found that, when considering application to a display utilizing microcavity effects or the like, 3,10PCA2Nbf(IV)-02 is a dopant useful in obtaining pure blue like NTSC standard, and 3,10FrA2Nbf(IV)-02 is a dopant useful in aiming at a deep blue region like BT.2020 standard.

Example 19

Synthesis Example 8

In this synthesis example, a method for synthesizing 3,10-bis[N-(9-phenyl-9H-carbazol-3-yl)-N-phenylamino]naphtho[2,3-b;7,6-b']bisbenzofuran (abbreviation: 3,10PCA2Nbf(II)) will be described in detail. The structural formula of 3,10PCA2Nbf(II) is shown below.

[Chemical Formula 102]

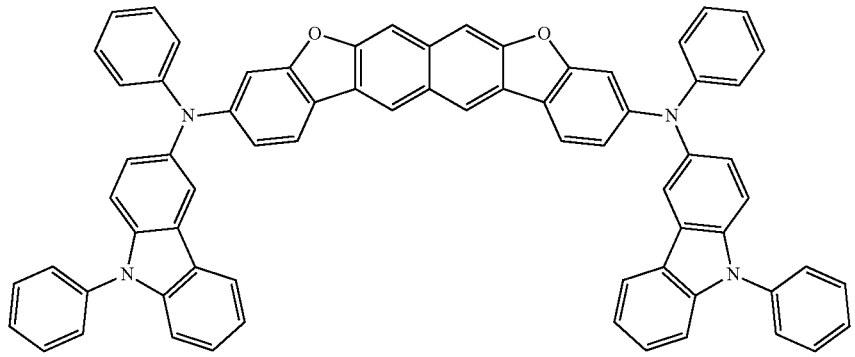

Step 1: Synthesis of 3,6-bis(4-chloro-2-fluorophenyl)-2,7-dimethoxynaphthalene

Into a 200 mL three-necked flask were put 3.0 g (8.7 mmol) of 3,6-dibromo-2,7-dimethoxynaphthalene, 3.3 g (19 mmol) of 4-chloro-2-fluorophenylboronic acid, 5.8 g (42 mmol) of potassium carbonate, and 0.13 g (0.43 mmol) of tris(2-methylphenyl)phosphine. To this mixture was added 85 mL of toluene. This mixture was degassed by being stirred while the pressure was reduced. To this mixture was added 19 mg (87 μmol) of palladium(II) acetate, and the mixture was stirred under a nitrogen stream at 60° C. for 14 hours and at 120° C. for 11.5 hours. Note that, in the middle of the stirring, 3.0 g (17 mmol) of 4-chloro-2-fluorophenylboronic acid and 4.8 g (35 mmol) of potassium carbonate were added to the mixture.

After the stirring, toluene was added to this mixture, which was then subjected to suction filtration through Florisil (manufactured by Wako Pure Chemical Industries, Ltd., Catalog Number: 540-00135), Celite (manufactured by Wako Pure Chemical Industries, Ltd., Catalog Number: 531-16855), and alumina to give a filtrate, and the filtrate was concentrated to give an oily substance. The obtained oily substance was purified by silica gel column chromatography (developing solvent: toluene:hexane=1:2). The obtained solid was purified by high performance liquid column chromatography. The high performance liquid column chromatography was performed using chloroform as a developing solvent. The fractions obtained were concentrated to give 5.8 g of a white solid, which was the target substance, in a yield of 76%. The synthesis scheme of Step 1 is shown below.

[Chemical Formula 103]

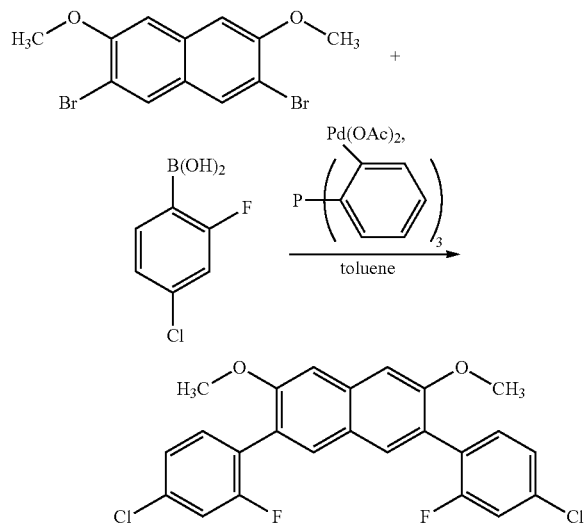

Step 2: Synthesis of 3,6-bis(4-chloro-2-fluorophenyl)-2,7-dihydroxynaphthalene

Into a 200 mL three-necked flask was put 5.8 g (13 mmol) of 3,6-bis(4-chloro-2-fluorophenyl)-2,7-dimethoxynaphthalene, and the air in the flask was replaced with nitrogen. Into this flask, 33 mL of dichloromethane was added. Into this solution, 29 mL of boron tribromide (approximately 1.0 mol/L of dichloromethane solution) and 40 mL of dichloromethane were dropped. After the dropping, this solution was stirred at room temperature. After the stirring, approximately 20 mL of water was added to this solution and the solution was stirred while being cooled with ice. After the stirring, the aqueous layer of this mixture was subjected to extraction with dichloromethane, and the solution of the extract and the organic layer were combined and washed with water and a saturated aqueous solution of sodium hydrogen carbonate. Magnesium sulfate was added to the organic layer to adsorb moisture, and then the resulting mixture was subjected to gravity filtration. The obtained filtrate was concentrated to give 5.7 g of a white solid. The synthesis scheme of Step 2 is shown below.

[Chemical Formula 104]

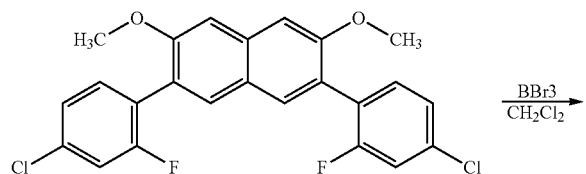

-continued

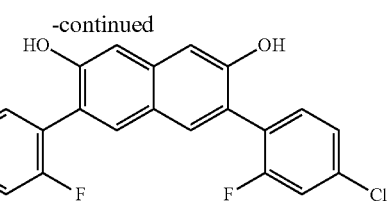

Step 3: Synthesis of 3,10-dichloronaphtho[2,3-b;7,6-b']bisbenzofuran

Into a 200 mL three-necked flask were put 2.5 g (5.7 mmol) of 3,6-bis(4-chloro-2-fluorophenyl)-2,7-dihydroxynaphthalene and 7.6 g (55 mmol) of potassium carbonate. To this mixture was added 137 mL of N-methyl-2-pyrrolidone, and this mixture was degassed by being stirred while the pressure was reduced. After the degassing, this mixture was stirred under a nitrogen stream at 120° C. for six hours. After the stirring, water was added to the mixture, and a precipitated solid was collected by filtration. This solid was washed with water and ethanol. Ethanol was added to the obtained solid, which was then stirred while being heated and filtered to give a solid. The obtained solid was recrystallized with toluene to give 4.4 g of a white solid in a yield of 86%. The synthesis scheme of Step 3 is shown below.

[Chemical Formula 105]

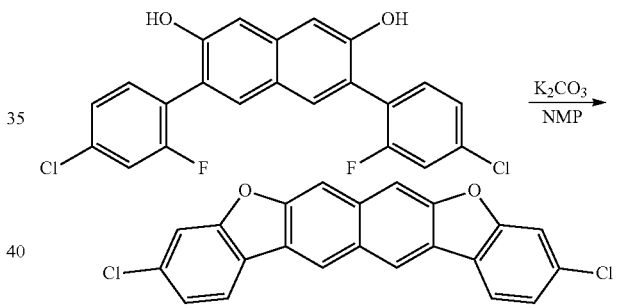

Step 4: Synthesis of 3,10-bis[N-(9-phenyl-9H-carbazol-3-yl)-N-phenylamino]naphtho[2,3-b;7,6-b']bisbenzofuran (abbreviation: 3,10PCA2Nbf(II)

Into a 200 mL three-necked flask were put 0.97 g (2.6 mmol) of 3,10-dichloronaphtho[2,3-b;7,6-b']bisbenzofuran, 2.4 g (6.4 mmol) of 3-anilino-9-phenylcarbazole, 92 mg (0.26 mmol) of di(1-adamantyl)-n-butylphosphine, and 1.5 g (15 mmol) of sodium tert-butoxide. To this mixture was added 25 mL of xylene. This mixture was degassed by being stirred while the pressure was reduced. To this mixture was added 30 mg (51 μmol) of bis(dibenzylideneacetone)palladium(0), and the mixture was stirred under a nitrogen stream at 150° C. for 14.5 hours.

After the stirring, toluene was added to this mixture, which was then subjected to suction filtration through Florisil, Celite, and alumina to give a filtrate. The obtained filtrate was concentrated to give a solid. This solid was purified by silica gel column chromatography (developing solvent: toluene:hexane=1:2) to give a solid. The obtained solid was reprecipitated with a mixed solvent of toluene and ethanol to give 2.6 g of a yellow solid. Then, 1.4 g of the obtained solid was purified by high performance liquid column chromatography. The high performance liquid column chromatography was performed using chloroform as a developing solvent. After the purification, toluene was added to the obtained solid, and suction filtration through Florisil, Celite, and alumina was conducted to give a filtrate. The obtained filtrate was concentrated to give a solid. The obtained solid was reprecipitated with a mixed solvent of toluene and ethanol to give 1.1 g of a yellow solid. By a train sublimation method, 1.1 g of the obtained solid was sublimated and purified. The sublimation purification was performed by heating at 393° C. under the conditions where the pressure was $1.9 \times 10^{-2}$ Pa and the argon flow rate was 0 mL/min. After the sublimation purification, 0.80 g of a yellow solid was obtained at a collection rate of 77%. The synthesis scheme of Step 4 is shown below.

eter, manufactured by Hitachi High-Technologies Corporation). The emission spectra were measured using a fluorescence spectrophotometer (FS920 manufactured by Hamamatsu Photonics K.K.). The emission quantum yield was measured using an absolute PL quantum yield measurement system (Quantaurus-QY manufactured by Hamamatsu Photonics K.K.).

As can be seen from FIG. 127, the toluene solution of 3,10PCA2Nbf(II) has absorption peaks at 413 nm, 392 nm, 353 nm, 320 nm, 300 nm, and 282 nm, and an emission wavelength peak at 443 nm (excitation wavelength 390 nm). In addition, as can be seen from FIG. 128, the thin film of 3,10PCA2Nbf(II) has absorption peaks at 416 nm, 394 nm, 356 nm, 325 nm, and 298 nm, and an emission wavelength peak at 492 nm (excitation wavelength 395 nm). These

[Chemical Formula 106]

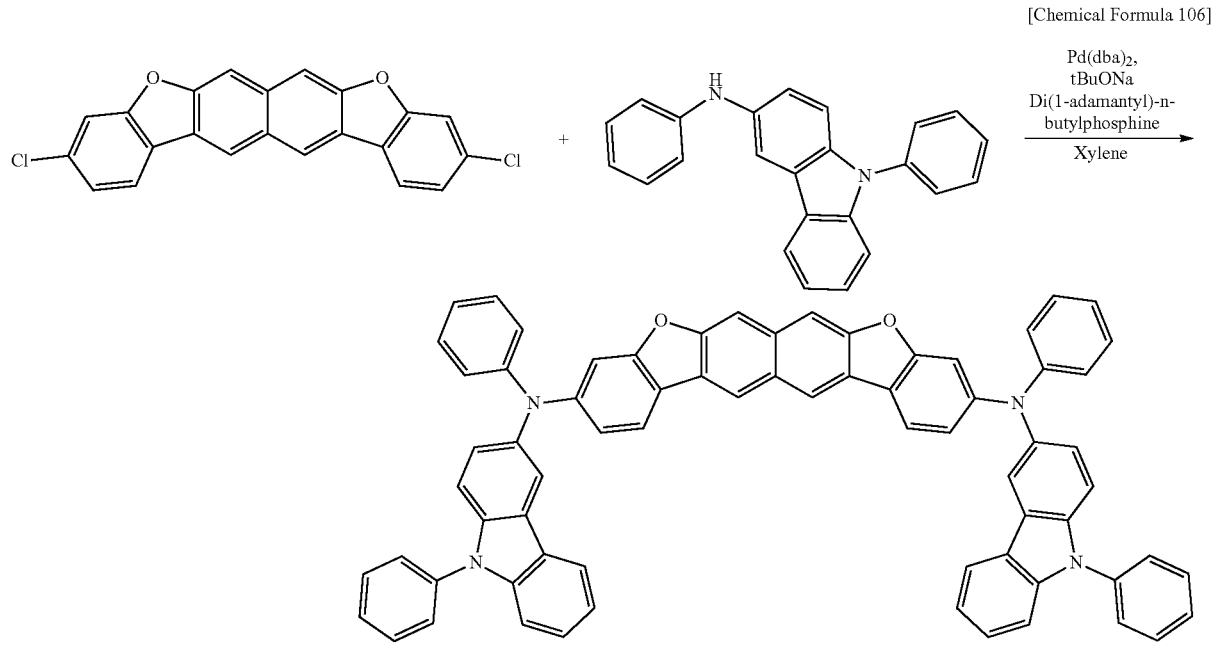

FIG. 126 shows $^1$H NMR data of the obtained solid, whose numerical data is given below. The data indicates that 3,10PCA2Nbf(II), which is an organic compound of one embodiment of the present invention, was obtained in this synthesis example.

$^1$H NMR (DMSO-d$_6$, 300 MHz): δ=7.01 (dd, J1=8.1 Hz, J2=1.8 Hz, 2H), 7.05-7.11 (m, 4H), 7.17-7.26 (m, 6H), 7.29-7.46 (m, 12H), 7.52-7.57 (m, 2H), 7.65-7.72 (m, 8H), 8.06 (d, J1=8.1 Hz, 2H), 8.10 (s, 2H), 8.16 (d, J1=1.8 Hz, 2H), 8.21 (d, J1=7.8 Hz, 2H), 8.61 (s, 2H).

Next, the measurement results of the absorption spectrum and emission spectrum of a toluene solution of 3,10PCA2Nbf(II) are shown in FIG. 127. In addition, the absorption spectrum and emission spectrum of a thin film of 3,10PCA2Nbf(II) are shown in FIG. 128. The solid thin film was formed over a quartz substrate by a vacuum evaporation method. The absorption spectrum of the toluene solution was measured using an ultraviolet-visible light spectrophotometer (V550 type manufactured by JASCO Corporation). The shown absorpotion spectrum is the one from which the spectrum of toluene alone in a quartz cell has been subtracted. The absorption spectrum of the thin film was measured using a spectrophotometer (U4100 Spectrophotomresults indicate that 3,10PCA2Nbf(II) emits blue light and can be used as a host for a light-emitting substance or a host for a substance that emits fluorescence in the visible region.

Furthermore, the measured emission quantum yield in the toluene solution was as high as 92%, which indicates that 3,10PCA2Nbf(II) is suitable as a light-emitting material.

In addition, 3,10PCA2Nbf(II) obtained in this example was analyzed by LC/MS analysis. The fabrication method of the sample, and the measurement method and conditions were similar to those of Synthesis Example 3 in Example 3.

A component with m/z=972.35, which is an ion derived from 3,10PCA2Nbf(II), was subjected to the MS$^2$ measurement by a Targeted-MS$^2$ method. For setting of the Targeted-MS$^2$, the mass range of a target ion was set to m/z=972.35±2.0 (isolation window=4) and detection was performed in a positive mode. Measurement was performed with energy NCE for accelerating the target ion in a collision cell set to 50. The obtained MS spectrum is shown in FIG. 129.

From the results in FIG. 129, it was found that product ions from 3,10PCA2Nbf(II) are detected mainly at around m/z=896, 729, 333, and 256. Note that the results shown in FIG. 129 exhibit characteristic results derived from 3,10PCA2Nbf(II) and therefore are important data for identifying 3,10PCA2Nbf(II) contained in a mixture.

Note that the product ion around m/z=896 is presumed to be a cation in the state where a phenyl group was eliminated from 3,10PCA2Nbf(II), which suggests that 3,10PCA2Nbf(II) contains a phenyl group. Furthermore, the product ion around m/z=729 is presumed to be a cation in the state where a 9-phenylcarbazolyl group was eliminated from 3,10PCA2Nbf(II), which suggests that 3,10PCA2Nbf(II) contains a 9-phenylcarbazolyl group.

Furthermore, the product ion around m/z=333 is presumed to be a cation in the state where a 3-[N-(9-phenyl-9H-carbazol-3-yl)-N-phenylamino]naphtho[2,3-b;7,6-b'] bisbenzofuranyl group was eliminated from 3,10PCA2Nbf (II), which suggests that 3,10PCA2Nbf(II) contains a 3-[N-(9-phenyl-9H-carbazol-3-yl)-N-phenylamino]naphtho[2,3-b;7,6-b']bisbenzofuranyl group.

Example 20

Synthesis Example 9

In this synthesis example, a method for synthesizing 2,9-bis[N-(dibenzofuran-3-yl)-N-phenylamino]naphtho[2,1-b;6,5-b']bisbenzofuran (abbreviation: 2,9FrA2Nbf(III)-02), which is shown in Embodiment 1, will be described in detail. The structural formula of 2,9FrA2Nbf(III)-02 is shown below.

[Chemical Formula 107]

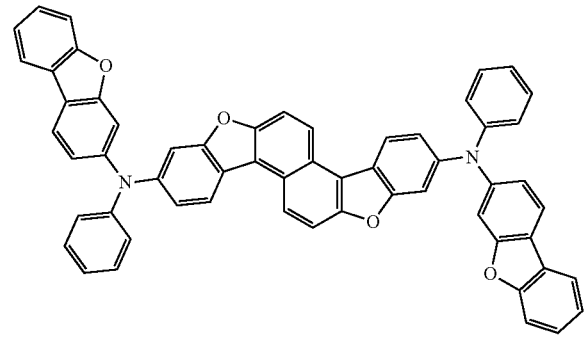

Step 1: Synthesis of 1,5-bis(4-chloro-2-fluorophenyl)-2,7-dihydroxynaphthalene

The synthesis was conducted in a similar manner to Step 1 of Synthesis Example 2 in Example 2.

Step 2: Synthesis of 2,9-dichloronaphtho[2,1-b;6,5-b']bisbenzofuran

The synthesis was conducted in a similar manner to Step 2 of Synthesis Example 2 in Example 2.

Step 3: Synthesis of 2,9-bis[N-(dibenzofuran-3-yl)-N-phenylamino]naphtho[2,1-b;6,5-b']bisbenzofuran (abbreviation: 2,9FrA2Nbf(III)-02)

Into a 200 mL three-necked flask were put 1.2 g (3.0 mmol) of 2,9-dichloronaphtho[2,1-b;6,5-b']bisbenzofuran, 2.0 g (7.7 mmol) of N-(dibenzofuran-3-yl)-N-phenylamine, 0.11 g (0.30 mmol) of di(1-adamantyl)-n-butylphosphine, and 1.8 g (18 mmol) of sodium tert-butoxide. To this mixture was added 30 mL of xylene. This mixture was degassed by being stirred while the pressure was reduced. To this mixture was added 35 mg (60 μmol) of bis(dibenzylideneacetone) palladium(0), and the mixture was stirred under a nitrogen stream at 150° C. for 21.5 hours. After the stirring, water and ethanol were added to this mixture, and after the irradiation with ultrasonic waves, the mixture was filtered to give a solid. This solid was purified by silica gel column chromatography (developing solvent: toluene). The obtained solid was recrystallized with toluene twice, so that 1.5 g of a yellow solid was obtained in a yield of 62%. By a train sublimation method, 1.5 g of the obtained solid was sublimated and purified. The sublimation purification was performed by heating at 365° C. under the conditions where the pressure was $1.9 \times 10^{-2}$ Pa and the argon flow rate was 0 mL/min. After the sublimation purification, 1.2 g of a yellow solid was obtained at a collection rate of 82%. The synthesis scheme of Step 3 is shown below.

[Chemical Formula 108]

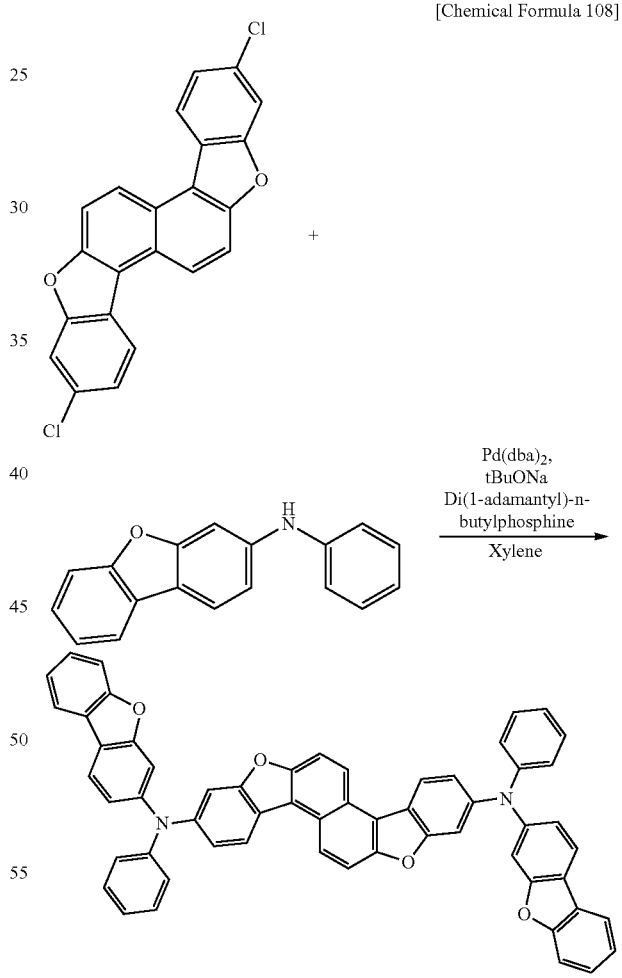

FIG. 130 shows ¹H NMR data of the obtained solid, whose numerical data is given below. The data indicates that 2,9FrA2Nbf(III)-02, which is an organic compound of one embodiment of the present invention, was obtained in this example.

¹H NMR (CD₂Cl₂, 300 MHz): δ=7.11-7.17 (m, 2H), 7.20 (dd, J1=8.4 Hz, J2=2.1 Hz, 2H), 7.24-7.28 (m, 4H), 7.30-

7.45 (m, 12H), 7.46 (d, J1=2.4 Hz, 2H), 7.53 (d, J1=8.4 Hz, 2H), 7.87 (d, J1=8.1 Hz, 2H), 7.91-7.96 (m, 4H), 8.33 (d, J1=8.4 Hz, 2H), 8.64 (d, J1=9.3 Hz, 2H).

Next, the measurement results of the absorption spectrum and emission spectrum of a toluene solution of 2,9FrA2Nbf (III)-02 are shown in FIG. 131. In addition, the absorption spectrum and emission spectrum of a thin film of 2,9FrA2Nbf(III)-02 are shown in FIG. 132. The solid thin film was formed over a quartz substrate by a vacuum evaporation method. The absorption spectrum of the toluene solution was measured using an ultraviolet-visible light spectrophotometer (V550 type manufactured by JASCO Corporation). The shown absorpotion spectrum is the one from which the spectrum of toluene alone in a quartz cell has been subtracted. The absorption spectrum of the thin film was measured using a spectrophotometer (U4100 Spectrophotometer, manufactured by Hitachi High-Technologies Corporation). The emission spectra were measured using a fluorescence spectrophotometer (FS920 manufactured by Hamamatsu Photonics K.K.). The emission quantum yield was measured using an absolute PL quantum yield measurement system (Quantaurus-QY manufactured by Hamamatsu Photonics K.K.).

As can be seen from FIG. 131, the toluene solution of 2,9FrA2Nbf(III)-02 has absorption peaks at 419 nm, 399 nm, 348 nm, 323 nm, 294 nm, and 282 nm, and emission wavelength peaks at 435 nm and 459 nm (excitation wavelength 398 nm). In addition, as can be seen from FIG. 132, the thin film of 2,9FrA2Nbf(III)-02 has absorption peaks at 425 nm, 404 nm, 352 nm, 325 nm, 299 nm, and 274 nm, and emission wavelength peaks at 452 nm and 473 nm (excitation wavelength 400 nm). These results indicate that 2,9FrA2Nbf(III)-02 emits blue light and can be used as a host for a light-emitting substance or a host for a substance that emits fluorescence in the visible region.

Furthermore, the measured emission quantum yield in the toluene solution was as high as 94%, which indicates that 2,9FrA2Nbf(III)-02 is suitable as a light-emitting material.

Subsequently, 2,9FrA2Nbf(III)-02 obtained in this example was analyzed by LC/MS analysis. The fabrication method of the sample, and the measurement method and conditions were similar to those of Synthesis Example 3 in Example 3.

A component with m/z=822.25, which is an ion derived from 2,9FrA2Nbf(III)-02, was subjected to the $MS^2$ measurement by a Targeted-$MS^2$ method. For setting of the Targeted-$MS^2$ the mass range of a target ion was set to m/z=822.25±2.0 (isolation window=4) and detection was performed in a positive mode. Measurement was performed with energy NCE for accelerating the target ion in a collision cell set to 60. The obtained MS spectrum is shown in FIG. 133.

From the results in FIG. 133, it was found that product ions from 2,9FrA2Nbf(III)-02 are detected mainly at around m/z=746, 656, 563, 487, 397, 258, and 182. Note that the results shown in FIG. 133 exhibit characteristic results derived from 2,9FrA2Nbf(III)-02 and therefore are important data for identifying 2,9FrA2Nbf(III)-02 contained in a mixture.

Note that the product ion around m/z=746 is presumed to be a cation in the state where a phenyl group was eliminated from 2,9FrA2Nbf(III)-02, which suggests that 2,9FrA2Nbf (III)-02 contains a phenyl group. Furthermore, the product ion around m/z=656 is presumed to be a cation in the state where a dibenzofuranyl group was eliminated from 2,9FrA2Nbf(III)-02, which suggests that 2,9FrA2Nbf(III)-02 contains a dibenzofuranyl group. Note that the product ion around m/z=563 is presumed to be a cation in the state where an N-(dibenzofuran-3-yl)-N-phenylamino group was eliminated from 2,9FrA2Nbf(III)-02, which suggests that 2,9FrA2Nbf(III)-02 contains an N-(dibenzofuran-3-yl)-N-phenylamino group. Furthermore, the product ion around n/z=258 is presumed to be a cation in the state where a 2-[N-(dibenzofuran-3-yl)-N-phenylamino]naphtho[2,1-b;6,5-b']bisbenzofuranyl group was eliminated from 2,9FrA2Nbf(III)-02, which suggests that 2,9FrA2Nbf(III)-02 contains a 2-[N-(dibenzofuran-3-yl)-N-phenylamino] naphtho[2,1-b;6,5-b']bisbenzofuranyl group.

Example 21

Synthesis Example 10

In this synthesis example, a method for synthesizing 2,9-bis[N-(dibenzofuran-4-yl)-N-phenylamino]-6,13-diphenylnaphtho[2,1-b;6,5-b']bisbenzofuran (abbreviation: ph-2,9FrA2Nbf(III)-II), which is an organic compound of one embodiment of the present invention, will be described in detail. The structural formula of ph-2,9FrA2Nbf(III)-II is shown below.

[Chemical Formula 109]

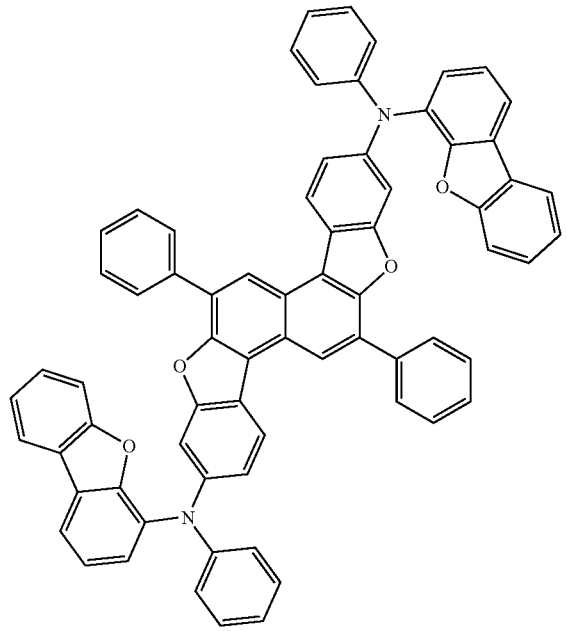

Step 1: Synthesis of
2,6-dimethoxy-3,7-diphenylnaphthalene

Into a 200 mL three-necked flask were put 3.1 g (7.1 mmol) of 3,7-diiodo-2,6-dimethoxynaphthalene, 3.5 g (16 mmol) of phenylboromic acid, 4.3 g (31 mmol) of potassium carbonate, and 0.22 g (0.72 mmol) of tris(2-methylphenyl) phosphine, and the air in the flask were replaced with nitrogen. To this mixture was added 50 mL of toluene. This mixture was degassed by being stirred while the pressure was reduced. To this mixture was added 43 mg (0.14 mmol) of palladium(II) acetate, and the mixture was stirred under a nitrogen stream at 120° C. for seven hours. After the stirring, toluene was added to this mixture, which was then subjected to suction filtration through Florisil, Celite, and alumina to give a filtrate. The filtrate was concentrated to give a solid. The obtained solid was purified by silica gel column chromatography (developing solvent: toluene). The obtained solid was recrystallized with a mixed solvent of toluene and ethyl acetate to give 2.2 g of a pale yellow solid in a yield of 90%. The synthesis scheme of Step 1 is shown below.

[Chemical Formula 110]

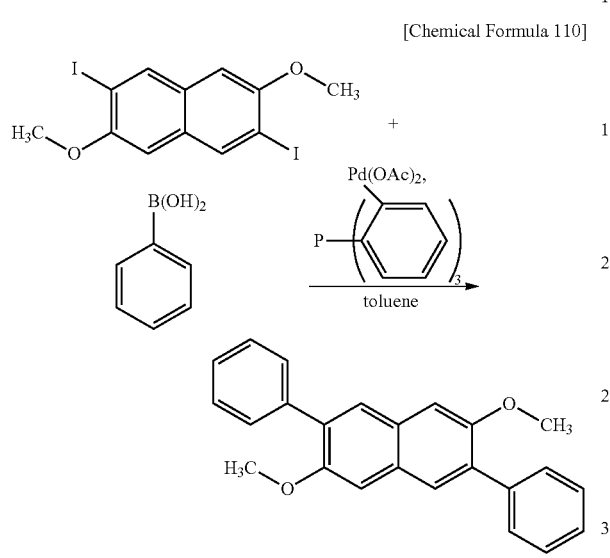

Given below is $^1$H NMR data of the obtained solid. The data indicates that 2,6-dimethoxy-3,7-diphenylnaphthalene was obtained.

$^1$H NMR (DMSO-d$_6$, 300 MHz): δ=3.85 (s, 6H), 7.34-7.49 (m, 8H), 7.55-7.59 (m, 4H), 7.77 (s, 2H).

Step 2: Synthesis of 2,6-bis(2-bromo-5-chlorophenoxy)-3,7-diphenylnaphthalene

Into a 100 mL three-necked flask was put 2.2 g (6.4 mmol) of 2,6-dimethoxy-3,7-diphenylnaphthalene, and the air in the flask was replaced with nitrogen. Into this flask was added 16 mL of dichloromethane. Into this solution, 14 mL (14 mmol) of boron tribromide (approximately 1.0 mol/L of dichloromethane solution) and 10 mL of dichloromethane were dropped. After the dropping, this solution was stirred at room temperature all night. After the stirring, approximately 20 mL of water was added to this solution and the solution was stirred while being cooled with ice. After the stirring, the aqueous layer of this mixture was subjected to extraction with dichloromethane, and the solution of the extract and the organic layer were combined and washed with water and a saturated aqueous solution of sodium hydrogen carbonate. The organic layer was dried using magnesium sulfate, and after the drying, this mixture was subjected to gravity filtration. The obtained filtrate was concentrated to give a white solid.

Into a 200 mL three-necked flask were put the obtained white solid, 4.2 g (20 mmol) of 1-bromo-4-chloro-2-fluorobenzene, and 6.1 g (19 mmol) of cesium carbonate. To this mixture was added 30 mL of N-methyl-2-pyrrolidone, and this mixture was degassed by being stirred while the pressure was reduced. After the degassing, this mixture was stirred under a nitrogen stream at 120° C. for seven hours. After the stirring, water was added to this mixture, and after the irradiation with ultrasonic waves, the mixture was filtered to give a solid. The obtained solid was washed with water and ethanol. This solid was purified by silica gel column chromatography (developing solvent: toluene). The obtained solid was recrystallized with a mixed solvent of toluene and ethyl acetate to give 1.9 g of a white solid in a yield of 42%. The synthesis scheme of Step 2 is shown below.

[Chemical Formula 111]

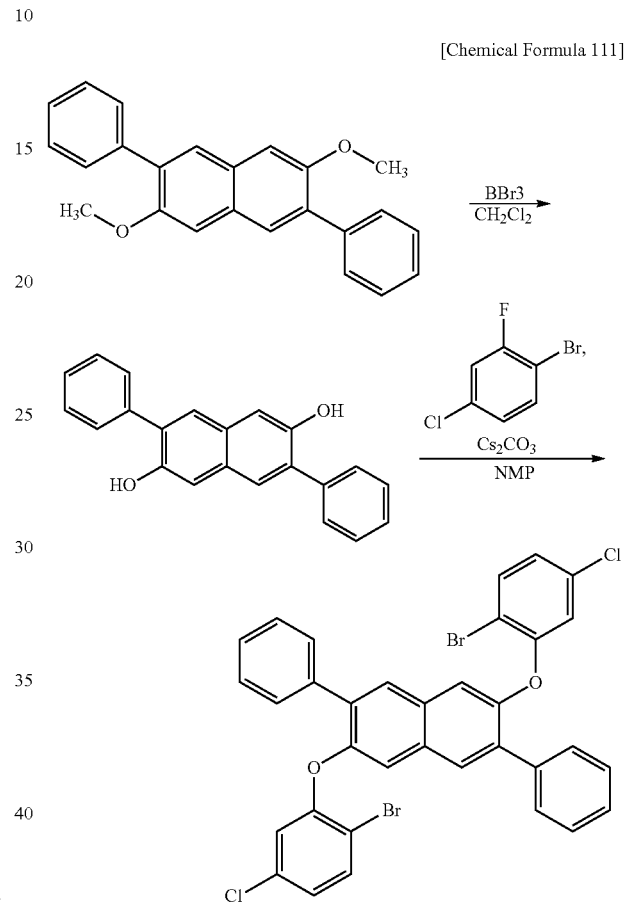

Given below is $^1$H NMR data of the obtained solid. The data indicates that 2,6-bis(2-bromo-5-chlorophenoxy)-3,7-diphenylnaphthalene was obtained.

$^1$H NMR (DMSO-d$_6$, 300 MHz): δ=7.06 (d, J1=2.4 Hz, 2H), 7.16 (dd, J1=9.0 Hz, J2=2.4 Hz, 2H), 7.32-7.46 (m, 6H), 7.54 (s, 2H), 7.67-7.35 (m, 6H), 8.08 (s, 2H).

Step 3: Synthesis of 2,9-dichloro-6,13-diphenylnaphtho[2,1-b;6,5-b']bisbenzofuran Into a 200 mL three-necked flask were put 1.8 g (2.7 mmol) of 2,6-bis(2-bromo-5-chlorophenoxy)-3,7-diphenylnaphthalene, 0.14 g (0.53 mol) of triphenylphosphine, and 2.1 g (6.4 mmol) of cesium carbonate. To this mixture was added 20 mL of N-methyl-2-pyrrolidone, and this mixture was degassed by being stirred while the pressure was reduced. After the degassing, this mixture was stirred under a nitrogen stream at 120° C. for 15.5 hours. After the stirring, water was added to this mixture, and after the irradiation with ultrasonic waves, the mixture was filtered to give a solid. The obtained solid was dissolved in toluene, and the solution was subjected to suction filtration through Florisil, Celite, and alumina to give a filtrate. The obtained filtrate was concentrated to give a solid. The obtained solid was recrystallized with toluene, so that 1.1 g of a pale yellow solid was obtained in a yield of 76%. The synthesis scheme of Step 3 is shown below.

[Chemical Formula 112]

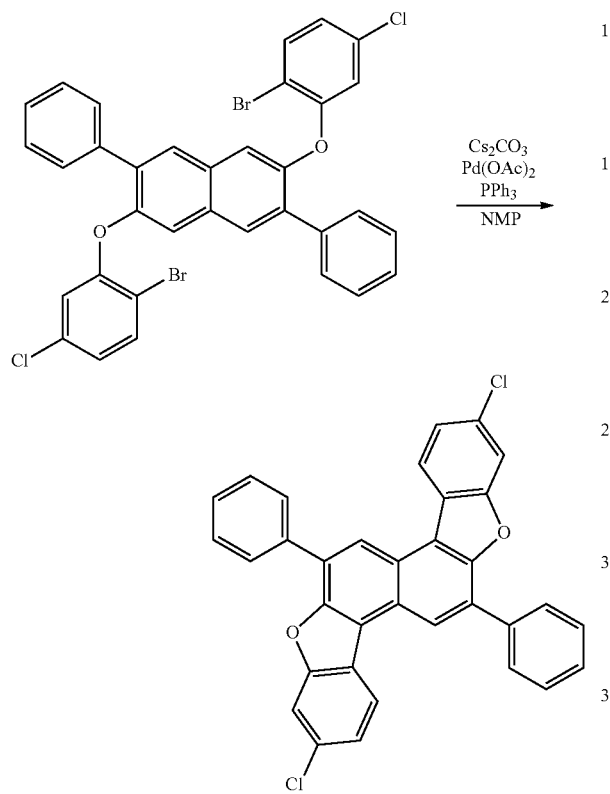

Given below is $^1$H NMR data of the obtained solid. The data indicates that 2,9-dichloro-6,13-diphenylnaphtho[2,1-b;6,5-b']bisbenzofuran was obtained.

$^1$H NMR (1,1,2,2-Tetrachloroethane-D2, 300 MHz): δ=7.56-7.74 (m, 8H), 7.86 (d, J1=2.1 Hz, 2H), 8.13 (d, J1=7.5 Hz, 4H), 8.46 (d, J1=8.7 Hz, 2H), 8.84 (s, 2H).

Step 4: Synthesis of 2,9-bis[N-(dibenzofuran-4-yl)-N-phenylamino]-6,13-diphenylnaphtho[2,1-b;6,5-b']bisbenzofuran (abbreviation: ph-2,9FrA2Nbf(III)-II)

Into a 200 mL three-necked flask were put 1.1 g (2.0 mmol) of 2,9-dichloro-6,13-diphenylnaphtho[2,1-b;6,5-b']bisbenzofuran, 1.3 g (5.0 mmol) of N-(dibenzofuran-4-yl)-N-phenylamine, 71 mg (0.20 mmol) of di(1-adamantyl)-n-butylphosphine, and 1.1 g (12 mmol) of sodium tert-butoxide. To this mixture was added 20 mL of xylene. This mixture was degassed by being stirred while the pressure was reduced. To this mixture was added 21 mg (40 μmol) of bis(dibenzylideneacetone)palladium(0), and the mixture was stirred under a nitrogen stream at 150° C. for 27 hours. After the stirring, water and ethanol were added to this mixture, and after the irradiation with ultrasonic waves, the mixture was filtered to give a solid.

This solid was purified by silica gel column chromatography (developing solvent: toluene). The obtained solid was recrystallized with toluene twice, so that 1.2 g of a yellow solid was obtained in a yield of 62%. By a train sublimation method, 1.1 g of the obtained solid was sublimated and purified. The sublimation purification was performed by heating at 390° C. under the conditions where the pressure was $1.6×10^{-2}$ Pa and the argon flow rate was 0 mL/min. After the sublimation purification, 0.95 g of a yellow solid was obtained at a collection rate of 88%. The synthesis scheme of Step 4 is shown below.

[Chemical Formula 113]

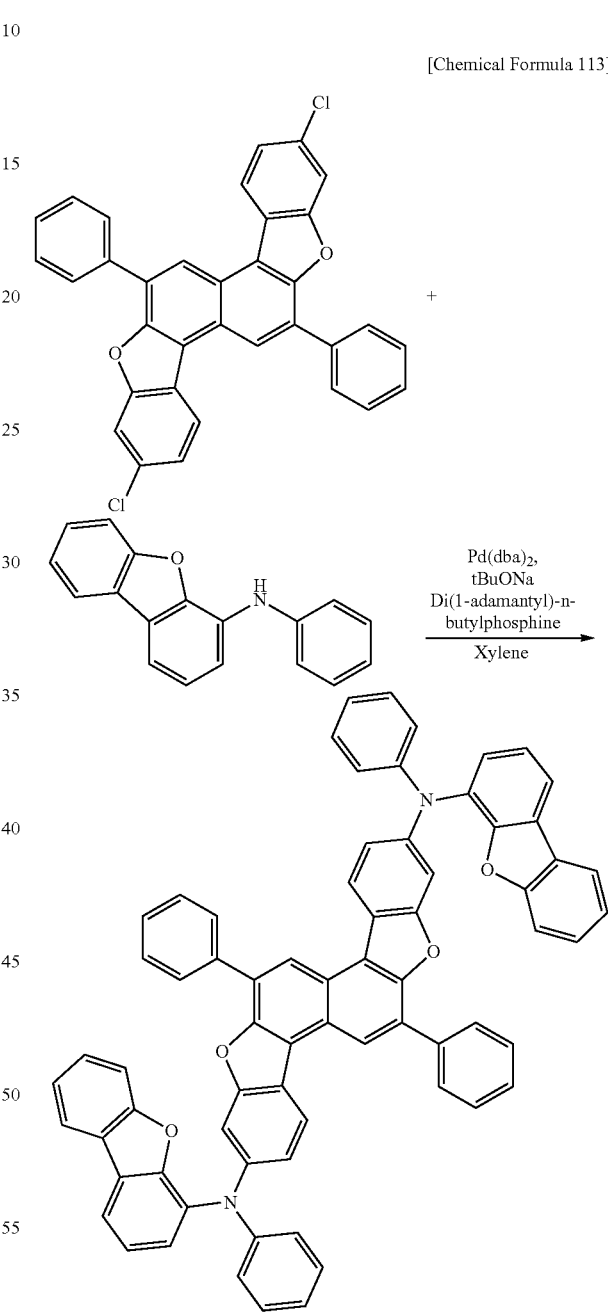

FIG. 134 shows $^1$H NMR data of the obtained solid, whose numerical data is given below. The data indicates that ph-2,9FrA2Nbf(III)-II was obtained.

$^1$H NMR (CD$_2$Cl$_2$, 300 MHz): δ=7.12 (tt, J1=6.9 Hz, J2=1.5 Hz, 2H), 7.23-7.28 (m, 6H), 7.30-7.48 (m, 18H), 7.53-7.58 (m, 4H), 7.87 (dd, J1=6.9 Hz, J2=1.5 Hz, 2H), 7.99-8.06 (m, 6H), 8.37 (d, J1=8.7 Hz, 2H), 8.72 (s, 2H).

Next, the measurement results of the absorption spectrum and emission spectrum of a toluene solution of ph-2,9FrA2Nbf(III)-II are shown in FIG. 135. In addition, the absorption spectrum and emission spectrum of a thin film of ph-2,9FrA2Nbf(III)-II are shown in FIG. 136. The solid thin film was formed over a quartz substrate by a vacuum evaporation method. The absorption spectrum of the toluene solution was measured using an ultraviolet-visible light spectrophotometer (V550 type manufactured by JASCO Corporation). The shown absorpotion spectrum is the one from which the spectrum of toluene alone in a quartz cell has been subtracted. The absorption spectrum of the thin film was measured using a spectrophotometer (U4100 Spectrophotometer, manufactured by Hitachi High-Technologies Corporation). The emission spectra were measured using a fluorescence spectrophotometer (FS920 manufactured by Hamamatsu Photonics K.K.). The emission quantum yield was measured using an absolute PL quantum yield measurement system (Quantaurus-QY manufactured by Hamamatsu Photonics K.K.).

As can be seen from FIG. 135, the toluene solution of ph-2,9FrA2Nbf(III)-II has absorption peaks at 429 nm, 409 nm, 367 nm, 351 nm, 313 nm, and 295 nm, and emission wavelength peaks at 462 nm and 483 nm (excitation wavelength 406 nm). In addition, as can be seen from FIG. 136, the thin film of ph-2,9FrA2Nbf(III)-II has absorption peaks at 437 nm, 420 nm, 373 nm, 325 nm, and 294 nm, and emission wavelength peaks at 487 nm and 513 nm (excitation wavelength 420 nm). These results indicate that ph-2,9FrA2Nbf(III)-II emits blue light and can be used as a host for a light-emitting substance or a host for a substance that emits fluorescence in the visible region.

Furthermore, the measured emission quantum yield in the toluene solution was as high as 98%, which indicates that ph-2,9FrA2Nbf(III)-II is suitable as a light-emitting material.

Subsequently, ph-2,9FrA2Nbf(III)-II obtained in this example was analyzed by LC/MS analysis. The fabrication method of the sample, and the measurement method and conditions were similar to those of Synthesis Example 3 in Example 3.

A component with m/z=974.31, which is an ion derived from ph-2,9FrA2Nbf(III)-II, was subjected to the MS$^2$ measurement by a Targeted-MS$^2$ method. For setting of the Targeted-MS$^2$, the mass range of a target ion was set to m/z=974.31±2.0 (isolation window=4) and detection was performed in a positive mode. Measurement was performed with energy NCE for accelerating the target ion in a collision cell set to 60. The obtained MS spectrum is shown in FIG. 137.

From the results in FIG. 137, it was found that product ions from ph-2,9FrA2Nbf(III)-II are detected mainly at around n/z=896, 715, 639, 549, and 275. Note that the results shown in FIG. 137 exhibit characteristic results derived from ph-2,9FrA2Nbf(III)-II and therefore are important data for identifying ph-2,9FrA2Nbf(III)-II contained in a mixture.

Note that the product ion around m/z=896 is presumed to be a cation in the state where a phenyl group was eliminated from ph-2,9FrA2Nbf(III)-II, which suggests that ph-2,9FrA2Nbf(III)-II contains a phenyl group. Furthermore, the product ion around m/z=715 is presumed to be a cation in the state where an N-(dibenzofuran-4-yl)-N-phenylamino group was eliminated from ph-2,9FrA2Nbf(III)-II, which suggests that ph-2,9FrA2Nbf(III)-II contains an N-(dibenzofuran-4-yl)-N-phenylamino group.

Furthermore, the product ion around m/z=257 is presumed to be a cation in the state where a 2-[N-(dibenzofuran-4-yl)-N-phenylamino]-6,13-diphenylnaphtho[2,1-b;6,5-b']bisbenzofuranyl group was eliminated from ph-2,9FrA2Nbf(III)-II, which suggests that ph-2,9FrA2Nbf(III)-II contains a 2-[N-(dibenzofuran-4-yl)-N-phenylamino]-6,13-diphenylnaphtho[2,1-b;6,5-b']bisbenzofuranyl group.

Example 22

Synthesis Example 11

In this synthesis example, a method for synthesizing 3,10-bis[N-(dibenzofuran-3-yl)-N-phenylamino]-6,13-diphenylnaphtho[2,3-b;6,7-b']bisbenzofuran (abbreviation: ph-3,10FrA2Nbf(IV)-02) will be described in detail. The structural formula of ph-3,10FrA2Nbf(IV)-02 is shown below.

[Chemical Formula 114]

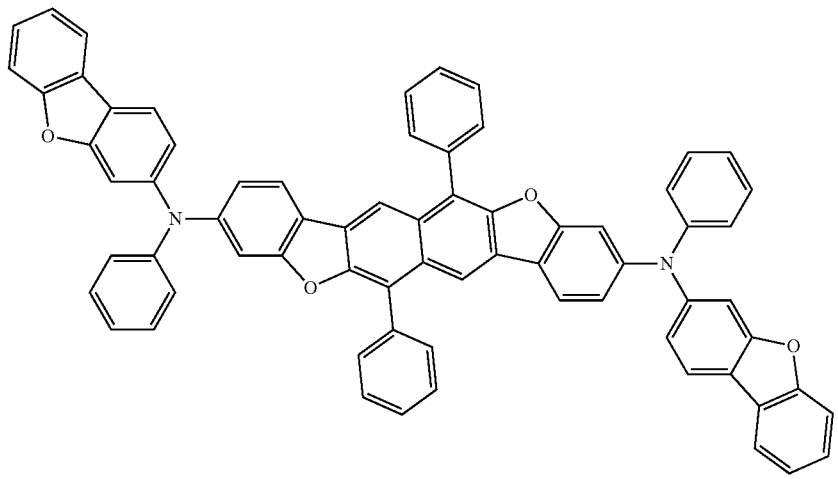

Step 1: Synthesis of 2,6-dihydroxy-1,5-diphenylnaphthalene

The synthesis was conducted in a similar manner to Step 1 of Synthesis Example 7 in Example 13.

Step 2: Synthesis of 2,6-bis(2-bromo-4-chlorophenoxy)-1,5-diphenylnaphthalene The synthesis was conducted in a similar manner to Step 2 of Synthesis Example 7 in Example 13.

Step 3: Synthesis of 3,10-dichloro-6,13-diphenylnaphtho[2,3-b;6,7-b']bisbenzofuran The synthesis was conducted in a similar manner to Step 3 of Synthesis Example 7 in Example 13.

Step 4: Synthesis of 3,10-bis[N-(dibenzofuran-3-yl)-N-phenylamino]-6,13-diphenylnaphtho[2,3-b;6,7-b']bisbenzofuran (abbreviation: ph-3,10FrA2Nbf (IV)-02)

Into a 200 mL three-necked flask were put 1.4 g (2.6 mmol) of 3,10-dichloro-6,13-diphenylnaphtho[2,3-b;6,7-b']bisbenzofuran, 1.7 g (6.4 mmol) of N-(dibenzofuran-3-yl)-N-phenylamine, 92 mg (0.26 mmol) of di(1-adamantyl)-n-butylphosphine, and 1.5 g (15 mmol) of sodium tert-butoxide. To this mixture was added 25 mL of xylene. This mixture was degassed by being stirred while the pressure was reduced. To this mixture was added 29 mg (51 μmol) of bis(dibenzylideneacetone)palladium(0), and the mixture was stirred under a nitrogen stream at 150° C. for 14.5 hours. After the stirring, toluene was added to this mixture, which was then subjected to suction filtration through Florisil, Celite, and alumina to give a filtrate. The obtained filtrate was concentrated to give a solid. This solid was purified by silica gel column chromatography (developing solvent: toluene:hexane=1:2 and then toluene:hexane=2:3) to give a solid.

The obtained solid was recrystallized with toluene, so that 2.0 g of a yellow solid was obtained in a yield of 78%. By a train sublimation method, 1.0 g of the obtained solid was sublimated and purified. The sublimation purification was performed by heating at 395° C. under the conditions where the pressure was $1.0 \times 10^{-2}$ Pa and the argon flow rate was 0 mL/min. After the sublimation purification, 0.90 g of a yellow solid was obtained at a collection rate of 88%. The synthesis scheme of Step 4 is shown below.

[Chemical Formula 115]

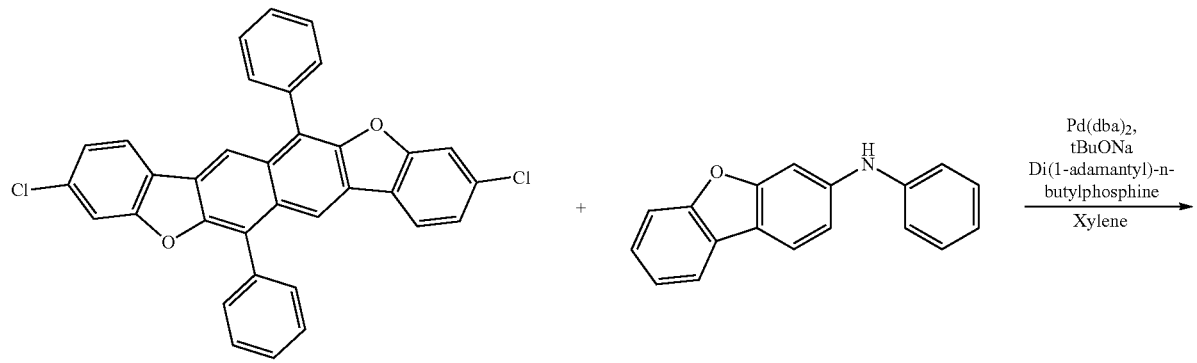

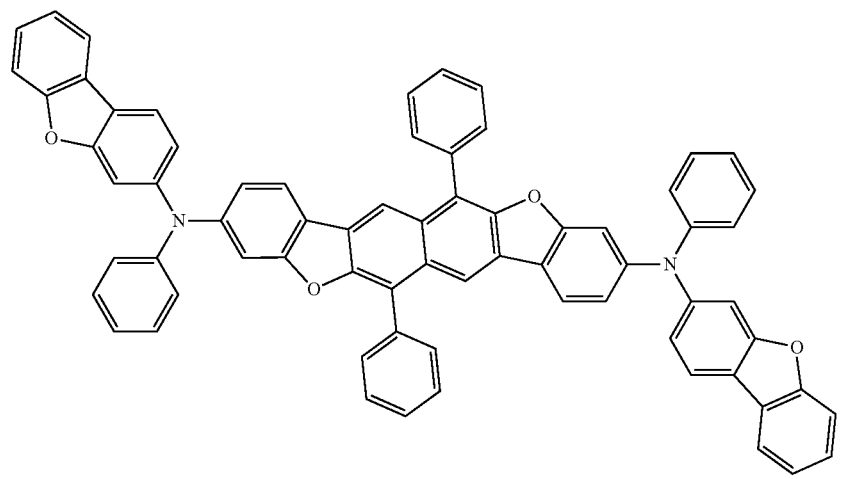

FIG. 138 shows $^1$H NMR data of the obtained solid, whose numerical data is given below. The data indicates that ph-3,10FrA2Nbf(IV)-02, which is an organic compound of one embodiment of the present invention, was obtained in this synthesis example.

$^1$H NMR (CD$_2$Cl$_2$, 300 MHz): δ=7.06-7.21 (m, 12H), 7.29-7.36 (m, 8H), 7.41 (dt, J1=1.5 Hz, J2=7.5 Hz, 2H), 7.50-7.57 (m, 4H), 7.60-7.70 (m, 8H), 7.79-7.85 (m, 4H), 7.90 (dd, J1=7.2 Hz, J2=0.9 Hz, 2H), 8.34 (s, 2H).

Next, the measurement results of the absorption spectrum and emission spectrum of a toluene solution of ph-3,10FrA2Nbf(IV)-02 are shown in FIG. 139. In addition, the absorption spectrum and emission spectrum of a thin film of ph-3,10FrA2Nbf(IV)-02 are shown in FIG. 140. The solid thin film was formed over a quartz substrate by a vacuum evaporation method. The absorption spectrum of the toluene solution was measured using an ultraviolet-visible light spectrophotometer (V550 type manufactured by JASCO Corporation). The shown absorpotion spectrum is the one from which the spectrum of toluene alone in a quartz cell has been subtracted. The absorption spectrum of the thin film was measured using a spectrophotometer (U4100 Spectrophotometer, manufactured by Hitachi High-Technologies Corporation). The emission spectra were measured using a fluorescence spectrophotometer (FS920 manufactured by Hamamatsu Photonics K.K.). The emission quantum yield was measured using an absolute PL quantum yield measurement system (Quantaurus-QY manufactured by Hamamatsu Photonics K.K.).

As can be seen from FIG. 139, the toluene solution of ph-3,10FrA2Nbf(IV)-02 has absorption peaks at 436 nm, 411 nm, 352 nm, 325 nm, and 281 nm, and emission wavelength peaks at 450 nm and 480 nm (excitation wavelength 412 nm). In addition, as can be seen from FIG. 140, the thin film of ph-3,10FrA2Nbf(IV)-02 has absorption peaks at 444 nm, 419 nm, 358 nm, 327 nm, 299 nm, and 262 nm, and emission wavelength peaks at 471 nm, 517 nm, and 552 nm (excitation wavelength 420 nm). These results indicate that ph-3,10FrA2Nbf(IV)-02 emits blue light and can be used as a host for a light-emitting substance or a host for a substance that emits fluorescence in the visible region.

Furthermore, the measured emission quantum yield in the toluene solution was as high as 93%, which indicates that ph-3,10FrA2Nbf(IV)-02 is suitable as a light-emitting material.

Next, ph-3,10FrA2Nbf(IV)-02 obtained in this example was analyzed by LC/MS analysis. The fabrication method of the sample, and the measurement method and conditions were similar to those of Synthesis Example 3 in Example 3.

A component with m/z=974.31, which is an ion derived from ph-3,10FrA2Nbf(IV)-02, was subjected to the MS$^2$ measurement by a Targeted-MS$^2$ method. For setting of the Targeted-MS$^2$, the mass range of a target ion was set to m/z=974.31±2.0 (isolation window=4) and detection was performed in a positive mode. Measurement was performed with energy NCE for accelerating the target ion in a collision cell set to 60. The obtained MS spectrum is shown in FIG. 141.

From the results in FIG. 141, it was found that product ions from ph-3,10FrA2Nbf(IV)-02 are detected mainly at around n/z=896, 820, 715, 639, 549, and 258. Note that the results shown in FIG. 141 exhibit characteristic results derived from ph-3,10FrA2Nbf(IV)-02 and therefore are important data for identifying ph-3,10FrA2Nbf(IV)-02 contained in a mixture.

Note that the product ion around i/z=896 is presumed to be a cation in the state where a phenyl group was eliminated from ph-3,10FrA2Nbf(IV)-02, which suggests that ph-3,10FrA2Nbf(IV)-02 contains a phenyl group. Furthermore, the product ion around n/z=715 is presumed to be a cation in the state where an N-(dibenzofuran-3-yl)-N-phenylamino group was eliminated from ph-3,10FrA2Nbf(IV)-02, which suggests that ph-3,10FrA2Nbf(IV)-02 contains an N-(dibenzofuran-3-yl)-N-phenylamino group.

Furthermore, the product ion around m/z=258 is presumed to be a cation in the state where a 3-[N-(dibenzofuran-3-yl)-N-phenylamino]-6,13-diphenylnaphtho[2,3-b;6,7-b']bisbenzofuranyl group was eliminated from ph-3,10FrA2Nbf(IV)-02, which suggests that ph-3,10FrA2Nbf(IV)-02 contains a 3-[N-(dibenzofuran-3-yl)-N-phenylamino]-6,13-diphenylnaphtho[2,3-b;6,7-b'] bisbenzofuranyl group.

Example 23

Synthesis Example 12

In this synthesis example, a method for synthesizing 3,10-bis[N-(dibenzofuran-3-yl)-N-(4-isopropylphenyl) amino]naphtho[2,3-b;6,7-b']bisbenzofuran (abbreviation: 3,10iPrFrA2Nbf(IV)-02) will be described in detail. The structural formula of 3,10iPrFrA2Nbf(IV)-02 is shown below.

[Chemical Formula 116]

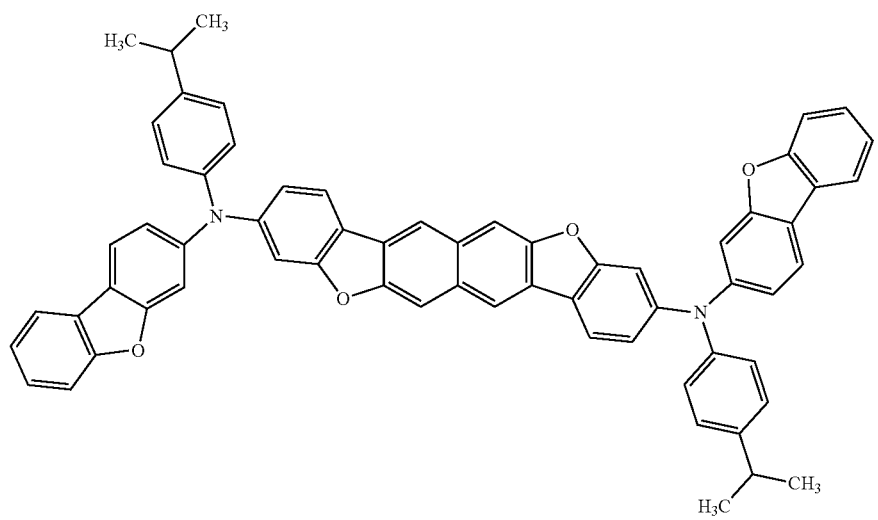

Step 1: Synthesis of 3,7-bis(4-chloro-2-fluorophenyl)-2,6-dimethoxynaphthalene The synthesis was conducted in a similar manner to Step 1 of Synthesis Example 1 in Example 1.

Step 2: Synthesis of 3,7-bis(4-chloro-2-fluorophenyl)-2,6-dihydroxynaphthalene The synthesis was conducted in a similar manner to Step 2 of Synthesis Example 1 in Example 1.

Step 3: Synthesis of 3,10-dichloronaphtho[2,3-b;6,7-b']bisbenzofuran

The synthesis was conducted in a similar manner to Step 3 of Synthesis Example 1 in Example 1.

Step 4: Synthesis of 3,10-bis[N-(dibenzofuran-3-yl)-N-(4-isopropylphenyl)amino]naphtho[2,3-b;6,7-b']bisbenzofuran (abbreviation: 3,10iPrFrA2Nbf (IV)-02)

Into a 200 mL three-necked flask were put, 1.0 g (2.8 mmol) of 3,10-dichloronaphtho[2,3-b;6,7-b']bisbenzofuran, 2.1 g (6.9 mmol) of N-(4-isopropylphenyl)-N-(dibenzofuran-3-yl)amine, 99 mg (0.28 mmol) of di(1-adamantyl)-n-butylphosphine, and 1.6 g (17 mmol) of sodium tert-butoxide. To this mixture was added 30 mL of xylene. This mixture was degassed by being stirred while the pressure was reduced. To this mixture was added 32 mg (55 µmol) of bis(dibenzylideneacetone)palladium(0), and the mixture was stirred under a nitrogen stream at 150° C. for 15 hours.

After the stirring, toluene was added to this mixture, which was then subjected to suction filtration through Florisil, Celite, and alumina to give a filtrate. The obtained filtrate was concentrated to give a solid. This solid was purified by silica gel column chromatography (developing solvent: toluene) to give a solid. The obtained solid was recrystallized with toluene twice, so that 1.9 g of a yellow solid was obtained in a yield of 77%. By a train sublimation method, 1.4 g of the obtained solid was sublimated and purified. The sublimation purification was performed by heating at 375° C. under the conditions where the pressure was $1.7 \times 10^{-2}$ Pa and the argon flow rate was 0 mL/min. After the sublimation purification, 1.2 g of a yellow solid was obtained at a collection rate of 87%. The synthesis scheme of Step 4 is shown below.

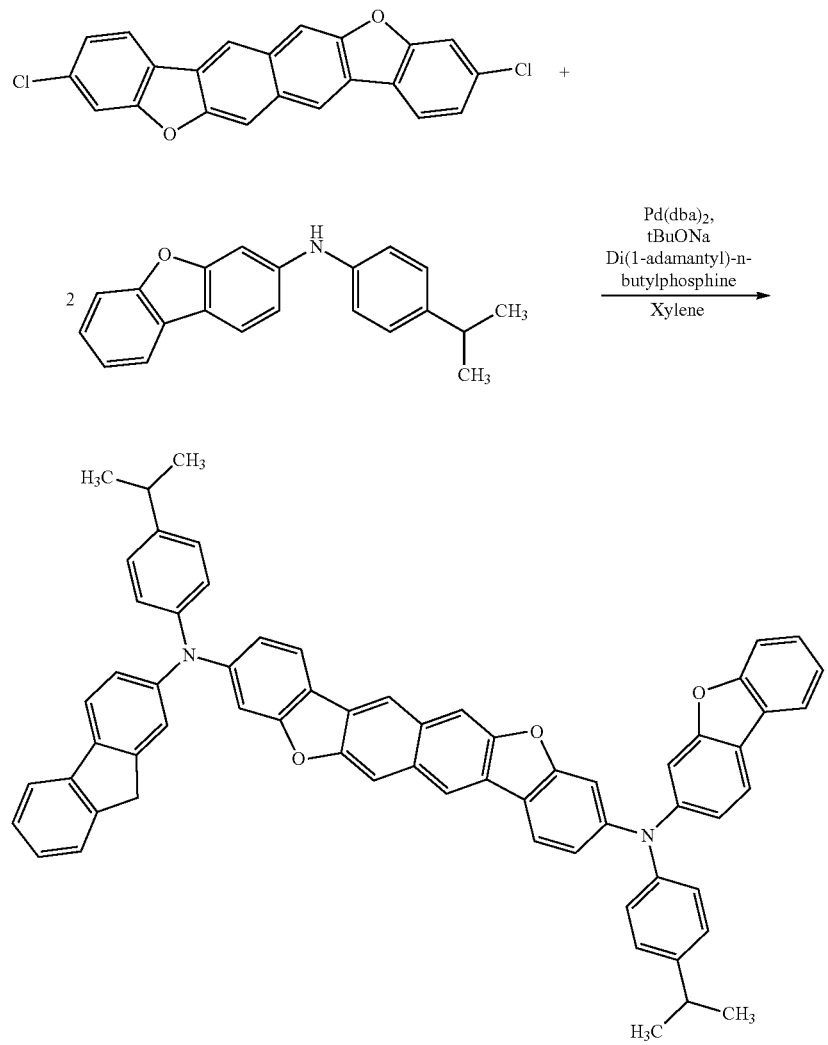

FIG. 142 shows $^1$H NMR data of the obtained solid, whose numerical data is given below. The data indicates that 3,10iPrFrA2Nbf(IV)-02, which is an organic compound of one embodiment of the present invention, was obtained in this synthesis example.

$^1$H NMR (CD$_2$Cl$_2$, 300 MHz): δ=1.29 (d, J1=7.5 Hz, 12H), 2.94 (sep, J1=7.5 Hz, 2H), 7.12-7.26 (m, 14H), 7.32-7.37 (m, 4H), 7.42 (dt, J1=7.2 Hz, J2=1.5 Hz, 2H), 7.53 (d, J1=7.8 Hz, 2H), 7.86 (d, J1=8.7 Hz, 2H), 7.90-7.95 (m, 4H), 8.00 (s, 2H), 8.40 (s, 2H).

Note that since 3,10iPrFrA2Nbf(IV)-02 contains an isopropyl group, which is a hydrocarbon group, its intermolecular force is relatively small; thus, the temperature for the sublimation purification could be low regardless of the high molecular weight.

Next, the measurement results of the absorption spectrum and emission spectrum of a toluene solution of 3,10iPrFrA2Nbf(IV)-02 are shown in FIG. 143. In addition, the absorption spectrum and emission spectrum of a thin film of 3,10iPrFrA2Nbf(IV)-02 are shown in FIG. 144. The solid thin film was formed over a quartz substrate by a vacuum evaporation method. The absorption spectrum of the toluene solution was measured using an ultraviolet-visible light spectrophotometer (V550 type manufactured by JASCO Corporation). The shown absorption spectrum is the one from which the spectrum of toluene alone in a quartz cell has been subtracted. The absorption spectrum of the thin film was measured using a spectrophotometer (U4100 Spectrophotometer, manufactured by Hitachi High-Technologies Corporation). The emission spectra were measured using a fluorescence spectrophotometer (FS920 manufactured by Hamamatsu Photonics K.K.). The emission quantum yield was measured using an absolute PL quantum yield measurement system (Quantaurus-QY manufactured by Hamamatsu Photonics K.K.).

As can be seen from FIG. 143, the toluene solution of 3,10iPrFrA2Nbf(IV)-02 has absorption peaks at 430 nm, 408 nm, 358 nm, and 281 nm, and emission wavelength peaks at 446 nm and 473 nm (excitation wavelength 410 nm). In addition, as can be seen from FIG. 144, the thin film of 3,10iPrFrA2Nbf(IV)-02 has absorption peaks at 435 nm, 413 nm, 359 nm, and 258 nm, and emission wavelength peaks at 468 nm and 493 nm (excitation wavelength 410 nm). These results indicate that 3,10iPrFrA2Nbf(IV)-02 emits blue light and can be used as a host for a light-emitting substance or a host for a substance that emits fluorescence in the visible region.

Furthermore, the measured emission quantum yield in the toluene solution was as high as 91%, which indicates that 3,10iPrFrA2Nbf(IV)-02 is suitable as a light-emitting material.

Next, 3,10iPrFrA2Nbf(IV)-02 obtained in this example was analyzed by LC/MS analysis. The fabrication method of the sample, and the measurement method and conditions were similar to those of Synthesis Example 3 in Example 3.

A component with m/z=906.35, which is an ion derived from 3,10iPrFrA2Nbf(IV)-02, was subjected to the MS$^2$ measurement by a Targeted-MS$^2$ method. For setting of the Targeted-MS$^2$, the mass range of a target ion was set to m/z=906.35±2.0 (isolation window=4) and detection was performed in a positive mode. Measurement was performed with energy NCE for accelerating the target ion in a collision cell set to 40 and 50. The obtained MS spectra are shown in FIGS. 145 (A) and (B). Note that FIGS. 145 (A) and (B) show the results when NCE is 40 and 50, respectively.

From the results in FIGS. 145 (A) and (B), it was found that product ions from 3,10iPrFrA2Nbf(IV)-02 are detected mainly at around m/z=891 and 740, when NCE is 40. Furthermore, it was found that product ions from 3,10iPrFrA2Nbf(IV)-02 are detected mainly at around n/z=891, 862, 773, 592, 487, and 258, when NCE is 50. Note that the results shown in FIGS. 145 (A) and (B) exhibit characteristic results derived from 3,10iPrFrA2Nbf(IV)-02 and therefore are important data for identifying 3,10iPrFrA2Nbf(IV)-02 contained in a mixture.

Note that the product ion around m/z=862 is presumed to be a cation in the state where an isopropyl group was eliminated from 3,10iPrFrA2Nbf(IV)-02, which suggests that 3,10iPrFrA2Nbf(IV)-02 contains an isopropyl group. Furthermore, the product ion around m/z=740 is presumed to be a cation in the state where a dibenzofuranyl group was eliminated from 3,10iPrFrA2Nbf(IV)-02, which suggests that 3,10iPrFrA2Nbf(IV)-02 contains a dibenzofuranyl group.

Example 24

Synthesis Example 13

In this synthesis example, a method for synthesizing 3,10-bis[N-(dibenzothiophen-2-yl)-N-phenylamino]naphtho[2,3-b;6,7-b']bisbenzofuran (abbreviation: 3,10ThA2Nbf (IV)) will be described in detail. The structural formula of 3,10ThA2Nbf(IV) is shown below.

[Chemical Formula 118]

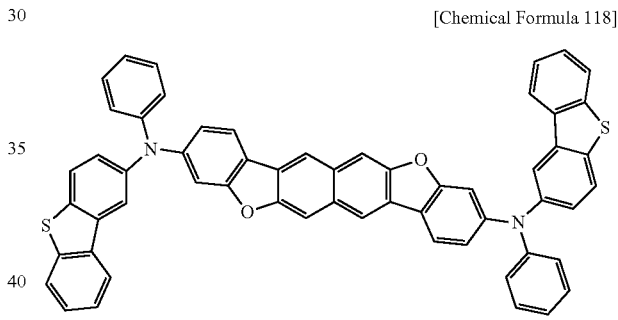

Step 1: Synthesis of 3,7-bis(4-chloro-2-fluorophenyl)-2,6-dimethoxynaphthalene

The synthesis was conducted in a similar manner to Step 1 of Synthesis Example 1 in Example 1.

Step 2: Synthesis of 3,7-bis(4-chloro-2-fluorophenyl)-2,6-dihydroxynaphthalene

The synthesis was conducted in a similar manner to Step 2 of Synthesis Example 1 in Example 1.

Step 3: Synthesis of 3,10-dichloronaphtho[2,3-b;6,7-b']bisbenzofuran

The synthesis was conducted in a similar manner to Step 3 of Synthesis Example 1 in Example 1.

Step 4: Synthesis of 3,10ThA2Nbf(IV)

Into a 200 mL three-necked flask were put 1.1 g (2.9 mmol) of 3,10-dichloronaphtho[2,3-b;6,7-b']bisbenzofuran, 2.0 g (7.3 mmol) of N-(dibenzothiophen-2-yl)-N-phenylamine, 0.11 g (0.29 mmol) of di(1-adamantyl)-n-butylphosphine, and 1.7 g (18 mmol) of sodium tert-butoxide. To this mixture was added 30 mL of xylene. This mixture was degassed by being stirred while the pressure was reduced. To this mixture was added 34 mg (58 µmol) of bis(dibenzylideneacetone)palladium(0), and the mixture was stirred under a nitrogen stream at 150° C. for 29 hours.

After the stirring, toluene was added to this mixture, which was then subjected to suction filtration through Florisil, Celite, and alumina, and the filtrate was concentrated to give a solid. This solid was purified by silica gel column chromatography (developing solvent: toluene) to give a solid. The obtained solid was recrystallized with toluene twice, so that 1.1 g of a yellow solid was obtained in a yield of 42%. By a train sublimation method, 1.0 g of the obtained solid was sublimated and purified. The sublimation purification was performed by heating at 385° C. under the conditions where the pressure was $2.0\times10^{-2}$ Pa and the argon flow rate was 0 mL/min. After the sublimation purification, 0.85 g of a yellow solid was obtained at a collection rate of 84%. The synthesis scheme of Step 4 is shown below.

[Chemical Formula 119]

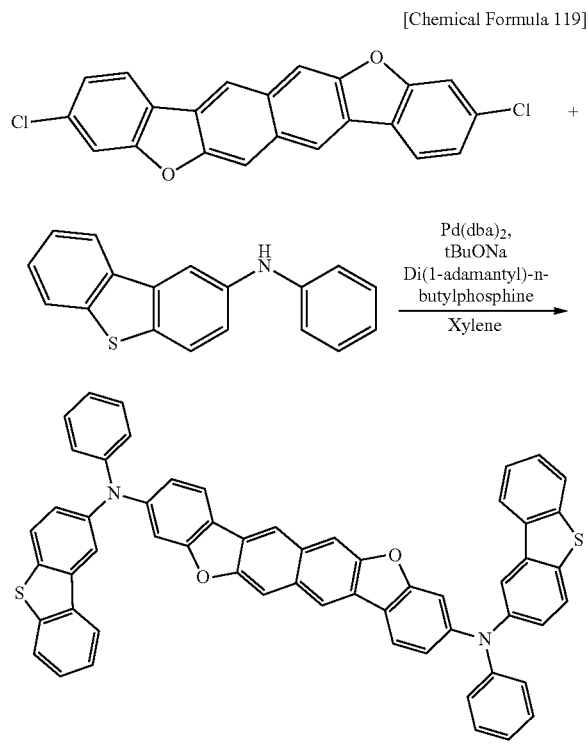

Next, the measurement results of the absorption spectrum and emission spectrum of a toluene solution of 3,10ThA2Nbf(IV) are shown in FIG. 146. In addition, the absorption spectrum and emission spectrum of a thin film of 3,10ThA2Nbf(IV) are shown in FIG. 147. The solid thin film was formed over a quartz substrate by a vacuum evaporation method. The absorption spectrum of the toluene solution was measured using an ultraviolet-visible light spectrophotometer (V550 type manufactured by JASCO Corporation). The shown absorpotion spectrum is the one from which the spectrum of toluene alone in a quartz cell has been subtracted. The absorption spectrum of the thin film was measured using a spectrophotometer (U4100 Spectrophotometer, manufactured by Hitachi High-Technologies Corporation). The emission spectra were measured using a fluorescence spectrophotometer (FS920 manufactured by Hamamatsu Photonics K.K.). The emission quantum yield was measured using an absolute PL quantum yield measurement system (Quantaurus-QY manufactured by Hamamatsu Photonics K.K.).

As can be seen from FIG. 146, the toluene solution of 3,10ThA2Nbf(IV) has absorption peaks at 426 nm, 403 nm, 309 nm, and 282 nm, and emission wavelength peaks at 441 nm and 466 nm (excitation wavelength 405 nm). In addition, as can be seen from FIG. 147, the thin film of 3,10ThA2Nbf (IV) has absorption peaks at 433 nm and 411 nm, and emission wavelength peaks at 466 nm and 493 nm (excitation wavelength 400 nm). These results indicate that 3,10ThA2Nbf(IV) emits blue light and can be used as a host for a light-emitting substance or a host for a substance that emits fluorescence in the visible region.

Next, 3,10ThA2Nbf(IV) obtained in this example was analyzed by LC/MS analysis. The fabrication method of the sample, and the measurement method and conditions were similar to those of Synthesis Example 3 in Example 3.

A component with m/z=854.21, which is an ion derived from 3,10ThA2Nbf(IV), was subjected to the $MS^2$ measurement by a Targeted-$MS^2$ method. For setting of the Targeted-$MS^2$, the mass range of a target ion was set to m/z=854.21±2.0 (isolation window=4) and detection was performed in a positive mode. Measurement was performed with energy NCE for accelerating the target ion in a collision cell set to 60. The obtained MS spectrum is shown in FIG. 148.

From the results in FIG. 148, it was found that product ions from 3,10ThA2Nbf(IV) are detected mainly at around m/z=776, 579, 503, 397, and 273. Note that the results shown in FIG. 148 exhibit characteristic results derived from 3,10ThA2Nbf(IV) and therefore are important data for identifying 3,10ThA2Nbf(IV) contained in a mixture.

Note that the product ion around m/z=776 is presumed to be a cation in the state where a phenyl group was eliminated from 3,10ThA2Nbf(IV), which suggests that 3,10ThA2Nbf (IV) contains a phenyl group. Furthermore, the product ion around m/z=579 is presumed to be a cation in the state where an N-(dibenzothiophen-2-yl)-N-phenylamino group was eliminated from 3,10ThA2Nbf(IV), which suggests that 3,10ThA2Nbf(IV) contains an N-(dibenzothiophen-2-yl)-N-phenylamino group.

Furthermore, the product ion around n/z=273 is presumed to be a cation in the state where a 3-[N-(dibenzothiophen-2-yl)-N-phenylamino]naphtho[2,3-b;6,7-b']bisbenzofuranyl group was eliminated from 3,10ThA2Nbf(IV), which suggests that 3,10ThA2Nbf(IV) contains a 3-[N-(dibenzothiophen-2-yl)-N-phenylamino]naphtho[2,3-b;6,7-b']bisbenzofuranyl group.

Example 25

Synthesis Example 14

In this synthesis example, a method for synthesizing 2,9-bis{N-[4-(9-phenyl-9H-carbazol-3-yl)phenyl]-N-phenylamino}naphtho[2,1-b;6,5-b']bisbenzofuran (abbreviation: 2,9PCBA2Nbf(III)) will be described in detail. The structural formula of 2,9PCBA2Nbf(III) is shown below.

[Chemical Formula 120]

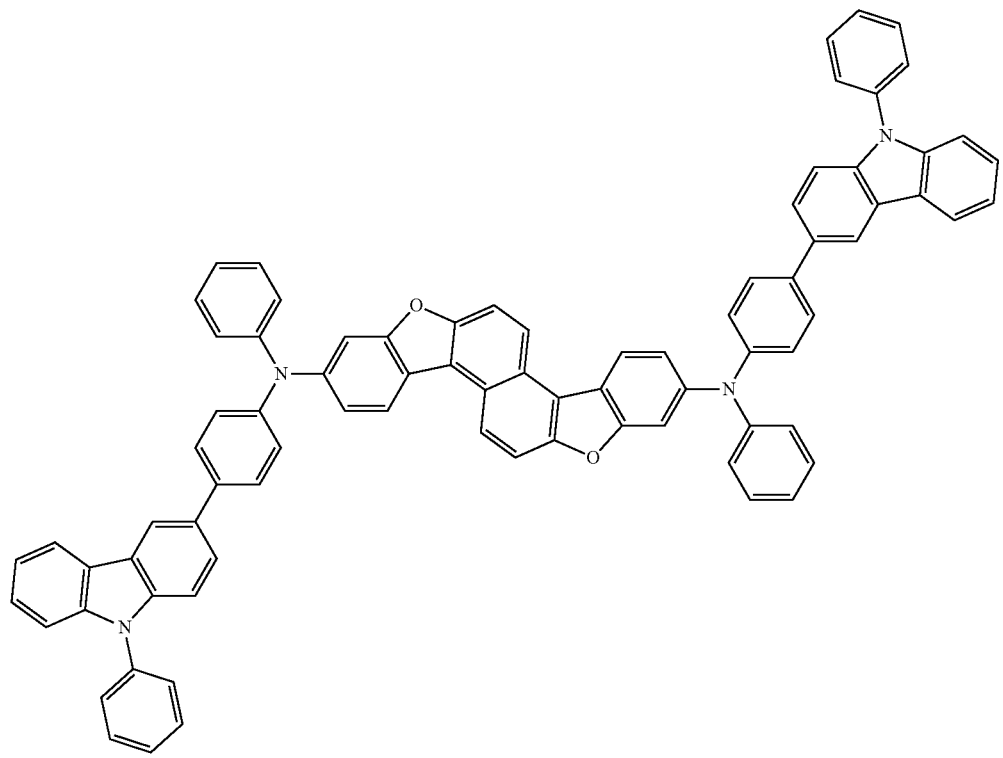

Step 1: Synthesis of 1,5-bis(4-chloro-2-fluorophenyl)-2,7-dihydroxynaphthalene

The synthesis was conducted in a similar manner to Step 1 of Synthesis Example 2 in Example 2.

Step 2: Synthesis of 2,9-dichloronaphtho[2,1-b;6,5-b']bisbenzofuran

The synthesis was conducted in a similar manner to Step 2 of Synthesis Example 2 in Example 2.

Step 3: Synthesis of 2,9PCBA2Nbf(III)

Into a 200 mL three-necked flask were put 0.84 g (2.2 mmol) of 2,9-dichloronaphtho[2,1-b;6,5-b']bismenzofuran, 2.3 g (5.6 mmol) of 3-[4-(4-phenylamino)phenyl]-9-phenyl-carbazole, 80 mg (0.22 mmol) of di(1-adamantyl)-n-butylphosphine, and 1.3 g (13 mmol) of sodium tert-butoxide. To this mixture was added 25 mL of xylene. This mixture was degassed by being stirred while the pressure was reduced. To this mixture was added 26 mg (44 μmol) of bis(dibenzylideneacetone)palladium(0), and the mixture was stirred under a nitrogen stream at 150° C. for 20 hours.

After the stirring, toluene was added to this mixture, which was then subjected to suction filtration through Florisil, Celite, and alumina to give a filtrate. The obtained filtrate was concentrated to give a solid. Toluene was added to the obtained solid, which was then stirred while being heated and was subjected to suction filtration, so that a solid was collected. Toluene was added again to the obtained solid, which was then stirred while being heated and was subjected to suction filtration, so that 1.4 g of a yellow solid was obtained in a yield of 56%. By a train sublimation method, 1.0 g of the obtained solid was sublimated and purified. The sublimation purification was performed by heating at 445° C. under the conditions where the pressure was $3.3 \times 10^{-2}$ Pa and the argon flow rate was 0 mL/min.

After the sublimation purification, 0.71 g of a yellow solid was obtained at a collection rate of 70%. The synthesis scheme of Step 3 is shown below.

[Chemical Formula 121]

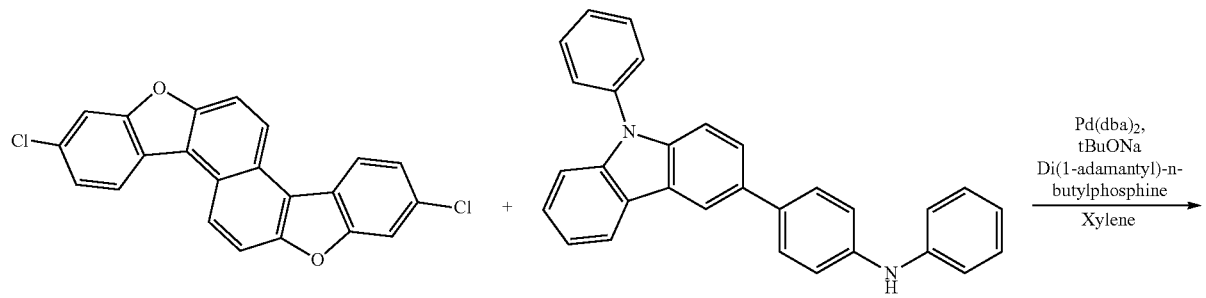

-continued

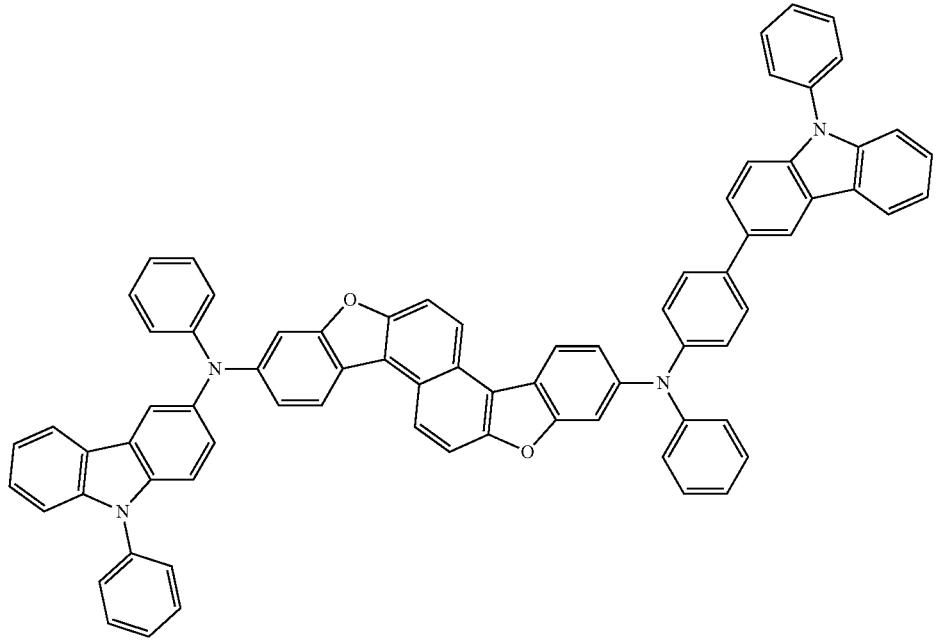

FIG. 149 shows ¹H NMR data of the obtained solid, whose numerical data is given below. The data indicates that 2,9PCBA2Nbf(III), which is an organic compound of one embodiment of the present invention, was obtained in this synthesis example.

¹H NMR (CD$_2$Cl$_2$, 300 MHz): δ=7.13 (t, J1=6.9 Hz, 2H), 7.25-7.40 (m, 16H), 7.43-7.54 (m, 10H), 7.60-7.73 (m, 14H), 7.97 (d, J1=9.3 Hz, 2H), 8.22 (d, J1=7.8 Hz, 2H), 8.34 (d, J1=8.7 Hz, 2H), 8.40 (d, J1=1.5 Hz, 2H), 8.66 (d, J1=8.7 Hz, 2H).

Next, the measurement results of the absorption spectrum and emission spectrum of a toluene solution of 2,9PCBA2Nbf(III) are shown in FIG. 150. In addition, the absorption spectrum and emission spectrum of a thin film of 2,9PCBA2Nbf(III) are shown in FIG. 151. The solid thin film was formed over a quartz substrate by a vacuum evaporation method. The absorption spectrum of the toluene solution was measured using an ultraviolet-visible light spectrophotometer (V550 type manufactured by JASCO Corporation). The shown absorpotion spectrum is the one from which the spectrum of toluene alone in a quartz cell has been subtracted. The absorption spectrum of the thin film was measured using a spectrophotometer (U4100 Spectrophotometer, manufactured by Hitachi High-Technologies Corporation). The emission spectra were measured using a fluorescence spectrophotometer (FS920 manufactured by Hamamatsu Photonics K.K.). The emission quantum yield was measured using an absolute PL quantum yield measurement system (Quantaurus-QY manufactured by Hamamatsu Photonics K.K.).

As can be seen from FIG. 150, the toluene solution of 2,9PCBA2Nbf(III) has absorption peaks at 421 nm, 402 nm, 329 nm, 298 nm, and 289 nm, and emission wavelength peaks at 439 nm and 465 nm (excitation wavelength 398 nm). In addition, as can be seen from FIG. 151, the thin film of 2,9PCBA2Nbf(III) has absorption peaks at 426 nm, 409 nm, 329 nm, and 285 nm, and an emission wavelength peak at 541 nm (excitation wavelength 430 nm). These results indicate that 2,9PCBA2Nbf(III) emits blue light and can be used as a host for a light-emitting substance or a host for a substance that emits fluorescence in the visible region.

Furthermore, the measured emission quantum yield in the toluene solution was as high as 88%, which indicates that 2,9PCBA2Nbf(III) is suitable as a light-emitting material.

Next, 2,9PCBA2Nbf(III) obtained in this example was analyzed by LC/MS analysis. The fabrication method of the sample, and the measurement method and conditions were similar to those of Synthesis Example 3 in Example 3.

A component with m/z=1124.41, which is an ion derived from 2,9PCBA2Nbf(III), was subjected to the MS² measurement by a Targeted-MS² method. For setting of the Targeted-MS², the mass range of a target ion was set to m/z=1124.41±2.0 (isolation window=4) and detection was performed in a positive mode. Measurement was performed with energy NCE for accelerating the target ion in a collision cell set to 60. The obtained MS spectrum is shown in FIG. 152.

From the results in FIG. 152, it was found that product ions from 2,9PCBA2Nbf(III) are detected mainly at around m/z=1046, 1019, 805, 714, 638, 409, 332, and 243. Note that the results shown in FIG. 152 exhibit characteristic results derived from 2,9PCBA2Nbf(III) and therefore are important data for identifying 2,9PCBA2Nbf(III) contained in a mixture.

Note that the product ion around m/z=1046 is presumed to be a cation in the state where a phenyl group was eliminated from 2,9PCBA2Nbf(III), which suggests that 2,9PCBA2Nbf(III) contains a phenyl group. Furthermore, the product ion around m/z=805 is presumed to be a cation in the state where a 4-(9-phenylcarbazol-3-yl)phenyl group was eliminated from 2,9PCBA2Nbf(III), which suggests that 2,9PCBA2Nbf(III) contains a 4-(9-phenylcarbazol-3-yl)phenyl group. Furthermore, the product ion around m/z=638 is presumed to be a cation in the state where an N-[4-(9-phenyl-9H-carbazol-3-yl)phenyl]-N-phenylamino group was eliminated from 2,9PCBA2Nbf(III), which suggests that 2,9PCBA2Nbf(III) contains an N-[4-(9-phenyl-9H-carbazol-3-yl)phenyl]-N-phenylamino group.

Furthermore, the product ion around m/z=409 is presumed to be a cation in the state where a 2-{N-[4-(9-phenyl-9H-carbazol-3-yl)phenyl]-N-phenylamino}naphtho[2,1-b;6,5-b']bisbenzofuranyl group was eliminated from 2,9PCBA2Nbf(III), which suggests that 2,9PCBA2Nbf(III) contains a 2-{N-[4-(9-phenyl-9H-carbazol-3-yl)phenyl]-N-phenylamino}naphtho[2,1-b;6,5-b']bisbenzofuranyl group.

Example 26

Synthesis Example 15

In this synthesis example, a method for synthesizing 3,10-bis[N-(dibenzofuran-3-yl)-N-(3,5-di-t-butylphenyl)amino]naphtho[2,3-b;6,7-b']bisbenzofuran (abbreviation: 3,10mmtBuFrA2Nbf(IV)-02) will be described in detail. The structural formula of 3,10mmtBuFrA2Nbf(IV)-02 is shown below.

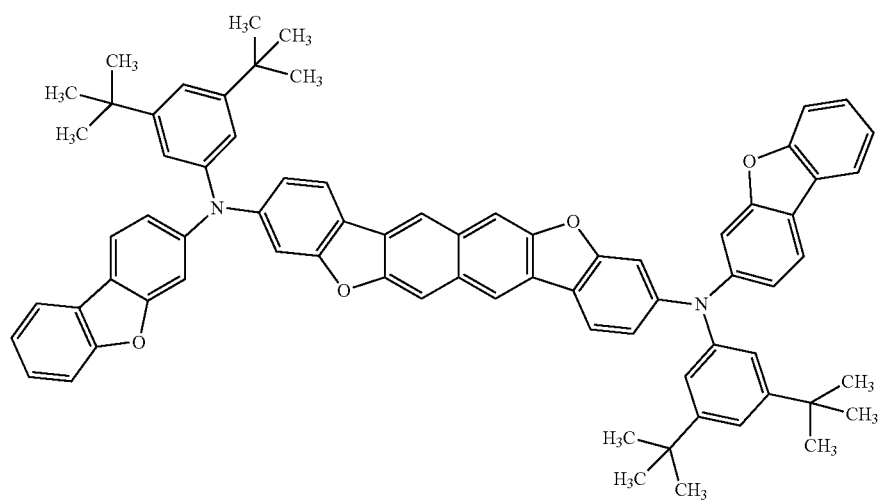

Step 1: Synthesis of 3,7-bis(4-chloro-2-fluorophenyl)-2,6-dimethoxynaphthalene

The synthesis was conducted in a similar manner to Step 1 of Synthesis Example 1 in Example 1.

Step 2: Synthesis of 3,7-bis(4-chloro-2-fluorophenyl)-2,6-dihydroxynaphthalene

The synthesis was conducted in a similar manner to Step 2 of Synthesis Example 1 in Example 1.

Step 3: Synthesis of 3,10-dichloronaphtho[2,3-b;6,7-b']bisbenzofuran

The synthesis was conducted in a similar manner to Step 3 of Synthesis Example 1 in Example 1.

Step 4: Synthesis of N-(dibenzofuran-3-yl)-N-(3,5-di-tert-butylphenyl)amine

Into a 200 mL three-necked flask were put 4.2 g (17 mmol) of 3-bromodibenzofuran, 5.2 g (25 mmol) of 3,5-di-tert-butylaniline, and 4.9 g (51 mmol) of sodium tert-butoxide. To this mixture were added 85 mL of toluene and 0.3 mL of a 10% hexane solution of tri(tert-butyl)phosphine, and the mixture was degassed by being stirred while the pressure was reduced. To this mixture was added 98 mg (0.17 mmol) of bis(dibenzylideneacetone)palladium(0), and the mixture was heated and stirred under a nitrogen stream at 120° C. for seven hours. After the stirring, toluene was added to this mixture, which was then subjected to suction filtration through Florisil, Celite, and alumina, and the filtrate was concentrated to give a solid. This solid was purified by silica gel column chromatography (developing solvent: toluene:hexane=1:3). The obtained solid was recrystallized with ethanol to give 3.7 g of a white solid in a yield of 59%. The synthesis scheme of Step 4 is shown below.

[Formula 122]

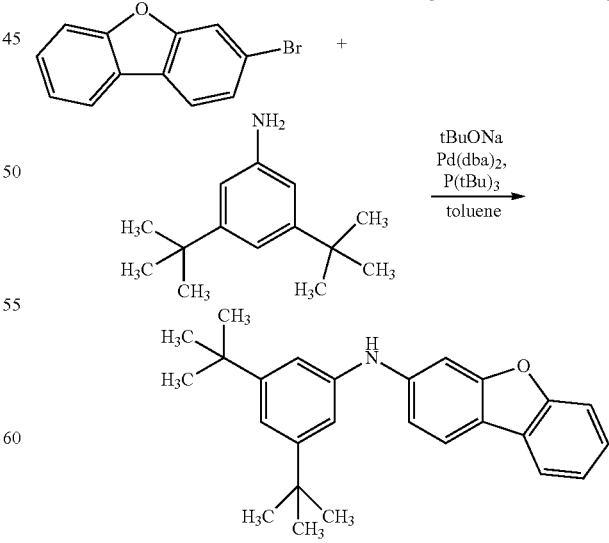

[Chemical Formula 123]

Given below is $^1$H NMR data of the obtained solid. The data indicates that N-(dibenzofuran-3-yl)-N-(3,5-di-tertbutylphenyl)amine, which is an organic compound of one embodiment of the present invention, was obtained in this synthesis example.

$^1$H NMR (DMSO-d$_6$, 300 MHz): δ=1.29 (s, 18H), 6.99 (t, J1=1.2 Hz, 1H), 7.03-7.07 (m, 3H), 7.24 (d, J1=2.1 Hz, 1H), 7.28-7.39 (m, 2H), 7.58 (dd, J1=7.2 Hz, J2=1.5 Hz, 1H), 7.89-7.95 (m, 2H), 8.48 (s, 1H).

Step 5: Synthesis of 3,10mmtBuFrA2Nbf(IV)-02

Into a 200 mL three-necked flask were put 0.90 g (2.4 mmol) of 3,10-dichloronaphtho[2,3-b;6,7-b']bisbenzofuran, 2.2 g (6.0 mmol) of N-(dibenzofuran-3-yl)-N-(3,5-di-tert-butylphenyl)amine, 86 mg (0.28 mmol) of di(1-adamantyl)-n-butylphosphine, and 1.4 g (14 mmol) of sodium tert-butoxide. To this mixture was added 25 mL of xylene. This mixture was degassed by being stirred while the pressure was reduced. To this mixture was added 27 mg (48 μmol) of bis(dibenzylideneacetone)palladium(0), and the mixture was stirred under a nitrogen stream at 150° C. for 27 hours.

After the stirring, toluene was added to this mixture, which was then subjected to suction filtration through Florisil, Celite, and alumina to give a filtrate. The obtained filtrate was concentrated to give a solid. This solid was purified by silica gel column chromatography (developing solvent: toluene) to give a solid. The obtained solid was recrystallized with toluene twice, so that 1.4 g of a yellow solid was obtained in a yield of 54%. By a train sublimation method, 1.1 g of the obtained solid was sublimated and purified. The sublimation purification was performed by heating at 365° C. under the conditions where the pressure was 2.1×10$^{-2}$ Pa and the argon flow rate was 0 mL/min.

After the sublimation purification, 1.0 g of a yellow solid was obtained at a collection rate of 95%. The synthesis scheme of Step 5 is shown below.

[Chemical Formula 124]

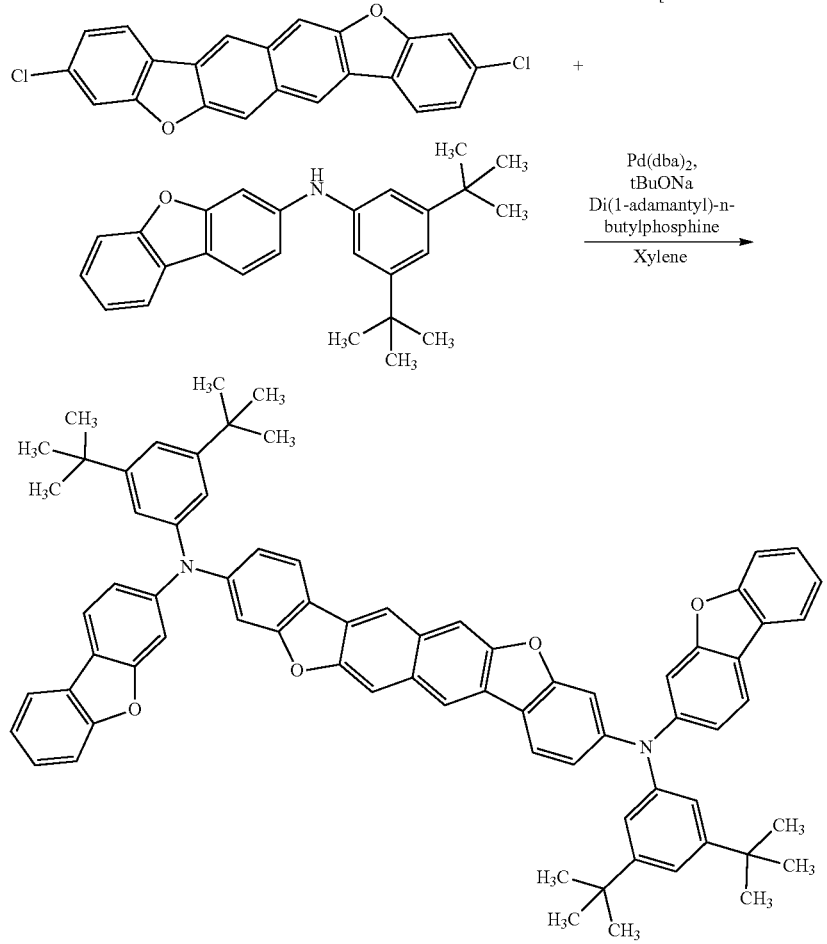

FIG. 153 shows $^1$H NMR data of the obtained solid, whose numerical data is given below. The data indicates that 3,10mmtBuFrA2Nbf(IV)-02, which is an organic compound of one embodiment of the present invention, was obtained in this synthesis example.

$^1$H NMR (CD$_2$Cl$_2$, 300 MHz): δ=1.28 (s, 36H), 7.10-7.15 (m, 6H), 7.19 (dd, J1=8.7 Hz, J2=1.8 Hz, 2H), 7.25-7.26 (m, 4H), 7.31-7.37 (m, 4H), 7.41 (dt, J1=8.4 Hz, J2=1.5 Hz, 2H), 7.52 (d, J1=7.8 Hz, 2H), 7.86 (d, J1=8.4 Hz, 2H), 7.90-7.94 (m, 4H), 8.00 (s, 2H), 8.39 (s, 2H).

Note that, in 3,10mmtBuFrA2Nbf(IV)-02, a tert-butyl group, which is a hydrocarbon group, is connected and thus the intermolecular force is relatively small; therefore, the temperature for the sublimation purification could be low regardless of the high molecular weight.

Next, the measurement results of the absorption spectrum and emission spectrum of a toluene solution of 3,10mmtBuFrA2Nbf(IV)-02 are shown in FIG. 154. The absorption spectrum of the toluene solution was measured using an ultraviolet-visible light spectrophotometer (V550 type manufactured by JASCO Corporation). The shown absorpotion spectrum is the one from which the spectrum of toluene alone in a quartz cell has been subtracted. The emission spectrum was measured using a fluorescence spectrophotometer (FS920 manufactured by Hamamatsu Photonics K.K.). The emission quantum yield was measured using an absolute PL quantum yield measurement system (Quantaurus-QY manufactured by Hamamatsu Photonics K.K.).

As can be seen from FIG. 154, the toluene solution of 3,10mmtBuFrA2Nbf(IV)-02 has absorption peaks at 431 nm, 408 nm, 383 nm, 351 nm, and 281 nm, and emission wavelength peaks at 445 nm and 473 nm (excitation wavelength 408 nm). The results indicate that 3,10mmtBuFrA2Nbf(IV)-02 emits blue light and can be used as a host for a light-emitting substance or a host for a substance that emits fluorescence in the visible region.

Furthermore, the measured emission quantum yield in the toluene solution was as high as 94%, which indicates that 3,10mmtBuFrA2Nbf(IV)-02 is suitable as a light-emitting material.

Next, 3,10mmtBuFrA2Nbf(IV)-02 obtained in this example was analyzed by LC/MS analysis. The fabrication method of the sample, and the measurement method and conditions were similar to those of Synthesis Example 3 in Example 3.

A component with m/z=1046.50, which is an ion derived from 3,10mmtBuFrA2Nbf(IV)-02, was subjected to the $MS^2$ measurement by a Targeted-$MS^2$ method. For setting of the Targeted-$MS^2$, the mass range of a target ion was set to m/z=1046.50±2.0 (isolation window=4) and detection was performed in a positive mode. Measurement was performed with energy NCE for accelerating the target ion in a collision cell set to 60. The obtained MS spectrum is shown in FIG. 155.

From the results in FIG. 155, it was found that product ions from 3,10mmtBuFrA2Nbf(IV)-02 are detected mainly at around m/z=1030, 1016, 974, 902, 677, 605, and 298.

Note that the results shown in FIG. 155 exhibit characteristic results derived from 3,10mmtBuFrA2Nbf(IV)-02 and therefore are important data for identifying 3,10mmtBuFrA2Nbf(IV)-02 contained in a mixture.

Note that the product ion around m/z=677 is presumed to be a cation in the state where an N-(dibenzofuran-3-yl)-N-(3,5-di-t-butylphenyl)amino group was eliminated from 3,10mmtBuFrA2Nbf(IV)-02, which suggests that 3,10mmtBuFrA2Nbf(IV)-02 contains an N-(dibenzofuran-3-yl)-N-(3,5-di-t-butylphenyl)amino group.

Example 27

Synthesis Example 16

In this synthesis example, a method for synthesizing 3,10-bis{N-[4-(dibenzofuran-4-yl)phenyl]-N-phenylamino}naphtho[2,3-b;6,7-b']bisbenzofuran (abbreviation: 3,10FrBA2Nbf(IV)-II), which is an organic compound of one embodiment of the present invention shown in Embodiment 1, will be described in detail. The structural formula of 3,10FrBA2Nbf(IV)-II is shown below.

[Chemical Formula 125]

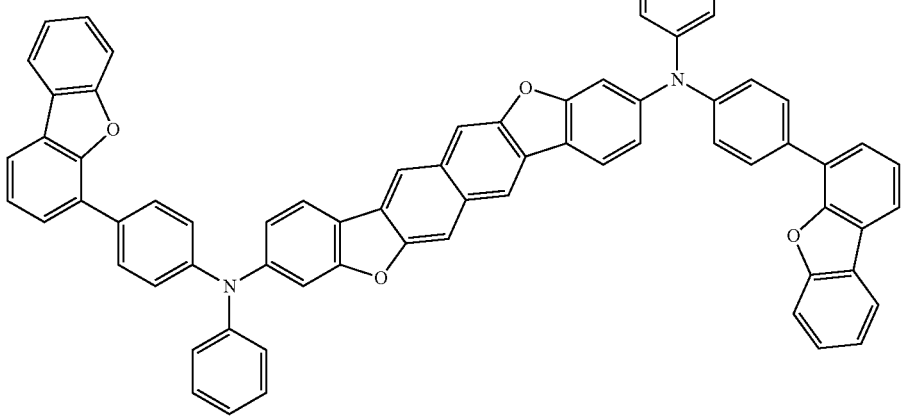

Step 1: Synthesis of 3,7-bis(4-chloro-2-fluorophenyl)-2,6-dimethoxynaphthalene

The synthesis was conducted in a similar manner to Step 1 of Synthesis Example 1 in Example 1.

Step 2: Synthesis of 3,7-bis(4-chloro-2-fluorophenyl)-2,6-dihydroxynaphthalene

The synthesis was conducted in a similar manner to Step 2 of Synthesis Example 1 in Example 1.

Step 3: Synthesis of 3,10-dichloronaphtho[2,3-b;6,7-b']bisbenzofuran

The synthesis was conducted in a similar manner to Step 3 of Synthesis Example 1 in Example 1.

Step 4: Synthesis of 3,10FrBA2Nbf(IV)-II

Into a 200 mL three-necked flask were put 1.0 g (2.6 mmol) of 3,10-dichloronaphtho[2,3-b;6,7-b']bisbenzofuran, 2.2 g (6.4 mmol) of 4-(dibenzofuran-4-yl)diphenylamine, 93 mg (0.26 mmol) of di(1-adamantyl)-n-butylphosphine, and 1.5 g (15 mmol) of sodium tert-butoxide. To this mixture was added 25 mL of xylene. This mixture was degassed by being stirred while the pressure was reduced. To this mixture was added 29 mg (52 µmol) of bis(dibenzylideneacetone) palladium(0), and the mixture was stirred under a nitrogen stream at 150° C. for 13 hours.

After the stirring, water and ethanol were added to the mixture, and after the irradiation with ultrasonic waves, the mixture was filtered, so that a solid was collected. The obtained solid was dissolved in toluene, and the solution was subjected to suction filtration through Florisil, Celite, and alumina to give a filtrate. The obtained filtrate was concentrated to give a solid. This solid was purified by silica gel column chromatography (developing solvent: toluene) to give a solid. The obtained solid was recrystallized with toluene twice, so that 1.5 g of a yellow solid was obtained in a yield of 60%. By a train sublimation method, 1.1 g of the obtained solid was sublimated and purified. The sublimation purification was performed by heating at 410° C. under the conditions where the pressure was $2.4 \times 10^{-2}$ Pa and the argon flow rate was 0 mL/min. After the sublimation purification, 0.84 g of a yellow solid was obtained at a collection rate of 74%. The synthesis scheme of Step 4 is shown below.

FIG. 156 shows $^1$H NMR data of the obtained solid, whose numerical data is given below. The data indicates that 3,10FrBA2Nbf(IV)-II, which is an organic compound of one embodiment of the present invention, was obtained in this synthesis example.

$^1$H NMR (CD$_2$Cl$_2$, 300 MHz): δ=7.14-7.21 (m, 4H), 7.27-7.44 (m, 16H), 7.46-7.53 (m, 4H), 7.62-7.67 (m, 4H), 7.89-7.92 (m, 4H), 7.95-7.99 (m, 4H), 8.02-8.05 (m, 4H), 8.43 (s, 2H).

Next, the measurement results of the absorption spectrum and emission spectrum of a toluene solution of 3,10FrBA2Nbf(IV)-II are shown in FIG. 157. In addition, the absorption spectrum and emission spectrum of a thin film of 3,10FrBA2Nbf(IV)-II are shown in FIG. 158. The solid thin film was formed over a quartz substrate by a vacuum evaporation method. The absorption spectrum of the toluene solution was measured using an ultraviolet-visible light spectrophotometer (V550 type manufactured by JASCO Corporation). The shown absorpotion spectrum is the one from which the spectrum of toluene alone in a quartz cell has been subtracted. The absorption spectrum of the thin film was measured using a spectrophotometer (U4100 Spectrophotometer, manufactured by Hitachi High-Technologies Corporation). The emission spectra were measured using a fluorescence spectrophotometer (FS920 manufactured by Hamamatsu Photonics K.K.). The emission quantum yield

[Chemical Formula 126]

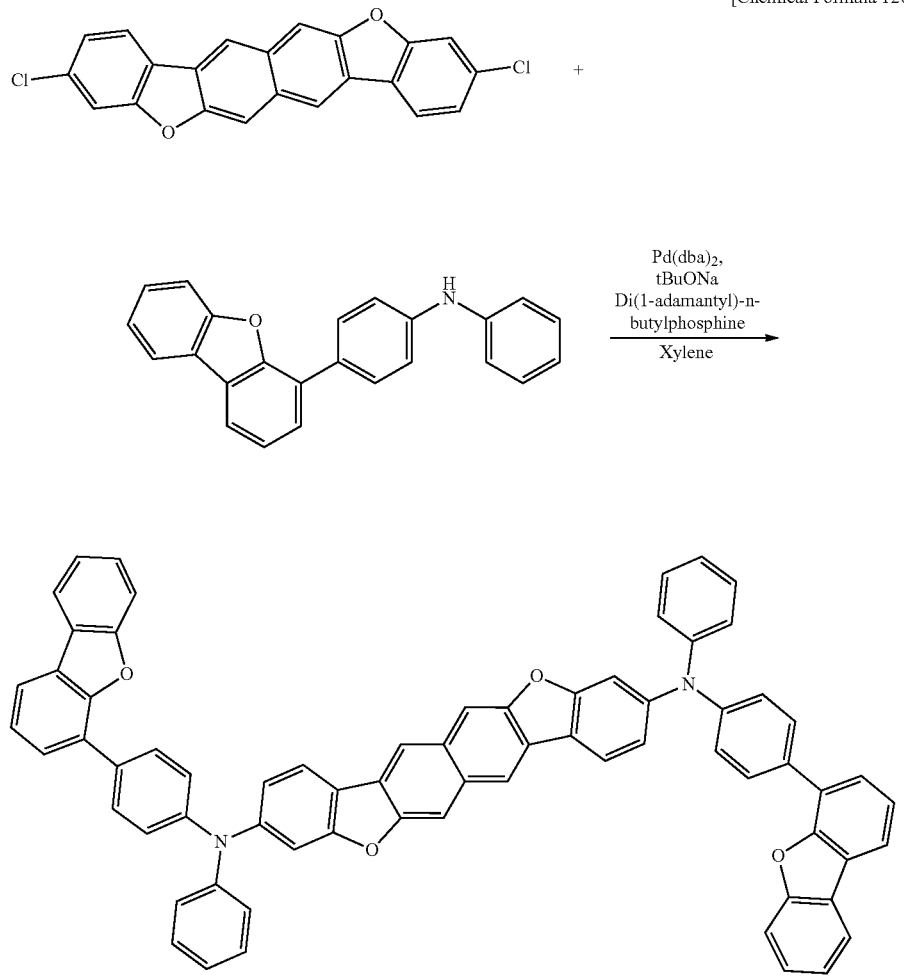

was measured using an absolute PL quantum yield measurement system (Quantaurus-QY manufactured by Hamamatsu Photonics K.K.).

As can be seen from FIG. 157, the toluene solution of 3,10FrBA2Nbf(IV)-II has absorption peaks at 427 nm, 404 nm, 341 nm, and 282 nm, and emission wavelength peaks at 442 nm and 466 nm (excitation wavelength 404 nm). In addition, as can be seen from FIG. 158, the thin film of 3,10FrBA2Nbf(IV)-II has absorption peaks at 434 nm, 412 nm, 351 nm, 286 nm, and 252 nm, and emission wavelength peaks at 465 nm and 486 nm (excitation wavelength 410 nm). These results indicate that 3,10FrBA2Nbf(IV)-II emits blue light and can be used as a host for a light-emitting substance or a host for a substance that emits fluorescence in the visible region.

Furthermore, the measured emission quantum yield in the toluene solution was as high as 93%, which indicates that 3,10FrBA2Nbf(IV)-II is suitable as a light-emitting material.

Next, 3,10FrBA2Nbf(IV)-II obtained in this example was analyzed by LC/MS analysis. The fabrication method of the sample, and the measurement method and conditions were similar to those of Synthesis Example 3 in Example 3.

A component with m/z=974.31, which is an ion derived from 3,10FrBA2Nbf(IV)-II, was subjected to the $MS^2$ measurement by a Targeted-$MS^2$ method. For setting of the Targeted-$MS^2$, the mass range of a target ion was set to m/z=974.31±2.0 (isolation window=4) and detection was performed in a positive mode. Measurement was performed with energy NCE for accelerating the target ion in a collision cell set to 60. The obtained MS spectrum is shown in FIG. 159.

From the results in FIG. 159, it was found that product ions from 3,10FrBA2Nbf(IV)-II are detected mainly at around m/z=896, 730, 639, 563, 397, 334, and 166. Note that the results shown in FIG. 159 exhibit characteristic results derived from 3,10FrBA2Nbf(IV)-II and therefore are important data for identifying 3,10FrBA2Nbf(IV)-II contained in a mixture.

Note that the product ion around m/z=896 is presumed to be a cation in the state where a phenyl group was eliminated from 3,10FrBA2Nbf(IV)-II, which suggests that 3,10FrBA2Nbf(IV)-II contains a phenyl group. Furthermore, the product ion around m/z=730 is presumed to be a cation in the state where a 4-(dibenzofuran-4-yl)phenyl group was eliminated from 3,10FrBA2Nbf(IV)-II, which suggests that 3,10FrBA2Nbf(IV)-II contains a 4-(dibenzofuran-4-yl)phenyl group.

Furthermore, the product ion around m/z=639 is presumed to be a cation in the state where a 4-(dibenzofuran-4-yl)diphenylamino group was eliminated from 3,10FrBA2Nbf(IV)-II, which suggests that 3,10FrBA2Nbf(IV)-II contains a 4-(dibenzofuran-4-yl)diphenylamino group.

Furthermore, the product ion around m/z=334 is presumed to be a cation in the state where a 3-{N-[4-(dibenzofuran-4-yl)phenyl]-N-phenylamino}naphtho[2,3-b;6,7-b'] bisbenzofuranyl group was eliminated from 3,10FrBA2Nbf(IV)-II, which suggests that 3,10FrBA2Nbf(IV)-II contains a 3-{N-[4-(dibenzofuran-4-yl)phenyl]-N-phenylamino}naphtho[2,3-b;6,7-b']bisbenzofuranyl group.

Example 28

In this example, light-emitting elements 10 to 15, which are light-emitting elements of one embodiment of the present invention described in Embodiments, will be described in detail. The structural formulae of organic compounds used in the light-emitting elements 10 to 15 are shown below.

[Chemical Formulae 127]

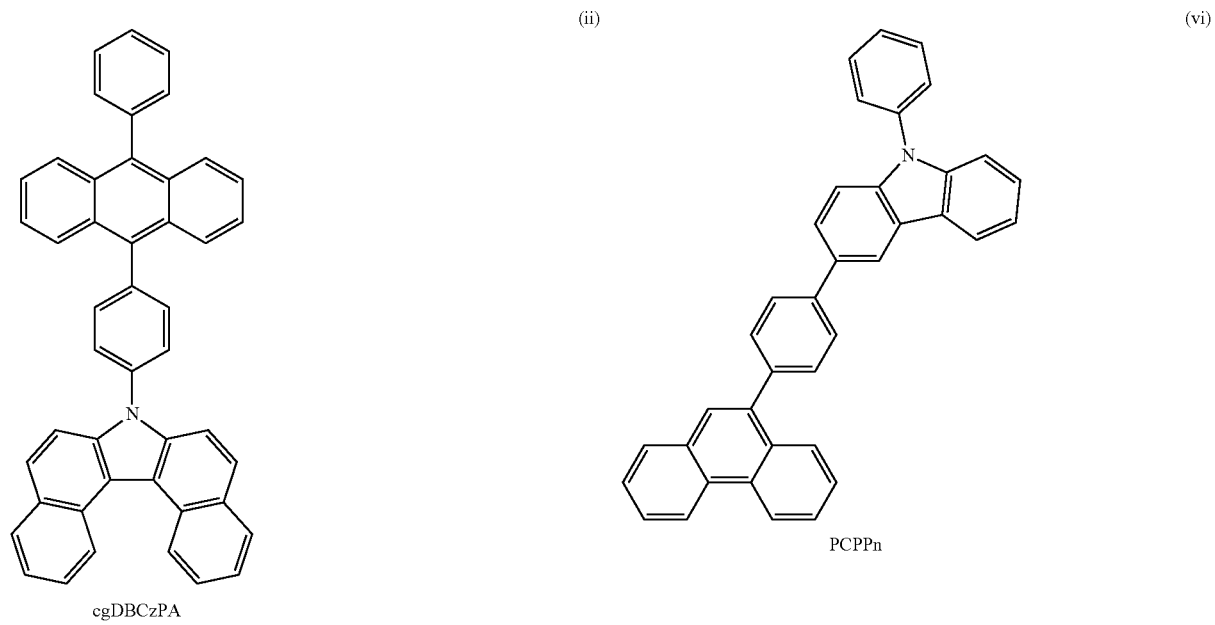

cgDBCzPA (ii)

PCPPn (vi)

(xii)
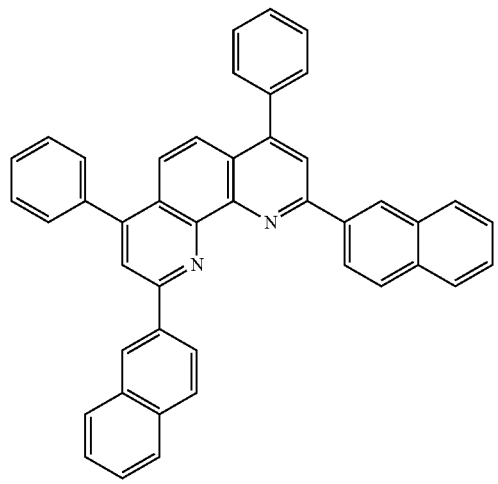
NBPhen
(xv)
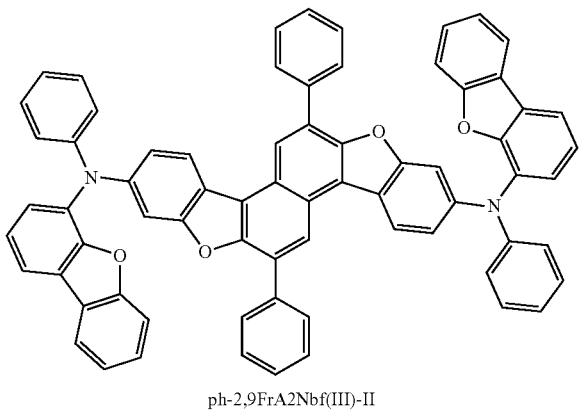
ph-2,9FrA2Nbf(III)-II
(xvi)
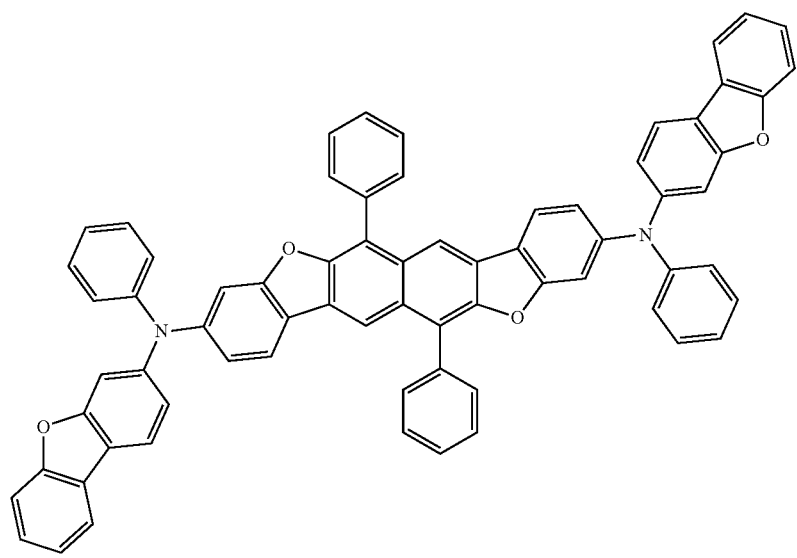
ph-3,10FrA2Nbf(IV)-02

[Chemical Formulae 128]
(xvii)
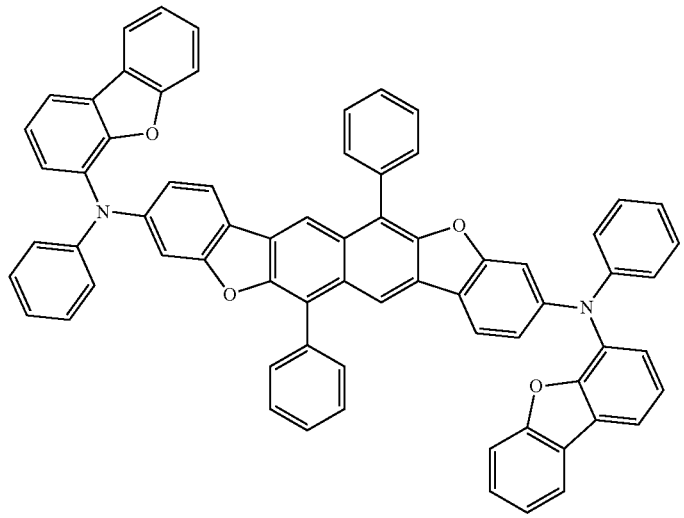
ph-3,10FrA2Nbf(IV)-II
(xviii)
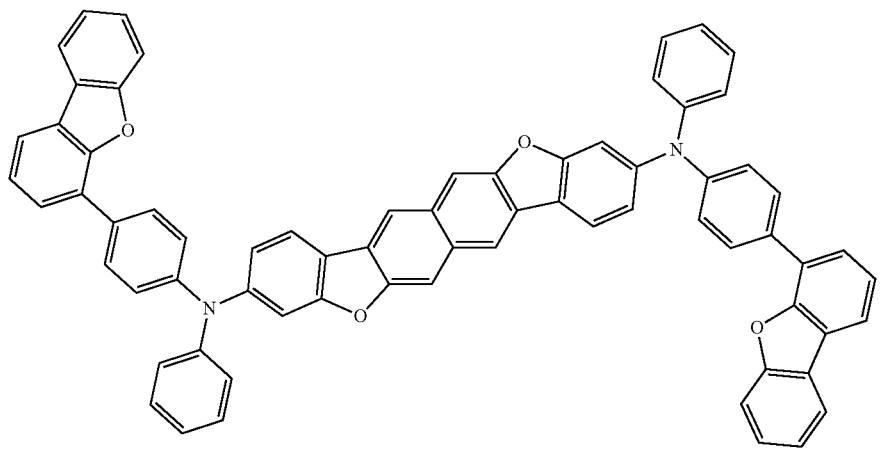
3,10FrBA2Nbf(IV)-II (xix)

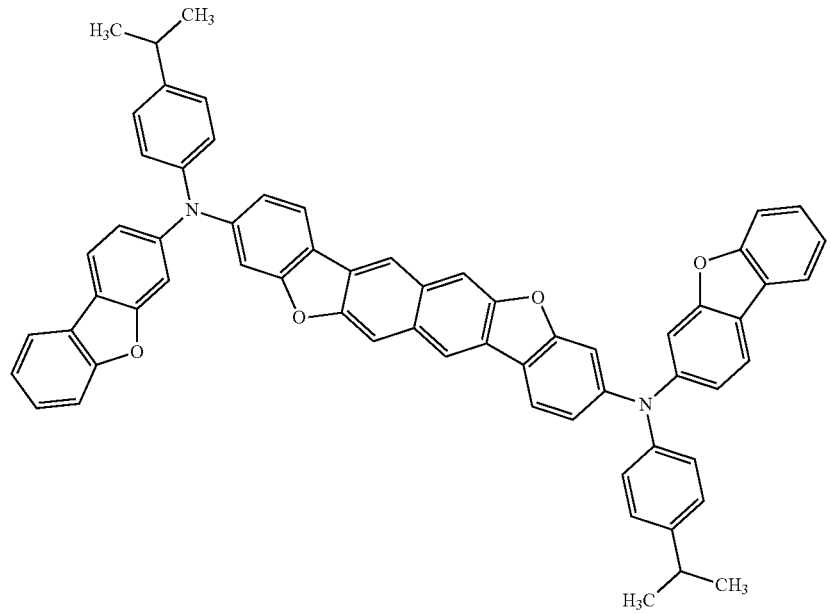

3,10iPrFrA2Nbf(IV)-02

(xx)

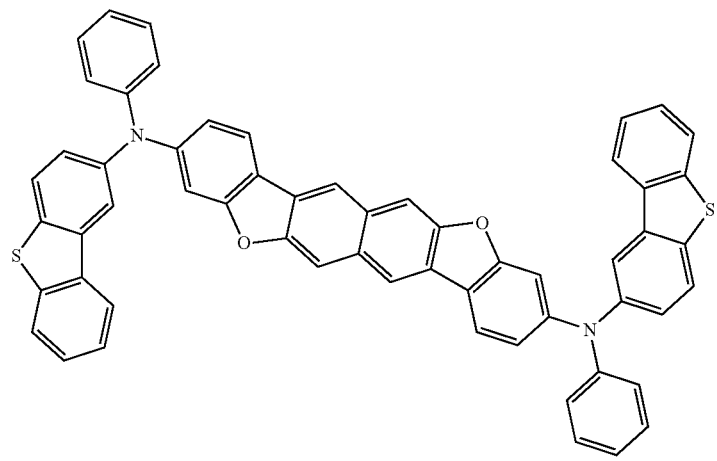

3,10ThA2Nbf(IV)

(Fabrication Method of Light-Emitting Element 10)

First, a film of indium tin oxide containing silicon oxide (ITSO) was formed on a glass substrate by a sputtering method, so that the anode 101 was formed. Note that the thickness was 70 nm and the area of the electrode was 4 mm$^2$ (2 mm×2 mm).

Next, in pretreatment for forming the light-emitting element over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to about $10^{-4}$ Pa, vacuum baking at 170° C. for 30 minutes was performed in a heating chamber in the vacuum evaporation apparatus, and then the substrate was naturally cooled down for about 30 minutes.

Next, the substrate on which the anode 101 was formed was fixed to a substrate holder provided in the vacuum evaporation apparatus such that the side on which the anode 101 was formed faced downward, and 3-[4-(9-phenanthryl)-phenyl]-9-phenyl-9H-carbazole (abbreviation: PCPPn) represented as the above structural formula (vi) and molybdenum(VI) oxide were deposited by co-evaporation on the anode 101 to have a weight ratio of 4:2 (=PCPPn:molybdenum oxide) to a thickness of 10 nm by an evaporation method using resistance heating, whereby the hole-injection layer 111 was formed.

Next, on the hole-injection layer 111, PCPPn was deposited by evaporation to a thickness of 30 nm to form the hole-transport layer 112.

Subsequently, 7-[4-(10-phenyl-9-anthryl)phenyl]-7H-dibenzo[c,g]carbazole (abbreviation: cgDBCzPA) represented as the above structural formula (ii) and 2,9-bis[N-(dibenzofuran-4-yl)-N-phenylamino]-6,13-diphenylnaphtho[2,1-b;6,5-b']bisbenzofuran (abbreviation: ph-2,9FrA2Nbf(III)-II) represented as the above structural formula (xv) were deposited by co-evaporation to have a weight ratio of 1:0.01 (=cgDBCzPA: ph-2,9FrA2Nbf(III)-II) to a thickness of 25 nm, whereby the light-emitting layer 113 was formed.

After that, on the light-emitting layer 113, cgDBCzPA was deposited by evaporation to a thickness of 15 nm, and 2,9-bis(naphthalen-2-yl)-4,7-diphenyl-1,10-phenanthroline (abbreviation: NBPhen) represented as the above structural formula (xii) was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115, and aluminum was deposited by evaporation to a thickness of 200 nm to form the cathode 102. Thus, the light-emitting element 10 of this example was fabricated.

(Fabrication Method of Light-Emitting Element 11)

The light-emitting element 11 was fabricated in a manner similar to that of the light-emitting element 10 except that 3,10-bis[N-(dibenzofuran-3-yl)-N-phenylamino]-6,13-diphenylnaphtho[2,3-b;6,7-b']bisbenzofuran (abbreviation: ph-3,10FrA2Nbf(IV)-02) represented as the above structural formula (xvi) was used instead of ph-2,9FrA2Nbf(III)-II in the light-emitting element 10.

(Fabrication Method of Light-Emitting Element 12)

The light-emitting element 12 was fabricated in a manner similar to that of the light-emitting element 10 except that 3,10-bis[N-(dibenzofuran-4-yl)-N-phenylamino]-6,13-diphenylnaphtho[2,3-b;6,7-b']bisbenzofuran (abbreviation: ph-3,10FrA2Nbf(IV)-II) represented as the above structural formula (xvii) was used instead of ph-2,9FrA2Nbf(III)-II in the light-emitting element 10.

(Fabrication Method of Light-Emitting Element 13)

The light-emitting element 13 was fabricated in a manner similar to that of the light-emitting element 10 except that 3,10-bis{N-[4-(dibenzofuran-4-yl)phenyl]-N-phenylamino}naphtho[2,3-b;6,7-b']bisbenzofuran (abbreviation: 3,10FrBA2Nbf(IV)-II) represented as the above structural formula (xviii) was used instead of ph-2,9FrA2Nbf(III)-II in the light-emitting element 10.

(Fabrication Method of Light-Emitting Element 14)

The light-emitting element 14 was fabricated in a manner similar to that of the light-emitting element 10 except that 3,10-bis[N-(dibenzofuran-3-yl)-N-(4-isopropylphenyl)amino]naphtho[2,3-b;6,7-b']bisbenzofuran (abbreviation: 3,10iPrFrA2Nbf(IV)-02) represented as the above structural formula (xix) was used instead of ph-2,9FrA2Nbf(III)-II in the light-emitting element 10.

(Fabrication Method of Light-Emitting Element 15)

The light-emitting element 15 was fabricated in a manner similar to that of the light-emitting element 10 except that 3,10-bis[N-(dibenzothiophen-2-yl)-N-phenylamino]naphtho[2,3-b;6,7-b']bisbenzofuran (abbreviation: 3,10ThA2Nbf(IV)) represented as the above structural formula (xx) was used instead of ph-2,9FrA2Nbf(III)-II in the light-emitting element 10.

The element structures of the light-emitting elements 10 to 15 are listed in the following table.

TABLE 19

| | Hole-injection layer | Hole-transport layer | Light-emitting layer | Electron-transport layer | | Electron-injection layer |
| --- | --- | --- | --- | --- | --- | --- |
| | 10 nm | 30 nm | 25 nm | 15 nm | 10 nm | 1 nm |
| Light-emitting element 10 | PCPPn:MoOx (4:2) | PCPPn | cgDBCzPA: ph-2,9FrA2Nbf(III)-II (1:0.01) | cgDBCzPA | NBPhen | LiF |
| Light-emitting element 11 | | | cgDBCzPA: ph-3,10FrA2Nbf(IV)-02 (1:0.01) | | | |
| Light-emitting element 12 | | | cgDBCzPA: ph-3,10FrA2Nbf(IV)-II (1:0.01) | | | |
| Light-emitting element 13 | | | cgDBCzPA: 3,10FrBA2Nbf(IV)-II (1:0.01) | | | |
| Light-emitting element 14 | | | cgDBCzPA: 3,10iPrFrA2Nbf(IV)-02 (1:0.01) | | | |
| Light-emitting element 15 | | | cgDBCzPA: 3,10ThA2Nbf(IV) (1:0.01) | | | |

Each of the light-emitting elements 10 to 15 was subjected to sealing with a glass substrate (a sealing material was applied to surround the element, followed by UV treatment and one-hour heat treatment at 80° C. at the time of sealing) in a glove box containing a nitrogen atmosphere so that the light-emitting element is not exposed to the air. Then, initial characteristics of these light-emitting elements were measured. Note that the measurement was carried out at room temperature.

Luminance-current density characteristics of the light-emitting elements 10 to 15 are shown in FIG. 160, current efficiency-luminance characteristics thereof are shown in FIG. 161, luminance-voltage characteristics thereof are shown in FIG. 162, current-voltage characteristics thereof are shown in FIG. 163, power efficiency-luminance characteristics thereof are shown in FIG. 164, external quantum efficiency-luminance characteristics thereof are shown in FIG. 165, and emission spectra thereof are shown in FIG. 166. In addition, their element characteristics at around a luminance of 1000 cd/m$^2$ are listed in Table 20.

light-emitting substances is suppressed and concentration quenching is inhibited, which probably resulted in their high external quantum efficiency.

In addition, these light-emitting elements were found to be light-emitting elements exhibiting favorable blue light emission. In particular, the light-emitting elements 11 to 15 exhibit significantly favorable blue color with the x-coordinate being 0.14 and the y-coordinate being 0.14 or less in the xy chromaticity diagram; among them, the light-emitting element 12, the light-emitting element 13, and the light-emitting element 15 exhibit significantly favorable blue color with the y-coordinate being 0.10 or less.

It is notable that the light-emitting elements of one embodiment of the present invention achieve significantly favorable external quantum efficiency and significantly favorable blue chromaticity at the same time. In this way, the light-emitting elements of one embodiment of the present invention are light-emitting elements with significantly

TABLE 20

|  | Voltage (V) | Current (mA) | Current density (mA/cm$^2$) | Chromaticity x | Chromaticity y | Current efficiency (cd/A) | Power efficiency (lm/W) | External quantum efficiency (%) |
| --- | --- | --- | --- | --- | --- | --- | --- | --- |
| Light-emitting element 10 | 3.0 | 0.19 | 4.7 | 0.14 | 0.24 | 19.6 | 20.5 | 12.6 |
| Light-emitting element 11 | 3.0 | 0.25 | 6.3 | 0.14 | 0.14 | 13.3 | 13.9 | 12.3 |
| Light-emitting element 12 | 3.1 | 0.43 | 10.9 | 0.14 | 0.10 | 9.8 | 9.9 | 11.3 |
| Light-emitting element 13 | 3.2 | 0.48 | 12.1 | 0.14 | 0.09 | 9.2 | 9.1 | 11.3 |
| Light-emitting element 14 | 3.1 | 0.31 | 7.7 | 0.14 | 0.12 | 11.3 | 11.5 | 11.6 |
| Light-emitting element 15 | 3.2 | 0.47 | 11.8 | 0.14 | 0.08 | 8.5 | 8.5 | 11.2 |

As can be seen from FIG. 160 to FIG. 166 and Table 20, the light-emitting elements 10 to 15 were found to be light-emitting elements exhibiting favorable characteristics, the external quantum efficiency at 1000 cd/m$^2$ being 11.2% to 12.6%. In particular, the light-emitting element 10, the light-emitting element 11, and the light-emitting element 14 were found to exhibit significantly favorable external quantum efficiency, an external quantum efficiency of 11.6% or higher.

The light-emitting element 10 and the light-emitting element 11 use, as the light-emitting substances, ph-2,9FrA2Nbf(III)-II and ph-3,10FrA2Nbf(IV)-02, respectively, in which a phenyl group, which is an aromatic hydrocarbon group, is connected to a naphthobisbenzofuran skeleton. Furthermore, the light-emitting element 14 uses 3,10iPrFrA2Nbf(IV)-02 as a light-emitting substance, and an isopropyl group, which is a hydrocarbon group, is connected to 3,10iPrFrA2Nbf(IV)-02. In this way, since these organic compounds contain the aromatic hydrocarbon group or the hydrocarbon group, intermolecular force between the favorable characteristics. In addition, the organic compounds of one embodiment of the present invention, which are dopants used in these light-emitting elements, were found to be organic compounds that emit light with favorable blue chromaticity at significantly high efficiency.

In addition, a graph of a change in luminance with driving time under the conditions where the current value was 2 mA and the current density was constant is shown in FIG. 167. As can be seen from FIG. 167, the light-emitting elements 10 to 15 maintain 80% or higher of the initial luminance even after 100 hours of driving, and in particular, the light-emitting elements 10 to 12 maintain 90% or higher, which indicates that they each have a favorable lifetime.

Example 29

In this example, light-emitting elements 16 to 18, which are light-emitting elements of one embodiment of the present invention described in Embodiments, will be described in detail. The structural formulae of organic compounds used in the light-emitting elements 16 to 18 are shown below.

[Chemical Formulae 129]
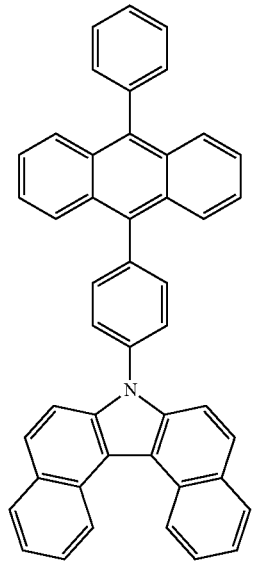
cgDBCzPA
(ii)
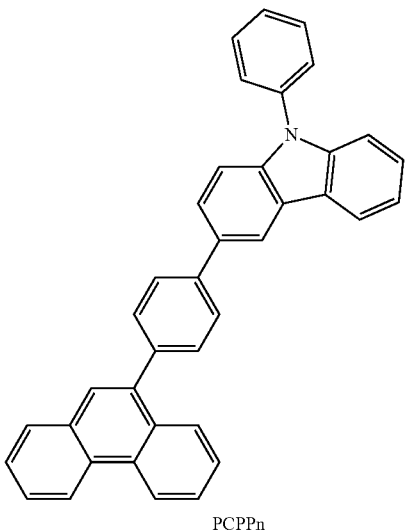
PCPPn
(vi)
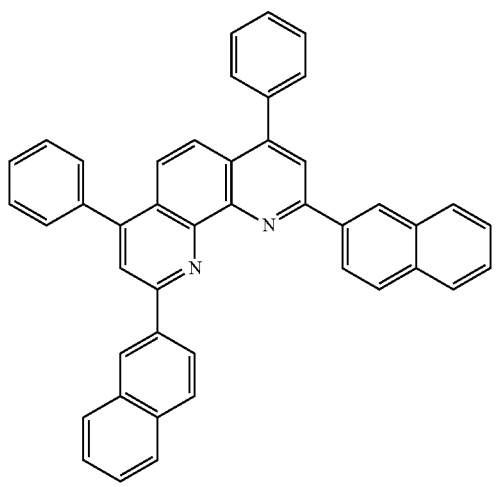
NBPhen
(xii)
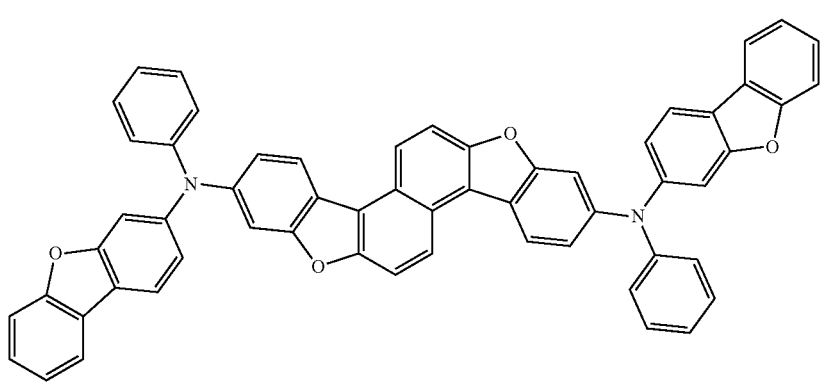
2,9FrA2Nbf(III)-02
(xxi)

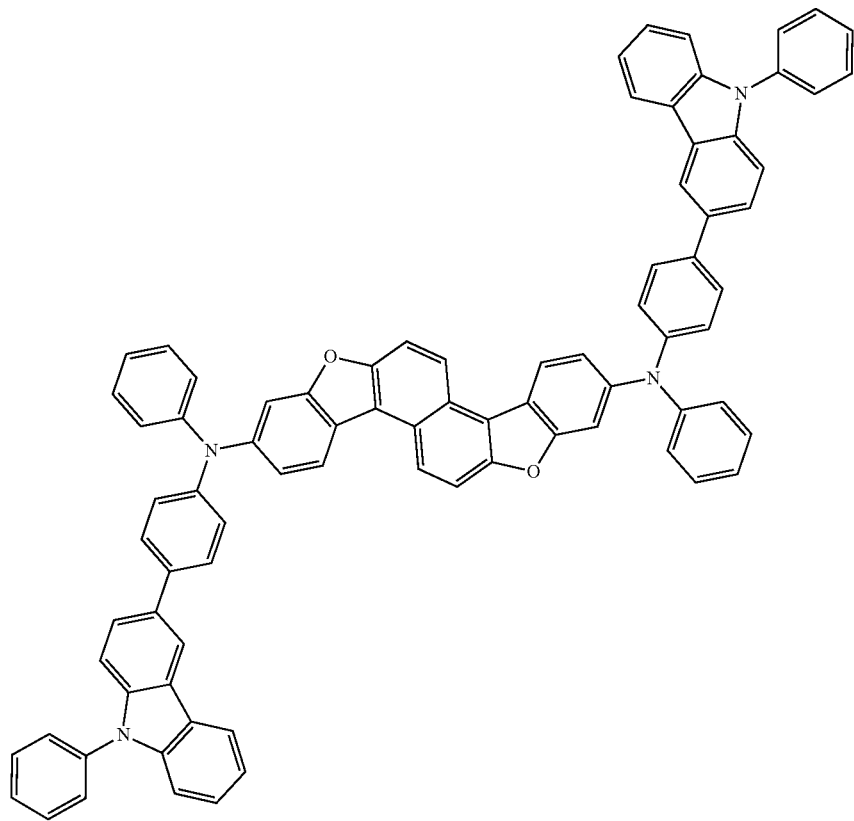

2,9PCBA2Nbf(III)

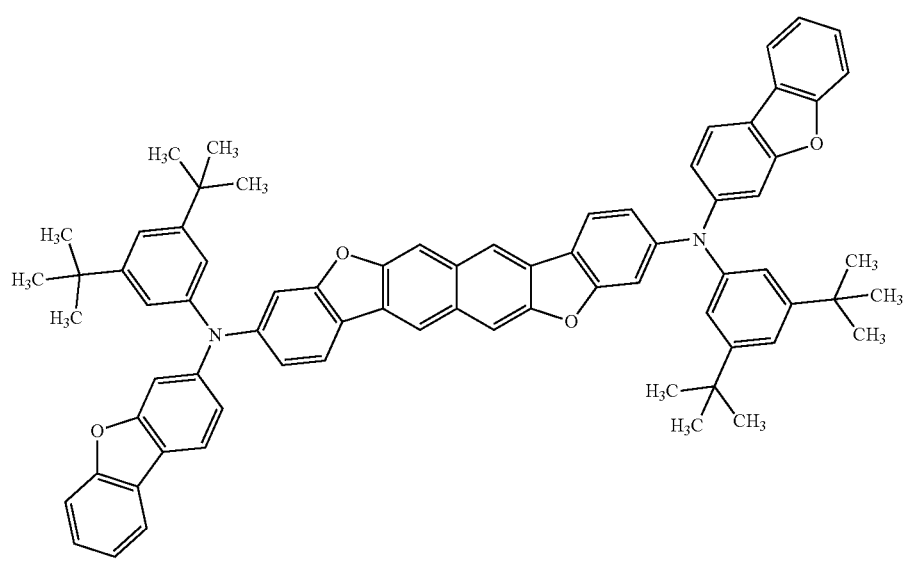

3,10mmtBuFrA2Nbf(IV)-02

(Fabrication Method of Light-Emitting Element 16)

First, a film of indium tin oxide containing silicon oxide (ITSO) was formed on a glass substrate by a sputtering method, so that the anode 101 was formed. Note that the thickness was 70 nm and the area of the electrode was 4 mm² (2 mm×2 mm).

Next, in pretreatment for forming the light-emitting element over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to about $10^{-4}$ Pa, vacuum baking at 170° C. for 30 minutes was performed in a heating chamber in the vacuum evaporation apparatus, and then the substrate was naturally cooled down for about 30 minutes.

Next, the substrate on which the anode 101 was formed was fixed to a substrate holder provided in the vacuum evaporation apparatus such that the side on which the anode 101 was formed faced downward, and 3-[4-(9-phenanthryl)-phenyl]-9-phenyl-9H-carbazole (abbreviation: PCPPn) represented as the above structural formula (vi) and molybdenum(VI) oxide were deposited by co-evaporation on the anode 101 to have a weight ratio of 4:2 (=PCPPn:molybdenum oxide) to a thickness of 10 nm by an evaporation method using resistance heating, whereby the hole-injection layer 111 was formed.

Next, on the hole-injection layer 111, PCPPn was deposited by evaporation to a thickness of 30 nm to form the hole-transport layer 112.

Subsequently, 7-[4-(10-phenyl-9-anthryl)phenyl]-7H-dibenzo[c,g]carbazole (abbreviation: cgDBCzPA) represented as the above structural formula (ii) and 2,9-bis[N-(dibenzofuran-3-yl)-N-phenylamino]naphtho[2,1-b;6,5-b'] bisbenzofuran (abbreviation: 2,9FrA2Nbf(III)-02) represented as the above structural formula (xxi) were deposited by co-evaporation to have a weight ratio of 1:0.01 (=cgDBCzPA: 2,9FrA2Nbf(III)-02) to a thickness of 25 nm, whereby the light-emitting layer 113 was formed.

phenylamino}naphtho[2,1-b;6,5-b']bisbenzofuran (abbreviation: 2,9PCBA2Nbf(III)) represented as the above structural formula (xxii) was used instead of 2,9FrA2Nbf(III)-02 in the light-emitting element 16, and that the weight ratio between cgDBCzPA and 2,9PCBA2Nbf(III) was set to 1:0.01 (=cgDBCzPA: 2,9PCBA2Nbf(III)).

(Fabrication Method of Light-Emitting Element 18)

The light-emitting element 18 was fabricated in a manner similar to that of the light-emitting element 16 except that 3,10-bis[N-(dibenzofuran-3-yl)-N-(3,5-di-t-butylphenyl) amino]naphtho[2,3-b;6,7-b']bisbenzofuran (abbreviation: 3,10mmtBuFrA2Nbf(IV)-02) represented as the above structural formula (xxiii) was used instead of 2,9FrA2Nbf(III)-02 in the light-emitting element 16, and that the weight ratio between cgDBCzPA and 3,10mmtBuFrA2Nbf(IV)-02 was set to 1:0.01 (=cgDBCzPA: 3,10mmtBuFrA2Nbf(IV)-02).

The element structures of the light-emitting elements 16 to 18 are listed in the following table.

TABLE 21

|  | Hole-injection layer 10 nm | Hole-transport layer 30 nm | Light-emitting layer 25 nm | Electron-transport layer | | Electron-injection layer 1 nm |
|---|---|---|---|---|---|---|
|  |  |  |  | 15 nm | 10 nm |  |
| Light-emitting element 16 | PCPPn: MoOx (4:2) | PCPPn | cgDBCzPA: 2,9FrA2Nbf(III)-02 (1:0.03) | cgDBCzPA | NBPhen | LiF |
| Light-emitting element 17 |  |  | cgDBCzPA: 2,9PCBA2Nbf(III) (1:0.01) |  |  |  |
| Light-emitting element 18 |  |  | cgDBCzPA: 3,10mmtBuFrA2Nbf(IV)-02 (1:0.01) |  |  |  |

After that, on the light-emitting layer 113, cgDBCzPA was deposited by evaporation to a thickness of 15 nm, and 2,9-bis(naphthalen-2-yl)-4,7-diphenyl-1,10-phenanthroline (abbreviation: NBPhen) represented as the above structural formula (xii) was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115, and aluminum was deposited by evaporation to a thickness of 200 nm to form the cathode 102. Thus, the light-emitting element 16 of this example was fabricated.

Each of the light-emitting elements 16 to 18 was subjected to sealing with a glass substrate (a sealing material was applied to surround the element, followed by UV treatment and one-hour heat treatment at 80° C. at the time of sealing) in a glove box containing a nitrogen atmosphere so that the light-emitting element is not exposed to the air. Then, initial characteristics of these light-emitting elements were measured. Note that the measurement was carried out at room temperature.

The element characteristics of the light-emitting elements 16 to 18 at around a luminance of 1000 cd/m$^2$ are listed in Table 22.

TABLE 22

|  | Voltage (V) | Current (mA) | Current density (mA/cm$^2$) | Chromaticity x | Chromaticity y | Current efficiency (cd/A) | Power efficiency (lm/W) | External quantum efficiency (%) |
|---|---|---|---|---|---|---|---|---|
| Light-emitting element 16 | 3.1 | 0.35 | 8.8 | 0.14 | 0.08 | 8.2 | 8.3 | 10.5 |
| Light-emitting element 17 | 3.1 | 0.33 | 8.2 | 0.15 | 0.14 | 11.2 | 11.4 | 9.6 |
| Light-emitting element 18 | 3.1 | 0.37 | 9.3 | 0.14 | 0.11 | 10.5 | 10.6 | 11.3 |

(Fabrication Method of Light-Emitting Element 17)

The light-emitting element 17 was fabricated in a manner similar to that of the light-emitting element 16 except that 2,9-bis{N-[4-(9-phenyl-9H-carbazol-3-yl)phenyl]-N-

As can be seen from Table 22, the light-emitting elements 16 to 18 were found to be light-emitting elements exhibiting favorable characteristics, the external quantum efficiency at 1000 cd/m$^2$ being 9.6% to 11.3%.

In addition, these light-emitting elements were found to be light-emitting elements exhibiting favorable blue light emission. In particular, the light-emitting element 16 exhibits significantly favorable blue color with the x-coordinate being 0.14 and the y-coordinate being 0.08 in the xy chromaticity diagram.

It is notable that the light-emitting elements of one embodiment of the present invention achieve significantly favorable external quantum efficiency and significantly favorable chromaticity at the same time. In this way, the light-emitting elements of one embodiment of the present invention are light-emitting elements with significantly favorable characteristics. In addition, the organic compounds of one embodiment of the present invention, which are dopants used in these light-emitting elements, were found to be organic compounds that emit light with favorable blue chromaticity at significantly high efficiency.

Among the three, the light-emitting element 18 uses the light-emitting substance 3,10mmtBuFrA2Nbf(IV)-02, and 3,10mmtBuFrA2Nbf(IV)-02 contains a tert-butyl group, which is a hydrocarbon group. Because of this, intermolecular force between the light-emitting substances was suppressed and concentration quenching was inhibited, which probably resulted in the high external quantum efficiency of 3,10mmtBuFrA2Nbf(IV)-02.

REFERENCE NUMERALS 101 anode
102 cathode
103 EL layer
111 hole-injection layer
112 hole-transport layer
113 light-emitting layer
114 electron-transport layer
115 electron-injection layer
116 charge-generation layer
117 P-type layer
118 electron-relay layer
119 electron-injection buffer layer
400 substrate
401 first electrode
403 EL layer
404 second electrode
405 sealant
406 sealant
407 sealing substrate
412 pad
420 IC chip
501 first electrode
502 second electrode
503 EL layer
511 first light-emitting unit
512 second light-emitting unit
513 charge-generation layer
601 driver circuit portion (source line driver circuit)
602 pixel portion
603 driver circuit portion (gate line driver circuit)
604 sealing substrate
605 sealant
607 space
608 wiring
609 FPC (flexible printed circuit)
610 element substrate
611 FET for switching
612 FET for current control
613 first electrode
614 insulator
616 EL layer
617 second electrode
618 light-emitting element
623 n-channel-type FET
624 p-channel-type FET
730 insulating film
770 planarization insulating film
772 conductive film
782 light-emitting element
783 droplet discharge apparatus
784 droplet
785 layer
786 layer containing light-emitting substance
788 conductive film
901 housing
902 liquid crystal layer
903 backlight unit
904 housing
905 driver IC
906 terminal
951 substrate
952 electrode
953 insulating layer
954 partition layer
955 EL layer
956 electrode
1001 substrate
1002 base insulating film
1003 gate insulating film
1006 gate electrode
1007 gate electrode
1008 gate electrode
1020 first interlayer insulating film
1021 second interlayer insulating film
1022 electrode
1024W first electrode of light-emitting element
1024R first electrode of light-emitting element
1024G first electrode of light-emitting element
1024B first electrode of light-emitting element
1025 partition
1028 EL layer
1029 cathode
1031 sealing substrate
1032 sealant
1033 transparent base material
1034R red coloring layer
1034G green coloring layer
1034B blue coloring layer
1035 black layer (black matrix)
1037 third interlayer insulating film
1040 pixel portion
1041 driver circuit portion
1042 peripheral portion
1400 droplet discharge apparatus
1402 substrate
1403 droplet discharge means
1404 imaging means
1405 head
1406 dotted line
1407 control means
1408 storage medium
1409 image processing means
1410 computer
1411 marker
1412 head
1413 material supply source 1414 material supply source
1415 material supply source
1416 head
2001 housing
2002 light source
3001 lighting device
5000 display region
5001 display region
5002 display region
5003 display region
5004 display region
5005 display region
7101 housing
7103 display portion
7105 stand
7107 display portion
7109 operation key
7110 remote controller
7201 main body
7202 housing
7203 display portion
7204 keyboard
7205 external connection port
7206 pointing device
7210 second display portion
7401 housing
7402 display portion
7403 operation button
7404 external connection port
7405 speaker
7406 microphone
9033 clasp
9034 switch
9035 power switch
9036 switch
9310 portable information terminal
9311 display panel
9312 display region
9313 hinge
9315 housing
9630 housing
9631 display portion
9631a display portion
9631b display portion
9632a touch panel region
9632b touch panel region
9633 solar cell
9634 charge and discharge control circuit
9635 battery
9636 DCDC converter
9637 operation key
9638 converter
9639 button

The invention claimed is:

1. An organic compound represented by a general formula (G1),

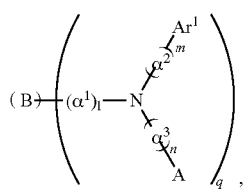

(G1)

wherein B represents any of a substituted or unsubstituted naphthobisbenzofuran skeleton, a substituted or unsubstituted naphthobisbenzothiophene skeleton, and a substituted or unsubstituted naphthobenzofuranobenzothiophene skeleton; a substituent in the substituted skeletons of the B is any of a hydrocarbon group having 1 to 10 carbon atoms, a cyclic hydrocarbon group having 3 to 10 carbon atoms, an aromatic hydrocarbon group having 6 to 14 carbon atoms, and a diarylamino group having 12 to 32 carbon atoms; $Ar^1$ is any of a substituted or unsubstituted aromatic hydrocarbon group having 6 to 25 carbon atoms, a substituted or unsubstituted dibenzofuranyl group, a substituted or unsubstituted dibenzothiophenyl group, and a substituted or unsubstituted carbazolyl group; a substituent in the substituted groups of the $Ar^1$ is any of hydrogen, a hydrocarbon group having 1 to 10 carbon atoms, a cyclic hydrocarbon group having 3 to 10 carbon atoms, and an aromatic hydrocarbon group having 6 to 14 carbon atoms; A is any of a substituted or unsubstituted dibenzofuranyl group, a substituted or unsubstituted dibenzothiophenyl group, and a substituted or unsubstituted carbazolyl group; a substituent in the substituted groups of A is any of a hydrocarbon group having 1 to 10 carbon atoms, a cyclic hydrocarbon group having 3 to 10 carbon atoms, an aromatic hydrocarbon group having 6 to 14 carbon atoms, and a diarylamino group having 12 to 32 carbon atoms; $\alpha^1$ to $\alpha^3$ are each independently a substituted or unsubstituted bivalent aromatic hydrocarbon group having 6 to 25 carbon atoms; a substituent of the bivalent aromatic hydrocarbon group is any of a hydrocarbon group having 1 to 10 carbon atoms, a cyclic hydrocarbon group having 3 to 10 carbon atoms, and an aromatic hydrocarbon group having 6 to 14 carbon atoms; and m each independently represent an integer of 0 to 2; n is 0, and q is 1 or 2.

2. The organic compound according to claim 1, wherein the 1 is 0.

3. The organic compound according to claim 1, represented by a general formula (G1-1),

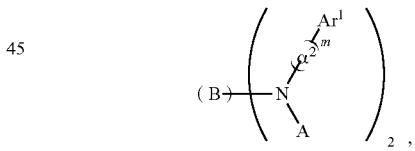

(G1-1)

wherein B is a group represented by a general formula (B1-1) or (B3-1); $Ar^1$ is a substituted or unsubstituted aromatic hydrocarbon group having 6 to 25 carbon atoms; a substituent of the substituted aromatic hydrocarbon group is any of hydrogen, a hydrocarbon group having 1 to 10 carbon atoms, a cyclic hydrocarbon group having 3 to 10 carbon atoms, and an aromatic hydrocarbon group having 6 to 14 carbon atoms; A is a group represented by a general formula (g0); m represents an integer of 0 to 2; $\alpha^2$ is a substituted or unsubstituted bivalent aromatic hydrocarbon group having 6 to 14 carbon atoms; a substituent of the substituted bivalent aromatic hydrocarbon group is any of a hydrocarbon group having 1 to 10 carbon atoms, a cyclic hydrocarbon group having 3 to 10 carbon atoms, an aromatic hydrocarbon group having 6 to 14 carbon atoms,

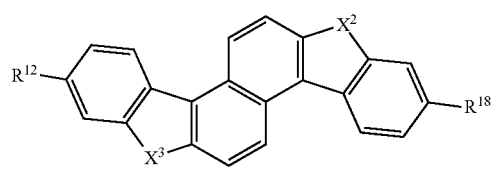

(B1-1)

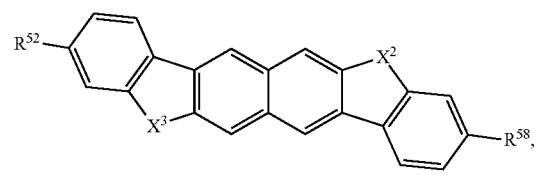

(B3-1)

wherein $X^2$ and $X^3$ each independently represent an oxygen atom or a sulfur atom, $R^{12}$, $R^{18}$, $R^{52}$, and $R^{58}$ represent a single bond,

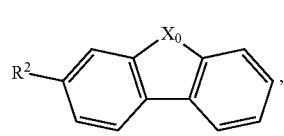

(g0)

wherein $X_0$ is an oxygen atom or a nitrogen atom to which a substituted or unsubstituted phenyl group is bonded; a substituent of the substituted phenyl group is any of a hydrocarbon group having 1 to 10 carbon atoms, a cyclic hydrocarbon group having 3 to 10 carbon atoms, an aromatic hydrocarbon group having 6 to 14 carbon atoms, and $R^2$ represents a single bond.

4. The organic compound according to claim 1, wherein the organic compound has a molecular weight of 1300 or less.

5. The organic compound according to claim 1, wherein the organic compound has a molecular weight of 1000 or less.

6. The organic compound according to claim 1, represented by any of the structural formulae (iii), (vii), (ix), (x), (xi), (xiii), (xv), (xvi), (xvii), (xviii), (xix), (xx), (xxi), (xxii), (xxiii), and (XXiv),

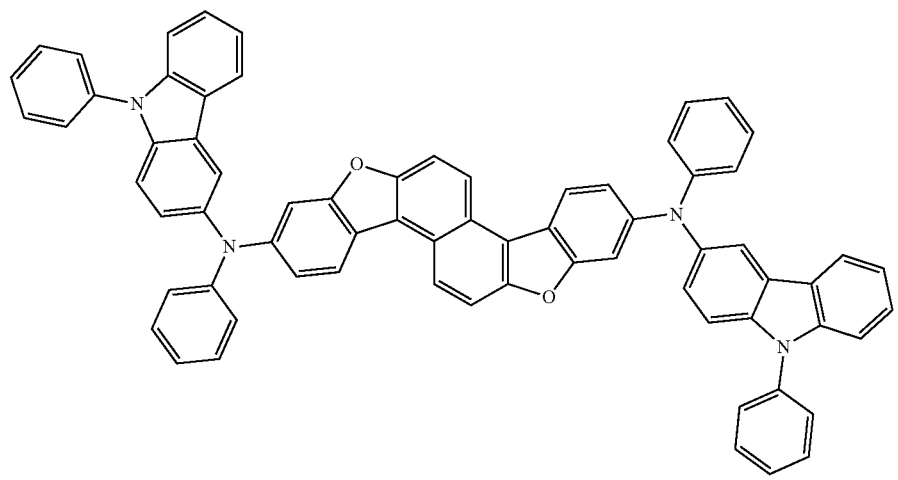

2,9PCA2Nbf(III)

(iii)

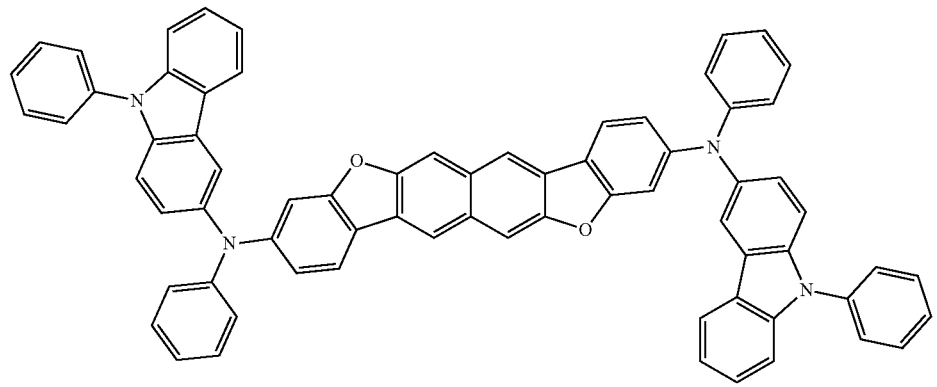

3,10PCA2Nbf(IV)

(vii)

(ix)
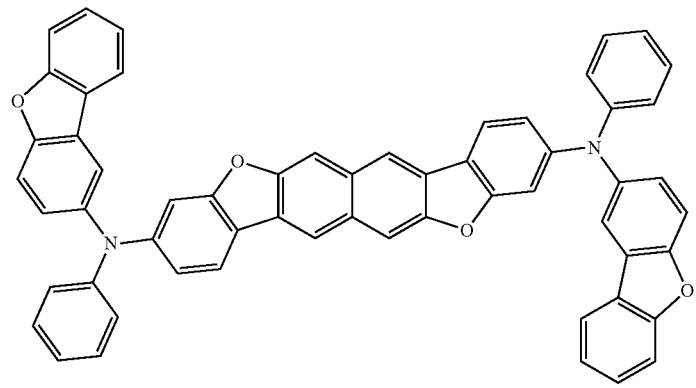
3,10FrA2Nbf(IV)
(x)
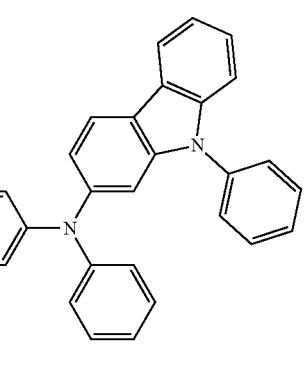
2,9PCA2Nbf (III)-02
(xi)
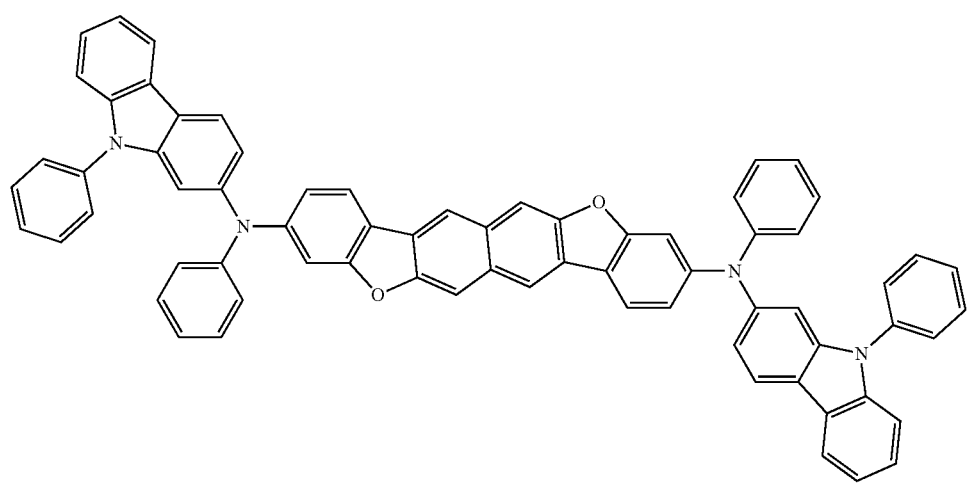
3,10PCA2Nbf (IV)-02

-continued
(xiii)
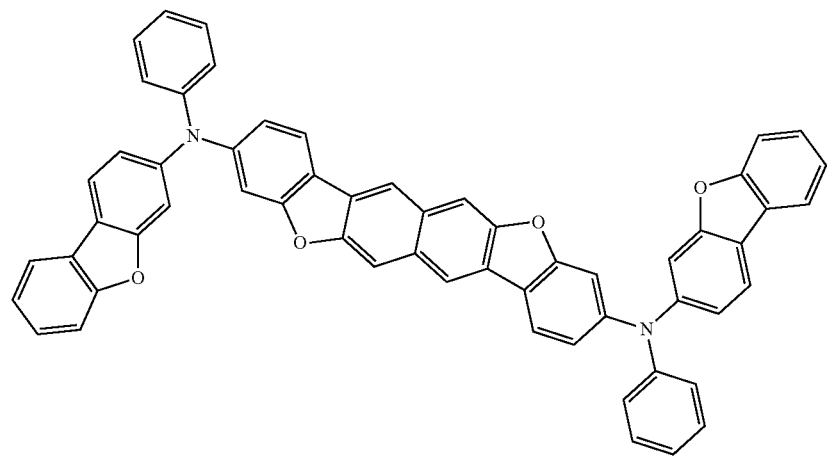
3,10FrA2Nbf (IV)-02
(xv)
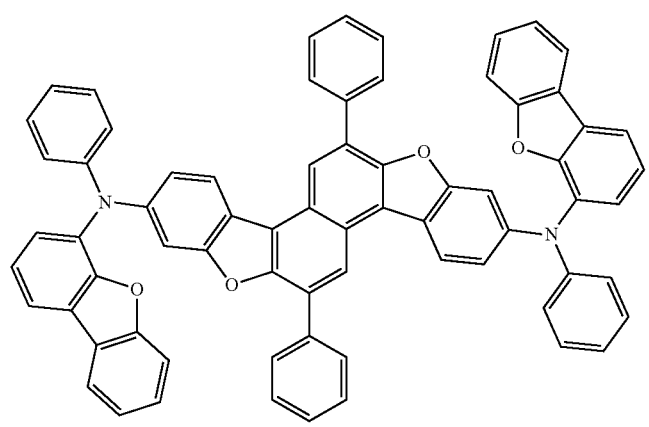
ph-2,9FrA2Nbf(III)-II
(xvi)
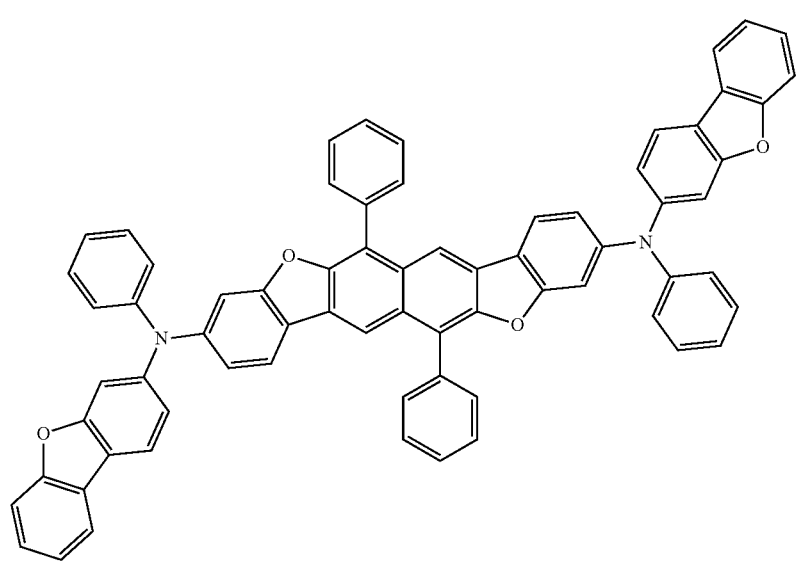
ph-3,10FrA2Nbf(IV)-02

(xvii)
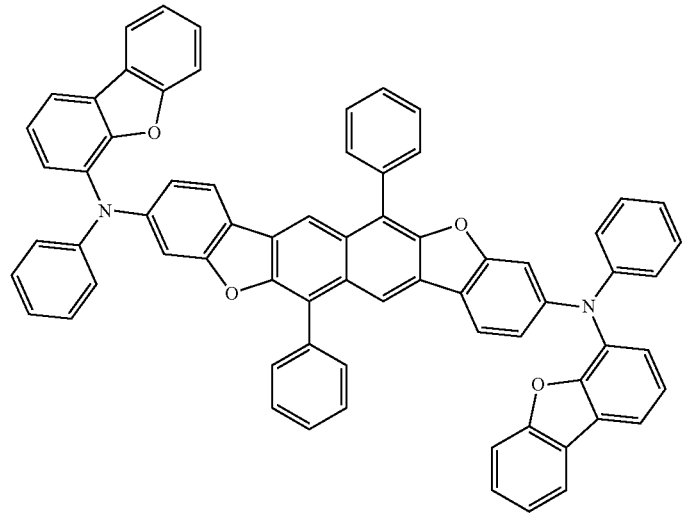
ph-3,10FrA2Nbf(IV)-II
(xviii)
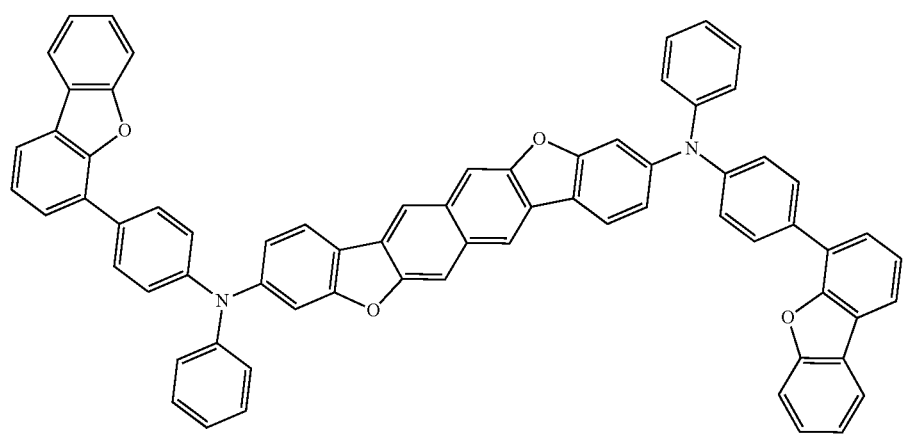
3,10FrBA2Nbf(IV)-II (xix)
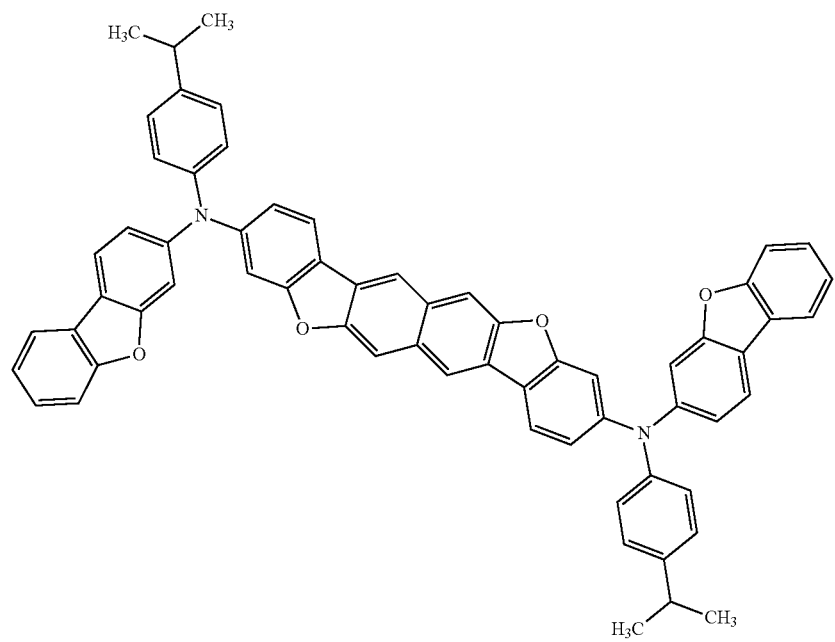
3,10iPrFrA2Nbf(IV)-02
(xx)
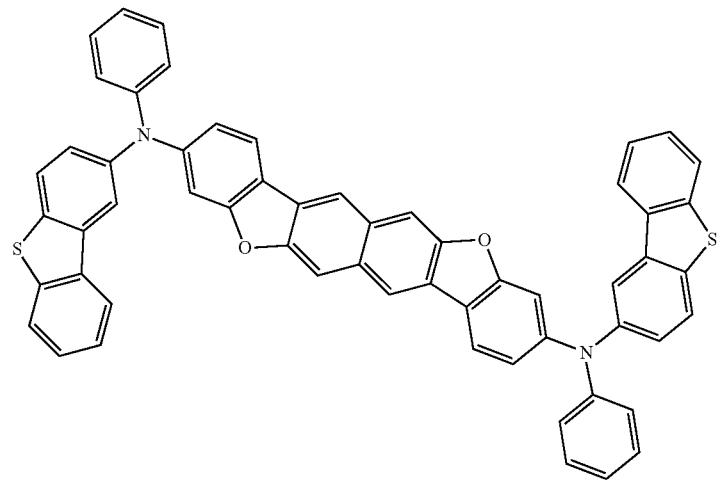
3,10ThA2Nbf(IV)
(xxi)
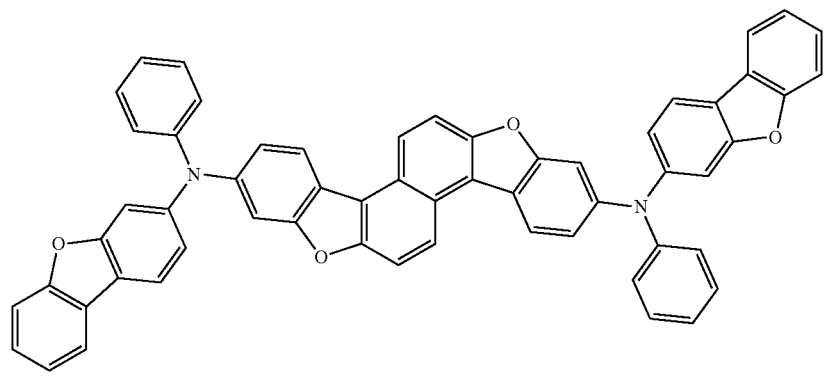
2,9FrA2Nbf(III)-02

-continued
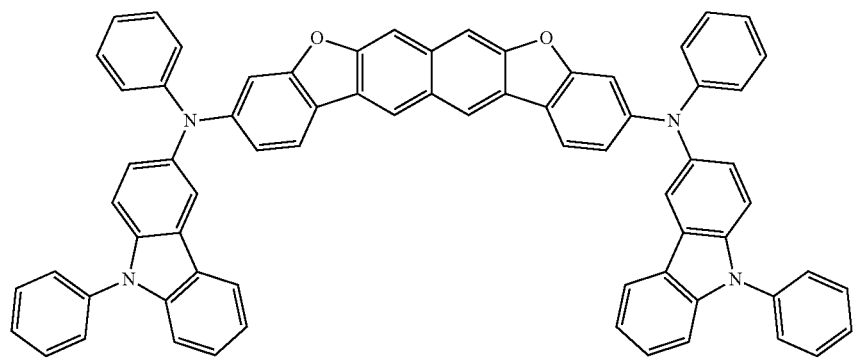
3,10PCA2Nbf(II)
(xxiv)
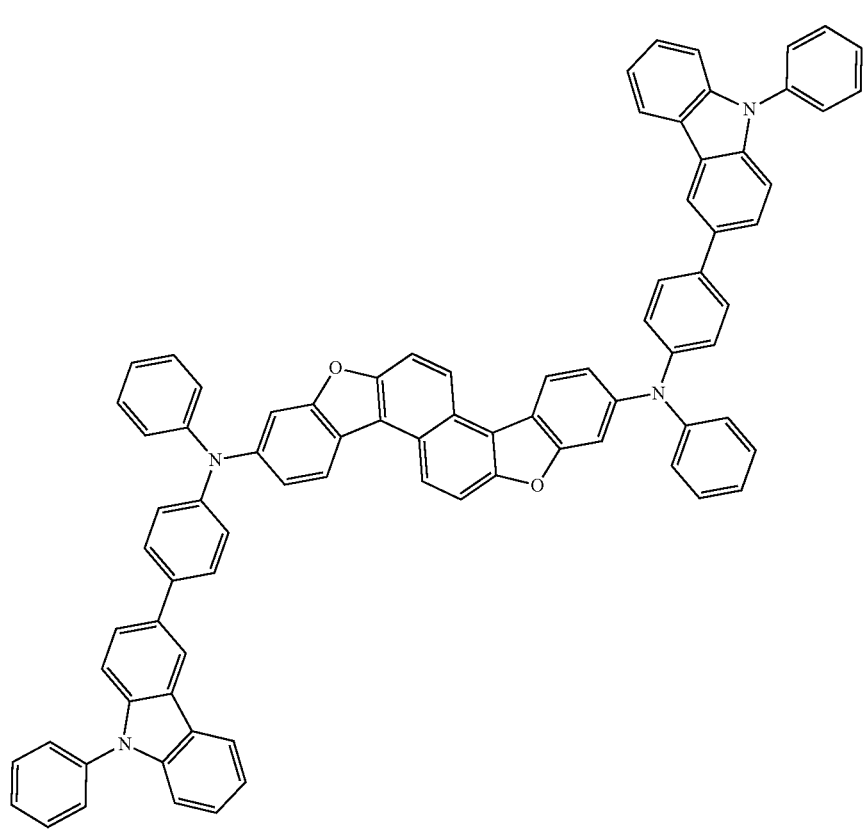
2,9PCBA2Nbf(III)
(xxii)

(xxiii)

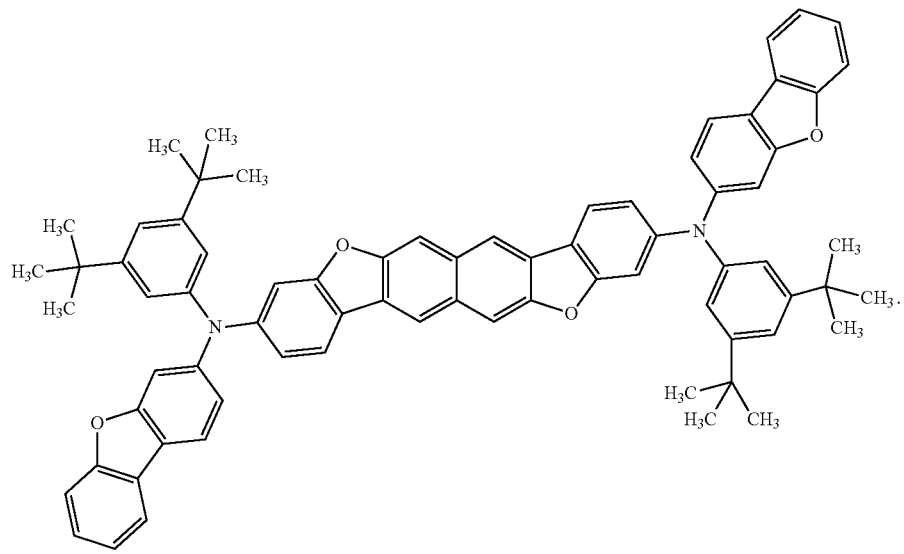

3,10mmtBuFrA2Nbf(IV)-02

7. An electronic device comprising the organic compound according to claim 1.

8. The organic compound according to claim 1, wherein the B is any of skeletons represented by a general formula (B1) to a general formula (B4),

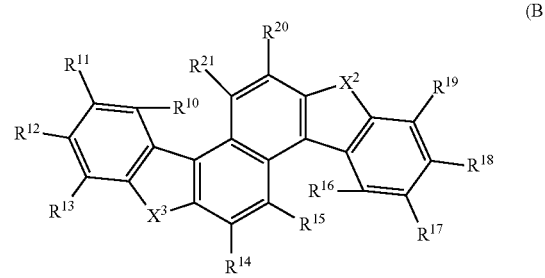
(B1)

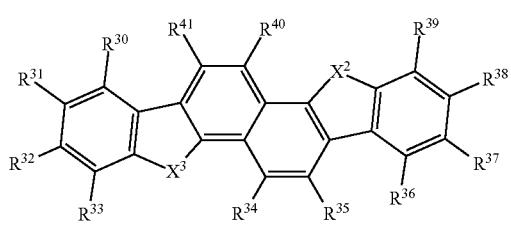
(B2)

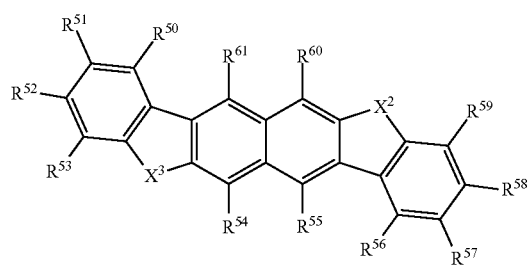
(B3)

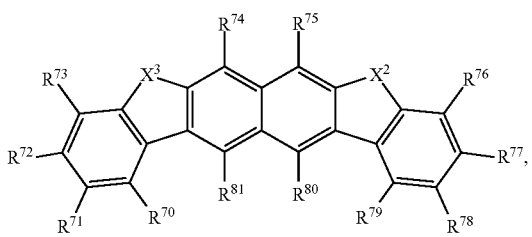
(B4)

wherein $X^2$ and $X^3$ each independently represent an oxygen atom or a sulfur atom; any one or two of $R^{10}$ to $R^{21}$ represent a single bond and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms; any one or two of $R^{30}$ to $R^{41}$ represent a single bond and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms; any one or two of $R^{50}$ to $R^{61}$ represent a single bond and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms; and any one or two of $R^{70}$ to $R^{81}$ represent a single bond and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms, and a substituent of the substituted aromatic hydrocarbon group and the substituted diarylamino group is any of a hydrocarbon group having 1 to 10 carbon atoms, a cyclic hydrocarbon group having 3 to 10 carbon atoms, an aromatic hydrocarbon group having 6 to 14 carbon atoms.

9. The organic compound according to claim 8, wherein the B is any of the skeletons represented by the general formula (B1) to general formula (B3).

10. The organic compound according to claim 8, wherein the $X^2$ and $X^3$ are each an oxygen atom.

11. The organic compound according to claim 1, wherein the B is a skeleton represented by a general formula (B1), (B1)

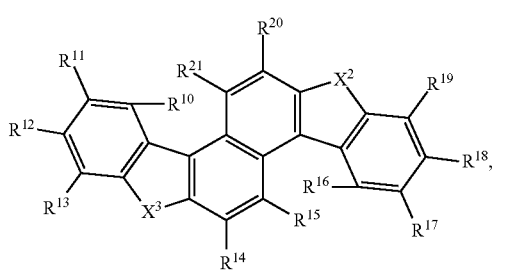

wherein $X^2$ and $X^3$ each independently represent an oxygen atom or a sulfur atom; one or two of $R^{10}$ to $R^{21}$ represent a single bond and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms, and a substituent of the substituted aromatic hydrocarbon group and the substituted diarylamino group is any of a hydrocarbon group having 1 to 10 carbon atoms, a cyclic hydrocarbon group having 3 to 10 carbon atoms, an aromatic hydrocarbon group having 6 to 14 carbon atoms.

12. The organic compound according to claim 11, wherein any one or two of $R^{11}$, $R^{12}$, $R^{17}$, and $R^{18}$ in the general formula (B1) represent a single bond.

13. The organic compound according to claim 11, wherein q in the general formula (G1) is 2, and one of $R^{11}$ and $R^{12}$ is a single bond and one of $R^{17}$ and $R^{18}$ is a single bond in the general formula (B1).

14. The organic compound according to claim 11, wherein q in the general formula (G1) is 2, and $R^{11}$ and $R^{17}$ in the general formula (B1) are a single bond.

15. The organic compound according to claim 11, wherein q in the general formula (G1) is 2, and $R^{12}$ and $R^{18}$ in the general formula (B1) are a single bond.

16. The organic compound according to claim 1, wherein the B is a skeleton represented by a general formula (B2), (B2)

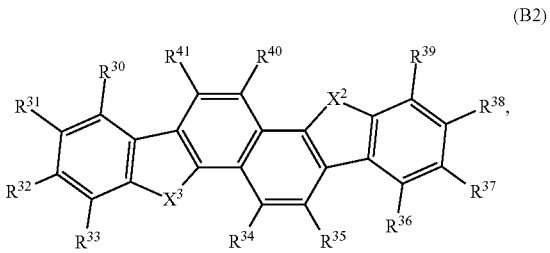

wherein $X^2$ and $X^3$ each independently represent an oxygen atom or a sulfur atom; one or two of $R^{30}$ to $R^{41}$ represent a single bond, and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms, and a substituent of the substituted aromatic hydrocarbon group and the substituted diarylamino group is any of a hydrocarbon group having 1 to 10 carbon atoms, a cyclic hydrocarbon group having 3 to 10 carbon atoms, an aromatic hydrocarbon group having 6 to 14 carbon atoms.

17. The organic compound according to claim 16, wherein any one or two of $R^{31}$, $R^{32}$, $R^{37}$, and $R^{38}$ in the general formula (B2) represent a single bond.

18. The organic compound according to claim 16, wherein q in the general formula (G1) is 2, and $R^{31}$ or $R^{32}$ and $R^{37}$ or $R^{38}$ in the general formula (B2) are a single bond.

19. The organic compound according to claim 16, wherein q in the general formula (G1) is 2, and $R^{31}$ and $R^{37}$ in the general formula (B2) are a single bond.

20. The organic compound according to claim 16, wherein q in the general formula (G1) is 2, and $R^{32}$ and $R^{38}$ in the general formula (B2) are a single bond.

21. The organic compound according to claim 1, wherein the B is a skeleton represented by a general formula (B3), (B3)

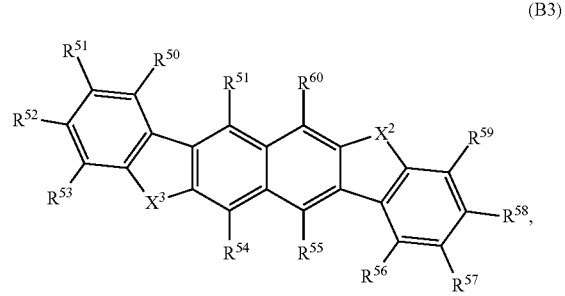

wherein $X^2$ and $X^3$ each independently represent an oxygen atom or a sulfur atom; any one or two of $R^{50}$ to $R^{61}$ represent a single bond, and the others each independently represent any of hydrogen, a hydrocarbon group having 1 to 10 carbon atoms, a cyclic hydrocarbon group having 3 to 10 carbon atoms, a substituted or unsubstituted aromatic hydrocarbon group having 6 to 14 carbon atoms, and a substituted or unsubstituted diarylamino group having 12 to 32 carbon atoms, and a substituent of the substituted aromatic hydrocarbon group and the substituted diarylamino group is any of a hydrocarbon group having 1 to 10 carbon atoms, a cyclic hydrocarbon group having 3 to 10 carbon atoms, an aromatic hydrocarbon group having 6 to 14 carbon atoms.

22. The organic compound according to claim 21, wherein any one or two of $R^{51}$, $R^{52}$, $R^{57}$, and $R^{58}$ in the general formula (B3) represent a single bond.

23. The organic compound according to claim 21, wherein q in the general formula (G1) is 2, and $R^{51}$ or $R^{52}$ and $R^{57}$ or $R^{58}$ in the general formula (B3) are a single bond.

24. The organic compound according to claim 21, wherein q in the general formula (G1) is 2, and $R^{51}$ and $R^{57}$ in the general formula (B3) are a single bond.

25. The organic compound according to claim 21, wherein q in the general formula (G1) is 2, and $R^{52}$ and $R^{58}$ in the general formula (B3) are a single bond.

26. A light-emitting element comprising the organic compound according to claim 1.

27. A light-emitting device comprising the light-emitting element according to claim 26, and a transistor or a substrate.

28. An electronic device comprising the light-emitting device according to claim 27 and a sensor, an operation button, a speaker, or a microphone.

29. A lighting device comprising the light-emitting device according to claim 27 and a housing.

30. The organic compound according to claim 1,
wherein $Ar^1$ is any of groups represented by the following general formulae (g1) and (g2), and A is any of groups represented by the general formulae (g1) and (g2), and $\alpha^1$ to $\alpha^3$ are each independently any of substituted or unsubstituted bivalent aromatic hydrocarbon groups having 6 to 14 carbon atoms; a substituent of the bivalent aromatic hydrocarbon group is any of a hydrocarbon group having 1 to 10 carbon atoms, a cyclic hydrocarbon group having 3 to 10 carbon atoms, an aromatic hydrocarbon group having 6 to 14 carbon atoms,

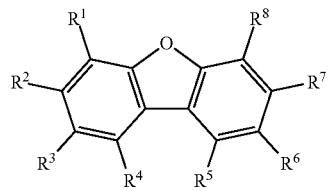

(g1)

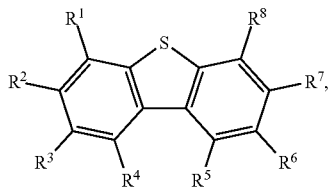

(g2)

wherein any one of $R^1$ to $R^8$ represents a single bond; the others each independently represent any of hydrogen, a hydrocarbon group having 1 to 10 carbon atoms, a cyclic hydrocarbon group having 3 to 10 carbon atoms, and a substituted or unsubstituted aromatic hydrocarbon group having 6 to 14 carbon atoms; a substituent of the substituted aromatic hydrocarbon group is any of a hydrocarbon group having 1 to 10 carbon atoms, a cyclic hydrocarbon group having 3 to 10 carbon atoms, an aromatic hydrocarbon group having 6 to 14 carbon atoms.

31. The organic compound according to claim 30, wherein A is the group represented by the general formula (g1).

32. The organic compound according to claim 30,
wherein, in the case where A and/or $Ar^1$ are/is each independently the group represented by the general formula (g1) or general formula (g2), any of $R^1$ to $R^3$ in the group B represented by the general formula (g1) or general formula (g2) is a single bond.

33. The organic compound according to claim 30, wherein the q is 2.

34. The organic compound according to claim 30,
wherein the A is the group represented by the general formula (g1),
wherein $R^2$ in the group represented by the general formula (g1) represents a single bond.

* * * * *